US011041173B2

(12) United States Patent
Zhang et al.

(10) Patent No.: US 11,041,173 B2
(45) Date of Patent: *Jun. 22, 2021

(54) DELIVERY, ENGINEERING AND OPTIMIZATION OF SYSTEMS, METHODS AND COMPOSITIONS FOR SEQUENCE MANIPULATION AND THERAPEUTIC APPLICATIONS

(71) Applicants: THE BROAD INSTITUTE, INC., Cambridge, MA (US); MASSACHUSETTS INSTITUTE OF TECHNOLOGY, Cambridge, MA (US)

(72) Inventors: Feng Zhang, Cambridge, MA (US); Randall Jeffrey Platt, Cambridge, MA (US); Guoping Feng, Cambridge, MA (US); Yang Zhou, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,603

(22) Filed: Nov. 11, 2016

(65) Prior Publication Data
US 2017/0107536 A1 Apr. 20, 2017

Related U.S. Application Data

(63) Continuation of application No. 14/481,339, filed on Sep. 9, 2014, now abandoned, which is a continuation of application No. PCT/US2013/074667, filed on Dec. 12, 2013.

(60) Provisional application No. 61/847,537, filed on Jul. 17, 2013, provisional application No. 61/835,931, filed on Jun. 17, 2013, provisional application No. 61/836,123, filed on Jun. 17, 2013, provisional application No. 61/828,130, filed on May 28, 2013, provisional application No. 61/819,803, filed on May 6, 2013, provisional application No. 61/814,263, filed
(Continued)

(51) Int. Cl.
| | | |
|---|---|---|
| C12N 15/85 | (2006.01) | |
| C12N 9/16 | (2006.01) | |
| C12N 15/31 | (2006.01) | |
| C12N 15/52 | (2006.01) | |
| C12N 15/63 | (2006.01) | |
| A61K 48/00 | (2006.01) | |
| C12N 15/90 | (2006.01) | |
| A01K 67/027 | (2006.01) | |
| C12N 9/22 | (2006.01) | |
| C12N 15/10 | (2006.01) | |
| C12N 15/86 | (2006.01) | |
| C12N 15/01 | (2006.01) | |
| C12N 15/82 | (2006.01) | |
| C12N 9/96 | (2006.01) | |

(52) U.S. Cl.
CPC ........ *C12N 15/907* (2013.01); *A01K 67/0275* (2013.01); *A01K 67/0278* (2013.01); *C12N 9/22* (2013.01); *C12N 9/96* (2013.01); *C12N 15/01* (2013.01); *C12N 15/102* (2013.01); *C12N 15/63* (2013.01); *C12N 15/8213* (2013.01); *C12N 15/85* (2013.01); *C12N 15/8509* (2013.01); *C12N 15/86* (2013.01); *C12N 15/90* (2013.01); *A01K 2217/05* (2013.01); *A01K 2217/052* (2013.01); *A01K 2217/07* (2013.01); *A01K 2217/072* (2013.01); *A01K 2227/105* (2013.01); *A01K 2267/03* (2013.01); *C12N 2800/22* (2013.01)

(58) Field of Classification Search
None
See application file for complete search history.

(56) References Cited

U.S. PATENT DOCUMENTS

| | | |
|---|---|---|
| 5,622,856 A | 4/1997 | Natsoulis |
| 6,251,677 B1 | 6/2001 | Wilson et al. |

(Continued)

FOREIGN PATENT DOCUMENTS

| | | |
|---|---|---|
| CN | 101228176 | 7/2008 |
| CN | 103388006 | 11/2013 |

(Continued)

OTHER PUBLICATIONS

Stratikopoulos et al, The hormonal action of IGF1 in postnatal mouse growth, 2008, PNAS, pp. 19378-19383.*

(Continued)

*Primary Examiner* — Maria Marvich
(74) *Attorney, Agent, or Firm* — Foley & Lardner LLP

(57) ABSTRACT

The invention provides for delivery, engineering and optimization of systems, methods, and compositions for manipulation of sequences and/or activities of target sequences. Provided are delivery systems and tissues or organ which are targeted as sites for delivery. Also provided are vectors and vector systems some of which encode one or more components of a CRISPR complex, as well as methods for the design and use of such vectors. Also provided are methods of directing CRISPR complex formation in eukaryotic cells to ensure enhanced specificity for target recognition and avoidance of toxicity and to edit or modify a target site in a genomic locus of interest to alter or improve the status of a disease or a condition.

15 Claims, 109 Drawing Sheets

Specification includes a Sequence Listing.

Related U.S. Application Data on Apr. 20, 2013, provisional application No. 61/806,375, filed on Mar. 28, 2013, provisional application No. 61/802,174, filed on Mar. 15, 2013, provisional application No. 61/791,409, filed on Mar. 15, 2013, provisional application No. 61/769,046, filed on Feb. 25, 2013, provisional application No. 61/758,468, filed on Jan. 30, 2013, provisional application No. 61/748,427, filed on Jan. 2, 2013, provisional application No. 61/736,527, filed on Dec. 12, 2012.

(56) References Cited

U.S. PATENT DOCUMENTS

| | | | |
|---|---|---|---|
| 7,601,492 | B2 | 10/2009 | Fu et al. |
| 7,691,995 | B2 | 4/2010 | Zamore et al. |
| 8,697,359 | B1 | 4/2014 | Zhang |
| 8,771,945 | B1 | 7/2014 | Zhang |
| 8,865,406 | B2 | 10/2014 | Zhang et al. |
| 8,871,445 | B2 * | 10/2014 | Cong ............... C12N 9/22 424/94.1 |
| 8,889,418 | B2 * | 11/2014 | Zhang ............... C12N 15/63 435/455 |
| 8,895,308 | B1 | 11/2014 | Zhang et al. |
| 8,932,814 | B2 * | 1/2015 | Cong ............... C12N 15/63 424/94.1 |
| 8,993,233 | B2 | 3/2015 | Zhang et al. |
| 8,945,839 | B2 | 8/2015 | Zhang |
| 9,512,446 | B1 | 12/2016 | Joung et al. |
| 9,549,901 | B2 | 1/2017 | Shi et al. |
| 9,597,357 | B2 | 3/2017 | Gregory et al. |
| 9,623,071 | B2 | 4/2017 | Guo et al. |
| 9,637,739 | B2 | 5/2017 | Siksnys et al. |
| 9,701,964 | B2 | 7/2017 | Clube et al. |
| 9,834,791 | B2 | 12/2017 | Zhang et al. |
| 9,873,894 | B2 | 1/2018 | Conway et al. |
| 10,301,651 | B2 | 5/2019 | Doudna et al. |
| 10,660,943 | B2 | 5/2020 | Bikard et al. |
| 2003/0186238 | A1 | 10/2003 | Allawi et al. |
| 2004/0111221 | A1 | 10/2004 | Beattie |
| 2005/0196851 | A1 | 9/2005 | Uckun |
| 2005/0220796 | A1† | 10/2005 | Dynan |
| 2006/0178297 | A1 | 8/2006 | Troy et al. |
| 2006/0234247 | A1 | 10/2006 | Puttaraju |
| 2007/0016012 | A1 | 1/2007 | Hartlep |
| 2007/0244031 | A1 | 10/2007 | Lu et al. |
| 2008/0293655 | A1 | 11/2008 | Aygun et al. |
| 2010/0055798 | A1 | 3/2010 | Battersby |
| 2010/0076057 | A1 | 3/2010 | Sontheimer |
| 2010/0081707 | A1 | 4/2010 | Ali et al. |
| 2010/0093617 | A1 | 4/2010 | Barrangou et al. |
| 2010/0233084 | A1 | 9/2010 | Narasimhaswamy et al. |
| 2011/0016540 | A1 | 1/2011 | Weinstein |
| 2011/0059502 | A1 | 3/2011 | Chalasani |
| 2011/0189776 | A1 | 8/2011 | Terns et al. |
| 2011/0223638 | A1 | 9/2011 | Wiedenheft et al. |
| 2011/0239315 | A1 | 9/2011 | Bonas et al. |
| 2012/0029891 | A1 | 2/2012 | Behlke et al. |
| 2013/0096182 | A1 | 4/2013 | Chatterjee et al. |
| 2013/0130248 | A1 | 5/2013 | Haurwitz et al. |
| 2013/0315831 | A1 | 11/2013 | Shi et al. |
| 2014/0068797 | A1 | 3/2014 | Doudna et al. |
| 2014/0294771 | A1 | 10/2014 | Schaffer et al. |
| 2014/0295557 | A1 | 10/2014 | Joung et al. |
| 2014/0315985 | A1 | 10/2014 | May et al. |
| 2014/0342456 | A1 | 11/2014 | Mali |
| 2014/0356956 | A1 | 12/2014 | Church et al. |
| 2014/0357530 | A1 | 12/2014 | Zhang et al. |
| 2015/0045546 | A1 | 2/2015 | Siksnys et al. |
| 2015/0071899 | A1 | 3/2015 | Liu et al. |
| 2015/0071903 | A1 | 3/2015 | Liu et al. |
| 2015/0071906 | A1 | 3/2015 | Liu et al. |
| 2015/0232881 | A1 | 8/2015 | Glucksmann et al. |
| 2015/0247150 | A1 | 9/2015 | Zhang et al. |
| 2015/0291965 | A1 | 10/2015 | Zhang et al. |
| 2015/0322457 | A1 | 11/2015 | Kim et al. |
| 2015/0353905 | A1 | 12/2015 | Weiss et al. |
| 2016/0017366 | A1 | 1/2016 | Chen et al. |
| 2016/0024510 | A1 | 1/2016 | Bikard |
| 2016/0024524 | A1 | 1/2016 | Joung et al. |
| 2016/0130609 | A1 | 5/2016 | Doudna et al. |
| 2016/0237456 | A1 | 8/2016 | Church et al. |
| 2016/0251648 | A1 | 9/2016 | Wang et al. |
| 2016/0281072 | A1 | 9/2016 | Zhang |
| 2016/0298135 | A1 | 10/2016 | Chen |
| 2016/0298137 | A1 | 10/2016 | Chen et al. |
| 2016/0324938 | A1 | 11/2016 | Bikard |
| 2016/0340662 | A1 | 11/2016 | Zhang et al. |
| 2017/0175144 | A1 | 6/2017 | Zhang et al. |
| 2018/0127783 | A1 | 5/2018 | Zhang et al. |
| 2018/0230495 | A1 | 8/2018 | Doudna et al. |
| 2019/0010471 | A1 | 1/2019 | Zhang et al. |
| 2020/0282026 | A1 | 9/2020 | Bikard et al. |
| 2020/0282027 | A1 | 9/2020 | Bikard et al. |
| 2021/0060140 | A1 | 3/2021 | Bikard et al. |
| 2021/0060141 | A1 | 3/2021 | Bikard et al. |

FOREIGN PATENT DOCUMENTS

| | | |
|---|---|---|
| CN | 112015013784 | 3/2014 |
| CN | 104854241 A | 8/2015 |
| EP | 2591770 | 5/2013 |
| EP | 2784162 | 1/2014 |
| EP | 2764103 | 8/2014 |
| EP | 2771468 | 9/2014 |
| EP | 2 828 386 A1 | 1/2015 |
| FR | 2872170 A1 | 12/2005 |
| IN | 49/2015 | 12/2015 |
| JP | 2004-519245 A | 7/2004 |
| JP | 2004-537285 A | 12/2004 |
| JP | 2005-509409 A | 4/2005 |
| JP | 2006-513694 A | 4/2006 |
| JP | 2006-518996 A | 8/2006 |
| JP | 2007-501626 A | 2/2007 |
| JP | 2009502170 | 1/2009 |
| JP | 2009-536827 A | 10/2009 |
| JP | 2010-522547 A | 7/2010 |
| JP | 2012-508235 | 4/2012 |
| JP | 2012-511332 A | 5/2012 |
| JP | 2012510812 | 5/2012 |
| JP | 2012-529287 A | 11/2012 |
| JP | 2013-500045 A | 1/2013 |
| JP | 2013-518602 A | 5/2013 |
| JP | 2013-544077 A | 12/2013 |
| JP | 2014-526279 A | 10/2014 |
| JP | 2015-523856 A | 8/2015 |
| JP | 2016-500262 A | 1/2016 |
| JP | 2016-501531 | 1/2016 |
| JP | 2016-501532 A | 1/2016 |
| JP | 2016000003 | 1/2016 |
| JP | 2016-025710 A | 2/2016 |
| JP | 2016-504026 A | 2/2016 |
| JP | 2016-505256 A | 2/2016 |
| JP | 2016502840 | 2/2016 |
| JP | 2016-093196 | 5/2016 |
| JP | 2016-516169 A | 6/2016 |
| JP | 2016-517954 A | 6/2016 |
| JP | 2016-131404 A | 7/2016 |
| JP | 2016-520317 A | 7/2016 |
| JP | 2016-521554 A | 7/2016 |
| JP | 2016-521975 A | 7/2016 |
| JP | 2016-521995 | 7/2016 |
| JP | 2016-523082 A | 8/2016 |
| JP | 2016-524472 | 8/2016 |
| JP | 6395765 | 10/2016 |
| JP | 2016182140 | 10/2016 |
| JP | 2017-501151 A | 1/2017 |
| JP | 2017-501699 | 1/2017 |
| RU | 2009136452 A | 4/2011 |
| WO | WO-02/074968 A1 | 9/2002 |
| WO | WO-02/080851 A2 | 10/2002 |
| WO | WO-03/014318 A2 | 2/2003 |
| WO | WO-03/104414 A2 | 12/2003 |
| WO | WO-2004/029219 A2 | 4/2004 |

(56) References Cited

FOREIGN PATENT DOCUMENTS

| WO | WO-2004/046321 A2 | 6/2004 |
|---|---|---|
| WO | WO-2004/062618 A2 | 7/2004 |
| WO | 2005/014791 | 2/2005 |
| WO | 2005049642 | 6/2005 |
| WO | 2007014275 | 2/2007 |
| WO | WO-2007/134161 A2 | 11/2007 |
| WO | 2008093152 | 8/2008 |
| WO | WO/2008/108989 | 9/2008 |
| WO | WO-2008/116860 A2 | 10/2008 |
| WO | WO/2010/054108 | 5/2010 |
| WO | 2010065123 | 6/2010 |
| WO | WO-2010/068816 A1 | 6/2010 |
| WO | 2010079430 | 7/2010 |
| WO | WO-2010/075424 A2 | 7/2010 |
| WO | WO-2010/143917 | 12/2010 |
| WO | 2011011767 | 1/2011 |
| WO | WO-2011/016840 A2 | 2/2011 |
| WO | WO-2011/036510 A1 | 3/2011 |
| WO | 2011064736 | 6/2011 |
| WO | WO-2011/076873 A1 | 6/2011 |
| WO | WO-2011/100058 | 8/2011 |
| WO | 2011146121 | 11/2011 |
| WO | WO-2012/012738 A1 | 1/2012 |
| WO | WO-2012/031205 | 3/2012 |
| WO | WO-2012/051343 A1 | 4/2012 |
| WO | 2012149470 | 11/2012 |
| WO | WO/2012/164565 | 12/2012 |
| WO | WO-2013/044008 A2 | 3/2013 |
| WO | WO-2013/052681 | 4/2013 |
| WO | WO-2013/155572 | 4/2013 |
| WO | WO-2013/071440 A1 | 5/2013 |
| WO | WO-2013/078400 A1 | 5/2013 |
| WO | WO2013/082519 | 6/2013 |
| WO | WO/2013/098244 | 7/2013 |
| WO | 2013130824 | 9/2013 |
| WO | WO 2013/141680 | 9/2013 |
| WO | WO 2013/142578 | 9/2013 |
| WO | WO-2013/176772 A1 | 11/2013 |
| WO | WO/2013176772 | 11/2013 |
| WO | WO-2014/165349 A1 | 3/2014 |
| WO | WO 2014/065596 | 5/2014 |
| WO | 2014093595 | 6/2014 |
| WO | 2014093622 | 6/2014 |
| WO | 2014093635 | 6/2014 |
| WO | 2014093661 | 6/2014 |
| WO | 2014093694 | 6/2014 |
| WO | 2014093701 | 6/2014 |
| WO | 2014093709 | 6/2014 |
| WO | 2014093718 | 6/2014 |
| WO | 2014099744 | 6/2014 |
| WO | WO 2014/09371 | 6/2014 |
| WO | WO 2014/089290 | 6/2014 |
| WO | WO 2014/093479 | 6/2014 |
| WO | WO-2014/093655 | 6/2014 |
| WO | WO 2014/099744 | 6/2014 |
| WO | WO 2014/099750 | 6/2014 |
| WO | WO-2015/031775 | 8/2014 |
| WO | WO-2014/144761 A2 | 9/2014 |
| WO | WO-2014/186585 A2 | 11/2014 |
| WO | 2014204724 | 12/2014 |
| WO | 2014204725 | 12/2014 |
| WO | 2014204727 | 12/2014 |
| WO | 2014204729 | 12/2014 |
| WO | WO-2014/191518 A1 | 12/2014 |
| WO | WO-2014/197568 A2 | 12/2014 |
| WO | WO-2014/197748 A2 | 12/2014 |
| WO | WO-2014/204726 | 12/2014 |
| WO | WO-2014/204728 | 12/2014 |
| WO | WO-2015/006747 A2 | 1/2015 |
| WO | WO-2015/035136 A2 | 3/2015 |
| WO | WO-2015/048577 | 4/2015 |
| WO | 2015065964 | 5/2015 |
| WO | WO-2015/070083 A1 | 5/2015 |
| WO | WO-2015/071474 A2 | 5/2015 |
| WO | 2015089419 | 6/2015 |
| WO | WO-2015/089351 A1 | 6/2015 |
| WO | WO-2015/089364 A1 | 6/2015 |
| WO | WO-2015/089427 A1 | 6/2015 |
| WO | WO-2015/113063 A1 | 7/2015 |
| WO | WO-2016/022866 A1 | 2/2016 |
| WO | WO-2016/141224 A1 | 9/2016 |
| WO | 2019093622 | 7/2017 |

OTHER PUBLICATIONS

Cong et al, Multiplex Genome Engineering Using CRISPR/Cas Systems, Science. Feb. 15, 2013; 339(6121): 819-823.*

Takara Bio USA, Inc, Lenti-X™ Tet-On® 3G CRISPR/Cas9 System User Manual, 2009, pp. 1-35.*

Andreas, et al. "Enhanced efficiency through nuclear localization signal fusion on phage C31-integrase: activity comparison with Cre and FLPe recombinase in mammalian cells" Nucleic Acids Research, 2002, 30(11):2299-2306.

Boch, et al. "Breaking the Code of DNA Binding Specificity of TAL—Type III Effecors" Science, 2009, 326:1509-1512.

Boch, et al. "Xanthomonas AvrBs3 Family-Type III Effectors: Discovery and Function" Annu. Rev. Phytopathol, 2010, Vo. 48:419-436.

Bogdanove, et al. "TAL Effectors:Customizable Proteins for DNA Targeting" Science, 2011, 333:1843-1846.

Briner, et al. "Guide RNA Functional Modules Direct Cas9 Activity and Orthogonality" Molecular Cell, Oct. 2014, 56:333-339.

Cermak, et al. Efficient design and assembly of custom TALEN and other TAL Effector-Based Constructs for DNA Targeting, Nucleic Acids Research (2011) vol. 39, No. 12, e82, p. 1-11.

Jieliang Chen, et al. "An Efficient Antiviral Strategy for Targeting Hepatitis B Virus Genome Using Transcription Activator-Like Effector Nucelases" Molecular Therapy, 2014, 22(2):303-311.

Cho, et al. "Generation of Transgenic Mice" Curr Protoc Cell Biol., 2011, 19.11.doi:10.1002/0471143030. cb1911s42.

Christian, et al. "Targeting DNA Double-Strand Breaks With TAL Effector Nucleases" Genetics, Oct. 2010, vol. 186:757-761.

Christian, et al. "Supporting Information-Targeting DNA Double-Strand Breaks With TAL Effector Nucleases" Genetics, 2010, DOI:10.1534/110.120717:1SI-8SI.

Cong, et al. "Comprehensive interrogation of natural TALE DNA-binding modules and transcriptional repressor domains" Nature Communications, 2012, 3:968, D0I:10/2038/ncomms1962.

CRISPR-associated endonuclease Cas9; Oct. 21, 2012, XP002738511M, http://ibis/exam/dbfetch.jsp?id=uniprot:J7RUA5.

"Crispr genome engineering" XP055167591, Oct. 5, 2013, https://web.archive.org/web/2013100500 [retrieved on Feb. 5, 2015.

Dahlman, et al. "In vivo endothelial siRNA delivery using polymeric nanoparticles with low molecular weight" Nat. Nanotechnol., 2014, 9(8)648-655. doi:10.1038/nnano.2014.84.

Dingwall, et al. "Abstract: A Polypeptide Domain That Specifies Migration of Nucleoplasmin into the Nucleus" Cell, 1982, 30(2):449-58.

Deltcheva, et al. "Supplementary Information: CRISPR RNA Maturation by Trans-Encoded Small RNA and Host Factor RNase III" www.Nature.com/doi:10.1038/nature09886:1-35.

Drittanti, et al. "High throughput production, screening and anyalysis of adeno-associated viral vectors" Gene Therapy, 2000, 7:924-929.

Ebina, et al. "Harnessing the CRISPR/Cas9 system to disrupt latent HIV-1 provirus" Scientific Reports, 2013, 2:2510, doi:10.1038/srep02510.

"Fixes, extra genomes, and improvements to the CRISPR Design Tool" Google Groups, XP055167583, Oct. 21, 2013, URL:https://groups.google.com/forum/#!topic/crispr/g9Q8U1tNSis [retrieved on Feb. 5, 2015].

Fu, et al. "High-frequency off-target mutagenesis induced by CRISPR-Cas nucleases in human cells", Nature Biotechnology, 2013, 31(9):822-826.

Garneau, et al. "The CRISPR-Cas bacterial immune systems cleaves bacteriophage and plasmid DNA" Nature, Nov. 2010, 468:67-71.

Geiβler, et al. "Trancscriptional Activators of Human Genes with Programmable DNA-Specificity" PLone, 2011, 6(5):e19509. doi:10.1371/hournal.pone.0019509.

(56) References Cited

OTHER PUBLICATIONS

Gilbert, et al. "CRISPR-Mediated Modular RNA-Guided Regulation of Transcription in Eukaryotes" Cell, Jul. 2013, 154:442-451.
Goldfarb, et al. "Synthetic peptides as nuclear localization signals" Nature, Aug. 1986, 322(14):641-644.
Gustafsson, et al. "Codon Bias and heterologous protein expression" TRENDS in Biotechnology, Jul. 2004, 22(7):346-353.
Haft, et al. "A Guild of 45 CRISPR-Associated (Cas) Protein Families and Multiple CRISPR/Cas Subtypes Exist in Prokaryotic Genomes" PLoS Computational Biology, 2005, 1(6):0474-0483.
Haft, D.H., "HMM Summary p. TIGR04330" 2012, XP-002757584, http://jcvi.org/cgi-bin/tigrfams/HmmReportPage.cgi?acc=TIGR04330.
Hale, et al. "RNA-Guided RNA Cleavage by a CRISPR RNA-Cas Protein Complex" Cell, 2009, 139:945-956.
Hale, et al. "Prokaryotic siliencing (psi) RNAs in Pyrococcus furiosus", RNA, 2008, 14:2572-2579.
Heintze, et al. "A CRISPR CASe for high-throughput silencing", Frontiers in Genetics, Oct. 2013, 4(193): DOI:10.3389/gfene.2013.00193.
Holmes, "CRISPR Genome Engineering Resources" XP055167586, Oct. 2, 2013, https://groups.google/forum/#!top1c/crispr/5BpJj_Y3jyG [retreieved on Feb. 5, 2015].
Holmes, "Understanding Scores" XP055167918, Oct. 23, 2013, https://groups.google.com/forum/#!profo_nt50txrP9Yb6e_LXccolb9hNf7gKeMLt6rgaVQ4fOsQ/crispr/fkhX7Fu3r-1/rziHxKT76pYJ [retrieved on Feb. 6, 2015].
Hsu, et al. "Development and Applications of CRISPR-Cas9 for Genome Engineering" Cell, Jun. 2014, 157:1262-1278.
Hsu et al., "Supplementary Information-DNA targeting specificity of RNA-guided Cas9 nucleases," Nature Biotechnology, 2013, doi:10.1038/nbt.2647.
Hwang Woong, et al. "Efficient In Vivo Genome Editing Usng RNA-Guided Nucleases" Nat. Biotechnol., 2013, 31(3):227.229. doi. 1.1038/mbt.2501.
Jiang, et al. "RNA-guided editing of bacterial genomes using CRISPR-Cas systems" Nature Biotechnology, 2013, 31(3):233-239.
Jinek, et al., "Figures and figure supplements—A Programmable Dual-RNA-Guided DNA Endonuclease in Adaptive Bacterial Immunity" eLife 2014;2:e00471.DOI:10.7554/eLife 00471.
Jao, et al. "Efficient multiplex biallelic zebrafish genome editing using a CRISPR nuclease system" Proceeding of the National Academy of Sciences, 2013, www.pnas.org/cgi/doi/10.1073/pnas.1308335110.
Kanasty, et al. "Delivery materials for siRNA therapeutics" Nature Materials, 2013, 12:967-977.
Karvelis, et al. "crRNA and tracrRNA guide Cas9-mediated DNA interference in Streptococcus thermophiles" RNA Biology, 2013, 10(5):841-851.
Karvelis, et al. "Supplemental Material to: crRNA and tracrRNA guide Cas9-mediated DNA interference in *Streptococcus thermophiles*" Landes Bioscience, 2013, 10(5), http://dx.doi.org/10.4161/ma.24203.
Kim, et al. "Crystal structure of Cas1 from Archaeoglobus fulgidus and characterization of its nucleolytic activity" Biochemical and Biophysical Research Communications, 2013, 441:720-725.
Larson, et al. "CRISPR interference (CRISPRi) for sequence-specific control of gene expression" Nature Protocols, 2013, 8(11):2180-2196.
Li, et al. "Multiplex and homologous recombination-mediated genome editing in *Arabidopsis* and Nicotaina benthamiana using guide RNA and Cas9" Nature Biotechnology, 2013, 31(9):688-691.
Luo, et al., "Highly parallel identification of essential genes in cancer cells", Proceeding of the National Academy of Sciences, 2008, 105(51);20380-20385.
Ma, et al. "A Guide RNA Sequence Design Platform for the CRISPR/Cas9 System for Model Organism Genomes", BioMed Research International, 2014, 2013:270805-4. http://dx.doi.org/10.1155/2014/270805.

Maeder, et al. "CRISPR RNA-guided activation of endogenous human genes" Nature Methods, 2013, 10(10):977-979. doi.10.1038/nmeth.2556.
Makarova et al. "Unification of Cas protein families and a simple scenario for the origin and evolution of CRISPR-Cas systms" Biology Direct, 2011, 6:38. http:///www.biology-direct.com/content/6/1/38.
Makarova, et al. "An updated evolutionary classification of CRISPR-Cas systems" Nature Reviews—Microbiology, 2015, 13:722-736.
Mali, et al. "RNA-Guided Human Genome engineering via Cas9" Science, 2013, DOI: 10.1126/SCIENCE.1232033.
U.S. Appl. No. 61/794,422, filed Mar. 15, 2013, Knight.
U.S. Appl. No. 61/769,046, filed Feb. 25, 2013, Zhang.
U.S. Appl. No. 61/835,931, filed Jun. 17, 2013, Zhang.
U.S. Appl. No. 61/748,427, filed Jan. 2, 2012, Zhang.
U.S. Appl. No. 61/757,972, filed Jan. 29, 2013, Zhang.
U.S. Appl. No. 61/768,959, filed Feb. 25, 2013, Zhang.
U.S. Appl. No. 61/791,409, filed Mar. 15, 2013, Zhang.
U.S. Appl. No. 61/817,324, filed Oct. 23, 2012, Seung Woo Kim.
U.S. Appl. No. 61/803,599, filed Mar. 20, 2013, Jin-Soo Kim.
U.S. Appl. No. 61/837,481, filed Jun. 20, 2013, Seung Woo Cho.
U.S. Appl. No. 61/765,576, filed Feb. 15, 2013, Wendell Lim.
U.S. Appl. No. 61/716,256, filed Oct. 10, 2012, Jinek.
U.S. Appl. No. 61/758,468, filed Jan. 30, 2013, Zhang.
U.S. Appl. No. 61/802,174, filed Mar. 15, 2013, Zhang.
U.S. Appl. No. 61/806,375, filed Mar. 28, 2013, Zhang.
U.S. Appl. No. 61/814,263, filed Apr. 20, 2013, Zhang.
U.S. Appl. No. 61/819,803, filed May 6, 2013, Zhang.
U.S. Appl. No. 61/828,130, filed May 28, 2013, Zhang.
U.S. Appl. No. 61/836,127, filed Jun. 17, 2013, Zhang.
U.S. Appl. No. 61/842,322, filed Jul. 2, 2013, Zhang.
U.S. Appl. No. 61/836,101, filed Jun. 17, 2013, Zhang.
U.S. Appl. No. 61/835,936, filed Jun. 17, 2013, Zhang.
Abudayyeh, et al. "C2c2 is a single-component programmable RNA-guided RNA-targeting CRISPR effector" Science, 2016, 10.1126/science.aaf5573 (2016).
Alberts, et al., Molecular Biology of the Cell, fourth edition, 2002, 671-676.
Au, et al. "Characterization of a baculovirus nuclear localization signal domain in the late express factor 3 protein" Virology, 2009, 385:209-217.
Ausubel, et al. "A Compendium of Methods from Current Protocols in Molecular Biology" Short Protocols in Molecular Biology, Fourth Edition, 1999, 9: 9-3-9-4.
Baiker, et al. "The Immediate-Early 63 Protein of Varicella-Zoster Virus: Analysis of Functional Domains Required for Replication In Vitro and for T-Cell and Skin Tropism in the SCIDhu Model In Vivo" Journal of Virology, 2004, 78(3):1181-1194.
Bauer, et al., "An Erythroid Enhancer of BCL11A Subject to Genetic Variation Determines Fetal Hemoglobin Level" Science, 2013, 342:253-257.
Bassett, et al. "Highly Efficient Targeted Mutagenesis of *Drosophila* with the CRISPR/Cas9 System" Cell Reports, 2013, 4:220-228.
Bassett, et al. "A Genome-Wide CRISPR Library for High-Throughput Genetic Screening in *Drosophila* Cells" Journal of Genetics and Genomics, 2015, 42:301-309.
Beerli, et al. "Toward controlling gene expression at will: Specific regulation of the erbB-2/HER-2 promoter by using polydactyl zinc finger proteins constructed from modular building blocks", Proc. Natl. Acad. Sci., 1998, 95:14628-14633.
Beerli, et al. "Positive and negative regulation of endogenous genes by designed transcription factors:" PNAS, 2000, 97(4):1495-1500.
Beerli, et al. "Enginnering polydactyl zinc-finger transcription factors" Nature Biotechnology, 2002, 20:135-141.
Birch, et al. "Plant Transformation: Problems and Strategies for Practical Application" Annu. Rev. Plant Physiol. Plant Mol. Biol., 1997, 48:297-326.
Bobis-Wozowicz, et al. "Targeted genome editing in pluripotent stem cells using zinc-finger nucleases" Methods, 2011, 53:339-346.
Boden, et al. "Efficient Gene Transfer of HIV-1-Specific Short Hairpin RNA into Human Lymphocytic Cells Using Recombinant Adeno-associated Virus Vectors" Molecular Therapy, 2004, 9(3):396-402.

(56) References Cited

OTHER PUBLICATIONS

Bouard, et al. "Themed Section: Vector Design and Drug Delivery Review, Viral vectors: from virology to transgene expression" British Journal of Pharmacology, 2009, 157:153-165.
Brouns, "A Swiss Army Knife of Immunity" Science, 2012, 337:808-809, DOI:10.1126/science.1227253.
Campeau, et al. "A Versatile Viral System for Expression and Depletion of Proteins in Mammalian Cells" PLoS One, 2009, 4(8):e6529.
Canver, et al. "BCL11A enhancer dissection by Cas9-mediated in situ saturating mutagenesis" Nature, 2015, 527:192-197, including Supplementary material.
Carr, et al. "Genome engineering" Nature Biotechnology, 2009, 27(12):1151-1162.
Carroll, "Progress and prospects: Zinc-finger nucleases as gene therapy agents" Gene Therapy, 2008, 15:1463-1468.
Carroll, "Genome Engineering With Zing-Finger Nucleases" Genetics, 2011, 188:773.782.
Chan, et al. "Characterization of the Kinetochore Binding Domain of CENP-E Reveals Interactions with the Kinetochore Proteins CENP-F and hBuBR1" The Journal of Cell Biology, 1998, 143:49-63.
Chan, Wai-Ting, et al. "Toxin-Antitoxin Genes of the Gram-Positive Pathogen *Streptococcus pneumoniae*: So Few and Yet So Many" Microbiology and Molecular Biology Reviews, 2012, 76(4):773-791.
Chang, et al. "Genome editing with RNA-guided Cas9 nuclease in Zebrafish embryos" Cell Research, 2013, 23:465-472.
Chen, Fuqiang et al. "High-frequency genome editing using ssDNA oligonucleotides with zinc-finger nucleases" Nature Methods, 2011, 8(9):753-755, including Supplemental Online Methods.
Chylinksi, et al. "Classification and evolution of type II CRISPR-Cas systems" Nucleic Acids Research, 2014, 42(10):6091-6105, doi:10.1093lnarlgku241.
Chiu, et al. "Engineered GFP as a vital reporter in plants" Current Biology, 1996, 6(3):325-330.
Clark, et al. A Tale of Two Nucleases: Gene Targeting for the Masses? Zebrafish, 2011, 8(3):147.149.
Costantino, et al., "Enhanced levels of λ Red-mediated recombinants in mismatch repair mutants" PNAS, 100(26):15748-15753.
"CRISPR-associated protein" UniProtKB/TrEMBL, Accession No. Q73QW6, uploaded Nov. 28, 2012, retrieved on Nov. 22, 2017, http://www.uniprot.org/uniprot/Q73Qw6.txt?version=4.
CRISPR-associated protein, Csn1 family, UniProtKB/TrEMBL, Accession No. DOW2Z9, uploaded Oct. 3, 2012, retrieved Nov. 22, 2017, http://www.uniprot.org/uniprot/DOW2Z9.txt?version=4.
CRISPR-associated protein, Csn2 family [*Staphylococcus pseudintermedius* ED99] GenBank, Accession No. ADX75954, uploaded on Nov. 21, 2011, retrieved on Nov. 22, 2017, http://www.uniprot.org/uniprot/G1UFN3.txt?version=3.
"Csn1 family CRISPR-associated protein" UniProtKB/TrEMBL, Accession No. J3TRJ9, uploaded Oct. 31, 2012, retrieved on Dec. 14, 2017, http://www.uniprot.org/uniprot/J3TRJ9.txt?version=2.
Dai, et al. "Genes:Structures and Regulation: The Transcription Factors GATA4 and dHAND Physically Interact to Synergistically Activate Cardiac Gene Expression through a p300-dependent Mechanism", J. Biol. Chem., 2002, 277:24390-24398.
Dicarlo, et al. "Genome engineering in *Saccharomyces cerevisiae* using CRISPTR-Cas systems", Nucleic Acids Research, 2013, 41(7):4336-4343, doi:10.1093/nar/gkt135.
Dingwall, et al. "The Nucleoplasmin Nuclear Location Sequence Is Larger and More Complex than That of SV-40 Large T Antigen" The Journal of Cell Biology, 1988, 107:841-849.
Do, et al. "Identification of multiple nuclear localization signals in murine Elf3, an ETS transcription factor" FEBS Letters, 2006, 580:1865-1871.
Doench, et al., "Rational design of highly active sgRNAs for CRISPR-Cas9-mediated gene inactivation" Nature Biotechnology, 2014, 32(12):1262-1267, including Supplementary material.

Dominguez, et al., "Beyond editing: repurposing CRISPR-Cas 9 for precision genome regulation and interrogation" Nat Rev Mol Cell Biol., 2016, 17(1):5-15, doi:10.1038/nrm.2015.2.
Dong, et al. "The crystal structure of Cpf1 in complex with CRISPR RNA" Nature, 2016, 532:523-525, including Research Letter, doi:10.1038/nature17944.
Dworetzky, et al. "The Effects of Variations in the Number and Sequence of Targeting Signals on Nuclear Uptake" The Journal of Cell Biology, 1988, 107:1279-1287.
Ellis, Hilary, et al. "High efficiency mutagenesis, repair, and engineering of chromosomal DNA using single-stranded oligonucleotids" PNAS, 2001, 98(12):6742-6746.
Espinoza, et al., "Characterization of the structure, function, and mechanism of B2 RNA, an ncRNA repressor of RNA polymerase II transcription" RNA, 2007, 13(4):583-596.
Fieck, et al. "Modifications of the *E.coli* Lac repressor for expression in eukaryotic cells: effects of nuclear signal sequences on protein activity and nuclear accumulation" Nucleic Acids Research, 1992, 20(7):1785-1791.
Fischer-Fantuzzi, et al. "Molecular and Cellular Biology" Mol. Cell. Biol., 1988, 8(12):5495, DOI:10.1128/MCB.8.12.5495.
Foecking, et al. "Powerful and versatile enhance-promoter unit for mammalian expression vectors" Gene, 1986, 101-105.
Freitas, et al. "Mechanisms and Signals for the Nuclear Import of Proteins" Current Genomics, 2009, 10:550-557.
Gaj, et al. "Targeted Gene knockout by direct delivery of zinc-finger nuclease proteins," Nature Methods, 2012, 9(8):805-807.
Gao, et al. "Engineered Cpf1 Enzymes with Altered PAM Specificities" BioRxiv Preprint, XP-002769442, 2016, doi:http://dx.doi.org/10.1101/091611, 1-13, including Figure Legends.
Gao, et al. "Engineered Cpf1 variants with altered PAM specificities" Nature Biotechnology, 2017, 1-4, doi:10.1038/nbt.3900, advanced online publication including Supplementary Information.
Garcia-Bustos, et al. "Nuclear protein localization" Biochimica et Biophysica Acta, 1991, 1071:83-101.
Garg, et al. "Engineering synthetic TAL effectors with orthogonal target sites" Nucleic Acids Research, 2012, 40(15):7584-7595, doi:10.1093/nar/gks404.
Genbank, Accession No. HE980450—"*Staphylococcus aureus* subsp. *aureus* ORFX gene and pseudo SCCmec-SCC-SCCCRISPR element, strain M06/0171", http://www.ncbi.nlm.nih.gov/nuccore/HE980450, Retrieved Aug. 18, 2016.
Gomaa, et al. "Programmable Removal of Bacterial Strains by Use of Genome-Targeting CRISPR-Cas Systems", MBio., 2014, 5(1):e00928-13.
Goncalves, et al. "Concerted nicking of donor and chromosomal acceptor DNA promotes homology-directed gene targeting in Human Cells" Nucleic Acids Research, 2012, 40(8):3443-3455.
Gratz, et al. "Genome Engineering of *Drosophila* with the CRISPR RNA-Guided Cas9 Nuclease" Genetics, 2013, 194:1029-1035.
Greenspan, et al. "Two Nuclear Location Signals in the Influenza Virus NS1 Nonstructural Protein" Journal of Virology, 1988, 62(8):3020-3026.
Greiger, et al. "Packaging Capacity of Adeno-Associated Virus Serotypes: Impact of Larger Genomes on Infectivity and Postentry Steps" Journal of Virology, 2005, 79(15): 9933-9944.
Grissa, et al. "CRISPRFinder: a web tool to identify clustered regularly interspaced short palindromic repeats" Nucleic Acids Research, 2007, 35:W52-W57, doi:10.1093/nar/gkm360.
Guan, et al. "Heritable endogenous gene regulation in plants with designed polydactyl zinc finger transcription factors" PNAS, 2002, 99(20):13296-13301.
Hicks, et al. "Protein Import Into the Nucleus: An Integrated View" Annu. Rev. Cell Dev. Biol., 1995, 11:155-88.
Ho, et al. "Targeting non-coding RNAs with the CRISPR/Cas9 system in human cell lines" Nucleic Acids Research, 2015, 43(3):e17, doi:10.1093/narlgku1198.
Hockemeyer, et al. "Highly efficient gene targeting of expressed and silent genes in human ESCs and iPSCs using zinc finger nucleases" Nat Biotechnol., 2009, 27(9):851-857, doi:10.1038/nbt.1562.
Incontro, et al. "Efficient, Complete Deletion of Synaptic Proteins using CRISPR" Cell, Neuron, 2014, 83:1051-1057.

(56) References Cited

OTHER PUBLICATIONS

Jinek, et al., "Supplementary Materials for a Programmable Dual-RNA-Guided DNA Endonuclease in Adaptive Bacterial Immunity" Science Express, 2012, DOI:10.1126/science.1225829.

Joshi, et al., "Evolution of I-SceI homing endonucleases with increased DNA recognition site specificity" Journal of Molecular Biology, 2011, 405(1):185-200; ePub: Oct. 26, 2010.

Joung, et al. "TALENs: a widely applicable technology for targeted genome editing" Nat Ref. Mol. Cell Biol., 2013, 14(1):49-55, doi:10.1038/nrm3586.

Kalderon, et al. "A Short Amino Acid Sequence Able to Specify Nuclear Location" Cell, 1984, 39:499-509.

Kiani, et al. "CAS9 gRNA engineering for genome editing, activation and repression" Nature Methods, Advanced Online Publication, 2015, DOI:10.1038/NMETH.3580.

Kinnevery, et al. "Emergence of Sequence Type 779 Methicillin-Resistant *Staphylococcus aureus* Harboring a Novel Pseudo *Staphylococcal* Cassette Chromosome mec (SCCmec)-SCC-SCC CRISPR Composite Element in Irish Hospitals" Antimicrobial Agents and Chemotherapy, 2013, 57(1):524-531.

Kleinstiver, et al. "Engineered CRISPR-Cas9 nucleases with altered PAM specificities" Nature, 2015, 523:481-485, including Research Letter, doi:10.1038/nature14592.

Kondo, et al. "Highly Improved Gene Targeting by Germline-Specific Cas9 Expression in *Drosphila*" Genetics, 2013, 195:715-721.

Kosugi, et al. "Six Classes of Nuclear Localization Signals Specific to Different Binding Grooves of Importin α . . . " The Journal of Biological Chemistry, 2009, 284(1):478-485.

Krauer, et al. "Identification of the nuclear localization signals within the Epstein-Barr virus EBNA-6 protein" Journal of General Virology, 2004, 85:165-172.

Kuhlman, et al. "Site-specific chromosomal integration of large synthetic constructs" Nucleic Acids Research, 2010, 38(6):1-10, doi:10.1093/nar/gkp1193.

Kuhlman, et al. "A place for everything" Chromosomal intergration of large constructs Bioengineered Bugs, Jul./Aug. 2010, 1(4)296-299.

Lanford, et al. "Induction of Nuclear Transport with a Synthetic Peptide Homologous to the SV40 T Antigen Transport Signal" Cell, 1986, 46:575-582.

Lange, et al. "Classical Nuclear Localization Signals: Definition, Function, and Interaction with Importin . . . " J. Biol. Chem., 2007, 282(8):5101-5105.

Lee, et al. "Correction of the F508 Mutation in the Cystic Fibrosis Transmembrane Conductance Regulator Gene by Zinc-Finger Nuclease Homology-Directed Repair" Bioresearch Open Access, 2012, 1(3):99-108.

Leenay, et al. "Identifying and Visualizing Functional PAM Diversity across CRISPR-Cas Systems" Molecular Cell, 2016, 62:137-147.

Lemay, et al. "Folding of the Adenine Riboswitch" Chemistry & Biology, 2006, 13:857-868.

Lewin, et al. "Nuclear localization sequences target proteins to the nucleus" Cells, 2006, 5:224.

Li, Ping, et al. "Biallelic knockout of α-1,3 galactosyltransferase gene in porcine liver-derived cells using zing finger nucleases" Journal of Surgical Research, 2013, E39-E45.

Li, Ting, et al. "Modularly assembled designer TAL effector nucleases for targeted gene knockout and gene replacement in eukaryotes" Nucleic Acids Research, 2011, 39(14):6315-6325.

Liu, et al. "Epstein-Barr Virus DNase Contains Two Nuclear Localization Signals Which Are Different in Sensitivity to the Hydrophobic Regions" Virology, 1998, 247:62-73.

Los, et al. "Halotag Technology: Cell Imaging and Protein Analysis" Cell Notes, 2006, 14:10-14.

Luo, Ming, et al. "Multiple Nuclear Localization Sequences Allow Modulation of 5-Lipoxygenase Nuclear Import" Traffic, 2004, 5:847-854.

Lyssenko, et al. "Cognate putative nuclear localization signal effects strong nuclear localization of a GFP reporter and facilitates gene expression studies in Caenorhabditis elegans" BioTechniques, 2007, 43:596-600.

Mahfouz, et al. "De novo-engineered transcription activator-like effector (TALE) hybrid nuclease with novel DNA binding specificity creates double-strand breaks" PNAS, 2011, 108(6):2623-2628.

Mahfouz, et al. "Targeted transcriptional repression using a chimeric TALE-SRDX repressor protein" Plant Mol Biol, 2012, 78:311-321.

Mincer, et al. "Simulations of nuclear pore transport yield mechanistic insights and quantitative predictions" PNAS, 2011, 108(31):E351-E358.

Morbitzer, et al. "Regulation of selected genome loci using de novo-engineered transcription activator-like effector (TALE)-type transcription factors" PNAS, 2010, 108(50):21617-21622.

Morbitzer, et al. "Assembly of custom TALE-type DNA binding domains by modular cloning" 2011, 39(13):5790-5799.

Morin, et al. "Nuclear Localization of the Adenovirus DNA-Binding Protein: Requirement for Two Signals and Complementation during Viral Infection" Molecular and Cellular Biology, 1989, 9(10):4372-4380.

Moscou, et al. "A Simple Cipher Governs DNA Regognition by TAL Effectors" Science, 2009, 326:1501.

Mussolino, et al. "TALE nucleases: tailored genome engineering made easy" Current Opinion in Biotechnology, 2012, 23(5):644-650.

Nagarajan, et al. "A Hierarchy of Nuclear Localization Signals Governs the Import of the Regulatory Factor X Complex Subunits and MHC Class II Expression" The Journal of Immunology, 2004, 173:410.419.

Nakai, et al. "PSORT: a program for detecting sorting signals in proteins and predicting their subcellular localization" Trends in Biochem Sciences, 1999 24:34-35.

Noguchi, et al. "PDX-1 Protein Containing Its Own Antennapedia-Like Protein Transduction Domain Can Transduce Pancreatic Duct and Islet Cells" Diabetes, 2003, 52:1732-1737.

O'Hare, et al. "Transformation of mouse fibroblasts to methotrexate resistance by a recombinant plasmid expressing a prokaryotic dihydrofolate reductase" Proc. Natl. Acad. Sci., 1981, 78(3):1527-1531.

Park, et al. "Regulation of Ribosomal S6 Kinase 2 by Mammalian Target of Rapamycin", The Journal of Biological Chemistry, 2002, 277(35):31423-31429.

Pattanayak, et al. "High-throughput profiling of off-target DNA cleavage reveals RNA-programmed Cas9 nuclease specificity" Nature Biotechnology, 2013, 31(9):839-843, including Supplementary Materials.

Perez-Pinera, et al. "Advances in Targeted Genome Editiong" Curr Opin Chem Biol., 2012, 16(3-4):268.277, doi:10.1016/j.cbpa.2012.06.007.

Planey, et al. "Mechanisms of Signal Transduction: Inhibition of Glucocorticoid-induced Apoptosis in 697 Pre-B Lymphocytes by the Mineralocorticoid Receptor N-terminal Domain", J. Biol. Chem., 2002, 277:42188-42196.

Porteus, et al. "Chimeric Nucleases Stimulate Gene Targeting in Human Cells", Science, 2003, 300:763.

Posfai, et al. "Markerless gene replacement in *Escherichia coli* stimulated by a double-strand break in the chromosome" Nucleic Acids Resarch, 1999, 27(22):4409-4415.

Primo, et al. "Lentiviral vectors for cutaneous RNA managing" Experimental Dermatology, 2012, 21:162-170.

"Putative uncharacterized protein" UniProtKB/TrEMBL, Accession No. Q6NK13, uploaded Jun. 13, 2012, retrieved on Nov. 22, 2017, http://www.uniprot.org/uniprot/Q6NK13.txt?version=43.

"Putative CRISPR-associated protein", UniProtKB/TrEMBL, Accession No. Q0P897, uploaded Oct. 3, 2012, retrieved on Nov. 22, 2017, http://www.uniprot.org/uniprot/Q0P897.txt?version=28.

Putative CRISPR associated protein, UniProtKB/TrEMBL, Accession No. G1UFN3, uploaded Oct. 3, 2012, retrieved on Nov. 22, 2017, http://www.uniprot.org/uniprot/G1UFN3.txt?version=3.

(56) References Cited

OTHER PUBLICATIONS

Radulovich, et al. "Modified gateway system for double shRNA expression and Cre/lox based gene expression" BMC Biotechnology, 2011, 11(24):1-9.
Rhun, et al. "Small RNAs in streptococci" RNA Biology, 2012, 9(4):414-426.
Roberts, et al. "The Effect of Protein Content on Nuclear Location Signal Function" Cell, 1987, 50:465-475.
Roberts, et al. "Nuclear location signal-mediated protein transport" Biochimica et Biophysica Acta, 1989, 1008:263-280.
Rodrigues, et al. "Red Fluorescent Protein (DsRed) as a Reporter in *Saccharomyces cerevisiae*" Journal of Bacteriology, 2001, 183(12):3791-3794.
Sambrook, et al., Molecular Cloning, A Laboratory Manual on the Web, 2001, Chapter 16.
Sander, et al. "CRISPR-Cas systems for editing, regulating and targeting genomes" Nature Biotechnology, 2014, 32:347-355.
Sanjana, et al. "A Transcription Activator-Like Effector (TALE) Toolbox for Genome Engineering" Nat. Protoc, 2011, 7(1):171-192, doi:10.1038/nprot.2011.431.
Sanjana, et al. "Improved vectors and genome-wide libraries for CRISPR screening", HHS Public Access Author Manuscript, 2014, 11(8):783-784.
Sato, et al. "Generation of Adeno-Associated Virus Vector Enabling Functional Expression of Oxytocin Receptor and Fluorescence Marker Genes Using the Human elF4G Internal Ribosome Entry Site Elemet" Biosci. Biotechno. Biochem, 2009, 73(9):2145-2148.
Sebastiani, et al. "BCL11A enhancer haplotypes and fetal hemoglobin in sickle cell anemia" Blood Cells, 2015, 54(3):1079-9796.
Sebo, et al. "A simplified and efficient germline-specific CRISPR/Cas9 system for *Drosophila* genomic engineering" Fly, 2014, 8(1):52-57.
Shalem, et al. "High-throughput functional genomics using CRISP-Cas9" Nature Reviews Genetics, 2015, 16(5):1471-0056.
Sharan, et al. "Recombineering: A Homologous Recombination-Based Method of Genetic Engineering" Nat. Protoc., 2009, 4(2):206-223, doi:10.1038/nprot.2008.227.
Shieh, et al. "Nuclear Targeting of the Maize R. Protein Requires Two Nuclear Localization Sequences" Plant Physiol, 1993, 101:353-361.
Siegl, et al. "I-Scel endonuclease: a new tool for DNA repair studies and genetic manipulations in streptomycetes" Appl Microbiol Bitotechnol, 2010, 87:1525-1532.
Singer, et al. "Applications of Lentiviral Vectors for shRNA Delivery and Transgenesis" Curr Gene Ther., 2008, 8(6):483-488.
Sung, et al. "An rpsL Cassette, Janus, for Gene Replacement through Negative Selectionin *Streptococcus pneumoniae*" Applied and Environmental Microbiology, 2001, 67(11):5190-5196.
Sung, et al. "The importance of valency in enhancing the import and cell routing potential of protein transduction domain-containing molecules" Biochimica et Biophysica Aeta, 2006, 1758:355-363.
Sung, Young Hoon, et al. "Mouse genetics: Catalogue and scissors" BMB Reports, 2012, 45(12):686-692.
Swarthout, et al. "Zinc Finger Nucleases: A new era for transgenic animals" Annals of Neurosciences, 2011, 18(1):25-28.
Tinland, et al. "The T-DNA-linked VirD2 protein contains two distinct functional nuclear localization signals" Proc. Natl. Acad. Sci, 1992, 89:7442-7446.
Tiscornia, et al. "Development of Lentiviral Vectors Expressing siRNA" Gene Transfer-Delivery and of DNA and Expression RNA—A Laboratory Manual, 2007, Chapter 3:23-34.
Type V CRISPR-associated protein Cpfi [*Acidaminococcus* sp. Bv3L6], 2017, NCBI Reference Sequence: WP_02173622.1, Non-redundant Protein Sequence.
Urrutia, et al. "KRAB-containing zing finger repressor proteins" Genome Biology, 2003, 4(10):231-231.8.
Urnov, et al. "Genome editing with engineered zinc finger nucleases" Nature Reviews, Genetics, 2010, 11:637-646.
Van Den Ackerveken, et al. "Recognition of the Bacterial Avirulence Protein AvrBs3 Occurs inside the Host Plant Cell" Cell, 1996, 87:1307-1316.
Van Nierop, et al. "Stimulation of homology-directed gene targeting at an endogenous human locus by a nicking endonuclease" Nucleic Acids Research, 2009, 37(17):5725-5736.
Villion, et al. "The double-edged sword of CRISPR-Cas systems" Cell Research, 2013, 23:15-17.
Wang, et al. "Genetic Screens in Human Cells Using the CRISPR-Cas9 System", Science, 2014, 343:80-84.
Welch, et al. "Designing Genes for Successful Protein Expression" Methods in Enzymology, 2011, 498:43-66, DOI: 10.1016/6978-0-12-385120-8.00003-6.
Wolff, et al. "Nuclear security breached" Nature Biotechnology, 2001, 19:1118-1120.
Wu, Yuxuan, et al. "Correction of a Genetic Disease in Mouse via Use of CRISPR-Cas9" Cell Stem Cell, 2013, 13:659-662.
Wu, Zhijian, et al. "Effect of Genome Size on AAV Vector Packaging" The American Society of Gene & Cell Therapy, (Jan. 2010), 18(1):80-86.
Xie, et al. "RNA-Guided Genome Editing in Plants Using a CRISPR-Cas System" Molecular Plant, 2013, 6(6):1975-1983.
Yaghmai, et al. "Optimized Regulation of Gene Expression Using Artificial Transcription Factors", Molecular Therapy, 2002, 5(6):685-694.
Yamano, et al. "Crystal Structure of Cpf1 in Complex with Guide RNA and Target DNA" Cell, 2016, 165:949-962.
Yang, et al. "One-Step Generation of Mice Carrying Reporter and Conditional Alleles by CRISPR/Cas-Mediated Genome Engineering" Cell, 2013, 154:1370-1379.
Yi, et al. "Current Advances in Retroviral Gene Therapy" Current Gene Therapy, 2011, 11:218:228.
Yu, et al. "An efficient recombination system for chromosome engineering in *Escherichia coli*" PNAS, 2000, 97(11):5978-5983.
Yu, Zhongshen, et al. "Highly Efficient Genome Modifications Mediated by CRISPR/Cas9 in *Drosophila*" Genetics, 2013, 195:289-291.
Mang, et al., Efficient Expression of CFTR Function with Adeno-Associated Virus Vectors that Carry Shortened CFTR Genes, PNAS (USA) (1998) vol. 95, p. 10158-10163.
Zhang, et al. "Optogenetic interrogation of neural circuits: technology for probing mammalian brain structures" Nat Protoc., 2010, 5(3):439-456, doi:10.1038/nprot.2009.226.
Zhou, et al. "High-throughput screening of a CRISPR/Cas9 library for functional genomics in human cells" Nature, 2014, 509:487-491.
Zolkiewska, et al. "ADAM Proteases:Ligand Processing and Modulation of the Notch Pathway" Cell Mol Life Sci, 2008, 65(13):2056-2068.
*The Broad Inst.* v. *The Regents of University of UCA*—Decision on Motions for Patent Interference No. 106,048 filed Feb. 15, 2017.
Press Release dated Jan. 15, 2018 "The Rockefeller University and Broad Institute of MIT and Harvard announce update to CRISPR-Cas9 Portfolio filed by Broad" Copyright by Broad Institute.
Mali, et al. "CAS9 transcriptional activators for target specificity screening and paired nickases for cooperative genome engineering" nature biotechnology, 2013, 31(9):833-840.
Mali, et al. "Supplementary Information: Use of adjacent sgRNA:Cas9 complexes for transcriptional activation and genome engineering" Nature Biotechnoly, doi:10.1037/nbt.2675.
Malina, et al. "Repurposing CRISPR/Cas9 for in situ functional assays" Genes & Development, 2013, 27:2602-2614.
Marraffini, et al. "Self vs. non-self discrimination during CRISPR RNA-directed immunity" Nature, 2010, 463(7280):568-571.
Miller, et al. "A TALE nuclease architecture for efficient genome editing" Nature Biotechnology, 2011, 29(2):143-150.
Mojica, et al. "Short motif sequences determine the targets of the prokaryotic CRISPR defence system", Microbiology, 2009, 155:733-740.
Nakamura, et al. "Codon usage tabulated from international DNA sequence databases: status for the year 2000" Nucleic Acids Research, 2000, 28(1): 292.

(56) References Cited

OTHER PUBLICATIONS

Nishimasu, et al. Crystal Structure of Cas9 in Complex with Guide RNA and Target DNA, Cell, 2014, 156:935-949.
Panyam, et al. "Biodegradable nanoparticles for drug and gene delivery to cells and tissue" Advanced Drug Delivery Reviews, 2003, 55:329-347.
Patterson, et al. "Codon optimization of bacterial luciferase (lux) for expression in mammalian cells" J. Ind. Microbio. Biotechnology, 2005, 32:115-123.
Pinera, et al. "RNA-guided gene activation by CRISPR-Cas9-based transcription factors" Nature Methods, 2013, 10(10):973-978.
Porteus, et al. "Gene targeting using zinc finger nucleases" Nature Biotechnology, 2005, 23(8):967-973.
Qi, et al. "Repurposing CRISPR as an RNA-Guided Platform for Sequence-Specific Control of Gene Expression" Cell, 2013, 152(5):1173-1183.
Ran, et al. "Genome engineering using the CRISPR-Cas9 system" Nature Protocols, 2013, 8(11):2281-2308.
Rand, et al. "Argonaute2 Cleaves the Anti-Guide Strand of siRNA during RISC Activation" Cell, 2005, 123:621-629.
Rebar, et al. "Induction of angiogenesis in a mouse model using engineered transcription factors" Nature Medicine, Dec. 2002, 8(12):1427-1432.
Sapranauskas, et al. "The *Streptococcus thermophilus* CRISPR-Cas system provides immunity in *Escherichia coli*" Nucleic Acids Research, 2011, 39(21): 9275-9282.
Schiffer, et al. "Predictors of Hepatitis B Cure Using Gene Therapy to Deliver DNA Cleavage Enzymes: A Mathematical Modeling Approach" PLOS Computational Biology 2013, 9(7):e1003131. www.ploscompbiol.org.
Scholze, et al. "TAL effector-DNA specificity" Virulence, 2010, 1(5):428-432, DOI:10.4161/viru.1.5.12863.
Schunder, et al. "First indication for a functional CRISPR/Cas system in Francisella tularensis" International Journal of Medical Microbiology, 2013, 303:1438-4221.
Schramm et al. "Recruitment of RNA polymerase III to its target promoters" Genes & Development, 2002, 16:2593-2620.
Seung Woo Cho, et al. "Analysis off-target effects of CRISPR/Cas-derived RNA-guided endonucleases and nickases" Genome Research, Nov. 2014, 24:132-141.
Shen, et al. "Efficient genome modification by CRISPR-Cas9 mickase with minimal off-target effects" 2014, Nature Methods, 11(4):399-404.
Sims, et al., "High-throughput RNA interference screening using pooled shRNA libraries and next generation sequencing", Genome Biology 12(10):R104, Oct. 2011.
Sosa, et a. "Animal transgenesis: an overiew" Brain Struct Funct, 2010, 214:91-109.
Terns, et al. "Crispr-based adaptive immune systems" Current Opinion in Microbiology, 2011, 14:321-327.
Tolia, et al. "Slicer and the Argonautes" Nature Chemical Biology, 2007, 3(1):36-43.
Trevino, et al. "Genome Editing Using Cas9 Nickases" Methods in Enxymology, 2014, 546:161-174.
Urnov, et al. "Highly efficient endogenous human gene correction using designed zinc-finger nucleases" Nature, 2005, 435:646-651.
Vestergaard, et al. "CRISPR adaptive immune systems of Archaea" RNA Biology, 2014, 11(2):156-167.
Xiao, et al. "Chromosomal deletions and inversions mediated by TALENs and CRIPPR/Cas in zebrafish" Nucleic Acids Research, 2013, 41(14):E141. doi:10.1093/nar/gkt464.
Xiao, et al. "Production of High-Titer Recombinant Adeno-Associated Virus Vectors in the Absence of Helper Adenovirus" Journal of Virology, 1998, 72(3):2224-2232.
Zetsche, et al. "CPF1 is a Single RNA-Guided Endonuclease of a Class 2 CRISPR-Cas System" Cell, 2015, 163:759-771.
Zhang, X. D., et al., "cSSMD: assessing collective activity for addressing off-target effects in genome-scale RNA interference screens", Bioinformatics (Oxford), 27(20);2775-2781, Oct. 2011.
Zhang, et al. "Efficient construction of sequence-specific TAL effectors for modulating mammalian transcription" nature biotechnology, 2011, 29(2):149-154.
Zhang, et al., "Optimized CRISPR Design", XP055167487, Oct. 23, 2013, URL:http//crispr.mit.edu/about[retrieved on Feb. 5, 2015].
Zhu, et al. "Crystal structure of Cmr2 suggests a nucleotide cyclase-related enzyme in type III CRISPR-Cas sytems" FEBS Letters, 2012, 939-945. Doi:10.1016/j.febslet2012.02.036.
PowerPoint slide entitled Development and Applications of CRISPR-Cas9 for Genome Editing dated Sep. 9, 2015.
PowerPoint slide entitled Interview Sep. 9, 2015.
David Bikard, et al., CRISPR Interference Can Prevent natural Transformation and Virulence Acquisition During In Vivo Bacterial Infection, Cell Host & Microbe (Aug. 2012) vol. 12, p. 177-186.
F. Zhang, PowerPoint Presentation "Development and Applications of CRISPR-Cas9 for Genome Editing" (Sep. 9, 2015).
Thomas J. Kowalski, PowerPoint Presentation "Interview Sep. 9, 2015".
A. P. Minton, How Can Biochemical Reactions Within Cells Differ From Use in Test Tubes? Journal of Cell Science (2006) vol. 119, p. 2863-2869.
R. John Ellis, Macromolecular Crowding: Obvious But Underappreciated, TRENDS in Biochemical Sciences (2001) vol. 26, No. 10, p. 597-604.
Glenn M. Sanders, et al., Use of a Macromolecular Crowding Agent to Dissect Interactions and Define Functions in Transcriptional Activation by a DNA-Tracking Protein: Bacteriophage T4 Gene 45 Protein and Late Transcription, PNAS (1994) vol. 91, p. 7703-7707.
Federal Circuit decision in *Dow Chemical Co. v. Nova Chemicals Corp.* Appeal Nos. 2014-1431, 2014-1462 (Fed. Cir. Aug. 28, 2015) (*Dow v. Nova*).
Baker, Gene Editing at CRISPR Speed, Nature Biotechnology 32(4):309-312 (Apr. 4, 2014).
Mukhopadyay, "On the Same Wavelength," ASBMBTODAY (Aug. 2014), available at http://www.asbmb.org/asbmbtoday/201408/Features/Doudna/.
Connor, "Scientific split—the human genome breakthrough dividing former colleagues," The Independent, Friday Apr. 25, 2014, available at http://www.independent.co.uk/news/science/scientific-split-the-human-genome-breakthrough-dividing-former-colleagues-9300456.html.
Nishimasu et al., "Crystal Structure of *Staphylococcus aureus* Cas9," Cell 162, 1113-1126, Aug. 27, 2015.
Grens, Enzyme Improves CRISPR A smaller Cas9 protein enables in vivo genome engineering via viral vectors, The Scientist, Apr. 1, 2015, available at: http://www.the-scientist.com//?articles.view/articleNo/42580/title/Enzyme-Improves-CRISPR/.
Anna Banaszewska, et al., Proprotein Convertase Subtilisin/Kexin Type 9: A New Target Molecule for Gene Therapy, Cellular & Molecular Biology Letters (2012) vol. 17, p. 228-239.
O. Hibbitt, et al., RNAi-Mediated Knockdown of HMG CoA Reductase Enhances Gene Expression From Physiologically Regulated Low-Density Lipoprotein Receptor Therapeutic Vectors In Vivo, Gene Therapy (2012) vol. 19, p. 463-467.
Annemart Koonmeef, et al., Apolipoprotein B Knockdown by AAV-Delivered shRNA Lowers Plasma Cholesterol in Mice, Molecular Therapy (2011) vol. 19, No. 4, p. 731-740.
Prashant Mali, et al., Supplemental), Materials for RNA-Guided Human Genome Engineering via Cas9, Science Express, Published Jan. 3, 2013, DOI: 10.1126/science.1232033.
S. Nomura, et al., Low-Density Lipoprotein Receptor Gene Therapy Using Helper-Dependent Adenovirus Produces Long-Term Protection Against Atherosclerosis in a Mouse Model of Familial Hypercholesterolemia, Gene Therapy (2004) vol. 11, p. 1540-1548.
Haoyi Wang, et al., One-Step General of Mice Carrying Mutations in Multiple Genes by CRISPR/Cas-Mediated Genome Engineering, Cell (2013) vol. 153, p. 910-918.
Krzysztof Chylinski, et al., The tractRNA and Cas9 Families of Type II CRISPR-Cas Immunity Systems, RNA Biology (2013) vol. 10, Issue 5, p. 726-737.
Woong Y. Hwang, et al., Efficient Genome Editing in Zebrafish Using a CRISPR-Cas System, Nature Biotechnology (2013) vol. 31, No. 3, p. 227-229.

(56) References Cited

OTHER PUBLICATIONS

Richard Gabriel, et al., An Unbiased Genome-Wide Analysis of Zinc-Finger Nuclease Specificity, Nature Biotechnology (2011) vol. 29, No. 9, p. 816-823.
B.L. Ellis, et al., Zinc-Finger Nuclease-Mediated Gene Correction using Single AAV Vector Transduction and Enhanced by Food and Drug Administration-Approved Drugs, Gene Therapy (2013) vol. 20, p. 35-42.
Eva-Maria Handel, et al., Versatile and Efficient Genome Editing in Human Cells by Combining Zinc-Finger Nucleases With Adeno-Associated Viral-Vectors, Human Gene Therapy (2012) vol. 23, p. 321-329.
Prashanth Asuri, et al., Directed Evolution of Adeno-Associated Virus for Enhanced Gene Delivery and Gene Targeting in Human Pluripotent Stem Cells, Molecular Therapy (2012) vol. 20, No. 2, p. 329-338.
Angelo Lombardo, et al., Gene Editing in Human Stem Cells Using Zinc Finger Nucleases and Integrase-Defective Lentiviral Vector Delivery, Nature Biotechnology (2007) vol. 25, No. 11, p. 1298-1306.
Brian C. Lewis, et al., The c-myc and PyMT Oncogenes Induce Different Tumor Types in a Somatic Mouse Model for Pancreatic Cancer, Genes & Development (2003) vol. 17, p. 3127-3138.
Klaus-Peter Janssen, et al., Mouse Models of K-ras-Initiated Carcinogenesis, Biochimicia et Biophysica Acta (2005) vol. 1756, p. 145-154.
Thomas Gaj, et al., ZFN, TALEN, and CRISPR/Cas-Based Methods for Genome Engineering, Trends in Biotechnology (2013) vol. 31, No. 7, p. 397-405.
Martin Jinek, et al., RNA-programmed genome editing in human cells; eLife 2013:e00471, p. 1-9.
Al-Attar et al., Clustered Regularly Interspaced Short Palindromic Repeats (CRISPRs): The Hallmark of an Ingenious Antiviral Defense Mechanism in Prokaryotes, *Biol Chem*. (2011) vol. 392, Issue 4, pp. 277-289.
Carroll, A CRISPR Approach to Gene Targeting, Molecular Therapy (2012) vol. 20, No. 9, p. 1658-1660.
Gasiunas, et al., Cas9-crRNA Ribonucleoprotein Complex Mediates Specific DNA cleavage for Adaptive Immunity in Bacteria, PNAS USA (2012) vol. 109, No. 39, p. E2579-E2586.
Hale et al., Essential Features and Rational Design of CRISPR RNAs That Function With the Cas RAMP Module Complex to Cleave RNAs, *Molecular Cell*,(2012) vol. 45, Issue 3, 292-302.
Jinek et al, A Programmable Dual-RNA-Guided DNA Endonuclease in Adaptive Bacterial Immunity, Science (2012) vol. 337, p. 816-821.
Makarova et al., Evolution and Classification of the CRISPR-CAS Systems, Nature Reviews Microbiology (2011) vol. 9, No. 6, p. 467-477.
Erik Sontheimer, Project 7: Establishing RNA-Directed DNA Targeting in Eukaryotic Cells; Project dates: Nov. 16, 2011 to Dec. 31, 2012 (Feb. 4, 2012).
Wiedenheft, et al., RNA-Guided Genetic Silencing Systems in Bacteria and Archaea, Nature (2012) vol. 482, p. 331-338.
Le Cong, et al., Multiplex Genome Engineering Using CRISPR-Cas Systems, Science (Feb. 2013) vol. 339, p. 819-823.
Le Cong, et al., Supplementary, Material: Multiplex Genome Engineering Using CRISPR-Cas Systems, Science Express (Jul. 5, 2012).
Seung Woo Cho, et al., Targeted Genome Engineering in Human Cells With the Cas9 RNA-Guided Endonuclease, Nature Biotechnology (Mar. 2013) vol. 31, No. 3, p. 230-232.
Seung Woo Cho, et al., Supplementary Information: Targeted Genome Engineering in Human Cells With the Cas9 RNA-Guided Endonuclease, Nature Biotechnology (Mar. 2013) vol. 31, No. 3, p. 1-10.
Le Cong, et al., Supplementary, Material: Multiplex Genome Engineering Using CRISPR-Cas Systems, Science Express (Jan. 3, 2013).

Kirill A. Datsenko, et al., Molecular Memory of Prior Infections Activates the CRISPR/Cas Adaptive Bacterial Immunity System, Nature Communications, Jul. 10, 2012, DOI:10.1038/ncomms1937.
Ksenia Pougach, et al., Transcription, Processing and Function of CRISPR Cassettes in *Escherichia coli*, Mol. Microbiol, Sep. 2010, 77(6), p. 1367-1379.
Ran et al., "In vivo genome editing using *Staphylococcus aureus* Cas9," Nature 520, 186-191 (Apr. 9, 2015) doi:10.1038/nature14299 (Published online Apr. 1, 2015).
Jinek et al., Science 2012, 337 :816-821 (Jinek 2012).
Jinek et al., eLife 2013;2:e00471 (published by eLife Jan. 29, 2013; manuscript posted by UCB online on Jan. 7, 2013, prior to the filing of Jinek P3, via Sanders, cited below) (Jinek 2013).
Barrangou, Nature Biotechnology 30(9): 836 -38 (Sep. 2012) (Barrangou 2012).
Carroll, Molecular Therapy 20(9): 1659-60 (Sep. 2012) (Carroll).
Cong et al., Science 2013; 339:819-823 (Published Online Jan. 3, 2013).
U.S. Appl. No. 61/736,527, filed Dec. 12, 2012, F. Zhang.
U.S. Appl. No. 61/757,640, filed Jan. 28, 2013, Jinek.
The CRISPR Revolution, Catalyst Magazine, College of Chemistry, University of California, Berkeley http://catalyst.berkeley.edu/slideshow/the-crispr-revolution/[Dec. 19, 2014 12:40:53] (Jul. 9, 2014) (CRISPR Revolution).
Sanders, UC Berkeley Jan. 7, 2013 Press Release, available at http://newscenter.berkeley.edu/2013/01/07/cheap-and-easy-technique-to-snip-dna-could-revolutionaize-gene-therapy/.
Pandika et al., www.ozy.com/rising-stars-and-provacateurs/jennifer-doudna-crispr-code-killer/4690; 2014 (Jul. 1, 2014).
Baohui Chen et al., "Dynamic Imaging of Genomic Loci in Living Human Cells by an Optimized CRISPR/Cas System," Cell 155, 1479-1491, Dec. 19, 2013.
Stolfi et al., "Tissue-specific genome editing in Ciona embryos by CRISPR/Cas9," Development (2014) 141, 4115-4120 doi:10.1242/dev.114488.
Hou et al., "Efficient genome engineering in human pluripotent stem cells using Cas9 from Neisseria meningitides," PNAS 110(39): 15644-15649 (Sep. 24, 2013).
Shen et al., "Generation of gene-modified mice via Cas9/RNA-mediated gene targeting," Cell Research (2013) 23:720-723. doi:10.1038/cr.2013.46; published online Apr. 2, 2013.
Morgan, W.F. et al., Inducible Expression and Cytogenetic Effects of the EcoRI Restriction Endonuclease in Chinese Hamster Ovary Cells, Mol. Cell. Biol. 1988, 8:4204-4211 (Oct. 1988).
Reiss, B. et al., RecA protein stimulates homologous recombination in plants, Proc. Natl. Acad. Sci. U.S.A. 1996, 93:3094-3098 (Apr. 2, 1996).
Sauer, B., Functional Expression of the cre-lox Site-Specific Recombination System in the Yeast *Saccharomyces cerevisiae*, Mol. Cell. Biol. 1987; 7:2087-2096 (Jun. 1987).
Sauer, B. et al., Site-specific DNA recombination in mammalian cells by the Cre recombinase of bacteriophage P1, Proc. Natl. Acad. Sci. U.S.A. 1988, 85:5166-5170 (Jul. 1988).
Raymond, C.S. et al., High-efficiency FLP and PhiC31 site-specific recombination in mammalian cells, PLoS One 2007, 2:e162 (Jan. 17, 2007).
Lombardo, A. et al., Gene editing in human stem cells using zinc finger nucleases and integrase-defective lentiviral vector delivery, Nat. Biotechnol. 2007, Nov. 2007; 25:1298-1306 (Nov. 2007). (Published online Oct. 28, 2007).
Li, H. et al., In vivo genome editing restores haemostasis in a mouse model of haemophilia, Nature 2011; 475:217-221 (Jun. 26, 2011) doi: 10.1038/nature10177.
Lambowitz and Zimmerly, Group II introns: mobile ribozymes that invade DNA, Cold Spring Harb Perspect Biol. 2011; 3:a003616 (Aug. 1, 2011).
Choulika, A. et al., Transfer of single gene-containing long tenninal repeats into the genome of mammalian cells by a retroviral vector carrying the cre gene and the loxP site, J. Virol. 1996, 70:1792-1798 (Mar. 1996).
Bergemann, J. et al., Excision of specific DNA-sequences from integrated retroviral vectors via site-specific recombination, Nucleic Acids Res. 1995, 23:4451-4456 (Nov. 11, 1995).

(56) References Cited

OTHER PUBLICATIONS

Meshorer and Misteli, Nature Reviews Molecular Cell Biology 7, 540-546 (Jul. 2006).
CRISPR-Cas Sytems, Barrangou and van der Oost (Eds)., Springer Heidelberg (2013; but written in 2012 before the publication of Cong et al.).
van der Oost, Science 339(6121): 768-770 (Feb. 15, 2013).
Horvath and Barrangou, in Horvath et al, Cell Research 23 (6):733-734 (Jun. 2013).
Mastroianni, M. et al Group II Intron-Based Gene Targeting Reactions in Eukaryotes, Plos One, 2008, 3:e3121 (Sep. 1, 2008).
Enyeart, P.J., et al., Biotechnological applications of mobile group II introns and their reverse transcriptases: gene targeting, RNA-seq, and non-coding RNA analysis, Mobile DNA 2014, 5:2 (Jan. 13, 2014).
Hsu et al., "DNA targeting specificity of RNA-guided Cas9 nucleases," Nature Biotechnology Letters, published online Jul. 21, 2013; doi:10.1038/nbt.2647.
Ran et al., "Double Nicking by RNA-Guided CRISPR Cas9 for Enhanced Genome Editing Specificity," Cell 154, 1-10, Sep. 12, 2013.
Konennann et al., "Genome-scale transcriptional activation by an engineered CRISPR-Cas9 complex," Nature 517:583-588 (2015).
Sidi Chen et al., "Genome-wide CRISPR Screen in a Mouse Model of Tumor Growth and Metastasis," Cell 160, 1-15 (2015).
Shalem et al., "Genome-Scale CRISPR-Cas9 Knockout Screening in Human Cells," Sciencexpress, http://www.sciencemag.org/content/early/recent, Dec. 12, 2013, 10.1126/science.1247005.
Nishimasu et al., "Crystal Structure of Cas9 in Complex with Guide RNA and Target DNA," Cell 156, 935-949 (2014).
Platt et al., "CRISPR-Cas9 Knockin Mice for Genome Editing and Cancer Modeling," Cell, 159(2):440-455 (2014).
Swiech et al., "In vivo interrogation of gene function in the mammalian brain using CRISPR-Cas9," Nature Biotechnology 33, 102-106 (2015).
Zetsche et al. "A split-Cas9 architecture for inducible genome editing and transcription modulation," Nature biotechnology, 33(2): 139-142 (2015).
Deltcheva et al., "CRISPR RNA maturation by trans-encoded small RNA and host factor RNase III," Nature. Mar. 31, 2011;471(7340):602-7. doi: 10.1038/nature09886.
*Manning* v. *Paradis*, 296 F.3d 1098 (Fed. Cir. 2012).
Cathy Cockrell, NewsCenter, "Berkeley's Wikipedian-in-residence is a first" (Feb. 25, 2014).
Wu et al., "Genome-wide binding of the CRISPR endonuclease Cas9 in mammalian cells", Nat Biotechnol. 2014, 32(7):670, doi: 10.1038/nbt.2889 (published online Apr. 20, 2014).
Christopher A. Cotropia & Mark A. Lemley, Copying in Patent Law, N. C. L. Rev., vol. 87, p. 1421, 2009; Stanford Public Law Working Paper No. 1270160.
*Rubin* v. *The General Hospital Corp.*, 2011-1439 (Fed. Cir. Mar. 28, 2013).
*Maxwell* v. *The Stanley Works*, 2006 WL 1967012, *5 (M.D. Tenn. Jul. 11, 2006).
*Huang* v. *California Institute of Technology*, 2004 WL 2296330 (C.D. Cal. Feb. 18, 2004).
*Ultra-Precision Mfg. Ltd.* v. *Ford Motor Co.*, 2004 WL 3507671, *7, *11-12 (E.D. Mich. Mar. 30, 2004).
*Arbitron, Inc.* v. *Kiefl*, No. 09-CV-04013 PAC, 2010 WL 3239414, at *1 (S.D.N. Y. Aug. 13, 2010).
Cong, et al., Oct. 5, 2012 Manuscript including Supplementary Materials, "CRISPR-Assisted Mammalian Genome Engineering," published as "Multiplex Genome Engineering Using CRISPR-Cas Systems," Science, vol. 339, pp. 819-823, dated Feb. 15, 2013, 36 pages.
Addgene, "gRNA_Cloning Vector", retrieved on Jan. 30, 2019, <https://www/addgenen.org/41824/>, 2 pages.
Allen, et al., "Liposomal drug delivery systems: From concept to clinical applications" Advanced Drug Delivery Reviews 65, Oct. 1, 2012, pp. 36-48.
Cho, Minseon, et al., "Quantitative selection and parallel characterization of aptamers," PNAS, Nov. 12, 2013, vol. 110, No. 46, pp. 18460-18465 (6 pages.).
Dean, "Recent Advances in Drug Design Methods: Where Will They Lead?", BioEssays, vol. 16, No. 9, Sep. 1994, pp. 683-687.
Gao, et al., "A Sustained, Cytoplasmic Transgene Expression System delivered by Cationic Liposomes", Biochemical and Biophysical Research Communications, vol. 200, No. 3, May 16, 1994, pp. 1201-1206.
Koo et al., "Measuring and Reducing Off-Target Activities of Programmable Nucleases Including CRISPR-Cas9", Molecules and Cells, vol. 38, No. 6, May 19, 2015, pp. 475-481.
Laganiere et. al., "An Engineered Zinc Finger Protein Activator of the Endogenous Glial Cell Line-Derived Neurotrophic Factor Gene Provides Functional Neuroprotection in a Rat Model of Parkinson's Disease", The Journal of Neuroscience (J. Neurosci.), Dec. 8, 2010, vol. 30, Issue 49, pp. 16469-16474.
Musunuru, "Abstract 18593: Use of a CRISPR/Cas System for Cardiovascular Disease Modeling and Therapeutic Applications", Circulation, vol. 128, No. 22, Suppl. 1, Nov. 26, 2013, 4 pages (Meeting info: American Heart Association, 2013 Scientific Sessions and Resuscitation Science Symposium, Dallas, TX, US, Nov. 16-20, 2013).
Swiech et al., "CRISPR-Mediated Genome Editing in the Mammalian Brain", Molecular Therapy, vol. 22, 749, May 2014, p. S289.
Symington et al., "Double-Strand Break End Resection and Repair Pathway Choice", Annual Review of Genetics 2011, vol. 45, Sep. 12, 2011, pp. 247-271.
Venken et al., "P[acman]: A BAC Transgenic Platform for Targeted Insertion of Large DNA Fragments in *D. melanogaster*", Science, vol. 314, No. 5806, Nov. 30, 2006, pp. 1747-1751.
Weber et al., "TALENs Targeting HBV: Designer Endonuclease Therapies for Viral Infections", Molecular Therapy, vol. 21, No. 10, Oct. 2013, pp. 1819-1821.
Xu, Zhi-Li et al., "Regulated gene expression from adenovirus vectors: a systematic comparison of various inducible systems," Gene, 2003, vol. 309, pp. 145-151 (7 pages).
Zhang, "Processing-Independent CRISPR RNAs Limit Natural Transformation in Neisseria meningitidis", Molecular Cell, vol. 50, May 23, 2013. pp. 488-503.
Zuris, et al., "Cationic lipid-mediated delivery of proteins enables efficient protein-based genome editing in vitro and in vivo" Nature Biotechnology, 2014, Advanced Online publication, doi:10.1038/nbt.3081.
Zuris, et al., Supplementary Information—"Cationic lipid-mediated delivery proteins enables efficient protein-based genome editing in vitro and in vivo" Nature Biotechnology, 2014, Advanced Online publication, doi:10.1038/nbt.3081.
U.S. Appl. No. 15/838,720, filed Dec. 12, 2017.
A. Amsterdam et al., "Identification of 315 genes essential for early zebrafish development," proc Natl Acad Sci., vol. 101, Aug. 31, 2004, pp. 12792-12797, 6 pages.
A. Fire et al., "Potent and specific genetic interference by double-stranded RNA in Caenorhabditis elegans," Nature, vol. 391, Feb. 19, 1998, pp. 806-811, 6 pages.
Subramanian et al., "Gene set enrichment analysis: a knowledge-based approach for interpreting genome-wide expression profiles," Proc Natl Acad Sci., vol. 102, Oct. 25, 2005, pp. 15545-15550, 6 pages.
A.C. Spradling et al., "The Berkeley Drosophila Genome Project Gene Disruption Project: Single P-Element Insertions Mutating 25% of Vital Drosophila Genes," Genetics, vol. 153, Sep. 1999, pp. 135-177, 43 pages.
A.H. Tong et al., "Global mapping of the yeast genetic interaction network," Science, vol. 303, Feb. 6, 2004, pp. 808-813, 6 pages.
A.L. Lin and D.H Gutmann, "Advances in the treatment of neurofibromatosis-associated tumours," Nature, vol. 10, Nov. 2013, pp. 616-624, 9 pages.
A.P. Blanchard and L. Hood, "Sequence to array: probing the genome's secrets," Nat Biotechnol, vol. 14, Dec. 14, 1996, p. 1649.
Autofluorescence MIT Flow Cytometry Core Facility (2018), 6 pages.

(56) References Cited

OTHER PUBLICATIONS

B. Langmead et al., "Ultrafast and memory-efficient alignment of short DNA sequences to the human genome," Genome biology, vol. 10, Mar. 4, 2009, 10 pages.
B. Langmead and S.L. Salzberg, "Fast gapped-read alignment with Bowtie 2," Nat Meth, vol. 9, 2012, pp. 357-359, 3 pages.
B. Scappini et al., "Changes associated with the development or resistance to imatinib (S11571) in two leukemia cell lines expressing p210 Bcr/Abl protein," Cancer, vol. 100, Apr. 1, 2004, pp. 1459-1471, 13 pages.
B. Sonnichsen et al., "Full-genome RNAi profiling of early embryogenesis in Caenorhabditis elegans," Nature, vol. 434, Mar. 24, 2005, pp. 462-469, 8 pages.
Bae, T. And Schneewind, O. "Allelic replacement in *Staphylococcus aureus* with inducible counter-selection," Plasmid, vol. 55, 2006, pp. 58-63, 6 pages.
Baena-Lopez, L., et al., "Accelerated homologous recombination and subsequent genome modification in *Drosophila*," Development, vol. 140, 2013, pp. 4818-4835, including Supplementary Material, 8 pages.
Balboa, et al., "Conditionally Stabilized dCas9 Activator for Controlling Gene Expression in Human Cell Reprogramming and Differentiation. (plus Supplemental Information)", Stem Cell Reports, vol. 5, Sep. 8, 2015, pp. 448-459, 12 pages.
Barrangou, R. et al., "CRISPR provides acquired resistance against viruses in prokaryotes," Science, vol. 315, Mar. 23, 2007, pp. 1709-1712, 6 pages.
Bennett, et al., "Stable transgene expression in rod photoreceptors after recombinant adeno-associated virus-mediated gene transfer to monkey retina", Proc. Natl. Acad. Sci., vol. 96, Aug. 1999, pp. 9920-9925.
Berns, K., et al., "A Large-Scale RNAi Screen in Human Cells Identifies New Components of the p53 Pathway," Nature, vol. 428, Mar. 25, 2004, pp. 431-437.
Bhaya, D., et al., "CRISPR-Cas Systems in Bacteria and Archaea: Versatile Small RNAs for Adaptive Defense and Regulation," Annual Review of Genetics, vol. 45, 2011, pp. 273-297, (27 pages).
Bikard, et al., Supplementary Information for: "CRISPR Interference Can Prevent Natural Transformation and Virulence Acquisition During in Vivo Bacterial Infection," Cell Host & Microbe, vol. 12, 2012, pp. 177-186.
Bloom, et al., "Inactivation of hepatitis B virus replication in cultured cells and in vivo with engineered transcription activator-like effector nucleases", Molecular Therapy, vol. 21, Oct. 2013, pp. 1889-1897.
Bohm et al., "The computer program LUDI: A new method for the de novo design of enzyme inhibitors", Journal of Computer-Aided Molecular Design, vol. 6, 1992, pp. 61-78.
Botta, S. et al, "Transcriptional Repression with Zinc-Finger and Tale Protein Scaffold", Molecular Therapy, 2013, Supplement 1, p. S208, Abstract No. 539.
Boutros, et al., "Genome-wide RNAi analysis of growth and viability in *Drosophila* cells," Science, American Association for the Advancement of Science, vol. 303, Feb. 6, 2004, pp. 832-835.
Branden, C., and Tooze, J., "Prediction, Engineering, and Design of Protein Structures: Introduction to Protein Structure," Garland Publishing, Inc., Chapter 16, 1991, p. 247.
Brouns, S., et al., "Small CRISPR RNAs Guide Antiviral Defense in Prokaryotes," Science, vol. 321, Aug. 15, 2008, pp. 960-964.
Brummelkamp TR et al., "A system for stable expression of short interfering RNAs in mammalian cells," Science, vol. 296, Apr. 19, 2002, pp. 550-553.
C. Cayrol et al., "The THAP-zinc finger protein THAP1 regulates endothelial cell proliferation through modulation of pRB/E2F cell-cycle target genes," Blood, vol. 109, 2007, pp. 584-594.
C. Trapnell et al., "Differential gene and transcript expression analysis of RNA-seq experiments with TopHat and Cufflinks," Nature protocols, vol. 7, 2012, p. 562.
C. Trapnell et al., "TopHat: discovering splice junctions with RNA-Seq.," Bioinformatics, vol. 25, 2009, pp. 1105-1111.
C.J, Echeverri et al., "Minimizing the risk of reporting false positives in large-scale RNAi screens," Nature methods, vol. 3, Oct. 2006, p. 777.
C.M Johannessen et al., "COT drives resistance to RAF inhibition through MAP kinase pathway reactivation," Nature, vol. 468, Dec. 16, 2010, p. 968.
C.M. Johnston et al., "Large-scale population study of human cell lines indicate that dosage compensation is virtually complete," PLoS Genet., vol. 4, Jan. 2008, pp. 88-98, 11 pages.
Carte, J., et al., "Cas6 is an endoribonuclease that generates guide RNAs for invader defense in prokaryotes," Genes Dev., vol. 22, 2008, pp. 3489-3496.
Chadderton, N., et al., "Improved Retinal Function in a Mouse Model of Dominant Retinitis Pigmentosa Following AAV-delivered Gene Therapy", Molecular Therapy, vol. 17, Apr. 2009, pp. 593-599.
Chevalier et al., "Homing endonuclease: structural and functional insight into the catalysts of intron/intein mobility," Oxford University Press., vol. 29, 2001, pp. 3757-3774.
Chinnasamy, D., et al., "Multicistronic lentiviral vectors containing the FMCV 2A Cleavage factor demonstrate robust expression of encoded genes at limiting MOI," Virology Journal, vol. 3, 2006, pp. 1-16.
Chou, JY, and Mansfield, BC., "Recombinant AAV-directed gene therapy for type I glycogen storage diseases," Expert Opinion on Biological Therapy, vol. 11, Aug. 2011, pp. 1011-1024.
Chylinski, et al., "Classification and evolution of type II CRISPR-Cas systems", Nucleic Acids Research, vol. 42, 2014, pp. 6091-6105, doi:10.1093InarIgku241.
Community Corner, "CRISPR technology for gene therapy," Nature Medicine, vol. 20, May 2014, pp. 476-477.
Cong, et al., Oct. 5, 2012 Manuscript including Supplementary Materials, "CRISPR-Assisted Mammalian Genome Engineering," published as "Multiplex Genome Engineering Using CRISPR-Cas Systems," Science, vol. 339, 2013, pp. 819-823.
Cong, L., et al., "In Vivo Genome Engineering With AAV Vector Carrying CRISPR-Cas9 System," Molecular Therapy, vol. 22, May 2014, Supplement 1, p. S214.
Cummings et al., "Fourteen and counting: unraveling trinucleotide repeat diseases", Human Molecular Genetics, vol. 9, 2000, pp. 909-916.
D.J. Burgess et al., "Topoisomerase levels determine chemotherapy response in vitro and in vivo," Proceedings of the National Academy of Sciences, vol. 105, Jul. 1, 2008, pp. 9053-9058.
Daoussi, F., et al., "Chromosomal context and epigenetic mechanisms control me efficacy or genome editing by rare-cutting designer endonucleases," Nucleic Acids Research, vol. 40, 2012, pp. 6367-6379.
Daley, J., and Wilson, T., "Rejoining of DNA Double-Strand Breaks as a Function of Overhang Length," Molecular and Cellular Biology, vol. 25, 2005, pp. 896-906.
Damian, M., and Porteus, M., "A Crisper Look at Genome Editing: RNA-guided Genome Modification," Molecular Therapy, vol. 21, Apr. 2013, pp. 720-722.
Database UniProtKB/TrEMBL [online], Accession No. Q0P897, "The genome sequence of the food-borne pathogen Campylobacter jejuni reveals hypervariable sequences," Subname: Full=Putative CRISPR-associated protein, Oct. 3, 2012 uploaded, [retrieved on Nov. 22, 2017], URL, http://www.uniprot.org/uniprot/Q0P897.txt?version=28, p. 1.
Database WPI, Week 201437 Thomson Scientific, London, GB; AN 2014-J79552, XP-002737563, 2 pages.
Deveau, H. et. al., "Phage Response to CRISPR-Encoded Resistance in *Streptococcus thermophilus*," Journal of Bacteriology, vol. 190, No. 4, Feb. 2008, pp. 1390-1400.
Deveau, H., et al., "CRISPR/Cas System and Its Role in Phage-Bacteria Interactions," The Annual Review of Microbiology, vol. 64, 2010, pp. 475-493.
E.S. Lander, "Initial impact of the sequencing of the human genome," Nature, vol. 470, Feb. 10,2011, p. 187-197.
Edgar, R. and Qimron, U., "The *Escherichia coli* CRISPR system protects from λ lysogenization, lysogens, and prophage induction," Journal of Bacteriology, vol. 192, Dec. 2010, pp. 6291-6294.

(56) References Cited

OTHER PUBLICATIONS

Esvelt et. al., "Orthogonal Cas9 proteins for RNA-guided gene regulation and editing", Nature Methods, vol. 10, No. 11, Nov. 2013 (available online Sep. 29, 2013), pp. 1116-1123.

Feldgarden et al., "*Staphylococcus aureus* M0408 acrHk-supercont1. 1, whole genome shotgun sequence", NCBI Reference Sequence: NK_KB821326.1, Direct Submission, Dec. 10, 2012, pp. 1-4.

Fischer, S. et al., "An archaeal immune system can detect multiple Protospacer Adjacent Motifs (PAMs) to target invader DNA," J. Biol. Chem., vol. 287, Sep. 28, 2012, pp. 33351-33363.

Flannery, J. G., "Ribozyme-Mediated Gene Therapy for Autosomal Dominant Retinal Degeneration", Retinal Degenerative Diseases and Experimental Therapy, 1999, pp. 277-291.

Fleming, J., et al., "Adeno-Associated Virus and Lentivirus Vectors Mediate Efficient and Sustained Transduction of Cultured Mouse and Human Dorsal Root Ganglia Sensory Neurons," Human Gene Therapy, vol. 12, Jan. 1, 2001, pp. 77-86.

Fonfara et al., "Phylogeny or Cas9 determines runctional excnangeability or dual-RNA and Cas9 among orthologous type II CRISPR-Cas systems", Nucleic Acids Research, 2014, vol. 42, No. 4, pp. 2577-2590.

Fu, et al., "Targeted genome editing in human cells using CRISPR/Cas nucleases and truncated guide RNAs", The Use of CRISPR/Cas9 ZFNs and Talens in Generating Site-Specific Genome Alterations; Elsivier Inc., 2014, pp. 21-45.

G. Giaever et al., "Functional profiling of the Saccharomyces cerevisiae genome," Nature, vol. 418, Jul. 25, 2002, pp. 387-391.

Guo et al., "Mismatch repair genes identified using genetic screens in Blm-deficient embryonic stem cells," Nature, vol. 429, Jun. 24, 2004, p. 891.

Gardlik, R., et al., "Vectors and delivery systems in gene therapy," Medical Science Monitor, vol. 11, No. 4, pp. RA110-121, dated Apr. 1, 2005, 12 pages.

Garriga-Canut, M., et al., "Synthetic zinc finger repressors reduce mutant huntingtin expression in the brain of R6/2 mice," Proceedings of the National Academy of Sciences, vol. 109, Oct. 10, 2012, pp. E3136-E3145.

Geisinger, et al., "In vivo blunt-end cloning through CRISPR/CAS9-facilitated non-homologous end-joining", Nucleic Acid Research Advance Access, vol. 44, 2016, pp. 1-15.

GenBank: "CRISPR-associated protein Cas9/Csn1 [*Staphylococcus aureus* subsp. aureus]", GenBank: CCK74173.1, Year: 2012, http://www.ncbi.nlm.nih.gov/protein/403411236?sat=16&satkey=13804560, dated Dec. 14, 2016, 2 pages.

Gibson, D.G. et al., "Enzymatic assembly of DNA molecules up to several hundred kilobases," Nat methods, vol. 6, 2009, pp. 343-345.

Greenwald, D L, et al., "Engineered Zinc Finger Nuclease-Mediated Homologous Recombination of the Human Rhodopsin Gene", Investigative Ophthalmology & Visual Science, vol. 51, Dec. 2010, pp. 6374-6380.

Grosse, et al. "Meganuclease-medicated Inhibition of HSV1 Infection in Cultured Cells", Molecular Therapy, vol. 19, No. 4, Apr. 1, 2011, pp. 694-702.

Gudbergsdottir, S. et al., "Dynamic properties of the Sulfolobus CRISPR/Cas and CRISPR/Cmr systems when challenged with vector-borne viral and plasmid genes and protospacers", Mol. Microbiology, vol. 79, 2011, pp. 35-49.

H. Davies et al., "Mutations of the BRAF gene in human cancer," Nature, vol. 417, Jun. 27, 2002, p. 949-954.

H.W Cheung et al., "Systematic investigation of genetic vulnerabilities across cancer cell lines reveals lineage-specific dependencies in ovarian cancer," Proceedings of the National Academy of Sciences, vol. 108, Jul. 26, 2011, p. 12372-12377.

Habib, N., Assignment to Broad Institute, dated Jun. 9, 2014, 4 pages.

Hall, B., et al., "Overview: Generation of Gene Knockout Mice," Current Protocols in Cell Biology, unit 19.12, suppl. 44, Sep. 2009, pp. 1-17.

Harrison, et al., "A CRISPR view of development", Genes & Development, vol. 28, 2014, pp. 1859-1872.

Hatoum-Aslan, A., et al., "Mature clustered, regularly interspaced, short palindromic repeats RNA (crRNA) length is measured by a ruler mechanism anchored at the precursor processing site," Proc. Natl. Acad. Sci., vol. 108, Dec. 27, 2011, p. 21218-21222.

Haurwitz, R.E., et al., "Sequence- and structure-specific RNA processing by a CRISPR endonuclease," Science, vol. 329, 2010, pp. 1355-1358.

Havarstein, L.S., et al., "An unmodified heptadecapeptide pheromone induces competence for genetic transformation in *Streptococcus pneumoniae*, " Proc. Natl. Acad. Sci., vol. 92, Nov. 1995, pp. 11140-11144.

Hemann et al., "An epi-allelic series of p53 hypomorphs created by stable RNAi produces distinct tumor phenotypes in vivo," Nat Genetics, vol. 33, Mar. 2003, pp. 396-400.

Hirano et al., "Structure and Engineering of Francisella novicida Cas9," Cell, vol. 164, Feb. 25, 2016, pp. 950-961.

Holkers, M., et al., "Adenoviral vector DNA for accurate genome editing with engineered nucleases," Nature Methods, vol. 11, 2014, pp. 1051-1057, (Only Abstract Available).

Horinouchi, S. and Weisblum, B., "Nucleotide sequence and functional map of pC194, a plasmid that specifies inducible chloramphenicol resistance," J. Bacteriology, vol. 150, May 1982, pp. 815-825.

Horton, R.M., "In Vitro recombination and Mutagenesis of DNA: SOEing Together Tailor-Made Genes," Methods Mol. Biology, vol. 15, 1993, pp. 251-261.

Horvath, P. and Barrangou, R. "CRISPR/Cas, the immune system of bacteria and archaea," Science, vol. 327, Jan. 8, 2010, pp. 167-170.

Hosaka, T. et al., "The novel mutation K87E in ribosomal protein S12 enhances protein synthesis activity during the late growth phase in *Escherichia coli*." Mol. Gen. Genomics, vol. 271, 2004, pp. 317-324.

Hoskins, J. et al., "Genome of the bacterium Streptococcus pneumoniae strain R6," Journal of Bacteriology, vol. 183, Oct. 2001, pp. 5709-5717.

Houdebine, L., "The methods to generate transgenic animals and to control transgene expression," Journal of Biotechnology, vol. 98, 2002, pp. 145-160.

Hung, S., et al., "AAV-Mediated CRISPR/Cas Gene Editing of Retinal Cells in Vivo," Investigative Ophthalmology & Visual Science, vol. 57, 2016, pp. 3470-3476.

Husmann, L.K.,et al., "Expression of the Arp protein, a member of the M protein family, is not sufficient to inhibit phagocytosis of *Streptococcus pyogenes*," Infection and immunity, vol. 63, Jan. 1995, pp. 345-348.

Hwang, W.Y., et al., "Efficient Genome Editing in Zebrafish Using a CRISPR-Cas System", Nature Biotechnology, vol. 31, No. 3, Jan. 29, 2013, pp. 227-229.

Ishino Y. et al., "Nucleotide sequence of the iap gene, responsible for alkaline phosphatase isozyme conversion in *Escherichia coli*, and identification of the gene product," J. Bacteriology, vol. 169, Dec. 1987, pp. 5429-5433, 5 pages.

Iwamoto et al., "A General Chemical Method to Regulate Protein Stability in the Mammalian Central Nervous System", Chemistry and Biology, Current Biology, vol. 17, Sep. 24, 2010, pp. 981-988, 8 pages.

J. Merkin et al., "Evolutionary dynamics of gene and isoform regulation in Mammalian tissues," Science, vol. 338, Dec. 21, 2012, p. 1593-1599, 7 pages. Includes Supplementary Information, 34 pages.

J.E. Carette et al., "Haploid genetic screens in human cells identify host factors used by pathogens," Science, vol. 326, Nov. 27, 2009, p. 1231-1235, 5 pages.

J.F. Rual et al., "Toward Improving Caenorhabditis elegans Phenome Mapping with an ORFeome-Based RNAi Library," Genome Research, vol. 14, 2004, pp. 2162-2168, 7 pages.

J.M. Engreitz et al., "The Xist lncRNA exploits three-dimensional genome architecture to spread across the X chromosome," Science, vol. 341, Aug. 16, 2013, pp. 1-8, 8 pages.

Jackson, A., et al., "Widespread siRNA "off-target" transcript silencing mediated by seed region sequence complementarity," RNA vol. 12, 2006, pp. 1179-1187, 10 pages.

(56) References Cited

OTHER PUBLICATIONS

Jansen R. et al., "Identification of genes that are associated with DNA repeats in prokaryotes," Molecular Microbiology, vol. 43, 2002, pp. 1565-1575, 11 pages.
Jiang, W., et al., "RNA-guided editing of bacterial genomes using CRISPR-Cas systems," Nature Biotechnology, vol. 31, Mar. 2013, pp. 233-239, 30 pages, including supplementary information.
Jinek, M., et al., "A Programmable Dual-RNA-Guided Dna Endonuclease in Adaptive Bacterial Immunity," Science, vol. 337, Aug. 17, 2012 pp. 816-821, including supplementary information, 45 pages.
JL. Mummery-Widmer et al., "Genome-wide analysis of Notch signalling in *Drosophila* by transgenic RNAi," Nature, vol. 458, Apr. 23, 2009, pp. 987-992, 6 pages. Includes Supplementary information, 2 pages.
Joseph, T., and Osman, R., "Thermodynamic basis of selectivity in guide-target-mismatched RNA interference," Proteins, vol. 80, 2012, pp. 1283-1298, 26 pages.
K. Yoshimoto et al., "Complex DNA repair pathways as possible therapeutic targets to overcome temozolomide resistance in glioblastoma," Front Oncology, vol. 2, Dec. 2012, pp. 1-8, 8 pages.
K.T Flaherty et al., "Inhibition of mutated, activated BRAF in metastatic melanoma," The New England Journal of Medicine, vol. 363, Aug. 26, 2010, pp. 1-22, 22 pages.
Kim, E., et al., "Precision genome engineering with programmable DNA-nicking enzymes," Genome Research, vol. 22, 2012, pp. 1327-1333, 8 pages.
Kim, S., et al., "CRISPER RNAs trigger innate immune responses in human cells," Genome Research, 2018, pp. 1-7, 8 pages.
Kleinstiver et al., "High-fidelity CRISP-Cas9 nucleases with no detectable genome-wide off-target effects", Nature, vol. 529, Jan. 28, 2016, pp. 490-495, 6 pages. Includes Supplementary information, 12 pages.
Koike-Yusa, H., et al., "Genome-wide recessive genetic screening in mammalian cells with a lentiviral CRISPR-guide RNA library," Nat Biotechnology, vol. 32, Mar. 2014, pp. 267-273, 7 pages. Including Supplemental information, 3 pages. doi:10.1038/nbt. 2800.
Kumar, M., et al., "Systematic Determination of the Packaging Limit of Lentiviral Vectors," Human Gene Therapy, vol. 12, Oct. 10,2001, pp. 1893-1905, 21 pages.
Kuwayama, H., "Enhancement or Homologous Recombination Efficiency by Homologous Oligonucleotides," Cell, 2012, pp. 233-244, 12 pages. IntechOpen, DOI: 10.5772/47779,.
Lebherz, C., et al., "Gene therapy with novel adeno-associated virus vectors substantially diminished atherosclerosis in a murine model of familial hypercholesterolemia," The Journal of Gene Medicine, vol. 6, 2004, pp. 663-672, 10 pages.
Levitt, J., et al., "Intrinsic fluorescence and redox changes associated with apoptosis of primary human epithelial cells," Journal of Biomedical Optics, vol. 11, No. 6, pp. 064012-1 to 064012-10, dated Nov./Dec. 2006, 10 pages.
Li et al., "Coevolution of CRISPR-Cas system with bacteria and phages", Hereditas, vol. 33, 2011, pp. 213-218, 6 pages, English abstract only.
M. Booker et al., "False negative rates in *Drosophila* cell-based RNAi screens: a case study," BMC Genomics, vol. 12, 2011, pp. 1-11, 11 pages.
M. Costanzo et al., "The genetic landscape of a cell," Science, vol. 327, Jan. 22, 2010, pp. 425-431, 8 pages.
Ma, M., et al., "A Guide RNA Sequence Design Platform for the CRISPR/Cas9 System for Model Organism Genomes," Hindawi, vol. 2013, 2013, pp. 1-5, 5 pages.
Maczuga, P., et al., "Embedding siRNA sequences targeting Apolipoprotein B100 in shRNA and miRNA scaffolds results in differential processing and in vivo efficacy," Molecular Therapy, vol. 21, 2013, pp. 217-227, 11 pages.
Maeder, M., and Gersbach, C., "Genome-editing Technologies for Gene and Cell Therapy," Molecular Therapy, vol. 24, 2016, pp. 430-446, 17 pages.

Maeder, M., et al., "Robust, synergistic regulation of human gene expression using Tale activators," Nature Methods, vol. 10, 2013, pp. 243-245, 3 pages. Including Supplemental information, 6 pages.
Mahfouz, M., et al., "De novo-engineered transcription activator-like effector (TALE) hybrid nuclease with novel DNA binding specificity creates double-strand breaks," Proceedings of the National Academy of Science, vol. 108, 2011, pp. 2623-2628, 6 pages.
Mali et al., "CAS9 transcriptional activators for target specificity screening and paired nickases for cooperative genome engineering", Nature Biotechnology, vol. 31, 2013, pp. 833-837, 5 pages.
Mali, et al., Supplementary Information for "Use of adjacent sgRNA: Cas9 complexes for transcriptional activation and genome engineering," Nature Biotechnology, pp. 1-36, 36 pages. doi:10. 1037/nbt.2675, Oct. 2013.
Mali, P., et al., "CAS9 transcriptional activators for target specificity screening and paired nickases for cooperative genome engineering," Nature Biotechnology, vol. 31, No. 9, pp. 833-838, dated Aug. 1, 2013, 44 pages. (Includes Supplemental Information).
Manjunath, N., et al., "Newer Gene Editing Technologies toward HIV Gene Therapy," Viruses, vol. 5, pp. 2748-2766, 2013, 19 pages.
Marraffini, L., "CRISPR-Cas Immunity against Phages: Its Effects on the Evolution and Survival of Bacterial Pathogens," PLOS, Dec. 12, 2013, pp. 1-6, 6 pages.
Marraffini, L., Assignment to Rockefeller University, dated Dec. 12, 2013, 3 pages.
Marraffini, L.A., et al., "Sortases and the art of anchoring proteins to the envelopes or gram-positive bacteria," Microbiol. Mol. Biology Review vol. 70, Mar. 2006, pp. 192-221, 3 pages.
Martin, M., "Cutadapt removes adapter sequences from high-throughput sequencing reads," EMBnet.journal, vol. 17, 2011, pp. 10-12, 3 pages.
Moffat J et al., "A lentiviral RNAi library for human and mouse genes applied to an arrayed viral high-content screen," Cell, vol. 124, Mar. 24, 2006, pp. 1283-98, 16 pages.
Mojica F. J. M et al., "Biological significance of a family of regularly spaced repeats in the genomes of Archaea, Bacteria and mitochondria," Molecular Microbiology, vol. 36, 2000, pp. 244-246, 3 pages.
Mojica, F. J., et al., Supplementary Material for: "Short Motif Sequences Determine the Targets of the Prokaryotic CRISPR Defence System," Microbiology, vol. 155, 2009, 37 pages.
Morris et al., "Distributed automated docking of flexible ligands to proteins: Parallel applications of AutoDock 2.4", Journal of Computer-Aided Molecular Design, 1996, vol. 10, pp. 293-304.
Motamedi, M.R., et al., "Double-strand-break repair recombination in *Escherichia coli*: physical evidence for a DNA replication mechanism in vivo," Genes Dev., vol. 13, 1999, pp. 2889-2903.
Muther, N., et al., "Viral Hybrid Vectors for Somatic Integration—Are They the Better Solution?" Viruses, vol. 1, 2009, pp. 1295-1324, 30 pages.
Ozawa, K., "Gene therapy using AAV," Virus, vol. 57, pp. 47-55, dated, 2007, 13 pages. (with English Abstract; No English Translation).
Paddison et al., "A resource for large-scale RNA-interference-based screens in mammals," Nature, vol. 428, Mar. 25, 2004, pp. 427-31, 5 pages.
Phillips, A., "The challenge of gene therapy and DNA delivery," The Journal of Pharmacy and Pharmacology, vol. 53, 2011, pp. 1169-1174, 6 pages.
Podbielski, A., et al., "R. Novel series of plasmid vectors for gene inactivation and expression analysis in group a streptococci (GAS)," Gene, vol. 177, 1996, pp. 137-147, 11 pages.
Pougach, K.S., et al., "CRISPR Adaptive Immunity Systems of Prokaryotes," Molecular Biology, vol. 46, Apr. 2012, pp. 195-203, 1 page (English Abstract).
Pride, D., et al., "Analysis of Streptococcal CRISPRs from Human Saliva Reveals Substantial Sequence Diversity Within and Between Subjects Over Time," Genome Research, vol. 21, 2011, pp. 126-136, 11 pages.
Qi, J., et al., "microRNAs regulate human embryonic stem cell division," Cell Cycle, vol. 8, 2009, pp. 3729-3741, 13 pages.

(56) References Cited

OTHER PUBLICATIONS

R. Rad et al., "PiggyBac transposon mutagenesis: a tool for cancer gene discovery in mice," Science, vol. 330, Nov. 19, 2010, p. 1104-1107, 4 pages.
R.D. Kolodner and G.I. Marsischy, "Eukaryotic DNA mismatch repair," Current Opinion in Genetics and Development, vol. 9, 1999, p. 89-96, 8 pages.
R.Renella et al., "Codanin-1 mutations in congenital dyserthropoietic anemia type 1 affect HP1α localization in erythroblasts," Blood, vol. 117, Jun. 2011, pp. 6928-6938, 11 pages.
Radecke, S., et al., "Zinc-finger Nuclease-induced Gene Repair With Oligodeoxynucleotides: Wanted and Unwanted Target Locus Modifications," Molecular Therapy, vol. 18, Apr. 2010, pp. 743-753, 11 pages.
Ran et al., "Double Nicking by RNA-guided CRISPR Cas9 for enhanced genome editing specificity", Cell, Sep. 12, 2013, vol. 154, pp. 1380-1389.
Ran, F.A., "CRISPR-Cas: Development and Applications for Mammalian Genome Editing", Ph.D. Dissertation, Harvard University, Apr. 2014, pp. 1-120.
Redeclaration—PTAB, *The Regents of the University of California v. The Broad Institute, Inc.*, filed Aug. 26, 2019, in Patent Interference No. 106,115 (DK), 20 pages.
Rho, M., et al., "Diverse CRISPRs Evolving in Human Microbiomes," PLOS Genetics, vol. 8, Jun. 2012 e1002441, 12 pages.
Rockefeller University and Broad Institute of MIT and Harvard announce update to CRISPR-Cas9 portfolio filed by Broad, Press Release dated Jan. 15, 2018, retrieved from: https://www.broadinstitute.org/news/rockefeller-university-and-broad-institute-mit-and-harvard-announce-update-crispr-cas9, 3 pages.
Rodriguez et al., "AAV-CRISPR: A New Therapeutic Approach to Nucleotide Repeat Diseases", Molecular Therapy, vol. 22, 2014, Supplement 1, Abstract 247, p. S94.
Rolling, "Recombinant AAV-mediated gene transfer to the retina: gene therapy perspectives", Gene Therapy, vol. 11, 2004, pp. S26-S32, 5 pages.
S. Huang et al., "MED12 Controls the Response to Multiple Cancer Drugs through Regulation of TGF-β; Receptor Signaling," Cell, vol. 151, 2012, pp. 937-950, 14 pages.
S. Konermann et al., "Optical control of mammalian endogenous transcription and epigenetic states," Nature, vol. 500, Aug. 22, 2013, pp. 472-476, 5 pages. Includes Supplemental Information, 13 pages.
S.H. Chen et al., "A Knockout Mouse Approach Reveals that TCTP Functions as an Essential Factor for Cell Proliferation and Survival in a Tissue-or Cell Type-specific Manner," Molecular Biology of the Cell, vol. 18, Jul. 2007, pp. 2525-2532, 8 pages.
S.R. Whittaker et al., "A Genome-Scale Rna Interference Screen Implicates NF1 Loss in Resistance to RAF Inhibition," Cancer Discovery, vol. 3, 2013, pp. 350-362, 14 pages.
S.S. Liu et al., "Identification and characterization of a novel gene, clorf109, encoding a CK2 substrate that is involved in cancer cell proliferation," Journal of Biomedical Science, vol. 19, 2012, 12 pages.
S.Xue and M. Barna, "Specialized ribosomes: a new frontier in gene regulation and organismal biology," Nat Rev Mol Cell Biology, vol. 13, Jun. 2012. Pages 355-369, 15 pages.
Sadowski, M., and Jones, D., "The sequence-structure reiationship and protein function prediction," Current Opinion in Structural Biology, vol. 19, 2009, pp. 357-362, 6 pages.
Sarra, G., et al., "Gene replacement therapy in the retinal degeneration slow (RDS) mouse: the effect on retinal degeneration following partial transduction of the retina", Human Molecular Genetics, vol. 10, 2001, pp. 2353-2361, 9 pages.
Schiffer, et al. "Targeted DNA Mutagenesis for the Cure of Chronic Viral Infections" Journal of Virology, vol. 86, No. 17, Jun. 20, 2012, pp. 8920-8936.
Seffernick, J., et al., "Melamine Deaminase and Atrazine Chlorohydrolase: 98 Percent Identical but Functionally Different," Journal of Bacteriology, vol. 183, No. 8, Apr. 2001, pp. 2405-2410, 6 pages.
Semenova, E. et al., "Interference by clustered regularly interspaced short palindromic repeat (CRISPR) RNA is governed by a seed sequence," Proc. Natl. Acad. Sci., vol. 108, Jun. 21, 2011, pp. 10089-10103, 7 pages.
Senis, E., et al., "Crispr/Cas9-mediated genome engineering: an adeno-associated viral (AAV) vector toolbox," Biotechnology Journal, vol. 9, 2014, pp. 1402-1412, 12 pages.
Senturk et al., "A rapid and tunable method to temporally control cas9 expression enables the identification of essential genes and the interrogation of functional gene interactions in vitro and in vivo," vol. 9, 2015, pp. 1-27, XP002756303, doi:10.1101/023366, Retrieved from the Internet: URL:http://biorxiv.org/content/early/2015/07/28/023366 [retrieved on Apr. 11, 2016).
Shengdar Tsai et al., "Dimeric CRISPR RNS-guided FokI nucleases for highly specific genome editing", Nature Biotechnology, vol. 32, Jun. 2014, pp. 569-576, 18 pages.
Slaymaker et al., "Rationally engineered Cas9 nucleases with improved specificity", Science, American Association for the Advancement of Science, U.S., vol. 351, Jan. 1, 2016, pp. 84-88.
Spencer, J.M., et al., "Development of a Nuclease Screen to Improve Cas9 Targeting Specificity", Molecular Therapy, May 2015, vol. 23, Suppl. 1, S136(340).
Stewart Sa et al., "Lentivirus-delivered stable gene silencing by RNAi in primary cells," RNA, vol. 9, 2003, pp. 493-501, 9 pages.
Stoller, J. and Aboussouan, L., "Alpha/-antitrypsin deficiency," The Lancet, Seminar, vol. 365, 2005, pp. 2225-2236, 12 pages.
Straub, C., et al., "CRISPR/Cas9-Mediated Gene Knock-Down in Post-Mitotic Neurons," PLOS One, vol. 9, Aug. 20, 2014, pp. 1-5, 6 pages.
Suzuki, K., et al., "In vivo genome editing via CRISPR/Cas9 mediated homology-independent targeted integration," Nature, vol. 540, 2015, pp. 1-44.
T. Horii et al., "Generation of an ICF Syndrome Model by Efficient Genome Editing of Human Induced Pluripotent Stem Cells Using the CRISPR System," International Journal of Molecular Sciences, vol. 14, 2013, p. 19774- 19781, 9 pages.
T.J. Cradick et al., "CRISPR/Cas9 systems targeting β-globin and CCR5 genes have substantial off-target activity," Nucleic Acids Research, vol. 41, 2013, 9584-9592, 9 pages.
I .Yan et al., "DNA mismatch repair (MMR) mediates 6-thioguanine genetoxicity by introducing single-strand breaks to signal a G2-M arrest in MMR-proficient RKO cells," Clinical Cancer Research, vol. 9, Jun. 2003, p. 2327-2334, 9 pages.
Tang, T., et al., "A mouse knockout library for secreted and transmembrane proteins," Nature Biotechnology, vol. 28, No. 7, Jul. 2010, pp. 749-755, pages. 7 pages. Including Supplemental information, 2 pages.
Trafton, A., "CRISPR-carrying nanoparticles edit the genome," MIT News, dated Nov. 13, 2017, 3 pages.
Tulpan, D., et al., "Free energy estimation of short DNA duplex hybridizations," BMC Bioinformatics, vol. 11, 2012, pp. 105-127, 23 pages.
V.N. Ngo et al., "A loss-of-function RNA interference screen for molecular targets in cancer," Nature, vol. 441, May 4, 2006, pp. 106-110, 5 pages.
Van Der Oost, "New tool for genome surgery", Science, vol. 339, Feb. 15, 2013, pp. 768-770, 3 pages.
Van Der Oost, J., et al., "CRISPR-based adaptive and heritable immunity in prokaryotes," Trends. Biochem. Sci., vol. 34, 2009, pp. 401-407, 7 pages.
W.G. Kaelin., "Use and Abuse of RNAi to Study Mammalian Gene Function," Science, vol. 337, Jul. 27, 2012, p. 421-422, 2 pages.
Wang, H.H. et al., "Genome-scale promoter engineering by coselection MAGE," Nat methods, vol. 9, Jun. 2012, pp. 591-593, 3 pages.
Wayengera, M., "Identity of zinc finger nucleases with specificity to herpes simplex virus type II genomic DNA; novel HSV-2 vaccine/therapy precursors", Theoretical Biology and Medical Modelling, vol. 8, No. 1, Jun. 24, 2011, p. 23.
Wayengera, M., "Zinc finger arrays binding human papillomavirus types 16 and 18 genomic DNA: precursors of gene-therapeutics for in-situ reversal of associated cervical neoplasia", Theoretical Biology and Medical Modeling, vol. 9, No. 1, Jul. 28, 2012, p. 30.

(56) References Cited

OTHER PUBLICATIONS

Wiedenheft, B. et al., "RNA-guided genetic silencing systems in bacteria and archaea", Nature, vol. 482, Feb. 16, 2012, pp. 331-338.
Wienert, B., et al., "In vitro transcribed guide RNAs trigger an innate immune response via the RIG-I pathway," BioRxiv Preprint, 2018, 1-28, 28 pages.
Witkowski, A., et al., "Conversion of a Beta-Ketoacyl Synthase to a Malonyl Decarboxylase by Replacement of the Active-Site Cysteine with Glutamine," Biochemistry, vol. 38, 1999, pp. 11643-11650, 8 pages.
Wittmann et al., "Engineered riboswitches: Expanding researchers' toolbox witn syntnetic RNA regulators", FEBS Letters, vol. 586, 2012, pp. 2076-2083, 8 pages.
X.Liu et al., "STAGA recruits Mediator to the MYC oncoprotein to stimulate transcription and cell proliferation," Molecular and cellular biology, vol. 28, Jan. 2008, p. 108-121, 14 pages.
Xiao, W., et al, "Gene Therapy Vectors Based on Adeno-Associated Virus Type 1", Journal of Virology, May 1999, vol. 73, No. 5, p. 3994-4003.
Yamada et al., "Crystal Structure of the Minimal Cas9 from Campylobacter jejuni Reveals the Molecular Diversity in the CRISPR-Cas9 Systems," Molecular Cell, vol. 65, Mar. 16, 2017, pp. 1109-1121.
Yanfang Fu et al., "Improving CRISPR-Cas nuclease specificity using truncated guide RNAs" (with Supplement Table), Nature Biotechnology, vol. 32, Mar. 2014, pp. 1-18.
Yin, H., et al., "Structure-guided chemical modification of guide RNA enables potent non-viral in vivo genome editing," Nature Biotechnology, vol. 35, Dec. 2017, pp. 1-22.
Yu, et al., "An efficient recombination system for chromosome engineering in *Escherichia coli*" PNAS, 2000, vol. 97, pp. 5978-5983, 6 pages.
Yu, W., et al., "NRL knockdown by AAV-delivered CRISPR/Cas9 prevents retinal degeneration in mice," Nature Communications, vol. 8, 2017, art. 14716, 15 pages.
Yusuke Miyazaki et al., Destabilizing Domains Derived from the Human Estrogen Receptor:, Journal of the American Chemical Society, vol. 134, Mar. 7, 2012, pp. 3942-3945, 4 pages.
Zahner, D. And Hakenbeck, R. "The *Streptococcus pneumoniae* beta-galactosidase is a surface protein," J. Bacteriology, vol. 182, Oct. 2000, pp. 5919-5921, 3 pages.
Zeng Yet Al., "Both natural and designed micro RNAs can inhibit the expression of cognate mRNAs when expressed in human cells," Mol Cell., vol. 9, Jun. 2002, pp. 1327-33, 7 pages.
Zuris, et al., "Cationic lipid-mediated delivery proteins enables efficient protein-based genome editing in vitro and in vivo", Nature Biotechnology, vol. 33, No. 1, Jan. 2015, pp. 73-80.
Anguela et al., "Robust ZFN-mediated geno1ne editing in adult hemophilic mice", Blood, vol. 122, No. 19, Nov. 7, 2013, (pp. 3283-3287).
Bikard et al., "Exploiting CRISPR-Cas nucleases to produce sequence-specific antimicrobials", Nature Biotechnology, vol. 32, No. 11, Nov. 2014 (pp. 1146-1151).
Chapdelaine et al., "Meganucleases can restore the reading frame of a mutated dystrophin", Gene Therapy, vol. 17, 2010 (pp. 846-858).
Database UniPro Accession No. J7RUA5, 2012, [online] downloaded from https:/lwww.uniprot.org/uniprol/J7RUA5 on Mar. 23, 2021 (10 pages).
Koonin et al., "Diversity, classification and evolution of CRISPR-Cas systems", Current Opinion in Microbiology vol. 37, 2017 (pp. 67-78).
Sorek et al., "CRISPR-Mediated Adaptive Immune Systems in Bacteria and Arches", Annual Review of Biochemistry, vol. 82, 2013, (pp. 237-266).
U.S. Appl. No. 14/054,414, filed Oct. 15, 2013.
U.S. Appl. No. 14/104,837, filed Dec. 12, 2013.
U.S. Appl. No. 14/104,900, filed Dec. 12, 2013.
U.S. Appl. No. 14/104,977, filed Dec. 12, 2013.
U.S. Appl. No. 14/104,990, filed Dec. 12, 2013.
U.S. Appl. No. 14/105,017, filed Dec. 12, 2013.
U.S. Appl. No. 14/105,031, filed Dec. 12, 2013.
U.S. Appl. No. 14/105,035, filed Dec. 12, 2013.
U.S. Appl. No. 14/183,429, filed Feb. 18, 2014.
U.S. Appl. No. 14/183,471, filed Feb. 18, 2014.
U.S. Appl. No. 14/183,486, filed Feb. 18, 2014.
U.S. Appl. No. 14/183,512, filed Feb. 18, 2014.
U.S. Appl. No. 14/222,930, filed Mar. 24, 2014.
U.S. Appl. No. 14/226,274, filed Mar. 26, 2014.
U.S. Appl. No. 14/256,912, filed Apr. 18, 2014.
U.S. Appl. No. 14/258,458, filed Apr. 22, 2014.
U.S. Appl. No. 14/259,420, filed Apr. 23, 2014.
U.S. Appl. No. 14/290,575, filed May 29, 2014.
U.S. Appl. No. 14/293,498, filed Jun. 2, 2014.
U.S. Appl. No. 14/293,674, filed Jun. 2, 2014.
U.S. Appl. No. 14/324,960, filed Jul. 7, 2014.
U.S. Appl. No. 14/463,253, filed Aug. 19, 2014.
U.S. Appl. No. 14/481,339, filed Sep. 9, 2014.
U.S. Appl. No. 14/497,627, filed Sep. 26, 2014.
U.S. Appl. No. 14/523,799, filed Oct. 24, 2014.
U.S. Appl. No. 14/681,382, filed Apr. 8, 2015.
U.S. Appl. No. 14/703,511, filed May 4, 2015.
U.S. Appl. No. 14/704,551, filed May 5, 2015.
U.S. Appl. No. 14/738,398, filed Jun. 12, 2015.
U.S. Appl. No. 14/738,483, filed Jun. 12, 2015.
U.S. Appl. No. 14/970,967, filed Dec. 16, 2015.
U.S. Appl. No. 14/971,169, filed Dec. 16, 2015.
U.S. Appl. No. 14/971,356, filed Dec. 16, 2015.
U.S. Appl. No. 14/972,523, filed Dec. 17, 2015.
U.S. Appl. No. 14/972,927, filed Dec. 17, 2015.
U.S. Appl. No. 14/973,062, filed Dec. 17, 2015.
U.S. Appl. No. 14/990,444, filed Jan. 7, 2016.
U.S. Appl. No. 14/991,083, filed Jan. 8, 2016.
U.S. Appl. No. 15/160,710, filed May 20, 2016.
U.S. Appl. No. 15/217,489, filed Jul. 22, 2016.
U.S. Appl. No. 15/229,702, filed Aug. 5, 2016.
U.S. Appl. No. 15/230,025, filed Aug. 5, 2016.
U.S. Appl. No. 15/230,161, filed Aug. 5, 2016.
U.S. Appl. No. 15/330,876, filed Nov. 7, 2016.
U.S. Appl. No. 15/430,260, filed Feb. 10, 2017.
U.S. Appl. No. 15/834,736, filed Dec. 7, 2017.
U.S. Appl. No. 15/838,064, filed Dec. 11, 2017.
U.S. Appl. No. 15/887,377, filed Feb. 2, 2018.
U.S. Appl. No. 15/967,464, filed Apr. 30, 2018.
U.S. Appl. No. 15/967,495, filed Apr. 30, 2018.
U.S. Appl. No. 15/967,510, filed Apr. 30, 2018.
U.S. Appl. No. 16/012,692, filed Jun. 19, 2018.
U.S. Appl. No. 16/177,403, filed Oct. 31, 2018.
U.S. Appl. No. 16/178,551, filed Nov. 1, 2018.
U.S. Appl. No. 16/445,150, filed Jun. 18, 2019.
U.S. Appl. No. 16/445,156, filed Jun. 18, 2019.
U.S. Appl. No. 16/525,531, filed Jul. 29, 2019.
U.S. Appl. No. 16/532,442, filed Aug. 5, 2019.
U.S. Appl. No. 16/535,043, filed Aug. 7, 2019.
U.S. Appl. No. 16/800,988, filed Feb. 25, 2020.
U.S. Appl. No. 16/844,548, filed Apr. 9, 2020.
U.S. Appl. No. 16/906,580, filed Jun. 19, 2020.
U.S. Appl. No. 16/938,110, filed Jul. 24, 2020.
U.S. Appl. No. 17/027,151, filed Sep. 21, 2020.
U.S. Appl. No. 17/034,754, filed Sep. 28, 2020.
U.S. Appl. No. 17/182,817, filed Feb. 23, 2020.
U.S. Appl. No. 17/201,347, filed Mar. 15, 2020.
Yang et al., "HIV-1 TAT-mediated protein transduction and subcellular localization using novel expression vectors," FEBS Letters 532:36-44, (2002).†
Raymond et al., High-Efficiency FLP and PhiC31 Site-Specific Recombination in Mammalian Cells, PLoS One 2(1):e162, (2007).†
Imagawa et al., "Two nuclear localization signals are required for nuclear translocation of nuclear factor 1-A," FEBS Letters 484:118-124, (2000).†
Kim et al., "High Cleavage Efficiency of a 2A Peptide Derived from Porcine Teschovirus-1 in Human Cell Lines, Zebrafish and Mice," PLoS One, 6(4):e18556, (2011).†

(56) References Cited

OTHER PUBLICATIONS

Madisen et al., "A robust and high-throughput Cre reporting and characterization system for the whole mouse brain," Nat. Neurosci., 13(1):133-140, (2010) (author manuscript; available in PMC Jul. 1, 2010).†

\* cited by examiner
† cited by third party

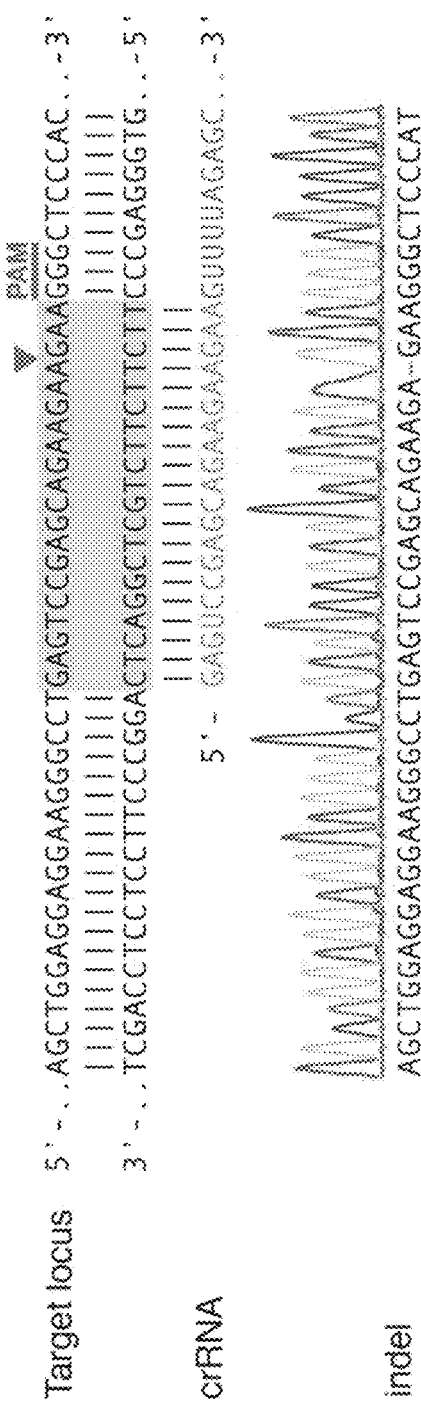

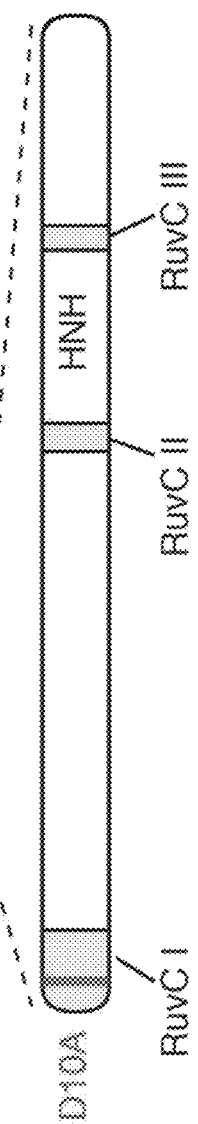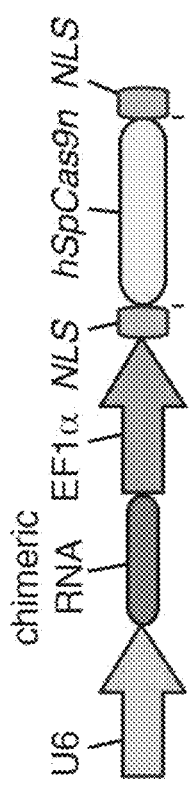
FIG. 4A
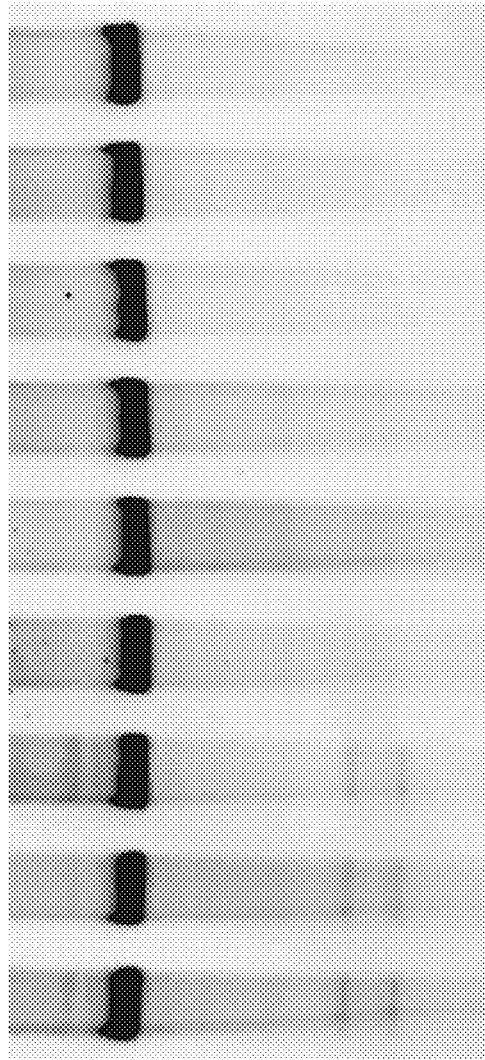
FIG. 4B

| Cas9 | target species | gene | protospacer ID | protospacer sequence (5' to 3') | PAM | strand | cell line tested | % indel (pre-crRNA + tracrRNA) | % indel (chimeric RNA) |
|---|---|---|---|---|---|---|---|---|---|
| S. pyogenes SF370 type II CRISPR | Homo sapiens | EMX1 | 1 | GGAGGGCCTGAGTCCGAGCAGAAGAAGAA | GGG | + | 293FT | 20 ± 1.8 | 6.7 ± 0.62 |
| | | EMX1 | 2 | CATTGGAGGTGACATCGATGTCCTCCCCAT | TGG | − | 293FT | 2.1 ± 0.31 | N.D. |
| | | EMX1 | 3 | GGACATCGATGTCACCTCCAATGACTAGGG | TGG | + | 293FT | 14 ± 1.1 | N.D. |
| | | EMX1 | 4 | CATCGATGTCCTCCCCATTGGCCTGCTTCG | TGG | − | 293FT | 11 ± 1.7 | N.D. |
| | | EMX1 | 5 | TTCGTGGCAATGCGCCACCGGTTGATGTGA | TGG | − | 293FT | 4.3 ± 0.46 | 2.1 ± 0.51 |
| | | EMX1 | 6 | TCGTGGCAATGCGCCACCGGTTGATGTGAT | TGG | − | 293FT | 4.0 ± 0.86 | 0.41 ± 0.25 |
| | | EMX1 | 7 | TCCAGCTTCTGCCGTTTGTACTTTGTCCTC | CGG | − | 293FT | 1.5 ± 0.12 | N.D. |
| | | EMX1 | 8 | GGAGGGAGGGCCACAGATAGAAACTCAGG | AGG | − | 293FT | 7.8 ± 0.83 | 2.3 ± 1.2 |
| | Homo sapiens | PVALB | 9 | AGGGCCGAGATTGGGTGTTCAGGGCAGAG | AGG | + | 293FT | 21 ± 2.6 | 6.5 ± 0.32 |
| | | PVALB | 10 | ATCAGAGGGGTGGCGAGAGGGCCGAGAT | TGG | + | 293FT | N.D. | N.D. |
| | | PVALB | 11 | GGTGGGCGAGAGGGCCGAGATTGGGTGTTC | AGG | + | 293FT | N.D. | N.D. |
| | Mus musculus | Th | 12 | CAAGCACTGAGTGCCATTAGTTAATGCAT | AGG | − | Neuro2A | 27 ± 4.3 | 4.1 ± 2.2 |
| | | Th | 13 | AATCATAGGGTACCACCCAGTGCCAG | TGG | − | Neuro2A | 4.8 ± 1.2 | N.D. |
| | | Th | 14 | ACACACATGGAAGCCTCTGGCCAGAA | GGG | + | Neuro2A | 11.3 ± 1.3 | N.D. |
| S. thermophilus LMD-9 CRISPR1 | Homo sapiens | EMX1 | 15 | GGAGGAGGTAGTATACAGAAACACAGAA | GTAGAAT | − | 293FT | 14 ± 0.88 | N.T. |
| | | EMX1 | 16 | AGAATGTACAGAGTCACAGAACTCAGCA | CTAGAAA | − | 293FT | 7.8 ± 0.77 | N.T. |

FIG. 5

FIG. 9C
| Chr | NGG median | NGG mean | NNAGAAW median | NNAGAAW mean |
|---|---|---|---|---|
| 1 | 7 | 12.8 | 67 | 115.8 |
| 2 | 8 | 12.7 | 64 | 100.8 |
| 3 | 8 | 13.0 | 63 | 98.5 |
| 4 | 9 | 14.0 | 61 | 94.5 |
| 5 | 8 | 13.1 | 63 | 97.9 |
| 6 | 8 | 13.1 | 63 | 98.5 |
| 7 | 8 | 12.4 | 64 | 102.9 |
| 8 | 8 | 12.8 | 64 | 100.9 |
| 9 | 7 | 13.9 | 65 | 120.5 |
| 10 | 7 | 12.1 | 66 | 107.0 |
| 11 | 7 | 12.0 | 65 | 105.8 |
| 12 | 8 | 12.4 | 65 | 103.5 |
| 13 | 8 | 13.6 | 62 | 94.6 |
| 14 | 8 | 12.0 | 65 | 101.5 |
| 15 | 7 | 11.5 | 68 | 107.7 |
| 16 | 7 | 11.7 | 74 | 136.8 |
| 17 | 6 | 10.3 | 76 | 127.9 |
| 18 | 8 | 13.4 | 63 | 101.8 |
| 19 | 6 | 9.4 | 82 | 145.4 |
| 20 | 7 | 11.1 | 72 | 121.8 |
| 21 | 7 | 13.4 | 64 | 111.4 |
| 22 | 6 | 9.2 | 85 | 140.3 |
| X | 8 | 13.2 | 63 | 99.0 |
| Y | 8 | 29.2 | 82 | 223.7 |
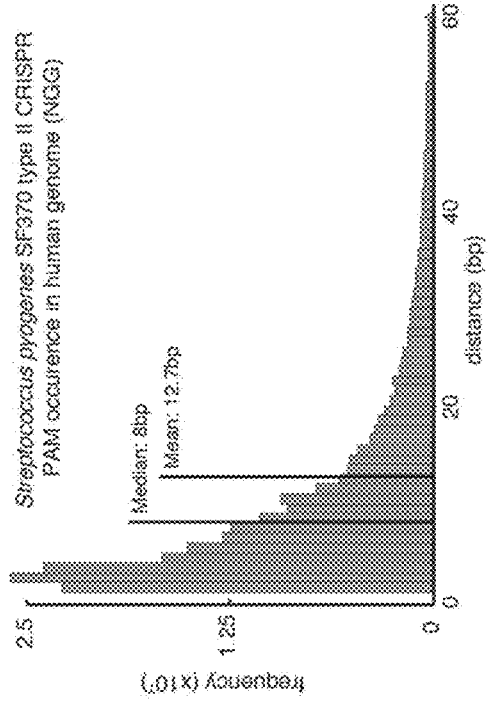
FIG. 9A
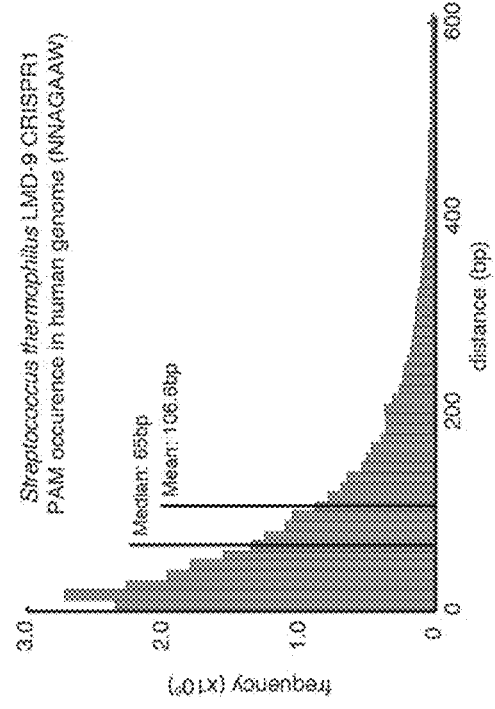
FIG. 9B FIG. 10A
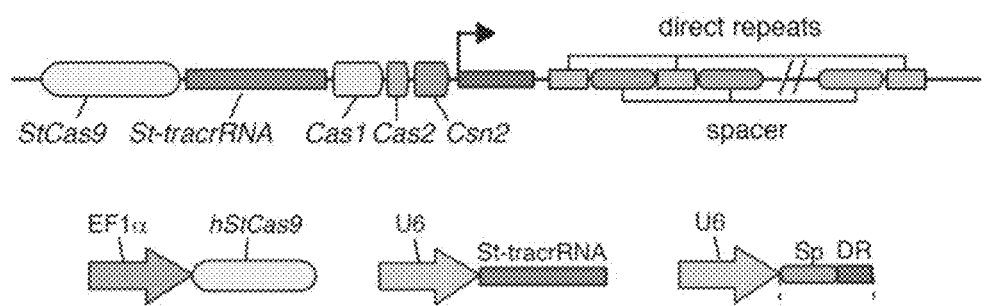
FIG. 10B
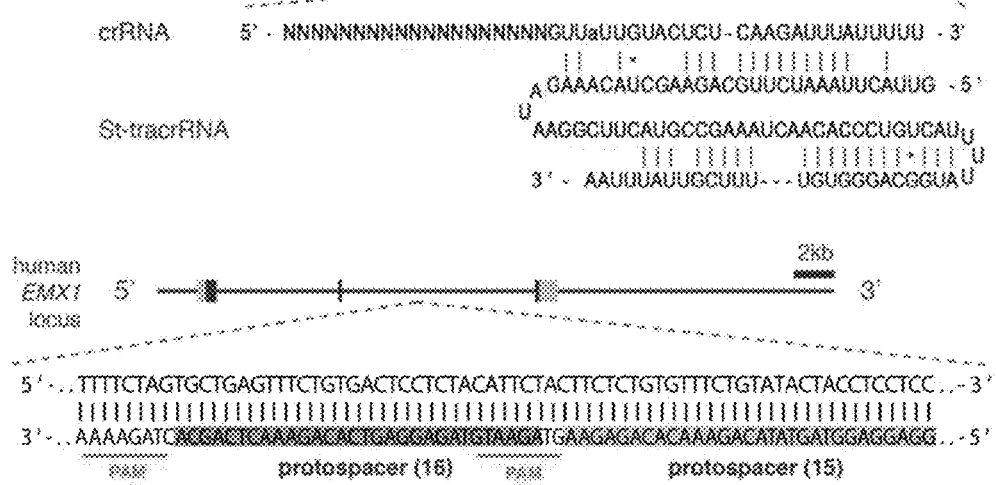
FIG. 10C

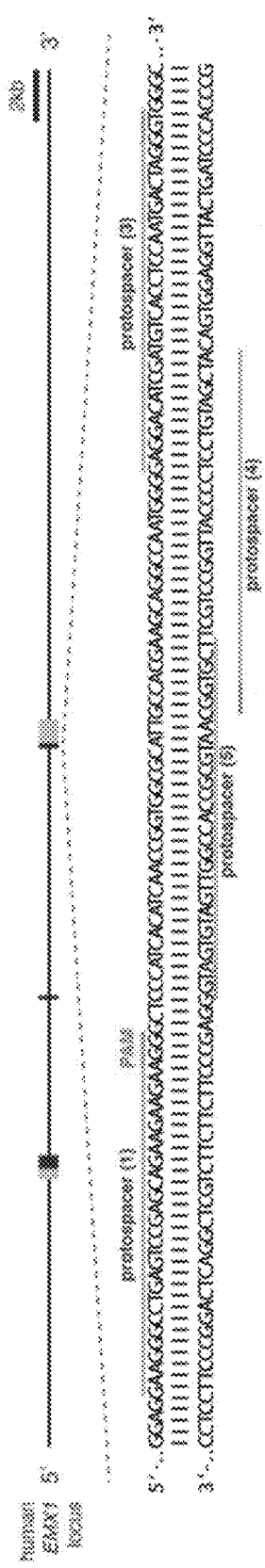
FIG. 11A
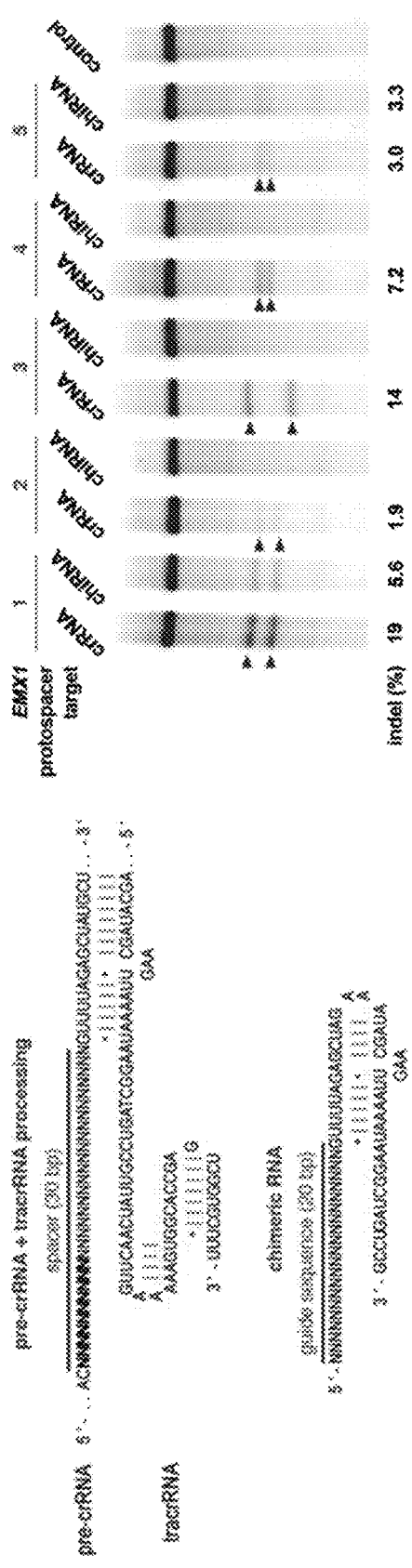
FIG. 11C
FIG. 11B

| Primer name | Assay | Genomic Target | Primer sequence |
|---|---|---|---|
| Sp-EMX1-F | SURVEYOR assay, sequencing | *EMX1* | AAAACCACCCTTCTCTCTGGC |
| Sp-EMX1-R | SURVEYOR assay, sequencing | *EMX1* | GGAGATTGGAGACACGGAGAG |
| Sp-PVALB-F | SURVEYOR assay, sequencing | *PVALB* | CTGGAAAGCCAATGCCTGAC |
| Sp-PVALB-R | SURVEYOR assay, sequencing | *PVALB* | GGCAGCAAACTCCTTGTCCT |
| Sp-Th-F | SURVEYOR assay, sequencing | *Th* | GTGCTTTGCAGAGGCCTACC |
| Sp-Th-R | SURVEYOR assay, sequencing | *Th* | CCTGGAGCGCATGCAGTAGT |
| St-EMX1-F | SURVEYOR assay, sequencing | *EMX1* | ACCTTCTGTGTTTCCACCATTC |
| St-EMX1-R | SURVEYOR assay, sequencing | *EMX1* | TTGGGGAGTGCACAGACTTC |
| Sp-EMX1-RFLP-F | RFLP, sequencing | *EMX1* | GGCTCCCTGGGTTCAAAGTA |
| Sp-EMX1-RFLP-R | RFLP, sequencing | *EMX1* | AGAGGGGTCTGGATGTCGTAA |
| Pb_EMX1_sp1 | Northern Blot Probe | Not applicable | TAGCTCTAAAACTTCTTCTTCTGCTCGGAC |
| Pb_tracrRNA | Northern Blot Probe | Not applicable | CTAGCCTTATTTTAACTTGCTATGCTGTTT |

SpCas9 mutation positions
hSpCas9

5' ATGGACAAGAAGTACAGCATCGGCCTGGACATCGGCACCAACTCTGTGGGCTGGGCCGTG 60 hSpCas9

D10

RuvCI

M D K K Y S I G L D I G T N S V G W A V
1 2 3 4 5 6 7 8 9 10 11 12 13 14 15 16 17 18 19 20

5' ATCACCGACGAGTACAAGGTGCCCAGCAAGAAATTCAAGGTGCTGGGCAACACCGACCGG 120 hSpCas9

R-3

I T D E Y K V P S K K F K V L G N T D R
21 22 23 24 25 26 27 28 29 30 31 32 33 34 35 36 37 38 39 40

5' CACAGCATCAAGAAGAACCTGATCGGAGCCCTGCTGTTCGACAGCGGCGAAACAGCCGAG 180 hSpCas9

H S I K K N L I G A L L F D S G E T A E
41 42 43 44 45 46 47 48 49 50 51 52 53 54 55 56 57 58 59 60

5' GCCACCCGGCTGAAGAGAACCGCCAGAAGAAGATACACCAGACGGAAGAACCGGATCTGC 240 hSpCas9

A T R L K R T A R R R Y T R R K N R I C
61 62 63 64 65 66 67 68 69 70 71 72 73 74 75 76 77 78 79 80

5' TATCTGCAAGAGATCTTCAGCAACGAGATGGCCAAGGTGGACGACAGCTTCTTCCACAGA 300 hSpCas9

Y L Q E I F S N E M A K V D D S F F H R
81 82 83 84 85 86 87 88 89 90 91 92 93 94 95 96 97 98 99 100

FIG. 24A hSpCas9

```
5'  CTGGAAGAGTCCTTCCTGGTGGAAGAGGATAAGAAGCACGAGCGGCACCCCATCTTCGGC  360
     L  E  E  S  F  L  V  E  E  D  K  K  H  E  R  H  P  I  F  G
    101 102 103 104 105 106 107 108 109 110 111 112 113 114 115 116 117 118 119 120

5'  AACATCGTGGACGAGGTGGCCTACCACGAGAAGTACCCCACCATCTACCACCTGAGAAAG  420
     N  I  V  D  E  V  A  Y  H  E  K  Y  P  T  I  Y  H  L  R  K
    121 122 123 124 125 126 127 128 129 130 131 132 133 134 135 136 137 138 139 140

5'  AAACTGGTGGACAGCACCGACAAGGCCGACCTGCGGCTGATCTATCTGGCCCTGGCCCAC  480
     K  L  V  D  S  T  D  K  A  D  L  R  L  I  Y  L  A  L  A  H
    141 142 143 144 145 146 147 148 149 150 151 152 153 154 155 156 157 158 159 160

5'  ATGATCAAGTTCCGGGGCCACTTCCTGATCGAGGGCGACCTGAACCCCGACAACAGCGAC  540
     M  I  K  F  R  G  H  F  L  I  E  G  D  L  N  P  D  N  S  D
    161 162 163 164 165 166 167 168 169 170 171 172 173 174 175 176 177 178 179 180

5'  GTGGACAAGCTGTTCATCCAGCTGGTGCAGACCTACAACCAGCTGTTCGAGGAAAACCCC  600
     V  D  K  L  F  I  Q  L  V  Q  T  Y  N  Q  L  F  E  E  N  P
    181 182 183 184 185 186 187 188 189 190 191 192 193 194 195 196 197 198 199 200

5'  ATCAACGCCAGCGGCGTGGACGCCAAGGCCATCCTGTCTGCCAGACTGAGCAAGAGCAGA  660
     I  N  A  S  G  V  D  A  K  A  I  L  S  A  R  L  S  K  S  R
    201 202 203 204 205 206 207 208 209 210 211 212 213 214 215 216 217 218 219 220
```

FIG. 24B hSpCas9

```
5' CGGCTGGAAAATCTGATCGCCCAGCTGCCCGGCGAGAAGAAGAATGGCCTGTTCGGCAAC 720
     R  L  E  N  L  I  A  Q  L  P  G  E  K  K  N  G  L  F  G  N
    221 222 223 224 225 226 227 228 229 230 231 232 233 234 235 236 237 238 239 240

5' CTGATTGCCCTGAGCCTGGGCCTGACCCCCAACTTCAAGAGCAACTTCGACCTGGCCGAG 780
     L  I  A  L  S  L  G  L  T  P  N  F  K  S  N  F  D  L  A  E
    241 242 243 244 245 246 247 248 249 250 251 252 253 254 255 256 257 258 259 260

5' GATGCCAAACTGCAGCTGAGCAAGGACACCTACGACGACGACCTGGACAACCTGCTGGCC 840
     D  A  K  L  Q  L  S  K  D  T  Y  D  D  D  L  D  N  L  L  A
    261 262 263 264 265 266 267 268 269 270 271 272 273 274 275 276 277 278 279 280

5' CAGATCGGCGACCAGTACGCCGACCTGTTTCTGGCCGCCAAGAACCTGTCCGACGCCATC 900
     Q  I  G  D  Q  Y  A  D  L  F  L  A  A  K  N  L  S  D  A  I
    281 282 283 284 285 286 287 288 289 290 291 292 293 294 295 296 297 298 299 300

5' CTGCTGAGCGACATCCTGAGAGTGAACACCGAGATCACCAAGGCCCCCCTGAGCGCCTCT 960
     L  L  S  D  I  L  R  V  N  T  E  I  T  K  A  P  L  S  A  S
    301 302 303 304 305 306 307 308 309 310 311 312 313 314 315 316 317 318 319 320

5' ATGATCAAGAGATACGACGAGCACCACCAGGACCTGACCCTGCTGAAAGCTCTCGTGCGG 1020
     M  I  K  R  Y  D  E  H  H  Q  D  L  T  L  L  K  A  L  V  R
    321 322 323 324 325 326 327 328 329 330 331 332 333 334 335 336 337 338 339 340
```

FIG. 24C hSpCas9

5' CAGCAGCTGCCTGAGAAGTACAAAGAGATTTTCTTCGACCAGAGCAAGAACGGCTACGCC 1080

Q Q L P E K Y K E I F F D Q S K N G Y A
341 342 343 344 345 346 347 348 349 350 351 352 353 354 355 356 357 358 359 360

5' GGCTACATTGACGGCGGAGCCAGCCAGGAAGAGTTCTACAAGTTCATCAAGCCCATCCTG 1140

G Y I D G G A S Q E E F Y K F I K P I L
361 362 363 364 365 366 367 368 369 370 371 372 373 374 375 376 377 378 379 380

5' GAAAAGATGGACGGCACCGAGGAACTGCTCGTGAAGCTGAACAGAGAGGACCTGCTGCGG 1200

E K M D G T E E L L V K L N R E D L L R
381 382 383 384 385 386 387 388 389 390 391 392 393 394 395 396 397 398 399 400

5' AAGCAGCGGACCTTCGACAACGGCAGCATCCCCCACCAGATCCACCTGGGAGAGCTGCAC 1260

K Q R T F D N G S I P H Q I H L G E L H
401 402 403 404 405 406 407 408 409 410 411 412 413 414 415 416 417 418 419 420

5' GCCATTCTGCGGCGGCAGGAAGATTTTTACCCATTCCTGAAGGACAACCGGGAAAAGATC 1320

A I L R R Q E D F Y P F L K D N R E K I
421 422 423 424 425 426 427 428 429 430 431 432 433 434 435 436 437 438 439 440

5' GAGAAGATCCTGACCTTCCGCATCCCCTACTACGTGGGCCCTCTGGCCAGGGGAAACAGC 1380

E K I L T F R I P Y Y V G P L A R G N S
441 442 443 444 445 446 447 448 449 450 451 452 453 454 455 456 457 458 459 460

FIG. 24D hSpCas9

```
5'  AGATTCGCCTGGATGACCAGAAAGAGCGAGGAAACCATCACCCCCTGGAACTTCGAGGAA  1440
     R  F  A  W  M  T  R  K  S  E  E  T  I  T  P  W  N  F  E  E
    461 462 463 464 465 466 467 468 469 470 471 472 473 474 475 476 477 478 479 480

5'  GTGGTGGACAAGGGCGCTTCCGCCCAGAGCTTCATCGAGCGGATGACCAACTTCGATAAG  1500
     V  V  D  K  G  A  S  A  Q  S  F  I  E  R  M  T  N  F  D  K
    481 482 483 484 485 486 487 488 489 490 491 492 493 494 495 496 497 498 499 500

5'  AACCTGCCCAACGAGAAGGTGCTGCCCAAGCACAGCCTGCTGTACGAGTACTTCACCGTG  1560
     N  L  P  N  E  K  V  L  P  K  H  S  L  L  Y  E  Y  F  T  V
    501 502 503 504 505 506 507 508 509 510 511 512 513 514 515 516 517 518 519 520

5'  TATAACGAGCTGACCAAAGTGAAATACGTGACCGAGGGAATGAGAAAGCCCGCCTTCCTG  1620
     Y  N  E  L  T  K  V  K  Y  V  T  E  G  M  R  K  P  A  F  L
    521 522 523 524 525 526 527 528 529 530 531 532 533 534 535 536 537 538 539 540

5'  AGCGGCGAGCAGAAAAAGGCCATCGTGGACCTGCTGTTCAAGACCAACCGGAAAGTGACC  1680
     S  G  E  Q  K  K  A  I  V  D  L  L  F  K  T  N  R  K  V  T
    541 542 543 544 545 546 547 548 549 550 551 552 553 554 555 556 557 558 559 560

5'  GTGAAGCAGCTGAAAGAGGACTACTTCAAGAAAATCGAGTGCTTCGACTCCGTGGAAATC  1740
     V  K  Q  L  K  E  D  Y  F  K  K  I  E  C  F  D  S  V  E  I
    561 562 563 564 565 566 567 568 569 570 571 572 573 574 575 576 577 578 579 580
```

FIG. 24E

```
hSpCas9
5'  TCCGGCGTGGAAGATCGGTTCAACGCCTCCCTGGGCACATACCACGATCTGCTGAAAATT
                                                                              1800
     S  G  V  E  D  R  F  N  A  S  L  G  T  Y  H  D  L  L  K  I
    581 582 583 584 585 586 587 588 589 590 591 592 593 594 595 596 597 598 599 600

5'  ATCAAGGACAAGGACTTCCTGGACAATGAGGAAAACGAGGACATTCTGGAAGATATCGTG
                                                                              1860
     I  K  D  K  D  F  L  D  N  E  E  N  E  D  I  L  E  D  I  V
    601 602 603 604 605 606 607 608 609 610 611 612 613 614 615 616 617 618 619 620

5'  CTGACCCTGACACTGTTTGAGGACAGAGAGATGATCGAGGAACGGCTGAAAACCTATGCC
                                                                              1920
     L  T  L  T  L  F  E  D  R  E  M  I  E  E  R  L  K  T  Y  A
    621 622 623 624 625 626 627 628 629 630 631 632 633 634 635 636 637 638 639 640

5'  CACCTGTTCGACGACAAAGTGATGAAGCAGCTGAAGCGGCGGAGATACACCGGCTGGGGC
                                                                              1980
     H  L  F  D  D  K  V  M  K  Q  L  K  R  R  R  Y  T  G  W  G
    641 642 643 644 645 646 647 648 649 650 651 652 653 654 655 656 657 658 659 660

5'  AGGCTGAGCCGGAAGCTGATCAACGGCATCCGGGACAAGCAGTCCGGCAAGACAATCCTG
                                                                              2040
     R  L  S  R  K  L  I  N  G  I  R  D  K  Q  S  G  K  T  I  L
    661 662 663 664 665 666 667 668 669 670 671 672 673 674 675 676 677 678 679 680

5'  GATTTCCTGAAGTCCGACGGCTTCGCCAACAGAAACTTCATGCAGCTGATCCACGACGAC
                                                                              2100
     D  F  L  K  S  D  G  F  A  N  R  N  F  M  Q  L  I  H  D  D
    681 682 683 684 685 686 687 688 689 690 691 692 693 694 695 696 697 698 699 700
```

FIG. 24F

```
hSpCas9
5'  AGCCTGACCTTTAAAGAGGACATCCAGAAAGCCCAGGTGTCCGGCCAGGGCGATAGCCTG
    ++++|++++|++++|++++|++++|++++|++++|++++|++++|++++|++++|++++|  2160
                              hSpCas9
     S   L   T   F   K   E   D   I   Q   K   A   Q   V   S   G   Q   G   D   S   L
    701 702 703 704 705 706 707 708 709 710 711 712 713 714 715 716 717 718 719 720

5'  CACGAGCACATTGCCAATCTGGCCGGCAGCCCCGCCATTAAGAAGGGCATCCTGCAGACA
    ++++|++++|++++|++++|++++|++++|++++|++++|++++|++++|++++|++++|  2220
                              hSpCas9
     H   E   H   I   A   N   L   A   G   S   P   A   I   K   K   G   I   L   Q   T
    721 722 723 724 725 726 727 728 729 730 731 732 733 734 735 736 737 738 739 740

5'  GTGAAGGTGGTGGACGAGCTCGTGAAAGTGATGGGCCGGCACAAGCCCGAGAACATCGTG
    ++++|++++|++++|++++|++++|++++|++++|++++|++++|++++|++++|++++|  2280
                              hSpCas9
                                                              RuvC II
     V   K   V   V   D   E   L   V   K   V   M   G   R   H   K   P   E   N   I   V
    741 742 743 744 745 746 747 748 749 750 751 752 753 754 755 756 757 758 759 760

5'  ATCGCCATGGCCAGAGAGAACCAGACCACCCAGAAGGGACAGAAGAACAGCCGCGAGAGA
    ++++|++++|++++|++++|++++|++++|++++|++++|++++|++++|++++|++++|  2340
                              hSpCas9
              RuvC II
              E
     I   A   M   A   R   E   N   Q   T   T   Q   K   G   Q   K   N   S   R   E   R
    761 762 763 764 765 766 767 768 769 770 771 772 773 774 775 776 777 778 779 780

5'  ATGAAGCGGATCGAAGAGGGCATCAAAGAGCTGGGCAGCCAGATCCTGAAAGAACACCCC
    ++++|++++|++++|++++|++++|++++|++++|++++|++++|++++|++++|++++|  2400
                              hSpCas9
     M   K   R   I   E   E   G   I   K   E   L   G   S   Q   I   L   K   E   H   P
    781 782 783 784 785 786 787 788 789 790 791 792 793 794 795 796 797 798 799 800
```

FIG. 24G hSpCas9

```
5'    GTGGAAAACACCCAGCTGCAGAACGAGAAGCTGTACCTGTACTACCTGCAGAATGGGCGG
      ++++|++++|++++|++++|++++|++++|++++|++++|++++|++++|++++|++++|  2460
      V  E  N  T  Q  L  Q  N  E  K  L  Y  L  Y  Y  L  Q  N  G  R
      801 802 803 804 805 806 807 808 809 810 811 812 813 814 815 816 817 818 819 820

5'    GATATGTACGTGGACCAGGAACTGGACATCAACCGGCTGTCCGACTACGATGTGGACGCC
      ++++|++++|++++|++++|++++|++++|++++|++++|++++|++++|++++|++++|  2520
      D  M  Y  V  D  Q  E  L  D  I  N  R  L  S  D  Y  D  V  D  A
      821 822 823 824 825 826 827 828 829 830 831 832 833 834 835 836 837 838 839 840

5'    ATCGTGCCTCAGAGCTTTCTGAAGGACGACTCCATCGACGCCAAGGTGCTGACCAGAAGC
      ++++|++++|++++|++++|++++|++++|++++|++++|++++|++++|++++|++++|  2580
      I  V  P  Q  S  F  L  K  D  D  S  I  D  A  K  V  L  T  R  S
      841 842 843 844 845 846 847 848 849 850 851 852 853 854 855 856 857 858 859 860

5'    GACAAGGCCCGGGGCAAGAGCGACAACGTGCCCTCCGAAGAGGTCGTGAAGAAGATGAAG
      ++++|++++|++++|++++|++++|++++|++++|++++|++++|++++|++++|++++|  2640
      D  K  A  R  G  K  S  D  N  V  P  S  E  E  V  V  K  K  M  K
      861 862 863 864 865 866 867 868 869 870 871 872 873 874 875 876 877 878 879 880

5'    AACTACTGGCGGCAGCTGCTGAACGCCAAGCTGATTACCCAGAGAAAGTTCGACAATCTG
      ++++|++++|++++|++++|++++|++++|++++|++++|++++|++++|++++|++++|  2700
      N  Y  W  R  Q  L  L  N  A  K  L  I  T  Q  R  K  F  D  N  L
      881 882 883 884 885 886 887 888 889 890 891 892 893 894 895 896 897 898 899 900
```

FIG. 24H

```
hSpCas9
5'  ACCAAGGCCGAGAGAGGCGGCCTGAGCGAACTGGATAAGGCCGGCTTCATCAAGAGACAG
                                                                          2760
              hSpCas9
     T  K  A  E  R  G  G  L  S  E  L  D  K  A  G  F  I  K  R  Q
    901 902 903 904 905 906 907 908 909 910 911 912 913 914 915 916 917 918 919 920

5'  CTGGTGGAAACCCGGCAGATCACAAAGCACGTGGCACAGATCCTGGACTCCCGGATGAAC
                                                                          2820
              hSpCas9
     L  V  E  T  R  Q  I  T  K  H  V  A  Q  I  L  D  S  R  M  N
    921 922 923 924 925 926 927 928 929 930 931 932 933 934 935 936 937 938 939 940

5'  ACTAAGTACGACGAGAATGACAAGCTGATCCGGGAAGTGAAAGTGATCACCCTGAAGTCC
                                                                          2880
              hSpCas9
     T  K  Y  D  E  N  D  K  L  I  R  E  V  K  V  I  T  L  K  S
    941 942 943 944 945 946 947 948 949 950 951 952 953 954 955 956 957 958 959 960

5'  AAGCTGGTGTCCGATTTCCGGAAGGATTTCCAGTTTTACAAAGTGCGCGAGATCAACAAC
                                                                          2940
              hSpCas9
     K  L  V  S  D  F  R  K  D  F  Q  F  Y  K  V  R  E  I  N  N
    961 962 963 964 965 966 967 968 969 970 971 972 973 974 975 976 977 978 979 980

5'  TACCACCACGCCCACGCCGCCTACCTGAACGCCGTCGTGGGAACCGCCCTGATCAAAAAG
                                                                          3000
              hSpCas9
            RuvC III
               D
     Y  H  H  A  H  A  A  Y  L  N  A  V  V  G  T  A  L  I  K  K
    981 982 983 984 985 986 987 988 989 990 991 992 993 994 995 996 997 998 999 1000
```

FIG. 24I

```
hSpCas9
5'  TACCCTAAGCTGGAAAGCGAGTTCGTGTACGGCGACTACAAGGTGTACGACGTGCGGAAG
                                                                      3060
          hSpCas9
     Y  P  K  L  E  S  E  F  V  Y  G  D  Y  K  V  Y  D  V  R  K
    1001 1002 1003 1004 1005 1006 1007 1008 1009 1010 1011 1012 1013 1014 1015 1016 1017 1018 1019 1020

5'  ATGATCGCCAAGAGCGAGCAGGAAATCGGCAAGGCTACCGCCAAGTACTTCTTCTACAGC
                                                                      3120
          hSpCas9
     M  I  A  K  S  E  Q  E  I  G  K  A  T  A  K  Y  F  F  Y  S
    1021 1022 1023 1024 1025 1026 1027 1028 1029 1030 1031 1032 1033 1034 1035 1036 1037 1038 1039 1040

5'  AACATCATGAACTTTTTCAAGACCGAGATTACCCTGGCCAACGGCGAGATCCGGAAGCGG
                                                                      3180
          hSpCas9
     N  I  M  N  F  F  K  T  E  I  T  L  A  N  G  E  I  R  K  R
    1041 1042 1043 1044 1045 1046 1047 1048 1049 1050 1051 1052 1053 1054 1055 1056 1057 1058 1059 1060

5'  CCTCTGATCGAGACAAACGGCGAAACCGGGGAGATCGTGTGGGATAAGGGCCGGGATTTT
                                                                      3240
          hSpCas9
     P  L  I  E  T  N  G  E  T  G  E  I  V  W  D  K  G  R  D  F
    1061 1062 1063 1064 1065 1066 1067 1068 1069 1070 1071 1072 1073 1074 1075 1076 1077 1078 1079 1080

5'  GCCACCGTGCGGAAAGTGCTGAGCATGCCCCAAGTGAATATCGTGAAAAAGACCGAGGTG
                                                                      3300
          hSpCas9
     A  T  V  R  K  V  L  S  M  P  Q  V  N  I  V  K  K  T  E  V
    1081 1082 1083 1084 1085 1086 1087 1088 1089 1090 1091 1092 1093 1094 1095 1096 1097 1098 1099 1100

5'  CAGACAGGCGGCTTCAGCAAAGAGTCTATCCTGCCCAAGAGGAACAGCGATAAGCTGATC
                                                                      3360
          hSpCas9
     Q  T  G  G  F  S  K  E  S  I  L  P  K  R  N  S  D  K  L  I
    1101 1102 1103 1104 1105 1106 1107 1108 1109 1110 1111 1112 1113 1114 1115 1116 1117 1118 1119 1120
```

FIG. 24J

FIG. 24K hSpCas9

```
5' CACTATGAGAAGCTGAAGGGCTCCCCCGAGGATAATGAGCAGAAACAGCTGTTTGTGGAA 3780
     H  Y  E  K  L  K  G  S  P  E  D  N  E  Q  K  Q  L  F  V  E
    1241 1242 1243 1244 1245 1246 1247 1248 1249 1250 1251 1252 1253 1254 1255 1256 1257 1258 1259 1260

5' CAGCACAAGCACTACCTGGACGAGATCATCGAGCAGATCAGCGAGTTCTCCAAGAGAGTG 3840
     Q  H  K  H  Y  L  D  E  I  I  E  Q  I  S  E  F  S  K  R  V
    1261 1262 1263 1264 1265 1266 1267 1268 1269 1270 1271 1272 1273 1274 1275 1276 1277 1278 1279 1280

5' ATCCTGGCCGACGCTAATCTGGACAAAGTGCTGTCCGCCTACAACAAGCACCGGGATAAG 3900
     I  L  A  D  A  N  L  D  K  V  L  S  A  Y  N  K  H  R  D  K
    1281 1282 1283 1284 1285 1286 1287 1288 1289 1290 1291 1292 1293 1294 1295 1296 1297 1298 1299 1300

5' CCCATCAGAGAGCAGGCCGAGAATATCATCCACCTGTTTACCCTGACCAATCTGGGAGCC 3960
     P  I  R  E  Q  A  E  N  I  I  H  L  F  T  L  T  N  L  G  A
    1301 1302 1303 1304 1305 1306 1307 1308 1309 1310 1311 1312 1313 1314 1315 1316 1317 1318 1319 1320

5' CCTGCCGCCTTCAAGTACTTTGACACCACCATCGACCGGAAGAGGTACACCAGCACCAAA 4020
     P  A  A  F  K  Y  F  D  T  T  I  D  R  K  R  Y  T  S  T  K
    1321 1322 1323 1324 1325 1326 1327 1328 1329 1330 1331 1332 1333 1334 1335 1336 1337 1338 1339 1340

5' GAGGTGCTGGACGCCACCCTGATCCACCAGAGCATCACCGGCCTGTACGAGACACGGATC 4080
     E  V  L  D  A  T  L  I  H  Q  S  I  T  G  L  Y  E  T  R  I
    1341 1342 1343 1344 1345 1346 1347 1348 1349 1350 1351 1352 1353 1354 1355 1356 1357 1358 1359 1360
```

FIG. 24L hSpCas9
5' GACCTGTCTCAGCTGGGAGGCGAC

```
    hSpCas9
 D   L   S   Q   L   G   G   D
1361 1362 1363 1364 1365 1366 1367 1368
```

Cas9 Expression in Mouse Hippocampus (AAV)
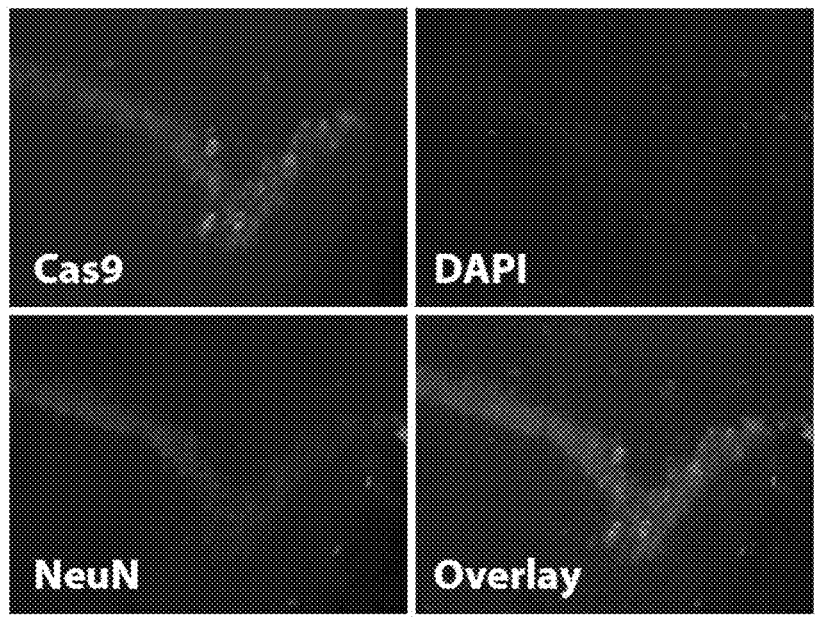
Cas9 Expression in Mouse Cortex (AAV)
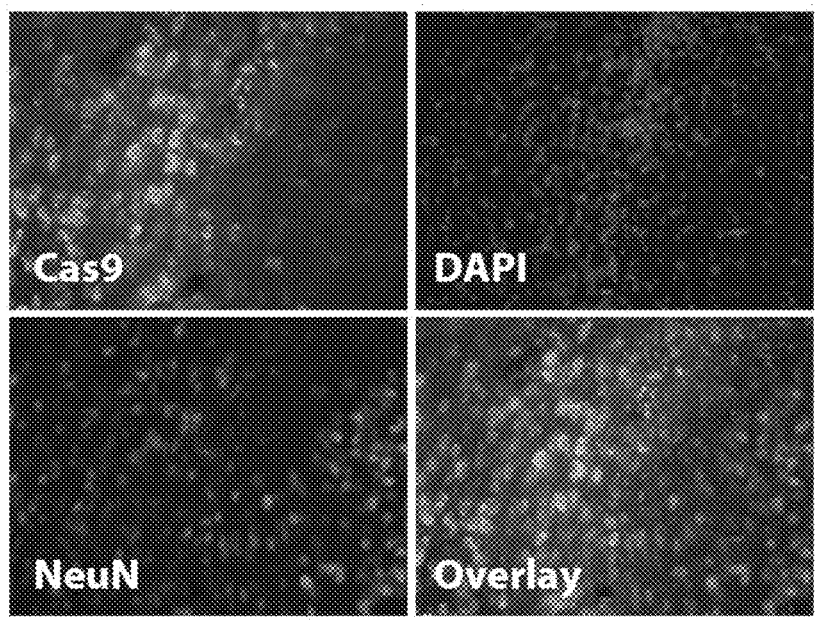
FIG. 27

FIG. 28A
GFP DNA
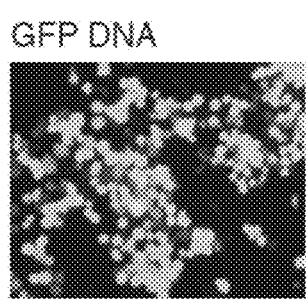
GFP RNA
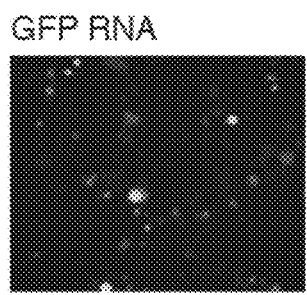
FIG. 28B
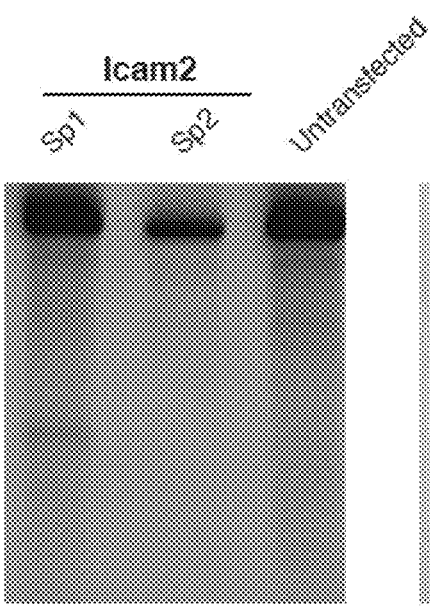
FIG. 28C
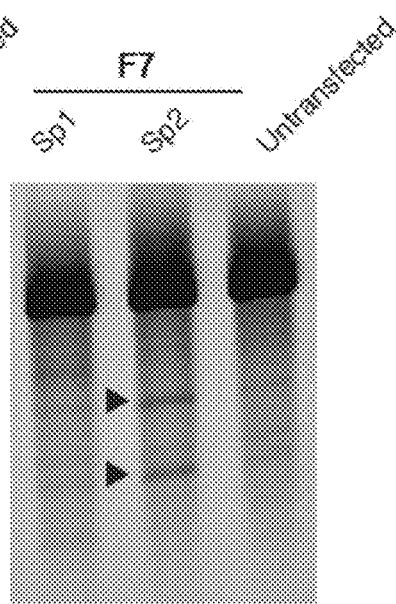

FIG. 30A
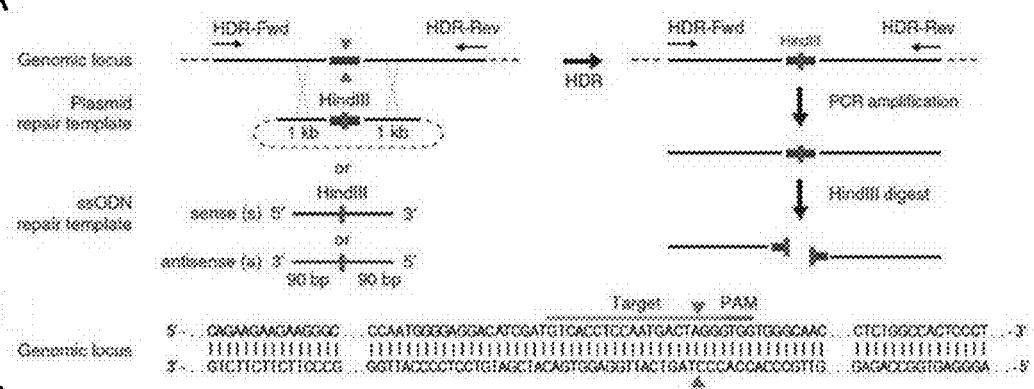
FIG. 30B
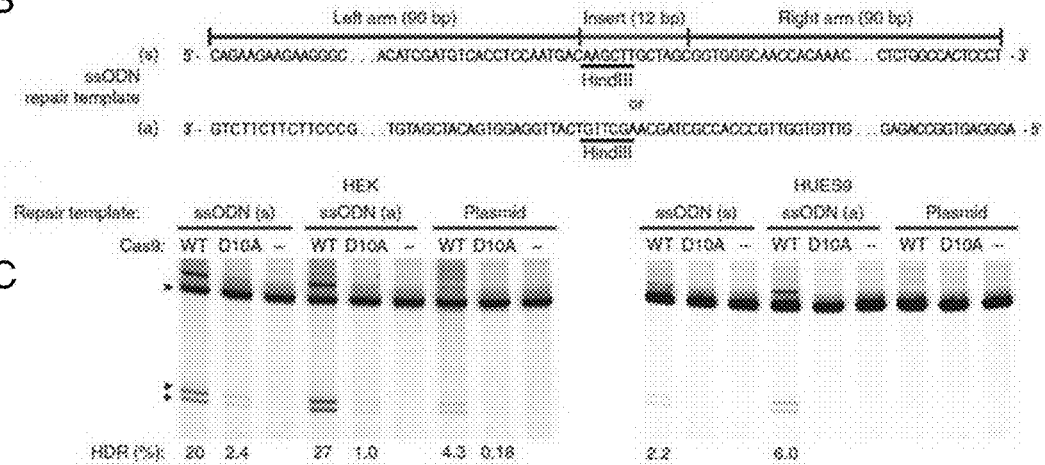
FIG. 30C

Repair Strategy for Cystic Fibrosis deltaF508 Mutation

GAA repeat expansion in *FXN* intron 1

Transcription repression likely due to aberrant
DNA structure or recruitment of heterchromatin
binding proteins to long GAA repeats

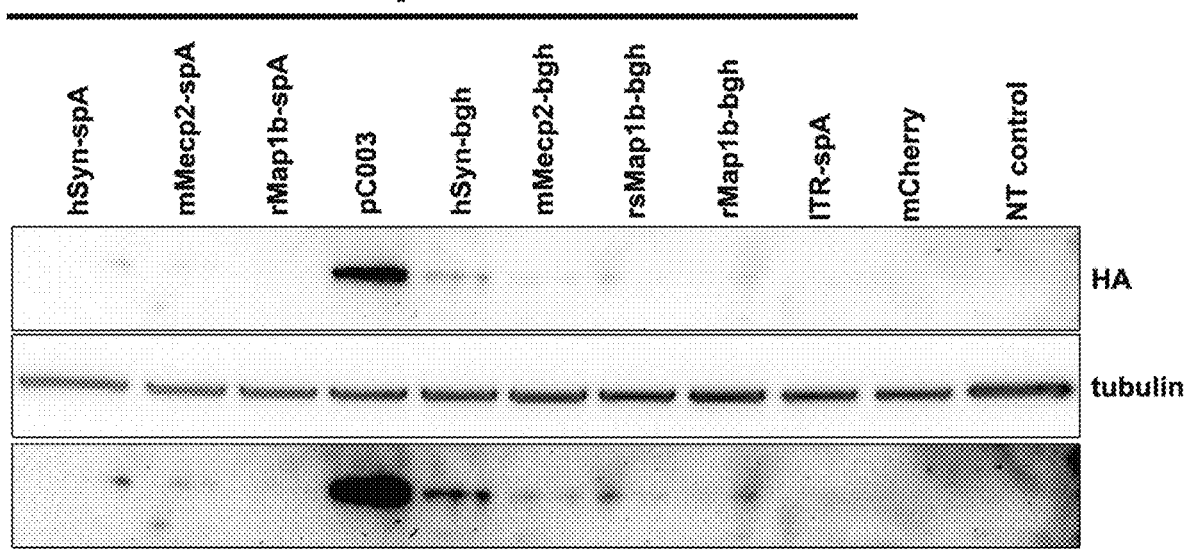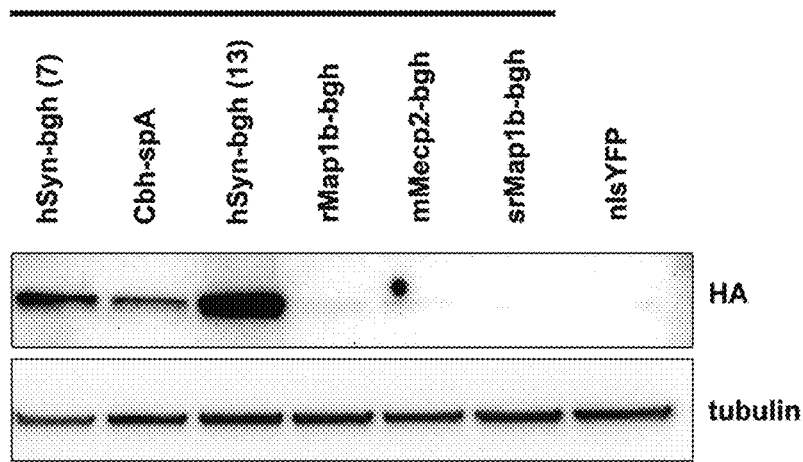
FIG. 42

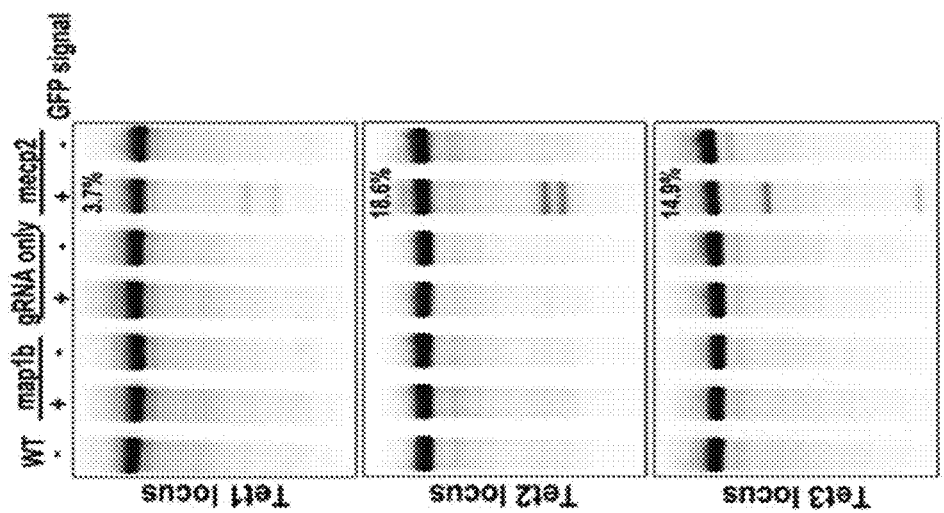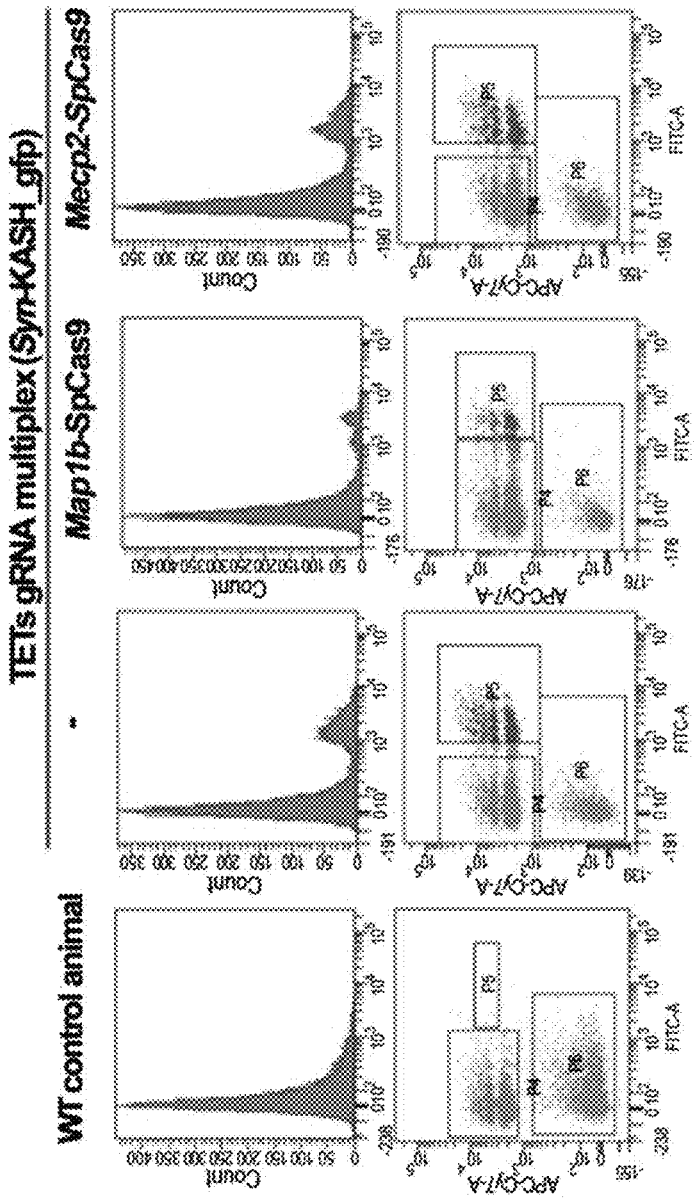
FIG. 49

| | pattern | overhang |
|---|---|---|
| 1 | CCnNNNNNNNNNNNNNNNNNnnnnnnnnnnNNNNNNNNNNNNNNNNNnGG | 38 |
| 2 | CCnNNNNNNNNNNNNNNNNNnnnnnnnNNNNNNNNNNNNNNNNNnGG | 34 |
| 3 | CCnNNNNNNNNNNNNNNNNNnnnnnNNNNNNNNNNNNNNNNNnGG | 30 |
| 4 | CCnNNNNNNNNNNNNNNNNNNNNNNNNNNNNNNNNNnGG | 26 |
| 5 | CCnNNNNNNNNNNNNNNNNNNNNNNNNNNNNNNNnGG | 22 |
| 6 | CCnNNNNNNNNNNNNNNNNNNNNNNNNNNNnGG | 18 |
| 7 | CCnNNNNNNNNNNNNNNNNNNNNNNNNnGG | 14 |
| 8 | CCnNNNNNNNNNNNNNNNNNNNNnGG | 10 |
| 9 | CCnNNNNNNNNNNNNNNnGG | 6 |
| 10 | CCnNNNNNNNNNNNnGG | 4 |
| 11 | CCnNNNNNNNNNnGG | 3 |
| 12 | CCnNNNNNNNNnGG | 2 |
| 13 | CCnNNNNNNNnGG | 1 |
| 14 | CCnNNNNNNnGG | 0 |
| 15 | CCnNNNNNnGG | 1 |
| 16 | CCnNNNNnGG | 2 |
| 17 | CCnNNNnGG | 3 |
| 18 | CCnnGG | 4 |
| 19 | CCGG | 8 |
| 20 | GGCC | 10 |
| 21 | GGNNCC | 12 |
| 22 | GGNNNCC | 14 |
| 23 | GGNNNNCC | 16 |
| 24 | GGNNNNNNNNCC | 20 |

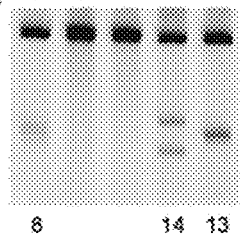

Pattern 1

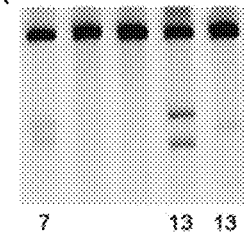

Pattern 2

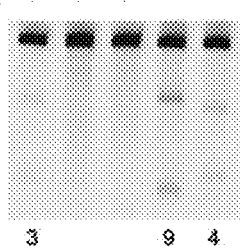

Pattern 3

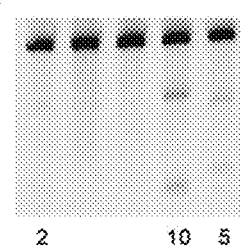

Pattern 4

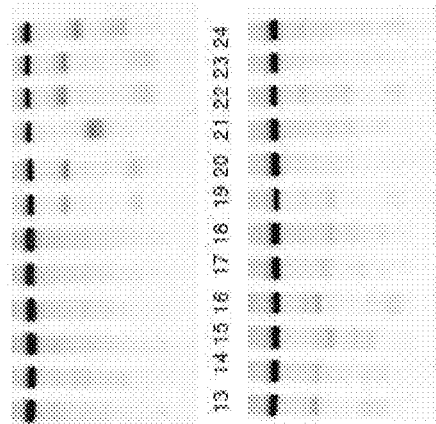

| lane # | Cas9 to use | Left gRNA | Right gRNA | Overhang (D10A) - number of bases protruding from 5' |
|---|---|---|---|---|
| 1 | D10A | left 23 | left 12 | -36 |
| 2 | D10A | right 4 | left 9 | -25 |
| 3 | D10A | left 23 | right 23 | -16 |
| 4 | D10A | right 7 | left 10 | -15 |
| 5 | D10A | right 16 | left 3 | -8 |
| 6 | D10A | right 22 | right 6 | 26 |
| 7 | D10A | left 12 | right 16 | 31 |
| 8 | D10A | left 12 | right 13 | 34 |
| 9 | D10A | left 10 | right 1 | 38 |
| 10 | D10A | right 23 | right 16 | 51 |
| 11 | D10A | right 23 | right 13 | 54 |
| 12 | D10A | left 3 | right 7 | 57 |
| 13 | D10A | left 12 | right 4 | 65 |
| 14 | D10A | left 3 | right 3 | 69 |
| 15 | D10A | left 3 | right 10 | 76 |
| 16 | D10A | right 23 | right 4 | 85 |
| 17 | D10A | left 12 | right 9 | 95 |
| 18 | D10A | left 12 | right 10 | 115 |
| 19 | D10A | right 23 | right 10 | 135 |
| 20 | D10A | left 12 | right 2 | 145 |
| 21 | D10A | left 12 | left 22 | 181 |
| 22 | D10A | right 23 | left 22 | 201 |
| 23 | D10A | left 12 | right 6 | 222 |
| 24 | D10A | right 23 | right 6 | 242 |

FIG. 54

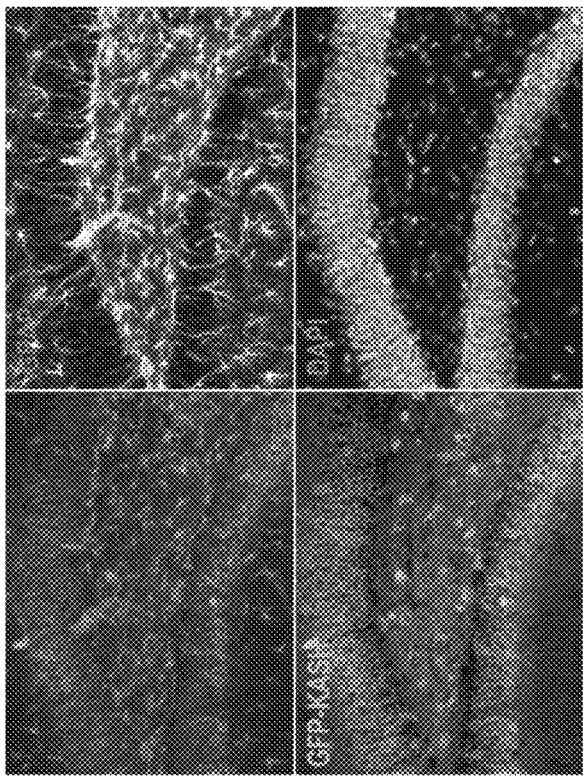
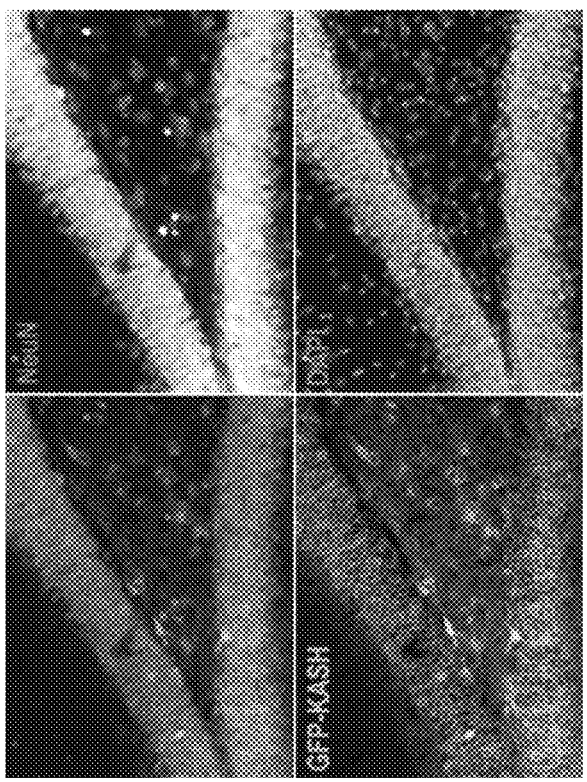
FIG. 57

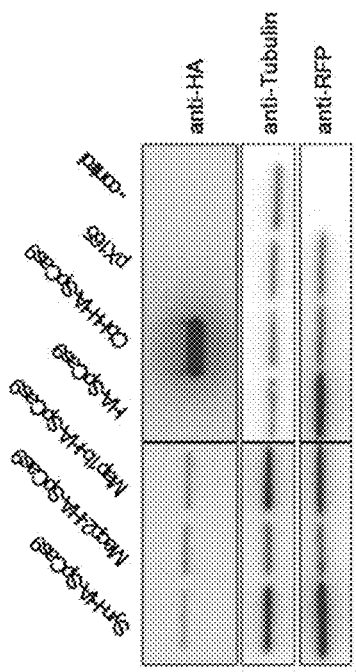
FIG. 63B
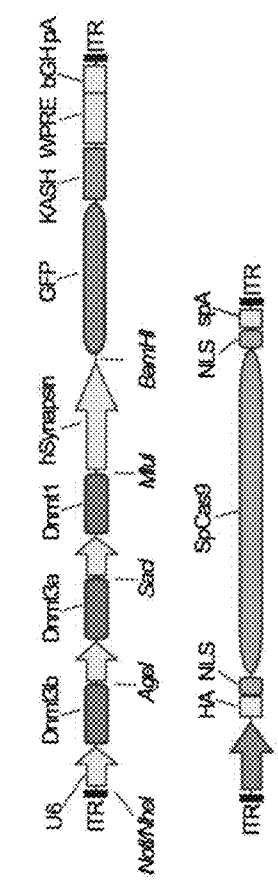
FIG. 63A
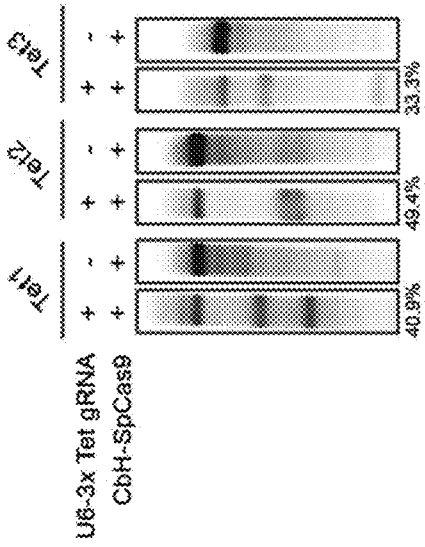
FIG. 63D
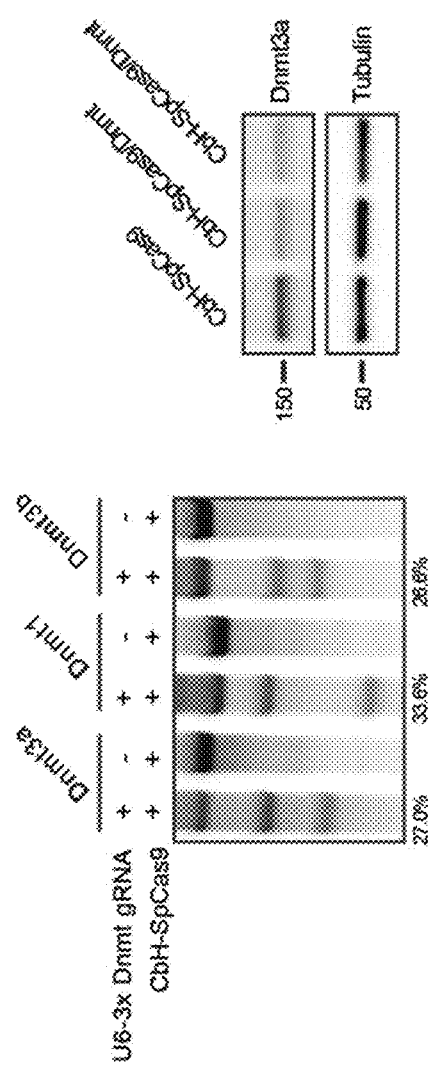
FIG. 63E
FIG. 63C FIG. 64A
FIG. 64B
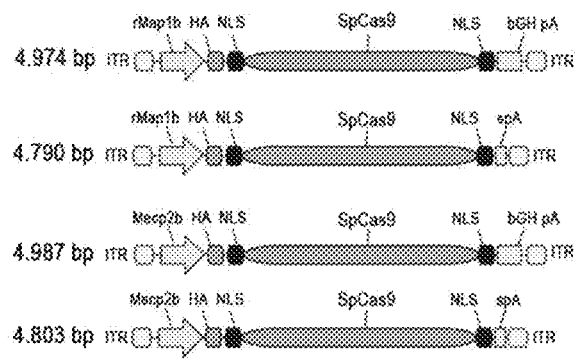
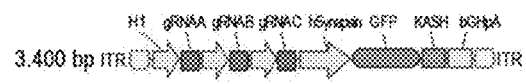
FIG. 64C
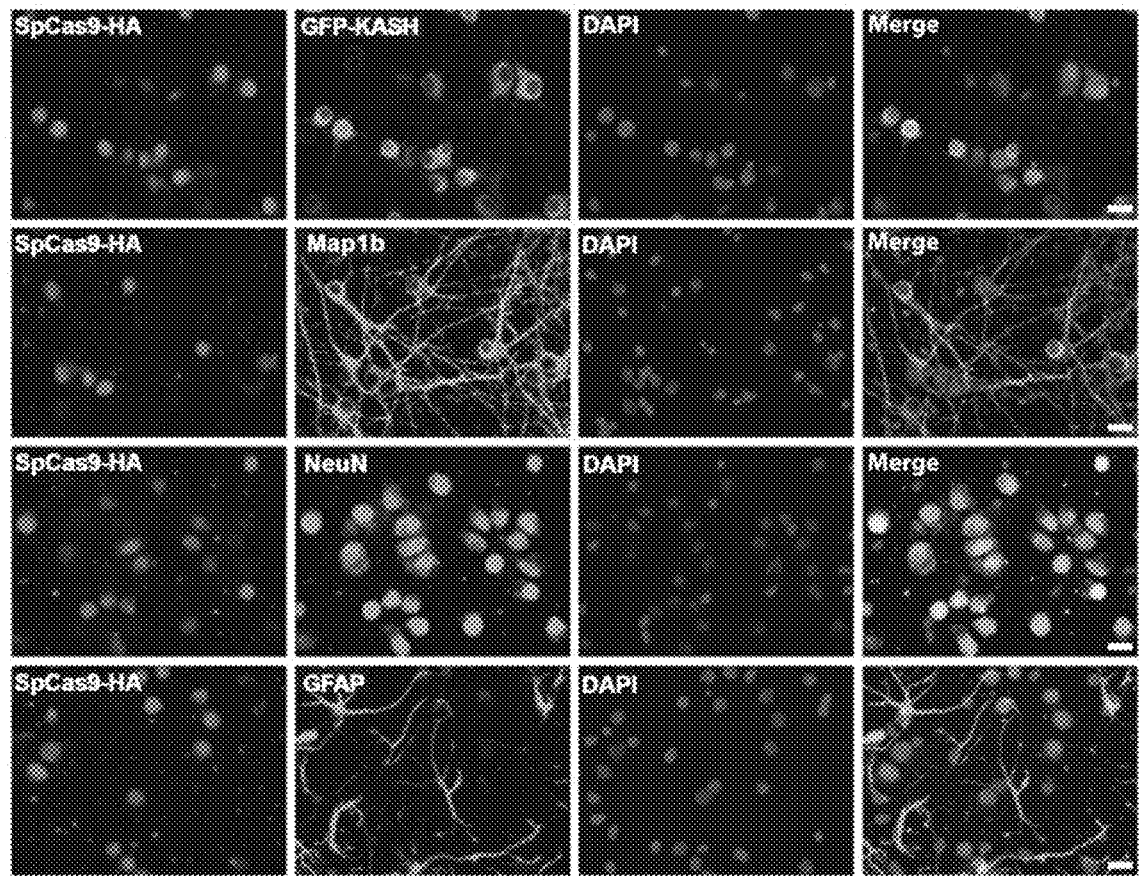
FIG. 64D

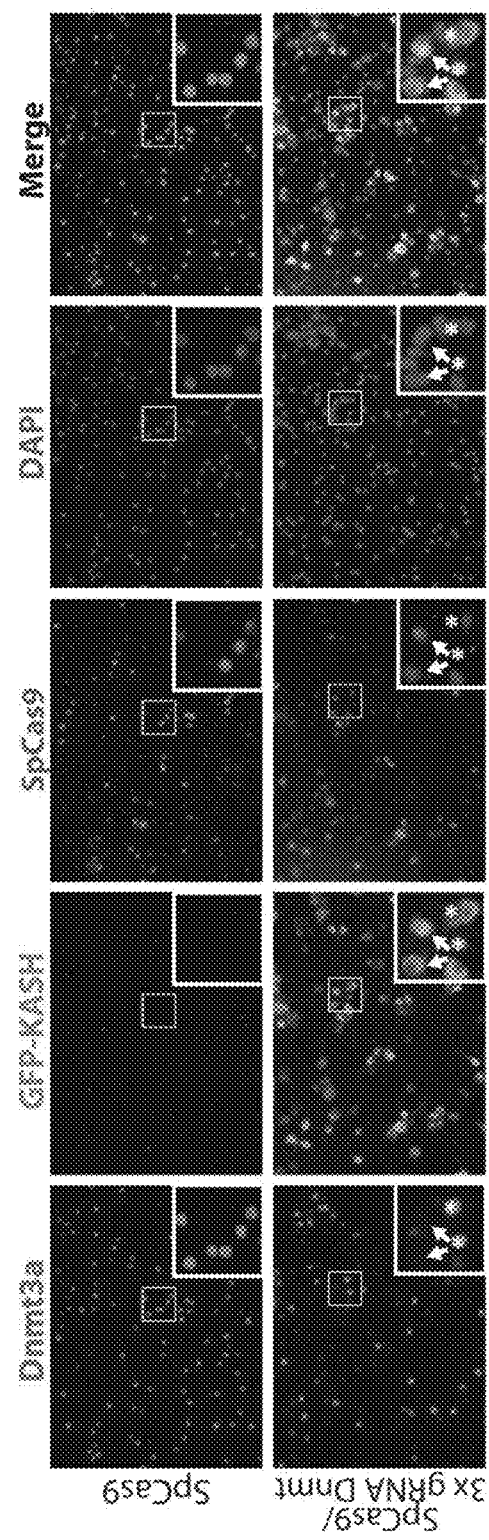
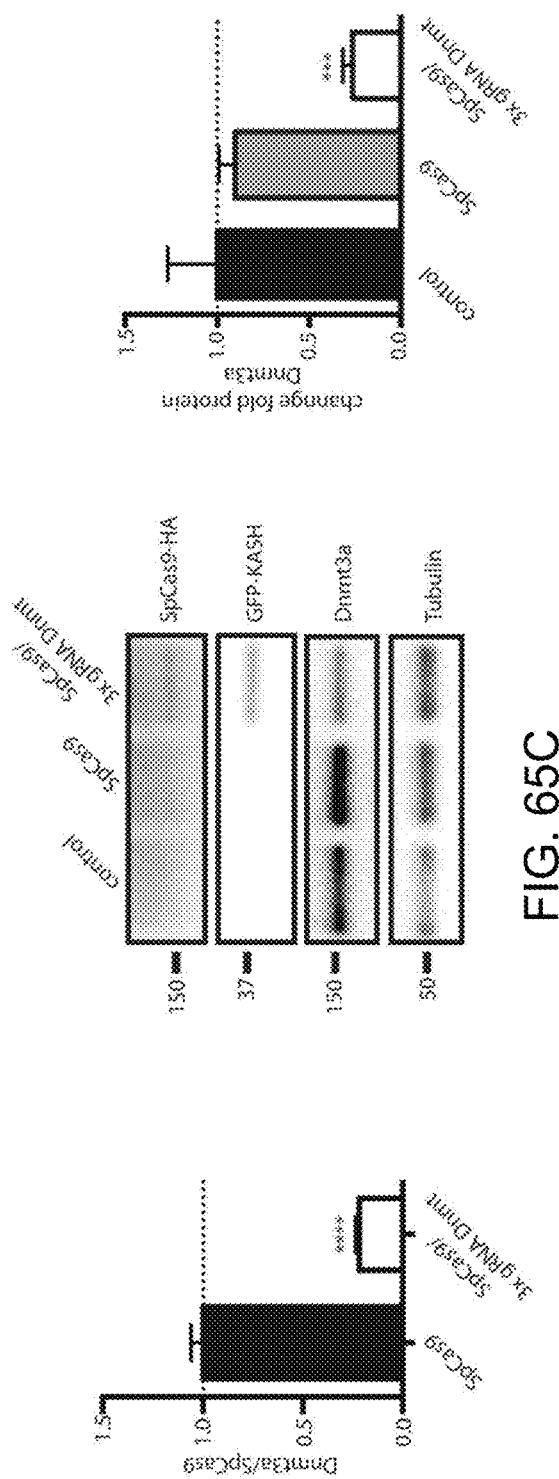
FIG. 65A
FIG. 65B
FIG. 65C
FIG. 65D

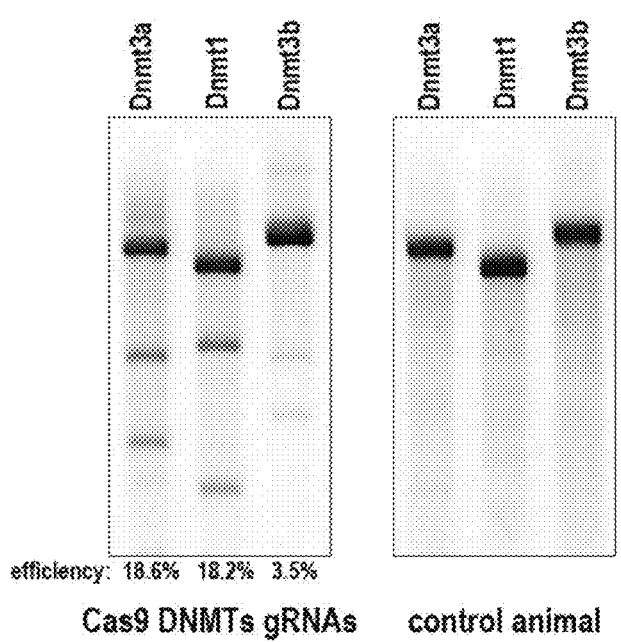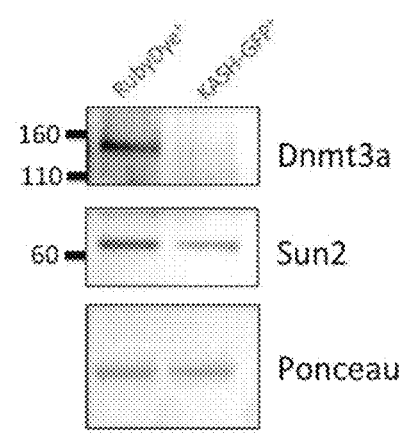

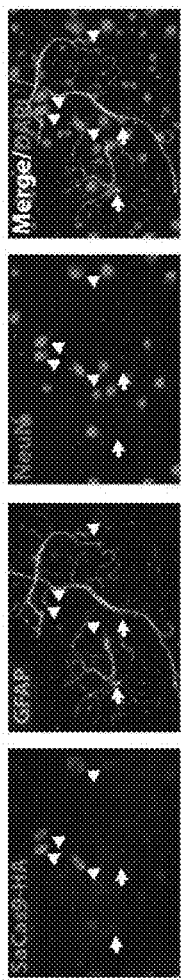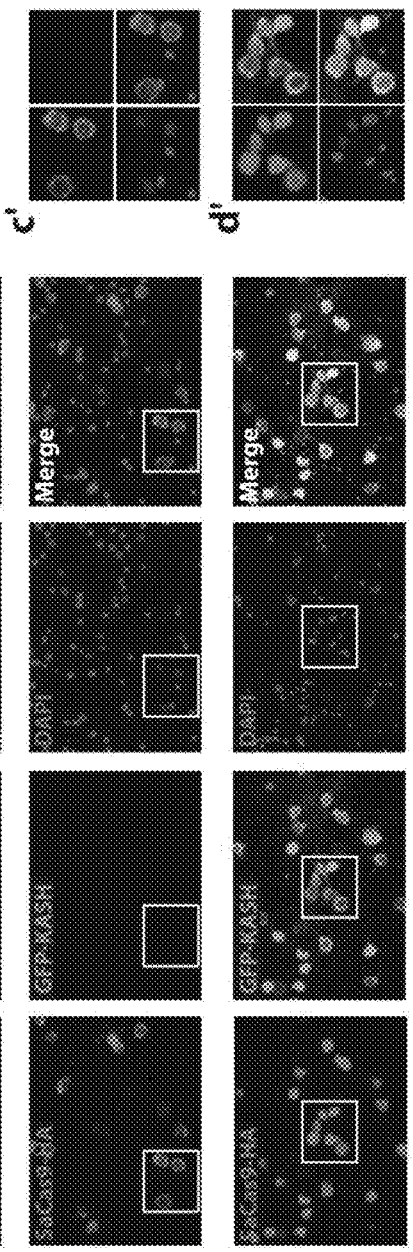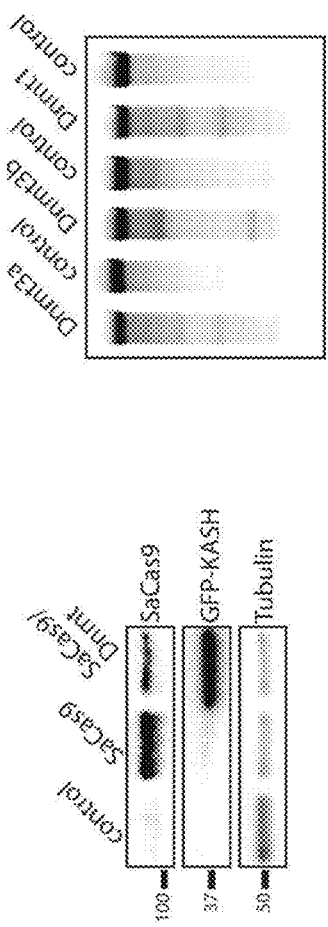
FIG. 67A  FIG. 67B  FIG. 67C  FIG. 67D  FIG. 67E  FIG. 67F FIG. 68A
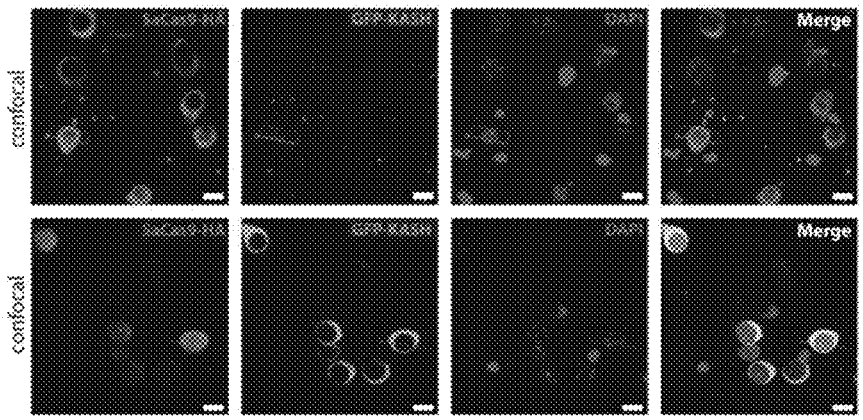
FIG. 68B
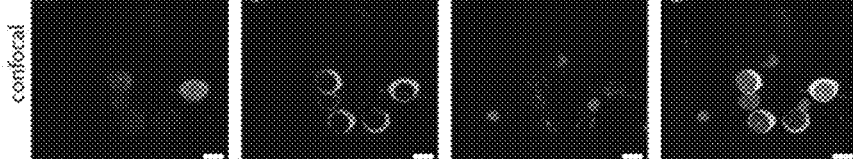
FIG. 68C
FIG. 68D
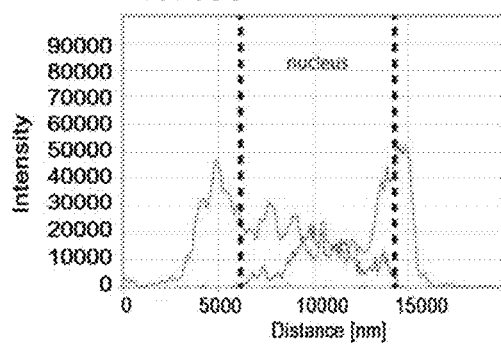
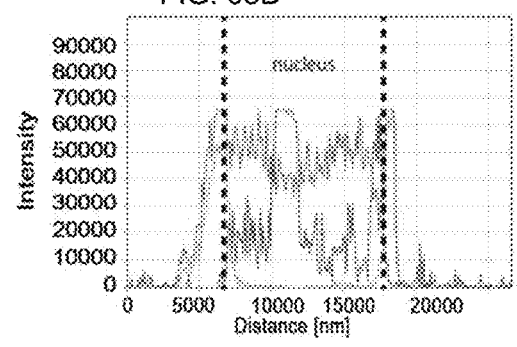
FIG. 68E
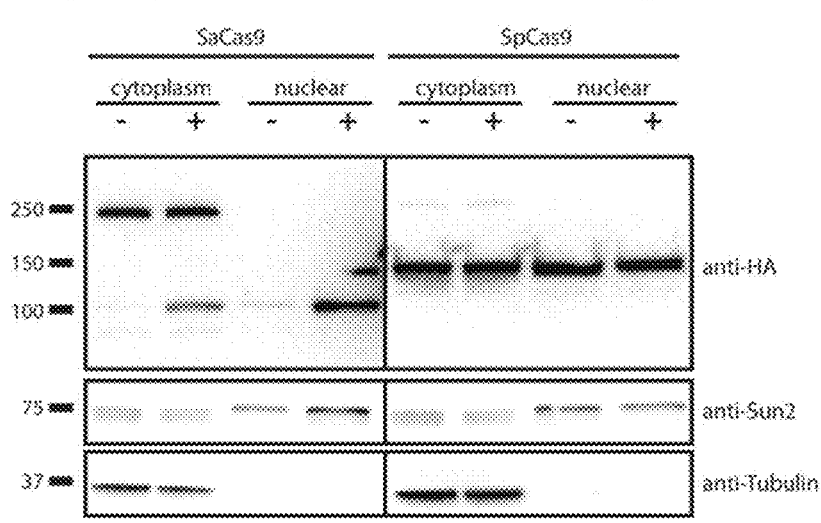

SEQUENCE LISTING

```
<160> NUMBER OF SEQ ID NOS: 451

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcactgaggg cctatttccc atgattc                                           27

<210> SEQ ID NO 2
<211> LENGTH: 20
<212> TYPE: DNA
<213> ORGANISM: Homo sapiens

<400> SEQUENCE: 2
tagggttagg ggccccaggc                                                   20

<210> SEQ ID NO 3
<211> LENGTH: 20
<212> TYPE: DNA
<213> ORGANISM: Homo sapiens

<400> SEQUENCE: 3
gagtccgagc agaagaagaa                                                   20

<210> SEQ ID NO 4
<211> LENGTH: 20
<212> TYPE: DNA
```

```
<213> ORGANISM: Homo sapiens

<400> SEQUENCE: 4
gagtcctagc aggagaagaa                                              20

<210> SEQ ID NO 5
<211> LENGTH: 20
<212> TYPE: DNA
<213> ORGANISM: Homo sapiens

<400> SEQUENCE: 5
gagtctaagc agaagaagaa                                              20

<210> SEQ ID NO 6
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(44)
<223> OTHER INFORMATION: a, c, u, g, unknown or other
<220> FEATURE:
<221> NAME/KEY: modified_base
<222> LOCATION: (47)..(60)
<223> OTHER INFORMATION: a, c, u, g, unknown or other

<400> SEQUENCE: 6
nnnnnnnnnn nnnnnnnnnn ccnnnnnnnn nnnnnnnnnn nnnnggnnnn nnnnnnnnnn   60

<210> SEQ ID NO 7
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(14)
<223> OTHER INFORMATION: a, c, u, g, unknown or other
<220> FEATURE:
<221> NAME/KEY: modified_base
<222> LOCATION: (17)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 7
nnnnnnnnnn nnnnccnnnn nnnnnnnnnn nnnnnnnngg nnnnnnnnnn nnnnnnnnnn   60

<210> SEQ ID NO 8
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
```

```
<221> NAME/KEY: modified_base
<222> LOCATION: (23)..(43)
<223> OTHER INFORMATION: a, c, u, g, unknown or other
<220> FEATURE:
<221> NAME/KEY: modified_base
<222> LOCATION: (46)..(60)
<223> OTHER INFORMATION: a, c, u, g, unknown or other

<400> SEQUENCE: 8 nnnnnnnnn nnnnnnnnn ccnnnnnnnn nnnnnnnnn nnggnnnnn nnnnnnnnn      60

<210> SEQ ID NO 9
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (18)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 9 nnnnnnnnn nnnnnccnnn nnnnnnnnnn nnnnnnnngg nnnnnnnnnn nnnnnnnnnn      60

<210> SEQ ID NO 10
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(42)
<223> OTHER INFORMATION: a, c, u, g, unknown or other
<220> FEATURE:
<221> NAME/KEY: modified_base
<222> LOCATION: (45)..(60)
<223> OTHER INFORMATION: a, c, u, g, unknown or other

<400> SEQUENCE: 10 nnnnnnnnn nnnnnnnnnn ccnnnnnnnn nnnnnnnnn nnggnnnnn nnnnnnnnn      60

<210> SEQ ID NO 11
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (18)..(38)
<223> OTHER INFORMATION: a, c, u, g, unknown or other
<220> FEATURE:
```

-continued

```
<221> NAME/KEY: modified_base
<222> LOCATION: (41)..(60)
<223> OTHER INFORMATION: a, c, u, g, unknown or other

<400> SEQUENCE: 11
nnnnnnnnnn nnnnccnnnn nnnnnnnnnn nnnnnnnngg nnnnnnnnnn nnnnnnnnnn      60

<210> SEQ ID NO 12
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(41)
<223> OTHER INFORMATION: a, c, u, g, unknown or other
<220> FEATURE:
<221> NAME/KEY: modified_base
<222> LOCATION: (44)..(60)
<223> OTHER INFORMATION: a, c, u, g, unknown or other

<400> SEQUENCE: 12
nnnnnnnnnn nnnnnnnnnn ccnnnnnnnn nnnnnnnnnn nggnnnnnnn nnnnnnnnnn      60

<210> SEQ ID NO 13
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(17)
<223> OTHER INFORMATION: a, c, u, g, unknown or other
<220> FEATURE:
<221> NAME/KEY: modified_base
<222> LOCATION: (20)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 13
nnnnnnnnnn nnnnnnnccn nnnnnnnnnn nnnnnnnngg nnnnnnnnnn nnnnnnnnnn      60

<210> SEQ ID NO 14
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(40)
<223> OTHER INFORMATION: a, c, u, g, unknown or other
<220> FEATURE:
<221> NAME/KEY: modified_base
<222> LOCATION: (43)..(60)
<223> OTHER INFORMATION: a, c, u, g, unknown or other
```

-continued

<400> SEQUENCE: 14
nnnnnnnnnn nnnnnnnnnn ccnnnnnnnn nnnnnnnnnn ggnnnnnnnn nnnnnnnnnn    60

<210> SEQ ID NO 15
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(18)
<223> OTHER INFORMATION: a, c, u, g, unknown or other
<220> FEATURE:
<221> NAME/KEY: modified_base
<222> LOCATION: (21)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 15
nnnnnnnnnn nnnnnnnncc nnnnnnnnnn nnnnnnnngg nnnnnnnnnn nnnnnnnnnn    60

<210> SEQ ID NO 16
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(39)
<223> OTHER INFORMATION: a, c, u, g, unknown or other
<220> FEATURE:
<221> NAME/KEY: modified_base
<222> LOCATION: (42)..(60)
<223> OTHER INFORMATION: a, c, u, g, unknown or other

<400> SEQUENCE: 16
nnnnnnnnnn nnnnnnnnnn ccnnnnnnnn nnnnnnnng gnnnnnnnnn nnnnnnnnnn    60

<210> SEQ ID NO 17
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: modified_base
<222> LOCATION: (22)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 17
nnnnnnnnnn nnnnnnnnnc cnnnnnnnnn nnnnnnnngg nnnnnnnnnn nnnnnnnnnn    60

```
<210> SEQ ID NO 18
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 18
nnnnnnnnnn nnnnnnnnnn ccnnnnnnnn nnnnnnnngg nnnnnnnnnn nnnnnnnnnn      60

<210> SEQ ID NO 19
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 19
nnnnnnnnnn nnnnnnnnnn ccnnnnnnnn nnnnnnnngg nnnnnnnnnn nnnnnnnnnn      60

<210> SEQ ID NO 20
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(37)
<223> OTHER INFORMATION: a, c, u, g, unknown or other
<220> FEATURE:
<221> NAME/KEY: modified_base
<222> LOCATION: (40)..(60)
<223> OTHER INFORMATION: a, c, u, g, unknown or other

<400> SEQUENCE: 20
nnnnnnnnnn nnnnnnnnnn ccnnnnnnnn nnnnnnnggn nnnnnnnnnn nnnnnnnnnn      60

<210> SEQ ID NO 21
<211> LENGTH: 60
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, u, g, unknown or other
<220> FEATURE:
<221> NAME/KEY: modified_base
<222> LOCATION: (24)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 21
nnnnnnnnnn nnnnnnnnnn nccnnnnnnn nnnnnnnngg nnnnnnnnnn nnnnnnnnnn       60

<210> SEQ ID NO 22
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(36)
<223> OTHER INFORMATION: a, c, u, g, unknown or other
<220> FEATURE:
<221> NAME/KEY: modified_base
<222> LOCATION: (39)..(60)
<223> OTHER INFORMATION: a, c, u, g, unknown or other

<400> SEQUENCE: 22
nnnnnnnnnn nnnnnnnnnn ccnnnnnnnn nnnnnnggnn nnnnnnnnnn nnnnnnnnnn       60

<210> SEQ ID NO 23
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: a, c, u, g, unknown or other
<220> FEATURE:
<221> NAME/KEY: modified_base
<222> LOCATION: (25)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 23
nnnnnnnnnn nnnnnnnnnn nnccnnnnnn nnnnnnnngg nnnnnnnnnn nnnnnnnnnn       60

<210> SEQ ID NO 24
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 24
nnnnnnnnnn nnnnnnnnnn ccnnnnnnnn nnnnggnnnn nnnnnnnnnn nnnnnnnnnn      60

<210> SEQ ID NO 25
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(23)
<223> OTHER INFORMATION: a, c, u, g, unknown or other
<220> FEATURE:
<221> NAME/KEY: modified_base
<222> LOCATION: (26)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 25
nnnnnnnnnn nnnnnnnnnn nnnccnnnnn nnnnnnnngg nnnnnnnnnn nnnnnnnnnn      60

<210> SEQ ID NO 26
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(34)
<223> OTHER INFORMATION: a, c, u, g, unknown or other
<220> FEATURE:
<221> NAME/KEY: modified_base
<222> LOCATION: (37)..(60)
<223> OTHER INFORMATION: a, c, u, g, unknown or other

<400> SEQUENCE: 26
nnnnnnnnnn nnnnnnnnnn ccnnnnnnnn nnnnggnnnn nnnnnnnnnn nnnnnnnnnn      60

<210> SEQ ID NO 27
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(24)
<223> OTHER INFORMATION: a, c, u, g, unknown or other
```

```
<220> FEATURE:
<221> NAME/KEY: modified_base
<222> LOCATION: (27)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 27
nnnnnnnnnn nnnnnnnnnn nnnnccnnnn nnnnnnnngg nnnnnnnnnn nnnnnnnnnn    60

<210> SEQ ID NO 28
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(33)
<223> OTHER INFORMATION: a, c, u, g, unknown or other
<220> FEATURE:
<221> NAME/KEY: modified_base
<222> LOCATION: (36)..(60)
<223> OTHER INFORMATION: a, c, u, g, unknown or other

<400> SEQUENCE: 28
nnnnnnnnnn nnnnnnnnnn ccnnnnnnnn nnnggnnnnn nnnnnnnnnn nnnnnnnnnn    60

<210> SEQ ID NO 29
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(25)
<223> OTHER INFORMATION: a, c, u, g, unknown or other
<220> FEATURE:
<221> NAME/KEY: modified_base
<222> LOCATION: (28)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 29
nnnnnnnnnn nnnnnnnnnn nnnnnccnnn nnnnnnnngg nnnnnnnnnn nnnnnnnnnn    60

<210> SEQ ID NO 30
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(32)
<223> OTHER INFORMATION: a, c, u, g, unknown or other
```

```
<220> FEATURE:
<221> NAME/KEY: modified_base
<222> LOCATION: (35)..(60)
<223> OTHER INFORMATION: a, c, u, g, unknown or other

<400> SEQUENCE: 30
nnnnnnnnnn nnnnnnnnnn ccnnnnnnnn nnggnnnnnn nnnnnnnnnn nnnnnnnnnn    60

<210> SEQ ID NO 31
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: a, c, u, g, unknown or other
<220> FEATURE:
<221> NAME/KEY: modified_base
<222> LOCATION: (29)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 31
nnnnnnnnnn nnnnnnnnnn nnnnnnccnn nnnnnnnngg nnnnnnnnnn nnnnnnnnnn    60

<210> SEQ ID NO 32
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(31)
<223> OTHER INFORMATION: a, c, u, g, unknown or other
<220> FEATURE:
<221> NAME/KEY: modified_base
<222> LOCATION: (34)..(60)
<223> OTHER INFORMATION: a, c, u, g, unknown or other

<400> SEQUENCE: 32
nnnnnnnnnn nnnnnnnnnn ccnnnnnnnn nggnnnnnnn nnnnnnnnnn nnnnnnnnnn    60

<210> SEQ ID NO 33
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(27)
<223> OTHER INFORMATION: a, c, u, g, unknown or other
<220> FEATURE:
<221> NAME/KEY: modified_base
<222> LOCATION: (30)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other
```

<400> SEQUENCE: 33
nnnnnnnnnn nnnnnnnnnn nnnnnnnccn nnnnnnnngg nnnnnnnnnn nnnnnnnnnn    60

<210> SEQ ID NO 34
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(30)
<223> OTHER INFORMATION: a, c, u, g, unknown or other
<220> FEATURE:
<221> NAME/KEY: modified_base
<222> LOCATION: (33)..(60)
<223> OTHER INFORMATION: a, c, u, g, unknown or other

<400> SEQUENCE: 34
nnnnnnnnnn nnnnnnnnnn ccnnnnnnnn ggnnnnnnnn nnnnnnnnnn nnnnnnnnnn    60

<210> SEQ ID NO 35
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(28)
<223> OTHER INFORMATION: a, c, u, g, unknown or other
<220> FEATURE:
<221> NAME/KEY: modified_base
<222> LOCATION: (31)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 35
nnnnnnnnnn nnnnnnnnnn nnnnnnnncc nnnnnnnngg nnnnnnnnnn nnnnnnnnnn    60

<210> SEQ ID NO 36
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(29)
<223> OTHER INFORMATION: a, c, u, g, unknown or other
<220> FEATURE:
<221> NAME/KEY: modified_base
<222> LOCATION: (32)..(60)
<223> OTHER INFORMATION: a, c, u, g, unknown or other

<400> SEQUENCE: 36
nnnnnnnnnn nnnnnnnnnn ccnnnnnnng gnnnnnnnnn nnnnnnnnnn nnnnnnnnnn    60

<210> SEQ ID NO 37
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(29)
<223> OTHER INFORMATION: a, c, u, g, unknown or other
<220> FEATURE:
<221> NAME/KEY: modified_base
<222> LOCATION: (32)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 37
nnnnnnnnnn nnnnnnnnnn nnnnnnnnnc cnnnnnnngg nnnnnnnnnn nnnnnnnnnn      60

<210> SEQ ID NO 38
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(28)
<223> OTHER INFORMATION: a, c, u, g, unknown or other
<220> FEATURE:
<221> NAME/KEY: modified_base
<222> LOCATION: (31)..(60)
<223> OTHER INFORMATION: a, c, u, g, unknown or other

<400> SEQUENCE: 38
nnnnnnnnnn nnnnnnnnnn ccnnnnnngg nnnnnnnnnn nnnnnnnnnn nnnnnnnnnn      60

<210> SEQ ID NO 39
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(30)
<223> OTHER INFORMATION: a, c, u, g, unknown or other
<220> FEATURE:
<221> NAME/KEY: modified_base
<222> LOCATION: (33)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 39
nnnnnnnnnn nnnnnnnnnn nnnnnnnnnn ccnnnnnngg nnnnnnnnnn nnnnnnnnnn      60

<210> SEQ ID NO 40
<211> LENGTH: 60

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(27)
<223> OTHER INFORMATION: a, c, u, g, unknown or other
<220> FEATURE:
<221> NAME/KEY: modified_base
<222> LOCATION: (30)..(60)
<223> OTHER INFORMATION: a, c, u, g, unknown or other

<400> SEQUENCE: 40
nnnnnnnnnn nnnnnnnnnn ccnnnnnggn nnnnnnnnnn nnnnnnnnnn nnnnnnnnnn       60

<210> SEQ ID NO 41
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(31)
<223> OTHER INFORMATION: a, c, u, g, unknown or other
<220> FEATURE:
<221> NAME/KEY: modified_base
<222> LOCATION: (34)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 41
nnnnnnnnnn nnnnnnnnnn nnnnnnnnnn nccnnnnngg nnnnnnnnnn nnnnnnnnnn       60

<210> SEQ ID NO 42
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(26)
<223> OTHER INFORMATION: a, c, u, g, unknown or other
<220> FEATURE:
<221> NAME/KEY: modified_base
<222> LOCATION: (29)..(60)
<223> OTHER INFORMATION: a, c, u, g, unknown or other

<400> SEQUENCE: 42
nnnnnnnnnn nnnnnnnnnn ccnnnnggnn nnnnnnnnnn nnnnnnnnnn nnnnnnnnnn       60

<210> SEQ ID NO 43
<211> LENGTH: 60
<212> TYPE: RNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (1)..(32)
<223> OTHER INFORMATION: a, c, u, g, unknown or other
<220> FEATURE:
<221> NAME/KEY: modified_base
<222> LOCATION: (35)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 43 nnnnnnnnn nnnnnnnnn nnnnnnnnn nnccnnnngg nnnnnnnnnn nnnnnnnnnn    60

<210> SEQ ID NO 44
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(25)
<223> OTHER INFORMATION: a, c, u, g, unknown or other
<220> FEATURE:
<221> NAME/KEY: modified_base
<222> LOCATION: (28)..(60)
<223> OTHER INFORMATION: a, c, u, g, unknown or other

<400> SEQUENCE: 44
nnnnnnnnnn nnnnnnnnnn ccnnnggnnn nnnnnnnnnn nnnnnnnnnn nnnnnnnnnn    60

<210> SEQ ID NO 45
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(33)
<223> OTHER INFORMATION: a, c, u, g, unknown or other
<220> FEATURE:
<221> NAME/KEY: modified_base
<222> LOCATION: (36)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 45
nnnnnnnnnn nnnnnnnnnn nnnnnnnnnn nnnccnnngg nnnnnnnnnn nnnnnnnnnn    60

<210> SEQ ID NO 46
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)

```
<223> OTHER INFORMATION: a, c, u, g, unknown or other
<220> FEATURE:
<221> NAME/KEY: modified_base
<222> LOCATION: (23)..(24)
<223> OTHER INFORMATION: a, c, u, g, unknown or other
<220> FEATURE:
<221> NAME/KEY: modified_base
<222> LOCATION: (27)..(60)
<223> OTHER INFORMATION: a, c, u, g, unknown or other

<400> SEQUENCE: 46
nnnnnnnnnn nnnnnnnnnn ccnnggnnnn nnnnnnnnnn nnnnnnnnnn nnnnnnnnnn      60

<210> SEQ ID NO 47
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(34)
<223> OTHER INFORMATION: a, c, u, g, unknown or other
<220> FEATURE:
<221> NAME/KEY: modified_base
<222> LOCATION: (37)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 47
nnnnnnnnnn nnnnnnnnnn nnnnnnnnnn nnnnccnngg nnnnnnnnnn nnnnnnnnnn      60

<210> SEQ ID NO 48
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(23)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 48
nnnnnnnnnn nnnnnnnnnn ccnggnnnnn nnnnnnnnnn nnnnnnnnnn nnnnnnnnnn      60

<210> SEQ ID NO 49
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(35)
<223> OTHER INFORMATION: a, c, u, g, unknown or other
<220> FEATURE:
<221> NAME/KEY: modified_base
<222> LOCATION: (38)..(38)
```

<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 49 nnnnnnnnn nnnnnnnnn nnnnnnnnn nnnnccngg nnnnnnnnn nnnnnnnnn        60

<210> SEQ ID NO 50
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 50 nnnnnnnnn nnnnnnnnn nccgnnnnn nnnnnnnnn nnnnnnnnn nnnnnnnnn        60

<210> SEQ ID NO 51
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(35)
<223> OTHER INFORMATION: a, c, u, g, unknown or other
<220> FEATURE:
<221> NAME/KEY: modified_base
<222> LOCATION: (40)..(60)
<223> OTHER INFORMATION: a, c, u, g, unknown or other

<400> SEQUENCE: 51 nnnnnnnnn nnnnnnnnn nnnnnnnnn nnnnccggn nnnnnnnnn nnnnnnnnn        60

<210> SEQ ID NO 52
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(23)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 52 nnnnnnnnn nnnnnnnnn nnnggnnnn nnnnnnnnn nnnnnnnnn nnnnnnnnn        60

<210> SEQ ID NO 53
<211> LENGTH: 60
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (1)..(33)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 53
nnnnnnnnnn nnnnnnnnnn nnnnnnnnnn nnnggccnnn nnnnnnnnnn nnnnnnnnnn      60

<210> SEQ ID NO 54
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 54
nnnnnnnnnn nnnnnnnnnn nncggnnnnn nnnnnnnnnn nnnnnnnnnn nnnnnnnnnn      60

<210> SEQ ID NO 55
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(32)
<223> OTHER INFORMATION: a, c, u, g, unknown or other
<220> FEATURE:
<221> NAME/KEY: modified_base
<222> LOCATION: (35)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 55
nnnnnnnnnn nnnnnnnnnn nnnnnnnnnn nnggnccnnn nnnnnnnnnn nnnnnnnnnn      60

<210> SEQ ID NO 56
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(31)
<223> OTHER INFORMATION: a, c, u, g, unknown or other
<220> FEATURE:
<221> NAME/KEY: modified_base
<222> LOCATION: (34)..(35)
<223> OTHER INFORMATION: a, c, u, g, unknown or other
<220> FEATURE:
<221> NAME/KEY: modified_base
```

<222> LOCATION: (38)..(60)
<223> OTHER INFORMATION: a, c, u, g, unknown or other

<400> SEQUENCE: 56
nnnnnnnnnn nnnnnnnnnn nnnnnnnnnn nggnnccnnn nnnnnnnnnn nnnnnnnnnn    60

<210> SEQ ID NO 57
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(30)
<223> OTHER INFORMATION: a, c, u, g, unknown or other
<220> FEATURE:
<221> NAME/KEY: modified_base
<222> LOCATION: (33)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 57
nnnnnnnnnn nnnnnnnnnn nnnnnnnnnn ggnnccnnn nnnnnnnnnn nnnnnnnnnn    60

<210> SEQ ID NO 58
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(29)
<223> OTHER INFORMATION: a, c, u, g, unknown or other
<220> FEATURE:
<221> NAME/KEY: modified_base
<222> LOCATION: (32)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 58
nnnnnnnnnn nnnnnnnnnn nnnnnnnnng gnnnccnnn nnnnnnnnnn nnnnnnnnnn    60

<210> SEQ ID NO 59
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(28)
<223> OTHER INFORMATION: a, c, u, g, unknown or other
<220> FEATURE:
<221> NAME/KEY: modified_base
<222> LOCATION: (31)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 59

```
nnnnnnnnnn nnnnnnnnnn nnnnnnnngg nnnnccnnn nnnnnnnnnn nnnnnnnnnn     60
```

<210> SEQ ID NO 60
<211> LENGTH: 9
<212> TYPE: PRT
<213> ORGANISM: Unknown
<220> FEATURE:
<223> OTHER INFORMATION: Description of Unknown:
      'LAGLIDADG' family motif peptide

<400> SEQUENCE: 60

Leu Ala Gly Leu Ile Asp Ala Asp Gly
1               5

<210> SEQ ID NO 61
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61

```
guuuuagagc ua                                                        12
```

<210> SEQ ID NO 62
<211> LENGTH: 7
<212> TYPE: PRT
<213> ORGANISM: Simian virus 40

<400> SEQUENCE: 62

Pro Lys Lys Lys Arg Lys Val
1               5

<210> SEQ ID NO 63
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 63

Lys Arg Pro Ala Ala Thr Lys Lys Ala Gly Gln Ala Lys Lys Lys Lys
1               5                   10                  15

<210> SEQ ID NO 64
<211> LENGTH: 9
<212> TYPE: PRT
<213> ORGANISM: Unknown
<220> FEATURE:
<223> OTHER INFORMATION: Description of Unknown:
      C-myc NLS sequence

<400> SEQUENCE: 64

Pro Ala Ala Lys Arg Val Lys Leu Asp
1               5

<210> SEQ ID NO 65
<211> LENGTH: 11
<212> TYPE: PRT
<213> ORGANISM: Unknown
<220> FEATURE:
<223> OTHER INFORMATION: Description of Unknown:
      C-myc NLS sequence

<400> SEQUENCE: 65

```
Arg Gln Arg Arg Asn Glu Leu Lys Arg Ser Pro
1               5                   10
```

<210> SEQ ID NO 66
<211> LENGTH: 38
<212> TYPE: PRT
<213> ORGANISM: Homo sapiens

<400> SEQUENCE: 66

```
Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
            35
```

<210> SEQ ID NO 67
<211> LENGTH: 42
<212> TYPE: PRT
<213> ORGANISM: Unknown
<220> FEATURE:
<223> OTHER INFORMATION: Description of Unknown:
      IBB domain from importin-alpha sequence

<400> SEQUENCE: 67

```
Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
            35                  40
```

<210> SEQ ID NO 68
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 68

```
Val Ser Arg Lys Arg Pro Arg Pro
1               5
```

<210> SEQ ID NO 69
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 69

```
Pro Pro Lys Lys Ala Arg Glu Asp
1               5
```

<210> SEQ ID NO 70
<211> LENGTH: 8
<212> TYPE: PRT
<213> ORGANISM: Homo sapiens

<400> SEQUENCE: 70

```
Pro Gln Pro Lys Lys Lys Pro Leu
1               5
```

<210> SEQ ID NO 71
<211> LENGTH: 12
<212> TYPE: PRT
<213> ORGANISM: Mus musculus

<400> SEQUENCE: 71

Ser Ala Leu Ile Lys Lys Lys Lys Lys Met Ala Pro
1               5                   10

<210> SEQ ID NO 72
<211> LENGTH: 5
<212> TYPE: PRT
<213> ORGANISM: Influenza virus

<400> SEQUENCE: 72

Asp Arg Leu Arg Arg
1               5

<210> SEQ ID NO 73
<211> LENGTH: 7
<212> TYPE: PRT
<213> ORGANISM: Influenza virus

<400> SEQUENCE: 73

Pro Lys Gln Lys Lys Arg Lys
1               5

<210> SEQ ID NO 74
<211> LENGTH: 10
<212> TYPE: PRT
<213> ORGANISM: Hepatitus delta virus

<400> SEQUENCE: 74

Arg Lys Leu Lys Lys Lys Ile Lys Lys Leu
1               5                   10

<210> SEQ ID NO 75
<211> LENGTH: 10
<212> TYPE: PRT
<213> ORGANISM: Mus musculus

<400> SEQUENCE: 75

Arg Glu Lys Lys Lys Phe Leu Lys Arg Arg
1               5                   10

<210> SEQ ID NO 76
<211> LENGTH: 20
<212> TYPE: PRT
<213> ORGANISM: Homo sapiens

<400> SEQUENCE: 76

Lys Arg Lys Gly Asp Glu Val Asp Gly Val Asp Glu Val Ala Lys Lys
1               5                   10                  15

Lys Ser Lys Lys
            20

<210> SEQ ID NO 77
<211> LENGTH: 17
<212> TYPE: PRT
<213> ORGANISM: Homo sapiens

<400> SEQUENCE: 77

Arg Lys Cys Leu Gln Ala Gly Met Asn Leu Glu Ala Arg Lys Thr Lys 1               5                   10                  15

Lys

<210> SEQ ID NO 78
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 78
nnnnnnnnnn nnnnnnnnnn nnagaaw                                              27

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 79
nnnnnnnnnn nnnnagaaw                                                       19

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 80
nnnnnnnnnn nnnnnnnnnn nnagaaw                                              27

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g

```
<220> FEATURE:
<221> NAME/KEY: modified_base
<222> LOCATION: (12)..(13)
<223> OTHER INFORMATION: a, c, t, g, unknown or other

<400> SEQUENCE: 81
nnnnnnnnnn nnnagaaw                                                       18

<210> SEQ ID NO 82
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 82
nnnnnnnnnn nnnnnnnnnn gtttttgtac tctcaagatt tagaaataaa tcttgcagaa          60
gctacaaaga taaggcttca tgccgaaatc aacaccctgt cattttatgg cagggtgttt         120
tcgttattta attttt                                                        137

<210> SEQ ID NO 83
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 83
nnnnnnnnnn nnnnnnnnnn gtttttgtac tctcagaaat gcagaagcta caaagataag          60
gcttcatgcc gaaatcaaca ccctgtcatt ttatggcagg gtgttttcgt tatttaattt         120
ttt                                                                      123

<210> SEQ ID NO 84
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 84
nnnnnnnnnn nnnnnnnnnn gtttttgtac tctcagaaat gcagaagcta caaagataag          60
gcttcatgcc gaaatcaaca ccctgtcatt ttatggcagg gtgttttttt                    110

<210> SEQ ID NO 85
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<221> NAME/KEY: modified_base
<222> LOCATION: (1)..(20)
<223> OTHER INFORMATION: a, c, t, g, unknown or other

<400> SEQUENCE: 85
nnnnnnnnnn nnnnnnnnnn gttttagagc tagaaatagc aagttaaaat aaggctagtc    60
cgttatcaac ttgaaaaagt ggcaccgagt cggtgctttt tt                      102

<210> SEQ ID NO 86
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 86
nnnnnnnnnn nnnnnnnnnn gttttagagc tagaaatagc aagttaaaat aaggctagtc    60
cgttatcaac ttgaaaaagt gttttttt                                       88

<210> SEQ ID NO 87
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 87
nnnnnnnnnn nnnnnnnnnn gttttagagc tagaaatagc aagttaaaat aaggctagtc    60
cgttatcatt tttttt                                                    76

<210> SEQ ID NO 88
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gttttagagc ta                                                        12

<210> SEQ ID NO 89
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tagcaagtta aaataaggct agtccgtttt t                                   31

<210> SEQ ID NO 90
<211> LENGTH: 27
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: a, c, t, g, unknown or other

<400> SEQUENCE: 90
nnnnnnnnnn nnnnnnnnnn nnagaaw                                           27

<210> SEQ ID NO 91
<211> LENGTH: 33
<212> TYPE: DNA
<213> ORGANISM: Homo sapiens

<400> SEQUENCE: 91
ggacatcgat gtcacctcca atgactaggg tgg                                    33

<210> SEQ ID NO 92
<211> LENGTH: 33
<212> TYPE: DNA
<213> ORGANISM: Homo sapiens

<400> SEQUENCE: 92
cattggaggt gacatcgatg tcctccccat tgg                                    33

<210> SEQ ID NO 93
<211> LENGTH: 33
<212> TYPE: DNA
<213> ORGANISM: Homo sapiens

<400> SEQUENCE: 93
ggaagggcct gagtccgagc agaagaagaa ggg                                    33

<210> SEQ ID NO 94
<211> LENGTH: 33
<212> TYPE: DNA
<213> ORGANISM: Homo sapiens

<400> SEQUENCE: 94
ggtggcgaga ggggccgaga ttgggtgttc agg                                    33

<210> SEQ ID NO 95
<211> LENGTH: 33
<212> TYPE: DNA
<213> ORGANISM: Homo sapiens

<400> SEQUENCE: 95
atgcaggagg gtggcgagag gggccgagat tgg                                    33

<210> SEQ ID NO 96
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aaactctaga gagggcctat ttcccatgat tc                                     32

<210> SEQ ID NO 97
<211> LENGTH: 153
<212> TYPE: DNA
```

-continued

<213> ORGANISM: Artificial Sequence
<220> FEATURE:
<223> OTHER INFORMATION: Description of Artificial Sequence: Synthetic primer

<400> SEQUENCE: 97
acctctagaa aaaaagcacc gactcggtgc cacttttca agttgataac ggactagcct    60
tattttaact tgctatgctg ttttgtttcc aaaacagcat agctctaaaa ccctagtca    120 ttggaggtga cggtgtttcg tcctttccac aag                                153

<210> SEQ ID NO 98
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
taatacgact cactatagga agtgcgccac catggcccca agaagaagc gg            52

<210> SEQ ID NO 99
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 99 ggttttttt tttttttttt tttttttttt ttttcttact ttttcttttt tgcctggccg    60

<210> SEQ ID NO 100
<211> LENGTH: 984
<212> TYPE: PRT
<213> ORGANISM: Campylobacter jejuni

<400> SEQUENCE: 100

Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
                20                  25                  30

Thr Lys Val Glu Asn Pro Lys Thr Gly Glu Ser Leu Ala Leu Pro Arg
            35                  40                  45

Arg Leu Ala Arg Ser Ala Arg Lys Arg Leu Ala Arg Arg Lys Ala Arg
        50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Asp Lys Glu Lys Gly Ala
    130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

```
Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
            195                 200                 205

Lys Lys Gln Arg Glu Phe Gly Phe Ser Phe Ser Lys Lys Phe Glu Glu
            210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
            245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
            275                 280                 285

Asp Asp Leu Asn Ala Leu Leu Asn Glu Val Leu Lys Asn Gly Thr Leu
            290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Tyr Lys
            325                 330                 335

Glu Phe Ile Lys Ala Leu Gly Glu His Asn Leu Ser Gln Asp Leu
            340                 345                 350

Asn Glu Ile Ala Lys Asp Ile Thr Leu Ile Lys Asp Glu Ile Lys Leu
            355                 360                 365

Lys Lys Ala Leu Ala Lys Tyr Asp Leu Asn Gln Asn Gln Ile Asp Ser
            370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
            405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
            435                 440                 445

Asn Pro Val Val Leu Arg Ala Ile Lys Glu Tyr Arg Lys Val Leu Asn
            450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
            485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
            515                 520                 525

Leu Phe Lys Glu Gln Lys Glu Phe Cys Ala Tyr Ser Gly Glu Lys Ile
            530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
            565                 570                 575

Val Phe Thr Lys Gln Asn Gln Glu Lys Leu Asn Gln Thr Pro Phe Glu
            580                 585                 590
```

Ala Phe Gly Asn Asp Ser Ala Lys Trp Gln Lys Ile Glu Val Leu Ala
            595                 600                 605

Lys Asn Leu Pro Thr Lys Lys Gln Lys Arg Ile Leu Asp Lys Asn Tyr
610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
            645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
            675                 680                 685

Ala Leu Arg His Thr Trp Gly Phe Ser Ala Lys Asp Arg Asn Asn His
            690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
            725                 730                 735

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
            755                 760                 765

Lys Ile Asp Glu Ile Phe Val Ser Lys Pro Glu Arg Lys Lys Pro Ser
            770                 775                 780

Gly Ala Leu His Glu Glu Thr Phe Arg Lys Glu Glu Phe Tyr Gln
785                 790                 795                 800

Ser Tyr Gly Gly Lys Glu Gly Val Leu Lys Ala Leu Glu Leu Gly Lys
            805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
            835                 840                 845

Ile Tyr Thr Met Asp Phe Ala Leu Lys Val Leu Pro Asn Lys Ala Val
850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
            885                 890                 895

Gln Thr Lys Asp Met Gln Glu Pro Glu Phe Val Tyr Tyr Asn Ala Phe
            900                 905                 910

Thr Ser Ser Thr Val Ser Leu Ile Val Ser Lys His Asp Asn Lys Phe
            915                 920                 925

Glu Thr Leu Ser Lys Asn Gln Lys Ile Leu Phe Lys Asn Ala Asn Glu
            930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
            965                 970                 975

Arg Gln Arg Glu Asp Phe Lys Lys
            980

<210> SEQ ID NO 101
<211> LENGTH: 91
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 101
tataatctca aagaaattt aaaaagggac taaaataaag agtttgcggg actctgcggg    60
gttacaatcc cctaaaaccg cttttaaaat t                                  91

<210> SEQ ID NO 102
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
attttaccat aaagaaattt aaaaagggac taaaac                             36

<210> SEQ ID NO 103
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 103
nnnnnnnnnn nnnnnnnnnn guuuuagucc cgaaagggac uaaauaaag aguuugcggg    60 acucugcggg guuacaaucc ccuaaaaccg cuuuu                              95

<210> SEQ ID NO 104
<211> LENGTH: 1115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Leu Phe Ile Ala Leu Lys Asn Met
                100                 105                 110

Val Lys His Arg Gly Ile Ser Tyr Leu Asp Asp Ala Ser Asp Gly
            115                 120                 125

Asn Ser Ser Val Gly Asp Tyr Ala Gln Ile Val Lys Glu Asn Ser Lys

```
              130                 135                 140
Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
    450                 455                 460

Thr Lys Tyr Ile Asp Glu Lys Leu Leu Thr Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
            500                 505                 510

Glu Asn Gln Thr Thr Gln Lys Gly Gln Lys Asn Ser Arg Glu Arg Met
        515                 520                 525

Lys Arg Ile Glu Glu Gly Ile Lys Glu Leu Gly Ser Gln Ile Leu Lys
    530                 535                 540

Glu His Pro Val Glu Asn Thr Gln Leu Gln Asn Glu Lys Leu Tyr Leu
545                 550                 555                 560
```

```
Tyr Tyr Leu Gln Asn Gly Arg Asp Met Tyr Val Asp Gln Glu Leu Asp
                565                 570                 575

Ile Asn Arg Leu Ser Asp Tyr Asp Val Asp His Ile Val Pro Gln Ser
                580                 585                 590

Phe Leu Lys Asp Asp Ser Ile Asp Asn Lys Val Leu Thr Arg Ser Asp
                595                 600                 605

Lys Asn Arg Gly Lys Ser Asp Asn Val Pro Ser Glu Glu Val Val Lys
                610                 615                 620

Lys Met Lys Asn Tyr Trp Arg Gln Leu Leu Asn Ala Lys Leu Ile Thr
625                 630                 635                 640

Gln Arg Lys Phe Asp Asn Leu Thr Lys Ala Glu Arg Gly Gly Leu Ser
                645                 650                 655

Glu Leu Asp Lys Ala Gly Phe Ile Lys Arg Gln Leu Val Glu Thr Arg
                660                 665                 670

Gln Ile Thr Lys His Val Ala Gln Ile Leu Asp Ser Arg Met Asn Thr
                675                 680                 685

Lys Tyr Asp Glu Asn Asp Lys Leu Ile Arg Glu Val Lys Val Ile Thr
                690                 695                 700

Leu Lys Ser Lys Leu Val Ser Asp Phe Arg Lys Asp Phe Gln Phe Tyr
705                 710                 715                 720

Lys Val Arg Glu Ile Asn Asn Tyr His His Ala His Asp Ala Tyr Leu
                725                 730                 735

Asn Ala Val Val Gly Thr Ala Leu Ile Lys Lys Tyr Pro Lys Leu Glu
                740                 745                 750

Ser Glu Phe Val Tyr Gly Asp Tyr Lys Val Tyr Asp Val Arg Lys Met
                755                 760                 765

Ile Ala Lys Ser Glu Gln Glu Ile Gly Lys Ala Thr Ala Lys Tyr Phe
                770                 775                 780

Phe Tyr Ser Asn Ile Met Asn Phe Phe Lys Thr Glu Ile Thr Leu Ala
785                 790                 795                 800

Asn Gly Glu Ile Arg Lys Arg Pro Leu Ile Glu Thr Asn Gly Glu Thr
                805                 810                 815

Gly Glu Ile Val Trp Asp Lys Gly Arg Asp Phe Ala Thr Val Arg Lys
                820                 825                 830

Val Leu Ser Met Pro Gln Val Asn Ile Val Lys Lys Thr Glu Val Gln
                835                 840                 845

Thr Gly Gly Phe Ser Lys Glu Ser Ile Leu Pro Lys Arg Asn Ser Asp
850                 855                 860

Lys Leu Ile Ala Arg Lys Lys Asp Trp Asp Pro Lys Lys Tyr Gly Gly
865                 870                 875                 880

Phe Asp Ser Pro Thr Val Ala Tyr Ser Val Leu Val Val Ala Lys Val
                885                 890                 895

Glu Lys Gly Lys Ser Lys Lys Leu Lys Ser Val Lys Glu Leu Leu Gly
                900                 905                 910

Ile Thr Ile Met Glu Arg Ser Ser Phe Glu Lys Asn Pro Ile Asp Phe
                915                 920                 925

Leu Glu Ala Lys Gly Tyr Lys Glu Val Lys Lys Asp Leu Ile Ile Lys
                930                 935                 940

Leu Pro Lys Tyr Ser Leu Phe Glu Leu Glu Asn Gly Arg Lys Arg Met
945                 950                 955                 960

Leu Ala Ser Ala Gly Glu Leu Gln Lys Gly Asn Glu Leu Ala Leu Pro
                965                 970                 975
```

-continued

```
Ser Lys Tyr Val Asn Phe Leu Tyr Leu Ala Ser His Tyr Glu Lys Leu
                980             985                 990

Lys Gly Ser Pro Glu Asp Asn Glu Gln Lys Gln Leu Phe Val Glu Gln
        995                 1000                1005

His Lys His Tyr Leu Asp Glu Ile Ile Glu Gln Ile Ser Glu Phe
    1010                1015                1020

Ser Lys Arg Val Ile Leu Ala Asp Ala Asn Leu Asp Lys Val Leu
    1025                1030                1035

Ser Ala Tyr Asn Lys His Arg Asp Lys Pro Ile Arg Glu Gln Ala
    1040                1045                1050

Glu Asn Ile Ile His Leu Phe Thr Leu Thr Asn Leu Gly Ala Pro
    1055                1060                1065

Ala Ala Phe Lys Tyr Phe Asp Thr Thr Ile Asp Arg Lys Arg Tyr
    1070                1075                1080

Thr Ser Thr Lys Glu Val Leu Asp Ala Thr Leu Ile His Gln Ser
    1085                1090                1095

Ile Thr Gly Leu Tyr Glu Thr Arg Ile Asp Leu Ser Gln Leu Gly
    1100                1105                1110

Gly Asp
    1115

<210> SEQ ID NO 105
<211> LENGTH: 1374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205
```

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

```
Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Thr Asn
                755                 760                 765

Glu Asp Asp Glu Lys Lys Ala Ile Gln Lys Ile Gln Lys Ala Asn Lys
770                 775                 780

Asp Glu Lys Asp Ala Ala Met Leu Lys Ala Ala Asn Gln Tyr Asn Gly
785                 790                 795                 800

Lys Ala Glu Leu Pro His Ser Val Phe His Gly His Lys Gln Leu Ala
                805                 810                 815

Thr Lys Ile Arg Leu Trp His Gln Gln Gly Glu Arg Cys Leu Tyr Thr
                820                 825                 830

Gly Lys Thr Ile Ser Ile His Asp Leu Ile Asn Asn Ser Asn Gln Phe
                835                 840                 845

Glu Val Asp His Ile Leu Pro Leu Ser Ile Thr Phe Asp Asp Ser Leu
850                 855                 860

Ala Asn Lys Val Leu Val Tyr Ala Thr Ala Asn Gln Glu Lys Gly Gln
865                 870                 875                 880

Arg Thr Pro Tyr Gln Ala Leu Asp Ser Met Asp Asp Ala Trp Ser Phe
                885                 890                 895

Arg Glu Leu Lys Ala Phe Val Arg Glu Ser Lys Thr Leu Ser Asn Lys
                900                 905                 910

Lys Lys Glu Tyr Leu Leu Thr Glu Glu Asp Ile Ser Lys Phe Asp Val
                915                 920                 925

Arg Lys Lys Phe Ile Glu Arg Asn Leu Val Asp Thr Arg Tyr Ala Ser
930                 935                 940

Arg Val Val Leu Asn Ala Leu Gln Glu His Phe Arg Ala His Lys Ile
945                 950                 955                 960

Asp Thr Lys Val Ser Val Val Arg Gly Gln Phe Thr Ser Gln Leu Arg
                965                 970                 975

Arg His Trp Gly Ile Glu Lys Thr Arg Asp Thr Tyr His His Ala
                980                 985                 990

Val Asp Ala Leu Ile Ile Ala Ala  Ser Ser Gln Leu Asn  Leu Trp Lys
                995                 1000                1005

Lys Gln  Lys Asn Thr Leu Val  Ser Tyr Ser Glu Asp  Gln Leu Leu
    1010                1015                1020

Asp Ile  Glu Thr Gly Glu Leu  Ile Ser Asp Asp Glu  Tyr Lys Glu
    1025                1030                1035

Ser Val  Phe Lys Ala Pro Tyr  Gln His Phe Val Asp  Thr Leu Lys
```

1040                1045                1050

Ser Lys Glu Phe Glu Asp Ser Ile Leu Phe Ser Tyr Gln Val Asp
    1055                1060                1065

Ser Lys Phe Asn Arg Lys Ile Ser Asp Ala Thr Ile Tyr Ala Thr
    1070                1075                1080

Arg Gln Ala Lys Val Gly Lys Asp Lys Ala Asp Glu Thr Tyr Val
    1085                1090                1095

Leu Gly Lys Ile Lys Asp Ile Tyr Thr Gln Asp Gly Tyr Asp Ala
    1100                1105                1110

Phe Met Lys Ile Tyr Lys Lys Asp Lys Ser Lys Phe Leu Met Tyr
    1115                1120                1125

Arg His Asp Pro Gln Thr Phe Glu Lys Val Ile Glu Pro Ile Leu
    1130                1135                1140

Glu Asn Tyr Pro Asn Lys Gln Ile Asn Glu Lys Gly Lys Glu Val
    1145                1150                1155

Pro Cys Asn Pro Phe Leu Lys Tyr Lys Glu Glu His Gly Tyr Ile
    1160                1165                1170

Arg Lys Tyr Ser Lys Lys Gly Asn Gly Pro Glu Ile Lys Ser Leu
    1175                1180                1185

Lys Tyr Tyr Asp Ser Lys Leu Gly Asn His Ile Asp Ile Thr Pro
    1190                1195                1200

Lys Asp Ser Asn Asn Lys Val Val Leu Gln Ser Val Ser Pro Trp
    1205                1210                1215

Arg Ala Asp Val Tyr Phe Asn Lys Thr Thr Gly Lys Tyr Glu Ile
    1220                1225                1230

Leu Gly Leu Lys Tyr Ala Asp Leu Gln Phe Glu Lys Gly Thr Gly
    1235                1240                1245

Thr Tyr Lys Ile Ser Gln Glu Lys Tyr Asn Asp Ile Lys Lys Lys
    1250                1255                1260

Glu Gly Val Asp Ser Asp Ser Glu Phe Lys Phe Thr Leu Tyr Lys
    1265                1270                1275

Asn Asp Leu Leu Leu Val Lys Asp Thr Glu Thr Lys Glu Gln Gln
    1280                1285                1290

Leu Phe Arg Phe Leu Ser Arg Thr Met Pro Lys Gln Lys His Tyr
    1295                1300                1305

Val Glu Leu Lys Pro Tyr Asp Lys Gln Lys Phe Glu Gly Gly Glu
    1310                1315                1320

Ala Leu Ile Lys Val Leu Gly Asn Val Ala Asn Ser Gly Gln Cys
    1325                1330                1335

Lys Lys Gly Leu Gly Lys Ser Asn Ile Ser Ile Tyr Lys Val Arg
    1340                1345                1350

Thr Asp Val Leu Gly Asn Gln His Ile Ile Lys Asn Glu Gly Asp
    1355                1360                1365

Lys Pro Lys Leu Asp Phe
    1370

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
Gly Gly Gly Gly Ser Gly Gly Gly Gly Ser Gly Gly Gly Gly Ser
1               5                   10                  15
```

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Glu Ala Ala Ala Lys Glu Ala Ala Ala Lys Glu Ala Ala Ala Lys
1               5                   10                  15
```

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Gly Gly Gly Gly Gly Ser Gly Gly Gly Gly Ser Gly Gly Gly Gly
1               5                   10                  15

Gly Ser
```

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gccaaattgg acgaccctcg cgg                                             23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cgaggagacc cccgtttcgg tgg                                             23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cccgccgccg ccgtggctcg agg                                             23

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 112
tgagctctac gagatccaca agg                                              23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ctcaaaattc ataccggttg tgg                                              23

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cgttaaacaa caaccggact tgg                                              23

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ttcaccccgc ggcgctgaat ggg                                              23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
accactacca gtccgtccac agg                                              23

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
agcctttctg aacacatgca cgg                                              23

<210> SEQ ID NO 118
<211> LENGTH: 39
<212> TYPE: DNA
<213> ORGANISM: Homo sapiens

<400> SEQUENCE: 118

```
cctgccatca atgtggccat gcatgtgttc agaaaggct                       39
```

<210> SEQ ID NO 119
<211> LENGTH: 39
<212> TYPE: DNA
<213> ORGANISM: Homo sapiens

<400> SEQUENCE: 119

```
cctgccatca atgtggccgt gcatgtgttc agaaaggct                       39
```

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120

```
cactgcttaa gcctcgctcg agg                                        23
```

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121

```
tcaccagcaa tattcgctcg agg                                        23
```

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      oligoneotide

<400> SEQUENCE: 122

```
caccagcaat attccgctcg agg                                        23
```

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123

```
tagcaacaga catacgctcg agg                                        23
```

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124

```
gggcagtagt aatacgctcg agg                                        23
```

<210> SEQ ID NO 125

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ccaattccca tacattattg tac                                              23

<210> SEQ ID NO 126
<211> LENGTH: 4677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
tctttcttgc gctatgacac ttccagcaaa aggtagggcg ggctgcgaga cggcttcccg       60
gcgctgcatg caacaccgat gatgcttcga ccccccgaag ctccttcggg gctgcatggg      120
cgctccgatg ccgctccagg gcgagcgctg tttaaatagc caggccccg attgcaaaga       180 cattatagcg agctaccaaa gccatattca aacacctaga tcactaccac ttctacacag      240
gccactcgag cttgtgatcg cactccgcta aggggcgcc tcttcctctt cgtttcagtc       300
acaacccgca aacatgtacc catacgatgt tccagattac gcttcgccga agaaaaagcg      360
caaggtcgaa gcgtccgaca agaagtacag catcggcctg gacatcggca ccaactctgt      420
gggctgggcc gtgatcaccg acgagtacaa ggtgcccagc aagaaattca aggtgctggg      480
caacaccgac cggcacagca tcaagaagaa cctgatcgga gccctgctgt tcgacagcgg      540
cgaaacagcc gaggccaccc ggctgaagag aaccgccaga agaagataca ccagacggaa      600
gaaccggatc tgctatctgc aagagatctt cagcaacgag atggccaagg tggacgacag      660
cttcttccac agactggaag agtccttcct ggtggaagag gataagaagc acgagcggca      720
ccccatcttc ggcaacatcg tggacgaggt ggcctaccac gagaagtacc ccaccatcta      780
ccacctgaga aagaaactgg tggacagcac cgacaaggcc gacctgcggc tgatctatct      840
ggccctggcc cacatgatca agttccgggg ccacttcctg atcgagggcg acctgaaccc      900
cgacaacagc gacgtggaca gctgttcat ccagctggtg cagacctaca accagctgtt       960
cgaggaaaac cccatcaacg ccagcggcgt ggacgccaag gccatcctgt ctgccagact     1020
gagcaagagc agacgctgg aaaatctgat cgcccagctg cccggcgaga agaagaatgg      1080
cctgttcggc aacctgattg ccctgagcct gggcctgacc cccaacttca gagcaacttt     1140
cgacctggcc gaggatgcca aactgcagct gagcaaggac acctacgacg acgacctgga     1200
caacctgctg gcccagatcg cgaccagta cgccgacctg tttctggccg ccaagaacct     1260
gtccgacgcc atcctgctga gcgacatcct gagagtgaac accgagatca ccaaggcccc     1320
cctgagcgcc tctatgatca agagatacga cgagcaccac caggacctga ccctgctgaa     1380
agctctcgtg cggcagcagc tgcctgagaa gtacaaagag attttcttcg accagagcaa     1440
gaacggctac gccggctaca ttgacggcgg agccagccag gaagagttct acaagttcat     1500
caagcccatc ctggaaaaga tggacggcac cgaggaactg ctcgtgaagc tgaacagaga     1560
ggacctgctg cggaagcagc ggaccttcga caacggcagc atcccccacc agatccacct     1620
gggagagctg cacgccattc tgcggcggca ggaagatttt tacccattcc tgaaggacaa     1680
ccgggaaaag atcgagaaga tcctgacctt ccgcatcccc tactacgtgg ccctctggc     1740
```

```
cagggggaaac agcagattcg cctggatgac cagaaagagc gaggaaacca tcaccccctg   1800
gaacttcgag gaagtggtgg acaagggcgc ttccgcccag agcttcatcg agcggatgac   1860
caacttcgat aagaacctgc ccaacgagaa ggtgctgccc aagcacagcc tgctgtacga   1920
gtacttcacc gtgtataacg agctgaccaa agtgaaatac gtgaccgagg aatgagaaa   1980 gcccgccttc ctgagcggcg agcagaaaaa ggccatcgtg gacctgctgt tcaagaccaa   2040
ccggaaagtg accgtgaagc agctgaaaga ggactacttc aagaaaatcg agtgcttcga   2100
ctccgtggaa atctccggcg tggaagatcg gttcaacgcc tccctgggca cataccacga   2160
tctgctgaaa attatcaagg acaaggactt cctggacaat gaggaaaacg aggacattct   2220
ggaagatatc gtgctgaccc tgacactgtt tgaggacaga gagatgatcg aggaacggct   2280
gaaaacctat gcccacctgt tcgacgacaa agtgatgaag cagctgaagc ggcggagata   2340
caccggctgg ggcaggctga gccggaagct gatcaacggc atccgggaca agcagtccgg   2400
caagacaatc ctggatttcc tgaagtccga cggcttcgcc aacagaaact tcatgcagct   2460
gatccacgac gacagcctga cctttaaaga ggacatccag aaagcccagg tgtccggcca   2520
gggcgatagc ctgcacgagc acattgccaa tctggccggc agccccgcca ttaagaaggg   2580
catcctgcag acagtgaagg tggtggacga gctcgtgaaa gtgatgggcc ggcacaagcc   2640
cgagaacatc gtgatcgaaa tggccagaga aaccagacc acccagaagg acagaagaa   2700 cagccgcgag agaatgaagc ggatcgaaga gggcatcaaa gagctgggca gccagatcct   2760
gaaagaacac cccgtggaaa cacccagct gcagaacgag aagctgtacc tgtactacct   2820
gcagaatggg cgggatatgt acgtggacca ggaactggac atcaaccggc tgtccgacta   2880
cgatgtggac catatcgtgc ctcagagctt tctgaaggac gactccatcg acaacaaggt   2940
gctgaccaga agcgacaaga accggggcaa gagcgacaac gtgccctccg aagaggtcgt   3000
gaagaagatg aagaactact ggcggcagct gctgaacgcc aagctgatta cccagagaaa   3060
gttcgacaat ctgaccaagg ccgagagagg cggcctgagc gaactggata aggccggctt   3120
catcaagaga cagctggtgg aaacccggca gatcacaaag cacgtggcac agatcctgga   3180
ctcccggatg aacactaagt acgacgagaa tgacaagctg atccgggaag tgaaagtgat   3240
caccctgaag tccaagctgg tgtccgattt ccggaaggat ttccagtttt acaaagtgcg   3300
cgagatcaac aactaccacc acgcccacga cgcctacctg aacgccgtcg tgggaaccgc   3360
cctgatcaaa aagtacccta agctggaaag cgagttcgtg tacggcgact acaaggtgta   3420
cgacgtgcgg aagatgatcg ccaagagcga gcaggaaatc ggcaaggcta ccgccaagta   3480
cttcttctac agcaacatca tgaactttt caagaccgag attaccctgg ccaacggcga   3540
gatccggaag cggcctctga tcgagacaaa cggcgaaacc ggggagatcg tgtgggataa   3600
gggccgggat tttgccaccg tgcggaaagt gctgagcatg ccccaagtga atatcgtgaa   3660
aaagaccgag gtgcagacag cgggcttcag caaagagtct atcctgccca gaggaacag   3720 cgataagctg atcgccagaa agaaggactg ggaccctaag aagtacggcg gcttcgacag   3780
ccccaccgtg gcctattctg tgctggtggt ggccaaagtg gaaagggca agtccaagaa   3840 actgaagagt gtgaaagagc tgctgggat caccatcatg gaaagaagca gcttcgaaaa   3900 gaatccatc gactttctgg aagccaaggg ctacaaagaa gtgaaaaagg acctgatcat   3960
caagctgcct aagtactccc tgttcgagct ggaaaacggc cggaagagaa tgctggcctc   4020
tgccggcgaa ctgcagaagg gaaacgaact ggccctgccc tccaaatatg tgaacttcct   4080
```

| | |
|---|---|
| gtacctggcc agccactatg agaagctgaa gggctccccc gaggataatg agcagaaaca | 4140 |
| gctgtttgtg gaacagcaca agcactacct ggacgagatc atcgagcaga tcagcgagtt | 4200 |
| ctccaagaga gtgatcctgg ccgacgctaa tctggacaaa gtgctgtccg cctacaacaa | 4260 |
| gcaccgggat aagcccatca gagagcaggc cgagaatatc atccacctgt ttaccctgac | 4320 |
| caatctggga gcccctgccg ccttcaagta ctttgacacc accatcgacc ggaagaggta | 4380 |
| caccagcacc aaagaggtgc tggacgccac cctgatccac cagagcatca ccggcctgta | 4440 |
| cgagacacgg atcgacctgt ctcagctggg aggcgacagc cccaagaaga agagaaaggt | 4500 |
| ggaggccagc taaggatccg gcaagactgg ccccgcttgg caacgcaaca gtgagcccct | 4560 |
| ccctagtgtg tttggggatg tgactatgta ttcgtgtgtt ggccaacggg tcaacccgaa | 4620 |
| cagattgata cccgccttgg catttcctgt cagaatgtaa cgtcagttga tggtact | 4677 |

<210> SEQ ID NO 127
<211> LENGTH: 3150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

| | |
|---|---|
| tctttcttgc gctatgacac ttccagcaaa aggtagggcg ggctgcgaga cggcttcccg | 60 |
| gcgctgcatg caacaccgat gatgcttcga ccccccgaag ctccttcggg gctgcatggg | 120 |
| cgctccgatg ccgctccagg cgagcgctg tttaaatagc caggccccg attgcaaaga | 180 |
| cattatagcg agctaccaaa gccatattca aacacctaga tcactaccac ttctacacag | 240 |
| gccactcgag cttgtgatcg cactccgcta aggggggcgcc tcttcctctt cgtttcagtc | 300 |
| acaacccgca acatgccta agaagaagag gaaggttaac acgattaaca tcgctaagaa | 360 |
| cgacttctct gacatcgaac tggctgctat cccgttcaac actctggctg accattacgg | 420 |
| tgagcgtttta gctcgcgaac agttggccct tgagcatgag tcttacgaga tgggtgaagc | 480 |
| acgcttccgc aagatgtttg agcgtcaact taaagctggt gaggttgcgg ataacgctgc | 540 |
| cgccaagcct ctcatcacta ccctactccc taagatgatt gcacgcatca acgactggtt | 600 |
| tgaggaagtg aaagctaagc gcggcaagcg cccgacagcc ttccagttcc tgcaagaaat | 660 |
| caagccggaa gccgtagcgt acatcaccat taagaccact ctggcttgcc taaccagtgc | 720 |
| tgacaataca accgttcagg ctgtagcaag cgcaatcggt cgggccattg aggacgaggc | 780 |
| tcgcttcggt cgtatccgtg accttgaagc taagcacttc aagaaaaacg ttgaggaaca | 840 |
| actcaacaag cgcgtagggc acgtctacaa gaaagcattt atgcaagttg tcgaggctga | 900 |
| catgctctct aagggtctac tcggtggcga ggcgtggtct tcgtggcata aggaagactc | 960 |
| tattcatgta ggagtacgct gcatcgagat gctcattgag tcaaccggaa tggttagctt | 1020 |
| acaccgccaa aatgctggcg tagtaggtca agactctgag actatcgaac tcgcacctga | 1080 |
| atacgctgag gctatcgcaa cccgtgcagg tgcgctggct ggcatctctc cgatgttcca | 1140 |
| accttgcgta gttcctccta gccgtggac tggcattact ggtggtggct attgggctaa | 1200 |
| cggtcgtcgt cctctggcgc tggtgcgtac tcacagtaag aaagcactga tgcgctacga | 1260 |
| agacgtttac atgcctgagg tgtacaaagc gattaacatt gcgcaaaaca ccgcatggaa | 1320 |
| aatcaacaag aaagtcctag cggtcgccaa cgtaatcacc aagtgaagc attgtccggt | 1380 |
| cgaggacatc cctgcgattg agcgtgaaga actcccgatg aaaccggaag acatcgacat | 1440 |

| | | | |
|---|---|---|---|
| gaatcctgag | gctctcaccg | cgtggaaacg | tgctgccgct gctgtgtacc gcaaggacaa | 1500 |
| ggctcgcaag | tctcgccgta | tcagccttga | gttcatgctt gagcaagcca ataagtttgc | 1560 |
| taaccataag | gccatctggt | tcccttacaa | catggactgg cgcggtcgtg tttacgctgt | 1620 |
| gtcaatgttc | aacccgcaag | gtaacgatat | gaccaaagga ctgcttacgc tggcgaaagg | 1680 |
| taaaccaatc | ggtaaggaag | gttactactg | gctgaaaatc cacggtgcaa actgtgcggg | 1740 |
| tgtcgacaag | gttccgttcc | ctgagcgcat | caagttcatt gaggaaaacc acgagaacat | 1800 |
| catggcttgc | gctaagtctc | cactggagaa | cacttggtgg gctgagcaag attctccgtt | 1860 |
| ctgcttcctt | gcgttctgct | ttgagtacgc | tggggtacag caccacggcc tgagctataa | 1920 |
| ctgctcccTT | ccgctggcgt | ttgacgggtc | ttgctctggc atccagcact tctccgcgat | 1980 |
| gctccgagat | gaggtaggtg | gtcgcgcggt | taacttgctt cctagtgaaa ccgttcagga | 2040 |
| catctacggg | attgttgcta | agaaagtcaa | cgagattcta caagcagacg caatcaatgg | 2100 |
| gaccgataac | gaagtagtta | ccgtgaccga | tgagaacact ggtgaaatct ctgagaaagt | 2160 |
| caagctgggc | actaaggcac | tggctggtca | atggctggct tacggtgtta ctcgcagtgt | 2220 |
| gactaagcgt | tcagtcatga | cgctggctta | cgggtccaaa gagttcggct tccgtcaaca | 2280 |
| agtgctggaa | gataccattc | agccagctat | tgattccggc aagggtctga tgttcactca | 2340 |
| gccgaatcag | gctgctggat | acatggctaa | gctgatttgg gaatctgtga gcgtgacggt | 2400 |
| ggtagctgcg | gttgaagcaa | tgaactggct | taagtctgct gctaagctgc tggctgctga | 2460 |
| ggtcaaagat | aagaagactg | gagagattct | tcgcaagcgt tgcgctgtgc attgggtaac | 2520 |
| tcctgatggt | ttccctgtgt | ggcaggaata | caagaagcct attcagacgc gcttgaacct | 2580 |
| gatgttcctc | ggtcagttcc | gcttacagcc | taccattaac accaacaaag atagcgagat | 2640 |
| tgatgcacac | aaacaggagt | ctggtatcgc | tcctaacttt gtacacagcc aagacggtag | 2700 |
| ccaccttcgt | aagactgtag | tgtgggcaca | cgagaagtac ggaatcgaat cttttgcact | 2760 |
| gattcacgac | tccttcggta | cgattccggc | tgacgctgcg aacctgttca agcagtgcg | 2820 |
| cgaaactatg | gttgacacat | atgagtcttg | tgatgtactg gctgatttct acgaccagtt | 2880 |
| cgctgaccag | ttgcacgagt | ctcaattgga | caaaatgcca gcacttccgg ctaaaggtaa | 2940 |
| cttgaacctc | cgtgacatct | tagagtcgga | cttcgcgttc gcgtaaggat ccggcaagac | 3000 |
| tggccccgct | tggcaacgca | acagtgagcc | cctccctagt gtgtttgggg atgtgactat | 3060 |
| gtattcgtgt | gttggccaac | gggtcaaccc | gaacagattg atacccgcct tggcatttcc | 3120 |
| tgtcagaatg | taacgtcagt | tgatggtact | | 3150 |

<210> SEQ ID NO 128
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (23)..(42)
<223> OTHER INFORMATION: a, c, t, g, unknown or other

<400> SEQUENCE: 128

| | | | |
|---|---|---|---|
| gaaattaata | cgactcacta | tannnnnnnn | nnnnnnnnnn nngttttaga gctagaaata | 60 |
| gcaagttaaa | ataaggctag | tccgttatca | acttgaaaaa gtggcaccga gtcggtgctt | 120 |
| ttttt | | | | 125 |

<210> SEQ ID NO 129
<211> LENGTH: 8452
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

| | | | | | |
|---|---|---|---|---|---|
| tgcggtattt | cacaccgcat | caggtggcac | ttttcgggga | aatgtgcgcg | gaacccctat | 60 |
| ttgtttattt | ttctaaatac | attcaaatat | gtatccgctc | atgagattat | caaaaaggat | 120 |
| cttcacctag | atccttttaa | attaaaaatg | aagttttaaa | tcaatctaaa | gtatatatga | 180 |
| gtaaacttgg | tctgacagtt | accaatgctt | aatcagtgag | gcacctatct | cagcgatctg | 240 |
| tctatttcgt | tcatccatag | ttgcctgact | ccccgtcgtg | tagataacta | cgatacggga | 300 |
| gggcttacca | tctggcccca | gtgctgcaat | gataccgcga | gacccacgct | caccggctcc | 360 |
| agatttatca | gcaataaacc | agccagccgg | aagggccgag | cgcagaagtg | gtcctgcaac | 420 |
| tttatccgcc | tccatccagt | ctattaattg | ttgccgggaa | gctagagtaa | gtagttcgcc | 480 |
| agttaatagt | ttgcgcaacg | ttgttgccat | tgctacaggc | atcgtggtgt | cacgctcgtc | 540 |
| gtttggtatg | gcttcattca | gctccggttc | ccaacgatca | aggcgagtta | catgatcccc | 600 |
| catgttgtgc | aaaaaagcgg | ttagctcctt | cggtcctccg | atcgttgtca | gaagtaagtt | 660 |
| ggccgcagtg | ttatcactca | tggttatggc | agcactgcat | aattctctta | ctgtcatgcc | 720 |
| atccgtaaga | tgcttttctg | tgactggtga | gtactcaacc | aagtcattct | gagaatagtg | 780 |
| tatgcggcga | ccgagttgct | cttgcccggc | gtcaatacgg | gataataccg | cgccacatag | 840 |
| cagaacttta | aaagtgctca | tcattggaaa | acgttcttcg | gggcgaaaac | tctcaaggat | 900 |
| cttaccgctg | ttgagatcca | gttcgatgta | acccactcgt | gcacccaact | gatcttcagc | 960 |
| atcttttact | ttcaccagcg | tttctgggtg | agcaaaaaca | ggaaggcaaa | atgccgcaaa | 1020 |
| aaagggaata | agggcgacac | ggaaatgttg | aatactcata | ctcttccttt | ttcaatatta | 1080 |
| ttgaagcatt | tatcagggtt | attgtctcat | gaccaaaatc | ccttaacgtg | agttttcgtt | 1140 |
| ccactgagcg | tcagaccccg | tagaaaagat | caaaggatct | tcttgagatc | ctttttttct | 1200 |
| gcgcgtaatc | tgctgcttgc | aaacaaaaaa | accaccgcta | ccagcggtgg | tttgtttgcc | 1260 |
| ggatcaagag | ctaccaactc | tttttccgaa | ggtaactggc | ttcagcagag | cgcagatacc | 1320 |
| aaatactgtt | cttctagtgt | agccgtagtt | aggccaccac | ttcaagaact | ctgtagcacc | 1380 |
| gcctacatac | ctcgctctgc | taatcctgtt | accagtggct | gttgccagtg | gcgataagtc | 1440 |
| gtgtcttacc | gggttggact | caagacgata | gttaccggat | aaggcgcagc | ggtcgggctg | 1500 |
| aacggggggt | tcgtgcacac | agcccagctt | ggagcgaacg | acctacaccg | aactgagata | 1560 |
| cctacagcgt | gagctatgag | aaagcgccac | gcttcccgaa | gggagaaagg | cggacaggta | 1620 |
| tccggtaagc | ggcagggtcg | gaacaggaga | gcgcacgagg | gagcttccag | ggggaaacgc | 1680 |
| ctggtatctt | tatagtcctg | tcgggtttcg | ccacctctga | cttgagcgtc | gatttttgtg | 1740 |
| atgctcgtca | ggggggcgga | gcctatggaa | aaacgccagc | aacgcggcct | ttttacggtt | 1800 |
| cctggccttt | tgctggcctt | ttgctcacat | gttctttcct | gcgttatccc | ctgattctgt | 1860 |
| ggataaccgt | attaccgcct | ttgagtgagc | tgataccgct | cgccgcagcc | gaacgaccga | 1920 |
| gcgcagcgag | tcagtgagcg | aggaagcggt | cgctgaggct | tgacatgatt | ggtgcgtatg | 1980 |
| tttgtatgaa | gctacaggac | tgatttggcg | ggctatgagg | cgggggaag | ctctggaagg | 2040 |

```
gccgcgatgg ggcgcgcggc gtccagaagg cgccatacgg cccgctggcg gcacccatcc    2100
ggtataaaag cccgcgaccc cgaacggtga cctccacttt cagcgacaaa cgagcactta    2160
tacatacgcg actattctgc cgctatacat aaccactcag ctagcttaag atcccatcaa    2220
gcttgcatgc cgggcgcgcc agaaggagcg cagccaaacc aggatgatgt ttgatggggt    2280
atttgagcac ttgcaacccct tatccggaag cccctggcc cacaaaggct aggcgccaat    2340
gcaagcagtt cgcatgcagc ccctggagcg gtgccctcct gataaaccgg ccagggggcc    2400
tatgttcttt acttttttac aagagaagtc actcaacatc ttaaaatggc caggtgagtc    2460
gacgagcaag cccggcggat caggcagcgt gcttgcagat ttgacttgca acgcccgcat    2520
tgtgtcgacg aaggcttttg gctcctctgt cgctgtctca agcagcatct aaccctgcgt    2580
cgccgtttcc atttgcagga gattcgaggt accatgtacc catacgatgt tccagattac    2640
gcttcgccga agaaaagcg caaggtcgaa gcgtccgaca agaagtacag catcggcctg    2700
gacatcggca ccaactctgt gggctgggcc gtgatcaccg acgagtacaa ggtgcccagc    2760
aagaaattca aggtgctggg caacaccgac cggcacagca tcaagaagaa cctgatcgga    2820
gccctgctgt tcgacagcgg cgaaacagcc gaggccaccc ggctgaagag aaccgccaga    2880
agaagataca ccagacggaa gaaccggatc tgctatctgc aagagatctt cagcaacgag    2940
atggccaagg tggacgacag cttcttccac agactggaag agtccttcct ggtggaagag    3000
gataagaagc acgagcggca ccccatcttc ggcaacatcg tggacgaggt ggcctaccac    3060
gagaagtacc ccaccatcta ccacctgaga aagaaactgg tggacagcac cgacaaggcc    3120
gacctgcggc tgatctatct ggccctggcc cacatgatca agttccgggg ccacttcctg    3180
atcgagggcg acctgaaccc cgacaacagc gacgtggaca gctgttcat ccagctggtg    3240 cagacctaca accagctgtt cgaggaaaac cccatcaacg ccagcggcgt ggacgccaag    3300
gccatcctgt ctgccagact gagcaagagc agacggctgg aaaatctgat cgcccagctg    3360
cccggcgaga agaagaatgg cctgttcggc aacctgattg ccctgagcct gggcctgacc    3420
cccaacttca gagcaacttt cgacctggcc gaggatgcca aactgcagct gagcaaggac    3480
acctacgacg acgacctgga caacctgctg gcccagatcg gcgaccagta cgccgacctg    3540
tttctggccg ccaagaacct gtccgacgcc atcctgctga gcgacatcct gagagtgaac    3600
accgagatca ccaaggcccc cctgagcgcc tctatgatca gagatacga cgagcaccac    3660 caggacctga ccctgctgaa agctctcgtg cggcagcagc tgcctgagaa gtacaaagag    3720
attttcttcg accagagcaa gaacggctac gccggctaca ttgacggcgg agccagccag    3780 gaaagagttct acaagttcat caagcccatc ctggaaaaga tggacggcac cgaggaactg    3840
ctcgtgaagc tgaacagaga ggacctgctg cggaagcagc ggaccttcga caacggcagc    3900
atcccccacc agatccacct gggagagctg cacgccattc tgcggcggca ggaagatttt    3960
tacccattcc tgaaggacaa ccgggaaaag atcgagaaga tcctgacctt ccgcatcccc    4020
tactacgtgg ccctctggc cagggggaaac agcagattcg cctggatgac cagaaagagc    4080
gaggaaacca tcaccccctg gaacttcgag gaagtggtgg acaagggcgc ttccgcccag    4140
agcttcatcg agcggatgac caacttcgat aagaacctgc ccaacgagaa ggtgctgccc    4200
aagcacagcc tgctgtacga gtacttcacc gtgtataacg agctgaccaa agtgaaatac    4260
gtgaccgagg aatgagaaa gcccgccttc ctgagcggcg agcagaaaaa ggccatcgtg    4320
gacctgctgt tcaagaccaa ccggaaagtg accgtgaagc agctgaaaga ggactacttc    4380
aagaaaatcg agtgcttcga ctccgtggaa atctccggcg tggaagatcg gttcaacgcc    4440
```

-continued

| | |
|---|---|
| tccctgggca cataccacga tctgctgaaa attatcaagg acaaggactt cctggacaat | 4500 |
| gaggaaaacg aggacattct ggaagatatc gtgctgaccc tgacactgtt tgaggacaga | 4560 |
| gagatgatcg aggaacggct gaaaacctat gcccacctgt tcgacgacaa agtgatgaag | 4620 |
| cagctgaagc ggcggagata caccggctgg ggcaggctga gccggaagct gatcaacggc | 4680 |
| atccgggaca agcagtccgg caagacaatc ctggatttcc tgaagtccga cggcttcgcc | 4740 |
| aacagaaact tcatgcagct gatccacgac gacagcctga cctttaaaga ggacatccag | 4800 |
| aaagcccagg tgtccggcca gggcgatagc ctgcacgagc acattgccaa tctggccggc | 4860 |
| agccccgcca ttaagaaggg catcctgcag acagtgaagg tggtggacga gctcgtgaaa | 4920 |
| gtgatgggcc ggcacaagcc cgagaacatc gtgatcgaaa tggccagaga gaaccagacc | 4980 |
| acccagaagg acagaagaa cagccgcgag agaatgaagc ggatcgaaga gggcatcaaa | 5040 |
| gagctgggca gccagatcct gaaagaacac cccgtggaaa cacccagct gcagaacgag | 5100 |
| aagctgtacc tgtactacct gcagaatggg cgggatatgt acgtggacca ggaactggac | 5160 |
| atcaaccggc tgtccgacta cgatgtggac catatcgtgc ctcagagctt tctgaaggac | 5220 |
| gactccatcg acaacaaggt gctgaccaga agcgacaaga accggggcaa gagcgacaac | 5280 |
| gtgccctccg aagaggtcgt gaagaagatg aagaactact ggcggcagct gctgaacgcc | 5340 |
| aagctgatta cccagagaaa gttcgacaat ctgaccaagg ccgagagagg cggcctgagc | 5400 |
| gaactggata aggccggctt catcaagaga cagctggtgg aaacccggca gatcacaaag | 5460 |
| cacgtggcac agatcctgga ctcccggatg aacactaagt acgacgagaa tgacaagctg | 5520 |
| atccgggaag tgaaagtgat caccctgaag tccaagctgg tgtccgattt ccggaaggat | 5580 |
| ttccagtttt acaaagtgcg cgagatcaac aactaccacc acgcccacga cgcctacctg | 5640 |
| aacgccgtcg tgggaaccgc cctgatcaaa aagtaccctaa agctggaaag cgagttcgtg | 5700 |
| tacggcgact acaaggtgta cgacgtgcgg aagatgatcg ccaagagcga gcaggaaatc | 5760 |
| ggcaaggcta ccgccaagta cttcttctac agcaacatca tgaactttt caagaccgag | 5820 |
| attaccctgg ccaacggcga gatccggaag cggcctctga tcgagacaaa cggcgaaacc | 5880 |
| ggggagatcg tgtgggataa gggccgggat tttgccaccg tgcggaaagt gctgagcatg | 5940 |
| ccccaagtga atatcgtgaa aaagaccgag gtgcagacag cggcttcag caaagagtct | 6000 |
| atcctgccca gaggaacag cgataagctg atcgccagaa agaaggactg ggaccctaag | 6060 |
| aagtacggcg gcttcgacag cccaccgtg gcctattctg tgctggtggt ggccaaagtg | 6120 |
| gaaagggca agtccaagaa actgaagagt gtgaaagagc tgctgggat caccatcatg | 6180 |
| gaaagaagca gcttcgagaa gaatcccatc gactttctgg aagccaaggg ctacaaagaa | 6240 |
| gtgaaaaagg acctgatcat caagctgcct aagtactccc tgttcgagct ggaaaacggc | 6300 |
| cggaagagaa tgctggcctc tgccggcgaa ctgcagaagg gaaacgaact ggccctgccc | 6360 |
| tccaaatatg tgaacttcct gtacctggcc agccactatg agaagctgaa gggctccccc | 6420 |
| gaggataatg agcagaaaca gctgtttgtg aacagcaca agcactacct ggacgagatc | 6480 |
| atcgagcaga tcagcgagtt ctccaagaga gtgatcctgg ccgacgctaa tctggacaaa | 6540 |
| gtgctgtccg cctacaacaa gcaccggat aagcccatca gagagcaggc cgagaatatc | 6600 |
| atccacctgt ttaccctgac caatctggga gcccctgccg ccttcaagta ctttgacacc | 6660 |
| accatcgacc ggaagaggta caccagcacc aaagaggtgc tggacgccac cctgatccac | 6720 |
| cagagcatca ccggcctgta cgagacacgg atcgacctgt ctcagctggg aggcgacagc | 6780 |

```
cccaagaaga agagaaaggt ggaggccagc taacatatga ttcgaatgtc tttcttgcgc    6840
tatgacactt ccagcaaaag gtagggcggg ctgcgagacg gcttcccggc gctgcatgca    6900
acaccgatga tgcttcgacc ccccgaagct ccttcggggc tgcatgggcg ctccgatgcc    6960
gctccagggc gagcgctgtt taaatagcca ggccccgat tgcaaagaca ttatagcgag     7020
ctaccaaagc catattcaaa cacctagatc actaccactt ctacacaggc cactcgagct    7080
tgtgatcgca ctccgctaag ggggcgcctc ttcctcttcg tttcagtcac aacccgcaaa    7140
catgacacaa gaatccctgt tacttctcga ccgtattgat tcggatgatt cctacgcgag    7200
cctgcggaac gaccaggaat tctgggaggt gagtcgacga gcaagcccgg cggatcaggc    7260
agcgtgcttg cagatttgac ttgcaacgcc cgcattgtgt cgacgaaggc ttttggctcc    7320
tctgtcgctg tctcaagcag catctaaccc tgcgtcgccg tttccatttg cagccgctgg    7380
cccgccgagc cctggaggag ctcgggctgc cggtgccgcc ggtgctgcgg gtgcccggcg    7440
agagcaccaa ccccgtactg gtcggcgagc ccggcccggt gatcaagctg ttcggcgagc    7500
actggtgcgg tccggagagc ctcgcgtcgg agtcggagge gtacgcggtc ctggcggacg    7560
ccccggtgcc ggtgccccgc ctcctcggcc gcggcgagct gcggcccggc accggagcct    7620
ggccgtggcc ctacctggtg atgagccgga tgaccggcac cacctggcgg tccgcgatgg    7680
acggcacgac cgaccggaac gcgctgctcg ccctggcccg cgaactcggc cgggtgctcg    7740
gccggctgca cagggtgccg ctgaccggga acaccgtgct cacccccat tccgaggtct     7800 tcccggaact gctgcgggaa cgccgcgcgg cgaccgtcga ggaccaccgc gggtggggct    7860
acctctcgcc ccggctgctg gaccgcctgg aggactggct gccggacgtg gacacgctgc    7920
tggccggccg cgaaccccgg ttcgtccacg gcgacctgca cggaccaac atcttcgtgg     7980 acctggccgc gaccgaggtc accgggatcg tcgacttcac cgacgtctat gcgggagact    8040
cccgctacag cctggtgcaa ctgcatctca acgccttccg gggcgaccgc gagatcctgg    8100
ccgcgctgct cgacggggcg cagtggaagc ggaccgagga cttcgcccgc gaactgctcg    8160
ccttcaccct cctgcacgac ttcgaggtgt tcgaggagac cccgctggat ctctccggct    8220
tcaccgatcc ggaggaactg gcgcagttcc tctgggggcc gccggacacc gcccccggcg    8280
cctgataagg atccggcaag actggccccg cttggcaacg caacagtgag cccctcccta    8340
gtgtgtttgg ggatgtgact atgtattcgt gtgttggcca acgggtcaac ccgaacagat    8400
tgatacccgc cttggcattt cctgtcagaa tgtaacgtca gttgatggta ct            8452
```

<210> SEQ ID NO 130
<211> LENGTH: 27
<212> TYPE: DNA
<213> ORGANISM: Homo sapiens

<400> SEQUENCE: 130

```
ccgtgccggg cggggagacc gccatgg                                           27
```

<210> SEQ ID NO 131
<211> LENGTH: 22
<212> TYPE: DNA
<213> ORGANISM: Homo sapiens

<400> SEQUENCE: 131

```
ggcccggctg tggctgagga gc                                                22
```

<210> SEQ ID NO 132
<211> LENGTH: 20

<212> TYPE: DNA
<213> ORGANISM: Homo sapiens

<400> SEQUENCE: 132
cggtctcccg cccggcacgg                                              20

<210> SEQ ID NO 133
<211> LENGTH: 26
<212> TYPE: DNA
<213> ORGANISM: Homo sapiens

<400> SEQUENCE: 133
gctcctcagc cacagccggg ccgggt                                       26

<210> SEQ ID NO 134
<211> LENGTH: 12
<212> TYPE: DNA
<213> ORGANISM: Homo sapiens

<400> SEQUENCE: 134
cgaccctgga aa                                                      12

<210> SEQ ID NO 135
<211> LENGTH: 14
<212> TYPE: DNA
<213> ORGANISM: Homo sapiens

<400> SEQUENCE: 135
ccccgccgcc accc                                                    14

<210> SEQ ID NO 136
<211> LENGTH: 18
<212> TYPE: DNA
<213> ORGANISM: Homo sapiens

<400> SEQUENCE: 136
tttccagggt cgccatgg                                                18

<210> SEQ ID NO 137
<211> LENGTH: 10
<212> TYPE: DNA
<213> ORGANISM: Homo sapiens

<400> SEQUENCE: 137
ggcggcgggg                                                         10

<210> SEQ ID NO 138
<211> LENGTH: 20
<212> TYPE: DNA
<213> ORGANISM: Homo sapiens

<400> SEQUENCE: 138
acccttgtta gccacctccc                                              20

<210> SEQ ID NO 139
<211> LENGTH: 20
<212> TYPE: DNA
<213> ORGANISM: Homo sapiens

<400> SEQUENCE: 139
gaacgcagtg ctcttcgaag                                              20

<210> SEQ ID NO 140

```
<211> LENGTH: 20
<212> TYPE: DNA
<213> ORGANISM: Homo sapiens

<400> SEQUENCE: 140
ctcacgccct gctccgtgta                                              20

<210> SEQ ID NO 141
<211> LENGTH: 20
<212> TYPE: DNA
<213> ORGANISM: Homo sapiens

<400> SEQUENCE: 141
ggcgacaact acttcctggt                                              20

<210> SEQ ID NO 142
<211> LENGTH: 20
<212> TYPE: DNA
<213> ORGANISM: Homo sapiens

<400> SEQUENCE: 142
ctcacgccct gctccgtgta                                              20

<210> SEQ ID NO 143
<211> LENGTH: 20
<212> TYPE: DNA
<213> ORGANISM: Homo sapiens

<400> SEQUENCE: 143
gggcgacaac tacttcctgg                                              20

<210> SEQ ID NO 144
<211> LENGTH: 20
<212> TYPE: DNA
<213> ORGANISM: Homo sapiens

<400> SEQUENCE: 144
cctcttcagg gccggggtgg                                              20

<210> SEQ ID NO 145
<211> LENGTH: 20
<212> TYPE: DNA
<213> ORGANISM: Homo sapiens

<400> SEQUENCE: 145
gaggacccag gtggaactgc                                              20

<210> SEQ ID NO 146
<211> LENGTH: 20
<212> TYPE: DNA
<213> ORGANISM: Homo sapiens

<400> SEQUENCE: 146
tcagctccag gcggtcctgg                                              20

<210> SEQ ID NO 147
<211> LENGTH: 20
<212> TYPE: DNA
<213> ORGANISM: Homo sapiens

<400> SEQUENCE: 147
agcagcagca gcagtggcag                                              20
```

```
<210> SEQ ID NO 148
<211> LENGTH: 20
<212> TYPE: DNA
<213> ORGANISM: Homo sapiens

<400> SEQUENCE: 148
tgggcaccgt cagctccagg                                              20

<210> SEQ ID NO 149
<211> LENGTH: 20
<212> TYPE: DNA
<213> ORGANISM: Homo sapiens

<400> SEQUENCE: 149
cagcagtggc agcggccacc                                              20

<210> SEQ ID NO 150
<211> LENGTH: 20
<212> TYPE: DNA
<213> ORGANISM: Homo sapiens

<400> SEQUENCE: 150
acctctcccc tggccctcat                                              20

<210> SEQ ID NO 151
<211> LENGTH: 20
<212> TYPE: DNA
<213> ORGANISM: Homo sapiens

<400> SEQUENCE: 151
ccaggaccgc ctggagctga                                              20

<210> SEQ ID NO 152
<211> LENGTH: 20
<212> TYPE: DNA
<213> ORGANISM: Homo sapiens

<400> SEQUENCE: 152
ccgtcagctc caggcggtcc                                              20

<210> SEQ ID NO 153
<211> LENGTH: 20
<212> TYPE: DNA
<213> ORGANISM: Homo sapiens

<400> SEQUENCE: 153
agcagcagca gcagtggcag                                              20

<210> SEQ ID NO 154
<211> LENGTH: 20
<212> TYPE: DNA
<213> ORGANISM: Homo sapiens

<400> SEQUENCE: 154
atgtgccaag caaagcctca                                              20

<210> SEQ ID NO 155
<211> LENGTH: 20
<212> TYPE: DNA
<213> ORGANISM: Homo sapiens

<400> SEQUENCE: 155
ttcggtcatg cccgtggatg                                              20
```

```
<210> SEQ ID NO 156
<211> LENGTH: 20
<212> TYPE: DNA
<213> ORGANISM: Homo sapiens

<400> SEQUENCE: 156
gtcgttgaaa ttcatcgtac                                              20

<210> SEQ ID NO 157
<211> LENGTH: 20
<212> TYPE: DNA
<213> ORGANISM: Homo sapiens

<400> SEQUENCE: 157
accacctgtg aagagtttcc                                              20

<210> SEQ ID NO 158
<211> LENGTH: 20
<212> TYPE: DNA
<213> ORGANISM: Homo sapiens

<400> SEQUENCE: 158
cgtcgttgaa attcatcgta                                              20

<210> SEQ ID NO 159
<211> LENGTH: 20
<212> TYPE: DNA
<213> ORGANISM: Homo sapiens

<400> SEQUENCE: 159
accacctgtg aagagtttcc                                              20

<210> SEQ ID NO 160
<211> LENGTH: 20
<212> TYPE: DNA
<213> ORGANISM: Mus musculus

<400> SEQUENCE: 160
gaacgcagtg cttttcgagg                                              20

<210> SEQ ID NO 161
<211> LENGTH: 20
<212> TYPE: DNA
<213> ORGANISM: Mus musculus

<400> SEQUENCE: 161
acccttgttg gccacctccc                                              20

<210> SEQ ID NO 162
<211> LENGTH: 20
<212> TYPE: DNA
<213> ORGANISM: Mus musculus

<400> SEQUENCE: 162
ggtgacaact actatctggt                                              20

<210> SEQ ID NO 163
<211> LENGTH: 20
<212> TYPE: DNA
<213> ORGANISM: Mus musculus

<400> SEQUENCE: 163
ctcacaccct gctccgtgta                                              20
```

<210> SEQ ID NO 164
<211> LENGTH: 20
<212> TYPE: DNA
<213> ORGANISM: Mus musculus

<400> SEQUENCE: 164
gggtgacaac tactatctgg                                               20

<210> SEQ ID NO 165
<211> LENGTH: 20
<212> TYPE: DNA
<213> ORGANISM: Mus musculus

<400> SEQUENCE: 165
ctcacaccct gctccgtgta                                               20

<210> SEQ ID NO 166
<211> LENGTH: 20
<212> TYPE: DNA
<213> ORGANISM: Mus musculus

<400> SEQUENCE: 166
cgagaacgca gtgcttttcg                                               20

<210> SEQ ID NO 167
<211> LENGTH: 20
<212> TYPE: DNA
<213> ORGANISM: Mus musculus

<400> SEQUENCE: 167
acccttgttg gccacctccc                                               20

<210> SEQ ID NO 168
<211> LENGTH: 20
<212> TYPE: DNA
<213> ORGANISM: Mus musculus

<400> SEQUENCE: 168
atgagccaag caaatcctca                                               20

<210> SEQ ID NO 169
<211> LENGTH: 20
<212> TYPE: DNA
<213> ORGANISM: Mus musculus

<400> SEQUENCE: 169
ttccgtcatg cccgtggaca                                               20

<210> SEQ ID NO 170
<211> LENGTH: 20
<212> TYPE: DNA
<213> ORGANISM: Mus musculus

<400> SEQUENCE: 170
cttcgttgaa aaccattgta                                               20

<210> SEQ ID NO 171
<211> LENGTH: 20
<212> TYPE: DNA
<213> ORGANISM: Mus musculus

<400> SEQUENCE: 171
ccacctctga agagtttcct                                              20

<210> SEQ ID NO 172
<211> LENGTH: 20
<212> TYPE: DNA
<213> ORGANISM: Mus musculus

<400> SEQUENCE: 172
cttcgttgaa aaccattgta                                              20

<210> SEQ ID NO 173
<211> LENGTH: 20
<212> TYPE: DNA
<213> ORGANISM: Mus musculus

<400> SEQUENCE: 173
accacctctg aagagtttcc                                              20

<210> SEQ ID NO 174
<211> LENGTH: 20
<212> TYPE: DNA
<213> ORGANISM: Mus musculus

<400> SEQUENCE: 174
cttccactca ctctgcgatt                                              20

<210> SEQ ID NO 175
<211> LENGTH: 20
<212> TYPE: DNA
<213> ORGANISM: Mus musculus

<400> SEQUENCE: 175
accatgtctc agtgtcaagc                                              20

<210> SEQ ID NO 176
<211> LENGTH: 20
<212> TYPE: DNA
<213> ORGANISM: Mus musculus

<400> SEQUENCE: 176
ggcggcaaca gcggcaacag                                              20

<210> SEQ ID NO 177
<211> LENGTH: 20
<212> TYPE: DNA
<213> ORGANISM: Mus musculus

<400> SEQUENCE: 177
actgctctgc gtggctgcgg                                              20

<210> SEQ ID NO 178
<211> LENGTH: 20
<212> TYPE: DNA
<213> ORGANISM: Mus musculus

<400> SEQUENCE: 178
ccgcagccac gcagagcagt                                              20

<210> SEQ ID NO 179
<211> LENGTH: 20
<212> TYPE: DNA
<213> ORGANISM: Mus musculus

<400> SEQUENCE: 179

```
gcacctctcc tcgccccgat                                               20

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gagggcctat ttcccatgat tcc                                           23

<210> SEQ ID NO 181
<211> LENGTH: 126
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (84)..(102)
<223> OTHER INFORMATION: a, c, t, g, unknown or other

<400> SEQUENCE: 181
aaaaaaagca ccgactcggt gccactttt caagttgata acggactagc cttatttaa     60 cttgctattt ctagctctaa aacnnnnnnn nnnnnnnnnn nnccggtgtt tcgtcctttc   120
cacaag                                                              126

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(24)
<223> OTHER INFORMATION: a, c, t, g, unknown or other

<400> SEQUENCE: 182
caccgnnnnn nnnnnnnnnn nnnn                                          24

<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)..(23)
<223> OTHER INFORMATION: a, c, t, g, unknown or other

<400> SEQUENCE: 183
aaacnnnnnn nnnnnnnnnn nnnc                                          24

<210> SEQ ID NO 184
<211> LENGTH: 126
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 184
aaaaaaagca ccgactcggt gccactttttt caagttgata acggactagc cttattttaa     60
cttgctattt ctagctctaa aacccctagt cattggaggt gaccggtgtt tcgtcctttc    120
cacaag                                                                126

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
caccgtcacc tccaatgact aggg                                             24

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186 aaaccctag tcattggagg tgac                                              24

<210> SEQ ID NO 187
<211> LENGTH: 192
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
cagaagaaga agggctccca tcacatcaac cggtggcgca ttgccacgaa gcaggccaat     60
ggggaggaca tcgatgtcac ctccaatgac aagcttgcta gcggtgggca accacaaacc    120
cacgagggca gagtgctgct tgctgctggc caggcccctg cgtgggccca agctggactc    180
tggccactcc ct                                                        192

<210> SEQ ID NO 188
<211> LENGTH: 192
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
agggagtggc cagagtccag cttgggccca cgcaggggcc tggccagcag caagcagcac     60
tctgccctcg tgggtttgtg gttgcccacc gctagcaagc ttgtcattgg aggtgacatc    120
gatgtcctcc ccattggcct gcttcgtggc aatgcgccac cggttgatgt gatgggagcc    180
cttcttcttc tg                                                        192

<210> SEQ ID NO 189
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 189
ccatcccctt ctgtgaatgt                                               20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ggagattgga gacacggaga                                               20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ggctccctgg gttcaaagta                                               20

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192 agagggtct ggatgtcgta a                                              21

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
cgccagggtt ttcccagtca cgac                                          24

<210> SEQ ID NO 194
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gagggtctcg tccttgcggc cgcgctagcg agggcctatt tcccatgatt c            51

<210> SEQ ID NO 195
<211> LENGTH: 133
<212> TYPE: DNA
<213> ORGANISM: Artificial Sequence
<220> FEATURE:
<223> OTHER INFORMATION: Description of Artificial Sequence: Synthetic

```
      primer
<220> FEATURE:
<221> NAME/KEY: modified_base
<222> LOCATION: (95)..(114)
<223> OTHER INFORMATION: a, c, t, g, unknown or other

<400> SEQUENCE: 195
ctcggtctcg gtaaaaaagc accgactcgg tgccactttt tcaagttgat aacggactag    60
ccttatttta acttgctatt tctagctcta aaacnnnnnn nnnnnnnnnn nnnnggtgtt   120
tcgtcctttc cac                                                      133

<210> SEQ ID NO 196
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gagggtctct ttaccggtga gggcctattt cccatgattc c                        41

<210> SEQ ID NO 197
<211> LENGTH: 133
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (95)..(114)
<223> OTHER INFORMATION: a, c, t, g, unknown or other

<400> SEQUENCE: 197
ctcggtctcc tcaaaaaagc accgactcgg tgccactttt tcaagttgat aacggactag    60
ccttatttta acttgctatt tctagctcta aaacnnnnnn nnnnnnnnnn nnnnggtgtt   120
tcgtcctttc cac                                                      133

<210> SEQ ID NO 198
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
gagggtctct ttgagctcga gggcctattt cccatgattc                          40

<210> SEQ ID NO 199
<211> LENGTH: 133
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (96)..(115)
<223> OTHER INFORMATION: a, c, t, g, unknown or other

<400> SEQUENCE: 199
ctcggtctcg cgtaaaaaag caccgactcg gtgccacttt ttcaagttga taacggacta    60
gccttatttt aacttgctat ttctagctct aaaacnnnnn nnnnnnnnnn nnnnnggtgt   120
```

<210> SEQ ID NO 200
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 200
gagggtctct tacgcgtgtg tctagac    27

<210> SEQ ID NO 201
<211> LENGTH: 98
<212> TYPE: DNA
<213> ORGANISM: Artificial Sequence
<220> FEATURE:
<223> OTHER INFORMATION: Description of Artificial Sequence: Synthetic primer

<400> SEQUENCE: 201
ctcggtctca aggacaggga agggagcagt ggttcacgcc tgtaatccca gcaatttggg    60
aggccaaggt gggtagatca cctgagatta ggagttgc    98

<210> SEQ ID NO 202
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 202
cctgtccttg cggccgcgct agcgagggcc    30

<210> SEQ ID NO 203
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 203
cacgcggccg caaggacagg gaagggagca g    31

<210> SEQ ID NO 204
<211> LENGTH: 327
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 204

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

```
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Arg Glu Glu Glu Glu Thr Asp Ser Arg Met Pro
                245                 250                 255

His Leu Asp Ser Pro Gly Ser Ser Gln Pro Arg Arg Ser Phe Leu Ser
            260                 265                 270

Arg Val Ile Arg Ala Ala Leu Pro Leu Gln Leu Leu Leu Leu Leu
        275                 280                 285

Leu Leu Leu Ala Cys Leu Leu Pro Ala Ser Glu Asp Asp Tyr Ser Cys
290                 295                 300

Thr Gln Ala Asn Asn Phe Ala Arg Ser Phe Tyr Pro Met Leu Arg Tyr
305                 310                 315                 320

Thr Asn Gly Pro Pro Pro Thr
                325

<210> SEQ ID NO 205
<211> LENGTH: 3243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
accggtgcca ccatgtaccc atacgatgtt ccagattacg cttcgccgaa gaaaaagcgc     60
aaggtcgaag cgtccatgaa aaggaactac attctgggc tggacatcgg gattacaagc    120
gtggggtatg ggattattga ctatgaaaca agggacgtga tcgacgcagg cgtcagactg    180
ttcaaggagg ccaacgtgga aaacaatgag ggacggagaa gcaagagggg agccaggcgc    240
ctgaaacgac ggagaaggca cagaatccag agggtgaaga aactgctgtt cgattacaac    300
ctgctgaccg accattctga gctgagtgga attaatcctt atgaagccag ggtgaaaggc    360
ctgagtcaga agctgtcaga ggaagagttt tccgcagctc tgctgcacct ggctaagcgc    420
cgaggagtgc ataacgtcaa tgaggtggaa gaggacaccg gcaacgagct gtctacaaag    480
```

```
gaacagatct cacgcaatag caaagctctg gaagagaagt atgtcgcaga gctgcagctg      540
gaacggctga agaaagatgg cgaggtgaga gggtcaatta ataggttcaa gacaagcgac      600
tacgtcaaag aagccaagca gctgctgaaa gtgcagaagg cttaccacca gctggatcag      660
agcttcatcg atacttatat cgacctgctg gagactcgga gaacctacta tgagggacca      720
ggagaaggga gccccttcgg atggaaagac atcaaggaat ggtacgagat gctgatggga      780
cattgcacct attttccaga gagctgaga agcgtcaagt acgcttataa cgcagatctg       840
tacaacgccc tgaatgacct gaacaacctg gtcatcacca gggatgaaaa cgagaaactg      900
gaatactatg agaagttcca gatcatcgaa acgtgttta agcagaagaa aaagcctaca       960
ctgaaacaga ttgctaagga gatcctggtc aacgaagagg acatcaaggg ctaccgggtg     1020
acaagcactg aaaaccaga gttcaccaat ctgaaagtgt atcacgatat taaggacatc      1080
acagcacgga aagaaatcat tgagaacgcc gaactgctgg atcagattgc taagatcctg     1140
actatctacc agagctccga ggacatccag gaagagctga ctaacctgaa cagcgagctg     1200
acccaggaag agatcgaaca gattagtaat ctgaaggggt acaccggaac acacaacctg     1260
tccctgaaag ctatcaatct gattctggat gagctgtggc atacaaacga caatcagatt     1320
gcaatcttta accggctgaa gctggtccca aaaaggtgg acctgagtca gcagaaagag       1380
atcccaacca cactggtgga cgatttcatt ctgtcacccg tggtcaagcg gagcttcatc     1440
cagagcatca aagtgatcaa cgccatcatc aagaagtacg gcctgcccaa tgatatcatt     1500
atcgagctgg ctaggagaa aacagcaag gacgcacaga gatgatcaa tgagatgcag         1560 aaacgaaacc ggcagaccaa tgaacgcatt gaagagatta ccgaactac cgggaaagag      1620 aacgcaaagt acctgattga aaaaatcaag ctgcacgata tgcaggaggg aaagtgtctg     1680
tattctctgg aggccatccc cctggaggac ctgctgaaca tccattcaa ctacgaggtc       1740 gatcatatta tccccagaag cgtgtccttc gacaattcct ttaacaacaa ggtgctggtc     1800
aagcaggaag agaactctaa aaagggcaat aggactcctt ccagtacct gtctagttca       1860 gattccaaga tctcttacga aacctttaaa aagcacattc tgaatctggc caaaggaaag     1920
ggccgcatca gcaagaccaa aaaggagtac ctgctggaag agcgggacat caacagattc     1980
tccgtccaga aggattttat taaccggaat ctggtggaca caagatacgc tactcgcggc     2040
ctgatgaatc tgctgcgatc ctatttccgg gtgaacaatc tggatgtgaa agtcaagtcc     2100
atcaacggcg ggttcacatc tttctgagg cgcaaatgga agtttaaaaa ggagcgcaac       2160
aaagggtaca agcaccatgc cgaagatgct ctgattatcg caaatgccga cttcatctttt   2220 aaggagtgga aaaagctgga caaagccaag aaagtgatgg agaaccagat gttcgaagag     2280
aagcaggccg aatctatgcc cgaaatcgag acagaacagg agtacaagga gattttcatc     2340
actcctcacc agatcaagca tatcaaggat ttcaaggact acaagtactc tcaccgggtg     2400
gataaaaagc ccaacagaga gctgatcaat gacaccctgt atagtacaag aaaagacgat     2460 aagggaata ccctgattgt gaacaatctg aacggactgt acgacaaaga taatgacaag       2520
ctgaaaaagc tgatcaacaa aagtcccgag aagctgctga tgtaccacca tgatcctcag     2580
acatatcaga aactgaagct gattatggag cagtacggcg acgagaagaa cccactgtat     2640
aagtactatg aagagactgg gaactacctg accaagtata gcaaaaagga taatggcccc     2700
gtgatcaaga gatcaagta ctatgggaac aagctgaatg cccatctgga catcacagac      2760
gattacccta cagtcgcaa caaggtggtc aagctgtcac tgaagccata cagattcgat     2820
gtctatctgg acaacggcgt gtataaattt gtgactgtca agaatctgga tgtcatcaaa     2880
```

```
aaggagaact actatgaagt gaatagcaag tgctacgaag aggctaaaaa gctgaaaaag   2940
attagcaacc aggcagagtt catcgcctcc ttttacaaca acgacctgat taagatcaat   3000
ggcgaactgt atagggtcat cggggtgaac aatgatctgc tgaaccgcat tgaagtgaat   3060
atgattgaca tcacttaccg agagtatctg gaaaacatga atgataagcg ccccccctcga  3120 attatcaaaa caattgcctc taagactcag agtatcaaaa agtactcaac cgacattctg   3180
ggaaacctgt atgaggtgaa gagcaaaaag caccctcaga ttatcaaaaa gggctaagaa   3240
ttc                                                                 3243
```

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
atctcttaga taccagcatc                                               20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tcaatctccc gatgggcacc                                               20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gcccatcggg agattgaggg                                               20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
acttcaacag cgtgccggag                                               20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ccgctgacca cacctgccag                                               20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tggcaggtgt ggtcagcggc                                              20

<210> SEQ ID NO 212
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212
gttttagagc tatgctgttt tgaatggtcc caaaacggaa gggcctgagt ccgagcagaa    60
gaagaagttt tagagctatg ctgttttgaa tggtcccaaa ac                      102

<210> SEQ ID NO 213
<211> LENGTH: 100
<212> TYPE: DNA
<213> ORGANISM: Homo sapiens

<400> SEQUENCE: 213
cggaggacaa agtacaaacg gcagaagctg gaggaggaag ggcctgagtc cgagcagaag    60
aagaagggct cccatcacat caaccggtgg cgcattgcca                         100

<210> SEQ ID NO 214
<211> LENGTH: 50
<212> TYPE: DNA
<213> ORGANISM: Homo sapiens

<400> SEQUENCE: 214
agctggagga ggaagggcct gagtccgagc agaagaagaa gggctcccac               50

<210> SEQ ID NO 215
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
gaguccgagc agaagaagaa guuuuagagc                                    30

<210> SEQ ID NO 216
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
agctggagga ggaagggcct gagtccgagc agaagagaag ggctcccac                49

<210> SEQ ID NO 217

```
<211> LENGTH: 53
<212> TYPE: DNA
<213> ORGANISM: Homo sapiens

<400> SEQUENCE: 217
ctggaggagg aagggcctga gtccgagcag aagaagaagg gctcccatca cat      53

<210> SEQ ID NO 218
<211> LENGTH: 52
<212> TYPE: DNA
<213> ORGANISM: Homo sapiens

<400> SEQUENCE: 218
ctggaggagg aagggcctga gtccgagcag aagagaaggg ctcccatcac at       52

<210> SEQ ID NO 219
<211> LENGTH: 54
<212> TYPE: DNA
<213> ORGANISM: Homo sapiens

<400> SEQUENCE: 219
ctggaggagg aagggcctga gtccgagcag aagaaagaag gctcccatc acat      54

<210> SEQ ID NO 220
<211> LENGTH: 50
<212> TYPE: DNA
<213> ORGANISM: Homo sapiens

<400> SEQUENCE: 220
ctggaggagg aagggcctga gtccgagcag aagaagggct cccatcacat          50

<210> SEQ ID NO 221
<211> LENGTH: 47
<212> TYPE: DNA
<213> ORGANISM: Homo sapiens

<400> SEQUENCE: 221
ctggaggagg aagggcctga gcccgagcag aagggctccc atcacat             47

<210> SEQ ID NO 222
<211> LENGTH: 48
<212> TYPE: DNA
<213> ORGANISM: Homo sapiens

<400> SEQUENCE: 222
ctggaggagg aagggcctga gtccgagcag aagaagaagg gctcccat            48

<210> SEQ ID NO 223
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
gaguccgagc agaagaagau                                            20

<210> SEQ ID NO 224
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 224 gauccgagc agaagaagua                                      20

<210> SEQ ID NO 225
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225 gauccgagc agaagaacaa                                      20

<210> SEQ ID NO 226
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226 gauccgagc agaagaugaa                                      20

<210> SEQ ID NO 227
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227 gauccgagc agaaguagaa                                      20

<210> SEQ ID NO 228
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228 gauccgagc agaugaagaa                                      20

<210> SEQ ID NO 229
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229 gauccgagc acaagaagaa                                      20

<210> SEQ ID NO 230
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 230
gaguccgagg agaagaagaa                                                    20

<210> SEQ ID NO 231
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
gaguccgugc agaagaagaa                                                    20

<210> SEQ ID NO 232
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
gagucggagc agaagaagaa                                                    20

<210> SEQ ID NO 233
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
gagaccgagc agaagaagaa                                                    20

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
aatgacaagc ttgctagcgg tggg                                               24

<210> SEQ ID NO 235
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
aaaacggaag ggcctgagtc cgagcagaag aagaagttt                               39

<210> SEQ ID NO 236
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
```
aaacaggggc cgagattggg tgttcagggc agaggtttt     39

<210> SEQ ID NO 237
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
aaaacggaag ggcctgagtc cgagcagaag aagaagtt     38

<210> SEQ ID NO 238
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
aacggaggga ggggcacaga tgagaaactc agggttttag     40

<210> SEQ ID NO 239
<211> LENGTH: 38
<212> TYPE: DNA
<213> ORGANISM: Homo sapiens

<400> SEQUENCE: 239
agcccttctt cttctgctcg gactcaggcc cttcctcc     38

<210> SEQ ID NO 240
<211> LENGTH: 40
<212> TYPE: DNA
<213> ORGANISM: Homo sapiens

<400> SEQUENCE: 240
cagggaggga ggggcacaga tgagaaactc aggaggcccc     40

<210> SEQ ID NO 241
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ggcaatgcgc caccggttga tgtgatggga gcccttctag gaggccccca gagcagccac     60
tggggcctca acactcaggc     80

<210> SEQ ID NO 242
<211> LENGTH: 33
<212> TYPE: DNA
<213> ORGANISM: Homo sapiens

<400> SEQUENCE: 242
catcgatgtc ctccccattg gcctgcttcg tgg     33

<210> SEQ ID NO 243
<211> LENGTH: 33
<212> TYPE: DNA
<213> ORGANISM: Homo sapiens

```
<400> SEQUENCE: 243
ttcgtggcaa tgcgccaccg gttgatgtga tgg                                    33

<210> SEQ ID NO 244
<211> LENGTH: 33
<212> TYPE: DNA
<213> ORGANISM: Homo sapiens

<400> SEQUENCE: 244
tcgtggcaat gcgccaccgg ttgatgtgat ggg                                    33

<210> SEQ ID NO 245
<211> LENGTH: 33
<212> TYPE: DNA
<213> ORGANISM: Homo sapiens

<400> SEQUENCE: 245
tccagcttct gccgtttgta ctttgtcctc cgg                                    33

<210> SEQ ID NO 246
<211> LENGTH: 33
<212> TYPE: DNA
<213> ORGANISM: Homo sapiens

<400> SEQUENCE: 246
ggagggaggg gcacagatga gaaactcagg agg                                    33

<210> SEQ ID NO 247
<211> LENGTH: 33
<212> TYPE: DNA
<213> ORGANISM: Homo sapiens

<400> SEQUENCE: 247
aggggccgag attgggtgtt cagggcagag agg                                    33

<210> SEQ ID NO 248
<211> LENGTH: 33
<212> TYPE: DNA
<213> ORGANISM: Mus musculus

<400> SEQUENCE: 248
caagcactga gtgccattag ctaaatgcat agg                                    33

<210> SEQ ID NO 249
<211> LENGTH: 33
<212> TYPE: DNA
<213> ORGANISM: Mus musculus

<400> SEQUENCE: 249
aatgcatagg gtaccaccca caggtgccag ggg                                    33

<210> SEQ ID NO 250
<211> LENGTH: 33
<212> TYPE: DNA
<213> ORGANISM: Mus musculus

<400> SEQUENCE: 250
acacacatgg gaaagcctct gggccaggaa agg                                    33

<210> SEQ ID NO 251
<211> LENGTH: 37
<212> TYPE: DNA
```

<213> ORGANISM: Homo sapiens

<400> SEQUENCE: 251
ggaggaggta gtatacagaa acacagagaa gtagaat                              37

<210> SEQ ID NO 252
<211> LENGTH: 37
<212> TYPE: DNA
<213> ORGANISM: Homo sapiens

<400> SEQUENCE: 252
agaatgtaga ggagtcacag aaactcagca ctagaaa                              37

<210> SEQ ID NO 253
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ggacgaaaca ccggaaccat tcaaaacagc atagcaagtt aaaataaggc tagtccgtta    60
tcaacttgaa aaagtggcac cgagtcggtg cttttttt                            98

<210> SEQ ID NO 254
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254
ggacgaaaca ccggtagtat taagtattgt tttatggctg ataaatttct ttgaatttct    60
ccttgattat ttgttataaa agttataaaa taatcttgtt ggaaccattc aaaacagcat   120
agcaagttaa aataaggcta gtccgttatc aacttgaaaa agtggcaccg agtcggtgct   180
tttttt                                                              186

<210> SEQ ID NO 255
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
gggttttaga gctatgctgt tttgaatggt cccaaaacgg gtcttcgaga agacgtttta    60
gagctatgct gttttgaatg gtcccaaaac ttttt                               95

<210> SEQ ID NO 256
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(34)
<223> OTHER INFORMATION: a, c, t, g, unknown or other

<400> SEQUENCE: 256
aaacnnnnnn nnnnnnnnnn nnnnnnnnnn nnnngt                                 36

<210> SEQ ID NO 257
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(36)
<223> OTHER INFORMATION: a, c, t, g, unknown or other

<400> SEQUENCE: 257
taaaacnnnn nnnnnnnnnn nnnnnnnnnn nnnnnn                                 36

<210> SEQ ID NO 258
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gtggaaagga cgaaacaccg ggtcttcgag aagacctgtt ttagagctag aaatagcaag       60
ttaaaataag gctagtccgt tttt                                              84

<210> SEQ ID NO 259
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other

<400> SEQUENCE: 259
nnnnnnnnnn nnnnnnnnng uuauuguacu cucaagauuu auuuuu                      46

<210> SEQ ID NO 260
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
guuacuuaaa ucuugcagaa gcuacaaaga uaaggcuuca ugccgaaauc aacacccugu       60
cauuuuaugg cagguguuu ucguuauuua a                                       91

<210> SEQ ID NO 261
<211> LENGTH: 70
<212> TYPE: DNA
<213> ORGANISM: Homo sapiens

<400> SEQUENCE: 261
ttttctagtg ctgagtttct gtgactcctc tacattctac ttctctgtgt ttctgtatac       60
tacctcctcc                                                              70

```
<210> SEQ ID NO 262
<211> LENGTH: 122
<212> TYPE: DNA
<213> ORGANISM: Homo sapiens

<400> SEQUENCE: 262
ggaggaaggg cctgagtccg agcagaagaa gaagggctcc catcacatca accggtggcg     60
cattgccacg aagcaggcca atggggagga catcgatgtc acctccaatg actagggtgg    120
gc                                                                   122

<210> SEQ ID NO 263
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(32)
<223> OTHER INFORMATION: a, c, u, g, unknown or other

<400> SEQUENCE: 263
acnnnnnnnn nnnnnnnnnn nnnnnnnnnn nnguuuuaga gcuaugcu                  48

<210> SEQ ID NO 264
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264
agcauagcaa guuaaaauaa ggcuaguccg uuaucaacuu gaaaaagugg caccgagucg     60
gugcuuu                                                               67

<210> SEQ ID NO 265
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 265
nnnnnnnnnn nnnnnnnnnn guuuuagagc uagaaauagc aaguuaaaau aaggcuaguc     60
cg                                                                   62

<210> SEQ ID NO 266
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
```

```
tgaatggtcc caaaacggaa gggcctgagt ccgagcagaa gaagaagttt tagagctatg    60
ctgttttgaa tgg                                                      73

<210> SEQ ID NO 267
<211> LENGTH: 69
<212> TYPE: DNA
<213> ORGANISM: Homo sapiens

<400> SEQUENCE: 267
ctggtcttcc acctctctgc cctgaacacc caatctcggc ccctctcgcc accctcctgc    60
atttctgtt                                                           69

<210> SEQ ID NO 268
<211> LENGTH: 138
<212> TYPE: DNA
<213> ORGANISM: Mus musculus

<400> SEQUENCE: 268
acccaagcac tgagtgccat tagctaaatg catagggtac cacccacagg tgccaggggc    60
ctttcccaaa gttcccagcc ccttctccaa cctttcctgg cccagaggct ttcccatgtg   120
tgtggctgga ccctttga                                                138

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
aaaaccaccc ttctctctgg c                                             21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
ggagattgga gacacggaga g                                             21

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
ctggaaagcc aatgcctgac                                               20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
```
ggcagcaaac tccttgtcct                                           20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
gtgctttgca gaggcctacc                                           20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
cctggagcgc atgcagtagt                                           20

<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
accttctgtg tttccaccat tc                                        22

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
ttggggagtg cacagacttc                                           20

<210> SEQ ID NO 277
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 277
tagctctaaa acttcttctt ctgctcggac                                30

<210> SEQ ID NO 278
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 278

```
ctagccttat tttaacttgc tatgctgttt                                        30

<210> SEQ ID NO 279
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 279
nnnnnnnnnn nnnnnnnnnn guuuuagagc uagaaauagc aaguuaaaau aaggcuaguc        60
cguuaucaac uugaaaaagu ggcaccgagu cggugcuuu                               99

<210> SEQ ID NO 280
<211> LENGTH: 12
<212> TYPE: DNA
<213> ORGANISM: Homo sapiens

<400> SEQUENCE: 280
tagcgggtaa gc                                                           12

<210> SEQ ID NO 281
<211> LENGTH: 12
<212> TYPE: DNA
<213> ORGANISM: Homo sapiens

<400> SEQUENCE: 281
tcggtgacat gt                                                           12

<210> SEQ ID NO 282
<211> LENGTH: 12
<212> TYPE: DNA
<213> ORGANISM: Homo sapiens

<400> SEQUENCE: 282
actccccgta gg                                                           12

<210> SEQ ID NO 283
<211> LENGTH: 12
<212> TYPE: DNA
<213> ORGANISM: Homo sapiens

<400> SEQUENCE: 283
actgcgtgtt aa                                                           12

<210> SEQ ID NO 284
<211> LENGTH: 12
<212> TYPE: DNA
<213> ORGANISM: Homo sapiens

<400> SEQUENCE: 284
acgtcgcctg at                                                           12

<210> SEQ ID NO 285
<211> LENGTH: 12
<212> TYPE: DNA
<213> ORGANISM: Homo sapiens

<400> SEQUENCE: 285
```
taggtcgacc ag                                                    12

<210> SEQ ID NO 286
<211> LENGTH: 12
<212> TYPE: DNA
<213> ORGANISM: Homo sapiens

<400> SEQUENCE: 286
ggcgttaatg at                                                    12

<210> SEQ ID NO 287
<211> LENGTH: 12
<212> TYPE: DNA
<213> ORGANISM: Homo sapiens

<400> SEQUENCE: 287
tgtcgcatgt ta                                                    12

<210> SEQ ID NO 288
<211> LENGTH: 12
<212> TYPE: DNA
<213> ORGANISM: Homo sapiens

<400> SEQUENCE: 288
atggaaacgc at                                                    12

<210> SEQ ID NO 289
<211> LENGTH: 12
<212> TYPE: DNA
<213> ORGANISM: Homo sapiens

<400> SEQUENCE: 289
gccgaattcc tc                                                    12

<210> SEQ ID NO 290
<211> LENGTH: 12
<212> TYPE: DNA
<213> ORGANISM: Homo sapiens

<400> SEQUENCE: 290
gcatggtacg ga                                                    12

<210> SEQ ID NO 291
<211> LENGTH: 12
<212> TYPE: DNA
<213> ORGANISM: Homo sapiens

<400> SEQUENCE: 291
cggtactctt ac                                                    12

<210> SEQ ID NO 292
<211> LENGTH: 12
<212> TYPE: DNA
<213> ORGANISM: Homo sapiens

<400> SEQUENCE: 292
gcctgtgccg ta                                                    12

<210> SEQ ID NO 293
<211> LENGTH: 12
<212> TYPE: DNA
<213> ORGANISM: Homo sapiens

<400> SEQUENCE: 293

```
tacggtaagt cg                                                    12

<210> SEQ ID NO 294
<211> LENGTH: 12
<212> TYPE: DNA
<213> ORGANISM: Homo sapiens

<400> SEQUENCE: 294
cacgaaatta cc                                                    12

<210> SEQ ID NO 295
<211> LENGTH: 12
<212> TYPE: DNA
<213> ORGANISM: Homo sapiens

<400> SEQUENCE: 295
aaccaagata cg                                                    12

<210> SEQ ID NO 296
<211> LENGTH: 12
<212> TYPE: DNA
<213> ORGANISM: Homo sapiens

<400> SEQUENCE: 296
gagtcgatac gc                                                    12

<210> SEQ ID NO 297
<211> LENGTH: 12
<212> TYPE: DNA
<213> ORGANISM: Homo sapiens

<400> SEQUENCE: 297
gtctcacgat cg                                                    12

<210> SEQ ID NO 298
<211> LENGTH: 12
<212> TYPE: DNA
<213> ORGANISM: Homo sapiens

<400> SEQUENCE: 298
tcgtcgggtg ca                                                    12

<210> SEQ ID NO 299
<211> LENGTH: 12
<212> TYPE: DNA
<213> ORGANISM: Homo sapiens

<400> SEQUENCE: 299
actccgtagt ga                                                    12

<210> SEQ ID NO 300
<211> LENGTH: 12
<212> TYPE: DNA
<213> ORGANISM: Homo sapiens

<400> SEQUENCE: 300
caggacgtcc gt                                                    12

<210> SEQ ID NO 301
<211> LENGTH: 12
<212> TYPE: DNA
<213> ORGANISM: Homo sapiens
```

```
<400> SEQUENCE: 301
tcgtatccct ac                                                          12

<210> SEQ ID NO 302
<211> LENGTH: 12
<212> TYPE: DNA
<213> ORGANISM: Homo sapiens

<400> SEQUENCE: 302
tttcaaggcc gg                                                          12

<210> SEQ ID NO 303
<211> LENGTH: 12
<212> TYPE: DNA
<213> ORGANISM: Homo sapiens

<400> SEQUENCE: 303
cgccggtgga at                                                          12

<210> SEQ ID NO 304
<211> LENGTH: 12
<212> TYPE: DNA
<213> ORGANISM: Homo sapiens

<400> SEQUENCE: 304
gaacccgtcc ta                                                          12

<210> SEQ ID NO 305
<211> LENGTH: 12
<212> TYPE: DNA
<213> ORGANISM: Homo sapiens

<400> SEQUENCE: 305
gattcatcag cg                                                          12

<210> SEQ ID NO 306
<211> LENGTH: 12
<212> TYPE: DNA
<213> ORGANISM: Homo sapiens

<400> SEQUENCE: 306
acaccggtct tc                                                          12

<210> SEQ ID NO 307
<211> LENGTH: 12
<212> TYPE: DNA
<213> ORGANISM: Homo sapiens

<400> SEQUENCE: 307
atcgtgccct aa                                                          12

<210> SEQ ID NO 308
<211> LENGTH: 12
<212> TYPE: DNA
<213> ORGANISM: Homo sapiens

<400> SEQUENCE: 308
gcgtcaatgt tc                                                          12

<210> SEQ ID NO 309
<211> LENGTH: 12
<212> TYPE: DNA
<213> ORGANISM: Homo sapiens
```

```
<400> SEQUENCE: 309
ctccgtatct cg                                                        12

<210> SEQ ID NO 310
<211> LENGTH: 12
<212> TYPE: DNA
<213> ORGANISM: Homo sapiens

<400> SEQUENCE: 310
ccgattcctt cg                                                        12

<210> SEQ ID NO 311
<211> LENGTH: 12
<212> TYPE: DNA
<213> ORGANISM: Homo sapiens

<400> SEQUENCE: 311
tgcgcctcca gt                                                        12

<210> SEQ ID NO 312
<211> LENGTH: 12
<212> TYPE: DNA
<213> ORGANISM: Homo sapiens

<400> SEQUENCE: 312
taacgtcgga gc                                                        12

<210> SEQ ID NO 313
<211> LENGTH: 12
<212> TYPE: DNA
<213> ORGANISM: Homo sapiens

<400> SEQUENCE: 313
aaggtcgccc at                                                        12

<210> SEQ ID NO 314
<211> LENGTH: 12
<212> TYPE: DNA
<213> ORGANISM: Homo sapiens

<400> SEQUENCE: 314
gtcggggact at                                                        12

<210> SEQ ID NO 315
<211> LENGTH: 12
<212> TYPE: DNA
<213> ORGANISM: Homo sapiens

<400> SEQUENCE: 315
ttcgagcgat tt                                                        12

<210> SEQ ID NO 316
<211> LENGTH: 12
<212> TYPE: DNA
<213> ORGANISM: Homo sapiens

<400> SEQUENCE: 316
tgagtcgtcg ag                                                        12

<210> SEQ ID NO 317
<211> LENGTH: 12
<212> TYPE: DNA
```

```
<213> ORGANISM: Homo sapiens

<400> SEQUENCE: 317
tttacgcaga gg                                                              12

<210> SEQ ID NO 318
<211> LENGTH: 12
<212> TYPE: DNA
<213> ORGANISM: Homo sapiens

<400> SEQUENCE: 318
aggaagtatc gc                                                              12

<210> SEQ ID NO 319
<211> LENGTH: 12
<212> TYPE: DNA
<213> ORGANISM: Homo sapiens

<400> SEQUENCE: 319
actcgatacc at                                                              12

<210> SEQ ID NO 320
<211> LENGTH: 12
<212> TYPE: DNA
<213> ORGANISM: Homo sapiens

<400> SEQUENCE: 320
cgctacatag ca                                                              12

<210> SEQ ID NO 321
<211> LENGTH: 12
<212> TYPE: DNA
<213> ORGANISM: Homo sapiens

<400> SEQUENCE: 321
ttcataaccg gc                                                              12

<210> SEQ ID NO 322
<211> LENGTH: 12
<212> TYPE: DNA
<213> ORGANISM: Homo sapiens

<400> SEQUENCE: 322
ccaaacggtt aa                                                              12

<210> SEQ ID NO 323
<211> LENGTH: 12
<212> TYPE: DNA
<213> ORGANISM: Homo sapiens

<400> SEQUENCE: 323
cgattccttc gt                                                              12

<210> SEQ ID NO 324
<211> LENGTH: 12
<212> TYPE: DNA
<213> ORGANISM: Homo sapiens

<400> SEQUENCE: 324
cgtcatgaat aa                                                              12

<210> SEQ ID NO 325
<211> LENGTH: 12
```

<212> TYPE: DNA
<213> ORGANISM: Homo sapiens

<400> SEQUENCE: 325
agtggcgatg ac                                                    12

<210> SEQ ID NO 326
<211> LENGTH: 12
<212> TYPE: DNA
<213> ORGANISM: Homo sapiens

<400> SEQUENCE: 326
cccctacggc ac                                                    12

<210> SEQ ID NO 327
<211> LENGTH: 12
<212> TYPE: DNA
<213> ORGANISM: Homo sapiens

<400> SEQUENCE: 327
gccaacccgc ac                                                    12

<210> SEQ ID NO 328
<211> LENGTH: 12
<212> TYPE: DNA
<213> ORGANISM: Homo sapiens

<400> SEQUENCE: 328
tgggacaccg gt                                                    12

<210> SEQ ID NO 329
<211> LENGTH: 12
<212> TYPE: DNA
<213> ORGANISM: Homo sapiens

<400> SEQUENCE: 329
ttgactgcgg cg                                                    12

<210> SEQ ID NO 330
<211> LENGTH: 12
<212> TYPE: DNA
<213> ORGANISM: Homo sapiens

<400> SEQUENCE: 330
actatgcgta gg                                                    12

<210> SEQ ID NO 331
<211> LENGTH: 12
<212> TYPE: DNA
<213> ORGANISM: Homo sapiens

<400> SEQUENCE: 331
tcacccaaag cg                                                    12

<210> SEQ ID NO 332
<211> LENGTH: 12
<212> TYPE: DNA
<213> ORGANISM: Homo sapiens

<400> SEQUENCE: 332
gcaggacgtc cg                                                    12

<210> SEQ ID NO 333

```
<211> LENGTH: 12
<212> TYPE: DNA
<213> ORGANISM: Homo sapiens

<400> SEQUENCE: 333
acaccgaaaa cg                                                          12

<210> SEQ ID NO 334
<211> LENGTH: 12
<212> TYPE: DNA
<213> ORGANISM: Homo sapiens

<400> SEQUENCE: 334
cggtgtattg ag                                                          12

<210> SEQ ID NO 335
<211> LENGTH: 12
<212> TYPE: DNA
<213> ORGANISM: Homo sapiens

<400> SEQUENCE: 335
cacgaggtat gc                                                          12

<210> SEQ ID NO 336
<211> LENGTH: 12
<212> TYPE: DNA
<213> ORGANISM: Homo sapiens

<400> SEQUENCE: 336
taaagcgacc cg                                                          12

<210> SEQ ID NO 337
<211> LENGTH: 12
<212> TYPE: DNA
<213> ORGANISM: Homo sapiens

<400> SEQUENCE: 337
cttagtcggc ca                                                          12

<210> SEQ ID NO 338
<211> LENGTH: 12
<212> TYPE: DNA
<213> ORGANISM: Homo sapiens

<400> SEQUENCE: 338
cgaaaacgtg gc                                                          12

<210> SEQ ID NO 339
<211> LENGTH: 12
<212> TYPE: DNA
<213> ORGANISM: Homo sapiens

<400> SEQUENCE: 339
cgtgccctga ac                                                          12

<210> SEQ ID NO 340
<211> LENGTH: 12
<212> TYPE: DNA
<213> ORGANISM: Homo sapiens

<400> SEQUENCE: 340
tttaccatcg aa                                                          12
```

```
<210> SEQ ID NO 341
<211> LENGTH: 12
<212> TYPE: DNA
<213> ORGANISM: Homo sapiens

<400> SEQUENCE: 341
cgtagccatg tt                                                          12

<210> SEQ ID NO 342
<211> LENGTH: 12
<212> TYPE: DNA
<213> ORGANISM: Homo sapiens

<400> SEQUENCE: 342
cccaaacggt ta                                                          12

<210> SEQ ID NO 343
<211> LENGTH: 12
<212> TYPE: DNA
<213> ORGANISM: Homo sapiens

<400> SEQUENCE: 343
gcgttatcag aa                                                          12

<210> SEQ ID NO 344
<211> LENGTH: 12
<212> TYPE: DNA
<213> ORGANISM: Homo sapiens

<400> SEQUENCE: 344
tcgatggtaa ac                                                          12

<210> SEQ ID NO 345
<211> LENGTH: 12
<212> TYPE: DNA
<213> ORGANISM: Homo sapiens

<400> SEQUENCE: 345
cgactttttg ca                                                          12

<210> SEQ ID NO 346
<211> LENGTH: 12
<212> TYPE: DNA
<213> ORGANISM: Homo sapiens

<400> SEQUENCE: 346
tcgacgactc ac                                                          12

<210> SEQ ID NO 347
<211> LENGTH: 12
<212> TYPE: DNA
<213> ORGANISM: Homo sapiens

<400> SEQUENCE: 347
acgcgtcaga ta                                                          12

<210> SEQ ID NO 348
<211> LENGTH: 12
<212> TYPE: DNA
<213> ORGANISM: Homo sapiens

<400> SEQUENCE: 348
cgtacggcac ag                                                          12
```

```
<210> SEQ ID NO 349
<211> LENGTH: 12
<212> TYPE: DNA
<213> ORGANISM: Homo sapiens

<400> SEQUENCE: 349
ctatgccgtg ca                                                          12

<210> SEQ ID NO 350
<211> LENGTH: 12
<212> TYPE: DNA
<213> ORGANISM: Homo sapiens

<400> SEQUENCE: 350
cgcgtcagat at                                                          12

<210> SEQ ID NO 351
<211> LENGTH: 12
<212> TYPE: DNA
<213> ORGANISM: Homo sapiens

<400> SEQUENCE: 351
aagatcggta gc                                                          12

<210> SEQ ID NO 352
<211> LENGTH: 12
<212> TYPE: DNA
<213> ORGANISM: Homo sapiens

<400> SEQUENCE: 352
cttcgcaagg ag                                                          12

<210> SEQ ID NO 353
<211> LENGTH: 12
<212> TYPE: DNA
<213> ORGANISM: Homo sapiens

<400> SEQUENCE: 353
gtcgtggact ac                                                          12

<210> SEQ ID NO 354
<211> LENGTH: 12
<212> TYPE: DNA
<213> ORGANISM: Homo sapiens

<400> SEQUENCE: 354
ggtcgtcatc aa                                                          12

<210> SEQ ID NO 355
<211> LENGTH: 12
<212> TYPE: DNA
<213> ORGANISM: Homo sapiens

<400> SEQUENCE: 355
gttaacagcg tg                                                          12

<210> SEQ ID NO 356
<211> LENGTH: 12
<212> TYPE: DNA
<213> ORGANISM: Homo sapiens

<400> SEQUENCE: 356
tagctaaccg tt                                                          12
```

```
<210> SEQ ID NO 357
<211> LENGTH: 12
<212> TYPE: DNA
<213> ORGANISM: Homo sapiens

<400> SEQUENCE: 357
agtaaaggcg ct                                                            12

<210> SEQ ID NO 358
<211> LENGTH: 12
<212> TYPE: DNA
<213> ORGANISM: Homo sapiens

<400> SEQUENCE: 358
ggtaatttcg tg                                                            12

<210> SEQ ID NO 359
<211> LENGTH: 15
<212> TYPE: DNA
<213> ORGANISM: Homo sapiens

<400> SEQUENCE: 359
cagaagaaga agggc                                                         15

<210> SEQ ID NO 360
<211> LENGTH: 51
<212> TYPE: DNA
<213> ORGANISM: Homo sapiens

<400> SEQUENCE: 360
ccaatgggga ggacatcgat gtcacctcca atgactaggg tggtgggcaa c                 51

<210> SEQ ID NO 361
<211> LENGTH: 15
<212> TYPE: DNA
<213> ORGANISM: Homo sapiens

<400> SEQUENCE: 361
ctctggccac tccct                                                         15

<210> SEQ ID NO 362
<211> LENGTH: 52
<212> TYPE: DNA
<213> ORGANISM: Homo sapiens

<400> SEQUENCE: 362
acatcgatgt cacctccaat gacaagcttg ctagcggtgg gcaaccacaa ac                52

<210> SEQ ID NO 363
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(25)
<223> OTHER INFORMATION: a, c, t, g, unknown or other

<400> SEQUENCE: 363
caccgnnnnn nnnnnnnnnn nnnnn                                              25
```

```
<210> SEQ ID NO 364
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(24)
<223> OTHER INFORMATION: a, c, t, g, unknown or other

<400> SEQUENCE: 364
aaacnnnnnn nnnnnnnnnn nnnnc                                         25

<210> SEQ ID NO 365
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
aacaccgggt cttcgagaag acctgtttta gagctagaaa tagcaagtta aaat         54

<210> SEQ ID NO 366
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
caaaacgggt cttcgagaag acgttttaga gctatgctgt tttgaatggt ccca         54

<210> SEQ ID NO 367
<211> LENGTH: 4104
<212> TYPE: DNA
<213> ORGANISM: Homo sapiens
<220> FEATURE:
<221> NAME/KEY: CDS
<222> LOCATION: (1)..(4104)

<400> SEQUENCE: 367 atg gac aag aag tac agc atc ggc ctg gac atc ggc acc aac tct gtg    48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc    96
Gly Trp Ala Val Ile Thr Asp Glu Tyr Lys Val Pro Ser Lys Lys Phe
            20                  25                  30 aag gtg ctg ggc aac acc gac cgg cac agc atc aag aag aac ctg atc   144
Lys Val Leu Gly Asn Thr Asp Arg His Ser Ile Lys Lys Asn Leu Ile
        35                  40                  45 gga gcc ctg ctg ttc gac agc ggc gaa aca gcc gag gcc acc cgg ctg   192
Gly Ala Leu Leu Phe Asp Ser Gly Glu Thr Ala Glu Ala Thr Arg Leu
    50                  55                  60 aag aga acc gcc aga aga aga tac acc aga cgg aag aac cgg atc tgc   240
Lys Arg Thr Ala Arg Arg Arg Tyr Thr Arg Arg Lys Asn Arg Ile Cys
65                  70                  75                  80 tat ctg caa gag atc ttc agc aac gag atg gcc aag gtg gac gac agc   288
Tyr Leu Gln Glu Ile Phe Ser Asn Glu Met Ala Lys Val Asp Asp Ser
                85                  90                  95 ttc ttc cac aga ctg gaa gag tcc ttc ctg gtg gaa gag gat aag aag   336
Phe Phe His Arg Leu Glu Glu Ser Phe Leu Val Glu Glu Asp Lys Lys
```

```
              100                 105                 110
cac gag cgg cac ccc atc ttc ggc aac atc gtg gac gag gtg gcc tac    384
His Glu Arg His Pro Ile Phe Gly Asn Ile Val Asp Glu Val Ala Tyr
        115                 120                 125 cac gag aag tac ccc acc atc tac cac ctg aga aag aaa ctg gtg gac    432
His Glu Lys Tyr Pro Thr Ile Tyr His Leu Arg Lys Lys Leu Val Asp
    130                 135                 140 agc acc gac aag gcc gac ctg cgg ctg atc tat ctg gcc ctg gcc cac    480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc    528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac    576
Asp Asn Ser Asp Val Asp Lys Leu Phe Ile Gln Leu Val Gln Thr Tyr
            180                 185                 190 aac cag ctg ttc gag gaa aac ccc atc aac gcc agc ggc gtg gac gcc    624
Asn Gln Leu Phe Glu Glu Asn Pro Ile Asn Ala Ser Gly Val Asp Ala
        195                 200                 205 aag gcc atc ctg tct gcc aga ctg agc aag agc aga cgg ctg gaa aat    672
Lys Ala Ile Leu Ser Ala Arg Leu Ser Lys Ser Arg Arg Leu Glu Asn
    210                 215                 220 ctg atc gcc cag ctg ccc ggc gag aag aag aat ggc ctg ttc ggc aac    720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc    768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac    816
Asp Leu Ala Glu Asp Ala Lys Leu Gln Leu Ser Lys Asp Thr Tyr Asp
            260                 265                 270 gac gac ctg gac aac ctg ctg gcc cag atc ggc gac cag tac gcc gac    864
Asp Asp Leu Asp Asn Leu Leu Ala Gln Ile Gly Asp Gln Tyr Ala Asp
        275                 280                 285 ctg ttt ctg gcc gcc aag aac ctg tcc gac gcc atc ctg ctg agc gac    912
Leu Phe Leu Ala Ala Lys Asn Leu Ser Asp Ala Ile Leu Leu Ser Asp
    290                 295                 300 atc ctg aga gtg aac acc gag atc acc aag gcc ccc ctg agc gcc tct    960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa   1008
Met Ile Lys Arg Tyr Asp Glu His His Gln Asp Leu Thr Leu Leu Lys
                325                 330                 335 gct ctc gtg cgg cag cag ctg cct gag aag tac aaa gag att ttc ttc   1056
Ala Leu Val Arg Gln Gln Leu Pro Glu Lys Tyr Lys Glu Ile Phe Phe
            340                 345                 350 gac cag agc aag aac ggc tac gcc ggc tac att gac ggc gga gcc agc   1104
Asp Gln Ser Lys Asn Gly Tyr Ala Gly Tyr Ile Asp Gly Gly Ala Ser
        355                 360                 365 cag gaa gag ttc tac aag ttc atc aag ccc atc ctg gaa aag atg gac   1152
Gln Glu Glu Phe Tyr Lys Phe Ile Lys Pro Ile Leu Glu Lys Met Asp
    370                 375                 380 ggc acc gag gaa ctg ctc gtg aag ctg aac aga gag gac ctg ctg cgg   1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg   1248
Lys Gln Arg Thr Phe Asp Asn Gly Ser Ile Pro His Gln Ile His Leu
                405                 410                 415 gga gag ctg cac gcc att ctg cgg cgg cag gaa gat ttt tac cca ttc   1296
```

|  |  |  |  |  |  |  |  |  |  |  |  |  |  |
|---|---|---|---|---|---|---|---|---|---|---|---|---|---|
| Gly | Glu | Leu | His | Ala | Ile | Leu | Arg | Arg | Gln | Glu | Asp | Phe | Tyr | Pro | Phe |
|  |  |  | 420 |  |  |  | 425 |  |  |  | 430 |  |  |

```
ctg aag gac aac cgg gaa aag atc gag aag atc ctg acc ttc cgc atc    1344
Leu Lys Asp Asn Arg Glu Lys Ile Glu Lys Ile Leu Thr Phe Arg Ile
        435                 440                 445 ccc tac tac gtg ggc cct ctg gcc agg gga aac agc aga ttc gcc tgg    1392
Pro Tyr Tyr Val Gly Pro Leu Ala Arg Gly Asn Ser Arg Phe Ala Trp
450                 455                 460 atg acc aga aag agc gag gaa acc atc acc ccc tgg aac ttc gag gaa    1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc    1488
Val Val Asp Lys Gly Ala Ser Ala Gln Ser Phe Ile Glu Arg Met Thr
        485                 490                 495 aac ttc gat aag aac ctg ccc aac gag aag gtg ctg ccc aag cac agc    1536
Asn Phe Asp Lys Asn Leu Pro Asn Glu Lys Val Leu Pro Lys His Ser
            500                 505                 510 ctg ctg tac gag tac ttc acc gtg tat aac gag ctg acc aaa gtg aaa    1584
Leu Leu Tyr Glu Tyr Phe Thr Val Tyr Asn Glu Leu Thr Lys Val Lys
                515                 520                 525 tac gtg acc gag gga atg aga aag ccc gcc ttc ctg agc ggc gag cag    1632
Tyr Val Thr Glu Gly Met Arg Lys Pro Ala Phe Leu Ser Gly Glu Gln
530                 535                 540 aaa aag gcc atc gtg gac ctg ctg ttc aag acc aac cgg aaa gtg acc    1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac    1728
Val Lys Gln Leu Lys Glu Asp Tyr Phe Lys Lys Ile Glu Cys Phe Asp
            565                 570                 575 tcc gtg gaa atc tcc ggc gtg gaa gat cgg ttc aac gcc tcc ctg ggc    1776
Ser Val Glu Ile Ser Gly Val Glu Asp Arg Phe Asn Ala Ser Leu Gly
                580                 585                 590 aca tac cac gat ctg ctg aaa att atc aag gac aag gac ttc ctg gac    1824
Thr Tyr His Asp Leu Leu Lys Ile Ile Lys Asp Lys Asp Phe Leu Asp
595                 600                 605 aat gag gaa aac gag gac att ctg gaa gat atc gtg ctg acc ctg aca    1872
Asn Glu Glu Asn Glu Asp Ile Leu Glu Asp Ile Val Leu Thr Leu Thr
610                 615                 620 ctg ttt gag gac aga gag atg atc gag gaa cgg ctg aaa acc tat gcc    1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac    1968
His Leu Phe Asp Asp Lys Val Met Lys Gln Leu Lys Arg Arg Arg Tyr
            645                 650                 655 acc ggc tgg ggc agg ctg agc cgg aag ctg atc aac ggc atc cgg gac    2016
Thr Gly Trp Gly Arg Leu Ser Arg Lys Leu Ile Asn Gly Ile Arg Asp
                660                 665                 670 aag cag tcc ggc aag aca atc ctg gat ttc ctg aag tcc gac ggc ttc    2064
Lys Gln Ser Gly Lys Thr Ile Leu Asp Phe Leu Lys Ser Asp Gly Phe
675                 680                 685 gcc aac aga aac ttc atg cag ctg atc cac gac gac agc ctg acc ttt    2112
Ala Asn Arg Asn Phe Met Gln Leu Ile His Asp Asp Ser Leu Thr Phe
690                 695                 700 aaa gag gac atc cag aaa gcc cag gtg tcc ggc cag ggc gat agc ctg    2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc    2208
His Glu His Ile Ala Asn Leu Ala Gly Ser Pro Ala Ile Lys Lys Gly
            725                 730                 735
```

-continued

| | |
|---|---|
| atc ctg cag aca gtg aag gtg gtg gac gag ctc gtg aaa gtg atg ggc<br>Ile Leu Gln Thr Val Lys Val Val Asp Glu Leu Val Lys Val Met Gly<br>740                               745                          750 | 2256 |
| cgg cac aag ccc gag aac atc gtg atc gcc atg gcc aga gag aac cag<br>Arg His Lys Pro Glu Asn Ile Val Ile Ala Met Ala Arg Glu Asn Gln<br>      755                       760                       765 | 2304 |
| acc acc cag aag gga cag aag aac agc cgc gag aga atg aag cgg atc<br>Thr Thr Gln Lys Gly Gln Lys Asn Ser Arg Glu Arg Met Lys Arg Ile<br>770                         775                      780 | 2352 |
| gaa gag ggc atc aaa gag ctg ggc agc cag atc ctg aaa gaa cac ccc<br>Glu Glu Gly Ile Lys Glu Leu Gly Ser Gln Ile Leu Lys Glu His Pro<br>785                         790                      795                     800 | 2400 |
| gtg gaa aac acc cag ctg cag aac gag aag ctg tac ctg tac tac ctg<br>Val Glu Asn Thr Gln Leu Gln Asn Glu Lys Leu Tyr Leu Tyr Tyr Leu<br>                 805                       810                      815 | 2448 |
| cag aat ggg cgg gat atg tac gtg gac cag gaa ctg gac atc aac cgg<br>Gln Asn Gly Arg Asp Met Tyr Val Asp Gln Glu Leu Asp Ile Asn Arg<br>820                         825                      830 | 2496 |
| ctg tcc gac tac gat gtg gac gcc atc gtg cct cag agc ttt ctg aag<br>Leu Ser Asp Tyr Asp Val Asp Ala Ile Val Pro Gln Ser Phe Leu Lys<br>      835                       840                       845 | 2544 |
| gac gac tcc atc gac gcc aag gtg ctg acc aga agc gac aag gcc cgg<br>Asp Asp Ser Ile Asp Ala Lys Val Leu Thr Arg Ser Asp Lys Ala Arg<br>850                         855                      860 | 2592 |
| ggc aag agc gac aac gtg ccc tcc gaa gag gtc gtg aag aag atg aag<br>Gly Lys Ser Asp Asn Val Pro Ser Glu Glu Val Val Lys Lys Met Lys<br>865                         870                      875                     880 | 2640 |
| aac tac tgg cgg cag ctg ctg aac gcc aag ctg att acc cag aga aag<br>Asn Tyr Trp Arg Gln Leu Leu Asn Ala Lys Leu Ile Thr Gln Arg Lys<br>                 885                       890                      895 | 2688 |
| ttc gac aat ctg acc aag gcc gag aga ggc ggc ctg agc gaa ctg gat<br>Phe Asp Asn Leu Thr Lys Ala Glu Arg Gly Gly Leu Ser Glu Leu Asp<br>900                         905                      910 | 2736 |
| aag gcc ggc ttc atc aag aga cag ctg gtg gaa acc cgg cag atc aca<br>Lys Ala Gly Phe Ile Lys Arg Gln Leu Val Glu Thr Arg Gln Ile Thr<br>      915                       920                       925 | 2784 |
| aag cac gtg gca cag atc ctg gac tcc cgg atg aac act aag tac gac<br>Lys His Val Ala Gln Ile Leu Asp Ser Arg Met Asn Thr Lys Tyr Asp<br>930                         935                      940 | 2832 |
| gag aat gac aag ctg atc cgg gaa gtg aaa gtg atc acc ctg aag tcc<br>Glu Asn Asp Lys Leu Ile Arg Glu Val Lys Val Ile Thr Leu Lys Ser<br>945                         950                      955                     960 | 2880 |
| aag ctg gtg tcc gat ttc cgg aag gat ttc cag ttt tac aaa gtg cgc<br>Lys Leu Val Ser Asp Phe Arg Lys Asp Phe Gln Phe Tyr Lys Val Arg<br>                 965                       970                      975 | 2928 |
| gag atc aac aac tac cac cac gcc cac gcc gcc tac ctg aac gcc gtc<br>Glu Ile Asn Asn Tyr His His Ala His Ala Ala Tyr Leu Asn Ala Val<br>980                         985                      990 | 2976 |
| gtg gga acc gcc ctg atc aaa aag  tac cct aag ctg gaa  agc gag ttc<br>Val Gly Thr Ala Leu Ile Lys Lys  Tyr Pro Lys Leu Glu  Ser Glu Phe<br>      995                         1000                   1005 | 3024 |
| gtg tac ggc gac tac aag gtg  tac gac gtg cgg aag  atg atc gcc<br>Val Tyr Gly Asp Tyr Lys Val  Tyr Asp Val Arg Lys  Met Ile Ala<br>   1010                       1015                 1020 | 3069 |
| aag agc gag cag gaa atc ggc  aag gct acc gcc aag  tac ttc ttc<br>Lys Ser Glu Gln Glu Ile Gly  Lys Ala Thr Ala Lys  Tyr Phe Phe<br>   1025                       1030                 1035 | 3114 |
| tac agc aac atc atg aac ttt  ttc aag acc gag att  acc ctg gcc<br>Tyr Ser Asn Ile Met Asn Phe  Phe Lys Thr Glu Ile  Thr Leu Ala<br>   1040                       1045                 1050 | 3159 |

-continued

```
aac ggc gag atc cgg aag cgg cct ctg atc gag aca aac ggc gaa      3204
Asn Gly Glu Ile Arg Lys Arg Pro Leu Ile Glu Thr Asn Gly Glu
    1055            1060                1065 acc ggg gag atc gtg tgg gat aag ggc cgg gat ttt gcc acc gtg      3249
Thr Gly Glu Ile Val Trp Asp Lys Gly Arg Asp Phe Ala Thr Val
1070            1075                1080 cgg aaa gtg ctg agc atg ccc caa gtg aat atc gtg aaa aag acc      3294
Arg Lys Val Leu Ser Met Pro Gln Val Asn Ile Val Lys Lys Thr
1085            1090                1095 gag gtg cag aca ggc ggc ttc agc aaa gag tct atc ctg ccc aag      3339
Glu Val Gln Thr Gly Gly Phe Ser Lys Glu Ser Ile Leu Pro Lys
1100            1105                1110 agg aac agc gat aag ctg atc gcc aga aag aag gac tgg gac cct      3384
Arg Asn Ser Asp Lys Leu Ile Ala Arg Lys Lys Asp Trp Asp Pro
    1115            1120                1125 aag aag tac ggc ggc ttc gac agc ccc acc gtg gcc tat tct gtg      3429
Lys Lys Tyr Gly Gly Phe Asp Ser Pro Thr Val Ala Tyr Ser Val
    1130            1135                1140 ctg gtg gtg gcc aaa gtg gaa aag ggc aag tcc aag aaa ctg aag      3474
Leu Val Val Ala Lys Val Glu Lys Gly Lys Ser Lys Lys Leu Lys
    1145            1150                1155 agt gtg aaa gag ctg ctg ggg atc acc atc atg gaa aga agc agc      3519
Ser Val Lys Glu Leu Leu Gly Ile Thr Ile Met Glu Arg Ser Ser
    1160            1165                1170 ttc gag aag aat ccc atc gac ttt ctg gaa gcc aag ggc tac aaa      3564
Phe Glu Lys Asn Pro Ile Asp Phe Leu Glu Ala Lys Gly Tyr Lys
    1175            1180                1185 gaa gtg aaa aag gac ctg atc atc aag ctg cct aag tac tcc ctg      3609
Glu Val Lys Lys Asp Leu Ile Ile Lys Leu Pro Lys Tyr Ser Leu
    1190            1195                1200 ttc gag ctg gaa aac ggc cgg aag aga atg ctg gcc tct gcc ggc      3654
Phe Glu Leu Glu Asn Gly Arg Lys Arg Met Leu Ala Ser Ala Gly
    1205            1210                1215 gaa ctg cag aag gga aac gaa ctg gcc ctg ccc tcc aaa tat gtg      3699
Glu Leu Gln Lys Gly Asn Glu Leu Ala Leu Pro Ser Lys Tyr Val
    1220            1225                1230 aac ttc ctg tac ctg gcc agc cac tat gag aag ctg aag ggc tcc      3744
Asn Phe Leu Tyr Leu Ala Ser His Tyr Glu Lys Leu Lys Gly Ser
    1235            1240                1245 ccc gag gat aat gag cag aaa cag ctg ttt gtg gaa cag cac aag      3789
Pro Glu Asp Asn Glu Gln Lys Gln Leu Phe Val Glu Gln His Lys
    1250            1255                1260 cac tac ctg gac gag atc atc gag cag atc agc gag ttc tcc aag      3834
His Tyr Leu Asp Glu Ile Ile Glu Gln Ile Ser Glu Phe Ser Lys
    1265            1270                1275 aga gtg atc ctg gcc gac gct aat ctg gac aaa gtg ctg tcc gcc      3879
Arg Val Ile Leu Ala Asp Ala Asn Leu Asp Lys Val Leu Ser Ala
    1280            1285                1290 tac aac aag cac cgg gat aag ccc atc aga gag cag gcc gag aat      3924
Tyr Asn Lys His Arg Asp Lys Pro Ile Arg Glu Gln Ala Glu Asn
    1295            1300                1305 atc atc cac ctg ttt acc ctg acc aat ctg gga gcc cct gcc gcc      3969
Ile Ile His Leu Phe Thr Leu Thr Asn Leu Gly Ala Pro Ala Ala
    1310            1315                1320 ttc aag tac ttt gac acc acc atc gac cgg aag agg tac acc agc      4014
Phe Lys Tyr Phe Asp Thr Thr Ile Asp Arg Lys Arg Tyr Thr Ser
    1325            1330                1335 acc aaa gag gtg ctg gac gcc acc ctg atc cac cag agc atc acc      4059
Thr Lys Glu Val Leu Asp Ala Thr Leu Ile His Gln Ser Ile Thr
```

```
                   1340              1345              1350 ggc ctg tac gag aca cgg atc gac ctg tct cag ctg gga ggc gac     4104
   Gly Leu Tyr Glu Thr Arg Ile Asp Leu Ser Gln Leu Gly Gly Asp
       1355              1360              1365
```

<210> SEQ ID NO 368
<211> LENGTH: 1368
<212> TYPE: PRT
<213> ORGANISM: Homo sapiens

<400> SEQUENCE: 368

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350
```

-continued

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Ala Met Ala Arg Glu Asn Gln
        755                 760                 765

```
Thr Thr Gln Lys Gly Gln Lys Asn Ser Arg Glu Arg Met Lys Arg Ile
770             775                 780
Glu Glu Gly Ile Lys Glu Leu Gly Ser Gln Ile Leu Lys Glu His Pro
785             790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp Ala Ile Val Pro Gln Ser Phe Leu Lys
                835                 840                 845
Asp Asp Ser Ile Asp Ala Lys Val Leu Thr Arg Ser Asp Lys Ala Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Ala Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
```

```
                1175                1180                1185

Glu Val Lys Lys Asp Leu Ile Ile Lys Leu Pro Lys Tyr Ser Leu
            1190                1195                1200

Phe Glu Leu Glu Asn Gly Arg Lys Arg Met Leu Ala Ser Ala Gly
            1205                1210                1215

Glu Leu Gln Lys Gly Asn Glu Leu Ala Leu Pro Ser Lys Tyr Val
            1220                1225                1230

Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys
            1250                1255                1260

His Tyr Leu Asp Glu Ile Ile Glu Gln Ile Ser Glu Phe Ser Lys
            1265                1270                1275

Arg Val Ile Leu Ala Asp Ala Asn Leu Asp Lys Val Leu Ser Ala
            1280                1285                1290

Tyr Asn Lys His Arg Asp Lys Pro Ile Arg Glu Gln Ala Glu Asn
            1295                1300                1305

Ile Ile His Leu Phe Thr Leu Thr Asn Leu Gly Ala Pro Ala Ala
            1310                1315                1320

Phe Lys Tyr Phe Asp Thr Thr Ile Asp Arg Lys Arg Tyr Thr Ser
            1325                1330                1335

Thr Lys Glu Val Leu Asp Ala Thr Leu Ile His Gln Ser Ile Thr
            1340                1345                1350

Gly Leu Tyr Glu Thr Arg Ile Asp Leu Ser Gln Leu Gly Gly Asp
            1355                1360                1365

<210> SEQ ID NO 369
<211> LENGTH: 26
<212> TYPE: DNA
<213> ORGANISM: Homo sapiens

<400> SEQUENCE: 369
tagggttagg ggccccaggc cggggt                                         26

<210> SEQ ID NO 370
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 370

His His His His His His
1               5

<210> SEQ ID NO 371
<211> LENGTH: 57
<212> TYPE: DNA
<213> ORGANISM: Homo sapiens
<220> FEATURE:
<221> NAME/KEY: CDS
<222> LOCATION: (1)..(57)

<400> SEQUENCE: 371 ggc acc att aaa gaa aat atc att ggt gtt tcc tat gat gaa tat aga    48
Gly Thr Ile Lys Glu Asn Ile Ile Gly Val Ser Tyr Asp Glu Tyr Arg
1               5                   10                  15 tac aga agc                                                         57
Tyr Arg Ser
```

<210> SEQ ID NO 372
<211> LENGTH: 19
<212> TYPE: PRT
<213> ORGANISM: Homo sapiens

<400> SEQUENCE: 372

Gly Thr Ile Lys Glu Asn Ile Ile Gly Val Ser Tyr Asp Glu Tyr Arg
1               5                   10                  15

Tyr Arg Ser

<210> SEQ ID NO 373
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(48)

<400> SEQUENCE: 373 att aaa gaa aat atc att ggc ttt gtt tcc tat gat gaa tat aga tac    48
Ile Lys Glu Asn Ile Ile Gly Phe Val Ser Tyr Asp Glu Tyr Arg Tyr
1               5                   10                  15

<210> SEQ ID NO 374
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Ile Lys Glu Asn Ile Ile Gly Phe Val Ser Tyr Asp Glu Tyr Arg Tyr
1               5                   10                  15

<210> SEQ ID NO 375
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(48)
<223> OTHER INFORMATION: a, c, t, g, unknown or other

<400> SEQUENCE: 375
ccnnnnnnnn nnnnnnnnnn nnnnnnnnnn nnnnnnnnnn nnnnnnnngg             50

<210> SEQ ID NO 376
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(44)
<223> OTHER INFORMATION: a, c, t, g, unknown or other

<400> SEQUENCE: 376
ccnnnnnnnn nnnnnnnnnn nnnnnnnnnn nnnnnnnnnn nnnngg                 46

<210> SEQ ID NO 377
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(40)
<223> OTHER INFORMATION: a, c, t, g, unknown or other

<400> SEQUENCE: 377
ccnnnnnnnn nnnnnnnnnn nnnnnnnnnn nnnnnnnnnn gg                              42

<210> SEQ ID NO 378
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(36)
<223> OTHER INFORMATION: a, c, t, g, unknown or other

<400> SEQUENCE: 378
ccnnnnnnnn nnnnnnnnnn nnnnnnnnnn nnnnnngg                                   38

<210> SEQ ID NO 379
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(32)
<223> OTHER INFORMATION: a, c, t, g, unknown or other

<400> SEQUENCE: 379
ccnnnnnnnn nnnnnnnnnn nnnnnnnnnn nngg                                       34

<210> SEQ ID NO 380
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(28)
<223> OTHER INFORMATION: a, c, t, g, unknown or other

<400> SEQUENCE: 380
ccnnnnnnnn nnnnnnnnnn nnnnnnnngg                                            30

<210> SEQ ID NO 381
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (3)..(24)
<223> OTHER INFORMATION: a, c, t, g, unknown or other

<400> SEQUENCE: 381
ccnnnnnnnn nnnnnnnnnn nnnngg                                      26

<210> SEQ ID NO 382
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(20)
<223> OTHER INFORMATION: a, c, t, g, unknown or other

<400> SEQUENCE: 382
ccnnnnnnnn nnnnnnnnnn gg                                          22

<210> SEQ ID NO 383
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(16)
<223> OTHER INFORMATION: a, c, t, g, unknown or other

<400> SEQUENCE: 383
ccnnnnnnnn nnnnnngg                                               18

<210> SEQ ID NO 384
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(14)
<223> OTHER INFORMATION: a, c, t, g, unknown or other

<400> SEQUENCE: 384
ccnnnnnnnn nnnngg                                                 16

<210> SEQ ID NO 385
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(13)
<223> OTHER INFORMATION: a, c, t, g, unknown or other

<400> SEQUENCE: 385
ccnnnnnnnn nnngg                                                  15

<210> SEQ ID NO 386
<211> LENGTH: 14
<212> TYPE: DNA
```

-continued

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(12)
<223> OTHER INFORMATION: a, c, t, g, unknown or other

<400> SEQUENCE: 386
ccnnnnnnnn nngg                                                        14

<210> SEQ ID NO 387
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(11)
<223> OTHER INFORMATION: a, c, t, g, unknown or other

<400> SEQUENCE: 387
ccnnnnnnnn ngg                                                         13

<210> SEQ ID NO 388
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(10)
<223> OTHER INFORMATION: a, c, t, g, unknown or other

<400> SEQUENCE: 388
ccnnnnnnnn gg                                                          12

<210> SEQ ID NO 389
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, c, t, g, unknown or other

<400> SEQUENCE: 389
ccnnnnnnng g                                                           11

<210> SEQ ID NO 390
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: a, c, t, g, unknown or other

<400> SEQUENCE: 390

```
ccnnnnnngg                                                                 10

<210> SEQ ID NO 391
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(10)
<223> OTHER INFORMATION: a, c, t, g, unknown or other

<400> SEQUENCE: 391
ggnnnnnnnn cc                                                              12

<210> SEQ ID NO 392
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
aaaaaaagca ccgactcggt gccactttt caagttgata acggactagc cttattttaa          60
cttgctattt ctagctctaa aactcacatc aaccggtggc gcaggtgttt cgtcctttcc        120
acaag                                                                     125

<210> SEQ ID NO 393
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
aaaaaaagca ccgactcggt gccactttt caagttgata acggactagc cttattttaa          60
cttgctattt ctagctctaa aactcacatc aaccggtggc gcaggtgttt cgtcctttcc        120
acaag                                                                     125

<210> SEQ ID NO 394
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
aaaaaaagca ccgactcggt gccactttt caagttgata acggactagc cttattttaa          60
cttgctattt ctagctctaa aacgaggaca aagtacaaac ggcggtgttt cgtcctttcc        120
acaag                                                                     125

<210> SEQ ID NO 395
<211> LENGTH: 125
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 395
aaaaaaagca ccgactcggt gccactttt caagttgata acggactagc cttattttaa      60
cttgctattt ctagctctaa aacgaggaca aagtacaaac ggcggtgttt cgtccttcc     120 acaag                                                                125

<210> SEQ ID NO 396
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
aaaaaaagca ccgactcggt gccactttt caagttgata acggactagc cttattttaa      60
cttgctattt ctagctctaa aacgtggcgc attgccacga agcggtgttt cgtccttcc     120 acaag                                                                125

<210> SEQ ID NO 397
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
aaaaaaagca ccgactcggt gccactttt caagttgata acggactagc cttattttaa      60
cttgctattt ctagctctaa aaccgagggc agagtgctgc ttgggtgttt cgtccttcc     120 acaag                                                                125

<210> SEQ ID NO 398
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
aaaaaaagca ccgactcggt gccactttt caagttgata acggactagc cttattttaa      60
cttgctattt ctagctctaa aacgagtccg agcagaagaa gaaggtgttt cgtccttcc     120 acaag                                                                125

<210> SEQ ID NO 399
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
aaaaaaagca ccgactcggt gccactttt caagttgata acggactagc cttattttaa      60
cttgctattt ctagctctaa aacgaggaca aagtacaaac ggcggtgttt cgtccttcc     120 acaag                                                                125

<210> SEQ ID NO 400
<211> LENGTH: 125
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
aaaaaaagca ccgactcggt gccactttt caagttgata acggactagc cttattttaa    60
cttgctattt ctagctctaa aacagcagaa gaagaagggc tccggtgttt cgtcctttcc  120
acaag                                                               125

<210> SEQ ID NO 401
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
aaaaaaagca ccgactcggt gccactttt caagttgata acggactagc cttattttaa    60
cttgctattt ctagctctaa aactcacatc aaccggtggc gcaggtgttt cgtcctttcc  120
acaag                                                               125

<210> SEQ ID NO 402
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
aaaaaaagca ccgactcggt gccactttt caagttgata acggactagc cttattttaa    60
cttgctattt ctagctctaa aaccctggc ccaggtgaag gtgggtgttt cgtcctttcc   120
acaag                                                               125

<210> SEQ ID NO 403
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
aaaaaaagca ccgactcggt gccactttt caagttgata acggactagc cttattttaa    60
cttgctattt ctagctctaa aactccctcc ctggcccagg tgaggtgttt cgtcctttcc  120
acaag                                                               125

<210> SEQ ID NO 404
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
aaaaaaagca ccgactcggt gccactttt caagttgata acggactagc cttattttaa    60
cttgctattt ctagctctaa aacgaaccgg aggacaaagt acaggtgttt cgtcctttcc  120
```

```
acaag                                                                  125

<210> SEQ ID NO 405
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
aaaaaaagca ccgactcggt gccactttt caagttgata acggactagc cttattttaa      60
cttgctattt ctagctctaa aacaggtgaa ggtgtggttc cagggtgttt cgtcctttcc    120
acaag                                                                 125

<210> SEQ ID NO 406
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
aaaaaaagca ccgactcggt gccactttt caagttgata acggactagc cttattttaa      60
cttgctattt ctagctctaa aacggtgaag gtgtggttcc agaggtgttt cgtcctttcc    120
acaag                                                                 125

<210> SEQ ID NO 407
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
aaaaaaagca ccgactcggt gccactttt caagttgata acggactagc cttattttaa      60
cttgctattt ctagctctaa aacgaaccgg aggacaaagt acaggtgttt cgtcctttcc    120
acaag                                                                 125

<210> SEQ ID NO 408
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
aaaaaaagca ccgactcggt gccactttt caagttgata acggactagc cttattttaa      60
cttgctattt ctagctctaa aaccctggc ccaggtgaag gtgggtgttt cgtcctttcc     120
acaag                                                                 125

<210> SEQ ID NO 409
<211> LENGTH: 125
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 409

```
aaaaaaagca ccgactcggt gccactttt caagttgata acggactagc cttattttaa    60
cttgctattt ctagctctaa aacaggtgaa ggtgtggttc cagggtgttt cgtcctttcc   120
acaag                                                              125
```

<210> SEQ ID NO 410
<211> LENGTH: 125
<212> TYPE: DNA
<213> ORGANISM: Artificial Sequence
<220> FEATURE:
<223> OTHER INFORMATION: Description of Artificial Sequence: Synthetic primer

<400> SEQUENCE: 410

```
aaaaaaagca ccgactcggt gccactttt caagttgata acggactagc cttattttaa    60
cttgctattt ctagctctaa aacgaggaca agtacaaac ggcggtgttt cgtcctttcc    120
acaag                                                              125
```

<210> SEQ ID NO 411
<211> LENGTH: 125
<212> TYPE: DNA
<213> ORGANISM: Artificial Sequence
<220> FEATURE:
<223> OTHER INFORMATION: Description of Artificial Sequence: Synthetic primer

<400> SEQUENCE: 411

```
aaaaaaagca ccgactcggt gccactttt caagttgata acggactagc cttattttaa    60
cttgctattt ctagctctaa aacgggaggg aggggcacag atgggtgttt cgtcctttcc   120
acaag                                                              125
```

<210> SEQ ID NO 412
<211> LENGTH: 125
<212> TYPE: DNA
<213> ORGANISM: Artificial Sequence
<220> FEATURE:
<223> OTHER INFORMATION: Description of Artificial Sequence: Synthetic primer

<400> SEQUENCE: 412

```
aaaaaaagca ccgactcggt gccactttt caagttgata acggactagc cttattttaa    60
cttgctattt ctagctctaa aaccaccttc acctgggcca gggggtgttt cgtcctttcc   120
acaag                                                              125
```

<210> SEQ ID NO 413
<211> LENGTH: 125
<212> TYPE: DNA
<213> ORGANISM: Artificial Sequence
<220> FEATURE:
<223> OTHER INFORMATION: Description of Artificial Sequence: Synthetic primer

<400> SEQUENCE: 413

```
aaaaaaagca ccgactcggt gccactttt caagttgata acggactagc cttattttaa    60
cttgctattt ctagctctaa aacaccctag tcattggagg tgaggtgttt cgtcctttcc   120
acaag                                                              125
```

<210> SEQ ID NO 414

<210> SEQ ID NO 414
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
aaaaaaagca ccgactcggt gccactttt caagttgata acggactagc cttatttaa    60 cttgctattt ctagctctaa aaccagagca gccactgggg cctggtgttt cgtcctttcc   120
acaag                                                              125

<210> SEQ ID NO 415
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
aaaaaaagca ccgactcggt gccactttt caagttgata acggactagc cttatttaa    60 cttgctattt ctagctctaa aaccaccttc acctgggcca ggggtgttt cgtcctttcc   120 acaag                                                              125

<210> SEQ ID NO 416
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
aaaaaaagca ccgactcggt gccactttt caagttgata acggactagc cttatttaa    60 cttgctattt ctagctctaa aaccccatt ggcctgcttc gtgggtgttt cgtcctttcc   120
acaag                                                              125

<210> SEQ ID NO 417
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
aaaaaaagca ccgactcggt gccactttt caagttgata acggactagc cttatttaa    60 cttgctattt ctagctctaa aacattggcc tgcttcgtgg caaggtgttt cgtcctttcc   120
acaag                                                              125

<210> SEQ ID NO 418
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
aaaaaaagca ccgactcggt gccactttt caagttgata acggactagc cttatttaa    60 cttgctattt ctagctctaa aactcctcct ccagcttctg ccgggtgttt cgtccttcc    120 acaag                                                               125

<210> SEQ ID NO 419
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
aaaaaaagca ccgactcggt gccactttt caagttgata acggactagc cttattttaa    60
cttgctattt ctagctctaa aaccctccag cttctgccgt ttgggtgttt cgtccttcc    120 acaag                                                               125

<210> SEQ ID NO 420
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
aaaaaaagca ccgactcggt gccactttt caagttgata acggactagc cttattttaa    60
cttgctattt ctagctctaa aacattggcc tgcttcgtgg caaggtgttt cgtccttcc    120 acaag                                                               125

<210> SEQ ID NO 421
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
aaaaaaagca ccgactcggt gccactttt caagttgata acggactagc cttattttaa    60
cttgctattt ctagctctaa aacgcagcaa gcagcactct gccggtgttt cgtccttcc    120 acaag                                                               125

<210> SEQ ID NO 422
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
aaaaaaagca ccgactcggt gccactttt caagttgata acggactagc cttattttaa    60
cttgctattt ctagctctaa aacttcttct tctgctcgga ctcggtgttt cgtccttcc    120 acaag                                                               125

<210> SEQ ID NO 423
<211> LENGTH: 125
<212> TYPE: DNA
<213> ORGANISM: Artificial Sequence
<220> FEATURE:
<223> OTHER INFORMATION: Description of Artificial Sequence: Synthetic primer

<400> SEQUENCE: 423
aaaaaaagca ccgactcggt gccactttt caagttgata acggactagc cttattttaa    60
cttgctattt ctagctctaa aacaccggag gacaaagtac aaggtgtttt cgtcctttcc   120
acaag                                                              125

<210> SEQ ID NO 424
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
aaaaaaagca ccgactcggt gccactttt caagttgata acggactagc cttattttaa    60
cttgctattt ctagctctaa aactcttctt ctgctcggac tcaggtgttt cgtcctttcc   120
acaag                                                              125

<210> SEQ ID NO 425
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
aaaaaaagca ccgactcggt gccactttt caagttgata acggactagc cttattttaa    60
cttgctattt ctagctctaa aacgttgatg tgatgggagc cctggtgttt cgtcctttcc   120
acaag                                                              125

<210> SEQ ID NO 426
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
aaaaaaagca ccgactcggt gccactttt caagttgata acggactagc cttattttaa    60
cttgctattt ctagctctaa aacgggccag ggagggaggg gcaggtgttt cgtcctttcc   120
acaag                                                              125

<210> SEQ ID NO 427
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 427
aaaaaaagca ccgactcggt gccactttt caagttgata acggactagc cttattttaa    60
cttgctattt ctagctctaa aacgggaggg aggggcacag atgggtgttt cgtcctttcc   120
acaag                                                              125

-continued

<210> SEQ ID NO 428
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 428
aaaaaaagca ccgactcggt gccactttt caagttgata acggactagc cttattttaa    60
cttgctattt ctagctctaa aacccggttc tggaaccaca cctggtgttt cgtccttcc   120 acaag                                                              125

<210> SEQ ID NO 429
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
aaaaaaagca ccgactcggt gccactttt caagttgata acggactagc cttattttaa    60
cttgctattt ctagctctaa aactcacctg ggccagggag ggaggtgttt cgtccttcc   120 acaag                                                              125

<210> SEQ ID NO 430
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
aaaaaaagca ccgactcggt gccactttt caagttgata acggactagc cttattttaa    60
cttgctattt ctagctctaa aactcacctg ggccagggag ggaggtgttt cgtccttcc   120 acaag                                                              125

<210> SEQ ID NO 431
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 431
aaaaaaagca ccgactcggt gccactttt caagttgata acggactagc cttattttaa    60
cttgctattt ctagctctaa aacgttctgg aaccacacct tcaggtgttt cgtccttcc   120 acaag                                                              125

<210> SEQ ID NO 432
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
aaaaaaagca ccgactcggt gccactttt caagttgata acggactagc cttattttaa    60

```
cttgctattt ctagctctaa aacgggaggg aggggcacag atgggtgttt cgtcctttcc    120
acaag                                                                125

<210> SEQ ID NO 433
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
aaaaaaagca ccgactcggt gccactttt caagttgata acggactagc cttatttaa     60 cttgctattt ctagctctaa aacgggccag ggagggaggg gcaggtgttt cgtcctttcc    120
acaag                                                                125

<210> SEQ ID NO 434
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
aaaaaaagca ccgactcggt gccactttt caagttgata acggactagc cttatttaa     60 cttgctattt ctagctctaa aacgttctgg aaccacacct tcaggtgttt cgtcctttcc    120
acaag                                                                125

<210> SEQ ID NO 435
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
aaaaaaagca ccgactcggt gccactttt caagttgata acggactagc cttatttaa     60 cttgctattt ctagctctaa aacaggtgaa ggtgtggttc cagggtgttt cgtcctttcc    120
acaag                                                                125

<210> SEQ ID NO 436
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 436
aaaaaaagca ccgactcggt gccactttt caagttgata acggactagc cttatttaa     60 cttgctattt ctagctctaa aacgaaccgg aggacaaagt acaggtgttt cgtcctttcc    120
acaag                                                                125

<210> SEQ ID NO 437
<211> LENGTH: 125
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 437
aaaaaaagca ccgactcggt gccactttt caagttgata acggactagc cttatttaa      60 cttgctattt ctagctctaa aaccaaaccc acgagggcag agtggtgttt cgtcctttcc    120
acaag                                                                125

<210> SEQ ID NO 438
<211> LENGTH: 125
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
aaaaaaagca ccgactcggt gccactttt caagttgata acggactagc cttatttaa      60 cttgctattt ctagctctaa aacgagtttc tcatctgtgc cccggtgttt cgtcctttcc    120
acaag                                                                125

<210> SEQ ID NO 439
<211> LENGTH: 684
<212> TYPE: DNA
<213> ORGANISM: Homo sapiens
<220> FEATURE:
<221> NAME/KEY: CDS
<222> LOCATION: (1)..(123)
<220> FEATURE:
<221> NAME/KEY: CDS
<222> LOCATION: (127)..(159)
<220> FEATURE:
<221> NAME/KEY: CDS
<222> LOCATION: (163)..(399)
<220> FEATURE:
<221> NAME/KEY: CDS
<222> LOCATION: (403)..(684)

<400> SEQUENCE: 439 aaa acc acc ctt ctc tct ggc cca ctg tgt cct ctt cct gcc ctg cca      48
Lys Thr Thr Leu Leu Ser Gly Pro Leu Cys Pro Leu Pro Ala Leu Pro
1               5                   10                  15 tcc cct tct gtg aat gtt aga ccc atg gga gca gct ggt cag agg gga      96
Ser Pro Ser Val Asn Val Arg Pro Met Gly Ala Ala Gly Gln Arg Gly
            20                  25                  30 ccc cgg cct ggg gcc cct aac cct atg tag cct cag tct tcc cat cag     144
Pro Arg Pro Gly Ala Pro Asn Pro Met     Pro Gln Ser Ser His Gln
        35                  40                  45 gct ctc agc tca gcc tga gtg ttg agg ccc cag tgg ctg ctc tgg ggg     192
Ala Leu Ser Ser Ala     Val Leu Arg Pro Gln Trp Leu Leu Trp Gly
    50                      55                  60 cct cct gag ttt ctc atc tgt gcc cct ccc tcc ctg gcc cag gtg aag     240
Pro Pro Glu Phe Leu Ile Cys Ala Pro Pro Ser Leu Ala Gln Val Lys
65                  70                  75 gtg tgg ttc cag aac cgg agg aca aag tac aaa cgg cag aag ctg gag     288
Val Trp Phe Gln Asn Arg Arg Thr Lys Tyr Lys Arg Gln Lys Leu Glu
        80                  85                  90 gag gaa ggg cct gag tcc gag cag aag aag aag ggc tcc cat cac atc     336
Glu Glu Gly Pro Glu Ser Glu Gln Lys Lys Lys Gly Ser His His Ile
95                  100                 105                 110 aac cgg tgg cgc att gcc acg aag cag gcc aat ggg gag gac atc gat     384
Asn Arg Trp Arg Ile Ala Thr Lys Gln Ala Asn Gly Glu Asp Ile Asp
            115                 120                 125
```

```
gtc acc tcc aat gac tag ggt ggg caa cca caa acc cac gag ggc aga       432
Val Thr Ser Asn Asp     Gly Gly Gln Pro Gln Thr His Glu Gly Arg
            130                 135                 140 gtg ctg ctt gct gct ggc cag gcc cct gcg tgg gcc caa gct gga ctc       480
Val Leu Leu Ala Ala Gly Gln Ala Pro Ala Trp Ala Gln Ala Gly Leu
                145                 150                 155 tgg cca ctc cct ggc cag gct ttg ggg agg cct gga gtc atg gcc cca       528
Trp Pro Leu Pro Gly Gln Ala Leu Gly Arg Pro Gly Val Met Ala Pro
        160                 165                 170 cag ggc ttg aag ccc ggg gcc gcc att gac aga ggg aca agc aat ggg       576
Gln Gly Leu Lys Pro Gly Ala Ala Ile Asp Arg Gly Thr Ser Asn Gly
    175                 180                 185 ctg gct gag gcc tgg gac cac ttg gcc ttc tcc tcg gag agc ctg cct       624
Leu Ala Glu Ala Trp Asp His Leu Ala Phe Ser Ser Glu Ser Leu Pro
190                 195                 200                 205 gcc tgg gcg ggc ccg ccc gcc acc gca gcc tcc cag ctg ctc tcc gtg       672
Ala Trp Ala Gly Pro Pro Ala Thr Ala Ala Ser Gln Leu Leu Ser Val
                210                 215                 220 tct cca atc tcc                                                       684
Ser Pro Ile Ser
        225

<210> SEQ ID NO 440
<211> LENGTH: 41
<212> TYPE: PRT
<213> ORGANISM: Homo sapiens

<400> SEQUENCE: 440

Lys Thr Thr Leu Leu Ser Gly Pro Leu Cys Pro Leu Pro Ala Leu Pro
1               5                   10                  15

Ser Pro Ser Val Asn Val Arg Pro Met Gly Ala Ala Gly Gln Arg Gly
            20                  25                  30

Pro Arg Pro Gly Ala Pro Asn Pro Met
        35                  40

<210> SEQ ID NO 441
<211> LENGTH: 11
<212> TYPE: PRT
<213> ORGANISM: Homo sapiens

<400> SEQUENCE: 441

Pro Gln Ser Ser His Gln Ala Leu Ser Ser Ala
1               5                   10

<210> SEQ ID NO 442
<211> LENGTH: 79
<212> TYPE: PRT
<213> ORGANISM: Homo sapiens

<400> SEQUENCE: 442

Val Leu Arg Pro Gln Trp Leu Leu Trp Gly Pro Pro Glu Phe Leu Ile
1               5                   10                  15

Cys Ala Pro Pro Ser Leu Ala Gln Val Lys Val Trp Phe Gln Asn Arg
            20                  25                  30

Arg Thr Lys Tyr Lys Arg Gln Lys Leu Glu Glu Glu Gly Pro Glu Ser
        35                  40                  45

Glu Gln Lys Lys Lys Gly Ser His His Ile Asn Arg Trp Arg Ile Ala
    50                  55                  60

Thr Lys Gln Ala Asn Gly Glu Asp Ile Asp Val Thr Ser Asn Asp
65                  70                  75
```

<210> SEQ ID NO 443
<211> LENGTH: 94
<212> TYPE: PRT
<213> ORGANISM: Homo sapiens

<400> SEQUENCE: 443

Gly Gly Gln Pro Gln Thr His Glu Gly Arg Val Leu Leu Ala Ala Gly
1               5                   10                  15

Gln Ala Pro Ala Trp Ala Gln Ala Gly Leu Trp Pro Leu Pro Gly Gln
            20                  25                  30

Ala Leu Gly Arg Pro Gly Val Met Ala Pro Gln Gly Leu Lys Pro Gly
        35                  40                  45

Ala Ala Ile Asp Arg Gly Thr Ser Asn Gly Leu Ala Glu Ala Trp Asp
    50                  55                  60

His Leu Ala Phe Ser Ser Glu Ser Leu Pro Ala Trp Ala Gly Pro Pro
65                  70                  75                  80

Ala Thr Ala Ala Ser Gln Leu Leu Ser Val Ser Pro Ile Ser
                85                  90

<210> SEQ ID NO 444
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 444
nnnnnnnnnn nnnnnnnnnn ngg                                      23

<210> SEQ ID NO 445
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other

<400> SEQUENCE: 445
nnnnnnnnnn nnngg                                               15

<210> SEQ ID NO 446
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 446
nnnnnnnnnn nnnnnnnnnn ngg                                                  23

<210> SEQ ID NO 447
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other

<400> SEQUENCE: 447
nnnnnnnnnn nngg                                                            14

<210> SEQ ID NO 448
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 448
nnnnnnnnnn nnnnnnnnnn nggng                                                25

<210> SEQ ID NO 449
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 449
```

```
nnnnnnnnnn nnnggng                                            17

<210> SEQ ID NO 450
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 450
nnnnnnnnnn nnnnnnnnnn nggng                                   25

<210> SEQ ID NO 451
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 451
nnnnnnnnnn nnggng                                             16
```

DELIVERY, ENGINEERING AND OPTIMIZATION OF SYSTEMS, METHODS AND COMPOSITIONS FOR SEQUENCE MANIPULATION AND THERAPEUTIC APPLICATIONS

RELATED APPLICATIONS AND INCORPORATION BY REFERENCE

This application is a continuation of U.S. patent application Ser. No. 14/481,339 filed Sep. 9, 2014, which claims priority to International Patent Application Number PCT/US13/74667 filed Dec. 12, 2013 which claims benefit of and priority to US provisional patent application No. 61/736,527 filed Dec. 12, 2012; 61/748,427 filed Jan. 2, 2013; 61/758,468 filed Jan. 30, 2013, 61/769,046 filed Feb. 25, 2013; 61/791,409 and 61/802,174 filed Mar. 15, 2013, 61/806,375 filed Mar. 28, 2013; 61/814,263 filed Apr. 20, 2013; 61/819,803 filed May 6, 2013; 61/828,130 filed May 28, 2013; 61/835,931 and 61/836,123 filed Jun. 17, 2013 and 61/847,537 filed Jul. 17, 2013.

Reference is also made to US provisional patent application No. 61/799,800 filed Mar. 15, 2013; 61/835,931, 61/835,936, 61/836,127, 61/836,101, 61/836,080 and 61/835,973 filed Jun. 17, 2013; 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under grant Number 1MH100706 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 10, 2018, is named 114203-5028_SL.txt and is 215,358 bytes in size.

FIELD OF THE INVENTION

The present invention generally relates to the delivery, engineering, optimization and therapeutic applications of systems, methods, and compositions used for the control of gene expression involving sequence targeting, such as genome perturbation or gene-editing, that relate to Clustered Regularly Interspaced Short Palindromic Repeats (CRISPR) and components thereof.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

SUMMARY OF THE INVENTION

The CRISPR-Cas system does not require the generation of customized proteins to target specific sequences but rather a single Cas enzyme can be programmed by a short RNA molecule to recognize a specific DNA target. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering, optimization and cell-type/tissue/organ specific delivery of these genome engineering tools, which are aspects of the claimed invention.

There exists a pressing need for alternative and robust systems and techniques for nucleic sequence targeting with a wide array of applications. Aspects of this invention address this need and provide related advantages. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

In one aspect, the invention provides methods for using one or more elements of a CRISPR-Cas system: The CRISPR complex of the invention provides an effective means for modifying a target polynucleotide. The CRISPR complex of the invention has a wide variety of utilities including modifying (e.g., deleting, inserting, translocating, inactivating, activating) a target polynucleotide in a multiplicity of cell types in various tissues and organs. As such the CRISPR complex of the invention has a broad spectrum of applications in, e.g., gene or genome editing, gene therapy, drug discovery, drug screening, disease diagnosis, and prognosis.

Aspects of the invention relate to Cas9 enzymes having improved targeting specificity in a CRISPR-Cas9 system having guide RNAs having optimal activity, smaller in length than wild-type Cas9 enzymes and nucleic acid molecules coding therefor, and chimeric Cas9 enzymes, as well as methods of improving the target specificity of a Cas9 enzyme or of designing a CRISPR-Cas9 system comprising designing or preparing guide RNAs having optimal activity and/or selecting or preparing a Cas9 enzyme having a smaller size or length than wild-type Cas9 whereby packaging a nucleic acid coding therefor into a delivery vector is more advanced as there is less coding therefor in the delivery vector than for wild-type Cas9, and/or generating chimeric Cas9 enzymes.

Also provided are uses of the present sequences, vectors, enzymes or systems, in medicine. Also provided are uses of the same in gene or genome editing.

In an additional aspect of the invention, a Cas9 enzyme may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (D10 and H840) in the RuvC and HNH catalytic domains, respectively. Further mutations have been characterized. In one aspect of the invention, the transcriptional activation domain may be VP64. In other aspects of the invention, the transcriptional repressor domain may be KRAB or SID4X. Other aspects of the invention relate to the mutated Cas 9 enzyme being fused to domains which include but are not limited to a transcriptional activator, repressor, a recombinase, a transposase, a histone remodeler, a demethylase, a DNA methyltransferase, a cryptochrome, a light inducible/controllable domain or a chemically inducible/controllable domain.

In a further embodiment, the invention provides for methods to generate mutant tracrRNA and direct repeat sequences or mutant chimeric guide sequences that allow for enhancing performance of these RNAs in cells. Aspects of the invention also provide for selection of said sequences.

Aspects of the invention also provide for methods of simplifying the cloning and delivery of components of the CRISPR complex. In the preferred embodiment of the invention, a suitable promoter, such as the U6 promoter, is amplified with a DNA oligo and added onto the guide RNA. The resulting PCR product can then be transfected into cells to drive expression of the guide RNA. Aspects of the invention also relate to the guide RNA being transcribed in vitro or ordered from a synthesis company and directly transfected.

In one aspect, the invention provides for methods to improve activity by using a more active polymerase. In a preferred embodiment, the expression of guide RNAs under the control of the T7 promoter is driven by the expression of the T7 polymerase in the cell. In an advantageous embodiment, the cell is a eukaryotic cell. In a preferred embodiment the eukaryotic cell is a human cell. In a more preferred embodiment the human cell is a patient specific cell.

In one aspect, the invention provides for methods of reducing the toxicity of Cas enzymes. In certain aspects, the Cas enzyme is any Cas9 as described herein, for instance any naturally-occurring bacterial Cas9 as well as any chimaeras, mutants, homologs or orthologs. In a preferred embodiment, the Cas9 is delivered into the cell in the form of mRNA. This allows for the transient expression of the enzyme thereby reducing toxicity. In another preferred embodiment, the invention also provides for methods of expressing Cas9 under the control of an inducible promoter, and the constructs used therein.

In another aspect, the invention provides for methods of improving the in vivo applications of the CRISPR-Cas system. In the preferred embodiment, the Cas enzyme is wildtype Cas9 or any of the modified versions described herein, including any naturally-occurring bacterial Cas9 as well as any chimaeras, mutants, homologs or orthologs. An advantageous aspect of the invention provides for the selection of Cas9 homologs that are easily packaged into viral vectors for delivery. Cas9 orthologs typically share the general organization of 3-4 RuvC domains and a HNH domain. The 5' most RuvC domain cleaves the non-complementary strand, and the HNH domain cleaves the complementary strand. All notations are in reference to the guide sequence.

The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Franciscilla novicida* type II CRISPR locus), and the conserved Asp residue (D10) is mutated to alanine to convert Cas9 into a complementary-strand nicking enzyme. Similarly, the conserved His and Asn residues in the HNH domains are mutated to Alanine to convert Cas9 into a non-complementary-strand nicking enzyme. In some embodiments, both sets of mutations may be made, to convert Cas9 into a non-cutting enzyme.

In some embodiments, the CRISPR enzyme is a type I or III CRISPR enzyme, preferably a type II CRISPR enzyme. This type II CRISPR enzyme may be any Cas enzyme. A preferred Cas enzyme may be identified as Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCas9, St1Cas9 and so forth. Further examples are provided herein. The skilled person will be able to determine appropriate corresponding residues in Cas9 enzymes other than SpCas9 by comparison of the relevant amino acid sequences. Thus, where a specific amino acid replacement is referred to using the SpCas9 numbering, then, unless the context makes it apparent this is not intended to refer to other Cas9 enzymes, the disclosure is intended to encompass corresponding modifications in other Cas9 enzymes.

An example of a codon optimized sequence, in this instance optimized for humans (i.e. being optimized for expression in humans) is provided herein, see the SaCas9 human codon optimized sequence. Whilst this is preferred, it will be appreciated that other examples are possible and codon optimization for a host species is known.

In further embodiments, the invention provides for methods of enhancing the function of Cas9 by generating chimeric Cas9 proteins. Chimeric Cas9 proteins chimeric Cas9s may be new Cas9 containing fragments from more than one naturally occurring Cas9. These methods may comprise fusing N-terminal fragments of one Cas9 homolog with C-terminal fragments of another Cas9 homolog. These methods also allow for the selection of new properties displayed by the chimeric Cas9 proteins.

It will be appreciated that in the present methods, where the organism is an animal or a plant, the modification may occur ex vivo or in vitro, for instance in a cell culture and in some instances not in vivo. In other embodiments, it may occur in vivo.

In one aspect, the invention provides a method of modifying an organism or a non-human organism by manipulation of a target sequence in a genomic locus of interest comprising: delivering a non-naturally occurring or engineered composition comprising:
A)—I. a CRISPR-Cas system chimeric RNA (chiRNA) polynucleotide sequence, wherein the polynucleotide sequence comprises:
(a) a guide sequence capable of hybridizing to a target sequence in a eukaryotic cell,
(b) a tracr mate sequence, and
(c) a tracr sequence, and
II. a polynucleotide sequence encoding a CRISPR enzyme comprising at least one or more nuclear localization sequences,
wherein (a), (b) and (c) are arranged in a 5' to 3' orientation, wherein when transcribed, the tracr mate sequence hybridizes to the tracr sequence and the guide sequence directs sequence-specific binding of a CRISPR complex to the target sequence, and
wherein the CRISPR complex comprises the CRISPR enzyme complexed with (1) the guide sequence that is hybridized to the target sequence, and (2) the tracr mate sequence that is hybridized to the tracr sequence and the polynucleotide sequence encoding a CRISPR enzyme is DNA or RNA, or
(B) I. polynucleotides comprising:
(a) a guide sequence capable of hybridizing to a target sequence in a eukaryotic cell, and
(b) at least one or more tracr mate sequences,
II. a polynucleotide sequence encoding a CRISPR enzyme, and
III. a polynucleotide sequence comprising a tracr sequence, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence, and the polynucleotide sequence encoding a CRISPR enzyme is DNA or RNA.

Any or all of the polynucleotide sequence encoding a CRISPR enzyme, guide sequence, tracr mate sequence or tracr sequence, may be RNA. The polynucleotides encoding the sequence encoding a CRISPR enzyme, the guide sequence, tracr mate sequence or tracr sequence may be RNA and may be delivered via liposomes, nanoparticles, exosomes, microvesicles, or a gene-gun.

It will be appreciated that where reference is made to a polynucleotide, which is RNA and is said to 'comprise' a feature such a tracr mate sequence, the RNA sequence includes the feature. Where the Polynucleotide is DNA and is said to comprise a feature such a tracr mate sequence, the DNA sequence is or can be transcribed into the RNA including the feature at issue. Where the feature is a protein, such as the CRISPR enzyme, the DNA or RNA sequence referred to is, or can be, translated (and in the case of DNA transcribed first).

Accordingly, in certain embodiments the invention provides a method of modifying an organism, e.g., mammal including human or a non-human mammal or organism by manipulation of a target sequence in a genomic locus of interest comprising delivering a non-naturally occurring or engineered composition comprising a viral or plasmid vector system comprising one or more viral or plasmid vectors operably encoding a composition for expression thereof, wherein the composition comprises: (A) a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to a target sequence in a eukaryotic cell, (b) a tracr mate sequence, and (c) a tracr sequence, and II. a second regulatory element operably linked to an enzyme-coding sequence encoding a CRISPR enzyme comprising at least one or more nuclear localization sequences (or optionally at least one or more nuclear localization sequences as some embodiments can involve no NLS), wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence, or (B) a non-naturally occurring or engineered composition comprising a vector system comprising one or more vectors comprising I. a first regulatory element operably linked to (a) a guide sequence capable of hybridizing to a target sequence in a eukaryotic cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence. In some embodiments, components I, II and III are located on the same vector. In other embodiments, components I and II are located on the same vector, while component III is located on another vector. In other embodiments, components I and III are located on the same vector, while component II is located on another vector. In other embodiments, components II and III are located on the same vector, while component I is located on another vector. In other embodiments, each of components I, II and III is located on different vectors. The invention also provides a viral or plasmid vector system as described herein.

Preferably, the vector is a viral vector, such as a lenti- or baculo- or preferably adeno-viral/adeno-associated viral vectors, but other means of delivery are known (such as yeast systems, microvesicles, gene guns/means of attaching vectors to gold nanoparticles) and are provided. In some embodiments, one or more of the viral or plasmid vectors may be delivered via liposomes, nanoparticles, exosomes, microvesicles, or a gene-gun.

By manipulation of a target sequence, Applicants also mean the epigenetic manipulation of a target sequence. This may be of the chromatin state of a target sequence, such as by modification of the methylation state of the target sequence (i.e. addition or removal of methylation or methylation patterns or CpG islands), histone modification, increasing or reducing accessibility to the target sequence, or by promoting 3D folding.

It will be appreciated that where reference is made to a method of modifying an organism or mammal including human or a non-human mammal or organism by manipulation of a target sequence in a genomic locus of interest, this may apply to the organism (or mammal) as a whole or just a single cell or population of cells from that organism (if the organism is multicellular). In the case of humans, for instance, Applicants envisage, inter alia, a single cell or a population of cells and these may preferably be modified ex vivo and then re-introduced. In this case, a biopsy or other tissue or biological fluid sample may be necessary. Stem cells are also particularly preferred in this regard. But, of course, in vivo embodiments are also envisaged.

In certain embodiments the invention provides a method of treating or inhibiting a condition caused by a defect in a target sequence in a genomic locus of interest in a subject (e.g., mammal or human). or a non-human subject (e.g., mammal) in need thereof comprising modifying the subject or a non-human subject by manipulation of the target sequence and wherein the condition is susceptible to treatment or inhibition by manipulation of the target sequence comprising providing treatment comprising: delivering a non-naturally occurring or engineered composition comprising an AAV or lentivirus vector system comprising one or more AAV or lentivirus vectors operably encoding a composition for expression thereof, wherein the target sequence is manipulated by the composition when expressed, wherein the composition comprises: (A) a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to a target sequence in a eukaryotic cell, (b) a tracr mate sequence, and (c) a tracr sequence, and II. a second regulatory element operably linked to an enzyme-coding sequence encoding a CRISPR enzyme comprising at least one or more nuclear localization sequences (or optionally at least one or more nuclear localization sequences as some embodiments can involve no NLS) wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence, or (B) a non-naturally occurring or engineered composition comprising a vector system comprising one or more vectors comprising I. a first regulatory element operably linked to (a) a guide sequence capable of hybridizing to a target sequence in a eukaryotic cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence. In some embodiments, components I, II and III are located on the same vector. In other embodiments, components I and II are located on the same vector, while component III is located on another vector. In other embodiments, components I and III are located on the same vector, while component II is located on another vector. In other embodiments, components II and III are located on the same vector, while component I is located on another vector. In other embodiments, each of components I, II and III is located on different vectors. The invention also provides a viral (e.g. AAV or lentivirus) vector system as described herein, and can be part of a vector system as described herein.

Some methods of the invention can include inducing expression. In some methods of the invention the organism or subject is a eukaryote (including mammal including human) or a non-human eukaryote or a non-human animal or a non-human mammal. In some embodiments, the organism or subject is a non-human animal, and may be an arthropod, for example, an insect, or may be a nematode. In some methods of the invention the organism or subject is a plant. In some methods of the invention the organism or subject is a mammal or a non-human mammal. A non-human mammal may be for example a rodent (preferably a mouse or a rat), an ungulate, or a primate. In some methods of the invention the organism or subject is algae, including microalgae, or is a fungus. In some methods of the invention the viral vector is an AAV or a lentivirus, and can be part of a vector system as described herein. In some methods of the invention the CRISPR enzyme is a Cas9. In some methods of the invention the expression of the guide sequence is under the control of the T7 promoter and is driven by the expression of T7 polymerase.

The invention in some embodiments comprehends a method of delivering a CRISPR enzyme comprising delivering to a cell mRNA encoding the CRISPR enzyme. In some of these methods the CRISPR enzyme is a Cas9.

The invention also provides methods of preparing the vector systems of the invention, in particular the viral vector systems as described herein. The invention in some embodiments comprehends a method of preparing the AAV of the invention comprising transfecting plasmid(s) containing or consisting essentially of nucleic acid molecule(s) coding for the AAV into AAV-infected cells, and supplying AAV rep and/or cap obligatory for replication and packaging of the AAV. In some embodiments the AAV rep and/or cap obligatory for replication and packaging of the AAV are supplied by transfecting the cells with helper plasmid(s) or helper virus(es). In some embodiments the helper virus is a poxvirus, adenovirus, herpesvirus or baculovirus. In some embodiments the poxvirus is a vaccinia virus. In some embodiments the cells are mammalian. cells. And in some embodiments the cells are insect cells and the helper virus is baculovirus. In other embodiments, the virus is a lentivirus.

In plants, pathogens are often host-specific. For example, *Fusarium oxysporum* f. sp. *lycopersici* causes tomato wilt but attacks only tomato, and *F. oxysporum* f *dianthii* *Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

The invention further comprehends a composition of the invention or a CRISPR enzyme thereof (including or alternatively mRNA encoding the CRISPR enzyme) for use in medicine or in therapy. In some embodiments the invention comprehends a composition according to the invention or a CRISPR enzyme thereof (including or alternatively mRNA encoding the CRISPR enzyme) for use in a method according to the invention. In some embodiments the invention provides for the use of a composition of the invention or a CRISPR enzyme thereof (including or alternatively mRNA encoding the CRISPR enzyme) in ex vivo gene or genome editing. In certain embodiments the invention comprehends use of a composition of the invention or a CRISPR enzyme thereof (including or alternatively mRNA encoding the CRISPR enzyme) in the manufacture of a medicament for ex vivo gene or genome editing or for use in a method according of the invention. The invention comprehends in some embodiments a composition of the invention or a CRISPR enzyme thereof (including or alternatively mRNA encoding the CRISPR enzyme), wherein the target sequence is flanked at its 3' end by a PAM (protospacer adjacent motif) sequence comprising 5'-motif, especially where the Cas9 is (or is derived from) *S. pyogenes* or *S. aureus* Cas9. For example, a suitable PAM is 5'-NRG or 5'-NNGRR (where N is any Nucleotide) for SpCas9 or SaCas9 enzymes (or derived enzymes), respectively, as mentioned below.

It will be appreciated that SpCas9 or SaCas9 are those from or derived from *S. pyogenes* or *S. aureus* Cas9.

Aspects of the invention comprehend improving the specificity of a CRISPR enzyme, e.g. Cas9, mediated gene targeting and reducing the likelihood of off-target modification by the CRISPR enzyme, e.g. Cas9. The invention in some embodiments comprehends a method of modifying an organism or a non-human organism by minimizing off-target modifications by manipulation of a first and a second target sequence on opposite strands of a DNA duplex in a genomic locus of interest in a cell comprising delivering a non-naturally occurring or engineered composition comprising:

I. a first CRISPR-Cas system chimeric RNA (chiRNA) polynucleotide sequence, wherein the first polynucleotide sequence comprises:
(a) a first guide sequence capable of hybridizing to the first target sequence,
(b) a first tracr mate sequence, and
(c) a first tracr sequence,
II. a second CRISPR-Cas system chiRNA polynucleotide sequence, wherein the second polynucleotide sequence comprises:
(a) a second guide sequence capable of hybridizing to the second target sequence,
(b) a second tracr mate sequence, and
(c) a second tracr sequence, and
III. a polynucleotide sequence encoding a CRISPR enzyme comprising at least one or more nuclear localization sequences and comprising one or more mutations, wherein (a), (b) and (c) are arranged in a 5' to 3' orientation, wherein when transcribed, the first and the second tracr mate sequence hybridize to the first and second tracr sequence respectively and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridized to the first target sequence, and (2) the first tracr mate sequence that is hybridized to the first tracr sequence, wherein the second CRISPR complex comprises the CRISPR enzyme complexed with (1) the second guide sequence that is hybridized to the second target sequence, and (2) the second tracr mate sequence that is hybridized to the second tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of the other strand near the second target sequence inducing a double strand break, thereby modifying the organism or the non-human organism by minimizing off-target modifications.

In some methods of the invention any or all of the polynucleotide sequence encoding the CRISPR enzyme, the first and the second guide sequence, the first and the second tracr mate sequence or the first and the second tracr sequence, is/are RNA. In further embodiments of the invention the polynucleotides encoding the sequence encoding the CRISPR enzyme, the first and the second guide sequence, the first and the second tracr mate sequence or the first and the second tracr sequence, is/are RNA and are delivered via liposomes, nanoparticles, exosomes, microvesicles, or a gene-gun. In certain embodiments of the invention, the first and second tracr mate sequence share 100% identity and/or the first and second tracr sequence share 100% identity. In some embodiments, the polynucleotides may be comprised within a vector system comprising one or more vectors. In preferred embodiments of the invention the CRISPR enzyme is a Cas9 enzyme, e.g. SpCas9. In an aspect of the invention the CRISPR enzyme comprises one or more mutations in a catalytic domain, wherein the one or more mutations are selected from the group consisting of D10A, E762A, H840A, N854A, N863A and D986A. In a highly preferred embodiment the CRISPR enzyme has the D10A mutation. In preferred embodiments, the first CRISPR enzyme has one or more mutations such that the enzyme is a complementary strand nicking enzyme, and the second CRISPR enzyme has one or more mutations such that the enzyme is a non-complementary strand nicking enzyme. Alternatively the first enzyme may be a non-complementary strand nicking enzyme, and the second enzyme may be a complementary strand nicking enzyme.

In preferred methods of the invention the first guide sequence directing cleavage of one strand of the DNA duplex near the first target sequence and the second guide sequence directing cleavage of the other strand near the second target sequence results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs.

The invention in some embodiments comprehends a method of modifying an organism or a non-human organism by minimizing off-target modifications by manipulation of a first and a second target sequence on opposite strands of a DNA duplex in a genomic locus of interest in a cell comprising delivering a non-naturally occurring or engineered composition comprising a vector system comprising one or more vectors comprising I. a first regulatory element operably linked to
(a) a first guide sequence capable of hybridizing to the first target sequence, and
(b) at least one or more tracr mate sequences, II. a second regulatory element operably linked to
(a) a second guide sequence capable of hybridizing to the second target sequence, and
(b) at least one or more tracr mate sequences, III. a third regulatory element operably linked to an enzyme-coding sequence encoding a CRISPR enzyme, and IV. a fourth regulatory element operably linked to a tracr sequence, wherein components I, II, III and IV are located on the same or different vectors of the system, when transcribed, the tracr mate sequence hybridizes to the tracr sequence and the first and the second guide sequence direct sequence-specific binding of a first and a second CRISPR complex to the first and second target sequences respectively, wherein the first CRISPR complex comprises the CRISPR enzyme complexed with (1) the first guide sequence that is hybridized to the first target sequence, and (2) the tracr mate sequence that is hybridized to the tracr sequence, wherein the second CRISPR complex comprises the CRISPR enzyme complexed with (1) the second guide sequence that is hybridized to the second target sequence, and (2) the tracr mate sequence that is hybridized to the tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of the other strand near the second target sequence inducing a double strand break, thereby modifying the organism or the non-human organism by minimizing off-target modifications.

The invention also provides a vector system as described herein. The system may comprise one, two, three or four different vectors. Components I, II, III and IV may thus be located on one, two, three or four different vectors, and all combinations for possible locations of the components are herein envisaged, for example: components I, II, III and IV can be located on the same vector; components I, II, III and IV can each be located on different vectors; components I, II, II I and IV may be located on a total of two or three different vectors, with all combinations of locations envisaged, etc.

In some methods of the invention any or all of the polynucleotide sequence encoding the CRISPR enzyme, the first and the second guide sequence, the first and the second tracr mate sequence or the first and the second tracr sequence, is/are RNA. In further embodiments of the invention the first and second tracr mate sequence share 100% identity and/or the first and second tracr sequence share 100% identity. In preferred embodiments of the invention the CRISPR enzyme is a Cas9 enzyme, e.g. SpCas9. In an aspect of the invention the CRISPR enzyme comprises one or more mutations in a catalytic domain, wherein the one or more mutations are selected from the group consisting of D10A, E762A, H840A, N854A, N863A and D986A. In a highly preferred embodiment the CRISPR enzyme has the D10A mutation. In preferred embodiments, the first CRISPR enzyme has one or more mutations such that the enzyme is a complementary strand nicking enzyme, and the second CRISPR enzyme has one or more mutations such that the enzyme is a non-complementary strand nicking enzyme. Alternatively the first enzyme may be a non-complementary strand nicking enzyme, and the second enzyme may be a complementary strand nicking enzyme. In a further embodiment of the invention, one or more of the viral vectors are delivered via liposomes, nanoparticles, exosomes, microvesicles, or a gene-gun.

In preferred methods of the invention the first guide sequence directing cleavage of one strand of the DNA duplex near the first target sequence and the second guide sequence directing cleavage of other strand near the second target sequence results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs.

The invention in some embodiments comprehends a method of modifying a genomic locus of interest by minimizing off-target modifications by introducing into a cell containing and expressing a double stranded DNA molecule encoding a gene product of interest an engineered, non-naturally occurring CRISPR-Cas system comprising a Cas protein having one or more mutations and two guide RNAs that target a first strand and a second strand of the DNA molecule respectively, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In preferred methods of the invention the Cas protein nicking each of the first strand and the second strand of the DNA molecule encoding the gene product results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs.

Embodiments of the invention also comprehend the guide RNAs comprising a guide sequence fused to a tracr mate sequence and a tracr sequence. In an aspect of the invention the Cas protein is codon optimized for expression in a eukaryotic cell, preferably a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations selected from the group consisting of D10A, E762A, H840A, N854A, N863A and D986A. In a highly preferred embodiment the Cas protein has the D10A mutation.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

The invention also comprehends an engineered, non-naturally occurring CRISPR-Cas system comprising a Cas protein having one or more mutations and two guide RNAs that target a first strand and a second strand respectively of a double stranded DNA molecule encoding a gene product in a cell, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In aspects of the invention the guide RNAs may comprise a guide sequence fused to a tracr mate sequence and a tracr sequence. In an embodiment of the invention the Cas protein is a type II CRISPR-Cas protein. In an aspect of the invention the Cas protein is codon optimized for expression in a eukaryotic cell, preferably a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations selected from the group consisting of D10A, E762A, H840A, N854A, N863A and D986A. In a highly preferred embodiment the Cas protein has the D10A mutation.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

The invention also comprehends an engineered, non-naturally occurring vector system comprising one or more vectors comprising:
a) a first regulatory element operably linked to each of two CRISPR-Cas system guide RNAs that target a first strand and a second strand respectively of a double stranded DNA molecule encoding a gene product,
b) a second regulatory element operably linked to a Cas protein,
wherein components (a) and (b) are located on same or different vectors of the system, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In aspects of the invention the guide RNAs may comprise a guide sequence fused to a tracr mate sequence and a tracr sequence. In an embodiment of the invention the Cas protein is a type II CRISPR-Cas protein. In an aspect of the invention the Cas protein is codon optimized for expression in a eukaryotic cell, preferably a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations selected from the group consisting of D10A, E762A, H840A, N854A, N863A and D986A. In a highly preferred embodiment the Cas protein has the D10A mutation.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. In preferred embodiments of the invention the vectors of the system are viral vectors. In a further embodiment, the vectors of the system are delivered via liposomes, nanoparticles, exosomes, microvesicles, or a gene-gun.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation Comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the CRISPR enzyme, the guide sequence linked to the tracr mate sequence, and the tracr sequence. In some embodiments, said Vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors drive expression of one or more of: the CRISPR enzyme, the guide sequence linked to the tracr mate sequence, and the tracr sequence.

In one aspect, the invention provides a method of generating a model eukaryotic cell comprising a mutated disease gene. In some embodiments, a disease gene is any gene associated with an increase in the risk of having or developing a disease. In some embodiments, the method comprises (a) introducing one or more vectors into a eukaryotic cell, wherein the one or more vectors drive expression of one or more of: a CRISPR enzyme, a guide sequence linked to a tracr mate sequence, and a tracr sequence; and (b) allowing a CRISPR complex to bind to a target polynucleotide to effect cleavage of the target polynucleotide within said disease gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect the invention provides for a method of selecting one or more prokaryotic cell(s) by introducing one or more mutations in a gene in the one or more prokaryotic cell (s), the method comprising: introducing one or more vectors into the prokaryotic cell (s), wherein the one or more vectors drive expression of one or more of: a CRISPR enzyme, a guide sequence linked to a tracr mate sequence, a tracr sequence, and an editing template; wherein the editing template comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, wherein binding of the CRISPR complex to the target polynucleotide induces cell death, thereby allowing one or more prokaryotic cell(s) in which one or more mutations have been introduced to be selected. In a preferred embodiment, the CRISPR enzyme is Cas9. In another aspect of the invention the cell to be selected may be a eukaryotic cell. Aspects of the invention allow for selection of specific cells without requiring a selection marker or a two-step process that may include a counter-selection system.

In one aspect, the invention provides for methods of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

In other embodiments, this invention provides a method of modifying expression of a polynucleotide in a eukaryotic cell. The method comprises increasing or decreasing expression of a target polynucleotide by using a CRISPR complex that binds to the polynucleotide.

Where desired, to effect the modification of the expression in a cell, one or more vectors comprising a tracr sequence, a guide sequence linked to the tracr mate sequence, a sequence encoding a CRISPR enzyme is delivered to a cell. In some methods, the one or more vectors comprises a regulatory element operably linked to an enzyme-coding sequence encoding said CRISPR enzyme comprising a nuclear localization sequence; and a regulatory element operably linked to a tracr mate sequence and one or more insertion sites for inserting a guide sequence upstream of the tracr mate sequence. When expressed, the guide sequence directs sequence-specific binding of a CRISPR complex to a target sequence in a cell. Typically, the CRISPR complex comprises a CRISPR enzyme complexed with (1) the guide sequence that is hybridized to the target sequence, and (2) the tracr mate sequence that is hybridized to the tracr sequence.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In certain embodiments, the CRISPR enzyme comprises one or more mutations selected from the group consisting of D10A, E762A, H840A, N854A, N863A or D986A and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain. In some embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

In some embodiments, the CRISPR enzyme is a type I or III CRISPR enzyme, but is preferably a type II CRISPR enzyme. This type II CRISPR enzyme may be any Cas enzyme. A Cas enzyme may be identified as Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth.

An example of a codon optimized sequence, in this instance optimized for humans (i.e. being optimized for expression in humans) is provided herein, see the SaCas9 human codon optimized sequence. Whilst this is preferred, it will be appreciated that other examples are possible and codon optimization for a host species is known.

Preferably, delivery is in the form of a vector which may be a viral vector, such as a lenti- or baculo- or preferably adeno-viral/adeno-associated viral vectors, but other means of delivery are known (such as yeast systems, microvesicles, gene guns/means of attaching vectors to gold nanoparticles) and are provided. A vector may mean not only a viral or yeast system (for instance, where the nucleic acids of interest may be operably linked to and under the control of (in terms of expression, such as to ultimately provide a processed RNA) a promoter), but also direct delivery of nucleic acids into a host cell. While in herein methods the vector may be a viral vector and this is advantageously an AAV, other viral vectors as herein discussed can be employed, such as lentivirus. For example, baculoviruses may be used for expression in insect cells. These insect cells may, in turn be useful for producing large quantities of further vectors, such as AAV or lentivirus vectors adapted for delivery of the present invention. Also envisaged is a method of delivering the present CRISPR enzyme comprising delivering to a cell mRNA encoding the CRISPR enzyme. It will be appreciated that in certain embodiments the CRISPR enzyme is truncated, and/or comprised of less than one thousand amino acids or less than four thousand amino acids, and/or is a nuclease or nickase, and/or is codon-optimized, and/or comprises one or more mutations, and/or comprises a chimeric CRISPR enzyme, and/or the other options as herein discussed. AAV and lentiviral vectors are preferred.

In certain embodiments, the target sequence is flanked or followed, at its 3' end, by a PAM suitable for the CRISPR enzyme, typically a Cas and in particular a Cas9.

For example, a suitable PAM is 5'-NRG or 5'-NNGRR for SpCas9 or SaCas9 enzymes (or derived enzymes), respectively.

It will be appreciated that SpCas9 or SaCas9 are those from or derived from *S. pyogenes* or *S. aureus* Cas9.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-F shows an exemplary CRISPR system, a possible mechanism of action, an example adaptation for expression in eukaryotic cells, and results of tests assessing nuclear localization and CRISPR activity. FIG. 2C discloses SEQ ID NOS 212 and 213, respectively, in order of appearance. FIG. 2E discloses SEQ ID NOS 214-216, respectively, in order of appearance. FIG. 2F discloses SEQ ID NOS 217-221, respectively, in order of appearance.

FIG. 3A discloses SEQ ID NOS 222, 215 and 223-233, respectively, in order of appearance. FIG. 3C discloses SEQ ID NO: 222.

FIG. 4A-G show an exemplary vector system and results for its use in directing homologous recombination in eukaryotic cells. FIG. 4E discloses SEQ ID NO: 234. FIG. 4F discloses SEQ ID NOS 235 and 236, respectively, in order of appearance. FIG. 4G discloses SEQ ID NOS 237-241, respectively, in order of appearance.

FIG. 5 provides a table of protospacer sequences (SEQ ID NOS 93, 92, 91, 242-247, 95, 94 and 248-252, respectively, in order of appearance) and summarizes modification efficiency results for protospacer targets designed based on exemplary *S. pyogenes* and *S. thermophilus* CRISPR systems with corresponding PAMs against loci in human and mouse genomes. Cells were transfected with Cas9 and either pre-crRNA/tracrRNA or chimeric RNA, and analyzed 72 hours after transfection. Percent indels are calculated based on Surveyor assay results from indicated cell lines (N=3 for all protospacer targets, errors are S.E.M., N.D. indicates not detectable using the Surveyor assay, and N.T. indicates not tested in this study).

FIG. 6A discloses SEQ ID NOS 253 and 254, respectively, in order of appearance.

FIG. 8A discloses SEQ ID NOS 255-257, respectively, in order of appearance. FIG. 8B discloses SEQ ID NOS 258, 182 and 183, respectively, in order of appearance.

FIG. 9A-C shows histograms of distances between adjacent *S. pyogenes* SF370 locus 1 PAM (NGG) (FIG. 9A) and *S. thermophilus* LMD9 locus 2 PAM (NNAGAAW) (FIG. 9B) in the human genome; and distances for each PAM by chromosome (Chr) (FIG. 9C).

FIG. 10A-D shows an exemplary CRISPR system, an example adaptation for expression in eukaryotic cells, and results of tests assessing CRISPR activity. FIG. 10B discloses SEQ ID NOS 259 and 260, respectively, in order of appearance. FIG. 10C discloses SEQ ID NO: 261.

FIG. 11A-C shows exemplary manipulations of a CRISPR system for targeting of genomic loci in mammalian cells. FIG. 11A discloses SEQ ID NO: 262. FIG. 11B discloses SEQ ID NOS 263-265, respectively, in order of appearance.

FIG. 12A discloses SEQ ID NO: 266.

FIG. 14 discloses SEQ ID NO: 261.

FIG. 15 provides a table of sequences (SEQ ID NOS 269-276, 191-192 and 277-278, respectively, in order of appearance) for primers and probes used for Surveyor, RFLP, genomic sequencing, and Northern blot assays.

FIG. 16A discloses SEQ ID NO: 279.

FIG. 18 discloses SEQ ID NOS 280-358, respectively, in order of appearance.

Figure 20B:
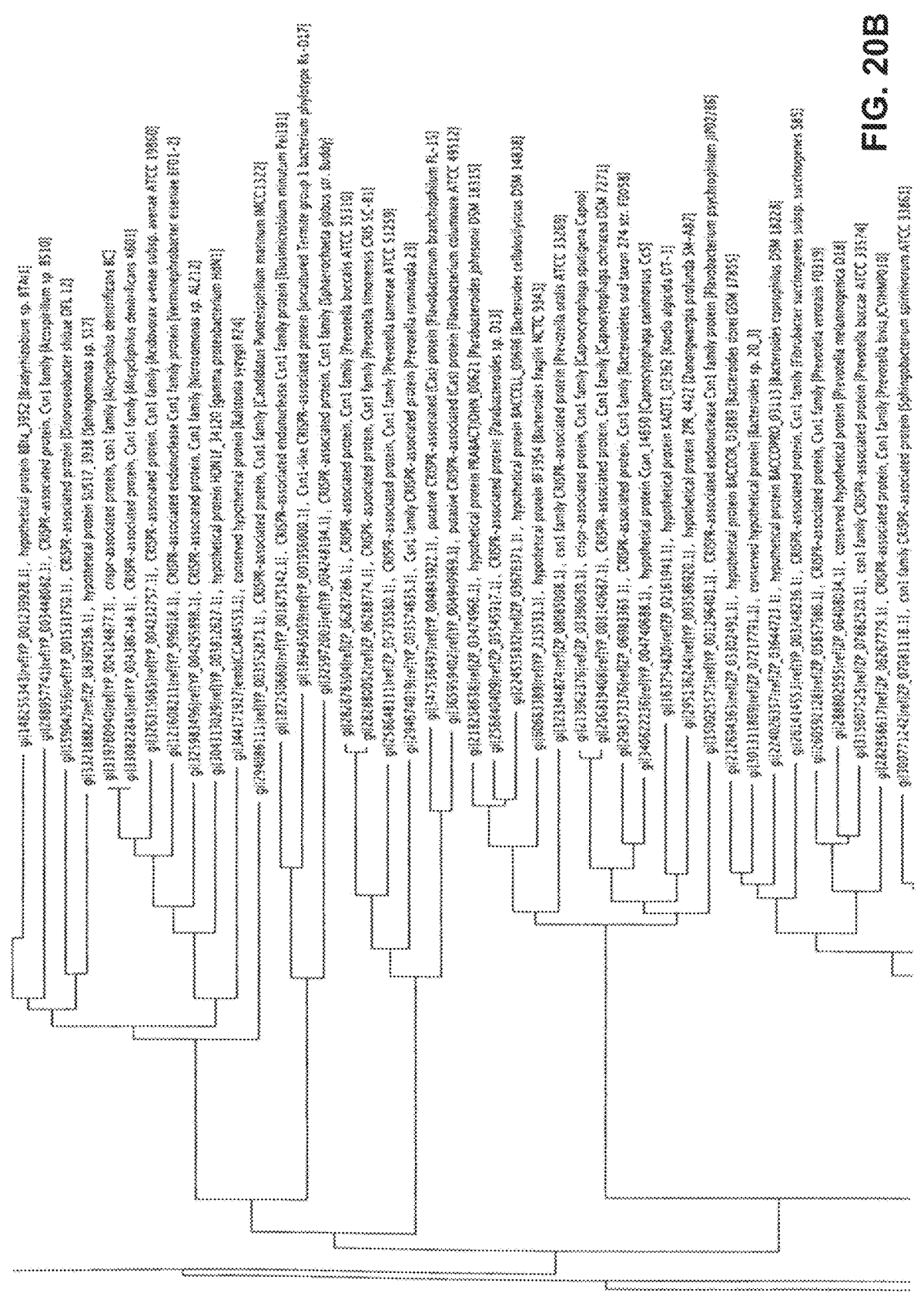
Figure 20D:
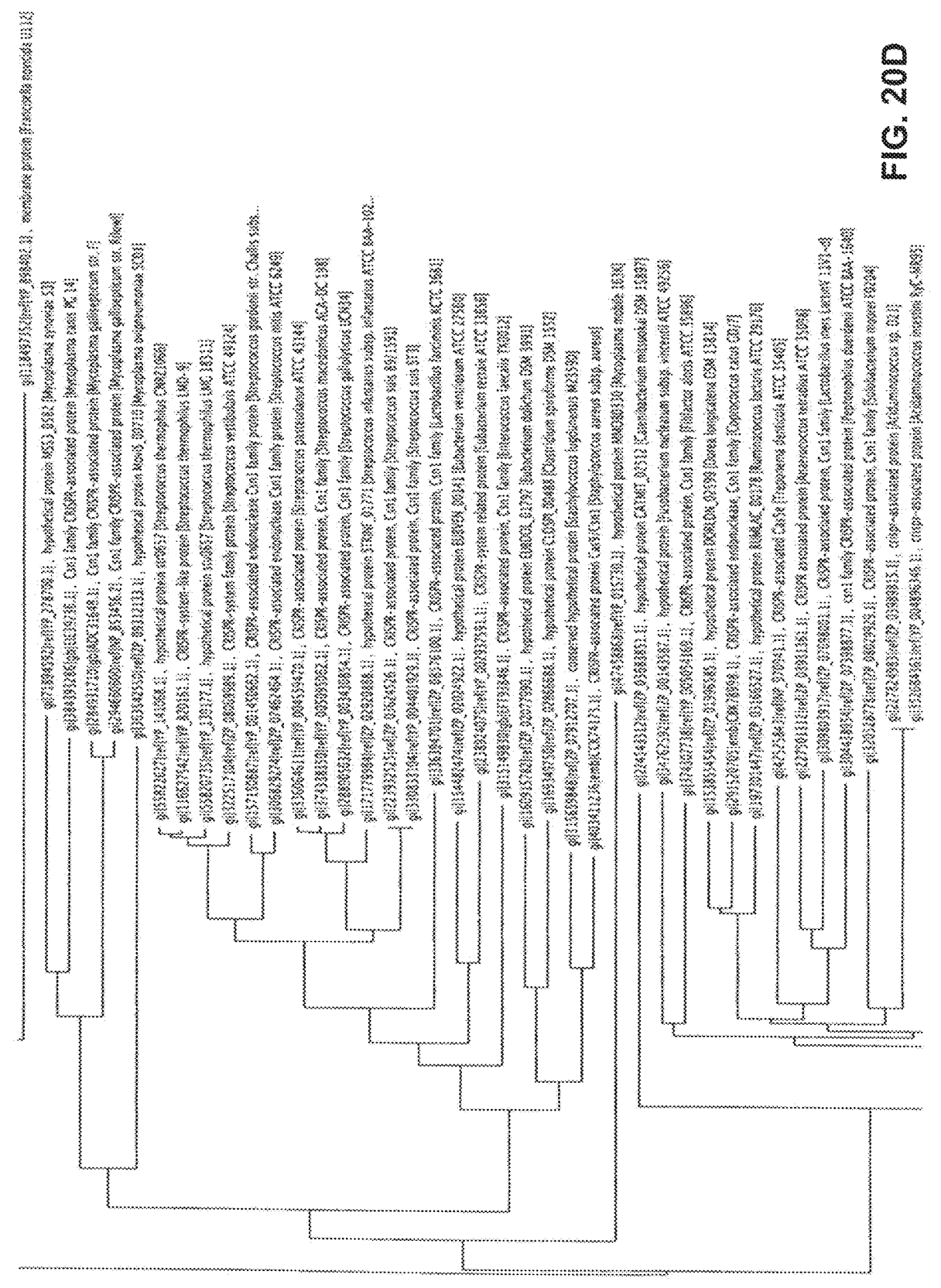

FIG. 20A-F shows the linear depiction of the phylogenetic analysis revealing five families of Cas9s, including three groups of large Cas9s (~1400 amino acids) and two of small Cas9s (~1100 amino acids).

FIG. 21C discloses SEQ ID NOS 359-361, 359, 362 and 361, respectively, in order of appearance.

FIG. 22A discloses SEQ ID NOS 363-365, respectively, in order of appearance. FIG. 22B discloses SEQ ID NO: 366.

FIG. 24A-M shows sequences where the mutation points are located within the SpCas9 gene. FIG. 24A-M discloses the nucleotide sequence as SEQ ID NO: 367 and the amino acid sequence as SEQ ID NO: 368.

FIG. 27 shows delivery and in vivo mouse brain Cas9 expression data.

FIG. 28A-C shows RNA delivery of Cas9 and chimeric RNA into cells (A) Delivery of a GFP reporter as either DNA or mRNA into Neuro-2A cells. (B) Delivery of Cas9 and chimeric RNA against the Icam2 gene as RNA results in cutting for one of two spacers tested. (C) Delivery of Cas9 and chimeric RNA against the F7 gene as RNA results in cutting for one of two spacers tested.

FIG. 30A-C shows anticipated results for HDR in HEK and HUES9 cells. (a) Either a targeting plasmid or an ssODN (sense or antisense) with homology arms can be used to edit the sequence at a target genomic locus cleaved by Cas9 (red triangle). To assay the efficiency of HDR, we introduced a HindIII site (red bar) into the target locus, which was PCR-amplified with primers that anneal outside of the region of homology. Digestion of the PCR product with HindIII reveals the occurrence of HDR events. (b) ssODNs, oriented in either the sense or the antisense (s or a) direction relative to the locus of interest, can be used in combination with Cas9 to achieve efficient HDR-mediated editing at the target locus. A minimal homology region of 40 bp, and preferably 90 bp, is recommended on either side of the modification (red bar). (c) Example of the effect of ssODNs on HDR in the EMX1 locus is shown using both wild-type Cas9 and Cas9 nickase (D10A). Each ssODN contains homology arms of 90 bp flanking a 12-bp insertion of two restriction sites. FIG. 30B discloses SEQ ID NOS 359-361, 359, 362 and 361, respectively, in order of appearance.

FIG. 31A discloses the nucleotide sequence as SEQ ID NO: 371 and the amino acid sequence as 372. FIG. 31B discloses SEQ ID NO: 279. FIG. 31C discloses the nucleotide sequence as SEQ ID NO: 373 and the amino acid sequence as SEQ ID NO: 374.

FIG. 42 shows expression of SpCas9 and SaCas9 in cortical primary neurons in culture 7 days after transduction. Representative Western blot of HA-tagged SpCas9 and SaCas9 versions under the control of different promoters and with bgh or short polyA (spA) sequences. Tubulin is loading control.

FIG. 49 shows efficiency of SpCas9 cleavage in the mouse brain. Mice were injected with AAV1/2 virus carrying gRNA multiplex targeting TET family genes loci together with SpCas9 viruses under control of 2 different promoters: mouse Mecp2 and rat Map1b. Three weeks after injection brain tissue was extracted, nuclei were prepped and sorted using FACS, based on the GFP expression driven by Synapsin promoter from gRNA multiplex construct. After gDNA extraction Surveyor assay was run. + indicates GFP positive nuclei and − control, GFP-negative nuclei from the same animal. Numbers on the gel indicate assessed SpCas9 efficiency.

FIG. 51 shows (top) a list of spacing (as indicated by the pattern of arrangement for two PAM sequences) between pairs of guide RNAs (SEQ ID NOS 375-391, respectively, in order of appearance). Only guide RNA pairs satisfying patterns 1, 2, 3, 4 exhibited indels when used with SpCas9 (D10A) nickase. (bottom) Gel images showing that combination of SpCas9(D10A) with pairs of guide RNA satisfying patterns 1, 2, 3, 4 led to the formation of indels in the target site.

FIG. 52 shows a list of U6 reverse primer sequences (SEQ ID NOS 392-438, respectively, in order of appearance) used to generate U6-guide RNA expression casssettes. Each primer needs to be paired with the U6 forward primer "gcactgagggcctatttcccatgattc" (SEQ ID NO: 1) to generate amplicons containing U6 and the desired guide RNA.

FIG. 53 discloses the nucleotide sequence as SEQ ID NO: 439 and the amino acid sequences as SEQ ID NOS 440-443, respectively, in order of appearance.

FIG. 54 shows on (right) a gel image indicating the formation of indels at the target site when variable 5' overhangs are present after cleavage by the Cas9 nickase targeted by different pairs of guide RNAs. on (left) a table indicating the lane numbers of the gel on the right and various parameters including identifying the guide RNA pairs used and the length of the 5' overhang present following cleavage by the Cas9 nickase.

FIG. 55 discloses the nucleotide sequence as SEQ ID NO: 439 and the amino acid sequences as SEQ ID NOS 440-443, respectively, in order of appearance.

FIG. 57 shows Syn_GFP-KASH expression 8 weeks after 3×gRNA virus injection is specific for neurons (NeuN positive cells) and not for glia cells (GFAP positive).

FIG. 63A-E shows SpCas9 in N2a cells. A) Targeting- and SpCas9 expression vector. B) Western Blot analysis of N2a cells expressing HA-tagged SpCas9 under the control of different promoters. C) Cutting efficiency of Dnmt loci. D) Western blot analysis demonstrating efficient knock down of Dnmt3a. e) Cutting efficiency of Tet loci.

FIG. 64A-D shows SpCas9 in primary neurons. A) Schematic overview of SpCas9 cloning strategies used in this study. Short promoters and short polyA for efficient packaging into AAV delivering system. B) Schematic overview of combined multiplex targeting and nuclear envelope labeling strategy. C) Western blot analysis showing expression of HA-tagged SpCas9 under the control of rMap1b and mMecp2 promoter and bGH and spA signal. D) Immunocytochemistry demonstrating co-expression of SpCas9 and GFP-KASH in primary neurons. SpCas9 under the control of the mMecp2 promoter is expressed in neurons (Map1b, NeuN) but not in astroglia cells (GFAP).

FIG. 65A-D shows knock down of Dnmt3a in primary neurons. A) Immunocytochemistry demonstrating efficient knock down of Dnmt3a after targeting with multiplex targeting vector and mMecp2-SpCas9. B) Quantification of Dnmt3a antibody staining in control and targeted neurons. C) Western blot analysis demonstrating reduced Dnmt3a protein level. D) Quantification of Western Blot analysis demonstrating a total knock down of Dnmt3a protein level of approx. 75% in a mixed primary neuron culture (neurons and astroglia).

FIG. 66A-B shows knock down of Dnmt3a in vivo. A) Cutting efficiency of Dnmt loci in the brain, 8 weeks after Mecp_SpCas9 virus injection in compare to control animals injected with Mecp2_SpCas9 virus only. B) Western blot analysis showing reduced Dnmt3a protein level in targeted neuronal nuclei (KASH-GFP positive) compared to control nuclei (RubyDye positive) after sorting cell nuclei using FACS.

FIG. 67A-F shows expression of SaCas9 in primary neurons. A) Size of SaCas9 expression vector using hSynapsin promoter and bGH signal. B) Expression of SaCas9 in primary neurons (NeuN) but not in astroglia (GFAP). C) Extranuclear localization of SaCas9 in absence of gRNA. C' Higher magnification of SaCas9 positive neurons shown in C). D) Nuclear localization of SaCas9 in presence of gRNA. D') Higher magnification of SaCas9 positive neurons shown in D). E) Western blot analysis demonstrating expression of HA-tagged SaCas9 and GFP-KASH. F) Cutting efficiency of Dnmt loci 1 week after AAV infection.

FIG. 68A-E shows gRNA dependent nuclear localization of SaCas9. A) Confocal imaging analysis demonstrating extranuclear localization of SaCas9 in absence of gRNA in primary neurons. B) Nuclear localization of SaCas9 in presence of gRNA. C) Line Scan analysis of confocal picture A) showing extranuclear localization of SaCas9 in absence of gRNA (red, SaCas9 signal; blue, DAPI signal; green, GFP-KASH signal. D) Line Scan analysis of confocal picture B) showing nuclear localization of SaCas9 in presence of gRNA (red, SaCas9 signal; blue, DAPI signal; green, GFP-KASH signal). E) Subcellular localization of SaCas9 and SpCas9 under conditions without (−) and with (+) gRNA in N2a cells. SaCas9 signal at 250 kDa in the cytoplasm fraction (Tubulin positive) indicating dimerization of SaCas9 in the cytoplasm. In the presence of gRNA a shift of SaCas9 protein into the nuclear fraction (Sun2 positive) is visible. SaCas9 signal at 100 kDa indicates a gRNA dependent formation of SaCas9 homomers and transport into the cell nucleus. In contrast, SpCas9 is mainly present as homomer and its nuclear localization is independent of gRNA.

Figure 1:
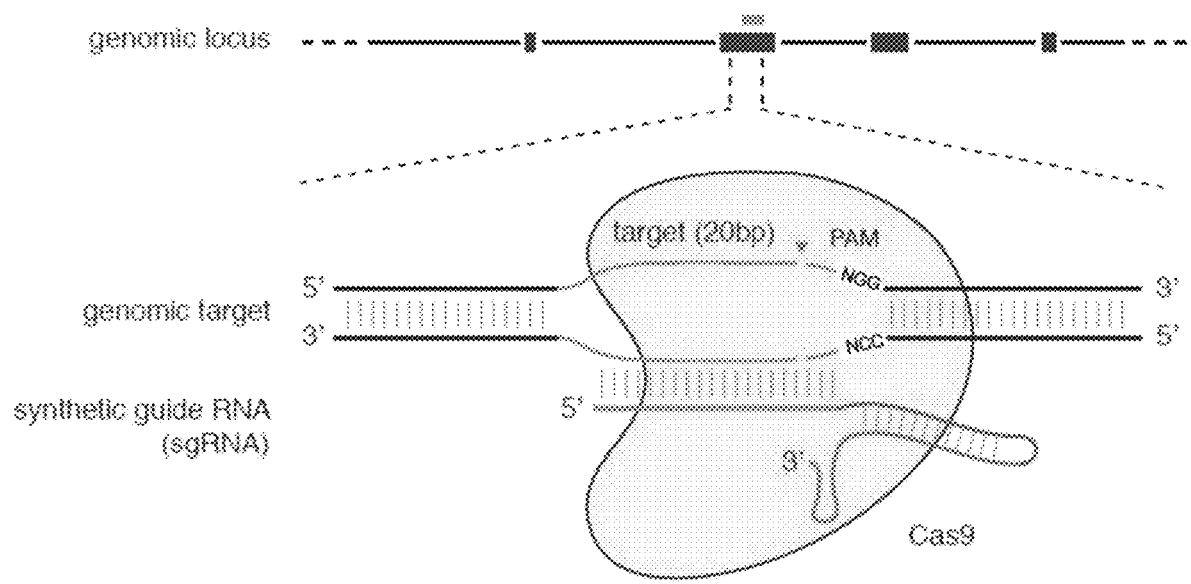
FIG. 1 shows a schematic model of the CRISPR system. The Cas9 nuclease from *Streptococcus pyogenes* (yellow) is targeted to genomic DNA by a synthetic guide RNA (sgRNA) consisting of a 20-nt guide sequence (blue) and a scaffold (red). The guide sequence base-pairs with the DNA target (blue), directly upstream of a requisite 5'-NGG protospacer adjacent motif (PAM; magenta), and Cas9 mediates a double-stranded break (DSB) ~3 bp upstream of the PAM (red triangle).

The figures herein are for illustrative purposes only and are not necessarily drawn to scale.

DETAILED DESCRIPTION OF THE INVENTION

The invention relates to the engineering and optimization of systems, methods and compositions used for the control of gene expression involving sequence targeting, such as genome perturbation or gene-editing, that relate to the CRISPR-Cas system and components thereof. In advantageous embodiments, the Cas enzyme is Cas9.

An advantage of the present methods is that the CRISPR system avoids off-target binding and its resulting side effects. This is achieved using systems arranged to have a high degree of sequence specificity for the target DNA.

Cas9

Cas9 optimization may be used to enhance function or to develop new functions, one can generate chimeric Cas9 proteins. Examples that the Applicants have generated are provided in Example 6. Chimeric Cas9 proteins can be made by combining fragments from different Cas9 homologs. For example, two example chimeric Cas9 proteins from the Cas9s described herein. For example, Applicants fused the N-term of St1Cas9 (fragment from this protein is in bold) with C-term of SpCas9. The benefit of making chimeric Cas9s include any or all of: reduced toxicity; improved expression in eukaryotic cells; enhanced specificity; reduced molecular weight of protein, for example, making the protein smaller by combining the smallest domains from different Cas9 homologs; and/or altering the PAM sequence requirement.

The Cas9 may be used as a generic DNA binding protein. For example, and as shown in Example 7, Applicants used Cas9 as a generic DNA binding protein by mutating the two catalytic domains (D10 and H840) responsible for cleaving both strands of the DNA target. In order to upregulate gene transcription at a target locus Applicants fused a transcriptional activation domain (VP64) to Cas9. Other transcriptional activation domains are known. As shown in Example 17, transcriptional activation is possible. As also shown in Example 17, gene repression (in this case of the beta-catenin gene) is possible using a Cas9 repressor (DNA-binding domain) that binds to the target gene sequence, thus repressing its activity.

Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual, and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed.

The viral vectors can be injected into the tissue of interest. For cell-type specific genome modification, the expression of Cas9 can be driven by a cell-type specific promoter. For example, liver-specific expression might use the Albumin promoter and neuron-specific expression might use the Synapsin I promoter.

Transgenic Animals and Plants

Figure 25A:
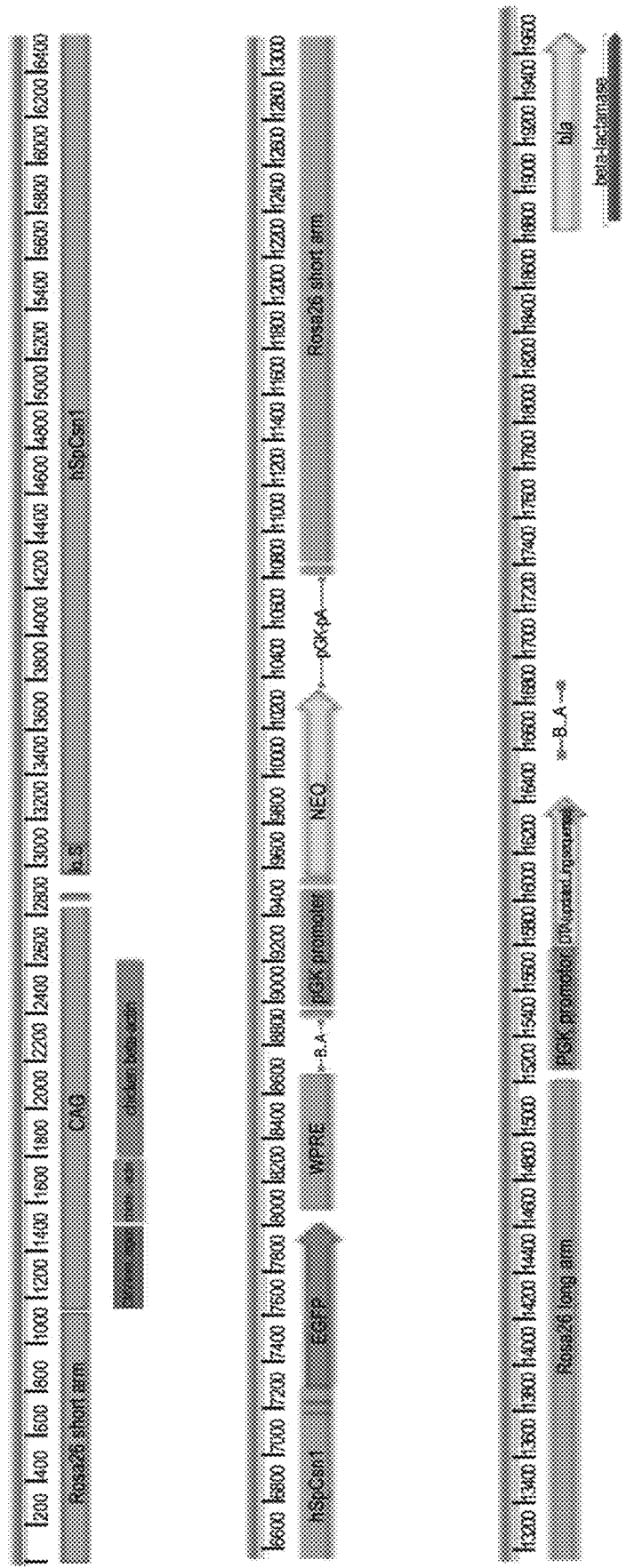
FIG. 25A shows the Conditional Cas9, Rosa26 targeting vector map.
Figure 25B:
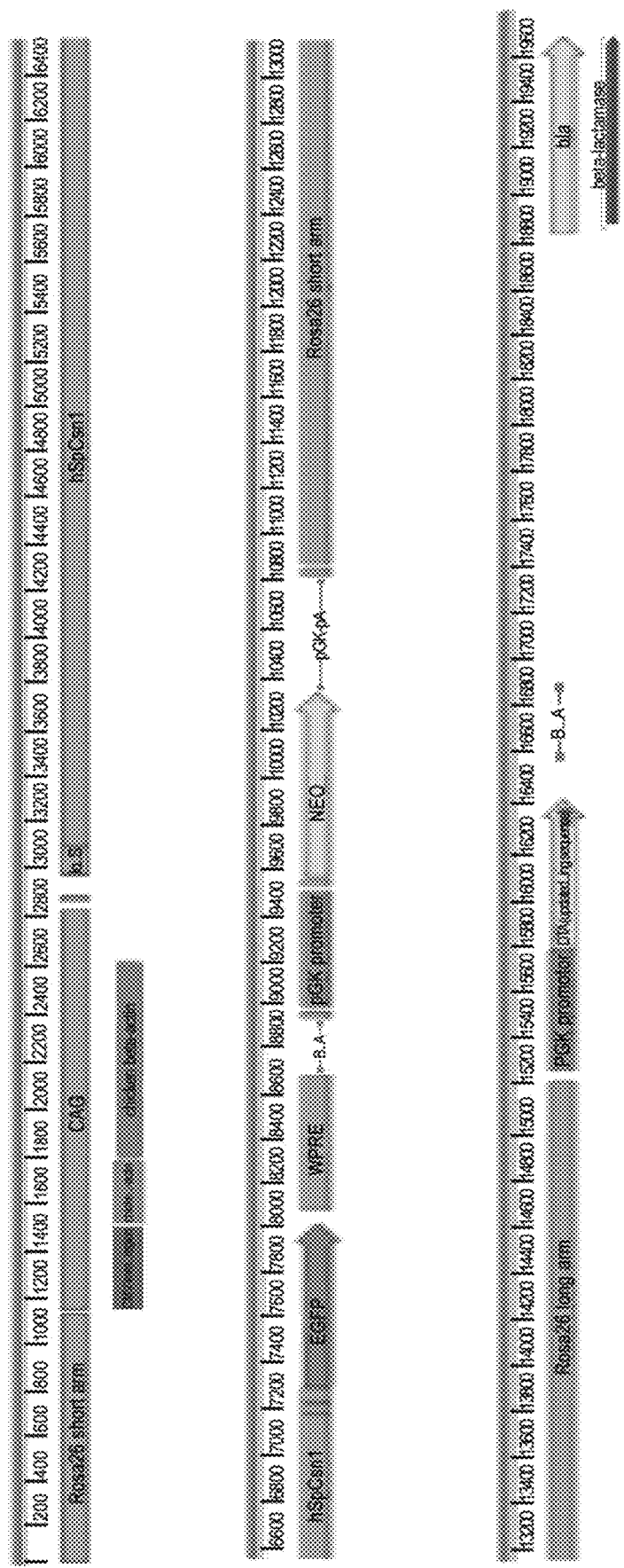
FIG. 25B shows the Constitutive Cas9, Rosa26 targeting vector map.
Figure 26:
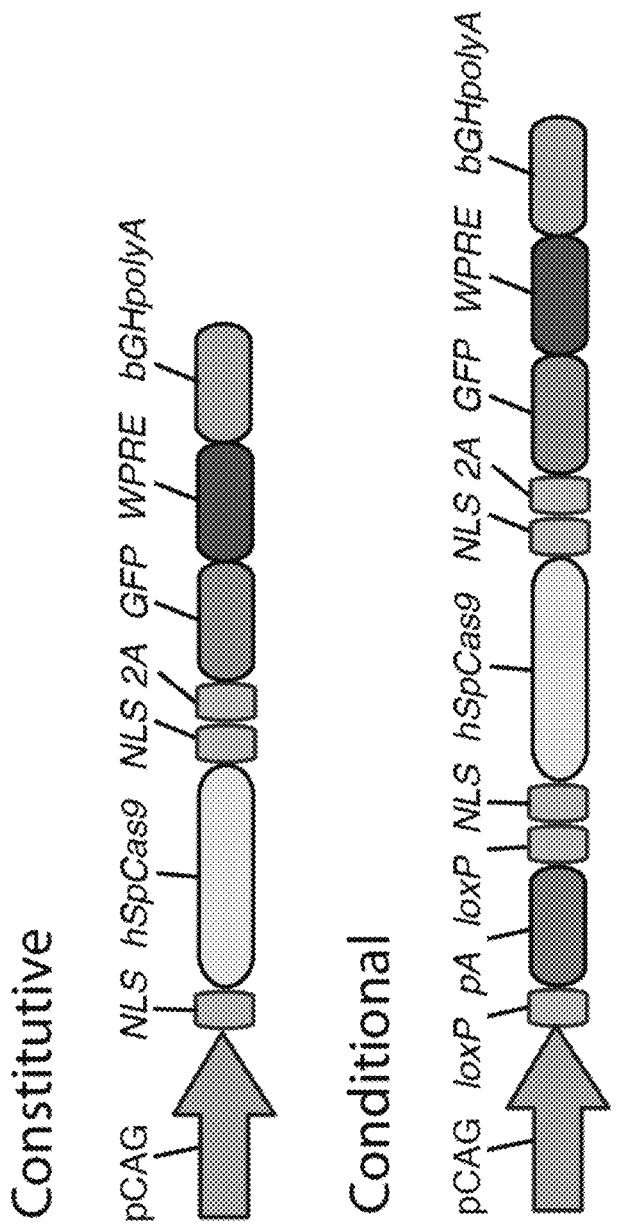
FIG. 26 shows a schematic of the important elements in the Constitutive and Conditional Cas9 constructs.

Transgenic animals are also provided. Preferred examples include animals comprising Cas9, in terms of polynucleotides encoding Cas9 or the protein itself. Mice, rats and rabbits are preferred. To generate transgenic mice with the constructs, as exemplified herein one may inject pure, linear DNA into the pronucleus of a zygote from a pseudo pregnant female, e.g. a CB56 female. Founders may then be identified, genotyped, and backcrossed to CB57 mice. The constructs may then be cloned and optionally verified, for instance by Sanger sequencing. Knock outs are envisaged where for instance one or more genes are knocked out in a model. However, are knockins are also envisaged (alone or in combination). An example knockin Cas9 mouse was generated and this is exemplified, but Cas9 knockins are preferred. To generate a Cas9 knock in mice one may target the same constitutive and conditional constructs to the Rosa26 locus, as described herein (FIGS. 25A-B and 26). Methods of US Patent Publication Nos. 20120017290 and 20110265198 assigned to Sangamo BioSciences, Inc. directed to targeting the Rosa locus may be modified to utilize the CRISPR Cas system of the present invention. In another embodiment, the methods of US Patent Publication No. 20130236946 assigned to Cellectis directed to targeting the Rosa locus may also be modified to utilize the CRISPR Cas system of the present invention.

Utility of the conditional Cas9 mouse: Applicants have shown in 293 cells that the Cas9 conditional expression construct can be activated by co-expression with Cre. Applicants also show that the correctly targeted R1 mESCs can have active Cas9 when Cre is expressed. Because Cas9 is followed by the P2A peptide cleavage sequence and then EGFP Applicants identify successful expression by observing EGFP. Applicants have shown Cas9 activation in mESCs. This same concept is what makes the conditional Cas9 mouse so useful. Applicants may cross their conditional Cas9 mouse with a mouse that ubiquitously expresses Cre (ACTB-Cre line) and may arrive at a mouse that expresses Cas9 in every cell. It should only take the delivery of chimeric RNA to induce genome editing in embryonic or adult mice. Interestingly, if the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue.

As mentioned above, transgenic animals are also provided, as are transgenic plants, especially crops and algae. The transgenic plants may be useful in applications outside of providing a disease model. These may include food or feed production through expression of, for instance, higher protein, carbohydrate, nutrient or vitamin levels than would normally be seen in the wildtype. In this regard, transgenic plants, especially pulses and tubers, and animals, especially mammals such as livestock (cows, sheep, goats and pigs), but also poultry and edible insects, are preferred.

Transgenic algae or other plants such as rape may be particularly useful in the production of vegetable oils or biofuels such as alcohols (especially methanol and ethanol), for instance. These may be engineered to express or overexpress high levels of oil or alcohols for use in the oil or biofuel industries.

Adeno Associated Virus (AAV)

In terms of in vivo delivery, AAV is advantageous over other viral vectors for a couple of reasons:

Low toxicity (this may be due to the purification method not requiring ultra centrifugation of cell particles that can activate the immune response)

Low probability of causing insertional mutagenesis because it doesn't integrate into the host genome.

AAV has a packaging limit of 4.5 or 4.75 Kb. This means that Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

| Species | Cas9 Size |
| --- | --- |
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Streptococcus thermophilus LMD-9 | 3396 |

These species are therefore, in general, preferred Cas9 species. Applicants have shown delivery and in vivo mouse brain Cas9 expression data.

Two ways to package Cas9 coding nucleic acid molecules, e.g., DNA, into viral vectors to mediate genome modification in vivo are preferred:

To achieve NHEJ-mediated gene knockout:
Single Virus Vector:
Vector containing two or more expression cassettes:
Promoter-Cas9 coding nucleic acid molecule-terminator
Promoter-gRNA1-terminator
Promoter-gRNA2-terminator
Promoter-gRNA(N)-terminator (up to size limit of vector)
Double Virus Vector:
Vector 1 containing one expression cassette for driving the expression of Cas9
Promoter-Cas9 coding nucleic acid molecule-terminator
Vector 2 containing one more expression cassettes for driving the expression of one or more guideRNAs
Promoter-gRNA1-terminator
Promoter-gRNA(N)-terminator (up to size limit of vector)

To mediate homology-directed repair. In addition to the single and double virus vector approaches described above, an additional vector is used to deliver a homology-direct repair template.

Promoter used to drive Cas9 coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce toxicity due to over expression of Cas9.

For ubiquitous expression, can use promoters: CMV, CAG, CBh, PGK, SV40, Ferritin heavy or light chains, etc.

For brain expression, can use promoters: SynapsinI for all neurons, CaMKIIalpha for excitatory neurons, GAD67 or GAD65 or VGAT for GABAergic neurons, etc.

For liver expression, can use Albumin promoter.
For lung expression, can use SP-B.
For endothelial cells, can use ICAM.
For hematopoietic cells can use IFNbeta or CD45.
For Osteoblasts can use OG-2.
Promoter used to drive guide RNA can include:
Pol III promoters such as U6 or H1
Use of Pol II promoter and intronic cassettes to express gRNA As to AAV, the AAV can be AAV1, AAV2, AAV5 or any combination thereof. One can select the AAV of the AAV with regard to the cells to be targeted; e.g., one can select AAV serotypes 1, 2, 5 or a hybrid or capsid AAV1, AAV2, AAV5 or any combination thereof for targeting brain or neuronal cells; and one can select AAV4 for targeting cardiac tissue. AAV8 is useful for delivery to the liver. The above promoters and vectors are preferred individually.

RNA delivery is also a useful method of in vivo delivery. FIG. 27 shows delivery and in vivo mouse brain Cas9 expression data. It is possible to deliver Cas9 and gRNA (and, for instance, HR repair template) into cells using liposomes or nanoparticles. Thus delivery of the CRISPR enzyme, such as a Cas9 and/or delivery of the RNAs of the invention may be in RNA form and via microvesicles, liposomes or nanoparticles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Various means of delivery are described herein, and further discussed in this section.

Viral delivery: The CRISPR enzyme, for instance a Cas9, and/or any of the present RNAs, for instance a guide RNA, can be delivered using adeno associated virus (AAV), lentivirus, adenovirus or other viral vector types, or combinations thereof. Cas9 and one or more guide RNAs can be packaged into one or more viral vectors. In some embodiments, the viral vector is delivered to the tissue of interest by, for example, an intramuscular injection, while other times the viral delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector chose, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, an adjuvant to enhance antigenicity, an immunostimulatory compound or molecule, and/or other compounds known in the art. The adjuvant herein may contain a suspension of minerals (alum, aluminum hydroxide, aluminum phosphate) on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages). Adjuvants also include immunostimulatory molecules, such as cytokines, costimulatory molecules, and for example, immunostimulatory DNA or RNA molecules, such as CpG oligonucleotides. Such a dosage formulation is readily ascertainable by one skilled in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^0$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg.

The doses herein are based on an average 70 kg individual. The frequency of administration is within the ambit of the medical or veterinary practitioner (e.g., physician, veterinarian), or scientist skilled in the art.

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 µg of lentiviral transfer plasmid (pCasES10) and the following packaging plasmids: 5 µg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4 C. They were then aliquotted and immediately frozen at −80 C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285, Published online 21 Nov. 2005 in Wiley InterScience (www.interscience.wiley.com). DOI: 10.1002/jgm.845). In another embodiment, RetinoStat®, an equine infectious anemia virus-based lentiviral gene therapy vector that expresses angiostatic proteins endostain and angiostatin that is delivered via a subretinal injection for the treatment of the web form of age-related macular degeneration is also contemplated (see, e.g., Binley et al., HUMAN GENE THERAPY 23:980-991 (September 2012)) may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of $2.5 \times 10^6$ CD34+ cells per kilogram patient weight may be collected and prestimulated for 16 to 20 hours in X-VIVO 15 medium (Lonza) containing 2 mML-glutamine, stem cell factor (100 ng/ml), Flt-3 ligand (Flt-3L) (100 ng/ml), and thrombopoietin (10 ng/ml) (CellGenix) at a density of $2 \times 10^6$ cells/ml. Prestimulated cells may be transduced with lentiviral at a multiplicity of infection of 5 for 16 to 24 hours in 75-cm$^2$ tissue culture flasks coated with fibronectin (25 mg/cm$^2$) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the train, see, e.g., US Patent Publication Nos. US20110293571; US20110293571, US20040013648, US20070025970, US20090111106 and U.S. Pat. No. 7,259,015.

RNA Delivery

RNA delivery: The CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce toxicity, the CRISPR enzyme and/or guide RNA can be modified using pseudo-U or 5-Methyl-C.

mRNA delivery methods are especially promising for liver delivery currently. In particular, for AAV8 is particularly preferred for delivery to the liver.

Nanoparticles

CRISPR enzyme mRNA and guide RNA may be delivered simultaneously using nanoparticles or lipid envelopes.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular deliver of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, nanoparticles that can deliver RNA to a cancer cell to stop tumor growth developed by Dan Anderson's lab at MIT may be used/and or adapted to the CRISPR Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the CRISPR Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The minoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 0110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30.-100 C., preferably at approximately 50.-90 C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 0110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas system of the present invention.

In another embodiment, lipid nanoparticles (LNPs) are contemplated. In particular, an antitransthyretin small interfering RNA encapsulated in lipid nanoparticles (see, e.g., Coelho et al., N Engl J Med 2013; 369:819-29) may be applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetampinophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as siRNA oligonucleotides may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 µg/ml levels may be contemplated, especially for a formulation containing DLinKC2-DMA.

Preparation of LNPs and CRISPR Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ω-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, Mo.). The specific CRISPR Cas RNA may be encapsulated in LNPs containing DLinDAP, DLinDMA, DLinK-DMA, and DLinKC2-DMA (cationic lipid:DSPC: CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/1 citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/1 citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, Calif.). The particle size for all three LNP systems may be ~70 nm in diameter. siRNA encapsulation efficiency may be determined by removal of free siRNA using VivaPureD MiniH columns (Sartorius Stedim Biotech) from samples collected before and after dialysis. The encapsulated RNA may be extracted from the eluted nanoparticles and quantified at 260 nm. siRNA to lipid ratio was determined by measurement of cholesterol content in vesicles using the Cholesterol E enzymatic assay from Wako Chemicals USA (Richmond, Va.).

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an siRNA to total lipid ratio of approximately 1:10 (wt:wt), followed by incubation for 30 minutes at 37° C. to form loaded LNPs. The mixture may be subsequently dialyzed overnight in PBS and filtered with a 0.45-um syringe filter.

Spherical Nucleic Acid (SNA™) constructs and other nanoparticles (particularly gold nanoparticles) are also contemplate as a means to delivery CRISPR/Cas system to intended targets. Significant data show that AuraSense Therapeutics' Spherical Nucleic Acid (SNA™) constructs, based upon nucleic acid-functionalized gold nanoparticles, are superior to alternative platforms based on multiple key success factors, such as:

High in vivo stability. Due to their dense loading, a majority of cargo (DNA or siRNA) remains bound to the constructs inside cells, conferring nucleic acid stability and resistance to enzymatic degradation.

Deliverability. For all cell types studied (e.g., neurons, tumor cell lines, etc.) the constructs demonstrate a transfection efficiency of 99% with no need for carriers or transfection agents.

Therapeutic targeting. The unique target binding affinity and specificity of the constructs allow exquisite specificity for matched target sequences (i.e., limited off-target effects).

Superior efficacy. The constructs significantly outperform leading conventional transfection reagents (Lipofectamine 2000 and Cytofectin).

Low toxicity. The constructs can enter a variety of cultured cells, primary cells, and tissues with no apparent toxicity.

No significant immune response. The constructs elicit minimal changes in global gene expression as measured by whole-genome microarray studies and cytokine-specific protein assays.

Chemical tailorability. Any number of single or combinatorial agents (e.g., proteins, peptides, small molecules) can be used to tailor the surface of the constructs.

This platform for nucleic acid-based therapeutics may be applicable to numerous disease states, including inflammation and infectious disease, cancer, skin disorders and cardiovascular disease.

Citable literature includes: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, doi.org/10.1002/sml1.201302143.

Self-assembling nanoparticles with siRNA may be constructed with polyethyleneimine (PEI) that is PEGylated with an Arg-Gly-Asp (RGD) peptide ligand attached at the distal end of the polyethylene glycol (PEG), for example, as a means to target tumor neovasculature expressing integrins and used to deliver siRNA inhibiting vascular endothelial growth factor receptor-2 (VEGF R2) expression and thereby tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas is envisioned for delivery in the self-assembling nanoparticles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclodo-decane-1,4,7,10-tetraacetic acid mono(N-hydroxysuccinimide ester) (DOTA-NHSester) was ordered from Macrocyclics (Dallas, Tex.). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, Calif.) to remove trace metal contaminants. Tf-targeted and nontargeted siRNA nanoparticles may be formed by using cyclodextrin-containing polycations. Typically, nanoparticles were formed in water at a charge ratio of 3 (+/−) and an siRNA concentration of 0.5 g/liter. One percent of the adamantane-PEG molecules on the surface of the targeted nanoparticles were modified with Tf (adamantane-PEG-Tf). The nanoparticles were suspended in a 5% (wt/vol) glucose carrier solution for injection.

Davis et al. (Nature, Vol 464, 15 Apr. 2010) conducts a siRNA clinical trial that uses a targeted nanoparticle-delivery system (clinical trial registration number NCT00689065). Patients with solid cancers refractory to standard-of-care therapies are administered doses of targeted nanoparticles on days 1, 3, 8 and 10 of a 21-day cycle by a 30-min intravenous infusion. The nanoparticles consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These nanoparticles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg m$^{-2}$ siRNA, respectively. Similar doses may also be contemplated for the CRISPR Cas system of the present invention. The delivery of the invention may be achieved with nanoparticles containing a linear, cyclodextrin-based polymer (CDP), a human transferrin protein (TF) targeting ligand displayed on the exterior of the nanoparticle to engage TF receptors (TFR) on the surface of the cancer cells and/or a hydrophilic polymer (for example, polyethylene glycol (PEG) used to promote nanoparticle stability in biological fluids).

Exosomes

Exosomes are endogenous nano-vesicles that transport RNAs and proteins which can deliver short interfering (si)RNA to the brain in mice. To reduce immunogenicity, Alvarez-Erviti et al. (2011, Nat Biotechnol 29: 341) used self-derived dendritic cells for exosome production. Targeting was achieved by engineering the dendritic cells to express Lamp2b, an exosomal membrane protein, fused to the neuron-specific RVG peptide3. Purified exosomes were loaded with exogenous siRNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by nanoparticle tracking analysis (NTA) and electron microscopy. Alvarez-Erviti et al. obtained 6-12 μg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled siRNA was used for the empirical optimization of the electroporation protocol. The amount of encapsulated siRNA was assayed after ultracentrifugation and lysis of exosomes. Electroporation at 400 V and 125 µF resulted in the greatest retention of siRNA and was used for all subsequent experiments.

Alvarez-Erviti et al. administered 150 µg of each BACE1 siRNA encapsulated in 150 µg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG pep tide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P<0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether siRNA-RVG exosomes induced immune responses in vivo by assessing IL-6, IP-10, TNFα and IFN-α serum concentrations. Following siRNA-RVG exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the CRISPR-Cas system of the present invention to therapeutic targets, especially neurodegenerative diseases. A dosage of about 100 to 1000 mg of CRISPR Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of siRNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading siRNA into exosomes. Finally, El-Andaloussi et al. outline how to use exosomes to efficiently deliver siRNA in vitro and in vivo in mouse brain. Examples of anticipated results in which exosome-mediated siRNA delivery is evaluated by functional assays and imaging are also provided. The entire protocol takes ~3 weeks. Delivery or administration according to the invention may be performed using exosomes produced from self-derived dendritic cells.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property might be useful in gene therapy.

Exosomes from plasma are prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas into exosomes may be conducted similarly to siRNA. The exosomes may be co-cultured with monocytes and lymphocytes isolated from the peripheral blood of healthy donors. Therefore, it may be contemplated that exosomes containing CRISPR Cas may be introduced to monocytes and lymphocytes of and autologously reintroduced into a human. Accordingly, delivery or administration according to the invention may beperformed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

Conventional liposome formulation is mainly comprised of natural phospholipids and lipids such as 1,2-distearoryl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at Cold Springs Harbor Protocol. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA may be contemplated for in vivo administration in liposomes.

In another embodiment, the CRISPR Cas system may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of abpit 1 or 2.5 mg/kg are also contemplated (see, e.g., Zimmerman et al., Nature Letters, Vol. 441, 4 May 2006). The SNALP formulation may contain the lipids 3-N-[(wmethoxypoly(ethylene glycol) 2000) carbamoyl]-!,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic siRNA during particle formation. When positively charged under increasingly acidic endosomal conditions, the ionizable lipid also mediates the fusion of SNALP with the endosomal membrane enabling release of siRNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALPsiRNA formulations. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC)—both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid were solubilized in ethanol at a molar ratio of 40:10: 40:10, respectively (see, Semple et al., Nature Niotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM Na2HPO4, 1 mM KH2PO4, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 µm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method may be extrapolated to the CRISPR Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate CRISPR Cas similar to SiRNA (see, e.g., Jayaraman, Angew. Chem. Int. Ed. 2012, 51, 8529-8533). A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11_0.04 (n=56), the particles may be extruded up to three times through 80 nm membranes prior to adding the CRISPR Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011) Published online 9 Jan. 2011) describes the use of lipid envelopes to deliver RNA. Use of lipid envelopes is also preferred in the present invention.

In another embodiment, lipids may be formulated with the CRISPR Cas system of the present invention to form lipid nanoparticles (LNPs). Lipids include, but are not limited to, DLin-KC2-DMA4, C12-200 and colipids disteroylphosphatidyl choline, cholesterol, and PEG-DMG may be formulated with CRISPR Cas instead of siRNA (see, e.g., Novobrantseva, Molecular Therapy—Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid:siRNA weight ratio may be ~12:1 and 9:1 in the case of DLin-KC2-DMA and C12-200 lipid nanoparticles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901, 708; 7,745,651; 7,803,397; 8,101,741; 8,188,263; 7,915, 399; 8,236,943 and 7,838,658 and European Pat. Nos 0.1766035; 1519714; 1781593 and 1664316), all of which may be used/and or adapted to the present invention.

The CRISPR Cas system may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid: fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart. Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered."

Supercharged Proteins

Supercharged proteins are a class of engineered or naturally occurring proteins with unusually high positive or negative net theoretical charge. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, siRNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of siRNA and plasmid DNA into mammalian cells are valuable both for research and therapeutic applications (Akinc et al., 2010, Nat. Biotech. 26, 561-569). Purified +36 GFP protein (or other superpositively charged protein) is mixed with siRNAs in the appropriate serum-free media and allowed to complex prior addition to cells. Inclusion of serum at this stage inhibits formation of the supercharged protein-siRNA complexes and reduces the effectiveness of the treatment. The following protocol has been found to be effective for a variety of cell lines (McNaughton et al., 2009, Proc. Natl. Acad. Sci. USA 106, 6111-6116). However, pilot experiments varying the dose of protein and siRNA should be performed to optimize the procedure for specific cell lines.

(1) One day before treatment, plate $1 \times 10^5$ cells per well in a 48-well plate.

(2) On the day of treatment, dilute purified+36 GFP protein in serumfree media to a final concentration 200 nM. Add siRNA to a final concentration of 50 nM. Vortex to mix and incubate at room temperature for 10 min.

(3) During incubation, aspirate media from cells and wash once with PBS.

(4) Following incubation of +36 GFP and siRNA, add the protein-siRNA complexes to cells.

(5) Incubate cells with complexes at 37 C for 4 h.

(6) Following incubation, aspirate the media and wash three times with 20 U/mL heparin PBS. Incubate cells with serum-containing media for a further 48 h or longer depending upon the assay for knockdown.

(7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications.

(1) One day before treatment, plate $1 \times 10^5$ per well in a 48-well plate.

(2) On the day of treatment, dilute purified b36 GFP protein in serumfree media to a final concentration 2 mM. Add 1 mg of plasmid DNA. Vortex to mix and incubate at room temperature for 10 min.

(3) During incubation, aspirate media from cells and wash once with PBS.

(4) Following incubation of b36 GFP and plasmid DNA, gently add the protein-DNA complexes to cells.

(5) Incubate cells with complexes at 37 C for 4 h.

(6) Following incubation, aspirate the media and wash with PBS. Incubate cells in serum-containing media and incubate for a further 24-48 h.

(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas system of the present invention.

Implantable Devices

In another embodiment, implantable devices are also contemplated for delivery of the CRISPR Cas system. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. The selection of drug is based on the advantageous of releasing drug locally and in prolonged period, where drug is released directly to the extracellular matrix (ECM) of the diseased area such as tumor, inflammation, degeneration or for symptomatic objectives, or to injured smooth muscle cells, or for prevention. One kind of drug is the gene silencing drugs based on RNA interference (RNAi), including but not limited to si RNA, sh RNA, or antisense RNA/DNA, ribozyme and nucleoside analogs. Therefore, this system may be used/and or adapted to the CRISPR Cas system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

As described in US Patent Publication 20110195123, there is provided a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 m$^3$ to 1000 mm$^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described in US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle. The site for local delivery also may optionally include sites enabling performing preventive activities including pregnancy, prevention of infection and aging.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear-auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a gene silencing biological RNAi drug, for example for localized cancer cases in breast, pancreas, brain, kidney, bladder, lung, and prostate as described below. Moreover, many drugs other than siRNA are applicable to be encapsulated in Loder, and can be used in association with this invention, as long as such drugs can be encapsulated with the Loder substrate, such as a matrix for example. Such drugs include approved drugs that are delivered today by methods other than of this invention, including Amphotericin B for fungal infection; antibiotics such as iii osteomyelitis; pain killers such as narcotics; anti degenerative such as in Alzheimer or Parkinson diseases in a Loder implanted in the vicinity of the spine in the case of back pain. Such a system may be used and/or adapted to deliver the CRISPR Cas system of the present invention.

For example, for specific applications such as prevention of growth or regrowth of smooth muscle cells (that are injured during a stenting procedure and as a result tend to proliferate), the drug may optionally be siRNA that silence smooth muscle cells, including H19 silencing, or a drug selected from the group consisting of taxol, rapamycin and rapamycin-analogs. In such cases the Loder is preferably either a Drug Eluting Stent (DES), with prolonged release at constant rate, or a dedicated device that is implanted separately, in association to the stent. All of this may be used/and or adapted to the CRISPR Cas system of the present invention.

As another example of a specific application, neuro and muscular degenerative diseases develop due, to abnormal gene expression. Local delivery of silencing RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the CRISPR Cas system of the present invention.

As yet another example of a specific application, psychiatric and cognitive disorders are treated with gene modifiers. Gene knockdown with silencing RNA is a treatment option. Loders locally delivering nucleotide based agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the CRISPR Cas system of the present invention.

As another example of a specific application, silencing of innate and/or adaptive immune mediators at local sites enables the prevention of organ transplant rejection. Local delivery of silencing RNAs and immunomodulating reagents with the Loder implanted into the transplanted organ and/or the implanted site renders local immune suppression by repelling immune cells such as CD8 activated against the transplanted organ. All of this may be used/and or adapted to the CRISPR Cas system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

CRISPR Enzyme mRNA and Guide RNA

CRISPR enzyme mRNA and guide RNA might also be delivered separately. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA.

Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA.

Additional administrations of CRISPR enzyme mRNA and/or guide RNA might be useful to achieve the most efficient levels of genome modification.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or animal model and using deep sequencing the analyze the extent of modification at potential off-target genomic loci. For example, for the guide sequence targeting 5'-GAGTCCGAGCAGAAGAAGAA-3' (SEQ ID NO: 3) in the EMX1 gene of the human genome, deep sequencing can be used to assess the level of modification at the following two off-target loci, 1: 5'-GAGTCCTAGCAGGAGAAGAA-3' (SEQ ID NO: 4) and 2: 5'-GAGTCTAAGCAGAAGAAGAA-3' (SEQ ID NO: 5). The concentration that gives the highest level of on-target modification while minimizing the level of off-target modification should be chosen for in vivo delivery.

Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences in red (single underline) and blue (double underline) respectively (these examples are based on the PAM requirement for *Streptococcus pyogenes* Cas9).

| Overhang length (bp) | Guide RNA design (guide sequence and PAM color coded) |
|---|---|
| 14 | (SEQ ID NO: 6)<br>5'-NNNNNNNNNNNNNNNNNNNNNNCCN................N...NNNNNNNNNNNNNNNN-3' |
| 13 | (SEQ ID NO: 7)<br>3'-NNNNNNNNNNNNNNNNNNNNNNN...N................NCCNNNNNNNNNNNNNNNN-5' |
| 12 | (SEQ ID NO: 8)<br>5'-NNNNNNNNNNNNNNNNNNNNNNNCC................N...NNNNNNNNNNNNNNNN-3' |
| 11 | (SEQ ID NO: 9)<br>3'-NNNNNNNNNNNNNNNNNNNNNNN...N................CCNNNNNNNNNNNNNNNN-5' |
| 10 | (SEQ ID NO: 10)<br>5'-NNNNNNNNNNNNNNNNNNNNNNNNC................N...NNNNNNNNNNNNNNNN-3' |
| 9 | (SEQ ID NO: 11)<br>3'-NNNNNNNNNNNNNNNNNNNNNNN...N................CCNNNNNNNNNNNNNNNN-5' |
| 8 | (SEQ ID NO: 12)<br>5'-NNNNNNNNNNNNNNNNNNNNNNNNN................N...NNNNNNNNNNNNNNNN-3' |
| 7 | (SEQ ID NO: 13)<br>3'-NNNNNNNNNNNNNNNNNNNNNNN...N................NNNNNNNNNNNNNNNNN-5' |
| 6 | (SEQ ID NO: 14)<br>5'-NNNNNNNNNNNNNNNNNNNNNNNNN................N...NNNNNNNNNNNNNNNN-3' |
| 5 | (SEQ ID NO: 15)<br>3'-NNNNNNNNNNNNNNNNNNNNNNN...N................NNNNNNNNNNNNNNNNN-5' |
| 4 | (SEQ ID NO: 16)<br>5'-NNNNNNNNNNNNNNNNNNNNNN................N...NNNNNNNNNNNNNNNNNN-3' |
| 3 | (SEQ ID NO: 17)<br>3'-NNNNNNNNNNNNNNNNNNNNNNN...N................NNNNNNNNNNNNNNNNN-5' |
| 2 | (SEQ ID NO: 18)<br>5'-NNNNNNNNNNNNNNNNNNNNN................N...NNNNNNNNNNNNNNNNNN-3' |
| 1 | (SEQ ID NO: 19)<br>3'-NNNNNNNNNNNNNNNNNNNNNNN...N................NNNNNNNNNNNNNNNNN-5' |
| blunt | (SEQ ID NO: 20)<br>5'-NNNNNNNNNNNNNNNNNNNN................N...NNNNNNNNNNNNNNNNNN-3' |
| 1 | (SEQ ID NO: 21)<br>3'-NNNNNNNNNNNNNNNNNNNNNNN...N................NNNNNNNNNNNNNNNNN-5' |
| 2 | (SEQ ID NO: 22)<br>5'-NNNNNNNNNNNNNNNNNNN................N...NNNNNNNNNNNNNNNNNNN-3' |
| 3 | (SEQ ID NO: 23)<br>3'-NNNNNNNNNNNNNNNNNNNNNNN...N................NNNNNNNNNNNNNNNNN-5' |
| 4 | (SEQ ID NO: 24)<br>5'-NNNNNNNNNNNNNNNNN................N...NNNNNNNNNNNNNNNNNNNN-3' |

-continued

| Overhang length (bp) | Guide RNA design (guide sequence and PAM color coded) |
|---|---|
| 5 | 3'-NNNNNNNNNNNNNNNNNNNN...N[guide+PAM]NNNNNNNNNNNNNNNNNNNN-5' (SEQ ID NO: 25) |
| 6 | 5'-NNNNNNNNNNNNN[guide+PAM]N...NNNNNNNNNNNNNNNNNNNNNNNN-3' (SEQ ID NO: 26) |
| 7 | 3'-NNNNNNNNNNNNNNNNNNNN...N[guide+PAM]NNNNNNNNNNNNNNNNNNNN-5' (SEQ ID NO: 27) |
| 8 | 5'-NNNNNNNNNNNNN[guide+PAM]N...NNNNNNNNNNNNNNNNNNNNNNNN-3' (SEQ ID NO: 28) |
| 9 | 3'-NNNNNNNNNNNNNNNNNNNN...N[guide+PAM]NNNNNNNNNNNNNNNNNNNN-5' (SEQ ID NO: 29) |
| 10 | 5'-NNNNNNNNNNNN[guide+PAM]N...NNNNNNNNNNNNNNNNNNNNNNNNN-3' (SEQ ID NO: 30) |
| 11 | 3'-NNNNNNNNNNNNNNNNNNNN...N[guide+PAM]NNNNNNNNNNNNNNNNNNNN-5' (SEQ ID NO: 31) |
| 12 | 5'-NNNNNNNNNNN[guide+PAM]N...NNNNNNNNNNNNNNNNNNNNNNNNNN-3' (SEQ ID NO: 32) |
| 13 | 3'-NNNNNNNNNNNNNNNNNNNN...N[guide+PAM]NNNNNNNNNNNNNNNNNNNN-5' (SEQ ID NO: 33) |
| 14 | 5'-NNNNNNNNNN[guide+PAM]N...NNNNNNNNNNNNNNNNNNNNNNNNNNN-3' (SEQ ID NO: 34) |
| 15 | 3'-NNNNNNNNNNNNNNNNNNNN...N[guide+PAM]NNNNNNNNNNNNNNNNNNNN-5' (SEQ ID NO: 35) |
| 16 | 5'-NNNNNNNN[guide+PAM]N...NNNNNNNNNNNNNNNNNNNNNNNNNNNNN-3' (SEQ ID NO: 36) |
| 17 | 3'-NNNNNNNNNNNNNNNNNNNN...N[guide+PAM]NNNNNNNNNNNNNNNNNNNN-5' (SEQ ID NO: 37) |
|  | 5'-NNNNNNN[guide+PAM]N...NNNNNNNNNNNNNNNNNNNNNNNNNNNNNN-3' (SEQ ID NO: 38) |
|  | 3'-NNNNNNNNNNNNNNNNNNNN...N[guide+PAM]NNNNNNNNNNNNNNNNNNNN-5' (SEQ ID NO: 39) |
|  | 5'-NNNNNN[guide+PAM]N...NNNNNNNNNNNNNNNNNNNNNNNNNNNNNNN-3' (SEQ ID NO: 40) |
|  | 3'-NNNNNNNNNNNNNNNNNNNN...N[guide+PAM]NNNNNNNNNNNNNNNNNNNN-5' (SEQ ID NO: 41) |
|  | 5'-NNNNN[guide+PAM]N...NNNNNNNNNNNNNNNNNNNNNNNNNNNNNNNN-3' (SEQ ID NO: 42) |
|  | 3'-NNNNNNNNNNNNNNNNNNNN...N[guide+PAM]NNNNNNNNNNNNNNNNNNNN-5' (SEQ ID NO: 43) |
|  | 5'-NNNN[guide+PAM]N...NNNNNNNNNNNNNNNNNNNNNNNNNNNNNNNNN-3' (SEQ ID NO: 44) |

-continued

Overhang
length (bp) Guide RNA design (guide sequence and PAM color coded)

```
                                                          (SEQ ID NO: 45)
3'-NNNNNNNNNNNNNNNNNNNNN N                 NNNNNNNNNNNNNNNNNN-5'

(SEQ ID NO: 46)
5'-NNN                  N NNNNNNNNNNNNNNNNNNNNNNNNNNNNNN-3'

(SEQ ID NO: 47)
3'-NNNNNNNNNNNNNNNNNNNN N                 NNNNNNNNNNNNNNNNNN-5'

(SEQ ID NO: 48)
5'-NN                   N NNNNNNNNNNNNNNNNNNNNNNNNNNNNNN-3'

(SEQ ID NO: 49)
3'-NNNNNNNNNNNNNNNNNNNNN N                 NNNNNNNNNNNNNNNNN-5'

(SEQ ID NO: 50)
5'-NN                   C NNNNNNNNNNNNNNNNNNNNNNNNNNNNNN-3'

(SEQ ID NO: 51)
3'-NNNNNNNNNNNNNNNNNNNNN C                 NNNNNNNNNNNNNNNNN-5'

(SEQ ID NO: 52)
5'-NN                   N NNNNNNNNNNNNNNNNNNNNNNNNNNNNNNN-3'

(SEQ ID NO: 53)
3'-NNNNNNNNNNNNNNNNNNNNNNCC N                 NNNNNNNNNNNNN-5'

(SEQ ID NO: 54)
5'-NN                   C NNNNNNNNNNNNNNNNNNNNNNNNNNNNNNN-3'

(SEQ ID NO: 55)
3'-NNNNNNNNNNNNNNNNNNNNNNNCCN N                 NNNNNNNNNNNN-5'

(SEQ ID NO: 54)
5'-NN                   C NNNNNNNNNNNNNNNNNNNNNNNNNNNNNNN-3'

(SEQ ID NO: 56)
3'-NNNNNNNNNNNNNNNNNNNNNNNCCNN N                 NNNNNNNNNNN-5'

(SEQ ID NO: 54)
5'-NN                   C NNNNNNNNNNNNNNNNNNNNNNNNNNNNNNN-3'

(SEQ ID NO: 57)
3'-NNNNNNNNNNNNNNNNNNNNNNNCCNNN N                 NNNNNNNNNN-5'

(SEQ ID NO: 54)
5'-NN                   C NNNNNNNNNNNNNNNNNNNNNNNNNNNNNNN-3'

(SEQ ID NO: 58)
3'-NNNNNNNNNNNNNNNNNNNNNNNCCNNNN N                 NNNNNNNNN-5'

(SEQ ID NO: 54)
5'-NN                   C NNNNNNNNNNNNNNNNNNNNNNNNNNNNNNN-3'

(SEQ ID NO: 59)
3'-NNNNNNNNNNNNNNNNNNNNNNNCCNNNNN N                 NNNNNNNN-5'
```

Further interrogation of the system have given Applicants evidence of the 5' overhang (see, e.g., Ran et al., Cell. 2013 Sep. 12; 154(6):1380-9 and U.S. Provisional Patent Application Ser. No. 61/871,301 filed Aug. 28, 2013). Applicants have further identified parameters that relate to efficient cleavage by the Cas9 nickase mutant when combined with two guide RNAs and these parameters include but are not limited to the length of the 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs or 1-34 base pairs. In other preferred methods of the invention the first guide sequence directing cleavage of one strand of the DNA duplex near the first target sequence and the second guide sequence directing cleavage of other strand near the second target sequence results in a blunt cut or a 3' overhang. In embodiments of the invention the 3' overhang is at most 150, 100 or 25 base pairs or at least 15, 10 or 1 base pairs. In preferred embodiments the 3' overhang is 1-100 basepairs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity.

Since Cas9n and Cas9H840A nick opposite strands of DNA, substitution of Cas9n with Cas9H840A with a given sgRNA pair should result in the inversion of the overhang type. For example, a pair of sgRNAs that will generate a 5' overhang with Cas9n should in principle generate the corresponding 3' overhang instead. Therefore, sgRNA pairs that lead to the generation of a 3' overhang with Cas9n might be used with Cas9H840A to generate a 5' overhang. Unexpectedly, Applicants tested Cas9H840A with a set of sgRNA pairs designed to generate both 5' and 3' overhangs (offset range from −278 to +58 bp), but were unable to observe indel formation. Further work may be needed to identify the necessary design rules for sgRNA pairing to allow double nicking by Cas9H840A.

Liver, Proprotein Convertase Subtilisin Kexin 9 (PCSK9)

Proprotein convertase subtilisin kexin 9 (PCSK9) is a member of the subtilisin serine protease family. PCSK9 is primarily expressed by the liver and is critical for the down regulation of hepatocyte LDL receptor expression. LDL-C levels in plasma are highly elevated in humans with gain of function mutations in PCSK9, classifying them as having severe hypercholesterolemia. Therefore, PCSK9 is an attractive target for CRISPR. PCS9K-targeted CRISPR may be formulated in a lipid particle and for example administered at about 15, 45, 90, 150, 250 and 400 µg/kg intraveneously.

Bailey et al. (J Mol Med (Berl). 1999 January; 77(1):244-9) discloses insulin delivery by ex-vivo somatic cell gene therapy involves the removal of non-B-cell somatic cells (e.g. fibroblasts) from a diabetic patient, and genetically altering them in vitro to produce and secrete insulin. The cells can be grown in culture and returned to the donor as a source of insulin replacement. Cells modified in this way could be evaluated before implantation, and reserve stocks could be cryopreserved. By using the patient's own cells, the procedure should obviate the need for immunosuppression and overcome the problem of tissue supply, while avoiding a recurrence of cell destruction. Ex-vivo somatic cell gene therapy requires an accessible and robust cell type that is amenable to multiple transfections and subject to controlled proliferation. Special problems associated with the use of non-B-cell somatic cells include the processing of proinsulin to insulin, and the conferment of sensitivity to glucose-stimulated proinsulin biosynthesis and regulated insulin release. Preliminary studies using fibroblasts, pituitary cells, kidney (COS) cells and ovarian (CHO) cells suggest that these challenges could be met, and that ex-vivo somatic cell gene therapy offers a feasible approach to insulin replacement therapy. The system of Bailey et al. may be used/and or adapted to the CRISPR Cas system of the present invention for delivery to the liver.

The methods of Sato et al. (Nature Biotechnology Volume 26 Number 4 Apr. 2008, Pages 431-442) may be applied to the CRISPR Cas system of the present invention for delivery to the liver. Sato et al. found that treatments with the siRNA-bearing vitamin A-coupled liposomes almost completely resolved liver fibrosis and prolonged survival in rats with otherwise lethal dimethylnitrosamine-induced liver cirrhosis in a dose- and duration-dependent manner. Cationic liposomes (Lipotrust) containing 0,0'-ditetradecanoyl-N-(a-trimethylammonioacetyl) diethanolamine chloride (DC-6-14) as a cationic lipid, cholesterol and dioleoylphosphatidylethanolamine at a molar ratio of 4:3:3 (which has shown high transfection efficiency under serumcontaining conditions for in vitro and in vivo gene delivery) were purchased from Hokkaido System Science. The liposomes were manufactured using a freeze-dried empty liposomes method and prepared at a concentration of 1 mM (DC-16-4) by addition of double-distilled water (DDW) to the lyophilized lipid mixture under vortexing before use. To prepare VA-coupled liposomes, 200 nmol of vitamin A (retinol, Sigma) dissolved in DMSO was mixed with the liposome suspensions (100 nmol as DC-16-4) by vortexing in a 1.5 ml tube at 25 1C. To prepare VA-coupled liposomes carrying siRNAgp46 (VA-lip-siRNAgp46), a solution of siRNAgp46 (580 pmol/ml in DDW) was added to the retinol-coupled liposome solution with stirring at 25 C. The ratio of siRNA to DC-16-4 was 1:11.5 (mol/mol) and the siRNA to liposome ratio (wt/wt) was 1:1. Any free vitamin A or siRNA that was not taken up by liposomes were separated from liposomal preparations using a microparittion system (VIVASPIN 2 concentrator 30,000 MWCO PES, VIVASCIENCE). The liposomal suspension was added to the filters and centrifuged at 1,500 g for 5 min 3 times at 25 1C. Fractions were collected and the material trapped in the filter was reconstituted with PBS to achieve the desired dose for in vitro or in vivo use. Three injections of 0.75 mg/kg siRNA were given every other day to rats. The system of Sato et al. may be used/and or adapted to the CRISPR Cas system of the present invention for delivery to the liver by delivering about 0.5 to 1 mg/kg of CRISPR Cas RNA in the liposomes as described by Sato et al. to humans.

The methods of Rozema et al. (PNAS, Aug. 7, 2007, vol. 104, no. 32) for a vehicle for the delivery of siRNA to hepatocytes both in vitro and in vivo, which Rozema et al. have named siRNA Dynamic PolyConjugates may also be applied to the present invention. Key features of the Dynamic Poly-Conjugate technology include a membrane-active polymer, the ability to reversibly mask the activity of this polymer until it reaches the acidic environment of endosomes, and the ability to target this modified polymer and its siRNA cargo specifically to hepatocytes in vivo after simple, low-pressure i.v. injection. SATA-modified siRNAs are synthesized by reaction of 5' aminemodified siRNA with 1 weight equivalents (wt eq) of Nsuccinimidyl-S-acetylthioacetate (SATA) reagent (Pierce) and 0.36 wt eq of NaHCO$_3$ in water at 4° C. for 16 h. The modified siRNAs are then precipitated by the addition of 9 vol of ethanol and incubation at ▯80° C. for 2 h. The precipitate is resuspended in 1X siRNA buffer (Dharmacon) and quantified by measuring absorbance at the 260-nm wavelength. PBAVE (30 mg/ml in 5 mMTAPS, pH 9) is modified by addition of 1.5 wt % SMPT (Pierce). After a 1-h incubation, 0.8 mg of SMPT-PBAVE was added to 400 µl of isotonic glucose solution containing 5 mM TAPS (pH 9). To this solution was added 50 µg of SATA-modified siRNA. For the dose-response experiments where [PBAVE] was constant, different amounts of siRNA are added. The mixture is then incubated for 16 h. To the solution is then added 5.6 mg of Hepes free base followed by a mixture of 3.7 mg of CDM-NAGand 1.9 mg of CDM-PEG. The solution is then incubated for at least 1 h at room temperature before injection. CDM-PEG and CDM-NAG are synthesized from the acid chloride generated by using oxalyl chloride. To the acid chloride is added 1.1 molar equivalents polyethylene glycol monomethyl ether (molecular weight average of 450) to generate CDM-PEG or (aminoethoxy)ethoxy-2-(acetylamino)-2-deoxy-β-D-glucopyranoside to generate CDM-NAG. The final product is purified by using reverse-phase HPLC with a 0.1% TFA water/acetonitrile gradient. About 25 to 50 µg of siRNA was delivered to mice. The system of Rozema et al. may be applied to the CRISPR Cas system of the present invention for delivery to the liver, for example by envisioning a dosage of about 50 to about 200 mg of CRISPR Cas for delivery to a human.

Bone

Oakes and Lieberman (Clin Orthop Relat Res. 2000 October; (379 Suppl):S101-12) discusses delivery of genes to the bone. By transferring genes into cells at a specific anatomic site, the osteoinductive properties of growth factors can be used at physiologic doses for a sustained period to facilitate a more significant healing response. The specific anatomic site, the quality of the bone, and the soft-tissue envelope, influences the selection of the target cells for regional gene therapy. Gene therapy vectors delivered to a treatment site in osteoconductive carriers have yielded promising results. Several investigators have shown exciting results using ex vivo and in vivo regional gene therapy in animal models. Such a system may be used/and or adapted to the CRISPR Cas system for delivery to the bone.

Brain

Delivery options for the brain include encapsulation of CRISPR enzyme and guide RNA in the form of either DNA or RNA into liposomes and conjugating to molecular Trojan horses for trans-blood brain barrier (BBB) delivery. Molecular Trojan horses have been shown to be effective for delivery of B-gal expression vectors into the brain of non-human primates. The same approach can be used to delivery vectors containing CRISPR enzyme and guide RNA. For instance, Xia C F and Boado R J, Pardridge W M ("Antibody-mediated targeting of siRNA via the human insulin receptor using avidin-biotin technology." Mol Pharm. 2009 May-June; 6(3):747-51. doi: 10.1021/mp800194) describes how delivery of short interfering RNA (siRNA) to cells in culture, and in vivo, is possible with combined use of a receptor-specific monoclonal antibody (mAb) and avidin-biotin technology. The authors also report that because the bond between the targeting mAb and the siRNA is stable with avidin-biotin technology, and RNAi effects at distant sites such as brain are observed in vivo following an intravenous administration of the targeted siRNA.

Zhang et al. (Mol Ther. 2003 January; 7(1):11-8.)) describe how expression plasmids encoding reporters such as luciferase were encapsulated in the interior of an "artificial virus" comprised of an 85 nm pegylated immunoliposome, which was targeted to the rhesus monkey brain in vivo with a monoclonal antibody (MAb) to the human insulin receptor (HIR). The HIRMAb enables the liposome carrying the exogenous gene to undergo transcytosis across the blood-brain barrier and endocytosis across the neuronal plasma membrane following intravenous injection. The level of luciferase gene expression in the brain was 50-fold higher in the rhesus monkey as compared to the rat. Widespread neuronal expression of the beta-galactosidase gene in primate brain was demonstrated by both histochemistry and confocal microscopy. The authors indicate that this approach makes feasible reversible adult transgenics in 24 hours. Accordingly, the use of immunoliposome is preferred. These may be used in conjunction with antibodies to target specific tissues or cell surface proteins.

Other means of delivery or RNA are also preferred, such as via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials; 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641).

Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then siRNA is loaded into the exosomes. Delivery or administration according to the invention can be performed with exosomes, in particular but not limited to the brain.

Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, Calif.) filled with phosphate-buffered saline (PBS) or free TocsiBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 µmol of CRISPR Cas targeted to the brain may becontemplated.

Zou et al. ((HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 µl of a recombinant lentivirus having a titer of $1\times10^9$ transducing units (TU)/ml by an intrathecal catheter. A similar dosage of CRISPR Cas expressed in a lentiviral vector targeted to the brain may be contemplated for humans in the present invention, for example, about 10-50 ml of CRISPR Cas targeted to the brain in a lentivirus having a titer of $1\times10^9$ transducing units (TU)/ml may becontemplated.

Targeted Deletion, Therapeutic Applications

Targeted deletion of genes is preferred. Examples are exemplified in Example 18. Preferred are, therefore, genes involved in cholesterol biosynthesis, fatty acid biosynthesis, and other metabolic disorders, genes encoding mis-folded proteins involved in amyloid and other diseases, oncogenes leading to cellular transformation, latent viral genes, and genes leading to dominant-negative disorders, amongst other disorders. As exemplified here, Applicants prefer gene delivery of a CRISPR-Cas system to the liver, brain, ocular, epithelial, hematopoetic, or another tissue of a subject or a patient in need thereof, suffering from metabolic disorders, amyloidosis and protein-aggregation related diseases, cellular transformation arising from genetic mutations and translocations, dominant negative effects of gene mutations, latent viral infections, and other related symptoms, using either viral or nanoparticle delivery system.

Therapeutic applications of the CRISPR-Cas system include Glaucoma, Amyloidosis, and Huntington's disease. These are exemplified in Example 20 and the features described therein are preferred alone or in combination.

Another example of a polyglutamine expansion disease that may be treated by the present invention includes spinocerebellar ataxia type 1 (SCA1). Upon intracerebellar injection, recombinant adenoassociated virus (AAV) vectors expressing short hairpin RNAs profoundly improve motor coordination, restored cerebellar morphology and resolved characteristic ataxin-1 inclusions in Purkinje cells of SCA1 mice (see, e.g., Xia et al., Nature Medicine, Vol. 10, No. 8, August 2004). In particular, AAV1 and AAV5 vectors are preferred and AAV titers of about $1\times10^{12}$ vector genomes/ml are desirable.

As an example, chronic infection by HIV-1 may be treated or prevented. In order to accomplish this, one may generate CRISPR-Cas guide RNAs that target the vast majority of the HIV-1 genome while taking into account HIV-1 strain variants for maximal coverage and effectiveness. One may accomplish delivery of the CRISPR-Cas system by conventional adenoviral or lentiviral-mediated infection of the host immune system. Depending on approach, host immune cells could be a) isolated, transduced with CRISPR-Cas, selected, and re-introduced in to the host or b) transduced in vivo by systemic delivery of the CRISPR-Cas system. The first approach allows for generation of a resistant immune population whereas the second is more likely to target latent viral reservoirs within the host. This is discussed in more detail in the Examples section.

In another example, US Patent Publication No. 20130171732 assigned to Sangamo BioSciences, Inc. relates to insertion of an anti-HIV transgene into the genome, methods of which may be applied to the CRISPR Cas system of the present invention. In another embodiment, the CXCR4 gene may be targeted and the TALE system of US Patent Publication No. 20100291048 assigned to Sangamo BioSciences, Inc. may be modified to the CRISPR Cas system of the present invention. The method of US Patent Publication Nos. 20130137104 and 20130122591 assigned to Sangamo BioSciences, Inc. and US Patent Publication No. 20100146651 assigned to Cellectis may be more generally applicable for transgene expression as it involves modifying a hypoxanthine-guanine phosphoribosyltransferase (HPRT) locus for increasing the frequency of gene modification.

It is also envisaged that the present invention generates a gene knockout cell library. Each cell may have a single gene knocked out. This is exemplified in Example 23.

One may make a library of ES cells where each cell has a single gene knocked out, and the entire library of ES cells will have every single gene knocked out. This library is useful for the screening of gene function in cellular processes as well as diseases. To make this cell library, one may integrate Cas9 driven by an inducible promoter (e.g. doxycycline inducible promoter) into the ES cell. In addition, one may integrate a single guide RNA targeting a specific gene in the ES cell. To make the ES cell library, one may simply mix ES cells with a library of genes encoding guide RNAs targeting each gene in the human genome. One may first introduce a single BxB1 attB site into the AAVS1 locus of the human ES cell. Then one may use the BxB1 integrase to facilitate the integration of individual guide RNA genes into the BxB1 attB site in AAVS1 locus. To facilitate integration, each guide RNA gene may be contained on a plasmid that carries of a single attP site. This way BxB1 will recombine the attB site in the genome with the attP site on the guide RNA containing plasmid. To generate the cell library, one may take the library of cells that have single guide RNAs integrated and induce Cas9 expression. After induction, Cas9 mediates double strand break at sites specified by the guide RNA.

Chronic administration of protein therapeutics may elicit unacceptable immune responses to the specific protein. The immunogenicity of protein drugs can be ascribed to a few immunodominant helper T lymphocyte (HTL) epitopes. Reducing the MHC binding affinity of these HTL epitopes contained within these proteins can generate drugs with lower immunogenicity (Tangri S, et al. ("Rationally engineered therapeutic proteins with reduced immunogenicity" J Immunol. 2005 Mar. 15; 174(6):3187-96.) In the present invention, the immunogenicity of the CRISPR enzyme in particular may be reduced following the approach first set out in Tangri et al with respect to erythropoietin and subsequently developed. Accordingly, directed evolution or rational design may be used to reduce the immunogenicity of the CRISPR enzyme (for instance a Cas9) in the host species (human or other species).

In Example 28, Applicants used 3 guideRNAs of interest and able to visualize efficient DNA cleavage in vivo occurring only in a small subset of cells. Essentially, what Applicants have shown here is targeted in vivo cleavage. In particular, this provides proof of concept that specific targeting in higher organisms such as mammals can also be achieved. It also highlights multiplex aspect in that multiple guide sequences (i.e. separate targets) can be used simultaneously (in the sense of co-delivery). In other words, Applicants used a multiple approach, with several different sequences targeted at the same time, but independently.

A suitable example of a protocol for producing AAV, a preferred vector of the invention is provided in Example 34.

Trinucleotide repeat disorders are preferred conditions to be treated. These are also exemplified herein.

For example, US Patent Publication No. 20110016540, describes use of zinc finger nucleases to genetically modify cells, animals and proteins associated with trinucleotide repeat expansion disorders. Trinucleotide repeat expansion disorders are complex, progressive disorders that involve developmental neurobiology and often affect cognition as well as sensori-motor functions.

Trinucleotide repeat expansion proteins are a diverse set of proteins associated with susceptibility for developing a trinucleotide repeat expansion disorder, the presence of a trinucleotide repeat expansion disorder, the severity of a trinucleotide repeat expansion disorder or any combination thereof. Trinucleotide repeat expansion disorders are divided into two categories determined by the type of repeat. The most common repeat is the triplet CAG, which, when present in the coding region of a gene, codes for the amino acid glutamine (Q). Therefore, these disorders are referred to as the polyglutamine (polyQ) disorders and comprise the following diseases: Huntington Disease (HD); Spinobulbar Muscular Atrophy (SBMA); Spinocerebellar Ataxias (SCA types 1, 2, 3, 6, 7, and 17); and Dentatorubro-Pallidoluysian Atrophy (DRPLA). The remaining trinucleotide repeat expansion disorders either do not involve the CAG triplet or the CAG triplet is not in the coding region of the gene and are, therefore, referred to as the non-polyglutamine disorders. The non-polyglutamine disorders comprise Fragile X Syndrome (FRAXA); Fragile XE Mental Retardation (FRAXE); Friedreich Ataxia (FRDA); Myotonic Dystrophy (DM); and Spinocerebellar Ataxias (SCA types 8, and 12).

The proteins associated with trinucleotide repeat expansion disorders are typically selected based on an experimental association of the protein associated with a trinucleotide repeat expansion disorder to a trinucleotide repeat expansion disorder. For example, the production rate or circulating concentration of a protein associated with a trinucleotide repeat expansion disorder may be elevated or depressed in a population having a trinucleotide repeat expansion disorder relative to a population lacking the trinucleotide repeat expansion disorder. Differences in protein levels may be assessed using proteomic techniques including but not limited to Western blot, immunohistochemical staining, enzyme linked immunosorbent assay (ELISA), and mass spectrometry. Alternatively, the proteins associated with trinucleotide repeat expansion disorders may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Non-limiting examples of proteins associated with trinucleotide repeat expansion disorders include AR (androgen receptor), FMR1 (fragile X mental retardation 1), HTT (huntingtin), DMPK (dystrophia myotonica-protein kinase), FXN (frataxin), ATXN2 (ataxin 2), ATN1 (atrophin 1), FEN1 (flap structure-specific endonuclease 1), TNRC6A (trinucleotide repeat containing 6A), PABPN1 (poly(A) binding protein, nuclear 1), JPH3 (junctophilin 3), MED15 (mediator complex subunit 15), ATXN1 (ataxin 1), ATXN3 (ataxin 3), TBP (TATA box binding protein), CACNA1A (calcium channel, voltage-dependent, P/Q type, alpha 1A subunit), ATXN80S (ATXN8 opposite strand (non-protein coding)), PPP2R2B (protein phosphatase 2, regulatory subunit B, beta), ATXN7 (ataxin 7), TNRC6B (trinucleotide repeat containing 6B), TNRC6C (trinucleotide repeat containing 6C), CELF3 (CUGBP, Elav-like family member 3), MAB21L1 (mab-21-like 1 (*C. elegans*)), MSH2 (mutS homolog 2, colon cancer, nonpolyposis type 1 (*E. coli*)), TMEM185A (transmembrane protein 185A), SIX5 (SIX homeobox 5), CNPY3 (canopy 3 homolog (zebrafish)), FRAXE (fragile site, folic acid type, rare, fra(X)(q28) E), GNB2 (guanine nucleotide binding protein (G protein), beta polypeptide 2), RPL14 (ribosomal protein L14), ATXN8 (ataxin 8), INSR (insulin receptor), TTR (transthyretin), EP400 (E1A binding protein p400), GIGYF2 (GRB10 interacting GYF protein 2), OGG1 (8-oxoguanine DNA glycosylase), STCI (stanniocalcin 1), CNDP1 (carnosine dipeptidase 1 (metallopeptidase M20 family)), C10orf2 (chromosome 10 open reading frame 2), MAML3 (mastermind-like 3 (*Drosophila*)), DKC1 (dyskeratosis congenita 1, dyskerin), PAXIP1 (PAX interacting (with transcription-activation domain) protein 1), CASK (calcium/calmodulin-dependent serine protein kinase (MAGUK family)), MAPT (microtubule-associated protein tau), SP1 (Sp1 transcription factor), POLG (polymerase (DNA directed), gamma), AFF2 (AF4/FMR2 family, member 2), THBS1 (thrombospondin 1), TP53 (tumor protein p53), ESR1 (estrogen receptor 1), CGGBP1 (CGG triplet repeat binding protein 1), ABT1 (activator of basal transcription 1), KLK3 (kallikrein-related peptidase 3), PRNP (prion protein), JUN (jun oncogene), KCNN3 (potassium intermediate/small conductance calcium-activated channel, subfamily N, member 3), BAX (BCL2-associated X protein), FRAXA (fragile site, folic acid type, rare, fra(X)(q27.3) A (macroorchidism, mental retardation)), KBTBD10 (kelch repeat and BTB (POZ) domain containing 10), MBNLI (muscleblind-like (*Drosophila*)), RAD51 (RAD51 homolog (RecA homolog, *E. coli*) (*S. cerevisiae*)), NCOA3 (nuclear receptor coactivator 3), ERDA1 (expanded repeat domain, CAG/CTG 1), TSC1 (tuberous sclerosis 1), COMP (cartilage oligomeric matrix protein), GCLC (glutamate-cysteine ligase, catalytic subunit), RRAD (Ras-related associated with diabetes), MSH3 (mutS homolog 3 (*E. coli*)), DRD2 (dopamine receptor D2), CD44 (CD44 molecule (Indian blood group)), CTCF (CCCTC-binding factor (zinc finger protein)), CCND 1 (cyclin D1), CLSPN (claspin homolog (*Xenopus laevis*)), MEF2A (myocyte enhancer factor 2A), PTPRU (protein tyrosine phosphatase, receptor type, U), GAPDH (glyceraldehyde-3-phosphate dehydrogenase), TRIM22 (tripartite motif-containing 22), WT1 (Wilms tumor 1), AHR (aryl hydrocarbon receptor), GPX1 (glutathione peroxidase 1), TPMT (thiopurine S-methyltransferase), NDP (Norrie disease (pseudoglioma)), ARX (aristaless related homeobox), MUS81 (MUS81 endonuclease homolog (*S. cerevisiae*)), TYR (tyrosinase (oculocutaneous albinism IA)), EGR1 (early growth response 1), UNG (uracil-DNA glycosylase), NUMBL (numb homolog (*Drosophila*)-like), FABP2 (fatty acid binding protein 2, intestinal), EN2 (engrailed homeobox 2), CRYGC (crystallin, gamma C), SRP14 (signal recognition particle 14 kDa (homologous Alu RNA binding protein)), CRYGB (crystallin, gamma B), PDCD1 (programmed cell death 1), HOXA1 (homeobox A1), ATXN2L (ataxin 2-like), PMS2 (PMS2 postmeiotic segregation increased 2 (*S. cerevisiae*)), GLA (galactosidase, alpha), CBL (Cas-Br-M (murine) ecotropic retroviral transforming sequence), FTH1 (ferritin, heavy polypeptide 1), IL12RB2 (interleukin 12 receptor, beta 2), OTX2 (orthodenticle homeobox 2), HOXA5 (homeobox A5); POLG2 (polymerase (DNA directed), gamma 2, accessory subunit), DLX2 (distal-less homeobox 2), SIRPA (signal-regulatory protein alpha), OTX1 (orthodenticle homeobox 1), AHRR (aryl-hydrocarbon receptor repressor), MANF (mesencephalic astrocyte-derived neurotrophic factor), TMEM158 (transmembrane protein 158 (gene/pseudogene)), and ENSG00000078687.

Preferred proteins associated with trinucleotide repeat expansion disorders include HTT (Huntingtin), AR (androgen receptor), FXN (frataxin), Atxn3 (ataxin), Atxn1 (ataxin), Atxn2 (ataxin), Atxn7 (ataxin), Atxn10 (ataxin), DMPK (dystrophia myotonica-protein kinase), Atn1 (atrophin 1), CBP (creb binding protein), VLDLR (very low density lipoprotein receptor), and any combination thereof.

According to another aspect, a method of gene therapy for the treatment of a subject having a mutation in the CFTR gene is provided and comprises administering a therapeutically effective amount of a CRISPR-Cas gene therapy particle, optionally via a biocompatible pharmaceutical carrier, to the cells of a subject. Preferably, the target DNA comprises the mutation deltaF508. In general, it is of preferred that the mutation is repaired to the wildtype. In this case, the mutation is a deletion of the three nucleotides that comprise the codon for phenylalanine (F) at position 508. Accordingly, repair in this instance requires reintroduction of the missing codon into the mutant.

To implement this Gene Repair Strategy, it is preferred that an adenovirus/AAV vector system is introduced into the host cell, cells or patient. Preferably, the system comprises a Cas9 (or Cas9 nickase) and the guide RNA along with a adenovirus/AAV vector system comprising the homology repair template containing the F508 residue. This may be introduced into the subject via one of the methods of delivery discussed earlier. The CRISPR-Cas system may be guided by the CFTRdelta 508 chimeric guide RNA. It targets a specific site of the CFTR genomic locus to be nicked or cleaved. After cleavage, the repair template is inserted into the cleavage site via homologous recombination correcting the deletion that results in cystic fibrosis or causes cystic fibrosis related symptoms. This strategy to direct delivery and provide systemic introduction of CRISPR systems with appropriate guide RNAs can be employed to target genetic mutations to edit or otherwise manipulate genes that cause metabolic, liver, kidney and protein diseases and disorders such as those in Table B.

Genome Editing

The CRISPR/Cas9 systems of the present invention can be used to correct genetic mutations that were previously attempted with limited success using TALEN and ZFN. For example, WO2013163628 A2, Genetic Correction of Mutated Genes, published application of Duke University describes efforts to correct, for example, a frameshift mutation which causes a premature stop codon and a truncated gene product that can be corrected via nuclease mediated non-homologous end joining such as those responsible for Duchenne Muscular Dystrophy, ("DMD") a recessive, fatal, X-linked disorder that results in muscle degeneration due to mutations in the dystrophin gene. The majority of dystrophin mutations that cause DMD are deletions of exons that disrupt the reading frame and cause premature translation termination in the dystrophin gene. Dystrophin is a cytoplasmic protein that provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

The methods of US Patent Publication No. 20130145487 assigned to Cellectis, which relates to meganuclease variants to cleave a target sequence from the human dystrophin gene (DMD), may also be modified to for the CRISPR Cas system of the present invention.

Blood

The present invention also contemplates delivering the CRISPR-Cas system to the blood.

The plasma exosomes of Wahlgren et al. (Nucleic Acids Research, 2012, Vol. 40, No. 17 e130) were previously described and may be utilized to deliver the CRISPR Cas system to the blood.

The CRISPR Cas system of the present invention is also contemplated to treat hemoglobinopathies, such as thalassemias and sickle cell disease. See, e.g., International Patent Publication No. WO 2013/126794 for potential targets that may be targeted by the CRISPR Cas system of the present invention.

US Patent Publication Nos. 20110225664, 20110091441, 20100229252, 20090271881 and 20090222937 assigned to Cellectis, relates to CREI variants, wherein at least one of the two I-CreI monomers has at least two substitutions, one in each of the two functional subdomains of the LAGLI-DADG core domain (SEQ ID NO: 60) situated respectively from positions 26 to 40 and 44 to 77 of I-CreI, said variant being able to cleave a DNA target sequence from the human interleukin-2 receptor gamma chain (IL2RG) gene also named common cytokine receptor gamma chain gene or gamma C gene. The target sequences identified in US Patent Publication Nos. 20110225664, 20110091441, 20100229252, 20090271881 and 20090222937 may be utilized for the CRISPR Cas system of the present invention.

Severe Combined Immune Deficiency (SCID) results from a defect in lymphocytes T maturation, always associated with a functional defect in lymphocytes B (Cavazzana-Calvo et al., Annu. Rev. Med., 2005, 56, 585-602; Fischer et al., Immunol. Rev., 2005, 203, 98-109). Overall incidence is estimated to 1 in 75 000 births. Patients with untreated SCID are subject to multiple opportunist micro-organism infections, and do generally not live beyond one year. SCID can be treated by allogenic hematopoietic stem cell transfer, from a familial donor. Histocompatibility with the donor can vary widely. In the case of Adenosine Deaminase (ADA) deficiency, one of the SCID forms, patients can be treated by injection of recombinant Adenosine Deaminase enzyme.

Since the ADA gene has been shown to be mutated in SCID patients (Giblett et al., Lancet, 1972, 2, 1067-1069), several other genes involved in SCID have been identified (Cavazzana-Calvo et. al., Annu. Rev. Med., 2005, 56, 585-602; Fischer et al., Immunol. Rev., 2005, 203, 98-109). There are four major causes for SCID: (i) the most frequent form of SCID, SCID-X1 (X-linked SCID or X-SCID), is caused by mutation in the IL2RG gene, resulting in the absence of mature T lymphocytes and NK cells. IL2RG encodes the gamma C protein (Noguchi, et al., Cell, 1993, 73, 147-157), a common component of at least five interleukin receptor complexes. These receptors activate several targets through the JAK3 kinase (Macchi et al., Nature, 1995, 377, 65-68), which inactivation results in the same syndrome as gamma C inactivation; (ii) mutation in the ADA gene results in a defect in purine metabolism that is lethal for lymphocyte precursors, which in turn results in the quasi absence of B, T and NK cells; (iii) V(D)J recombination is an essential step in the maturation of immunoglobulins and T lymphocytes receptors (TCRs). Mutations in Recombination Activating Gene 1 and 2 (RAG1 and RAG2) and Artemis, three genes involved in this process, result in the absence of mature T and B lymphocytes; and (iv) Mutations in other genes such as CD45, involved in T cell specific signaling have also been reported, although they represent a minority of cases (Cavazzana-Calvo et al., Annu. Rev. Med., 2005, 56, 585-602; Fischer et al., Immunol. Rev., 2005, 203, 98-109).

Since when their genetic bases have been identified, the different SCID forms have become a paradigm for gene therapy approaches (Fischer et al., Immunol. Rev., 2005, 203, 98-109) for two major reasons. First, as in all blood diseases, an ex vivo treatment can be envisioned. Hematopoietic Stem Cells (HSCs) can be recovered from bone marrow, and keep their pluripotent properties for a few cell divisions. Therefore, they can be treated in vitro, and then reinjected into the patient, where they repopulate the bone marrow. Second, since the maturation of lymphocytes is impaired in SCID patients, corrected cells have a selective advantage. Therefore, a small number of corrected cells can restore a functional immune system. This hypothesis was validated several times by (i) the partial restoration of immune functions associated with the reversion of mutations in SCID patients (Hirschhorn et al., Nat. Genet., 1996, 13, 290-295; Stephan et al., N. Engl. J. Med., 1996, 335, 1563-1567; Bousso et al., Proc. Natl., Acad. Sci. USA, 2000, 97, 274-278; Wada et al., Proc. Natl. Acad. Sci. USA, 2001, 98, 8697-8702; Nishikomori et al., Blood, 2004, 103, 4565-4572), (ii) the correction of SCID-X1 deficiencies in vitro in hematopoietic cells (Candotti et al., Blood, 1996, 87, 3097-3102; Cavazzana-Calvo et-al., Blood, 1996, Blood, 88, 3901-3909; Taylor et al., Blood, 1996, 87, 3103-3107; Hacein-Bey et al., Blood, 1998, 92, 4090-4097), (iii) the correction of SCID-X1 (Soudais et al., Blood, 2000, 95, 3071-3077; Tsai et al., Blood, 2002, 100, 72-79), JAK-3 (Bunting et al., Nat. Med., 1998, 4, 58-64; Bunting et al., Hum. Gene Ther., 2000, 11, 2353-2364) and RAG2 (Yates et al., Blood, 2002, 100, 3942-3949) deficiencies in vivo in animal models and (iv) by the result of gene therapy clinical trials (Cavazzana-Calvo et al., Science, 2000, 288, 669-672; Aiuti et al., Nat. Med., 2002; 8, 423-425; Gaspar et al., Lancet, 2004, 364, 2181-2187).

US Patent Publication No. 20110182867 assigned to the Children's Medical Center Corporation and the President and Fellows of Harvard College relates to methods and uses of modulating fetal hemoglobin expression (HbF) in a hematopoietic progenitor cells via inhibitors of BCL11A expression or activity, such as RNAi and antibodies. The targets disclosed in US Patent Publication No. 20110182867, such as BCL11A, may be targeted by the CRISPR Cas system of the present invention for modulating fetal hemoglobin expression. See also Bauer et al. (Science 11 Oct. 2013: Vol. 342 no. 6155 pp. 253-257) and Xu et al. (Science 18 Nov. 2011: Vol. 334 no. 6058 pp. 993-996) for additional BCL11A targets.

Ears

The present invention also contemplates delivering the CRISPR-Cas system to one or both ears.

Researchers are looking into whether gene therapy could be used to aid current deafness treatments—namely, cochlear implants. Deafness is often caused by lost or damaged hair cells that cannot relay signals to auditory neurons. In such cases, cochlear implants may be used to respond to sound and transmit electrical signals to the nerve cells. But these neurons often degenerate and retract from the cochlea as fewer growth factors are released by impaired hair cells.

US patent application 20120328580 describes injection of a pharmaceutical composition into the ear (e.g., auricular administration), such as into the luminae of the cochlea (e.g., the Scala media, Sc vestibulae, and Sc tympani), e.g., using a syringe, e.g., a single-dose syringe. For example, one or more of the compounds described herein can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlear capsule. Other inner ear administration methods are known in the art (see, e.g., Salt and Plontke, Drug Discovery Today, 10:1299-1306, 2005).

In another mode of administration, the pharmaceutical composition can be administered in situ, via a catheter or pump. A catheter or pump can, for example, direct a pharmaceutical composition into the cochlear luminae or the round window of the ear and/or the lumen of the colon. Exemplary drug delivery apparatus and methods suitable for administering one or more of the compounds described herein into an ear, e.g., a human ear, are described by McKenna et al., (U.S. Publication No. 2006/0030837) and Jacobsen et al., (U.S. Pat. No. 7,206,639). In some embodiments, a catheter or pump can be positioned, e.g., in the ear (e.g., the outer, middle, and/or inner ear) of a patient during a surgical procedure. In some embodiments, a catheter or pump can be positioned, e.g., in the ear (e.g., the outer, middle, and/or inner ear) of a patient without the need for a surgical procedure.

Alternatively or in addition, one or more of the compounds described herein can be administered in combination with a mechanical device such as a cochlear implant or a hearing aid, which is worn in the outer ear. An exemplary cochlear implant that is suitable for use with the present invention is described by Edge et al., (U.S. Publication No. 2007/0093878).

In some embodiments, the modes of administration described above may be combined in any order and can be simultaneous or interspersed.

Alternatively or in addition, the present invention may be administered according to any of the Food and Drug Administration approved methods, for example, as described in CDER Data Standards Manual, version number 004 (which is available at fda.give/cder/dsm/DRG/drg00301.htm).

In general, the cell therapy methods described in US patent application 20120328580 can be used to promote complete or partial differentiation of a cell to or towards a mature cell type of the inner ear (e.g., a hair cell) in vitro. Cells resulting from such methods can then be transplanted or implanted into a patient in need of such treatment. The cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described below.

Cells suitable for use in the present invention include, but are not limited to, cells that are capable of differentiating completely or partially into a mature cell of the inner ear, e.g., a hair cell (e.g., an inner and/or outer hair cell), when contacted, e.g., in vitro, with one or more of the compounds described herein. Exemplary cells that are capable of differentiating into a hair cell include, but are not limited to stem cells (e.g., inner ear stem cells, adult stem cells, bone marrow derived stem cells, embryonic stem cells, mesenchymal stem cells, skin stem cells, iPS cells, and fat derived stem cells), progenitor cells (e.g., inner ear progenitor cells), support cells (e.g., Deiters' cells, pillar cells, inner phalangeal cells, tectal cells and Hensen's cells), and/or germ cells. The use of stem cells for the replacement of inner ear sensory cells is described in Li et al., (U.S. Publication No. 2005/0287127) and Li et al., (U.S. patent Ser. No. 11/953, 797). The use of bone marrow derived stem cells for the replacement of inner ear sensory cells is described in Edge et al., PCT/US2007/084654. iPS cells are described, e.g., at Takahashi et al., Cell, Volume 131, Issue 5, Pages 861-872 (2007); Takahashi and Yamanaka, Cell 126, 663-76 (2006); Okita et al., Nature 448, 260-262 (2007); Yu, J. et al., Science 318(5858):1917-1920 (2007); Nakagawa et al., Nat. Biotechnol. 26:101-106 (2008); and Zaehres and Scholer, Cell 131(5):834-835 (2007).

Such suitable cells can be identified by analyzing (e.g., qualitatively or quantitatively) the presence of one or more tissue specific genes. For example, gene expression can be detected by detecting the protein product of one or more tissue-specific genes. Protein detection techniques involve staining proteins (e.g., using cell extracts or whole cells) using antibodies against the appropriate antigen. In this case, the appropriate antigen is the protein product of the tissue-specific gene expression. Although, in principle, a first antibody (i.e., the antibody that binds the antigen) can be labeled, it is more common (and improves the visualization) to use a second antibody directed against the first (e.g., an anti-IgG). This second antibody is conjugated either with fluorochromes, or appropriate enzymes for colorimetric reactions, or gold beads (for electron microscopy), or with the biotin-avidin system, so that the location of the primary antibody, and thus the antigen, can be recognized.

The CRISPR Cas molecules of the present invention may be delivered to the ear by direct application of pharmaceutical composition to the outer ear, with compositions modified from US Published application, 20110142917. In some embodiments the pharmaceutical composition is applied to the ear canal. Delivery to the ear may also be refered to as aural or otic delivery.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Qi et al. discloses methods for efficient siRNA transfection to the inner ear through the intact round window by a novel proteidic delivery technology which may be applied to the CRISPR Cas system of the present invention (see, e.g., Qi et al., Gene Therapy (2013), 1-9). In particular, a TAT double stranded RNA-binding domains (TAT-DRBDs), which can transfect Cy3-labeled siRNA into cells of the inner ear, including the inner and outer hair cells, crista ampullaris, macula utriculi and macula sacculi, through intact round-window permeation was successful for delivering double stranded siRNAs in vivo for treating various inner ear ailments and preservation of hearing function. About 40 μl of 10 mM RNA may be contemplated as the dosage for administration to the ear.

According to Rejali et al. (Hear Res. 2007 June; 228(1-2):180-7), cochlear implant function can be improved by good preservation of the spiral ganglion neurons, which are the target of electrical stimulation by the implant and brain derived neurotrophic factor (BDNF) has previously been shown to enhance spiral ganglion survival in experimentally deafened ears. Rejali et al. tested a modified design of the cochlear implant electrode that includes a coating of fibroblast cells transduced by a viral vector with a BDNF gene insert. To accomplish this type of ex vivo gene transfer, Rejali et al. transduced guinea pig fibroblasts with an adenovirus with a BDNF gene cassette insert, and determined that these cells secreted BDNF and then attached BDNF-secreting cells to the cochlear implant electrode via an agarose gel, and implanted the electrode in the scala tympani. Rejali et al. determined that the BDNF expressing electrodes were able to preserve significantly more spiral ganglion neurons in the basal turns of the cochlea after 48 days of implantation when compared to control electrodes and demonstrated the feasibility of combining cochlear implant therapy with ex vivo gene transfer for enhancing spiral ganglion neuron survival. Such a system may be applied to the CRISPR Cas system of the present invention for delivery to the ear.

Mukherjea et al. (Antioxidants & Redox Signaling, Volume 13, Number 5, 2010) document that knockdown of NOX3 using short interfering (si) RNA abrogated cisplatin ototoxicity, as evidenced by protection of OHCs from damage and reduced threshold shifts in auditory brainstem responses (ABRs). Different doses of siNOX3 (0.3, 0.6, and 0.9 μg) were administered to rats and NOX3 expression was evaluated by real time RT-PCR. The lowest dose of NOX3 siRNA used (0.3 μg) did not show any inhibition of NOX3 mRNA when compared to transtympanic administration of scrambled siRNA or untreated cochleae. However, administration of the higher doses of NOX3 siRNA (0.6 and 0.9 μg) reduced NOX3 expression compared to control scrambled siRNA. Such a system may be applied to the CRISPR Cas system of the present invention for transtympanic administration with a dosage of about 2 mg to about 4 mg of CRISPR Cas for administration to a human.

Jung et al. (Molecular Therapy, vol. 21 no. 4, 834-841 April 2013) demonstrate that Hes5 levels in the utricle decreased after the application of siRNA and that the number of hair cells in these utricles was significantly larger than following control treatment. The data suggest that siRNA technology may be useful for inducing repair and regeneration in the inner ear and that the Notch signaling pathway is a potentially useful target for specific gene expression inhibition. Jung et al. injected 8 μg of Hes5 siRNA in 2 μl volume, prepared by adding sterile normal saline to the lyophilized siRNA to a vestibular epithelium of the ear. Such a system may be applied to the CRISPR Cas system of the present invention for administration to the vestibular epithelium of the ear with a dosage of about 1 to about 30 mg of CRISPR Cas for administration to a human.

Eyes

The present invention also contemplates delivering the CRISPR-Cas system to one or both eyes.

In yet another aspect of the invention, the CRISPR-Cas system may be used to correct ocular defects that arise from several genetic mutations further described in Genetic Diseases of the Eye, Second Edition, edited by Elias I. Traboulsi, Oxford University Press, 2012.

For administration to the eye, lentiviral vectors, in particular equine infectious anemia viruses (EIAV) are particularly preferred.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285, Published online 21 Nov. 2005 in Wiley InterScience (www.interscience.wiley.com). DOI: 10.1002/jgm.845). The vectors are contemplated to have cytomegalovirus (CMV) promoter driving expression of the target gene. Intracameral, subretinal, intraocular and intravitreal injections are all contemplated (see, e.g., Balagaan, J Gene Med 2006; 8: 275-285, Published online 21 Nov. 2005 in Wiley InterScience (www.interscience.wiley.com). DOI: 10.1002/jgm.845). Intraocular injections may be performed with the aid of an operating microscope. For subretinal and intravitreal injections, eyes may be prolapsed by gentle digital pressure and fundi visualised using a contact lens system consisting of a drop of a coupling medium solution on the cornea covered with a glass microscope slide coverslip. For subretinal injections, the tip of a 10-mm 34-gauge needle, mounted on a 5-μl Hamilton syringe may be advanced under direct visualisation through the superior equatorial sclera tangentially towards the posterior pole until the aperture of the needle was visible in the subretinal space. Then, 2 μl of vector suspension may be injected to produce a superior bullous retinal detachment, thus confirming subretinal vector administration. This approach creates a self-sealing sclerotomy allowing the vector suspension to be retained in the subretinal space until it is absorbed by the RPE, usually within 48 h of the procedure. This procedure may be repeated in the inferior hemisphere to produce an inferior retinal detachment. This technique results in the exposure of approximately 70% of neurosensory retina and RPE to the vector suspension. For intravitreal injections, the needle tip may be advanced through the sclera 1 mm posterior to the corneoscleral limbus and 2 μl of vector suspension injected into the vitreous cavity. For intracameral injections, the needle tip may be advanced through a corneoscleral limbal paracentesis, directed towards the central cornea, and 2 μl of vector suspension may be injected. For intracameral injections, the needle tip may be advanced through a corneoscleral limbal paracentesis, directed towards the central cornea, and 2 μl of vector suspension may be injected. These vectors may be injected at titres of either $1.0$-$1.4 \times 10^{10}$ or $1.0$-$1.4 \times 10^{9}$ transducing units (TU)/ml.

In another embodiment, RetinoStat®, an equine infectious anemia virus-based lentiviral gene therapy vector that expresses angiostatic proteins endostain and angiostatin that is delivered via a subretinal injection for the treatment of the web form of age-related macular degeneration is also contemplated (see, e.g., Binley et al., HUMAN GENE THERAPY 23:980-991 (September 2012)). Such a vector may be modified for the CRISPR-Cas system of the present invention. Each eye may be treated with either RetinoStat® at a dose of $1.1 \times 10^{5}$ transducing units per eye (TU/eye) in a total volume of 100 μl In another embodiment, an E1-, partial E3-, E4-deleted adenoviral vector may be contemplated for delivery to the eye. Twenty-eight patients with advanced neovascular age-related macular degeneration (AMD) were given a single intravitreous injection of an E1-, partial E3-, E4-deleted adenoviral vector expressing human pigment ep-ithelium-derived factor (AdPEDF.11) (see, e.g., Campochiaro et al., Human Gene Therapy 17:167-176 (February 2006)). Doses ranging from $10^{6}$ to $10^{9.5}$ particle units (PU) were investigated and there were no serious adverse events related to AdPEDF.11 and no dose-limiting toxicities (see, e.g., Campochiaro et al., Human Gene Therapy 17:167-176 (February 2006)). Adenoviral vector-mediated ocular gene transfer appears to be a viable approach for the treatment of ocular disorders and could be applied to the CRISPR Cas system.

In another embodiment, the sd-rxRNA® system of RXi Pharmaceuticals may be used/and or adapted for delivering CRISPR Cas to the eye. In this system, a single intravitreal administration of 3 μg of sd-rxRNA results in sequence-specific reduction of PPIB mRNA levels for 14 days. The the sd-rxRNA® system may be applied to the CRISPR Cas system of the present invention, contemplating a dose of about 3 to 20 mg of CRISPR administered to a human.

Millington-Ward et al. (Molecular Therapy, vol. 19 no. 4, 642-649 April 2011) describes adeno-associated virus (AAV) vectors to deliver an RNA interference (RNAi)-based rhodopsin suppressor and a codon-modified rhodopsin replacement gene resistant to suppression due to nucleotide alterations at degenerate positions over the RNAi target site. An injection of either $6.0 \times 10^{8}$ vp or $1.8 \times 10^{10}$ vp AAV were subretinally injected into the eyes by Millington-Ward et al. The AAV vectors of Millington-Ward et al. may be applied to the CRISPR Cas system of the present invention, contemplating a dose of about $2 \times 10^{11}$ to about $6 \times 10^{13}$ vp administered to a human.

Dalkara et al. (Sci Transl Med 5, 189ra76 (2013)) also relates to in vivo directed evolution to fashion an AAV vector that delivers wild-type versions of defective genes throughout the retina after noninjurious injection into the eyes' vitreous humor. Dalkara describes a a 7mer peptide display library and an AAV library constructed by DNA shuffling of cap genes from AAV1, 2, 4, 5, 6, 8, and 9. The rcAAV libraries and rAAV vectors expressing GFP under a CAG' or Rho promoter were packaged and and deoxyribonuclease-resistant genomic titers were obtained through quantitative PCR. The libraries were pooled, and two rounds of evolution were performed, each consisting of initial library diversification followed by three in vivo selection steps. In each such step, P30 rho-GFP mice were intravitreally injected with 2 ml of iodixanol-purified, phosphate-buffered saline (PBS)-dialyzed library with a genomic titer of about $1 \times 10^{12}$ vg/ml. The AAV vectors of Dalkara et al. may be applied to the CRISPR Cas system of the present invention, contemplating a dose of about $1 \times 10^{15}$ to about $1 \times 10^{16}$ vg/ml administered to a human.

In another embodiment, the rhodopsin gene may be targeted for the treatment of retinitis pigmentosa (RP), wherein the system of US Patent Publication No. 20120204282 assigned to Sangamo BioSciences, Inc. may be modified in accordance of the CRISPR Cas system of the present invention.

In another embodiment, the methods of US Patent Publication No. 20130183282 assigned to Cellectis, which is directed to methods of cleaving a target sequence from the human rhodopsin gene, may also be modified to the CRISPR Cas system of the present invention.

US Patent Publication No. 20130202678 assigned to Academia Sinica relates to methods for treating. retinopathies and sight-threatening ophthalmologic disorders relating to delivering of the Puf-A gene (which is expressed in retinal ganglion and pigmented cells of eye tissues and displays a unique anti-apoptotic activity) to the sub-retinal or intravitreal space in the eye. In particular, desirable targets are zgc:193933, prdm1a, spata2, tex10, rbb4, ddx3, zp2.2, Blimp-1 and HtrA2, all of which may be targeted by the CRISPR Cas system of the present invention.

Wu (Cell Stem Cell, 13:659-62, 2013) designed a guide RNA that led Cas9 to a single base pair mutation that causes cataracts in mice, where it induced DNA cleavage. Then using either the other wild-type allele or oligos given to the zygotes repair mechanisms corrected the sequence of the broken allele and corrected the cataract-causing genetic defect in mutant mouse.

US Patent Publication No. 20120159653, describes use of zinc finger nucleases to genetically modify cells, animals and proteins associated with macular degeration (MD). Macular degeneration (MD) is the primary cause of visual impairment in the elderly, but is also a hallmark symptom of childhood diseases such as Stargardt disease, Sorsby fundus, and fatal childhood neurodegenerative diseases, with an age of onset as young as infancy. Macular. degeneration results in a loss of vision in the center of the visual field (the macula) because of damage to the retina. Currently existing animal models do not recapitulate major hallmarks of the disease as it is observed in humans. The available animal models comprising mutant genes encoding proteins associated with MD also produce highly variable phenotypes, making translations to human disease and therapy development problematic.

One aspect of US Patent Publication No. 20120159653 relates to editing of any chromosomal sequences that encode proteins associated with MD which may be applied to the CRISPR Cas system of the present invention. The proteins associated with MD are typically selected based on an experimental association of the protein associated with MD to an MD disorder. For example, the production rate or circulating concentration of a protein associated with MD may be elevated or depressed in a population having an MD disorder relative to a population lacking the MD disorder. Differences in protein levels may be assessed using proteomic techniques including but not limited to Western blot, immunohistochemical staining, enzyme linked immunosorbent assay (ELISA), and mass spectrometry. Alternatively, the proteins associated with MD may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with MD include but are not limited to the following proteins: (ABCA4) ATP-binding cassette, sub-family A (ABC1), member 4 ACHM1 achromatopsia (rod monochromacy) 1 ApoE Apolipoprotein E (ApoE) C1QTNF5 (CTRP5) C1q and tumor necrosis factor related protein 5 (C1QTNF5) C2 Complement component 2 (C2) C3 Complement components (C3) CCL2 Chemokine (C-C motif) Ligand 2 (CCL2) CCR2 Chemokine (C-C motif) receptor 2 (CCR2) CD36 Cluster of Differentiation 36 CFB Complement factor B CFH Complement factor CFH H CFHR1 complement factor H-related 1 CFHR3 complement factor H-related 3 CNGB3 cyclic nucleotide gated channel beta 3 CP ceruloplasmin (CP) CRP C reactive protein (CRP) CST3 cystatin C or cystatin 3 (CST3) CTSD Cathepsin D (CTSD) CX3CR1 chemokine (C-X3-C motif) receptor 1 ELOVL4 Elongation of very long chain fatty acids 4 ERCC6 excision repair cross-complementing rodent repair deficiency, complementation group 6 FBLN5 Fibulin-5 FBLN5 Fibulin 5 FBLN6 Fibulin 6 FSCN2 fascin (FSCN2) HMCN1 Hemicentrin 1 HMCN1 hemicentin 1 HTRA1 HtrA serine peptidase 1 (HTRA1) HTRA1 HtrA serine peptidase 1 IL-6 Interleukin 6 IL-8 Interleukin 8 LOC387715 Hypothetical protein PLEKHA1 Pleckstrin homology domain-containing family A member 1 (PLEKHA1) PROM1 Prominin 1 (PROM1 or CD133) PRPH2 Peripherin-2 RPGR retinitis pigmentosa GTPase regulator SERPING1 serpin peptidase inhibitor, clade G, member 1 (C1-inhibitor) TCOF1 Treacle TIMP3 Metalloproteinase inhibitor 3 (TIMP3) TLR3 Toll-like receptor 3

The identity of the protein associated with MD whose chromosomal sequence is edited can and will vary. In preferred embodiments, the proteins associated with MD whose chromosomal sequence is edited may be the ATP-binding cassette, sub-family A (ABC1) member 4 protein (ABCA4) encoded by the ABCR gene, the apolipoprotein E protein (APOE) encoded by the APOE gene, the chemokine (C-C motif) Ligand 2 protein (CCL2) encoded by the CCL2 gene, the chemokine (C-C motif) receptor 2 protein (CCR2) encoded by the CCR2 gene, the ceruloplasmin protein (CP) encoded by the CP gene, the cathepsin D protein (CTSD) encoded by the CTSD gene, or the metalloproteinase inhibitor 3 protein (TIMP3) encoded by the TIMP3 gene. In an exemplary embodiment, the genetically modified animal is a rat, and the edited chromosomal sequence encoding the protein associated with MD may be: (ABCA4) ATP-binding cassette, NM_000350 sub-family A (ABC1), member 4 APOE Apolipoprotein E NM 138828 (APOE) CCL2 Chemokine (C-C NM_031530 motif) Ligand 2 (CCL2) CCR2 Chemokine (C-C NM_021866 motif) receptor 2 (CCR2) CP ceruloplasmin (CP) NM_012532 CTSD Cathepsin D (CTSD) NM_134334 TIMP3 Metalloproteinase NM_012886 inhibitor 3 (TIMP3) The animal or cell may comprise 1, 2, 3, 4, 5, 6, 7 or more disrupted chromosomal sequences encoding a protein associated with MD and zero, 1, 2, 3, 4, 5, 6, 7 or more chromosomally integrated sequences encoding the disrupted protein associated with MD.

The edited or integrated chromosomal sequence may be modified to encode an altered protein associated with MD. Several mutations in MD-related chromosomal sequences have been associated with MD. Non-limiting examples of mutations in chromosomal sequences associated with MD include those that may cause MD including in the ABCR protein, E471K (i.e. glutamate at position 471 is changed to lysine), R1129L (i.e. arginine at position 1129 is changed to leucine), T1428M (i.e. threonine at position 1428 is changed to methionine), R1517S (i.e. arginine at position 1517 is changed to serine), I1562T (i.e. isoleucine at position 1562 is changed to threonine), and G1578R (i.e. glycine at position 1578 is changed to arginine); in the CCR2 protein, V64I (i.e. valine at position 192 is changed to isoleucine); in CP protein, G969B (i.e. glycine at position 969 is changed to asparagine or aspartate); in TIMP3 protein, S156C (i.e. serine at position 156 is changed to cysteine), G166C (i.e. glycine at position 166 is changed to cysteine), G167C (i.e. glycine at position 167 is changed to cysteine), Y168C (i.e. tyrosine at position 168 is changed to cysteine), S170C (i.e. serine at position 170 is changed to cysteine), Y172C (i.e. tyrosine at position 172 is changed to cysteine) and S181C (i.e. serine at position 181 is changed to cysteine). Other associations of genetic variants in MD-associated genes and disease are known in the art.

Heart

The present invention also contemplates delivering the CRISPR-Cas system to the heart. For the heart, a myocardium tropic adena-associated virus (AAVM) is preferred, in particular AAVM41 which showed preferential gene transfer in the heart (see, e.g., Lin-Yanga et al., PNAS, Mar. 10, 2009, vol. 106, no. 10). Administration may be systemic or local. A dosage of about 1-10×10$^{14}$ vector genomes are contemplated for systemic administration. See also, e.g., Eulalio et al. (2012) Nature 492: 376 and Somasuntharam et al. (2013) Biomaterials 34: 7790.

For example, US Patent Publication No. 20110023139, describes use of zinc finger nucleases to genetically modify cells, animals and proteins associated with cardiovascular disease. Cardiovascular diseases generally include high blood pressure, heart attacks, heart failure, and stroke and TIA. Any chromosomal sequence involved in cardiovascular disease or the protein encoded by any chromosomal sequence involved in cardiovascular disease may be utilized in the methods described in this disclosure. The cardiovascular-related proteins are typically selected based on an experimental association of the cardiovascular-related protein to the development of cardiovascular disease. For example, the production rate or circulating concentration of a cardiovascular-related protein may be elevated or depressed in a population having a cardiovascular disorder relative to a population lacking the cardiovascular disorder. Differences in protein levels may be assessed using proteomic techniques including but not limited to Western blot, immunohistochemical staining, enzyme linked immunosorbent assay (ELISA), and mass spectrometry. Alternatively, the cardiovascular-related proteins may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of example, the chromosomal sequence may comprise, but is not limited to, IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), CTSK (cathepsin K), PTGIR (prostaglandin 12 (prostacyclin) receptor (IP)), KCNJ11 (potassium inwardly-rectifying channel, subfamily J, member 11), INS (insulin), CRP (C-reactive protein, pentraxin-related), PDGFRB (platelet-derived growth factor receptor, beta polypeptide), CCNA2 (cyclin A2), PDGFB (platelet-derived growth factor beta polypeptide (simian sarcoma viral (v-sis) oncogene homolog)), KCNJ5 (potassium inwardly-rectifying channel, subfamily J, member 5), KCNN3 (potassium intermediate/small conductance calcium-activated channel, subfamily N, member 3), CAPN10 (calpain 10), PTGES (prostaglandin E synthase), ADRA2B (adrenergic, alpha-2B-, receptor), ABCGS (ATP-binding cassette, sub-family G (WHITE), member 5), PRDX2 (peroxiredoxin 2), CAPN5 (calpain 5), PARP14 (poly (ADP-ribose) polymerase family, member 14), MEX3C (mex-3 homolog C (C. elegans)), ACE angiotensin I converting enzyme (peptidyl-dipeptidase A) 1), TNF (tumor necrosis factor (TNF superfamily, member 2)), IL6 (interleukin 6 (interferon, beta 2)), STN (statin), SERPINE1 (serpin peptidase inhibitor, clade E (nexin, plasminogen activator inhibitor type 1), member 1), ALB (albumin), ADIPOQ (adiponectin, C IQ and collagen domain containing), APOB (apolipoprotein B (including Ag(x) antigen)), APOE (apolipoprotein E), LEP (leptin), MTHFR (5,10-methylenetetrahydrofolate reductase (NADPH)), APOA1 (apolipoprotein A-I), EDN1 (endothelin 1), NPPB (natriuretic peptide precursor B), NOS3 (nitric oxide synthase 3 (endothelial cell)), PPARG (peroxisome proliferator-activated receptor gamma), PLAT (plasminogen activator, tissue), PTGS2 (prostaglandin-endoperoxide synthase 2 (prostaglandin G/H synthase and cyclooxygenase)), CETP (cholesteryl ester transfer protein, plasma), AGTR1 (angiotensin II receptor, type 1), HMGCR (3-hydroxy-3-methylglutaryl-Coenzyme A reductase), IGF1 (insulin-like growth factor 1 (somatomedin C)), SELE (selectin E), REN (renin), PPARA (peroxisome proliferator-activated receptor alpha), PON1 (paraoxonase 1), KNG1 (kininogen 1), CCL2 (chemokine (C-C motif) ligand 2), LPL (lipoprotein lipase), VWF (von Willebrand factor), F2 (coagulation factor II (thrombin)), ICAM1 (intercellular adhesion molecule 1), TGFB1 (transforming growth factor, beta 1), NPPA (natriuretic peptide precursor A), IL10 (interleukin 10), EPO (erythropoietin), SOD1 (superoxide dismutase 1, soluble), VCAM1 (vascular cell adhesion molecule 1), IFNG (interferon, gamma), LPA (lipoprotein, Lp(a)), MPO (myeloperoxidase), ESR1 (estrogen receptor 1), MAPK1 (mitogen-activated protein kinase 1), HP (haptoglobin), F3 (coagulation factor III (thromboplastin, tissue factor)), CST3 (cystatin C), COG2 (component of oligomeric golgi complex 2), MMP9 (matrix metallopeptidase 9 (gelatinase B, 92 kDa gelatinase, 92 kDa type IV collagenase)), SERPINC1 (serpin peptidase inhibitor, clade C (antithrombin), member 1), F8 (coagulation factor VIII, procoagulant component), HMOX1 (heme oxygenase (decycling) 1), APOC3 (apolipoprotein C-III), IL8 (interleukin 8), PROK1 (prokineticin 1), CBS (cystathionine-beta-synthase), NOS2 (nitric oxide synthase 2, inducible), TLR4 (toll-like receptor 4), SELP (selectin P (granule membrane protein 140 kDa, antigen CD62)), ABCAI (ATP-binding cassette, sub-family A (ABC1), member 1), AGT (angiotensinogen (serpin peptidase inhibitor, clade A, member 8)), LDLR (low density lipoprotein receptor), GPT (glutamic-pyruvate transaminase (alanine aminotransferase)), VEGFA (vascular endothelial growth factor A), NR3C2 (nuclear receptor subfamily 3, group C, member 2), IL18 (interleukin 18 (interferon-gamma-inducing factor)), NOS1 (nitric oxide synthase 1 (neuronal)), NR3C1 (nuclear receptor subfamily 3, group C, member 1 (glucocorticoid receptor)), FGB (fibrinogen beta chain), HGF (hepatocyte growth factor (hepapoietin A; scatter factor)), IL1A (interleukin 1, alpha), RETN (resistin), AKT1 (v-akt murine thymoma viral oncogene homolog 1), LIPC (lipase, hepatic), HSPD1 (heat shock 60 kDa protein 1 (chaperonin)), MAPK14 (mitogen-activated protein kinase 14), SPP1 (secreted phosphoprotein 1), ITGB3 (integrin, beta 3 (platelet glycoprotein 111a, antigen CD61)), CAT (catalase), UTS2 (urotensin 2), THBD (thrombomodulin), F10 (coagulation factor X), CP (ceruloplasmin (ferroxidase)), TNFRSF11B (tumor necrosis factor receptor superfamily, member 11b), EDNRA (endothelin receptor type A), EGFR (epidermal growth factor receptor (erythroblastic leukemia viral (v-erb-b) oncogene homolog, avian)), MMP2 (matrix metallopeptidase 2 (gelatinase A, 72 kDa gelatinase, 72 kDa type IV collagenase)), PLG (plasminogen), NPY (neuropeptide Y), RHOD (ras homolog gene family, member D), MAPK8 (mitogen-activated protein kinase 8), MYC (v-myc myelocytomatosis viral oncogene homolog (avian)), FN1 (fibronectin 1), CMA1 (chymase 1, mast cell), PLAU (plasminogen activator, urokinase), GNB3 (guanine nucleotide binding protein (G protein), beta polypeptide 3), ADRB2 (adrenergic, beta-2-, receptor, surface), APOA5 (apolipoprotein A-V), SOD2 (superoxide dismutase 2, mitochondrial), F5 (coagulation factor V (proaccelerin, labile factor)), VDR (vitamin D (1,25-dihydroxyvitamin D3) receptor), ALOXS (arachidonate 5-lipoxygenase), HLA-DRB1 (major histocompatibility complex, class II, DR beta 1), PARP1 (poly (ADP-ribose) polymerase 1), CD40LG (CD40 ligand), PON2 (paraoxonase 2), AGER (advanced glycosylation end product-specific receptor), IRS1 (insulin receptor substrate 1), PTGS1 (prostaglandin-endoperoxide synthase 1 (prostaglandin G/H synthase and cyclooxygenase)), ECE1 (endothelin converting enzyme 1), F7 (coagulation factor VII (serum prothrombin conversion accelerator)), URN (interleukin 1 receptor antagonist), EPHX2 (epoxide hydrolase 2, cytoplasmic), IGFBP1 (insulin-like growth factor binding protein 1), MAPK10 (mitogen-activated protein kinase 10), FAS (Fas (TNF receptor superfamily, member 6)), ABCB1 (ATP-binding cassette, subfamily B (MDR/TAP), member 1), JUN (jun oncogene), IGFBP3 (insulin-like growth factor binding protein 3), CD14 (CD14 molecule), PDE5A (phosphodiesterase 5A, cGMP-specific), AGTR2 (angiotensin II receptor, type 2), CD40 (CD40 molecule, TNF receptor superfamily member 5), LCAT (lecithin-cholesterol acyltransferase), CCR5 (chemokine (C-C motif) receptor 5), MMP1 (matrix metallopeptidase 1 (interstitial collagenase)), TIMP1 (TIMP metallopeptidase inhibitor 1), ADM (adrenomedullin), DYT10 (dystonia 10), STAT3 (signal transducer and activator of transcription 3 (acute-phase response factor)), MMP3 (matrix metallopeptidase 3 (stromelysin 1, progelatinase)), ELN (elastin), USF1 (upstream transcription factor 1), CFH (complement factor H), HSPA4 (heat shock 70 kDa protein 4), MMP12 (matrix metallopeptidase 12 (macrophage elastase)), MME (membrane metallo-endopeptidase), F2R (coagulation factor II (thrombin) receptor), SELL (selectin L), CTSB (cathepsin B), ANXA5 (annexin A5), ADRB1 (adrenergic, beta-1-, receptor), CYBA (cytochrome b-245, alpha polypeptide), FGA (fibrinogen alpha chain), GGT1 (gamma-glutamyltransferase 1), LIPG (lipase, endothelial), HIF1A (hypoxia inducible factor 1, alpha subunit (basic helix-loop-helix transcription factor)), CXCR4 (chemokine (C-X-C motif) receptor 4), PROC (protein C (inactivator of coagulation factors Va and VIIIa)), SCARB1 (scavenger receptor Class B, member 1), CD79A (CD79a molecule, immunoglobulin-associated alpha), PLTP (phospholipid transfer protein), ADD1 (adducin 1 (alpha)), FGG (fibrinogen gamma chain), SAA1 (serum amyloid A1), KCNH2 (potassium voltage-gated channel, subfamily H (eag-related), member 2), DPP4 (dipeptidyl-peptidase 4), G6PD (glucose-6-phosphate dehydrogenase), NPR1 (natriuretic peptide receptor A/guanylate cyclase A (atrionatriuretic peptide receptor A)), VTN (vitronectin), KIAA0101 (KIAA0101), FOS (FBJ murine osteosarcoma viral oncogene homolog), TLR2 (toll-like receptor 2), PPIG (peptidylprolyl isomerase G (cyclophilin G)), IL1R1 (interleukin 1 receptor, type I), AR (androgen receptor), CYP1A1 (cytochrome P450, family 1, subfamily A, polypeptide 1), SERPINA1 (serpin peptidase inhibitor, clade A (alpha-1 antiproteinase, antitrypsin), member 1), MTR (5-methyltetrahydrofolate-homocysteine methyltransferase), RBP4 (retinol binding protein 4, plasma), APOA4 (apolipoprotein A-IV), CDKN2A (cyclin-dependent kinase inhibitor 2A (melanoma, p16, inhibits CDK4)), FGF2 (fibroblast growth factor 2 (basic)), EDNRB (endothelin receptor type B), ITGA2 (integrin, alpha 2 (CD49B, alpha 2 subunit of VLA-2 receptor)), CABIN1 (calcineurin binding protein 1), SHBG (sex hormone-binding globulin), HMGB1 (high-mobility group box 1), HSP90B2P (heat shock protein 90 kDa beta (Grp94), member 2 (pseudogene)), CYP3A4 (cytochrome P450, family 3, subfamily A, polypeptide 4), GJA1 (gap junction protein, alpha 1, 43 kDa), CAV1 (caveolin 1, caveolae protein, 22 kDa), ESR2 (estrogen receptor 2 (ER beta)), LTA (lymphotoxin alpha (TNF superfamily, member 1)), GDF15 (growth differentiation factor 15), BDNF (brain-derived neurotrophic factor), CYP2D6 (cytochrome P450, family 2, subfamily D, polypeptide 6), NGF (nerve growth factor (beta polypeptide)), SP1 (Sp1 transcription factor), TGIF1 (TGFB-induced factor homeobox 1), SRC (v-src sarcoma (Schmidt-Ruppin A-2) viral oncogene homolog (avian)), EGF (epidermal growth factor (beta-urogastrone)), PIK3CG (phosphoinositide-3-kinase, catalytic, gamma polypeptide), HLA-A (major histocompatibility complex, class I, A), KCNQ1 (potassium voltage-gated channel, KQT-like subfamily, member 1), CNR1 (cannabinoid receptor 1 (brain)), FBN1 (fibrillin 1), CHKA (choline kinase alpha), BEST1 (bestrophin 1), APP (amyloid beta (A4) precursor protein), CTNNB1 (catenin (cadherin-associated protein), beta 1, 88 kDa), IL2 (interleukin 2), CD36 (CD36 molecule (thrombospondin receptor)), PRKAB1 (protein kinase, AMP-activated, beta 1 non-catalytic subunit), TPO (thyroid peroxidase), ALDH7A1 (aldehyde dehydrogenase 7 family, member A1), CX3CR1 (chemokine (C-X3-C motif) receptor 1), TH (tyrosine hydroxylase), F9 (coagulation factor IX), GH1 (growth hormone 1), TF (transferrin), HFE (hemochromatosis), IL17A (interleukin 17A), PTEN (phosphatase and tensin homolog), GSTM1 (glutathione S-transferase mu 1), DMD (dystrophin), GATA4 (GATA binding protein 4), F13A1 (coagulation factor XIII, A1 polypeptide), TTR (transthyretin), FABP4 (fatty acid binding protein 4, adipocyte), PON3 (paraoxonase 3), APOC1 (apolipoprotein C-I), INSR (insulin receptor), TNFRSF1B (tumor necrosis factor receptor superfamily, member 1B), HTR2A (5-hydroxytryptamine (serotonin) receptor 2A), CSF3 (colony stimulating factor 3 (granulocyte)), CYP2C9 (cytochrome P450, family 2, subfamily C, polypeptide 9), TXN (thioredoxin), CYPI1B2 (cytochrome P450, family 11, subfamily B, polypeptide 2), PTH (parathyroid hormone), CSF2 (colony stimulating factor 2 (granulocyte-macrophage)), KDR (kinase insert domain receptor (a type III receptor tyrosine kinase)), PLA2G2A (phospholipase A2, group IIA (platelets, synovial fluid)), B2M (beta-2-microglobulin), THBS1 (thrombospondin 1), GCG (glucagon), RHOA (ras homolog gene family, member A), ALDH2 (aldehyde dehydrogenase 2 family (mitochondrial)), TCF7L2 (transcription factor 7-like 2 (T-cell specific, HMG-box)), BDKRB2 (bradykinin receptor B2), NFE2L2 (nuclear factor (erythroid-derived 2)-like 2), NOTCH1 (Notch homolog 1, translocation-associated (*Drosophila*)), UGT1A1 (UDP glucuronosyltransferase 1 family, polypeptide A1), IFNA1 (interferon, alpha 1), PPARD (peroxisome proliferator-activated receptor delta), SIRT1 (sirtuin (silent mating type information regulation 2 homolog) 1 (*S. cerevisiae*)), GNRH1 (gonadotropin-releasing hormone 1 (luteinizing-releasing hormone)), PAPPA (pregnancy-associated plasma protein A, pappalysin 1), ARR3 (arrestin 3, retinal (X-arrestin)), NPPC (natriuretic peptide precursor C), AHSP (alpha hemoglobin stabilizing protein), PTK2 (PTK2 protein tyrosine kinase 2), IL13 (interleukin 13), MTOR (mechanistic target of rapamycin (serine/threonine kinase)), ITGB2 (integrin, beta 2 (complement component 3 receptor 3 and 4 subunit)), GSTT1 (glutathione S-transferase theta 1), IL6ST (interleukin 6 signal transducer (gp130, oncostatin M receptor)), CPB2 (carboxypeptidase B2 (plasma)), CYP1A2 (cytochrome P450, family 1, subfamily A, polypeptide 2), HNF4A (hepatocyte nuclear factor 4, alpha), SLC6A4 (solute carrier family 6 (neurotransmitter transporter, serotonin), member 4), PLA2G6 (phospholipase A2, group VI (cytosolic, calcium-independent)), TNFSF11 (tumor necrosis factor (ligand) superfamily, member 11), SLC8A1 (solute carrier family 8 (sodium/calcium exchanger), member 1), F2RL1 (coagulation factor II (thrombin) receptor-like 1), AKR1A1 (aldo-keto reductase family 1, member A1 (aldehyde reductase)), ALDH9A1 (aldehyde dehydrogenase 9 family, member A1), BGLAP (bone gamma-carboxyglutamate (gla) protein), MTTP (microsomal triglyceride transfer protein), MTRR (5-methyltetrahydrofolate-homocysteine methyltransferase reductase), SULT1A3 (sulfotransferase family, cytosolic, 1A, phenol-preferring, member 3), RAGE (renal tumor antigen), C4B (complement component 4B (Chido blood group), P2RY12 (purinergic receptor P2Y, G-protein coupled, 12), RNLS (renalase, FAD-dependent amine oxidase), CREB1 (cAMP responsive element binding protein 1), POMC (proopiomelanocortin), RAC1 (ras-related C3 botulinum toxin substrate 1 (rho family, small GTP binding protein Rac1)), LMNA (lamin NC), CD59 (CD59 molecule, complement regulatory protein), SCN5A (sodium channel, voltage-gated, type V, alpha subunit), CYP1B1 (cytochrome P450, family 1, subfamily B, polypeptide 1), MIF (macrophage migration inhibitory factor (glycosylation-inhibiting factor)), MMP13 (matrix metallopeptidase 13 (collagenase 3)), TIMP2 (TIMP metallopeptidase inhibitor 2), CYP19A1 (cytochrome P450, family 19, subfamily A, polypeptide 1), CYP21A2 (cytochrome P450, family 21, subfamily A, polypeptide 2), PTPN22 (protein tyrosine phosphatase, non-receptor type 22 (lymphoid)), MYH14 (myosin, heavy chain 14, non-muscle), MBL2 (mannose-binding lectin (protein C) 2, soluble (opsonic defect)), SELPLG (selectin P ligand), AOC3 (amine oxidase, copper containing 3 (vascular adhesion protein 1)), CTSL1 (cathepsin L1), PCNA (proliferating cell nuclear antigen), IGF2 (insulin-like growth factor 2 (somatomedin A)), ITGB1 (integrin, beta 1 (fibronectin receptor, beta polypeptide, antigen CD29 includes MDF2, MSK12)), CAST (calpastatin), CXCL12 (chemokine (C-X-C motif) ligand 12 (stromal cell-derived factor 1)), IGHE (immunoglobulin heavy constant epsilon), KCNE1 (potassium voltage-gated channel, Isk-related family, member 1), TFRC (transferrin receptor (p90, CD71)), COL1A1 (collagen, type I, alpha 1), COL1A2 (collagen, type I, alpha 2), IL2RB (interleukin 2 receptor, beta), PLA2G10 (phospholipase A2, group X), ANGPT2 (angiopoietin 2), PROCR (protein C receptor, endothelial (EPCR)), NOX4 (NADPH oxidase 4), HAMP (hepcidin antimicrobial peptide), PTPN11 (protein tyrosine phosphatase, non-receptor type 11), SLC2A1 (solute carrier family 2 (facilitated glucose transporter), member 1), IL2RA (interleukin 2 receptor, alpha), CCL5 (chemokine (C-C motif) ligand 5), IRF1 (interferon regulatory factor 1), CFLAR (CASP8 and FADD-like apoptosis regulator), CALCA (calcitonin-related polypeptide alpha), EIF4E (eukaryotic translation initiation factor 4E), GSTP1 (glutathione S-transferase pi 1), JAK2 (Janus kinase 2), CYP3A5 (cytochrome P450, family 3, subfamily A, polypeptide 5), HSPG2 (heparan sulfate proteoglycan 2), CCL3 (chemokine (C-C motif) ligand 3), MYD88 (myeloid differentiation primary response gene (88)), VIP (vasoactive intestinal peptide), SOAT1 (sterol O-acyltransferase 1), ADRBK1 (adrenergic, beta, receptor kinase 1), NR4A2 (nuclear receptor subfamily 4, group A, member 2), MMP8 (matrix metallopeptidase 8 (neutrophil collagenase)), NPR2 (natriuretic peptide receptor B/guanylate cyclase B (atrionatriuretic peptide receptor B)), GCH1 (GTP cyclohydrolase 1), EPRS (glutamyl-prolyl-tRNA synthetase), PPARGC1A (peroxisome proliferator-activated receptor gamma, coactivator 1 alpha), F12 (coagulation factor XII (Hageman factor)), PECAM1 (platelet/endothelial cell adhesion molecule), CCL4 (chemokine (C-C motif) ligand 4), SERPINA3 (serpin peptidase inhibitor, clade A (alpha-1 antiproteinase, antitrypsin), member 3), CASR (calcium-sensing receptor), GJA5 (gap junction protein, alpha 5, 40 kDa), FABP2 (fatty acid binding protein 2, intestinal), TTF2 (transcription termination factor, RNA polymerase II), PROS1 (protein S (alpha)), CTF1 (cardiotrophin 1), SGCB (sarcoglycan, beta (43 kDa dystrophin-associated glycoprotein)), YME1L1 (YME1-like 1 (S. cerevisiae)), CAMP (cathelicidin antimicrobial peptide), ZC3H12A (zinc finger CCCH-type containing 12A), AKR1B1 (aldo-keto reductase family 1, member B1 (aldose reductase)), DES (desmin), MMP1 (matrix metallopeptidase 7 (matrilysin, uterine)), AHR (aryl hydrocarbon receptor), CSF1 (colony stimulating factor 1 (macrophage)), HDAC9 (histone deacetylase 9), CTGF (connective tissue growth factor), KCNMA1 (potassium large conductance calcium-activated channel, subfamily M, alpha member 1), UGT1A (UDP glucuronosyltransferase 1 family, polypeptide A complex locus), PRKCA (protein kinase C, alpha), COMT (catechol-.beta.-methyltransferase), S100B (S100 calcium binding protein B), EGR1 (early growth response 1), PRL (prolactin), IL15 (interleukin 15), DRD4 (dopamine receptor D4), CAMK2G (calcium/calmodulin-dependent protein kinase II gamma), SLC22A2 (solute carrier family 22 (organic cation transporter), member 2), CCL11 (chemokine (C-C motif) ligand 11), PGF (B321 placental growth factor), THPO (thrombopoietin), GP6 (glycoprotein VI (platelet)), TACR1 (tachykinin receptor 1), NTS (neurotensin), HNF1A (HNF1 homeobox A), SST (somatostatin), KCND 1 (potassium voltage-gated channel, Shal-related subfamily, member 1), LOC646627 (phospholipase inhibitor), TBXAS1 (thromboxane A synthase 1 (platelet)), CYP2J2 (cytochrome P450, family 2, subfamily J, polypeptide 2), TBXA2R (thromboxane A2 receptor), ADH1C (alcohol dehydrogenase 1C (class I), gamma polypeptide), ALOX12 (arachidonate 12-lipoxygenase), AHSG (alpha-2-HS-glycoprotein), BHMT (betaine-homocysteine methyltransferase), GJA4 (gap junction protein, alpha 4, 37 kDa), SLC25A4 (solute carrier family 25 (mitochondrial carrier; adenine nucleotide translocator), member 4), ACLY (ATP citrate lyase), ALOXSAP (arachidonate 5-lipoxygenase-activating protein), NUMA1 (nuclear mitotic apparatus protein 1), CYP27B1 (cytochrome P450, family 27, subfamily B, polypeptide 1), CYSLTR2 (cysteinyl leukotriene receptor 2), SOD3 (superoxide dismutase 3, extracellular), LTC4S (leukotriene C4 synthase), UCN (urocortin), GHRL (ghrelin/obestatin prepropeptide), APOC2 (apolipoprotein C-II), CLEC4A (C-type lectin domain family 4, member A), KBTBD10 (kelch repeat and BTB (POZ) domain containing 10), TNC (tenascin C), TYMS (thymidylate synthetase), SHCI (SHC (Src homology 2 domain containing) transforming protein 1), LRP1 (low density lipoprotein receptor-related protein 1), SOCS3 (suppressor of cytokine signaling 3), ADH1B (alcohol dehydrogenase 1B (class I), beta polypeptide), KLK3 (kallikrein-related peptidase 3), HSD11B1 (hydroxysteroid (11-beta) dehydrogenase 1), VKORC1 (vitamin K epoxide reductase complex, subunit 1), SERPINB2 (serpin peptidase inhibitor, clade B (ovalbumin), member 2), TNS1 (tensin 1), RNF19A (ring finger protein 19A), EPOR (erythropoietin receptor), ITGAM (integrin, alpha M (complement component 3 receptor 3 subunit)), PITX2 (paired-like homeodomain 2), MAPK7 (mitogen-activated protein kinase 7), FCGR3A (Fc fragment of IgG, low affinity IIIa, receptor (CD16a)), LEPR (leptin receptor), ENG (endoglin), GPX1 (glutathione peroxidase 1), GOT2 (glutamic-oxaloacetic transaminase 2, mitochondrial (aspartate aminotransferase 2)), HRH1 (histamine receptor H1), NR1I2 (nuclear receptor subfamily 1, group I, member 2), CRH (corticotropin releasing hormone), HTR1A (5-hydroxytryptamine (serotonin) receptor 1A), VDAC1 (voltage-dependent anion channel 1), HPSE (heparanase), SFTPD (surfactant protein D), TAP2 (transporter 2, ATP-binding cassette, sub-family B (MDR/TAP)), RNF123 (ring finger protein 123), PTK2B (PTK2B protein tyrosine kinase 2 beta), NTRK2 (neurotrophic tyrosine kinase, receptor, type 2), IL6R (interleukin 6 receptor), ACHE (acetylcholinesterase (Yt blood group)), GLP1R (glucagon-like peptide 1 receptor), GHR (growth hormone receptor), GSR (glutathione reductase), NQO1 (NAD(P)H dehydrogenase, quinone 1), NR5A1 (nuclear receptor subfamily 5, group A, member 1), GJB2 (gap junction protein, beta 2, 26 kDa), SLC9A1 (solute carrier family 9 (sodium/hydrogen exchanger), member 1), MAOA (monoamine oxidase A), PCSK9 (proprotein convertase subtilisin/kexin type 9), FCGR2A (Fc fragment of IgG, low affinity IIa, receptor (CD32)), SERPINF1 (serpin peptidase inhibitor, clade F (alpha-2 antiplasmin, pigment epithelium derived factor), member 1), EDN3 (endothelin 3), DHFR (dihydrofolate reductase), GAS6 (growth arrest-specific 6), SMPD1 (sphingomyelin phosphodiesterase 1, acid lysosomal), UCP2 (uncoupling protein 2 (mitochondrial, proton carrier)), TFAP2A (transcription factor AP-2 alpha (activating enhancer binding protein 2 alpha)), C4BPA (complement component 4 binding protein, alpha), SERPINF2 (serpin peptidase inhibitor, clade F (alpha-2 antiplasmin, pigment epithelium derived factor), member 2), TYMP (thymidine phosphorylase), ALPP (alkaline phosphatase, placental (Regan isozyme)), CXCR2 (chemokine (C-X-C motif) receptor 2), SLC39A3 (solute carrier family 39 (zinc transporter), member 3), ABCG2 (ATP-binding cassette, sub-family G (WHITE), member 2), ADA (adenosine deaminase), JAK3 (Janus kinase 3), HSPA1A (heat shock 70 kDa protein 1A), FASN (fatty acid synthase), FGF1 (fibroblast growth factor 1 (acidic)), F11 (coagulation factor XI), ATP7A (ATPase, Cu++ transporting, alpha polypeptide), CR1 (complement component (3b/4b) receptor 1 (Knops blood group)), GFAP (glial fibrillary acidic protein), ROCK1 (Rho-associated, coiled-coil containing protein kinase 1), MECP2 (methyl CpG binding protein 2 (Rett syndrome)), MYLK (myosin light chain kinase), BCHE (butyrylcholinesterase), LIPE (lipase, hormone-sensitive), PRDX5 (peroxiredoxin 5), ADORA1 (adenosine A1 receptor), WRN (Werner syndrome, RecQ helicase-like), CXCR3 (chemokine (C-X-C motif) receptor 3), CD81 (CD81 molecule), SMAD7 (SMAD family member 7), LAMC2 (laminin, gamma 2), MAP3K5 (mitogen-activated protein kinase kinase kinase 5), CHGA (chromogranin A (parathyroid secretory protein 1)), IAPP (islet amyloid polypeptide), RHO (rhodopsin), ENPP1 (ectonucleotide pyrophosphatase/phosphodiesterase 1), PTHLH (parathyroid hormone-like hormone), NRG1 (neuregulin 1), VEGFC (vascular endothelial growth factor C), ENPEP (glutamyl aminopeptidase (aminopeptidase A)), CEBPB (CCAAT/enhancer binding protein (C/EBP), beta), NAGLU (N-acetylglucosaminidase, alpha-), F2RL3 (coagulation factor II (thrombin) receptor-like 3), CX3CL1 (chemokine (C-X3-C motif) ligand 1), BDKRB1 (bradykinin receptor B1), ADAMTS13 (ADAM metallopeptidase with thrombospondin type 1 motif, 13), ELANE (elastase, neutrophil expressed), ENPP2 (ectonucleotide pyrophosphatase/phosphodiesterase 2), CISH (cytokine inducible SH2-containing protein), GAST (gastrin), MYOC (myocilin, trabecular meshwork inducible glucocorticoid response), ATP1A2 (ATPase, Na+/K+ transporting, alpha 2 polypeptide), NF1 (neurofibromin 1), GJB1 (gap junction protein, beta 1, 32 kDa), MEF2A (myocyte enhancer factor 2A), VCL (vinculin), BMPR2 (bone morphogenetic protein receptor, type II (serine/threonine kinase)), TUBB (tubulin, beta), CDC42 (cell division cycle 42 (GTP binding protein, 25 kDa)), KRT18 (keratin 18), HSF1 (heat shock transcription factor 1), MYB (v-myb myeloblastosis viral oncogene homolog (avian)), PRKAA2 (protein kinase, AMP-activated, alpha 2 catalytic subunit), ROCK2 (Rho-associated, coiled-coil containing protein kinase 2), TFPI (tissue factor pathway inhibitor (lipoprotein-associated coagulation inhibitor)), PRKG1 (protein kinase, cGMP-dependent, type I), BMP2 (bone morphogenetic protein 2), CTNND1 (catenin (cadherin-associated protein), delta 1), CTH (cystathionase (cystathionine gamma-lyase)), CTSS (cathepsin S), VAV2 (vav 2 guanine nucleotide exchange factor), NPY2R (neuropeptide Y receptor Y2), IGFBP2 (insulin-like growth factor binding protein 2, 36 kDa), CD28 (CD28 molecule), GSTA1 (glutathione S-transferase alpha 1), PPIA (peptidylprolyl isomerase A (cyclophilin A)), APOH (apolipoprotein H (beta-2-glycoprotein S100A8 (S100 calcium binding protein A8), IL11 (interleukin 11), ALOX15 (arachidonate 15-lipoxygenase), FBLN1 (fibulin 1), NR1H3 (nuclear receptor subfamily 1, group H, member 3), SCD (stearoyl-CoA desaturase (delta-9-desaturase)), GIP (gastric inhibitory polypeptide), CHGB (chromogranin B (secretogranin 1)), PRKCB (protein kinase C, beta), SRD5A1 (steroid-5-alpha-reductase, alpha polypeptide 1 (3-oxo-5 alpha-steroid delta 4-dehydrogenase alpha 1)), HSD11B2 (hydroxysteroid (11-beta) dehydrogenase 2), CALCRL (calcitonin receptor-like), GALNT2 (UDP-N-acetyl-alpha-D-galactosamine:polypeptide N-acetylgalactosaminyltransferase 2 (GalNAc-T2)), ANGPTL4 (angiopoietin-like 4), KCNN4 (potassium intermediate/small conductance calcium-activated channel, subfamily N, member 4), PIK3C2A (phosphoinositide-3-kinase, class 2, alpha polypeptide), HBEGF (heparin-binding EGF-like growth factor), CYP7A1 (cytochrome P450, family 7, subfamily A, polypeptide 1), HLA-DRB5 (major histocompatibility complex, class II, DR beta 5), BNIP3 (BCL2/adenovirus E1B 19 kDa interacting protein 3), GCKR (glucokinase (hexokinase 4) regulator), S100A12 (S100 calcium binding protein A12), PADI4 (peptidyl arginine deiminase, type IV), HSPA14 (heat shock 70 kDa protein 14), CXCR1 (chemokine (C-X-C motif) receptor 1), H19 (H19, imprinted maternally expressed transcript (non-protein coding)), KRTAP19-3 (keratin associated protein 19-3), IDDM2 (insulin-dependent diabetes mellitus 2), RAC2 (ras-related C3 botulinum toxin substrate 2 (rho family, small GTP binding protein Rac2)), RYR1 (ryanodine receptor 1 (skeletal)), CLOCK (clock homolog (mouse)), NGFR (nerve growth factor receptor (TNFR superfamily, member 16)), DBH (dopamine beta-hydroxylase (dopamine beta-monooxygenase)), CHRNA4 (cholinergic receptor, nicotinic, alpha 4), CACNA1C (calcium channel, voltage-dependent, L type, alpha 1C subunit), PRKAG2 (protein kinase, AMP-activated, gamma 2 non-catalytic subunit), CHAT (choline acetyltransferase), PTGDS (prostaglandin D2 synthase 21 kDa (brain)), NR1H2 (nuclear receptor subfamily 1, group H, member 2), TEK (TEK tyrosine kinase, endothelial), VEGFB (vascular endothelial growth factor B), MEF2C (myocyte enhancer factor 2C), MAPKAPK2 (mitogen-activated protein kinase-activated protein kinase 2), TNFRSF11A (tumor necrosis factor receptor superfamily, member 11a, NFKB activator), HSPA9 (heat shock 70 kDa protein 9 (mortalin)), CYSLTR1 (cysteinyl leukotriene receptor 1), MAT1A (methionine adenosyltransferase I, alpha), OPRL1 (opiate receptor-like 1), IMPA1 (inositol (myo)-1(or 4)-monophosphatase 1), CLCN2 (chloride channel 2), DLD (dihydrolipoamide dehydrogenase), PSMA6 (proteasome (prosome, macropain) subunit, alpha type, 6), PSMB8 (proteasome (prosome, macropain) subunit, beta type, 8 (large multifunctional peptidase 7)), CHI3L1 (chitinase 3-like 1 (cartilage glycoprotein-39)), ALDH1B1 (aldehyde dehydrogenase 1 family, member B1), PARP2 (poly (ADP-ribose) polymerase 2), STAR (steroidogenic acute regulatory protein), LBP (lipopolysaccharide binding protein), ABCC6 (ATP-binding cassette, sub-family C(CFTR/MRP), member 6), RGS2 (regulator of G-protein signaling 2, 24 kDa), EFNB2 (ephrin-B2), GJB6 (gap junction protein, beta 6, 30 kDa), APOA2 (apolipoprotein A-II), AMPD1 (adenosine monophosphate deaminase 1), DYSF (dysferlin, limb girdle muscular dystrophy 2B (autosomal recessive)), FDFT1 (farnesyl-diphosphate farnesyltransferase 1), EDN2 (endothelin 2), CCR6 (chemokine (C-C motif) receptor 6), GJB3 (gap junction protein, beta 3, 31 kDa), IL1RL1 (interleukin 1 receptor-like 1), ENTPD1 (ectonucleoside triphosphate diphosphohydrolase 1), BBS4 (Bardet-Biedl syndrome 4), CELSR2 (cadherin, EGF LAG seven-pass G-type receptor 2 (flamingo homolog, *Drosophila*)), F11R (F11 receptor), RAPGEF3 (Rap guanine nucleotide exchange factor (GEF) 3), HYAL1 (hyaluronoglucosaminidase 1), ZNF259 (zinc finger protein 259), ATOX1 (ATX1 antioxidant protein 1 homolog (yeast)), ATF6 (activating transcription factor 6), KHK (ketohexokinase (fructokinase)), SAT1 (spermidine/spermine N1-acetyltransferase 1), GGH (gamma-glutamyl hydrolase (conjugase, folylpolygammaglutamyl hydrolase)), TIMP4 (TIMP metallopeptidase inhibitor 4), SLC4A4 (solute carrier family 4, sodium bicarbonate cotransporter, member 4), PDE2A (phosphodiesterase 2A, cGMP-stimulated), PDE3B (phosphodiesterase 3B, cGMP-inhibited), FADS1 (fatty acid desaturase 1), FADS2 (fatty acid desaturase 2), TMSB4X (thymosin beta 4, X-linked), TXNIP (thioredoxin interacting protein), LIMS1 (LIM and senescent cell antigen-like domains 1), RHOB (ras homolog gene family, member B), LY96 (lymphocyte antigen 96), FOXO1 (forkhead box 01), PNPLA2 (patatin-like phospholipase domain containing 2), TRH (thyrotropin-releasing hormone), GJC1 (gap junction protein, gamma 1, 45 kDa), SLC17A5 (solute carrier family 17 (anion/sugar transporter), member 5), FTO (fat mass and obesity associated), GJD2 (gap junction protein, delta 2, 36 kDa), PSRC1 (proline/serine-rich coiled-coil 1), CASP12 (caspase 12 (gene/pseudogene)), GPBAR1 (G protein-coupled bile acid receptor 1), PXK (PX domain containing serine/threonine kinase), IL33 (interleukin 33), TRIB1 (tribbles homolog 1 (*Drosophila*)), PBX4 (pre-B-cell leukemia homeobox 4), NUPR1 (nuclear protein, transcriptional regulator, 1), 15-Sep(15 kDa selenoprotein), CILP2 (cartilage intermediate layer protein 2), TERC (telomerase RNA component), GGT2 (gamma-glutamyltransferase 2), MT-CO1 (mitochondrially encoded cytochrome c oxidase I), and UOX (urate oxidase, pseudogene).

In an additional embodiment, the chromosomal sequence may further be selected from Pon1 (paraoxonase 1), LDLR (LDL receptor), ApoE (Apolipoprotein E), Apo B-100 (Apolipoprotein B-100), ApoA (Apolipoprotein(a)), ApoA1 (Apolipoprotein A1), CBS (Cystathione B-synthase), Glycoprotein IIb/IIb, MTHRF (5,10-methylenetetrahydrofolate reductase (NADPH)), and combinations thereof. In one iteration, the chromosomal sequences and proteins encoded by chromosomal sequences involved in cardiovascular disease may be chosen from Cacna1C, Sod1, Pten, Ppar(alpha), Apo E, Leptin, and combinations thereof.

Kidneys

The present invention also contemplates delivering the CRISPR-Cas system to the kidney. Delivery strategies to induce cellular uptake of the therapeutic nucleic acid include physical force or vector systems such as viral-, lipid- or complex-based delivery, or nanocarriers. From the initial applications with less possible clinical relevance, when nucleic acids were addressed to renal cells with hydrodynamic high pressure injection systemically, a wide range of gene therapeutic viral and non-viral carriers have been applied already to target posttranscriptional events in different animal kidney disease models in vivo (Csaba Révész and Peter Hamar (2011). Delivery Methods to Target RNAs in the Kidney, Gene Therapy Applications, Prof. Chunsheng Kang (Ed.), ISBN: 978-953-307-541-9, InTech. Delivery methods to the kidney are summarized as follows:

| Delivery method | Carrier | Target RNA | Disease | Model | Functional assays | Author |
|---|---|---|---|---|---|---|
| Hydrodynamic/Lipid | TransIT In Vivo Gene Delivery System, DOTAP | p85α | Acute renal injury | Ischemia-reperfusion | Uptake, biodistribution | Larson et al., Surgery, (August 2007), Vol. 142, No. 2, pp. (262-269) |
| Hydrodynamic/Lipid | Lipofectamine 2000 | Fas | Acute renal injury | Ischemia-reperfusion | Blood urea nitrogen, Fas Immunohistochemistry, apoptosis, histological scoring | Hamar et al., Proc Natl Acad Sci, (October 2004), Vol. 101, No. 41, pp. (14883-14888) |
| Hydrodynamic | n.a. | Apoptosis cascade elements | Acute renal injury | Ischemia-reperfusion | n.a. | Zheng et al., Am J Pathol, (October 2008), Vol. 173, No. 4, pp. (973-980) |
| Hydrodynamic | n.a. | Nuclear factor kappa-b (NFkB) | Acute renal injury | Ischemia-reperfusion | n.a. | Feng et al., Transplantation, (May 2009), Vol. 87, No. 9, pp. (1283-1289) |

| Delivery method | Carrier | Target RNA | Disease | Model | Functional assays | Author |
|---|---|---|---|---|---|---|
| Hydrodynamic/ Viral | Lipofectamine 2000 | Apoptosis antagonizing transcription factor (AATF) | Acute renal injury | Ischemia-reperfusion | Apoptosis, oxidative stress, caspase activation, membrane lipid peroxidation | Xie & Guo, Am Soc Nephrol, (December 2006), Vol. 17, No. 12, pp. (3336-3346) |
| Hydrodynamic | pBAsi mU6 Neo/ TransIT-EE Hydrodynamic Delivery System | Gremlin | Diabetic nephropathy | Streptozotozin-induced diabetes | Proteinuria, serum creatinine, glomerular and tubular diameter, collagen type IV/BMP7 expression | Q. Zhang et al., PloS ONE, (July 2010), Vol. 5, No. 7, e11709, pp. (1-13) |
| Viral/Lipid | pSUPER vector/Lipofectamine | TGF-β type II receptor | Interstitial renal fibrosis | Unilateral urethral obstruction | α-SMA expression, collagen content, | Kushibikia et al., J Controlled Release, (July 2005), Vol. 105, No. 3, pp. (318-331) |
| Viral | Adeno-associated virus-2 | Mineral corticoid receptor | Hypertension caused renal damage | Cold-induced hypertension | blood pressure, serum albumin, serum urea nitrogen, serum creatinine, kidney weight, urinary sodium | Wang et al., Gene Therapy, (July 2006), Vol. 13, No. 14, pp. (1097-1103) |
| Hydrodynamic/ Viral | pU6 vector | Luciferase | n.a. | n.a. | uptake | Kobayashi et al., Journal of Pharmacology and Experimental Therapeutics, (February 2004), Vol. 308, No. 2, pp. (688-693) |
| Lipid | Lipoproteins, albumin | apoB1, apoM | n.a. | n.a. | Uptake, binding affinity to lipoproteins and albumin | Wolfrum et al., Nature Biotechnology, (September 2007), Vol. 25, No. 10, pp. (1149-1157) |
| Lipid | Lipofectamine2000 | p53 | Acute renal injury | Ischemic and cisplatin-induced acute injury | Histological scoring, apoptosis | Molitoris et al., J Am Soc Nephrol, (August 2009), Vol. 20, No. 8, pp. (1754-1764) |
| Lipid | DOTAP/DOPE, DOTAP/DOPE/ DOPE-PEG2000 | COX-2 | Breast adeno-carcinoma | MDA-MB-231 breast cancer xenograft-bearing mouse | Cell viability, uptake | Mikhaylova et al., Cancer Gene Therapy (March 2011), Vol. 16, No. 3, pp. (217-226) |
| Lipid | Cholesterol | 12/15-lipoxygenase | Diabetic nephropathy | Streptozotocin-induced diabetes | Albuminuria, urinary creatinine, histology, type I and IV collagen, TGF-β, fibronectin, plasminogen activator inhibitor 1 | Yuan et al., Am J Physiol Renal Physiol, (June 2008), Vol. 295, pp. (F605-F617) |
| Lipid | Lipofectamine 2000 | Mitochondrial membrane 44 (TIM44) | Diabetic nephropathy | Streptozotocin-induced diabetes | Cell proliferation and apoptosis, histology, ROS, mitochondrial import of Mn-SOD and glutathione peroxidase, cellular membrane polarization | Y. Zhang et al., J Am Soc Nephrol, (April 2006), Vol. 17, No. 4, pp. (1090-1101) |
| Hydrodynamic/ Lipid | Proteoliposome | RLIP76 | Renal carcinoma | Caki-2 kidney cancer xenograft-bearing mouse | uptake | Singhal et al., Cancer Res, (May 2009), Vol. 69, No. 10, pp. (4244-4251) |

| Delivery method | Carrier | Target RNA | Disease | Model | Functional assays | Author |
|---|---|---|---|---|---|---|
| Polymer | PEGylated PEI | Luciferase pGL3 | n.a. | n.a. | Uptake, biodistribution, erythrocyte aggregation | Malek et al., Toxicology and Applied Pharmacology, (April 2009), Vol. 236, No. 1, pp. (97-108) |
| Polymer | PEGylated poly-L-lysine | MAPK1 | Lupus glomerulonephritis | Glomerulonephritis | Proteinuria, glomerulosclerosis, TGF-β, fibronectin, plasminogen activator inhibitor 1 | Shimizu et al., J Am Soc Nephrology, (April 2010), Vol. 21, No. 4, pp. (622-633) |
| Polymer/Nano particle | Hyaluronic acid/ Quantum dot/PEI | VEGF | Kidney cancer/ melanoma | B16F1 melanoma tumor-bearing mouse | Biodistribution, citotoxicity, tumor volume, endocytosis | Jiang et al., Molecular Pharmaceutics, (May-June 2009), Vol. 6, No. 3, pp. (727-737) |
| Polymer/Nano particle | PEGylated polycaprolactone nanofiber | GAPDH | n.a. | n.a. | cell viability, uptake | Cao et al, J Controlled Release, (June 2010), Vol. 144, No. 2, pp. (203-212) |
| Aptamer | Spiegelmer mNOX-E36 | CC chemokine ligand 2 | Glomerulosclerosis | Uninephrectomized mouse | urinary albumin, urinary creatinine, histopathology, glomerular filtration rate, macrophage count, serum Ccl2, Mac-2+, Ki-67+ | Ninichuk et al., Am J Pathol, (March 2008), Vol. 172, No. 3, pp. (628-637) |
| Aptamer | Aptamer NOX-F37 | vasopressin (AVP) | Congestive heart failure | n.a. | Binding affinity to D-AVP, Inhibition of AVP Signaling, Urine osmolality and sodium concentration, | Purschke et al., Proc Natl Acad Sci, (March 2006), Vol. 103, No. 13, pp. (5173-5178) |

Yuan et al. (Am J Physiol Renal Physiol 295: F605-F617, 2008) investigated whether in vivo delivery of small interfering RNAs (siRNAs) targeting the 12/15-lipoxygenase (12/15-LO) pathway of arachidonate acid metabolism can ameliorate renal injury and diabetic nephropathy (DN) in a streptozotocininjected mouse model of type 1 diabetes. To achieve greater in vivo access and siRNA expression in the kidney, Yuan et al. used double-stranded 12/15-LO siRNA oligonucleotides conjugated with cholesterol. About 400 μg of siRNA was injected subcutaneously into mice. The method of Yuang et al. may be applied to the CRISPR Cas system of the present invention contemplating a 1-2 g subcutaneous injection of CRISPR Cas conjugated with cholesterol to a human for delivery to the kidneys.

Molitoris et al. (J Am Soc Nephrol 20: 1754-1764, 2009) exploited proximal tubule cells (PTCs), as the site of oligonucleotide reabsorption within the kidney to test the efficacy of siRNA targeted to p53, a pivotal protein in the apoptotic pathway, to prevent kidney injury. Naked synthetic siRNA to p53 injected intravenously 4 h after ischemic injury maximally protected both PTCs and kidney function. Molitoris et al.'s data indicates that rapid delivery of siRNA to proximal tubule cells follows intravenous administration. For dose-response analysis, rats were injected with doses of siP53, 0.33; 1, 3, or 5 mg/kg, given at the same four time points, resulting in cumulative doses of 1.32; 4, 12, and 20 mg/kg, respectively. All siRNA doses tested produced a SCr reducing effect on day one with higher doses being effective over approximately five days compared With PBS-treated ischemic control rats. The 12 and 20 mg/kg cumulative doses provided the best protective effect. The method of Molitoris et al. may be applied to the CRISPR Cas system of the present invention contemplating 12 and 20 mg/kg cumulative doses to a human for delivery to the kidneys.

Thompson et al. (Nucleic Acid Therapeutics, Volume 22, Number 4, 2012) reports the toxicological and pharmacokinetic properties of the synthetic, small interfering RNA I5NP following intravenous administration in rodents and nonhuman primates. I5NP is designed to act via the RNA interference (RNAi) pathway to temporarily inhibit expression of the pro-apoptotic protein p53 and is being developed to protect cells from acute ischemia/reperfusion injuries such as acute kidney injury that can occur during major cardiac surgery and delayed graft function that can occur following renal transplantation. Doses of 800 mg/kg 15NP in rodents, and 1,000 mg/kg I5NP in nonhuman primates, were required to elicit adverse effects, which in the monkey were isolated to direct effects on the blood that included a sub-clinical activation of complement and slightly increased clotting times. In the rat, no additional adverse effects were observed with a rat analogue of I5NP, indicating that the effects likely represent class effects of synthetic RNA duplexes rather than toxicity related to the intended pharmacologic activity of I5NP. Taken together, these data support clinical testing of intravenous administration of I5NP for the preservation of renal function following acute ischemia/reperfusion injury. The no observed adverse effect level (NOAEL) in the monkey was 500 mg/kg. No effects on cardiovascular, respiratory, and neurologic parameters were observed in monkeys following i.v. administration at dose levels up to 25 mg/kg. Therefore, a similar dosage may be contemplated for intravenous administration of CRISPR Cas to the kidneys of a human.

Shimizu et al. (J Am Soc Nephrol 21: 622-633, 2010) developed a system to target delivery of siRNAs to glomeruli via poly(ethylene glycol)-poly(L-lysine)-based vehicles. The siRNA/nanocarrier complex was approximately 10 to 20 nm in diameter, a size that would allow it to move across the fenestrated endothelium to access to the mesangium. After intraperitoneal injection of fluorescence-labeled siRNA/nanocarrier complexes, Shimizu et al. detected siRNAs in the blood circulation for a prolonged time. Repeated intraperitoneal administration of a mitogen-activated protein kinase 1 (MAPK1) siRNA/nanocarrier complex suppressed glomerular MAPK1 mRNA and protein expression in a mouse model of glomerulonephritis. For the investigation of siRNA accumulation, Cy5-labeled siRNAs complexed with PIC nanocarriers (0.5 ml, 5 nmol of siRNA content), naked Cy5-labeled siRNAs (0.5 ml, 5 nmol), or Cy5-labeled siRNAs encapsulated in HVJ-E (0.5 ml, 5 nmol of siRNA content) were administrated to BALB-c mice. The method of Shimizu et al. may be applied to the CRISPR Cas system of the present invention contemplating a dose of about of 10-20 µmol CRISPR Cas complexed with nanocarriers in about 1-2 liters to a human for intraperitoneal administration and delivery to the kidneys.

Lungs

The present invention also contemplates delivering the CRISPR-Cas system to one or both lungs.

Although AAV-2-based vectors were originally proposed for CFTR delivery to CF airways, other serotypes such as AAV-1, AAV-5, AAV-6, and AAV-9 exhibit improved gene transfer efficiency in a variety of models of the lung epithelium (see, e.g., Li et al., Molecular Therapy, vol. 17 no. 12, 2067-277 December 2009). AAV-1 was demonstrated to be ~100-fold more efficient than AAV-2 and AAV-5 at transducing human airway epithelial cells in vitro, 5 although AAV-1 transduced murine tracheal airway epithelia in vivo with an efficiency equal to that of AAV-5. Other studies have shown that AAV-5 is 50-fold more efficient than AAV-2 at gene delivery to human airway epithelium (HAE) in vitro and significantly more efficient in the mouse lung airway epithelium in vivo. AAV-6 has also been shown to be more efficient than AAV-2 in human airway epithelial cells in vitro and murine airways in vivo.8 The more recent isolate, AAV-9, was shown to display greater gene transfer efficiency than AAV-5 in murine nasal and alveolar epithelia in vivo with gene expression detected for over 9 months suggesting AAV may enable long-term gene expression in vivo, a desirable property for a CFTR gene delivery vector. Furthermore, it was demonstrated that AAV-9 could be readministered to the murine lung with no loss of CFTR expression and minimal immune consequences. CF and non-CF HAE cultures may be inoculated on the apical surface with 100 µl of AAV vectors for hours (see, e.g., Li et al., Molecular Therapy, vol. 17 no. 12, 2067-277 December 2009). The MOI may vary from $1 \times 10^3$ to $4 \times 10^5$ vector genomes/cell, depending on virus concentration and purposes of the experiments. The above cited vectors are contemplated for the delivery and/or administration of the invention.

Zamora et al. (Am J Respir Crit Care Med Vol 183. pp 531-538, 2011) reported an example of the application of an RNA interference therapeutic to the treatment of human infectious disease and also a randomized trial of an antiviral drug in respiratory syncytial virus (RSV)-infected lung transplant recipients. Zamora et al. performed a randomized, double-blind, placebocontrolled trial in LTX recipients with RSV respiratory tract infection. Patients were permitted to receive standard of care for RSV. Aerosolized ALN-RSV01 (0.6 mg/kg) or placebo was administered daily for 3 days. This study demonstrates that an RNAi therapeutic targeting RSV can be safely administered to LTX recipients with RSV infection. Three daily doses of ALN-RSV01 did not result in any exacerbation of respiratory tract symptoms or impairment of lung function and did not exhibit any systemic proinflammatory effects, such as induction of cytokines or CRP. Pharmacokinetics showed only low, transient systemic exposure after inhalation, consistent with preclinical animal data showing that ALN-RSV01, administered intravenously or by inhalation, is rapidly cleared from the circulation through exonucleasemediated digestion and renal excretion. The method of Zamora et al. may be applied to the CRISPR Cas system of the present invention and an aerosolized CRISPR Cas, for example with a dosage of 0.6 mg/kg, may be contemplated for the present invention.

For an example of CFTRdelta508 chimeric guide RNA, see Example 22 which demonstrates gene transfer or gene delivery of a CRISPR-Cas system in airways of subject or a patient in need thereof, suffering from cystic fibrosis or from cystic fibrosis (CF) related symptoms, using adeno-associated virus (AAV) particles. In particular, they exemplify a repair strategy for Cystic Fibrosis delta F508 mutation. This type of strategy should apply across all organisms. With particular reference to CF, suitable patients may include: Human, non-primate human, canine, feline, bovine, equine and other domestic animals. In this instance, Applicants utilized a CRISPR-Cas system comprising a Cas9 enzyme to target deltaF508 or other CFTR-inducing mutations.

The treated subjects in this instance receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector. In this instance, the following constructs are provided as examples: Cbh or EF1a promoter for Cas9, U6 or H1 promoter for chimeric guide RNA): A preferred arrangement is to use a CFTRdelta508 targeting chimeric guide, a repair template for deltaF508 mutation and a codon optimized Cas9 enzyme (preferred Cas9s are those with nuclease or nickase activity) with optionally one or more nuclear localization signal or sequence(s) (NLS(s)), e.g., two (2) NLSs. Constructs without NLS are also envisaged.

In order to identify the Cas9 target site, Applicants analyzed the human CFTR genomic locus and identified the Cas9 target site. Preferably, in general and in this CF case, the PAM may contain a NGG or a NNAGAAW motif Accordingly, in the case of CF, the present method comprises manipulation of a target sequence in a genomic locus of interest comprising delivering a non-naturally occurring or engineered composition comprising a viral vector system comprising one or more viral vectors operably encoding a composition for expression thereof, wherein the composition comprises:

a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to the CF target sequence in a suitable mammalian cell,
(b) a tracr mate sequence, and
(c) a tracr sequence, and
II. a second regulatory element operably linked to an enzyme-coding sequence encoding a CRISPR enzyme comprising at least one or more nuclear localization sequences, wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and
wherein the CRISPR complex comprises the CRISPR enzyme complexed with (1) the guide sequence that is hybridized to the target sequence, and (2) the tracr mate sequence that is hybridized to the tracr sequence. In respect of CF, preferred target DNA sequences comprise the CFTRdelta508 mutation. A preferred PAM is described above. A preferred CRISPR enzyme is any Cas (described herein, but particularly that described in Example 22).

Alternatives to CF include any genetic disorder and examples of these are well known. Another preferred method or use of the invention is for correcting defects in the EMP2A and EMP2B genes that have been identified to be associated with Lafora disease.

In some embodiments, a "guide sequence" may be distinct from "guide RNA". A guide sequence may refer to an approx. 20 bp sequence, within the guide RNA, that specifies the target site.

In some embodiments, the Cas9 is (or is derived from) SpCas9. In such embodiments, preferred mutations are at any or all or positions 10, 762, 840, 854, 863 and/or 986 of SpCas9 or corresponding positions in other Cas9s (which may be ascertained for instance by standard sequence comparison tools. In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. These are advantageous as they provide nickase activity. Such mutations may be applied to all aspects of the present invention, not only treatment of CF.

Schwank et al. (Cell Stem Cell, 13:653-58, 2013) used CRISPR/Cas9 to correct a defect associated with cystic fibrosis in human stem cells. The team's target was the gene for an ion channel, cystic fibrosis transmembrane conductor receptor (CFTR). A deletion in CFTR causes the protein to misfold in cystic fibrosis patients. Using cultured intestinal stem cells developed from cell samples from two children with cystic fibrosis, Schwank et al. were able to correct the defect using CRISPR along with a donor plasmid containing the reparative sequence to be inserted. The researchers then grew the cells into intestinal "organoids," or miniature guts, and showed that they functioned normally. In this case, about half of clonal organoids underwent the proper genetic correction.

Muscles

The present invention also contemplates delivering the CRISPR-Cas system to muscle(s).

Bortolanza et al. (Molecular Therapy vol. 19 no. 11, 2055-264 November 2011) shows that systemic delivery of RNA interference expression cassettes in the FRG1 mouse, after the onset of facioscapulohumeral muscular dystrophy (FSHD), led to a dose-dependent long-term FRG1 knockdown without signs of toxicity. Bortolanza et al. found that a single intravenous injection of $5\times10^{12}$ vg of rAAV6-sh1FRG1 rescues muscle histopathology and muscle function of FRG1 mice. In detail, 200 μl containing $2\times10^{12}$ or $5\times10^{12}$ vg of vector in physiological solution were injected into the tail vein using a 25-gauge Terumo syringe. The method of Bortolanza et al. may be applied to an AAV expressing CRISPR Cas and injected into humans at a dosage of about $2\times10^{15}$ or $2\times10^{16}$ vg of vector.

Dumonceaux et al. (Molecular Therapy vol. 18 no. 5, 881-887 May 2010) inhibit the myostatin pathway using the technique of RNA interference directed against the myostatin receptor AcvRIIb mRNA (sh-AcvRIIb). The restoration of a quasi-dystrophin was mediated by the vectorized U7 exon-skipping technique (U7-DYS). Adeno-associated vectors carrying either the sh-AcvrIIb construct alone, the U7-DYS construct alone, or a combination of both constructs were injected in the tibialis anterior (TA) muscle of dystrophic mdx mice. The injections were performed with $10^{11}$ AAV viral genomes. The method of Dumonceaux et al. may be applied to an AAV expressing CRISPR Cas and injected into humans, for example, at a dosage of about $10^{14}$ to about $10^{15}$ vg of vector.

Kinouchi et al. (Gene Therapy (2008) 15, 1126-1130) report the effectiveness of in vivo siRNA delivery into skeletal muscles of normal or diseased mice through nanoparticle formation of chemically unmodified siRNAs with atelocollagen (ATCOL). ATCOL-mediated local application of siRNA targeting myostatin, a negative regulator of skeletal muscle growth, in mouse skeletal muscles or intravenously, caused a marked increase in the muscle mass within a few weeks after application. These results imply that ATCOL-mediated application of siRNAs is a powerful tool for future therapeutic use for diseases including muscular atrophy. Mst-siRNAs (final concentration, 10 mM) were mixed with ATCOL (final concentration for local administration, 0.5%) (AteloGene, Kohken, Tokyo, Japan) according to the manufacturer's instructions. After anesthesia of mice (20-week-old male C57BL/6) by Nembutal (25 mg/kg, i.p.), the Mst-siRNA/ATCOL complex was injected into the masseter and biceps femoris muscles. The method of Kinouchi et al. may be applied to CRISPR Cas and injected into a human, for example, at a dosage of about 500 to 1000 ml of a 40 μM solution into the muscle.

Hagstrom et al. (Molecular Therapy Vol. 10, No. 2, August 2004) describe an intravascular, nonviral methodology that enables efficient and repeatable delivery of nucleic acids to muscle cells (myofibers) throughout the limb muscles of mammals. The procedure involves the injection of naked plasmid DNA or siRNA into a distal vein of a limb that is transiently isolated by a tourniquet or blood pressure cuff. Nucleic acid delivery to myofibers is facilitated by its rapid injection in sufficient volume to enable extravasation of the nucleic acid solution into muscle tissue. High levels of transgene expression in skeletal muscle were achieved in both small and large animals with minimal toxicity. Evidence of siRNA delivery to limb muscle was also obtained. For plasmid DNA intravenous injection into a rhesus monkey, a threeway stopcock was connected to two syringe pumps (Model PHD 2000; Harvard Instruments), each loaded with a single syringe. Five minutes after a papaverine injection, pDNA (15.5 to 25.7 mg in 40-100 ml saline) was injected at a rate of 1.7 or 2.0 ml/s. This could be scaled up for plasmid DNA expressing CRISPR Cas of the present invention with an injection of about 300 to 500 mg in 800 to 2000 ml saline for a human. For adenoviral vector injections into a rat, 2×10⁹ infectious particles were injected in 3 ml of normal saline solution (NSS). This could be scaled up for an adenoviral vector expressing CRISPR Cas of the present invention with an injection of about 1×10¹³ infectious particles were injected in 10 liters of NSS for a human. For siRNA, a rat was injected into the great saphenous vein with 12.5 µg of a siRNA and a primate was injected injected into the great saphenous vein with 750 µg of a siRNA. This could be scaled up for a CRISPR Cas of the present invention, for example, with an injection of about 15 to about 50 mg into the great saphenous vein of a human.

Skin

The present invention also contemplates delivering the CRISPR-Cas system to the skin.

Hickerson et al. (Molecular Therapy—Nucleic Acids (2013) 2, e129) relates to a motorized microneedle array skin delivery device for delivering self-delivery (sd)-siRNA to human and murine skin. The primary challenge to translating siRNA-based skin therapeutics to the clinic is the development of effective delivery systems. Substantial effort has been invested in a variety of skin delivery technologies with limited success. In a clinical study in which skin was treated with siRNA, the exquisite pain associated with the hypodermic needle injection precluded enrollment of additional patients in the trial, highlighting the need for improved, more "patient-friendly" (i.e., little or no pain) delivery approaches. Microneedles represent an efficient way to deliver large charged cargos including siRNAs across the primary barrier, the stratum corneum, and are generally regarded as less painful than conventional hypodermic needles. Motorized "stamp type" microneedle devices, including the motorized microneedle array (MMNA) device used by Hickerson et al., have been shown to be safe in hairless mice studies and cause little or no pain as evidenced by (i) widespread use in the cosmetic industry and (ii) limited testing in which nearly all volunteers found use of the device to be much less painful than a flushot, suggesting siRNA delivery using this device will result in much less pain than was experienced in the previous clinical trial using hypodermic needle injections. The MMNA device (marketed as Triple-M or Tri-M by Bomtech Electronic Co, Seoul, South Korea) was adapted for delivery of siRNA to mouse and human skin. sd-siRNA solution (up to 300 µl of 0.1 mg/ml RNA) was introduced into the chamber of the disposable Tri-M needle cartridge (Bomtech), which was set to a depth of 0.1 mm. For treating human skin, deidentified skin (obtained immediately following surgical procedures) was manually stretched and pinned to a cork platform before treatment. All intradermal injections were performed using an insulin syringe with a 28-gauge 0.5-inch needle. The MMNA device and method of Hickerson et al. could be used and/or adapted to deliver the CRISPR Cas of the present invention, for example, at a dosage of up to 300 µl of 0.1 mg/ml CRISPR Cas to the skin.

Leachman et al. (Molecular Therapy, vol. 18 no. 2, 442-446 February 2010) relates to a phase Ib clinical trial for treatment of a rare skin disorder pachyonychia congenita (PC), an autosomal dominant syndrome that includes a disabling plantar keratoderma, utilizing the first short-interfering RNA (siRNA)-based therapeutic for skin. This siRNA, called TD101, specifically and potently targets the keratin 6a (K6a) N171K mutant mRNA without affecting wild-type K6a mRNA. The dose-escalation schedule is presented below:

| Week | Dose no. | Days | Volume (ml) | Concentration of TD101 (mg/ml) | Total dose TD101 (mg) |
|---|---|---|---|---|---|
| 1 | 1-2 | 1-7 | 0.1 | 1.0 | 0.10 |
| 2 | 3-4 | 8-14 | 0.25 | 1.0 | 0.25 |
| 3 | 5-6 | 15-21 | 0.50 | 1.0 | 0.50 |
| 4 | 7-8 | 22-28 | 1.0 | 1.0 | 1.0 |
| 5 | 9-10 | 29-35 | 1.5 | 1.0 | 1.5 |
| 6 | 11-12 | 36-42 | 2.0 | 1.0 | 2.0 |
| 7 | 13-14 | 43-49 | 2.0 | 1.5 | 3.0 |
| 8 | 15-16 | 50-56 | 2.0 | 2.0 | 4.0 |
| 9 | 17-18 | 57-63 | 2.0 | 2.5 | 5.0 |
| 10 | 19-20 | 64-70 | 2.0 | 3.0 | 6.0 |
| 11 | 21-22 | 71-77 | 2.0 | 3.5 | 7.0 |
| 12 | 23-24 | 78-84 | 2.0 | 4.0 | 8.0 |
| 13 | 25-26 | 85-91 | 2.0 | 4.5 | 9.0 |
| 14 | 27-28 | 92-98 | 2.0 | 5.0 | 10.0 |
| 15 | 29-30 | 99-105 | 2.0 | 6.0 | 12.0 |
| 16 | 31-32 | 106-112 | 2.0 | 7.0 | 14.0 |
| 17 | 33 | 113-119 | 2.0 | 8.5 | 17.0 |

Initially, 0.1 ml of a 1.0 mg/ml solution of TD101 or vehicle alone (Dulbecco's phosphate-buffered saline without calcium or magnesium) was administered to symmetric calluses. Six rising dose-volumes were completed without an adverse reaction to the increases: 0.1, 0.25, 0.5, 1.0, 1.5, and 2.0 ml of a 1.0 mg/ml solution of TD101 solution per injection. As the highest planned volume (2.0 ml) was well tolerated, the concentration of TD101 was then increased each week from 1 mg/ml up to a final concentration of 8.5 mg/ml. Similar dosages are contemplated for the administration of a CRISPR Cas that specifically and potently targets the keratin 6a (K6a) N171K mutant mRNA.

Zheng et al. (PNAS, Jul. 24, 2012, vol. 109, no. 30, 11975-11980) show that spherical nucleic acid nanoparticle conjugates (SNA-NCs), gold cores surrounded by a dense shell of highly oriented, covalently immobilized siRNA, freely penetrate almost 100% of keratinocytes in vitro, mouse skin, and human epidermis within hours after application. Zheng et al. demonstrated that a single application of 25 nM epidermal growth factor receptor (EGFR) SNA-NCs for 60 h demonstrate effective gene knockdown in human skin. A similar dosage may be contemplated for CRISPR Cas immobilized in SNA-NCs for administration to the skin.

Hepatitis Viruses

The present invention may also be applied to treat hepatitis B virus (HBV). However, the CRISPR Cas system must be adapted to avoid the shortcomings of RNAi, such as the risk of oversatring endogenous small RNA pathways, by for example, optimizing dose and sequence (see, e.g., Grimm et al., Nature vol. 441, 26 May 2006). For example, low doses, such as about 1-10×10¹⁴ particles per humane are contemplated.

In another embodiment, the CRISPR Cas system directed against HBV may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of CRISPR Cas targeted to HBV RNA in a SNALP are contemplated. The daily treatment may be over about three days and then weekly for about five weeks.

In another embodiment, the system of Chen et al. (Gene Therapy (2007) 14, 11-19) may be used/and or adapted for the CRISPR Cas system of the present invention. Chen et al. use a double-stranded adenoassociated virus 8-pseudotyped vector (dsAAV2/8) to deliver shRNA. A single administration of dsAAV2/8 vector (1×10¹² vector genomes per mouse), carrying HBV-specific shRNA, effectively suppressed the steady level of HBV protein, mRNA and replicative DNA in liver of HBV transgenic mice, leading to up to 2-3 $\log_{10}$ decrease in HBV load in the circulation. Significant HBV suppression sustained for at least 120 days after vector administration. The therapeutic effect of shRNA was target sequence dependent and did not involve activation of interferon. For the present invention, a CRISPR Cas system directed to HBV may be cloned into an AAV vector, such as a dsAAV2/8 vector and administered to a human, for example, at a dosage of about $1\times10^{15}$ vector genomes to about $1\times10^{16}$ vector genomes per human.

In another embodiment, the method of Wooddell et al. (Molecular Therapy vol. 21 no. 5, 973-985 May 2013) may be used/and or adapted to the CRISPR Cas system of the present invention. Woodell et al. show that simple coinjection of a hepatocyte-targeted, N-acetylgalactosamine-conjugated melittin-like peptide (NAG-MLP) with a liver-tropic cholesterol-conjugated siRNA (chol-siRNA) targeting coagulation factor VII (F7) results in efficient F7 knockdown in mice and nonhuman primates without changes in clinical chemistry or induction of cytokines. Using transient and transgenic mouse models of HBV infection, Wooddell et al. show that a single coinjection of NAG-MLP with potent chol-siRNAs targeting conserved HBV sequences resulted in multilog repression of viral RNA, proteins, and viral DNA with long duration of effect. Intraveinous coinjections, for example, of about 6 mg/kg of NAG-MLP and 6 mg/kg of HBV specific CRISPR Cas may be envisioned for the present invention. In the alternative, about 3 mg/kg of NAG-MLP and 3 mg/kg of HBV specific CRISPR Cas may be delivered on day one, followed by administration of about about 2-3 mg/kg of NAG-MLP and 2-3 mg/kg of HBV specific CRISPR Cas two weeks later.

The present invention may also be applied to treat hepatitis C virus (HCV). The methods of Roelvinki et al. (Molecular Therapy vol. 20 no. 9, 1737-1749 September 2012) may be applied to the CRISPR Cas system. For example, an AAV vector such as AAV8 may be a contemplated vector and for example a dosage of about $1.25\times10^{11}$ to $1.25\times10^{13}$ vector genomes per kilogram body weight (vg/kg) may be contemplated.

It will be readily apparent that a host of other diseases can be treated in a similar fashion. Some examples of genetic diseases caused by mutations are provided herein, but many more are known. The above strategy can be applied to these diseases.

Huntington's Disease (HD)

RNA interference (RNAi) offers therapeutic potential for this disorder by reducing the expression of HTT, the disease-causing gene of Huntington's disease (see, e.g., McBride et al., Molecular Therapy vol. 19 no. 12 Dec. 2011, pp. 2152-2162), therefore Applicant postulates that it may be used/and or adapted to the CRISPR-Cas system. The CRISPR-Cas system may be generated using an algorithm to reduce the off-targeting potential of antisense sequences. The CRISPR-Cas sequences may target either a sequence in exon 52 of mouse, rhesus or human huntingtin and expressed in a viral vector, such as AAV. Animals, including humans, may be injected with about three microinjections per hemisphere (six injections total): the first 1 mm rostral to the anterior commissure (12 µl) and the two remaining injections (12 µl and 10 µl, respectively) spaced 3 and 6 mm caudal to the first injection with 1e12 vg/ml of AAV at a rate of about 1 µl/minute, and the needle was left in place for an additional 5 minutes to allow the injectate to diffuse from the needle tip.

DiFiglia et al. (PNAS, Oct. 23, 2007, vol. 104, no. 43, 17204-17209) observed that single administration into the adult striatum of an siRNA targeting Htt can silence mutant Htt, attenuate neuronal pathology, and delay the abnormal behavioral phenotype observed in a rapid-onset, viral transgenic mouse model of HD. DiFiglia injected mice intristriatally with 2 µl of Cy3-labeled cc-siRNA-Htt or unconjugated siRNA-Htt at 10 µM. A similar dosage of CRISPR Cas targeted to Htt may be contemplated for humans in the present invention, for example, about 5-10 ml of 10 µM CRISPR Cas targeted to Htt may be injected intrastriatally.

In another example, Boudreau et al. (Molecular Therapy vol. 17 no. 6 Jun. 2009) injects 5 µl of recombinant AAV serotype 2/1 vectors expressing htt-specific RNAi virus (at $4\times10^{12}$ viral genomes/ml) into the straiatum. A similar dosage of CRISPR Cas targeted to Htt may be contemplated for humans in the present invention, for example, about 10-20 ml of $4\times10^{12}$ viral genomes/ml) CRISPR Cas targeted to Htt may be injected intrastriatally.

In another example, a CRISPR Cas targeted to HTT may be administered continuously (see, e.g., Yu et al., Cell 150, 895-908, Aug. 31, 2012). Yu et al. utilizes osmotic pumps delivering 0.25 ml/hr (Model 2004) to deliver 300 mg/day of ss-siRNA or phosphate-buffered saline (PBS) (Sigma Aldrich) for 28 days, and pumps designed to deliver 0.5 µl/hr (Model 2002) were used to deliver −75 mg/day of the positive control MOE ASO for 14 days. Pumps (Durect Corporation) were filled with ss-siRNA or MOE diluted in sterile PBS and then incubated at 37 C for 24 or 48 (Model 2004) hours prior to implantation. Mice were anesthetized with 2.5% isofluorane, and a midline incision was made at the base of the skull. Using stereotaxic guides, a cannula was implanted into the right lateral ventricle and secured with Loctite adhesive. A catheter attached to an Alzet osmotic mini pump was attached to the cannula, and the pump was placed subcutaneously in the midscapular area. The incision was closed with 5.0 nylon sutures. A similar dosage of CRISPR Cas targeted to Htt may be contemplated for humans in the present invention, for example, about 500 to 1000 g/day CRISPR Cas targeted to Htt may be administered.

In another example of continuous infusion, Stiles et al. (Experimental Neurology 233 (2012) 463-471) implanted an intraparenchymal catheter with a titanium needle tip into the right putamen. The catheter was connected to a SynchroMed® II Pump (Medtronic Neurological, Minneapolis, Minn.) subcutaneously implanted in the abdomen. After a 7 day infusion of phosphate buffered saline at 6 µL/day, pumps were re-filled with test article and programmed for continuous delivery for 7 days. About 2.3 to 11.52 mg/d of siRNA were infused at varying infusion rates of about 0.1 to 0.5 µL/min. A similar dosage of CRISPR Cas targeted to Htt may be contemplated for humans in the present invention, for example, about 20 to 200 mg/day CRISPR Cas targeted to Htt may be administered.

In another example, the methods of US Patent Publication No. 20130253040 assigned to Sangamo may also be also be adapted from TALES to the CRISPR Cas system of the present invention for treating Huntington's Disease.

Nucleic Acids, Amino Acids and Proteins

The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$ Highly permissive (very low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "domain" or "protein domain" refers to a part of a protein sequence that may exist and function independently of the rest of the protein chain.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capplng region of the dTALEs described herein have sequences that are at least 95% identical or share identity to the capplng region amino acid sequences provided herein.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity.

However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4$^{th}$ Ed. —Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health).

Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" *Comput. Appl. Biosci.* 9: 745-756) (Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| Set | | Sub-set | |
|---|---|---|---|
| Hydrophobic | F W Y H K M I L V<br>A G C | Aromatic<br>Aliphatic | F W Y H<br>I L V |
| Polar | W Y H K R E D C S<br>T N Q | Charged<br>Positively charged<br>Negatively charged | H K R E D<br>H K R<br>E D |
| Small | V C A G S P T N D | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

Vectors

In one aspect, the invention provides for vectors that are used in the engineering and optimization of CRISPR-Cas systems.

A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 61). This may be followed by the loop sequence GAAA as shown. Both of these are preferred examples. Applicants have demonstrated Cas9-mediated indels at the human EMX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1a promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces cerivisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. Cell 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

Regulatory Elements

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In embodiments of the invention the terms guide sequence and guide RNA are used interchangeably. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell.

In some embodiments, direct repeats may be identified in silico by searching for repetitive motifs that fulfill any or all of the following criteria:
1. found in a 2 Kb window of genomic sequence flanking the type II CRISPR locus;
2. span from 20 to 50 bp; and
3. interspaced by 20 to 50 bp.

In some embodiments, 2 of these criteria may be used, for instance 1 and 2, 2 and 3, or 1 and 3. In some embodiments, all 3 criteria may be used.

In some embodiments, candidate tracrRNA may be subsequently predicted by sequences that fulfill any or all of the following criteria:
1. sequence homology to direct repeats (motif search in Geneious with up to 18-bp mismatches);
2. presence of a predicted Rho-independent transcriptional terminator in direction of transcription; and
3. stable hairpin secondary structure between tracrRNA and direct repeat.

In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

In preferred embodiments of the invention, the CRISPR system is a type II CRISPR system and the Cas enzyme is Cas9, which catalyzes DNA cleavage. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defence in bacteria and archaea, Mole Cell 2010, Jan. 15; 37(1): 7.

Figure 2A:
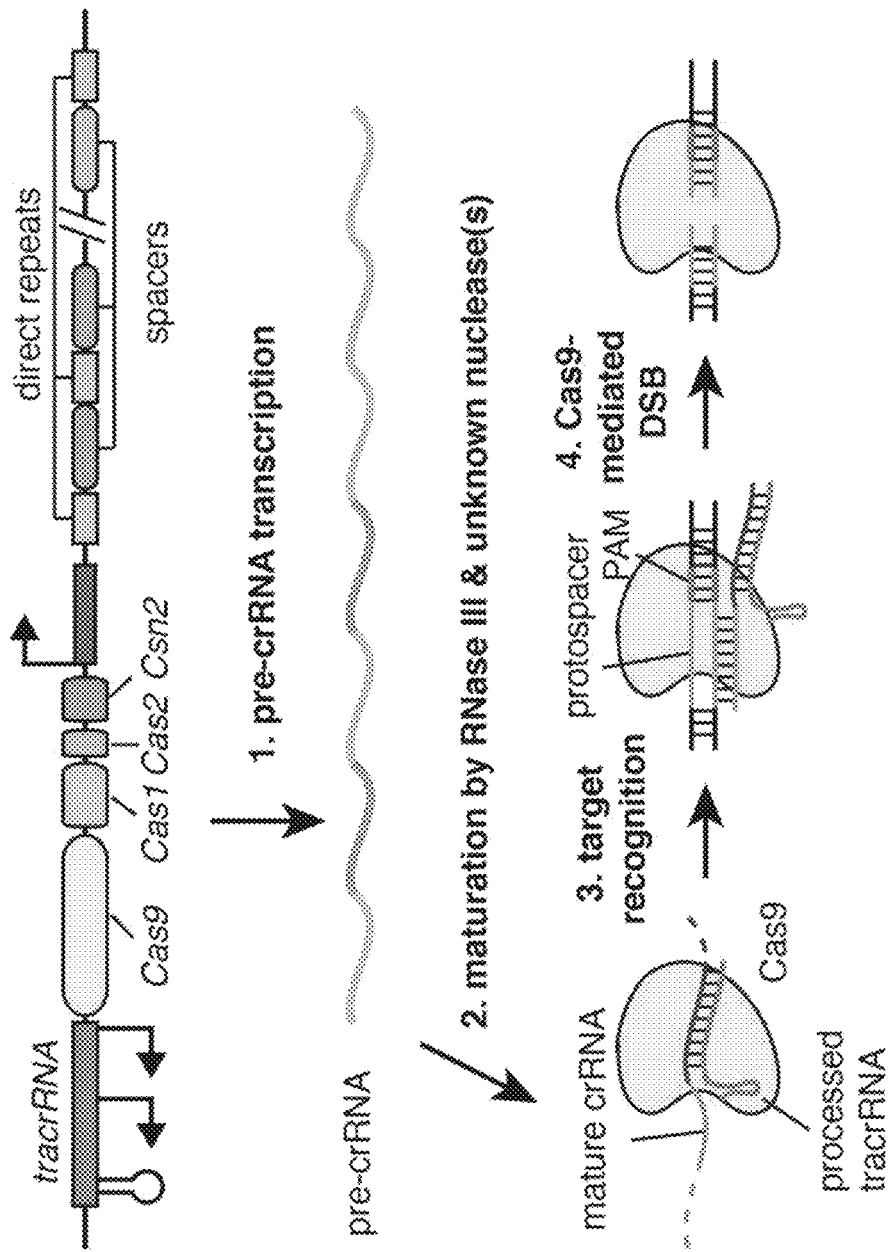
Figure 2B:
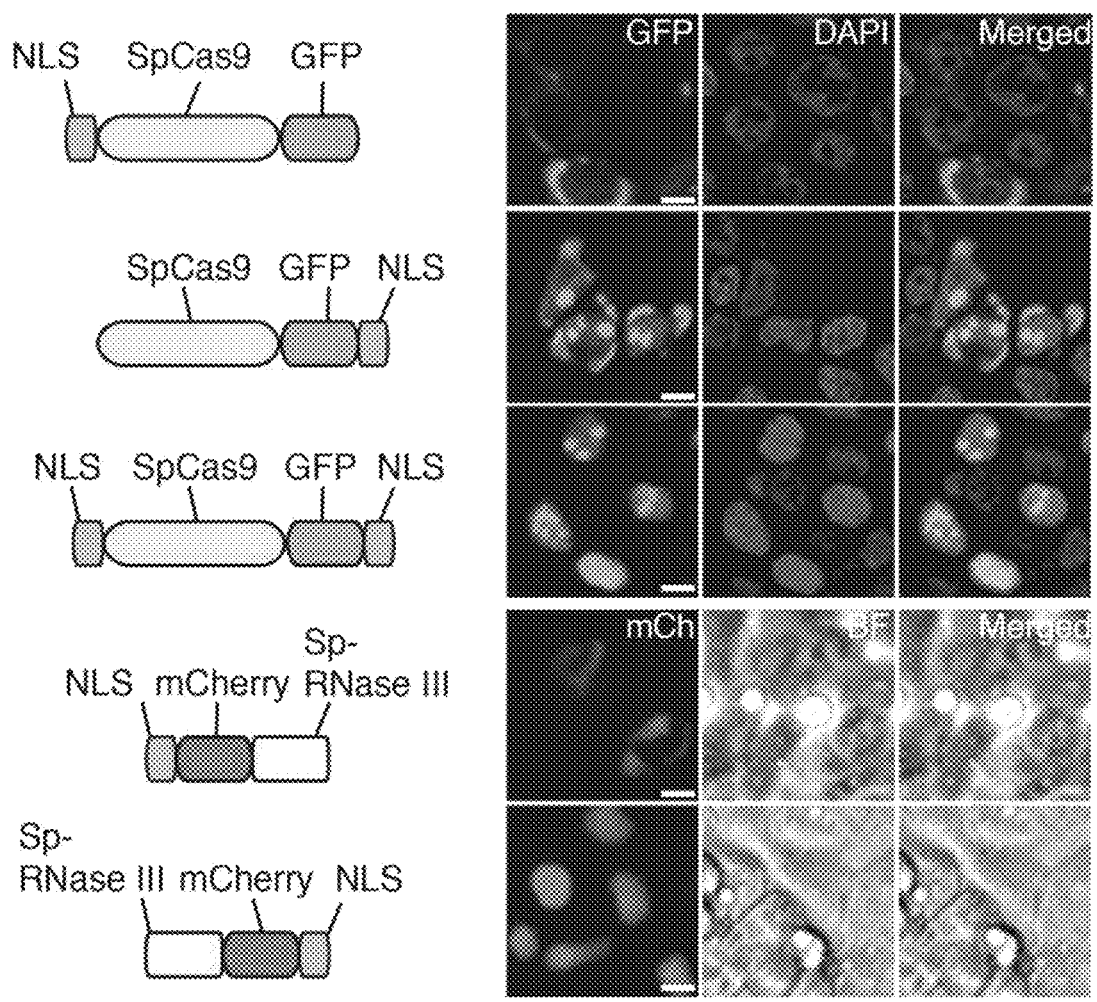
Figure 2C:
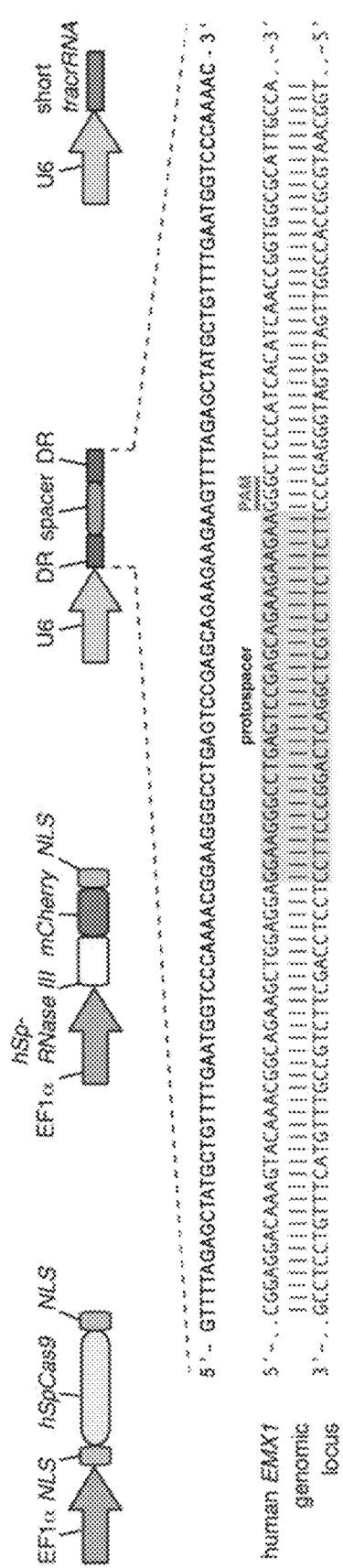

The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps (FIG. 2A). First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer (FIG. 2A). FIG. 2B demonstrates the nuclear localization of the codon optimized Cas9. To promote precise transcriptional initiation, the RNA polymerase III-based U6 promoter was selected to drive the expression of tracrRNA (FIG. 2C). Similarly, a U6 promoter-based construct was developed to express a pre-crRNA array consisting of a single spacer flanked by two direct repeats (DRs, also encompassed by the term "tracr-mate sequences"; FIG. 2C). The initial spacer was designed to target a 33-base-pair (bp) target site (30-bp protospacer plus a 3-bp CRISPR motif (PAM) sequence satisfying the NGG recognition motif of Cas9) in the human EMX1 locus (FIG. 2C), a key gene in the development of the cerebral cortex.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, 11840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred.

An aspartate-to-alanine substitution (D10A) in the RuvC I catalytic domain of SpCas9 was engineered to convert the nuclease into a nickase (SpCas9n) (see e.g. Sapranauskas et al., 2011, Nucleic Acis Research, 39: 9275; Gasiunas et al., 2012, Proc. Natl. Acad. Sci. USA, 109:E2579), such that nicked genomic DNA undergoes the high-fidelity homology-directed repair (HDR). Surveyor assay confirmed that SpCas9n does not generate indels at the EMX1 protospacer target. Co-expression of EMX1-targeting chimeric crRNA (having the tracrRNA component as well) with SpCas9 produced indels in the target site, whereas co-expression with SpCas9n did not (n=3). Moreover, sequencing of 327 amplicons did not detect any indels induced by SpCas9n. The same locus was selected to test CRISPR-mediated HR by co-transfecting HEK 293FT cells with the chimeric RNA targeting EMX1, hSpCas9 or hSpCas9n, as well as a HR template to introduce a pair of restriction sites (HindIII and NheI) near the protospacer.

Preferred orthologs are described herein. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in Streptococcus pyogenes. However, it will be appreciated that this invention includes many more Cas9s from other species of microbes, such as SpCas9, SaCa9, St1Cas9 and so forth.

Codon Optimization

An example of a codon optimized sequence, in this instance optimized for humans (i.e. being optimized for expression in humans) is provided herein, see the SaCas9 human codon optimized sequence. Whilst this is preferred, it will be appreciated that other examples are possible and codon optimization for a host species is known.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded.

In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ (visited Jul. 9, 2002), and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

Nuclear Localization Sequences (NLSs)

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 62); the NLS from nucleoplasmin (e.g. the nucleoplasmin bipartite NLS with the sequence KRPAATKKAGQAKKKK (SEQ ID NO: 63)); the c-myc NLS having the amino acid sequence PAAKRVKLD (SEQ ID NO: 64) or RQRRNELKRSP (SEQ ID NO: 65); the hRNPA1 M9 NLS having the sequence NQSSNFGPMKGGNFGGRSSGPYGGGGQYFAK-PRNQGGY (SEQ ID NO: 66); the sequence RMRIZFKNKGKDTAELRRRRVEVSVELRKAKKD-EQILKRRNV (SEQ ID NO: 67) of the IBB domain from importin-alpha; the sequences VSRKRPRP (SEQ ID NO: 68) and PPKKARED (SEQ ID NO: 69) of the myoma T protein; the sequence PQPKKKPL (SEQ ID NO: 70) of human p53; the sequence SALIKKKKMAP (SEQ ID NO: 71) of mouse c-abl IV; the sequences DRLRR (SEQ ID NO: 72) and PKQKKRK (SEQ ID NO: 73) of the influenza virus NS1; the sequence RKLKKKIKKL (SEQ ID NO: 74) of the Hepatitis virus delta antigen; the sequence REKKKFLKRR (SEQ ID NO: 75) of the mouse Mx1 protein; the sequence KRKGDEVDGVDEVAKKKSKK (SEQ ID NO: 76) of the human poly(ADP-ribose) polymerase; and the sequence RKCLQAGMNLEARKTKK (SEQ ID NO: 77) of the steroid hormone receptors (human) glucocorticoid.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Guide Sequence

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com); ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length, The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNNXGG (SEQ ID NO: 444) where NNNNNNNNNNNNXGG (SEQ ID NO: 445) (N is A, G, T, or C; and X can be anything) has a single occurrence in the genome. A unique target sequence in a genome may include an S. pyogenes Cas9 target site of the form MMMMMMMMNNNNNNNNNNNXGG (SEQ ID NO: 446) where NNNNNNNNNNNXGG (SEQ ID NO: 447) (N is A, G, T, or C; and X can be anything) has a single occurrence in the genome. For the S. thermophilus CRISPR1 Cas9, a unique target sequence in a genome may include a Cas9 target site of the form MMMMMMMMNNNNNNNNNNNNXXAGAAW (SEQ ID NO: 78) where NNNNNNNNNNXXAGAAW (SEQ ID NO: 79) (N is A, G, T, or C; X can be anything; and W is A or T) has a single occurrence in the genome. A unique target sequence in a genome may include an S. thermophilus CRISPR1 Cas9 target site of the form MMMMMMMMNNNNNNNNNNNXXAGAAW (SEQ ID NO: 80) where NNNNNNNNNNNXXAGAAW (SEQ ID NO: 81) (N is A, G, T, or C; X can be anything; and W is A or T) has a single occurrence in the genome. For the S. pyogenes Cas9, a unique target sequence in a genome may include a Cas9 target site of the form MMMMMMMMNNNNNNNNNNNNXGGXG (SEQ ID NO: 448) where NNNNNNNNNNNNXGGXG (SEQ ID NO: 449) (N is A, G, T, or C; and X can be anything) has a single occurrence in the genome. A unique target sequence in a genome may include an S. pyogenes Cas9 target site of the form MMMMMMMMNNNNNNNNNNNXGGXG (SEQ ID NO: 450) where NNNNNNNNNNNXGGXG (SEQ ID NO: 451) (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and P A Carr and G M Church, 2009, Nature Biotechnology 27(12): 1151-62).

Tracr Mate Sequence

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactctcaagatttaGAAAtaaatcttgcagaagctacaaagataa ggcttcatgccgaaatcaacaccctgtcattttatggcagggtgttttcgttatttaaTTTTTT (SEQ ID NO: 82); (2) NNNNNNNNNNNNNNNNNNNNgttttgtactctcaGAAAtgcagaagctacaaagataaggcttcatgccg aaatcaacaccctgtcattttatggcagggtgttttcgttatttaaTTTTT (SEQ ID NO: 83); (3) NNNNNNNNNNNNNNNNNNNNgttttgtactctcaGAAAtgcagaagctacaaagataaggcttcatgccg aaatcaacaccctgtcattttatggcagggtgtTTTTTT (SEQ ID NO: 84); (4) NNNNNNNNNNNNNNNNNNNNgtttagagctaGAAAtagcaagttaaaataaggctagtccgttatcaactt gaaaaagtggcaccgagtcggtgcTTTTTT (SEQ ID NO: 85); (5) NNNNNNNNNNNNNNNNNNNNgtttagagctaGAAATAGcaagttaaaataaggctagtccgttatcaac ttgaaaaagtgTTTTTTT (SEQ ID NO: 86); and (6) NNNNNNNNNNNNNNNNNNNNgtttagagctagAAATAGcaagttaaaataaggctagtccgttatcaTT TTTTT (SEQ ID NO: 87). In some embodiments, sequences (1) to (3) are used in combination with Cas9 from S. thermophilus CRISPR1. In some embodiments, sequences (4) to (6) are used in combination with Cas9 from S. pyogenes. In some embodiments, the tracr sequence is a separate transcript from a transcript comprising the tracr mate sequence.

Recombination Template

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

Fusion Protein

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

Inducible System

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

Delivery

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and animals comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700).

In another embodiment, Cocal vesiculovirus envelope pseudotyped retroviral vector particles are contemplated (see, e.g., US Patent Publication No. 20120164118 assigned to the Fred Hutchinson Cancer Research Center). Cocal virus is in the Vesiculovirus genus, and is a causative agent of vesicular stomatitis in mammals. Cocal virus was originally isolated from mites in Trinidad (Jonkers et al., Am. J. Vet. Res. 25:236-242 (1964)), and infections have been identified in Trinidad, Brazil, and Argentina from insects, cattle, and horses. Many of the vesiculoviruses that infect mammals have been isolated from naturally infected arthropods, suggesting that they are vector-borne. Antibodies to vesiculoviruses are common among people living in rural areas where the viruses are endemic and laboratory-acquired; infections in humans usually result in influenza-like symptoms. The Cocal virus envelope glycoprotein shares 71.5% identity at the amino acid level with VSV-G Indiana, and phylogenetic comparison of the envelope gene of vesiculoviruses shows that Cocal virus is serologically distinct from, but most closely related to, VSV-G Indiana strains among the vesiculoviruses. Jonkers et al., Am. J. Vet. Res. 25:236-242 (1964) and Travassos da Rosa et al., Am. J. Tropical Med. & Hygiene 33:999-1006 (1984). The Cocal vesiculovirus envelope pseudotyped retroviral vector particles may include for example, lentiviral, alpharetroviral, betaretroviral, gammaretroviral, deltaretroviral, and epsilonretroviral vector particles that may comprise retroviral Gag, Pol, and/or one or more accessory protein(s) and a Cocal vesiculovirus envelope protein. Within certain aspects of these embodiments, the Gag, Pol, and accessory proteins are lentiviral and/or gammaretroviral.

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system.

Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and v2 cells or PA317 cells, which package retrovirus. Viral vectors used in gene therapy are usually generated by producer a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV Vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

Accordingly, AAV is considered an ideal candidate for use as a transducing vector. Such AAV transducing vectors can comprise sufficient cis-acting functions to replicate in the presence of adenovirus or herpesvirus or poxvirus (e.g., vaccinia virus) helper functions provided in trans. Recombinant AAV (rAAV) can be used to carry exogenous genes into cells of a variety of lineages. In these vectors, the AAV cap and/or rep genes are deleted from the viral genome and replaced with a DNA segment of choice. Current AAV vectors may accommodate up to 4300 bases of inserted DNA.

There are a number of ways to produce rAAV, and the invention provides rAAV and methods for preparing rAAV. For example, plasmid(s) containing or consisting essentially of the desired viral construct are transfected into AAV-infected cells. In addition, a second or additional helper plasmid is cotransfected into these cells to provide the AAV rep and/or cap genes which are obligatory for replication and packaging of the recombinant viral construct. Under these conditions, the rep and/or cap proteins of AAV act in trans to stimulate replication and packaging of the rAAV construct. Two to Three days after transfection, rAAV is harvested. Traditionally rAAV is harvested from the cells along with adenovirus. The contaminating adenovirus is then inactivated by heat treatment. In the instant invention, rAAV is advantageously harvested not from the cells themselves, but from cell supernatant. Accordingly, in an initial aspect the invention provides for preparing rAAV, and in addition to the foregoing, rAAV can be prepared by a method that comprises or consists essentially of: infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus(s) provides the cap and/or rev function that the rAAV lacks); or infecting susceptible cells with a rAAV containing exogenous DNA including DNA for expression, wherein the recombinant lacks functioning cap and/or rep, and transfecting said cells with a plasmid supplying cap and/or rep function that the rAAV lacks; or infecting susceptible cells with a rAAV containing exogenous DNA including DNA for expression, wherein the recombinant lacks functioning cap and/or rep, wherein said cells supply cap and/or rep function that the recombinant lacks; or transfecting the susceptible cells with an AAV lacking functioning cap and/or rep and plasmids for inserting exogenous DNA into the recombinant so that the exogenous DNA is expressed by the recombinant and for supplying rep and/or cap functions whereby transfection results in an rAAV containing the exogenous DNA including DNA for expression that lacks functioning cap and/or rep.

The rAAV can be from an AAV as herein described, and advantageously can be an rAAV1, rAAV2, AAV5 or rAAV having hybrid or capsid which may comprise AAV1, AAV2, AAV5 or any combination thereof. One can select the AAV of the rAAV with regard to the cells to be targeted by the rAAV; e.g., one can select AAV serotypes 1, 2, 5 or a hybrid or capsid AAV1, AAV2, AAV5 or any combination thereof for targeting brain or neuronal cells; and one can select AAV4 for targeting cardiac tissue.

In addition to 293 cells, other cells that can be used in the practice of the invention and the relative infectivity of certain AAV serotypes in vitro as to these cells (see Grimm, D. et al, J. Virol. 82: 5887-5911 (2008) are as follows:

case proteins), e.g., Cas9 and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator . . . Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn).

Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKn, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat,

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

The invention provides rAAV that contains or consists essentially of an exogenous nucleic acid molecule encoding a CRISPR (Clustered Regularly Interspaced Short Palindromic Repeats) system, e.g., a plurality of cassettes comprising or consisting a first cassette comprising or consisting essentially of a promoter, a nucleic acid molecule encoding a CRISPR-associated (Cas) protein (putative nuclease or heli- J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, 1169, 11B54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. Methods for producing transgenic animals and plants are known in the art, and generally begin with a method of cell transfection, such as described herein.

In another embodiment, a fluid delivery device with an array of needles (see, e.g., US Patent Publication No. 20110230839 assigned to the Fred Hutchinson Cancer Research Center) may be contemplated for delivery of CRISPR Cas to solid tissue. A device of US Patent Publication No. 20110230839 for delivery of a fluid to a solid tissue may comprise a plurality of needles arranged in an array; a plurality of reservoirs, each in fluid communication with a respective one of the plurality of needles; and a plurality of actuators operatively coupled to respective ones of the plurality of reservoirs and configured to control a fluid pressure within the reservoir. In certain embodiments each of the plurality of actuators may comprise one of a plurality of plungers, a first end of each of the plurality of plungers being received in a respective one of the plurality of reservoirs, and in certain further embodiments the plungers of the plurality of plungers are operatively coupled together at respective second ends so as to be simultaneously depressable. Certain still further embodiments may comprise a plunger driver configured to depress all of the plurality of plungers at a selectively variable rate. In other embodiments each of the plurality of actuators may comprise one of a plurality of fluid transmission lines having first and second ends, a first end of each of the plurality of fluid transmission lines being coupled to a respective one of the plurality of reservoirs. In other embodiments the device may comprise a fluid pressure source, and each of the plurality of actuators comprises a fluid coupling between the fluid pressure source and a respective one of the plurality of reservoirs. In further embodiments the fluid pressure source may comprise at least one of a compressor, a vacuum accumulator, a peristaltic pump, a master cylinder, a microfluidic pump, and a valve. In another embodiment, each of the plurality of needles may comprise a plurality of ports distributed along its length.

Modifying a Target

In one aspect, the invention provides for methods of modifying a target polynucleotide in a eukaryotic cell, which may be in vivo, ex vivo or in vitro. In some embodiments, the method comprises sampling a cell or population of cells from a human or non-human animal, or a plant, and modifying the cell or cells. Culturing may occur at any stage ex vivo. The cell or cells may even be re-introduced into the non-human animal or plant. For re-introduced cells it is particularly preferred that the cells are stem cells.

In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence. Similar considerations and conditions apply as above for methods of modifying a target polynucleotide.

Kits

In one aspect, the invention provides kits containing any one or more of the elements disclosed in the above methods and compositions. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allows to provide all elements of the systems of the invention.

CRISPR Complex

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell.

Figure 29:
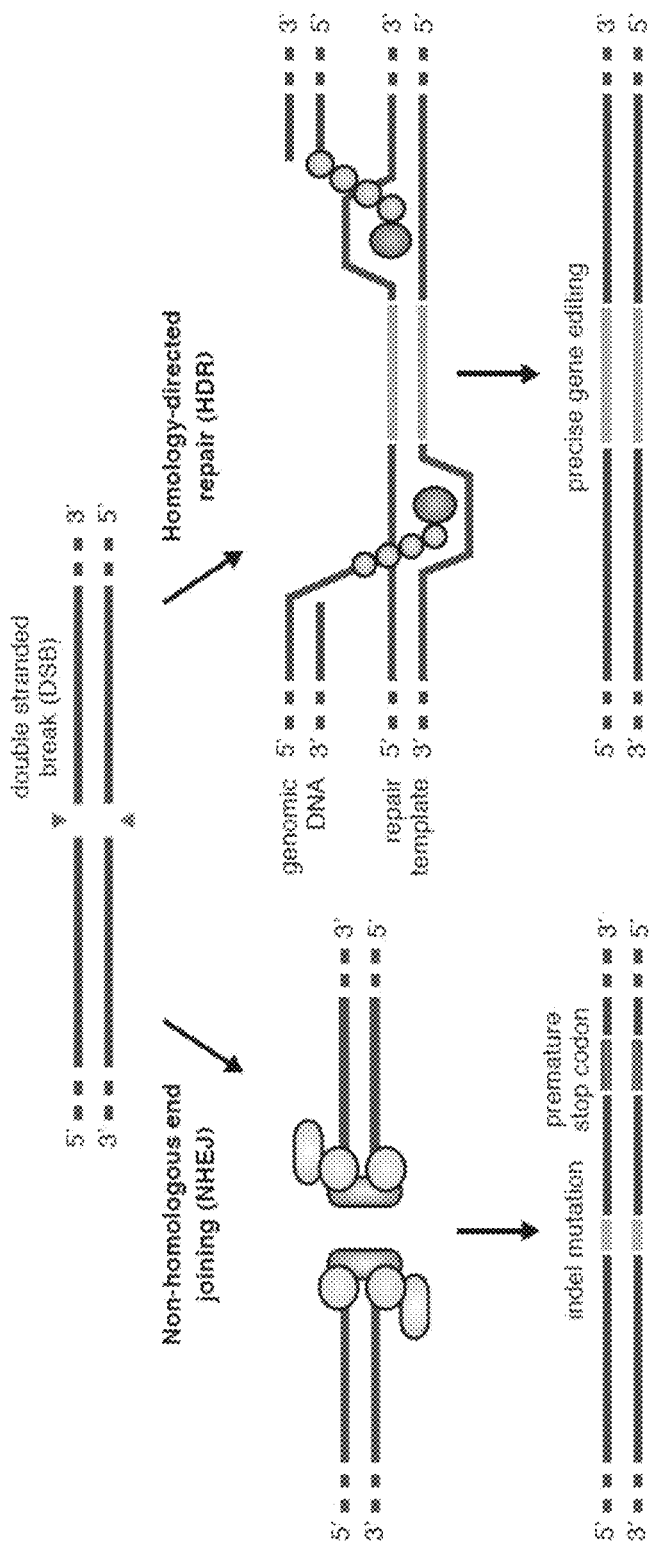
FIG. 29 shows how DNA double-strand break (DSB) repair promotes gene editing. In the error-prone non-homologous end joining (NHEJ) pathway, the ends of a DSB are processed by endogenous DNA repair machineries and rejoined together, which can result in random insertion/deletion (indel) mutations at the site of junction. Indel mutations occurring within the coding region of a gene can result in frame-shift and a premature stop codon, leading to gene knockout. Alternatively, a repair template in the form of a plasmid or single-stranded oligodeoxynucleotides (ssODN) can be supplied to leverage the homology-directed repair (HDR) pathway, which allows high fidelity and precise editing.

The break created by the CRISPR complex can be repaired by a repair processes such as the error prone non-homologous end joining (NHEJ) pathway or the high fidelity homology-directed repair (HDR) (FIG. 29). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome.

Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996).

In an exemplary method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template.

In other embodiments, this invention provides a method of modifying expression of a polynucleotide in a eukaryotic cell. The method comprises increasing or decreasing expression of a target polynucleotide by using a CRISPR complex that binds to the polynucleotide.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences.

The inactivated target sequence may include a deletion mutation (i.e., deletion of one or more nucleotides), an insertion mutation (i.e., insertion of one or more nucleotides), or a nonsense mutation (i.e., substitution of a single nucleotide for another nucleotide such that a stop codon is introduced): In some methods, the inactivation of a target sequence results in "knock-out" of the target sequence.

Disease Models

A method of the invention may be used to create a plant, an animal or cell that may be used as a disease model. As used herein, "disease" refers to a disease, disorder, or indication in a subject. For example, a method of the invention may be used to create an animal or cell that comprises a modification in one or more nucleic acid sequences associated with a disease, or a plant, animal or cell in which the expression of one or more nucleic acid sequences associated with a disease are altered. Such a nucleic acid sequence may encode a disease associated protein sequence or may be a disease associated control sequence. Accordingly, it is understood that in embodiments of the invention, a plant, subject, patient, organism or cell can be a non-human subject, patient, organism or cell. Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants. In the instance where the cell is in cultured, a cell line may be established if appropriate culturing conditions are met and preferably if the cell is suitably adapted for this purpose (for instance a stem cell). Bacterial cell lines produced by the invention are also envisaged. Hence, cell lines are also envisaged.

In some methods, the disease model can be used to study the effects of mutations on the animal or cell and development and/or progression of the disease using measures commonly used in the study of the disease. Alternatively, such a disease model is useful for studying the effect of a pharmaceutically active compound on the disease.

In some methods, the disease model can be used to assess the efficacy of a potential gene therapy strategy. That is, a disease-associated gene or polynucleotide can be modified such that the disease development and/or progression is inhibited or reduced. In particular, the method comprises modifying a disease-associated gene or polynucleotide such that an altered protein is produced and, as a result, the animal or cell has an altered response. Accordingly, in some methods, a genetically modified animal may be compared with an animal predisposed to development of the disease such that the effect of the gene therapy event may be assessed.

In another embodiment, this invention provides a method of developing a biologically active agent that modulates a cell signaling event associated with a disease gene. The method comprises contacting a test compound with a cell comprising one or more vectors that drive expression of one or more of a CRISPR enzyme, a guide sequence linked to a tracr mate sequence, and a tracr sequence; and detecting a change in a readout that is indicative of a reduction or an augmentation of a cell signaling event associated with, e.g., a mutation in a disease gene contained in the cell.

A cell model or animal model can be constructed in combination with the method of the invention for screening a cellular function change. Such a model may be used to study the effects of a genome sequence modified by the CRISPR complex of the invention on a cellular function of interest. For example, a cellular function model may be used to study the effect of a modified genome sequence on intracellular signaling or extracellular signaling. Alternatively, a cellular function model may be used to study the effects of a modified genome sequence on sensory perception. In some such models, one or more genome sequences associated with a signaling biochemical pathway in the model are modified.

Several disease models have been specifically investigated. These include de novo autism risk genes CHD8, KATNAL2, and SCN2A; and the syndromic autism (Angelman Syndrome) gene UBE3A. These genes and resulting autism models are of course preferred, but serve to show the broad applicability of the invention across genes and corresponding models.

An altered expression of one or more genome sequences associated with a signaling biochemical pathway can be determined by assaying for a difference in the mRNA levels of the corresponding genes between the test model cell and a control cell, when they are contacted with a candidate agent. Alternatively, the differential expression of the sequences associated with a signaling biochemical pathway is determined by detecting a difference in the level of the encoded polypeptide or gene product.

To assay for an agent-induced alteration in the level of mRNA transcripts or corresponding polynucleotides, nucleic acid contained in a sample is first extracted according to standard methods in the art. For instance, mRNA can be isolated using various lytic enzymes or chemical solutions according to the procedures set forth in Sambrook et al. (1989), or extracted by nucleic-acid-binding resins following the accompanying instructions provided by the manufacturers. The mRNA contained in the extracted nucleic acid sample is then detected by amplification procedures or conventional hybridization assays (e.g. Northern blot analysis) according to methods widely known in the art or based on the methods exemplified herein.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015:

In yet another aspect, conventional hybridization assays using hybridization probes that share sequence homology with sequences associated with a signaling biochemical pathway can be performed. Typically, probes are allowed to form stable complexes with the sequences associated with a signaling biochemical pathway contained within the biological sample derived from the test subject in a hybridization reaction. It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

An agent-induced change in expression of sequences associated with a signaling biochemical pathway can also be determined by examining the corresponding gene products. Determining the protein level typically involves a) contacting the protein contained in a biological sample with an agent that specifically bind to a protein associated with a signaling biochemical pathway; and (b) identifying any agent:protein complex so formed. In one aspect of this embodiment, the agent that specifically binds a protein associated with a signaling biochemical pathway is an antibody, preferably a monoclonal antibody.

The reaction is performed by contacting the agent with a sample of the proteins associated with a signaling biochemical pathway derived from the test samples under conditions that will allow a complex to form between the agent and the proteins associated with a signaling biochemical pathway. The formation of the complex can be detected directly or indirectly according to standard procedures in the art. In the direct detection method, the agents are supplied with a detectable label and unreacted agents may be removed from the complex; the amount of remaining label thereby indicating the amount of complex formed. For such method, it is preferable to select labels that remain attached to the agents even during stringent washing conditions. It is preferable that the label does not interfere with the binding reaction. In the alternative, an indirect detection procedure may use an agent that contains a label introduced either chemically or enzymatically. A desirable label generally does not interfere with binding or the stability of the resulting agent:polypeptide complex. However, the label is typically designed to be accessible to an antibody for an effective binding and hence generating a detectable signal.

A wide variety of labels suitable for detecting protein levels are known in the art. Non-limiting examples include radioisotopes, enzymes, colloidal metals, fluorescent compounds, bioluminescent compounds, and chemiluminescent compounds.

The amount of agent:polypeptide complexes formed during the binding reaction can be quantified by standard quantitative assays. As illustrated above, the formation of agent:polypeptide complex can be measured directly by the amount of label remained at the site of binding. In an alternative, the protein associated with a signaling biochemical pathway is tested for its ability to compete with a labeled analog for binding sites on the specific agent. In this competitive assay, the amount of label captured is inversely proportional to the amount of protein sequences associated with a signaling biochemical pathway present in a test sample.

A number of techniques for protein analysis based on the general principles outlined above are available in the art. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

Antibodies that specifically recognize or bind to proteins associated with a signaling biochemical pathway are preferable for conducting the aforementioned protein analyses. Where desired, antibodies that recognize a specific type of post-translational modifications (e.g., signaling biochemical pathway inducible modifications) can be used. Post-translational modifications include but are not limited to glycosylation, lipidation, acetylation, and phosphorylation. These antibodies may be purchased from commercial vendors. For example, anti-phosphotyrosine antibodies that specifically recognize tyrosine-phosphorylated proteins are available from a number of vendors including Invitrogen and Perkin Elmer. Anti-phosphotyrosine antibodies are particularly useful in detecting proteins that are differentially phosphorylated on their tyrosine residues in response to an ER stress. Such proteins include but are not limited to eukaryotic translation initiation factor 2 alpha (eIF-2a). Alternatively, these antibodies can be generated using conventional polyclonal or monoclonal antibody technologies by immunizing a host animal or an antibody-producing cell with a target protein that exhibits the desired post-translational modification.

In practicing the subject method, it may be desirable to discern the expression pattern of an protein associated with a signaling biochemical pathway in different bodily tissue, in different cell types, and/or in different subcellular structures. These studies can be performed with the use of tissue-specific, cell-specific or subcellular structure specific antibodies capable of binding to protein markers that are preferentially expressed in certain tissues, cell types, or subcellular structures.

An altered expression of a gene associated with a signaling biochemical pathway can also be determined by examining a change in activity of the gene product relative to a control cell. The assay for an agent-induced change in the activity of a protein associated with a signaling biochemical pathway will dependent on the biological activity and/or the signal transduction pathway that is under investigation. For example, where the protein is a kinase, a change in its ability to phosphorylate the downstream substrate(s) can be determined by a variety of assays known in the art. Representative assays include but are not limited to immunoblotting and immunoprecipitation with antibodies such as anti-phosphotyrosine antibodies that recognize phosphorylated proteins. In addition, kinase activity can be detected by high throughput chemiluminescent assays such as AlphaScreen™ (available from Perkin Elmer) and eTag™ assay (Chan-Hui, et al. (2003) Clinical Immunology 111: 162-174).

Where the protein associated with a signaling biochemical pathway is part of a signaling cascade leading to a fluctuation of intracellular pH condition, pH sensitive molecules such as fluorescent pH dyes can be used as the reporter molecules. In another example where the protein associated With a signaling biochemical pathway is an ion channel, fluctuations in membrane potential and/or intracellular ion concentration can be monitored. A number of commercial kits and high-throughput devices are particularly suited for a rapid and robust screening for modulators of ion channels. Representative instruments include FLIPR™ (Molecular Devices, Inc.) and VIPR (Aurora Biosciences). These instruments are capable of detecting reactions in over 1000 sample wells of a microplate simultaneously, and providing real-time measurement and functional data within a second or even a minisecond.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme.

The target polynucleotide of a CRISPR complex may include a number of disease-associated genes and polynucleotides as well as signaling biochemical pathway-associated genes and polynucleotides as listed in U.S. provisional patent applications 61/736,527 and 61/748,427 having Broad reference BI-2011/008/WSGR Docket No. 44063-701.101 and BI-2011/008/WSGR Docket No. 44063-701.102 respectively, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from U.S. Provisional application 61/736,527 filed Dec. 12, 2012. Such genes, proteins and pathways may be the target polynucleotide of a CRISPR complex.

TABLE A

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Nctsn); PEN-2 |
| Others | Nos1; Parp1; Nat1; Nat2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, |

TABLE B-continued

| | |
|---|---|
| | LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), Il-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2 Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's |

TABLE B-continued

| | |
|---|---|
| | Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE C

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; |

TABLE C-continued

| CELLULAR FUNCTION | GENES |
|---|---|
| | DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |

TABLE C-continued

| CELLULAR FUNCTION | GENES |
| --- | --- |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2: ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2: MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |

TABLE C-continued

| CELLULAR FUNCTION | GENES |
|---|---|
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |

TABLE C-continued

| CELLULAR FUNCTION | GENES |
|---|---|
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKC1; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |

TABLE C-continued

| CELLULAR FUNCTION | GENES |
| --- | --- |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/ Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRKIB |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |

TABLE C-continued

| CELLULAR FUNCTION | GENES |
| --- | --- |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4fl or Brn3a); Numb; Reln |

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011-Medical). Specific aspects of tandem repeat sequences have been found to be responsible for more than twenty human diseases (New insights into repeat instability: role of RNA-DNA hybrids. McIvor E I, Polak U, Napierala M. RNA Biol. 2010 September-October; 7(5):551-8). The CRISPR-Cas system may be harnessed to correct these defects of genomic instability.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology:20; 2009).

The methods of US Patent Publication No. 20110158957 assigned to Sangamo BioSciences, Inc. involved in inactivating T cell receptor (TCR) genes may also be modified to the CRISPR Cas system of the present invention. In another example, the methods of US Patent Publication No. 20100311124 assigned to Sangamo BioSciences, Inc. and US Patent Publication No. 20110225664 assigned to Cellectis, which are both involved in inactivating glutamine synthetase gene expression genes may also be modified to the CRISPR Cas system of the present invention.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

In some embodiments, the condition may be neoplasia. In some embodiments, where the condition is neoplasia, the genes to be targeted are any of those listed in Table A (in this case PTEN and so forth). In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion-related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

For example, US Patent Publication No. 20110023145, describes use of zinc finger nucleases to genetically modify cells, animals and proteins associated with autism spectrum disorders (ASD). Autism spectrum disorders (ASDs) are a group of disorders characterized by qualitative impairment in social interaction and communication, and restricted repetitive and stereotyped patterns of behavior, interests, and activities. The three disorders, autism, Asperger syndrome (AS) and pervasive developmental disorder-not otherwise specified (PDD-NOS) are a continuum of the same disorder with varying degrees of severity, associated intellectual functioning and medical conditions. ASDs are predominantly genetically determined disorders with a heritability of around 90%.

US Patent Publication No. 20110023145 comprises editing of any chromosomal sequences that encode proteins associated with ASD which may be applied to the CRISPR Cas system of the present invention. The proteins associated with ASD are typically selected based on an experimental association of the protein associated with ASD to an incidence or indication of an ASD. For example, the production rate or circulating concentration of a protein associated with ASD may be elevated or depressed in a population having an ASD relative to a population lacking the ASD. Differences in protein levels may be assessed using proteomic techniques including but not limited to Western blot, immunohistochemical staining, enzyme linked immunosorbent assay (ELISA), and mass spectrometry. Alternatively, the proteins associated with ASD may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Non limiting examples of disease states or disorders that may be associated with proteins associated with ASD include autism, Asperger syndrome (AS), pervasive developmental disorder-not otherwise specified (PDD-NOS), Rett's syndrome, tuberous sclerosis, phenylketonuria, Smith-Lemli-Opitz syndrome and fragile X syndrome. By way of non-limiting example, proteins associated with ASD include but are not limited to the following proteins: ATP10C aminophospholipid-MET MET receptor transporting ATPase tyrosine kinase (ATP10C) BZRAP1 MGLUR5 (GRM5) Metabotropic glutamate receptor 5 (MGLUR5) CDH10 Cadherin-10 MGLUR6 (GRM6) Metabotropic glutamate receptor 6 (MGLUR6) CDH9 Cadherin-9 NLGN1 Neuroligin-1 CNTN4 Contactin-4 NLGN2 Neuroligin-2 CNTNAP2 Contactin-associated SEMA5A Neuroligin-3 protein-like 2 (CNTNAP2) DHCR7 7-dehydrocholesterol NLGN4X Neuroligin-4 X-reductase (DHCR7) linked DOC2A Double C2-like domain-NLGN4Y Neuroligin-4 Y-containing protein alpha linked DPP6 Dipeptidyl NLGN5 Neuroligin-5 aminopeptidase-like protein 6 EN2 engrailed 2 (EN2) NRCAM Neuronal cell adhesion molecule (NR-CAM) MDGA2 fragile X mental retardation NRXN1 Neurexin-1 1 (MDGA2) FMR2 (AFF2) AF4/FMR2 family member 2 OR4M2 Olfactory receptor (AFF2) 4M2 FOXP2 Forkhead box protein P2 OR4N4 Olfactory receptor (FOXP2) 4N4 FXR1 Fragile X mental OXTR oxytocin receptor retardation, autosomal (OXTR) homolog 1 (FXR1) FXR2 Fragile X mental PAH phenylalanine retardation, autosomal hydroxylase (PAH) homolog 2 (FXR2) GABRA1 Gamma-aminobutyric acid PTEN Phosphatase and receptor subunit alpha-1 tensin homologue (GABRA1) (PTEN) GABRA5 GABAA (.gamma.-aminobutyric PTPRZ1 Receptor-type acid) receptor alpha 5 tyrosine-protein subunit (GABRA5) phosphatase zeta (PTPRZ1) GABRB1 Gamma-aminobutyric acid RELN Reelin receptor subunit beta-1 (GABRB1) GABRB3 GABAA (.gamma.-aminobutyric RPL10 60S ribosomal acid) receptor .beta.3 subunit protein L10 (GABRB3) GABRG1 Gamma-aminobutyric acid SEMA5A Semaphorin-5A receptor subunit gamma-1 (SEMA5A) (GABRG1) HIRIP3 HIRA-interacting protein 3 SEZ6L2 seizure related 6 homolog (mouse)-like 2 HOXA1 Homeobox protein Hox-A1 SHANK3 SH3 and multiple (HOXA1) ankyrin repeat domains 3 (SHANK3) IL6 Interleukin-6 SHBZRAP1 SH3 and multiple ankyrin repeat domains 3 (SHBZRAP1) LAMB1 Laminin subunit beta-1 SLC6A4 Serotonin (LAMB1) transporter (SERT) MAPK3 Mitogen-activated protein TAS2R1 Taste receptor kinase 3 type 2 member 1 TAS2R1 MAZ Myc-associated zinc finger TSC1 Tuberous sclerosis protein protein 1 MDGA2 MAM domain containing TSC2 Tuberous sclerosis glycosylphosphatidylinositol protein 2 anchor 2 (MDGA2) MECP2 Methyl CpG binding UBE3A Ubiquitin protein protein 2 (MECP2) ligase E3A (UBE3A) MECP2 methyl CpG binding WNT2 Wingless-type protein 2 (MECP2) MMTV integration site family, member 2 (WNT2)

The identity of the protein associated with ASD whose chromosomal sequence is edited can and will vary. In preferred embodiments, the proteins associated with ASD whose chromosomal sequence is edited may be the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, the fragile X mental retardation autosomal homolog 2 protein (FXR2) encoded by the FXR2 gene, the MAM domain containing glycosylphosphatidylinositol anchor 2 protein (MDGA2) encoded by the MDGA2 gene, the methyl CpG binding protein 2 (MECP2) encoded by the MECP2 gene, the metabotropic glutamate receptor 5 (MGLUR5) encoded by the MGLUR5-1 gene (also termed GRM5), the neurexin 1 protein encoded by the NRXN1 gene, or the semaphorin-5A protein (SEMASA) encoded by the SEMASA gene. In an exemplary embodiment, the genetically modified animal is a rat, and the edited chromosomal sequence encoding the protein associated with ASD is as listed below: BZRAP1 benzodiazapine receptor XM_002727789, (peripheral) associated XM_213427, protein 1 (BZRAP1) XM_002724533, XM_001081125 AFF2 (FMR2) AF4/FMR2 family member 2 XM_219832, (AFF2) XM_001054673 FXR1 Fragile X mental NM_001012179 retardation, autosomal homolog 1 (FXR1) FXR2 Fragile X mental NM_001100647 retardation, autosomal homolog 2 (FXR2) MDGA2 MAM domain containing NM_199269 glycosylphosphatidylinositol anchor 2 (MDGA2) MECP2 Methyl CpG binding NM_022673 protein 2 (MECP2) MGLUR5 Metabotropic glutamate NM_017012 (GRM5) receptor 5 (MGLUR5) NRXN1 Neurexin-1 NM_021767 SEMASA Semaphorin-5A (SEMASA) NM_001107659

Exemplary animals or cells may comprise one, two, three, four, five, six, seven, eight, or nine or more inactivated chromosomal sequences encoding a protein associated with ASD, and zero, one, two, three, four, five, six, seven, eight, nine or more chromosomally integrated sequences encoding proteins associated with ASD. The edited or integrated chromosomal sequence may be modified to encode an altered protein associated with ASD. Non-limiting examples of mutations in proteins associated with ASD include the L18Q mutation in neurexin 1 where the leucine at position 18 is replaced with a glutamine, the R451C mutation in neuroligin 3 where the arginine at position 451 is replaced with a cysteine, the R87W mutation in neuroligin 4 where the arginine at position 87 is replaced with a tryptophan, and the I425V mutation in serotonin transporter where the isoleucine at position 425 is replaced with a valine. A number of other mutations and chromosomal rearrangements in ASD-related chromosomal sequences have been associated with ASD and are known in the art. See, for example, Freitag et al. (2010) Eur. Child. Adolesc. Psychiatry 19:169-178, and Bucan et al. (2009) PLoS Genetics 5: e1000536, the disclosure of which is incorporated by reference herein in its entirety.

Examples of proteins associated with Parkinson's disease include but are not limited to α-synuclein, DJ-1, LRRK2, PINK1, Parkin, UCHL1, Synphilin-1, and NURR1.

Examples of addiction-related proteins may include ABAT for example.

Examples of inflammation-related proteins may include the monocyte chemoattractant protein-1 (MCP1) encoded by the Ccr2 gene, the C-C chemokine receptor type 5 (CCR5) encoded by the Ccr5 gene, the IgG receptor IIB (FCGR2b, also termed CD32) encoded by the Fcgr2b gene, or the Fc epsilon R1g (FCER1g) protein encoded by the Fcer1g gene, for example.

Examples of cardiovascular diseases associated proteins may include IL1B (interleukin 1, beta), XDH (xanthine dehydrogenase), TP53 (tumor protein p53), PTGIS (prostaglandin I2 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

For example, US Patent Publication No. 20110023153, describes use of zinc finger nucleases to genetically modify cells, animals and proteins associated with Alzheimer's Disease. Once modified cells and animals may be further tested using known methods to study the effects of the targeted mutations on the development and/or progression of AD using measures commonly used in the study of AD—such as, without limitation, learning and memory, anxiety, depression, addiction, and sensory motor functions as well as assays that measure behavioral, functional, pathological, metabolic and biochemical function.

The present disclosure comprises editing of any chromosomal sequences that encode proteins associated with AD. The AD-related proteins are typically selected based on an experimental association of the AD-related protein to an AD disorder. For example, the production rate or circulating concentration of an AD-related protein may be elevated or depressed in a population having an AD disorder relative to a population lacking the AD disorder. Differences in protein levels may be assessed using proteomic techniques including but not limited to Western blot, immunohistochemical staining, enzyme linked immunosorbent assay (ELISA), and mass spectrometry. Alternatively, the AD-related proteins may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

By way of non-limiting example, proteins associated with AD include but are not limited to the proteins listed as follows: Chromosomal Sequence Encoded Protein ALAS2 Delta-aminolevulinate synthase 2 (ALAS2) ABCA1 ATP-binding cassette transporter (ABCA1) ACE Angiotensin I-converting enzyme (ACE) APOE Apolipoprotein E precursor (APOE) APP amyloid precursor protein (APP) AQP1 aquaporin 1 protein (AQP1) BIN1 Myc box-dependent-interacting protein 1 or bridging integrator 1 protein (BIN1) BDNF brain-derived neurotrophic factor (BDNF) BTNL8 Butyrophilin-like protein 8 (BTNL8) C1ORF49 chromosome 1 open reading frame 49 CDH4 Cadherin-4 CHRNB2 Neuronal acetylcholine receptor subunit beta-2 CKLFSF2 CKLF-like MARVEL transmembrane domain-containing protein 2 (CKLFSF2) CLEC4E C-type lectin domain family 4, member e (CLEC4E) CLU clusterin protein (also known as apolipoprotein J) CR1 Erythrocyte complement receptor 1 (CR1, also known as CD35, C3b/C4b receptor and immune adherence receptor) CR1L Erythrocyte complement receptor 1 (CR1L) CSF3R granulocyte colony-stimulating factor 3 receptor (CSF3R) CST3 Cystatin C or cystatin 3 CYP2C Cytochrome P450 2C DAPK1 Death-associated protein kinase 1 (DAPK1) ESR1 Estrogen receptor 1 FCAR Fc fragment of IgA receptor (FCAR, also known as CD89) FCGR3B Fc fragment of IgG, low affinity IIIb, receptor (FCGR3B or CD16b) FFA2 Free fatty acid receptor 2 (FFA2) FGA Fibrinogen (Factor I) GAB2 GRB2-associated-binding protein 2 (GAB2) GAB2 GRB2-associated-binding protein 2 (GAB2) GALP Galanin-like peptide GAPDHS Glyceraldehyde-3-phosphate dehydrogenase, spermatogenic (GAPDHS) GMPB GMBP HP Haptoglobin (HP) HTR7 5-hydroxytryptamine (serotonin) receptor 7 (adenylate cyclase-coupled) IDE Insulin degrading enzyme IF127 IF127 IFI6 Interferon, alpha-inducible protein 6 (IFI6) IFIT2 Interferon-induced protein with tetratricopeptide repeats 2 (IFIT2) IL1RN interleukin-1 receptor antagonist (IL-1RA) IL8RA Interleukin 8 receptor, alpha (IL8RA or CD181) IL8RB Interleukin 8 receptor, beta (IL8RB) JAG1 Jagged 1 (JAG1) KCNJ15 Potassium inwardly-rectifying channel, subfamily J, member 15 (KCNJ15) LRP6 Low-density lipoprotein receptor-related protein 6 (LRP6) MAPT microtubule-associated protein tau (MAPT) MARK4 MAP/microtubule affinity-regulating kinase 4 (MARK4) MPHOSPH1 M-phase phosphoprotein 1 MTHFR 5,10-methylenetetrahydrofolate reductase MX2 Interferon-induced GTP-binding protein Mx2 NBN Nibrin, also known as NBN NCSTN Nicastrin NIACR2 Niacin receptor 2 (NIACR2, also known as GPR109B) NMNAT3 nicotinamide nucleotide adenylyltransferase 3 NTM Neurotrimin (or HNT) ORM1 Orosmucoid 1 (ORM1) or Alpha-1-acid glycoprotein 1 P2RY13 P2Y purinoceptor 13 (P2RY13) PBEF1 Nicotinamide phosphoribosyltransferase (NAmPRTase or Nampt) also known as pre-B-cell colony-enhancing factor 1 (PBEF1) or visfatin PCK1 Phosphoenolpyruvate carboxykinase PICALM phosphatidylinositol binding clathrin assembly protein (PICALM) PLAU Urokinase-type plasminogen activator (PLAU) PLXNC1 Plexin C1 (PLXNC1) PRNP Prion protein PSEN1 presenilin 1 protein (PSEN1) PSEN2 presenilin 2 protein (PSEN2) PTPRA protein tyrosine phosphatase receptor type A protein (PTPRA) RALGPS2 Ral GEF with PH domain and SH3 binding motif 2 (RALGPS2) RGSL2 regulator of G-protein signaling like 2 (RGSL2) SELENBP1 Selenium binding protein 1 (SELNBP1) SLC25A37 Mitoferrin-1 SORL1 sortilin-related receptor L (DLR class) A repeats-containing protein (SORL1) TF Transferrin TFAM Mitochondrial transcription factor A TNF Tumor necrosis factor TNFRSF10C Tumor necrosis factor receptor superfamily member 10C (TNFRSF10C) TNFSF10 Tumor necrosis factor receptor superfamily, (TRAIL) member 10a (TNFSF10) UBA1 ubiquitin-like modifier activating enzyme 1 (UBA1) UBA3 NEDD8-activating enzyme E1 catalytic subunit protein (UBE1C) UBB ubiquitin B protein (UBB) UBQLN1 Ubiquilin-1 UCHL1 ubiquitin carboxyl-terminal esterase L1 protein (UCHL1) UCHL3 ubiquitin carboxyl-terminal hydrolase isozyme L3 protein (UCHL3) VLDLR very low density lipoprotein receptor protein (VLDLR)

In exemplary embodiments, the proteins associated with AD whose chromosomal sequence is edited may be the very low density lipoprotein receptor protein (VLDLR) encoded by the VLDLR gene, the ubiquitin-like modifier activating enzyme 1 (UBA1) encoded by the UBA1 gene, the NEDD8-activating enzyme E1 catalytic subunit protein (UBE1C) encoded by the UBA3 gene, the aquaporin 1 protein (AQP1) encoded by the AQP1 gene, the ubiquitin carboxyl-terminal esterase L1 protein (UCHL1) encoded by the UCHL1 gene, the ubiquitin carboxyl-terminal hydrolase isozyme L3 protein (UCHL3) encoded by the UCHL3 gene, the ubiquitin B protein (UBB) encoded by the UBB gene, the microtubule-associated protein tau (MAPT) encoded by the MAPT gene, the protein tyrosine phosphatase receptor type A protein (PTPRA) encoded by the PTPRA gene, the phosphatidylinositol binding clathrin assembly protein (PICALM) encoded by the PICALM gene, the clusterin protein (also known as apolipoprotein J) encoded by the CLU gene, the presenilin 1 protein encoded by the PSEN1 gene, the presenilin 2 protein encoded by the PSEN2 gene, the sortilin-related receptor L (DLR class) A repeats-containing protein (SORL1) protein encoded by the SORL1 gene, the amyloid precursor protein (APP) encoded by the APP gene, the Apolipoprotein E precursor (APOE) encoded by the APOE gene, or the brain-derived neurotrophic factor (BDNF) encoded by the BDNF gene. In an exemplary embodiment, the genetically modified animal is a rat, and the edited chromosomal sequence encoding the protein associated with AD is as as follows: APP amyloid precursor protein (APP) NM_019288 AQP1 aquaporin 1 protein (AQP1) NM_012778 BDNF Brain-derived neurotrophic factor NM_012513 CLU clusterin protein (also known as NM_053021 apolipoprotein J) MAPT microtubule-associated protein NM_017212 tau (MAPT) PICALM phosphatidylinositol binding NM_053554 clathrin assembly protein (PICALM) PSEN1 presenilin 1 protein (PSEN1) NM_019163 PSEN2 presenilin 2 protein (PSEN2) NM_031087 PTPRA protein tyrosine phosphatase NM_012763 receptor type A protein (PTPRA) SORL1 sortilin-related receptor L (DLR NM_053519, class) A repeats-containing XM_001065506, protein (SORL1) XM_217115 UBA1 ubiquitin-like modifier activating NM_001014080 enzyme 1 (UBA1) UBA3 NEDD8-activating enzyme E1 NM_057205 catalytic subunit protein (UBE1C) UBB ubiquitin B protein (UBB) NM_138895 UCHL1 ubiquitin carboxyl-terminal NM_017237 esterase L1 protein (UCHL1) UCHL3 ubiquitin carboxyl-terminal NM_001110165 hydrolase isozyme L3 protein (UCHL3) VLDLR very low density lipoprotein NM_013155 receptor protein (VLDLR)

The animal or cell may comprise 1, 2, 3, 4, 5, 6, 7, 8, 9, 10, 11, 12, 13, 14, 15 or more disrupted chromosomal sequences encoding a protein associated with AD and zero, 1, 2, 3, 4, 5, 6, 7, 8, 9, 10, 11, 12, 13, 14, 15 or more chromosomally integrated sequences encoding a protein associated with AD.

The edited or integrated chromosomal sequence may be modified to encode an altered protein associated with AD. A number of mutations in AD-related chromosomal sequences have been associated with AD. For instance, the V717I (i.e. valine at position 717 is changed to isoleucine) missense mutation in APP causes familial AD. Multiple mutations in the presenilin-1 protein, such as H163R (i.e. histidine at position 163 is changed to arginine), A246E (i.e. alanine at position 246 is changed to glutamate), L286V (i.e. leucine at position 286 is changed to valine) and C410Y (i.e. cysteine at position 410 is changed to tyrosine) cause familial Alzheimer's type 3. Mutations in the presenilin-2 protein, such as N141I (i.e. asparagine at position 141 is changed to isoleucine), M239V (i.e. methionine at position 239 is changed to valine), and D439A (i.e. aspartate at position 439 is changed to alanine) cause familial Alzheimer's type 4.

Other associations of genetic variants in AD-associated genes and disease are known in the art. See, for example, Waring et al. (2008) Arch. Neurol. 65:329-334, the disclosure of which is incorporated by reference herein in its entirety.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, for example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C-C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch2, Notch 3, or Notch 4, for example.

Examples of proteins associated with a secretase disorder may include PSENEN (presenilin enhancer 2 homolog (*C. elegans*)), CTSB (cathepsin B), PSEN1 (presenilin 1), APP (amyloid beta (A4) precursor protein), APH1B (anterior pharynx defective 1 homolog B (*C. elegans*)), PSEN2 (presenilin 2 (Alzheimer disease 4)), or BACE1 (beta-site APP-cleaving enzyme 1), for example.

For example, US Patent Publication No. 20110023146, describes use of zinc finger nucleases to genetically modify cells, animals and proteins associated with secretase-associated disorders. Secretases are essential for processing pre-proteins into their biologically active forms. Defects in various components of the secretase pathways contribute to many disorders, particularly those with hallmark amyloidogenesis or amyloid plaques, such as Alzheimer's disease (AD).

A secretase disorder and the proteins associated with these disorders are a diverse set of proteins that effect susceptibility for numerous disorders, the presence of the disorder, the severity of the disorder, or any combination thereof. The present disclosure comprises editing of any chromosomal sequences that encode proteins associated with a secretase disorder. The proteins associated with a secretase disorder are typically selected based on an experimental association of the secretase-related proteins with the development of a secretase disorder. For example, the production rate or circulating concentration of a protein associated with a secretase disorder may be elevated or depressed in a population with a secretase disorder relative to a population without a secretase disorder. Differences in protein levels may be assessed using proteomic techniques including but not limited to Western blot, immunohistochemical staining, enzyme linked immunosorbent assay (ELISA), and mass spectrometry. Alternatively, the protein associated with a secretase disorder may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with a secretase disorder include PSENEN (presenilin enhancer 2 homolog (*C. elegans*)), CTSB (cathepsin B), PSEN1 (presenilin 1), APP (amyloid beta (A4) precursor protein), APH1B (anterior pharynx defective 1 homolog B (*C. elegans*)), PSEN2 (presenilin 2 (Alzheimer disease 4)), BACE1 (beta-site APP-cleaving enzyme 1), ITM2B (integral membrane protein 2B), CTSD (cathepsin D), NOTCH1 (Notch homolog 1, translocation-associated (*Drosophila*)), TNF (tumor necrosis factor (TNF superfamily, member 2)), INS (insulin), DYT10 (dystonia 10), ADAM17 (ADAM metallopeptidase domain 17), APOE (apolipoprotein E), ACE (angiotensin I converting enzyme (peptidyl-dipeptidase A) 1), STN (statin), TP53 (tumor protein p53), IL6 (interleukin 6 (interferon, beta 2)). NGFR (nerve growth factor receptor (TNFR superfamily, member 16)), IL1B (interleukin 1, beta), ACHE (acetylcholinesterase (Yt blood group)), CTNNB1 (catenin (cadherin-associated protein), beta 1, 88 kDa), IGF1 (insulin-like growth factor 1 (somatomedin C)), IFNG (interferon, gamma), NRG1 (neuregulin 1), CASP3 (caspase 3, apoptosis-related cysteine peptidase), MAPK1 (mitogen-activated protein kinase 1), CDH1 (cadherin 1, type 1, E-cadherin (epithelial)), APBB1 (amyloid beta (A4) precursor protein-binding, family B, member 1 (Fe65)), HMGCR (3-hydroxy-3-methylglutaryl-Coenzyme A reductase), CREB1 (cAMP responsive element binding protein 1), PTGS2 (prostaglandin-endoperoxide synthase 2 (prostaglandin G/H synthase and cyclooxygenase)), HES1 (hairy and enhancer of split 1, (*Drosophila*)), CAT (catalase), TGFB1 (transforming growth factor, beta 1), ENO2 (enolase 2 (gamma, neuronal)), ERBB4 (v-erb-a erythroblastic leukemia viral oncogene homolog 4 (avian)), TRAPPC10 (trafficking protein particle complex 10), MAOB (monoamine oxidase B), NGF (nerve growth factor (beta polypeptide)), MMP12 (matrix metallopeptidase 12 (macrophage elastase)), JAG1 (jagged 1 (Alagille syndrome)), CD40LG (CD40 ligand), PPARG (peroxisome proliferator-activated receptor gamma), FGF2 (fibroblast growth factor 2 (basic)), IL3 (interleukin 3 (colony-stimulating factor, multiple)), LRP1 (low density lipoprotein receptor-related protein 1), NOTCH4 (Notch homolog 4 (*Drosophila*)), MAPK8 (mitogen-activated protein kinase 8), PREP (prolyl endopeptidase), NOTCH3 (Notch homolog 3 (*Drosophila*)), PRNP (prion protein), CTSG (cathepsin G), EGF (epidermal growth factor (beta-urogastrone)), REN (renin), CD44 (CD44 molecule (Indian blood group)), SELP (selectin P (granule membrane protein 140 kDa, antigen CD62)), GHR (growth hormone receptor), ADCYAP1 (adenylate cyclase activating polypeptide 1 (pituitary)), INSR (insulin receptor), GFAP (glial fibrillary acidic protein), MMP3 (matrix metallopeptidase 3 (stromelysin 1, progelatinase)), MAPK10 (mitogen-activated protein kinase 10), SP1 (Sp1 transcription factor), MYC (v-myc myelocytomatosis viral oncogene homolog (avian)), CTSE (cathepsin E), PPARA (peroxisome proliferator-activated receptor alpha), JUN (jun oncogene), TIMP1 (TIMP metallopeptidase inhibitor 1), IL5 (interleukin 5 (colony-stimulating factor, eosinophil)), IL1A (interleukin 1, alpha), MMP9 (matrix metallopeptidase 9 (gelatinase B, 92 kDa gelatinase, 92 kDa type IV collagenase)), HTR4 (5-hydroxytryptamine (serotonin) receptor 4), HSPG2 (heparan sulfate proteoglycan 2), KRAS (v-Ki-ras2 Kirsten rat sarcoma viral oncogene homolog), CYCS (cytochrome c, somatic), SMG1 (SMG1 homolog, phosphatidylinositol 3-kinase-related kinase (*C. elegans*)), IL1R1 (interleukin 1 receptor, type I), PROK1 (prokineticin 1), MAPK3 (mitogen-activated protein kinase 3), NTRK1 (neurotrophic tyrosine kinase, receptor, type 1), IL13 (interleukin 13), MME (membrane metallo-endopeptidase), TKT (transketolase), CXCR2 (chemokine (C-X-C motif) receptor 2), IGF1R (insulin-like growth factor 1 receptor), RARA (retinoic acid receptor, alpha), CREBBP (CREB binding protein), PTGS1 (prostaglandin-endoperoxide synthase 1 (prostaglandin G/H synthase and cyclooxygenase)), GALT (galactose-1-phosphate uridylyltransferase), CHRM1 (cholinergic receptor, muscarinic 1), ATXN1 (ataxin 1), PAWR (PRKC, apoptosis, WT1, regulator), NOTCH2 (Notch homolog 2 (*Drosophila*)), M6PR (mannose-6-phosphate receptor (cation dependent)), CYP46A1 (cytochrome P450, family 46, subfamily A, polypeptide 1), CSNK1 D (casein kinase 1, delta), MAPK14 (mitogen-activated protein kinase 14), PRG2 (proteoglycan 2, bone marrow (natural killer cell activator, eosinophil granule major basic protein)), PRKCA (protein kinase C, alpha), L1 CAM (L1 cell adhesion molecule), CD40 (CD40 molecule, TNF receptor superfamily member 5), NR1I2 (nuclear receptor subfamily 1, group I, member 2), JAG2 (jagged 2), CTNND1 (catenin (cadherin-associated protein), delta 1), CDH2 (cadherin 2, type 1, N-cadherin (neuronal)), CMA1 (chymase 1, mast cell), SORT1 (sortilin 1), DLK1 (delta-like 1 homolog (*Drosophila*)), THEM4 (thioesterase superfamily member 4), JUP (junction plakoglobin), CD46 (CD46 molecule, complement regulatory protein), CCL11 (chemokine (C-C motif) ligand 11), CAV3 (caveolin 3), RNASE3 (ribonuclease, RNase A family, 3 (eosinophil cationic protein)), HSPA8 (heat shock 70 kDa protein 8), CASP9 (caspase 9, apoptosis-related cysteine peptidase), CYP3A4 (cytochrome P450, family 3, subfamily A, polypeptide 4), CCR3 (chemokine (C-C motif) receptor 3), TFAP2A (transcription factor AP-2 alpha (activating enhancer binding protein 2 alpha)), SCP2 (sterol carrier protein 2), CDK4 (cyclin-dependent kinase 4), HIF1A (hypoxia inducible factor 1, alpha subunit (basic helix-loop-helix transcription factor)), TCF7L2 (transcription factor 7-like 2 (T-cell specific, HMG-box)), IL1R2 (interleukin 1 receptor, type II), B3GALTL (beta 1,3-galactosyltransferase-like), MDM2 (Mdm2 p53 binding protein homolog (mouse)), RELA (v-rel reticuloendotheliosis viral oncogene homolog A (avian)), CASP7 (caspase 7, apoptosis-related cysteine peptidase), IDE (insulin-degrading enzyme), FABP4 (fatty acid binding protein 4, adipocyte), CASK (calcium/calmodulin-dependent serine protein kinase (MAGUK family)), ADCYAP1R1 (adenylate cyclase activating polypeptide 1 (pituitary) receptor type I), ATF4 (activating transcription factor 4 (tax-responsive enhancer element B67)), PDGFA (platelet-derived growth factor alpha polypeptide), C21 or f33 (chromosome 21 open reading frame 33), SCG5 (secretogranin V (7B2 protein)), RNF123 (ring finger protein 123), NFKB1 (nuclear factor of kappa light polypeptide gene enhancer in B-cells 1), ERBB2 (v-erb-b2 erythroblastic leukemia viral oncogene homolog 2, neuro/glioblastoma derived oncogene homolog (avian)), CAV1 (caveolin 1, caveolae protein, 22 kDa), MMP1 (matrix metallopeptidase 7 (matrilysin, uterine)), TGFA (transforming growth factor, alpha), RXRA (retinoid X receptor, alpha), STX1A (syntaxin 1A (brain)), PSMC4 (proteasome (prosome, macropain) 26S subunit, ATPase, 4), P2RY2 (purinergic receptor P2Y, G-protein coupled, 2), TNFRSF21 (tumor necrosis factor receptor superfamily, member 21), DLG1 (discs, large homolog 1 (*Drosophila*)), NUMBL (numb homolog (*Drosophila*)-like), SPN (sialophorin), PLSCR1 (phospholipid scramblase 1), UBQLN2 (ubiquilin 2), UBQLN1 (ubiquilin 1), PCSK7 (proprotein convertase subtilisin/kexin type 7), SPON1 (spondin 1, extracellular matrix protein), SILV (silver homolog (mouse)), QPCT (glutaminyl-peptide cyclotransferase), HESS (hairy and enhancer of split 5 (*Drosophila*)), GCC1 (GRIP and coiled-coil domain containing 1), and any combination thereof.

The genetically modified animal or cell may comprise 1, 2, 3, 4, 5, 6, 7, 8, 9, 10 or more disrupted chromosomal sequences encoding a protein associated with a secretase disorder and zero, 1, 2, 3, 4, 5, 6, 7, 8, 9, 10 or more chromosomally integrated sequences encoding a disrupted protein associated with a secretase disorder.

Examples' of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

For example, US Patent Publication No. 20110023144, describes use of zinc finger nucleases to genetically modify cells, animals and proteins associated with amyotrophyic lateral sclerosis (ALS) disease. ALS is characterized by the gradual steady degeneration of certain nerve cells in the brain cortex, brain stem, and spinal cord involved in voluntary movement.

Motor neuron disorders and the proteins associated with these disorders are a diverse set of proteins that effect susceptibility for developing a motor neuron disorder, the presence of the motor neuron disorder, the severity of the motor neuron disorder or any combination thereof. The present disclosure comprises editing of any chromosomal sequences that encode proteins associated with ALS disease, a specific motor neuron disorder. The proteins associated with ALS are typically selected based on an experimental association of ALS-related proteins to ALS. For example, the production rate or circulating concentration of a protein associated with ALS may be elevated or depressed in a population with ALS relative to a population without ALS. Differences in protein levels may be assessed using proteomic techniques including but not limited to Western blot, immunohistochemical staining, enzyme linked immunosorbent assay (ELISA), and mass spectrometry. Alternatively, the proteins associated with ALS may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with ALS include but are not limited to the following proteins: SOD1 superoxide dismutase 1, ALS3 amyotrophic lateral soluble sclerosis 3 SETX senataxin ALS5 amyotrophic lateral sclerosis 5 FUS fused in sarcoma ALS7 amyotrophic lateral sclerosis 7 ALS2 amyotrophic lateral DPP6 Dipeptidyl-peptidase 6 sclerosis 2 NEFH neurofilament, heavy PTGS1 prostaglandin-polypeptide endoperoxide synthase 1 SLC1A2 solute carrier family 1 TNFRSF10B tumor necrosis factor (glial high affinity receptor superfamily, glutamate transporter), member 10b member 2 PRPH peripherin HSP90AA1 heat shock protein 90 kDa alpha (cytosolic), class A member 1 GRIA2 glutamate receptor, IFNG interferon, gamma ionotropic, AMPA 2 S 1 00B S100 calcium binding FGF2 fibroblast growth factor 2 protein B AOX1 aldehyde oxidase 1 CS citrate synthase TARDBP TAR DNA binding protein TXN thioredoxin RAPH1 Ras association MAP3K5 mitogen-activated protein (RaIGDS/AF-6) and kinase 5 pleckstrin homology domains 1 NBEAL1 neurobeachin-like 1 GPX1 glutathione peroxidase 1 ICA1L islet cell autoantigen RAC1 ras-related C3 botulinum 1.69 kDa-like toxin substrate 1 MAPT microtubule-associated ITPR2 inositol 1,4,5-protein tau triphosphate receptor, type 2 ALS2CR4 amyotrophic lateral GLS glutaminase sclerosis 2 (juvenile) chromosome region, candidate 4 ALS2CR8 amyotrophic lateral CNTFR ciliary neurotrophic factor sclerosis 2 (juvenile) receptor chromosome region, candidate 8 ALS2CR11 amyotrophic lateral FOLH1 folate hydrolase 1 sclerosis 2 (juvenile) chromosome region, candidate 11 FAM117B family with sequence P4HB prolyl 4-hydroxylase, similarity 117, member B beta polypeptide CNTF ciliary neurotrophic factor SQSTM1 sequestosome 1 STRADB STE20-related kinase NAIP NLR family, apoptosis adaptor beta inhibitory protein YWHAQ tyrosine 3-SLC33A1 solute carrier family 33 monooxygenase/tryptoph (acetyl-CoA transporter), an 5-monooxygenase member 1 activation protein, theta polypeptide TRAK2 trafficking protein, FIG. 4 FIG. 4 homolog, SAC1 kinesin binding 2 lipid phosphatase domain containing NIF3L1 NIF3 NGG1 interacting INA internexin neuronal factor 3-like 1 intermediate filament protein, alpha PARD3B par-3 partitioning COX8A cytochrome c oxidase defective 3 homolog B subunit VIIIA CDK15 cyclin-dependent kinase HECW1 HECT, C2 and WW 15 domain containing E3 ubiquitin protein ligase 1 NOS 1 nitric oxide synthase 1 MET met proto-oncogene SOD2 superoxide dismutase 2, HSPB1 heat shock 27 kDa mitochondrial protein 1 NEFL neurofilament, light CTSB cathepsin B polypeptide ANG angiogenin, HSPA8 heat shock 70 kDa ribonuclease, RNase A protein 8 family, 5 VAPB VAMP (vesicle ESR1 estrogen receptor 1 associated membrane protein)-associated protein B and C SNCA synuclein, alpha HGF hepatocyte growth factor CAT catalase ACTB actin, beta NEFM neurofilament, medium TH tyrosine hydroxylase polypeptide BCL2 B-cell CLL/lymphoma 2 FAS Fas (TNF receptor superfamily, member 6) CASP3 caspase 3, apoptosis-CLU clusterin related cysteine peptidase SMN1 survival of motor neuron G6PD glucose-6-phosphate 1, telomeric dehydrogenase BAX BCL2-associated X HSF1 heat shock transcription protein factor 1 RNF19A ring finger protein 19A JUN jun oncogene ALS2CR12 amyotrophic lateral HSPA5 heat shock 70 kDa sclerosis 2 (juvenile) protein 5 chromosome region, candidate 12 MAPK14 mitogen-activated protein IL10 interleukin 10 kinase 14 APEX1 APEX nuclease TXNRD1 thioredoxin reductase 1 (multifunctional DNA repair enzyme) 1 NOS2 nitric oxide synthase 2, TIMP1 TIMP metallopeptidase inducible inhibitor 1 CASP9 caspase 9, apoptosis-XIAP X-linked inhibitor of related cysteine apoptosis peptidase GLG1 golgi glycoprotein 1 EPO erythropoietin VEGFA vascular endothelial ELN elastin growth factor A GDNF glial cell derived NFE2L2 nuclear factor (erythroid-neurotrophic factor derived 2)-like 2 SLC6A3 solute carrier family 6 HSPA4 heat shock 70 kDa (neurotransmitter protein 4 transporter, dopamine), member 3 APOE apolipoprotein E PSMB8 proteasome (prosome, macropain) subunit, beta type, 8 DCTN1 dynactin 1 TIMP3 TIMP metallopeptidase inhibitor 3 KIFAP3 kinesin-associated SLC1A1 solute carrier family 1 protein 3 (neuronal/epithelial high affinity glutamate transporter, system Xag), member 1 SMN2 survival of motor neuron CCNC cyclin C 2, centromeric MPP4 membrane protein, STUB 1 STIP1 homology and U-palmitoylated 4 box containing protein 1 ALS2 amyloid beta (A4) PRDX6 peroxiredoxin 6 precursor protein SYP synaptophysin CABIN1 calcineurin binding protein 1 CASP1 caspase 1, apoptosis-GART phosphoribosylglycinami related cysteine de formyltransferase, peptidase phosphoribosylglyciriami de synthetase, phosphoribosylaminoimi dazole synthetase CDK5 cyclin-dependent kinase 5 ATXN3 ataxin 3 RTN4 reticulon 4 C1QB complement component 1, q subcomponent, B chain VEGFC nerve growth factor HTT huntingtin receptor PARK7 Parkinson disease 7 XDH xanthine dehydrogenase GFAP glial fibrillary acidic MAP2 microtubule-associated protein protein 2 CYCS cytochrome c, somatic FCGR3B Fc fragment of IgG, low affinity Mb, CCS copper chaperone for UBL5 ubiquitin-like 5 superoxide dismutase MMP9 matrix metallopeptidase SLC18A3 solute carrier family 18 9 ((vesicular acetylcholine), member 3 TRPM7 transient receptor HSPB2 heat shock 27 kDa potential cation channel, protein 2 subfamily M, member 7 AKT1 v-akt murine thymoma DERL1 Der1-like domain family, viral oncogene homolog 1 member 1 CCL2 chemokine (C-C motif) NGRN neugrin, neurite ligand 2 outgrowth associated GSR glutathione reductase TPPP3 tubulin polymerization-promoting protein family member 3 APAF1 apoptotic peptidase BTBD10 BTB (POZ) domain activating factor 1 containing 10 GLUD1 glutamate CXCR4 chemokine (C-X-C motif) dehydrogenase 1 receptor 4 SLC1A3 solute carrier family 1 FLT1 fms-related tyrosine (glial high affinity glutamate transporter), member 3 kinase 1 PON1 paraoxonase 1 AR androgen receptor LIF leukemia inhibitory factor ERBB3 v-erb-b2 erythroblastic leukemia viral oncogene homolog 3 LGALS1 lectin, galactoside-CD44 CD44 molecule binding, soluble, 1 TP53 tumor protein p53 TLR3 toll-like receptor 3 GRIA1 glutamate receptor, GAPDH glyceraldehyde-3-ionotropic, AMPA 1 phosphate dehydrogenase GRIK1 glutamate receptor, DES desmin ionotropic, kainate 1 CHAT choline acetyltransferase FLT4 fms-related tyrosine kinase 4 CHMP2B chromatin modifying BAG 1 BCL2-associated protein 2B athanogene MT3 metallothionein 3 CHRNA4 cholinergic receptor, nicotinic, alpha 4 GSS glutathione synthetase BAK1 BCL2-antagonist/killer 1 KDR kinase insert domain GSTP1 glutathione S-transferase receptor (a type III pi 1 receptor tyrosine kinase) OGG1 8-oxoguanine DNA IL6 interleukin 6 (interferon, glycosylase beta 2).

The animal or cell may comprise 1, 2, 3, 4, 5, 6, 7, 8, 9, 10 or more disrupted chromosomal sequences encoding a protein associated with ALS and zero, 1, 2, 3, 4, 5, 6, 7, 8, 9, 10 or more chromosomally integrated sequences encoding the disrupted protein associated with ALS. Preferred proteins associated with ALS include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-1D adrenergic receptor for Alpha-1D adrenoreceptor), for example.

Examples of proteins associated with Immunodeficiency may include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor). FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 [ataxin 2-binding protein 1], AADAT [aminoadipate aminotransferase], AANAT [arylalkylamine N-acetyltransferase], ABAT [4-aminobutyrate aminotransferase], ABCA1 [ATP-binding cassette, sub-family A (ABC1), member 1], or ABCA13 [ATP-binding cassette, sub-family A (ABC1), member 13], for example.

Further examples of preferred conditions treatable with the present system include may be selected from: Aicardi-Goutières Syndrome; Alexander Disease; Allan-Herndon-Dudley Syndrome; POLG-Related Disorders; Alpha-Mannosidosis (Type II and III); Alström Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy; Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LIS1-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile), MAPT-Related Disorders; MECP2-Related Disorders; Rhizomelic Chondrodysplasia Punctata Type 1; Roberts Syndrome; Sandhoff Disease; Schindler Disease—Type 1; Adenosine Deaminase Deficiency; Smith-Lemli-Opitz Syndrome; Spinal Muscular Atrophy; Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

As will be apparent, it is envisaged that the present system can be used to target any polynucleotide sequence of interest. Some examples of conditions or diseases that might be usefully treated using the present system are included in the Tables above and examples of genes currently associated with those conditions are also provided there. However, the genes exemplified are not exhaustive.

For example, "wild type StCas9" refers to wild type Cas9 from S thermophilus, the protein sequence of which is given in the SwissProt database under accession number G3ECR1. Similarly, S pyogenes Cas9 is included in SwissProt under accession number Q99ZW2.

The ability to use CRISPR-Cas systems to perform efficient and cost effective gene editing and manipulation will allow the rapid selection and comparison of single and and multiplexed genetic manipulations to transform such genomes for improved production and enhanced traits. In this regard reference is made to US patents and publications: U.S. Pat. No. 6,603,061—Agrobacterium-Mediated Plant Transformation Method; U.S. Pat. No. 7,868,149-Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics:advances and applications" Nat Rev Genet. 2011 Dec. 29; 13(2):85-96 are also herein incorporated by reference in their entirety.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: CRISPR Complex Activity in the Nucleus of a Eukaryotic Cell

An example type II CRISPR system is the type II CRISPR locus from Streptococcus pyogenes SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps (FIG. 2A). First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer (FIG. 2A). This example describes an example process for adapting this RNA-programmable nuclease system to direct CRISPR complex activity in the nuclei of eukaryotic cells.

Cell Culture and Transfection

Human embryonic kidney (HEK) cell line HEK 293FT (Life Technologies) was maintained in Dulbecco's modified Eagle's Medium (DMEM) supplemented with 10% fetal bovine serum (HyClone), 2 mM GlutaMAX (Life Technologies), 100 U/mL penicillin, and 100 µg/mL streptomycin at 37° C. with 5% CO2 incubation. Mouse neuro2A (N2A) cell line (ATCC) was maintained with DMEM supplemented with 5% fetal bovine serum (HyClone), 2 mM GlutaMAX (Life Technologies), 100 U/mL penicillin, and 100 µg/mL streptomycin at 37° C. with 5% $CO_2$.

HEK 293FT or N2A cells were seeded into 24-well plates (Corning) one day prior to transfection at a density of 200,000 cells per well. Cells were transfected using Lipofectamine 2000 (Life Technologies) following the manufacturer's recommended protocol. For each well of a 24-well plate a total of 800 ng of plasmids were used.

Surveyor Assay and Sequencing Analysis for Genome Modification

HEK 293FT or N2A cells were transfected with plasmid DNA as described above. After transfection, the cells were incubated at 37° C. for 72 hours before genomic DNA extraction. Genomic DNA was extracted using the QuickExtract DNA extraction kit (Epicentre) following the manufacturer's protocol. Briefly, cells were resuspended in QuickExtract solution and incubated at 65° C. for 15 minutes and 98° C. for 10 minutes. Extracted genomic DNA was immediately processed or stored at −20° C.

Figure 7:
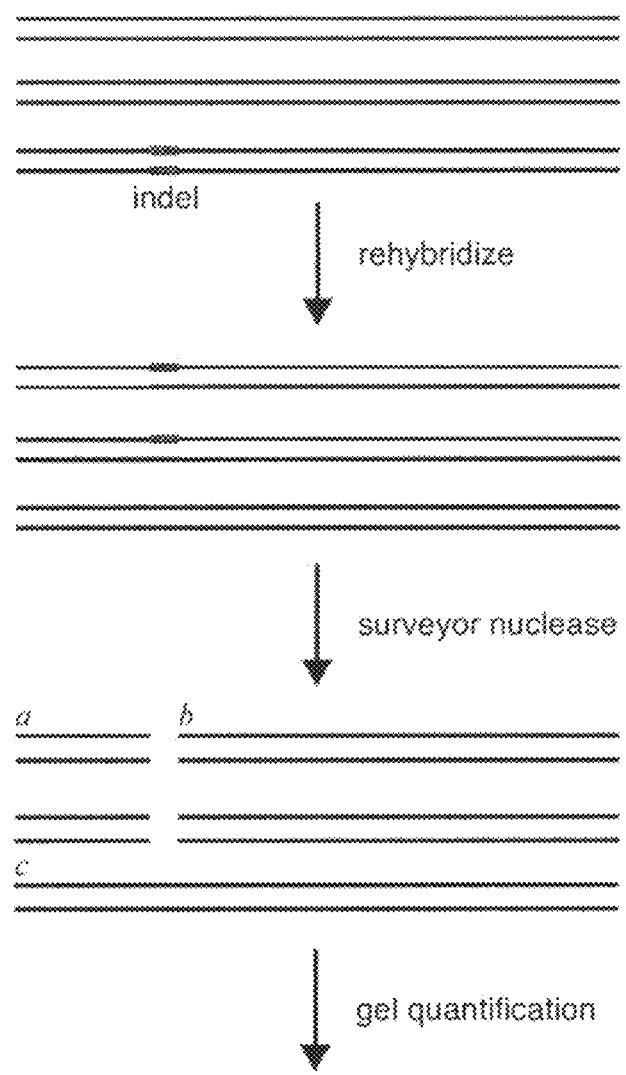
FIG. 7 shows a schematic of a surveyor nuclease assay for detection of double strand break-induced micro-insertions and -deletions.

The genomic region surrounding a CRISPR target site for each gene was PCR amplified, and products were purified using QiaQuick Spin Column (Qiagen) following manufacturer's protocol. A total of 400 ng of the purified PCR products were mixed with 2 µl 10× Taq polymerase PCR buffer (Enzymatics) and ultrapure water to a final volume of 20 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products were treated with Surveyor nuclease and Surveyor enhancer S (Transgenomics) following the manufacturer's recommended protocol, and analyzed on 4-20% Novex TBE poly-acrylamide gels (Life Technologies). Gels were stained with SYBR Gold DNA stain (Life Technologies) for 30 minutes and imaged with a Gel Doc gel imaging system (Bio-rad). Quantification was based on relative band intensities, as a measure of the fraction of cleaved DNA. FIG. 7 provides a schematic illustration of this Surveyor assay.

Restriction fragment length polymorphism assay for detection of homologous recombination.

HEK 293FT and N2A cells were transfected with plasmid DNA, and incubated at 37° C. for 72 hours before genomic DNA extraction as described above. The target genomic region was PCR amplified using primers outside the homology arms of the homologous recombination (HR) template. PCR products were separated on a 1% agarose gel and extracted with MinElute GelExtraction Kit (Qiagen). Purified products were digested with HindIII (Fermentas) and analyzed on a 6% Novex TBE poly-acrylamide gel (Life Technologies).

RNA secondary structure prediction and analysis

RNA secondary structure prediction was performed using the online webserver RNAfold developed at Institute for Theoretical Chemistry at the University of Vienna, using the centroid structure prediction algorithm (see e.g. A. R. Gruber et al., 2008, Cell 106(1): 23-24; and P A Carr and G M Church, 2009, Nature Biotechnology 27(12): 1151-62).

RNA Purification

HEK 293FT cells were maintained and transfected as stated above. Cells were harvested by trypsinization followed by washing in phosphate buffered saline (PBS). Total cell RNA was extracted with TRI reagent (Sigma) following manufacturer's protocol. Extracted total RNA was quantified using Naonodrop (Thermo Scientific) and normalized to same concentration.

Northern Blot Analysis of crRNA and tracrRNA Expression in Mammalian Cells

RNAs were mixed with equal volumes of 2× loading buffer (Ambion), heated to 95° C. for 5 min, chilled on ice for 1 min, and then loaded onto 8% denaturing polyacrylamide gels (SequaGel, National Diagnostics) after pre-running the gel for at least 30 minutes. The samples were electrophoresed for 1.5 hours at 40 W limit. Afterwards, the RNA was transferred to Hybond N+ membrane (GE Healthcare) at 300 mA in a semi-dry transfer apparatus (Bio-rad) at room temperature for 1.5 hours. The RNA was crosslinked to the membrane using autocrosslink button on Stratagene UV Crosslinker the Stratalinker (Stratagene). The membrane was pre-hybridized in ULTRAhyb-Oligo Hybridization Buffer (Ambion) for 30 min with rotation at 42° C., and probes were then added and hybridized overnight. Probes were ordered from IDT and labeled with [gamma-$^{32}$P] ATP (Perkin Elmer) with T4 polynucleotide kinase (New England Biolabs). The membrane was washed once with pre-warmed (42° C.) 2×SSC, 0.5% SDS for 1 min followed by two 30 minute washes at 42° C. The membrane was exposed to a phosphor screen for one hour or overnight at room temperature and then scanned with a phosphorimager (Typhoon).

Bacterial CRISPR System Construction and Evaluation

Figure 6A:
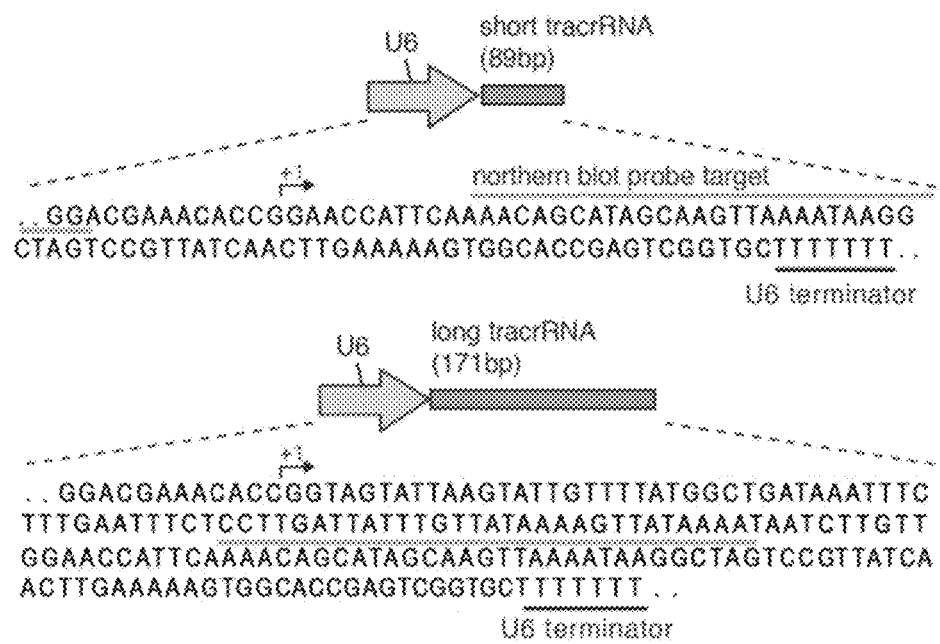
FIG. 6A-C shows a comparison of different tracrRNA transcripts for Cas9-mediated gene targeting.
Figure 6B:
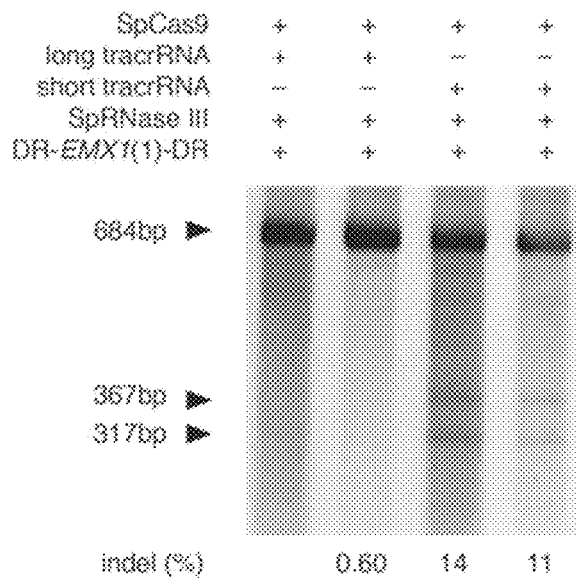
Figure 6C:
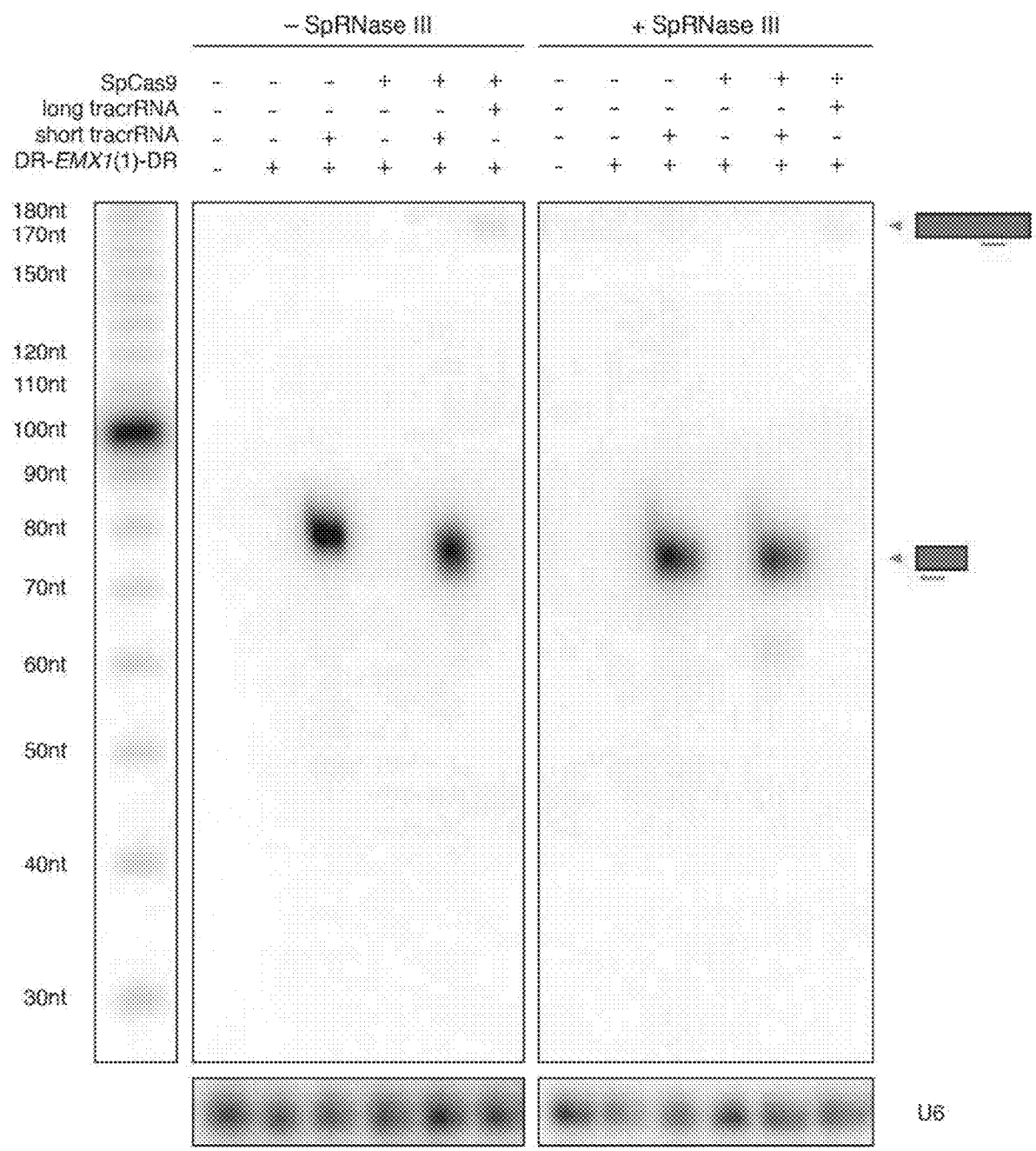

CRISPR locus elements, including tracrRNA, Cas9, and leader were PCR amplified from *Streptococcus pyogenes* SF370 genomic DNA with flanking homology arms for Gibson Assembly. Two BsaI type IIS sites were introduced in between two direct repeats to facilitate easy insertion of spacers (FIG. 8). PCR products were cloned into EcoRV-digested pACYC184 downstream of the tet promoter using Gibson Assembly Master Mix (NEB). Other endogenous CRISPR system elements were omitted, with the exception of the last 50 bp of Csn2. Oligos (Integrated DNA Technology) encoding spacers with complimentary overhangs were cloned into the BsaI-digested vector pDC000 (NEB) and then ligated with T7 ligase (Enzymatics) to generate pCRISPR plasmids. Challenge plasmids containing spacers with PAM expression in mammalian cells (expression constructs illustrated in FIG. 6A, with functionality as determined by results of the Surveyor assay shown in FIG. 6B). Transcription start sites are marked as +1, and transcription terminator and the sequence probed by northern blot are also indicated. Expression of processed tracrRNA was also confirmed by Northern blot. FIG. 6C shows results of a Northern blot analysis of total RNA extracted from 293FT cells transfected with U6 expression constructs carrying long or short tracrRNA, as well as SpCas9 and DR-EMX1(1)-DR. Left and right panels are from 293FT cells transfected without or with SpRNase III, respectively. U6 indicate loading control blotted with a probe targeting human U6 snRNA. Transfection of the short tracrRNA expression construct led to abundant levels of the processed form of tracrRNA (~75 bp). Very low amounts of long tracrRNA are detected on the Northern blot.

To promote precise transcriptional initiation, the RNA polymerase III-based U6 promoter was selected to drive the expression of tracrRNA (FIG. 2C). Similarly, a U6 promoter-based construct was developed to express a pre-crRNA array consisting of a single spacer flanked by two direct repeats (DRs, also encompassed by the term "tracr-mate sequences"; FIG. 2C). The initial spacer was designed to target a 33-base-pair (bp) target site (30-bp protospacer plus a 3-bp CRISPR motif (PAM) sequence satisfying the NGG recognition motif of Cas9) in the human EMX1 locus (FIG. 2C), a key gene in the development of the cerebral cortex.

Figure 2D:
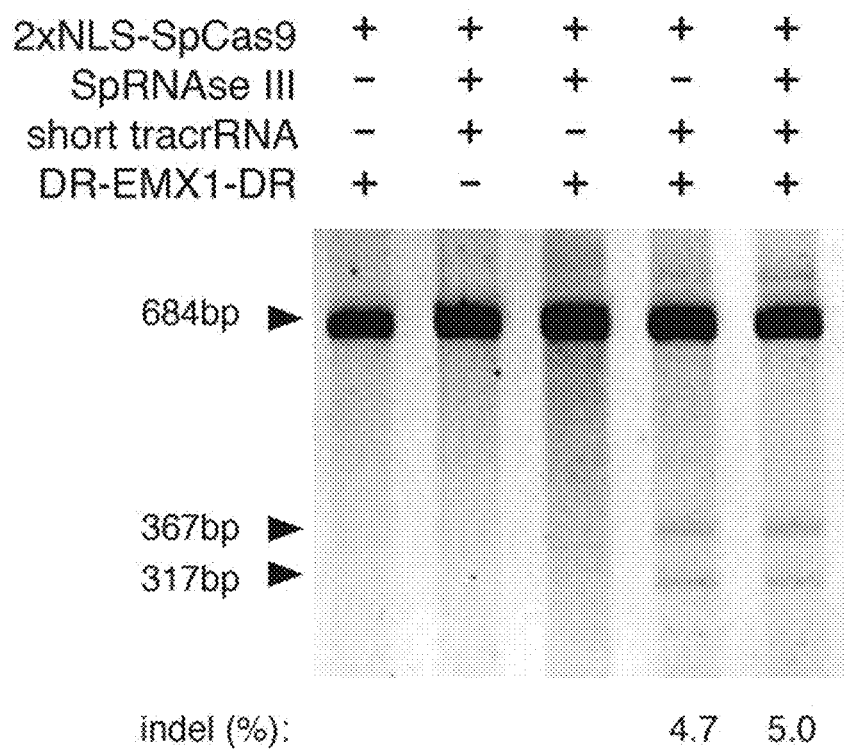

To test whether heterologous expression of the CRISPR system (SpCas9, SpRNase III, tracrRNA, and pre-crRNA) in mammalian cells can achieve targeted cleavage of mammalian chromosomes, HEK 293FT cells were transfected with combinations of CRISPR components. Since DSBs in mammalian nuclei are partially repaired by the non-homologous end joining (NHEJ) pathway, which leads to the formation of indels, the Surveyor assay was used to detect potential cleavage activity at the target EMX1 locus (FIG. 7) (see e.g. Guschin et al., 2010, Methods Mol Biol 649: 247). Co-transfection of all four CRISPR components was able to induce up to 5.0% cleavage in the protospacer (see FIG. 2D). Co-transfection of all CRISPR components minus SpRNase III also induced up to 4.7% indel in the protospacer, suggesting that there may be endogenous mammalian RNases that are capable of assisting with crRNA maturation, such as for example the related Dicer and Drosha enzymes. Removing any of the remaining three components abolished the genome cleavage activity of the CRISPR system (FIG. 2D). Sanger sequencing of amplicons containing the target locus verified the cleavage activity: in 43 sequenced clones, 5 mutated alleles (11.6%) were found. Similar experiments using a variety of guide sequences produced indel percentages as high as 29% (see FIGS. 3-6, 10, and 11). These results define a three-component system for efficient CRISPR-mediated genome modification in mammalian cells. To optimize the cleavage efficiency, Applicants also tested whether different isoforms of tracrRNA affected the cleavage efficiency and found that, in this example system, only the short (89-bp) transcript form was able to mediate cleavage of the human EMX1 genomic locus (FIG. 6B).

Figure 12A:
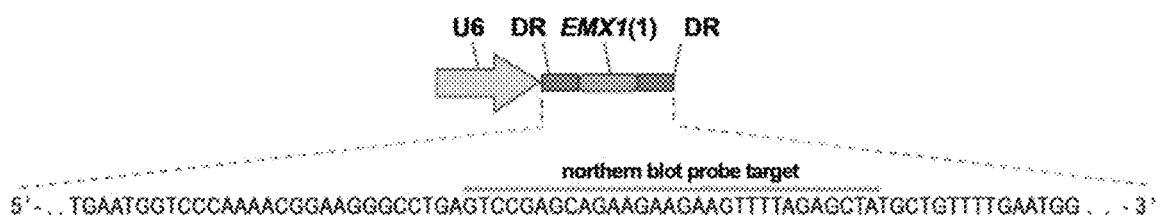
FIG. 12A-B shows the results of a Northern blot analysis of crRNA processing in mammalian cells.
Figure 12B:
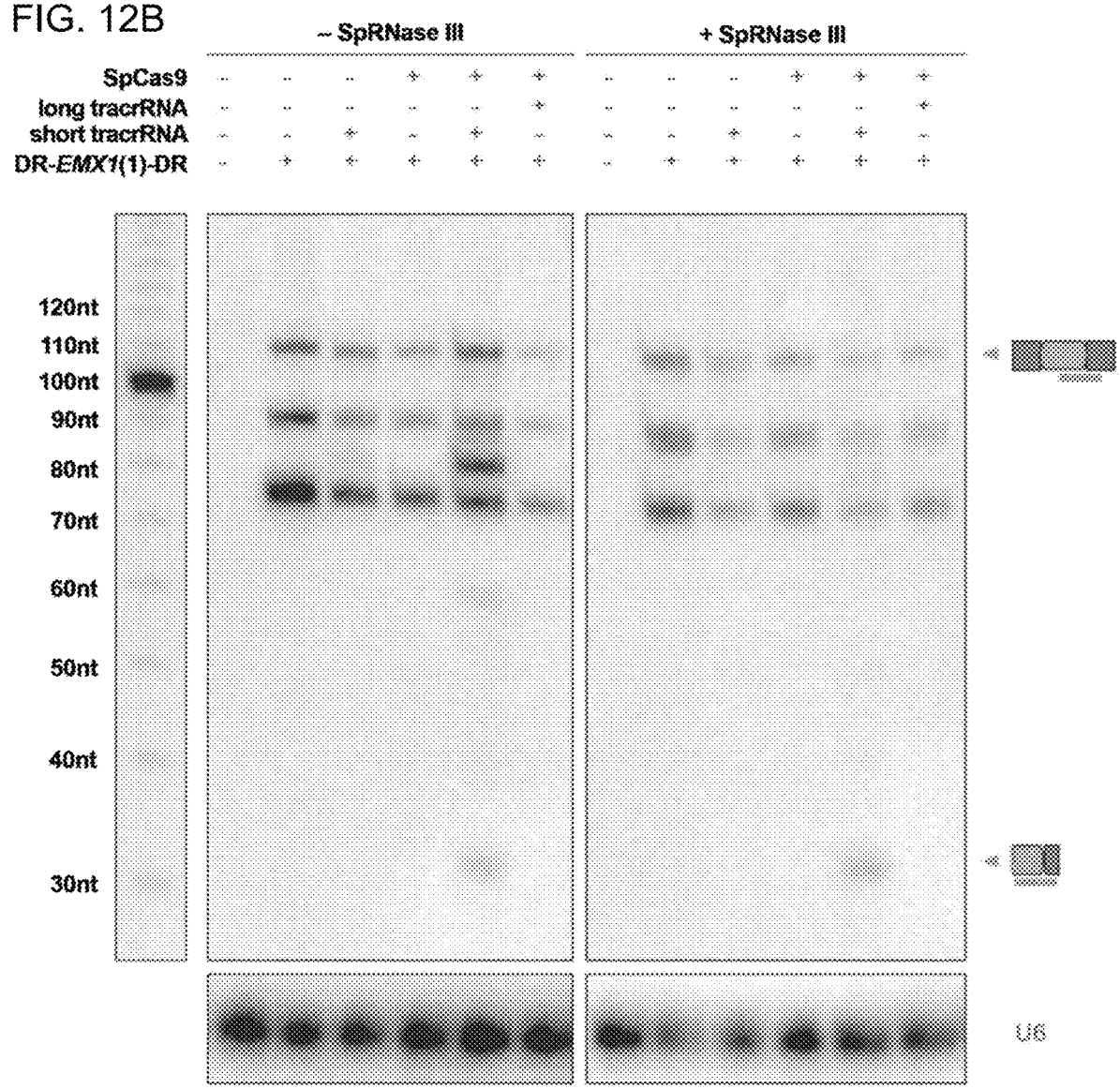

FIG. 12 provides an additional Northern blot analysis of crRNA processing in mammalian cells. FIG. 12A illustrates a schematic showing the expression vector for a single spacer flanked by two direct repeats (DR-EMX1(1)-DR). The 30 bp spacer targeting the human EMX1 locus protospacer 1 (see FIG. 6) and the direct repeat sequences are shown in the sequence beneath FIG. 12A. The line indicates the region whose reverse-complement sequence was used to generate Northern blot probes for EMX1(1) crRNA detection. FIG. 12B shows a Northern blot analysis of total RNA extracted from 293FT cells transfected with U6 expression constructs carrying DR-EMX1(1)-DR. Left and right panels are from 293FT cells transfected without or with SpRNase III respectively. DR-EMX1(1)-DR was processed into mature crRNAs only in the presence of SpCas9 and short tracrRNA and was not dependent on the presence of SpRNase III. The mature crRNA detected from transfected 293FT total RNA is ~33 bp and is shorter than the 39-42 bp mature crRNA from *S. pyogenes*. These results demonstrate that a CRISPR system can be transplanted into eukaryotic cells and reprogrammed to facilitate cleavage of endogenous mammalian target polynucleotides.

FIG. 2 illustrates the bacterial CRISPR system described in this example. FIG. 2A illustrates a schematic showing the CRISPR locus 1 from *Streptococcus pyogenes* SF370 and a proposed mechanism of CRISPR-mediated DNA cleavage by this system. Mature crRNA processed from the direct repeat-spacer array directs Cas9 to genomic targets consisting of complimentary protospacers and a protospacer-adjacent motif (PAM). Upon target-spacer base pairing, Cas9 mediates a double-strand break in the target DNA. FIG. 2B illustrates engineering of *S. pyogenes* Cas9 (SpCas9) and RNase III (SpRNase III) with nuclear localization signals (NLSs) to enable import into the mammalian nucleus. FIG. 2C illustrates mammalian expression of SpCas9 and SpRNase III driven by the constitutive EF1a promoter and tracrRNA and pre-crRNA array (DR-Spacer-DR) driven by the RNA Pol3 promoter U6 to promote precise transcription initiation and termination. A protospacer from the human EMX1 locus with a satisfactory PAM sequence is used as the spacer in the pre-crRNA array. FIG. 2D illustrates surveyor nuclease assay for SpCas9-mediated minor insertions and deletions. SpCas9 was expressed with and without SpRNase III, tracrRNA, and a pre-crRNA array carrying the EMX1-target spacer. FIG. 2E illustrates a schematic representation of base pairing between target locus and EMX1-targeting crRNA, as well as an example chromatogram showing a micro deletion adjacent to the SpCas9 cleavage site. FIG. 2F illustrates mutated alleles identified from sequencing analysis of 43 clonal amplicons showing a variety of micro insertions and deletions. Dashes indicate deleted bases, and non-aligned or mismatched bases indicate insertions or mutations. Scale bar=10 μm.

Figure 8A:
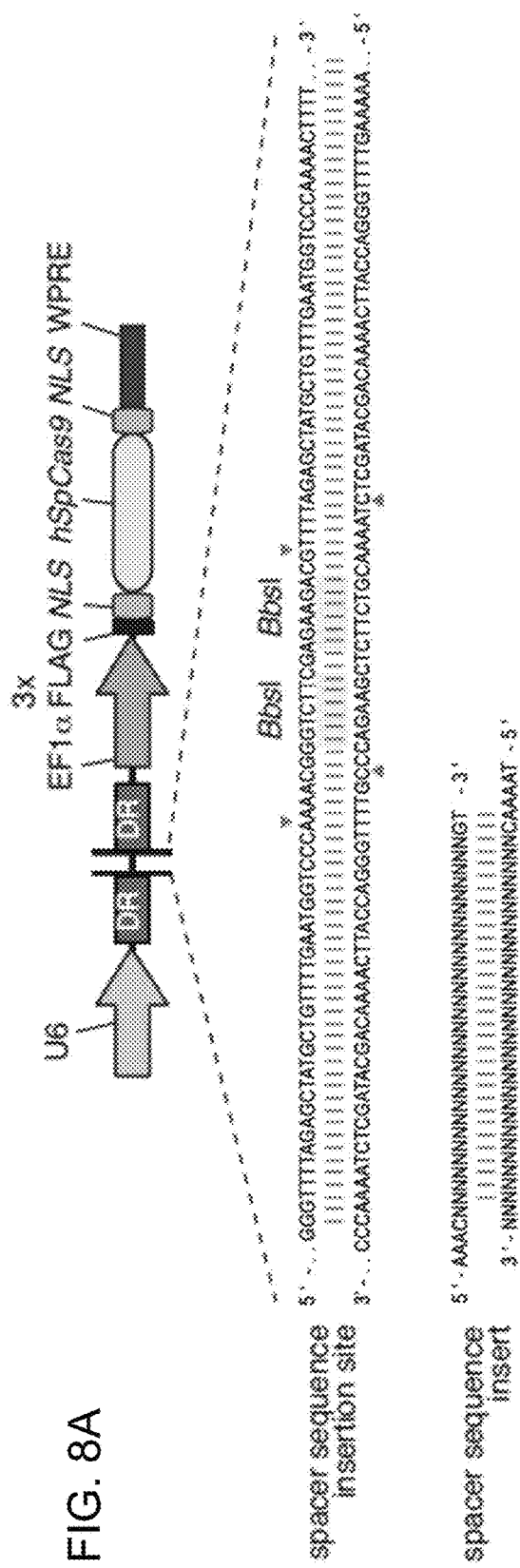
FIG. 8A-B shows exemplary bicistronic expression vectors for expression of CRISPR system elements in eukaryotic cells.
Figure 8B:
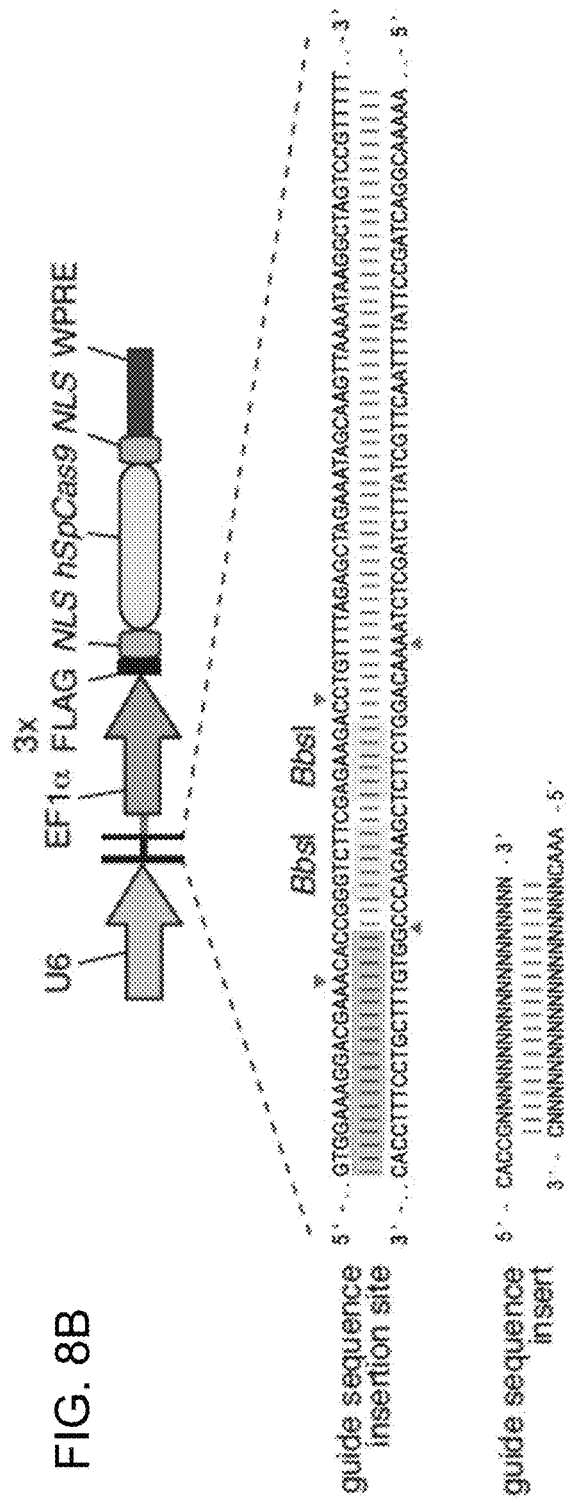

To further simplify the three-component system, a chimeric crRNA-tracrRNA hybrid design was adapted, where a mature crRNA (comprising a guide sequence) may be fused to a partial tracrRNA via a stem-loop to mimic the natural crRNA:tracrRNA duplex. To increase co-delivery efficiency, a bicistronic expression vector was created to drive co-expression of a chimeric RNA and SpCas9 in transfected cells. In parallel, the bicistronic vectors were used to express a pre-crRNA (DR-guide sequence-DR) with SpCas9, to induce processing into crRNA with a separately expressed tracrRNA (compare FIG. 11B top and bottom). FIG. 8 provides schematic illustrations of bicistronic expression vectors for pre-crRNA array (FIG. 8A) or chimeric crRNA (represented by the short line downstream of the guide sequence insertion site and upstream of the EF1a promoter in FIG. 8B) with hSpCas9, showing location of various elements and the point of guide sequence insertion. The expanded sequence around the location of the guide sequence insertion site in FIG. 8B also shows a partial DR sequence (GTTTTAGAGCTA (SEQ ID NO: 88)) and a partial tracrRNA sequence (TAGCAAGT-TAAAATAAGGCTAGTCCGTTTTT (SEQ ID NO: 89)). Guide sequences can be inserted between BbsI sites using annealed oligonucleotides. Sequence design for the oligonucleotides are shown below the schematic illustrations in FIG. 8, with appropriate ligation adapters indicated. WPRE represents the Woodchuck hepatitis virus post-transcriptional regulatory element. The efficiency of chimeric RNA-mediated cleavage was tested by targeting the same EMX1 locus described above. Using both Surveyor assay and Sanger sequencing of amplicons, Applicants confirmed that the chimeric RNA design facilitates cleavage of human EMX1 locus with approximately a 4.7% modification rate (FIG. 3).

Figure 13A:
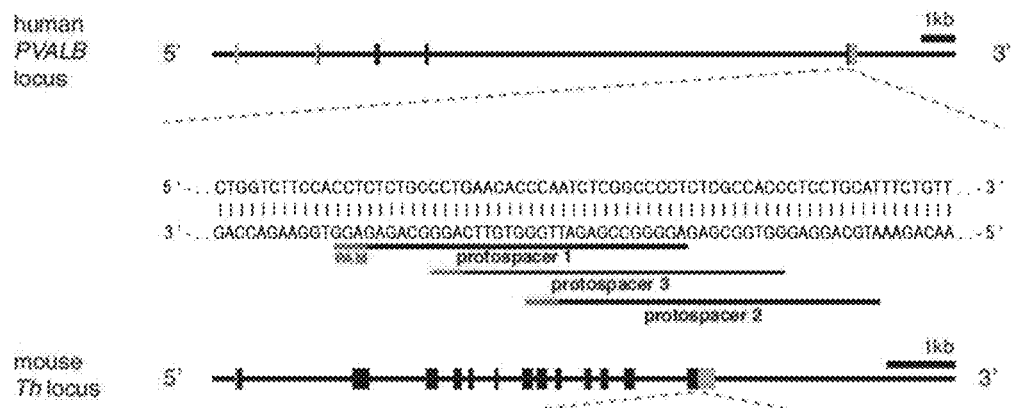
FIG. 13A-B shows an exemplary selection of protospacers in the human PVALB (SEQ ID NO: 267) and mouse Th loci (SEQ ID NO: 268).
Figure 13B:
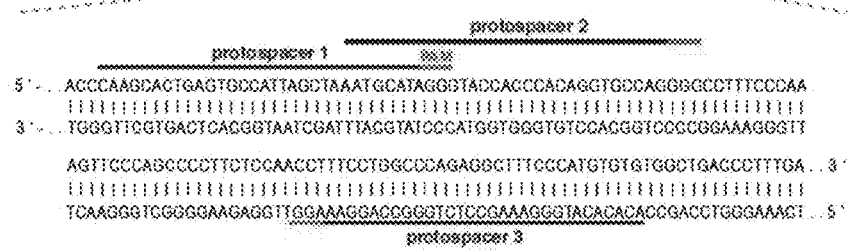

Generalizability of CRISPR-mediated cleavage in eukaryotic cells was tested by targeting additional genomic loci in both human and mouse cells by designing chimeric RNA targeting multiple sites in the human EMX1 and PVALB, as well as the mouse Th loci. FIG. 13 illustrates the selection of some additional targeted protospacers in human PVALB (FIG. 13A) and mouse Th (FIG. 13B) loci. Schematics of the gene loci and the location of three protospacers within the last exon of each are provided. The underlined sequences include 30 bp of protospacer sequence and 3 bp at the 3' end corresponding to the PAM sequences. Protospacers on the sense and anti-sense strands are indicated above and below the DNA sequences, respectively. A modification rate of 6.3% and 0.75% was achieved for the human PVALB and mouse Th loci respectively, demonstrating the broad applicability of the CRISPR system in modifying different loci across multiple organisms (FIG. 5). While cleavage was only detected with one out of three spacers for each locus using the chimeric constructs, all target sequences were cleaved with efficiency of indel production reaching 27% when using the co-expressed pre-crRNA arrangement (FIGS. 6 and 13).

FIG. 11 provides a further illustration that SpCas9 can be reprogrammed to target multiple genomic loci in mammalian cells. FIG. 11A provides a schematic of the human EMX1 locus showing the location of five protospacers, indicated by the underlined sequences. FIG. 11B provides a schematic of the pre-crRNA/trcrRNA complex showing hybridization between the direct repeat region of the pre-crRNA and tracrRNA (top), and a schematic of a chimeric RNA design comprising a 20 bp guide sequence, and tracr mate and tracr sequences consisting of partial direct repeat and tracrRNA sequences hybridized in a hairpin structure (bottom). Results of a Surveyor assay comparing the efficacy of Cas9-mediated cleavage at five protospacers in the human EMX1 locus is illustrated in FIG. 11C. Each protospacer is targeted using either processed pre-crRNA/tracrRNA complex (crRNA) or chimeric RNA (chiRNA).

Since the secondary structure of RNA can be crucial for intermolecular interactions, a structure prediction algorithm based on minimum free energy and Boltzmann-weighted structure ensemble was used to compare the putative secondary structure of all guide sequences used in the genome targeting experiment (see e.g. Gruber et al., 2008, Nucleic Acids Research, 36: W70). Analysis revealed that in most cases, the effective guide sequences in the chimeric crRNA context were substantially free of secondary structure motifs, whereas the ineffective guide sequences were more likely to form internal secondary structures that could prevent base pairing with the target protospacer DNA. It is thus possible that variability in the spacer secondary structure might impact the efficiency of CRISPR-mediated interference when using a chimeric crRNA.

Figure 22A:
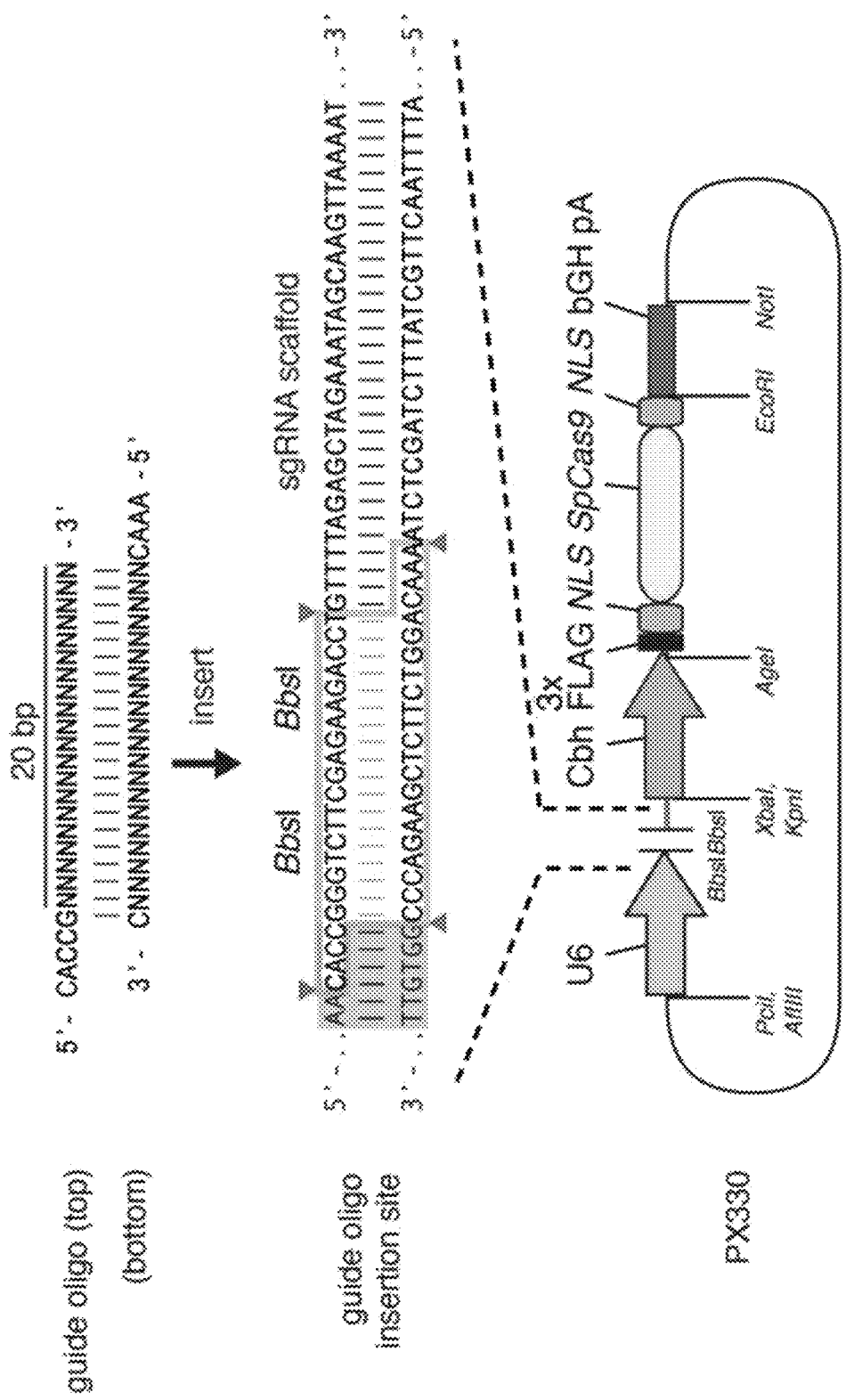
FIG. 22A-B shows single vector designs for SpCas9.
Figure 22B:
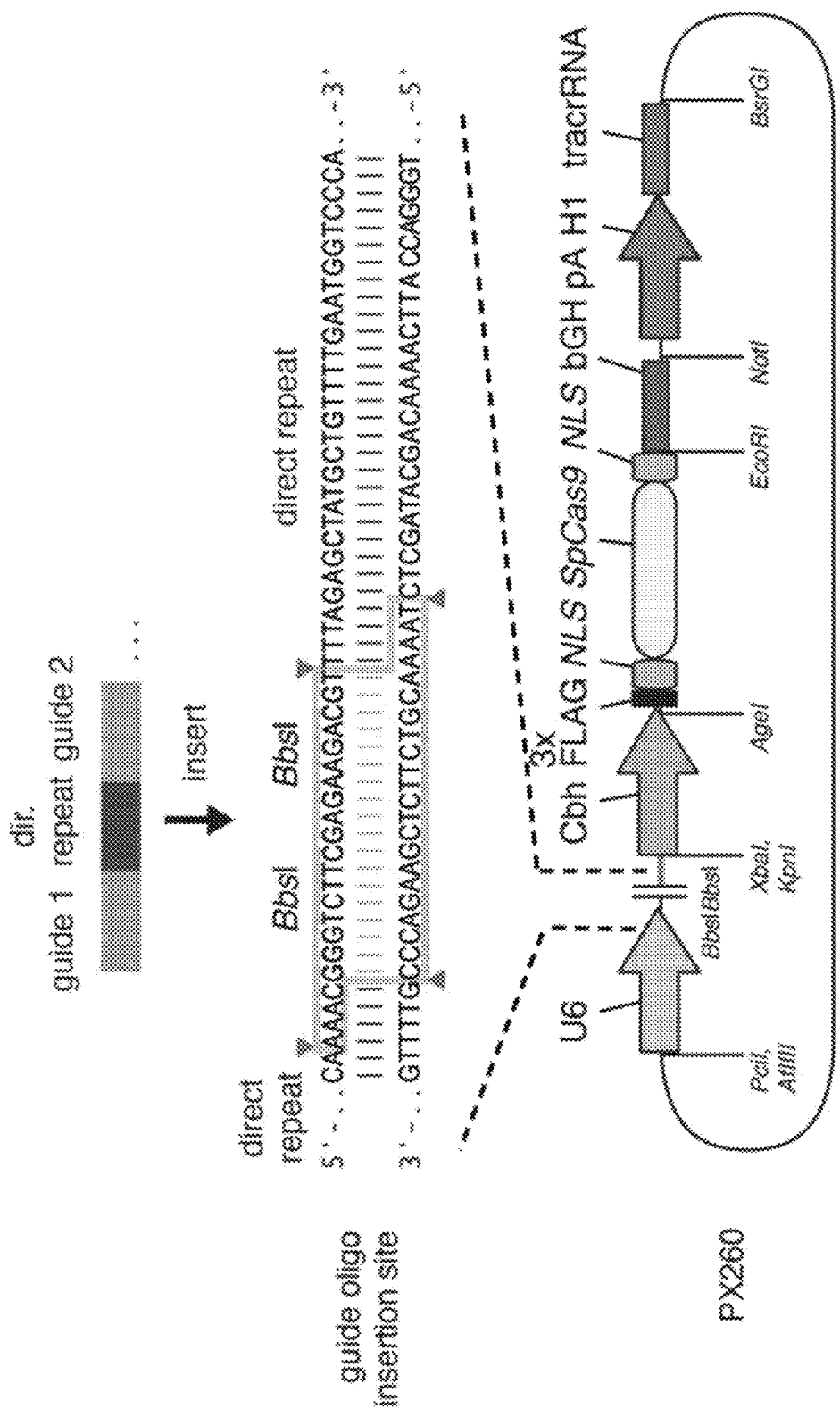

Further vector designs for SpCas9 are shown in FIG. 22, which illustrates single expression vectors incorporating a U6 promoter linked to an insertion site for a guide oligo, and a Cbh promoter linked to SpCas9 coding sequence. The vector shown in FIG. 22b includes a tracrRNA coding sequence linked to an H1 promoter.

Figure 3A:
FIG. 3A-D shows results of an evaluation of SpCas9 specificity for an example target.
Figure 3B:
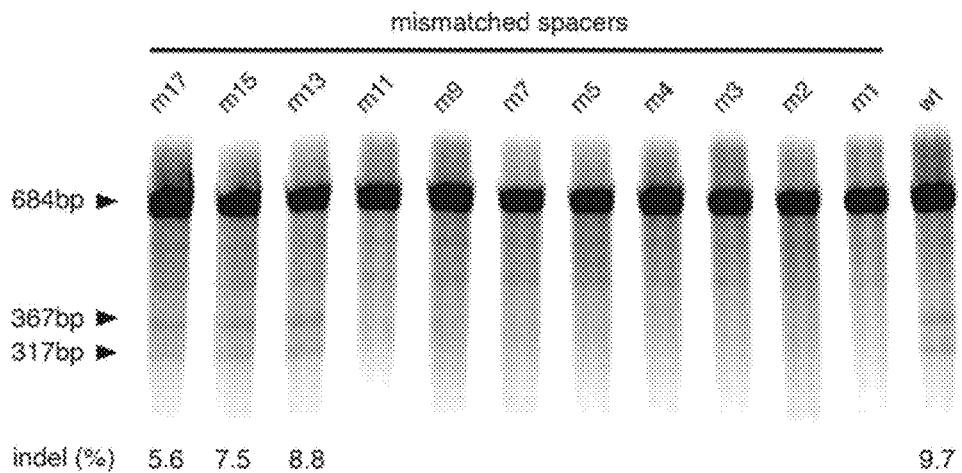
Figure 3C:

In the bacterial assay, all spacers facilitated efficient CRISPR interference (FIG. 3C). These results suggest that there may be additional factors affecting the efficiency of CRISPR activity in mammalian cells.

Figure 3D:
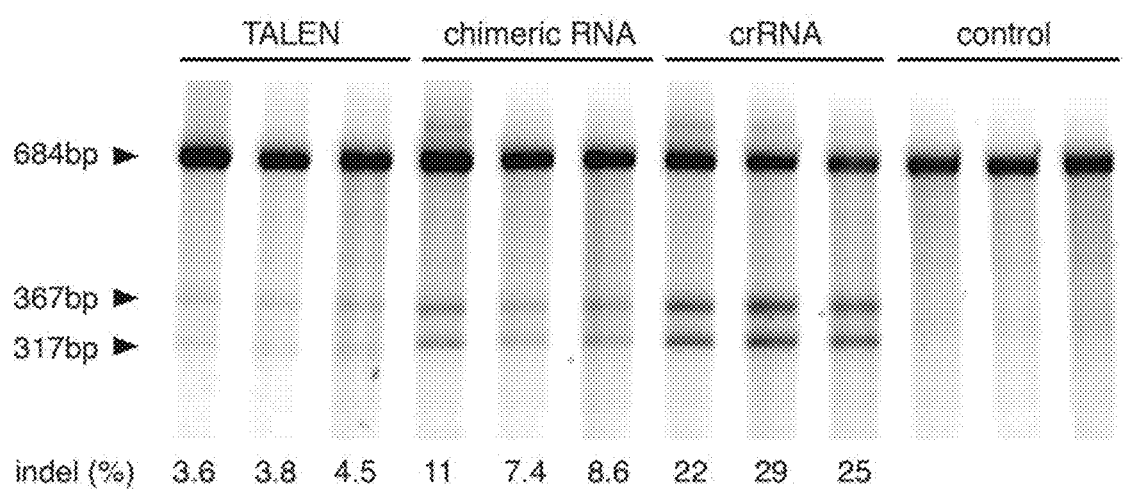

To investigate the specificity of CRISPR-mediated cleavage, the effect of single-nucleotide mutations in the guide sequence on protospacer cleavage in the mammalian genome was analyzed using a series of EMX1-targeting chimeric crRNAs with single point mutations (FIG. 3A). FIG. 3B illustrates results of a Surveyor nuclease assay comparing the cleavage efficiency of Cas9 when paired with different mutant chimeric RNAs. Single-base mismatch up to 12-bp 5' of the PAM substantially abrogated genomic cleavage by SpCas9, whereas spacers with mutations at farther upstream positions retained activity against the original protospacer target (FIG. 3B). In addition to the PAM, SpCas9 has single-base specificity within the last 12-bp of the spacer. Furthermore, CRISPR is able to mediate genomic cleavage as efficiently as a pair of TALE nucleases (TALEN) targeting the same EMX1 protospacer. FIG. 3C provides a schematic showing the design of TALENs targeting EMX1, and FIG. 3D shows a Surveyor gel comparing the efficiency of TALEN and Cas9 (n=3).

Figure 4C:
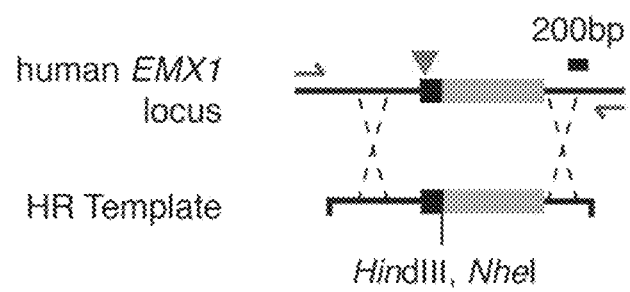
Figure 4D:
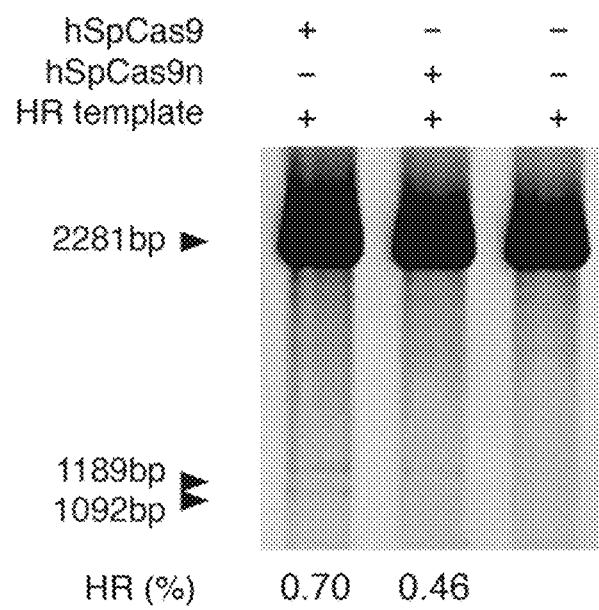
Figure 4E:
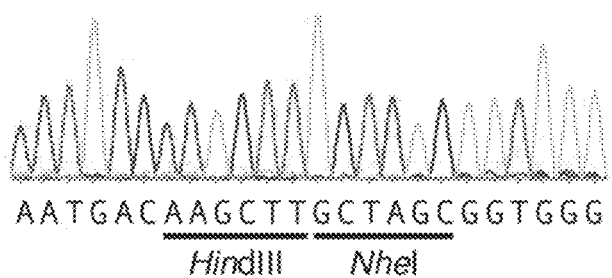

Having established a set of components for achieving CRISPR-mediated gene editing in mammalian cells through the error-prone NHEJ mechanism, the ability of CRISPR to stimulate homologous recombination (HR), a high fidelity gene repair pathway for making precise edits in the genome, was tested. The wild type SpCas9 is able to mediate site-specific DSBs, which can be repaired through both NHEJ and HR. In addition, an aspartate-to-alanine substitution (D10A) in the RuvC I catalytic domain of SpCas9 was engineered to convert the nuclease into a nickase (SpCas9n; illustrated in FIG. 4A) (see e.g. Sapranausaks et al., 2011, Nucleic Acids Resch, 39: 9275; Gasiunas et al., 2012, Proc. Natl. Acad. Sci, USA, 109:E2579), such that nicked genomic DNA undergoes the high-fidelity homology-directed repair (HDR). Surveyor assay confirmed that SpCas9n does not generate indels at the EMX1 protospacer target. As illustrated in FIG. 4B, co-expression of EMX1-targeting chimeric crRNA with SpCas9 produced indels in the target site, whereas co-expression with SpCas9n did not (n=3). Moreover, sequencing of 327 amplicons did not detect any indels induced by SpCas9n. The same locus was selected to test CRISPR-mediated HR by co-transfecting HEK 293FT cells with the chimeric RNA targeting EMX1, hSpCas9 or hSpCas9n, as well as a HR template to introduce a pair of restriction sites (HindIII and NheI) near the protospacer. FIG. 4C provides a schematic illustration of the HR strategy, with relative locations of recombination points and primer annealing sequences (arrows). SpCas9 and SpCas9n indeed catalyzed integration of the HR template into the EMX1 locus. PCR amplification of the target region followed by restriction digest with HindIII revealed cleavage products corresponding to expected fragment sizes (arrows in restriction fragment length polymorphism gel analysis shown in FIG. 4D), with SpCas9 and SpCas9n mediating similar levels of HR efficiencies. Applicants further verified HR using Sanger sequencing of genomic amplicons (FIG. 4E). These results demonstrate the utility of CRISPR for facilitating targeted gene insertion in the mammalian genome. Given the 14-bp (12-bp from the spacer and 2-bp from the PAM) target specificity of the wild type SpCas9, the availability of a nickase can significantly reduce the likelihood of off-target modifications, since single strand breaks are not substrates for the error-prone NHEJ pathway.

Figure 4F:
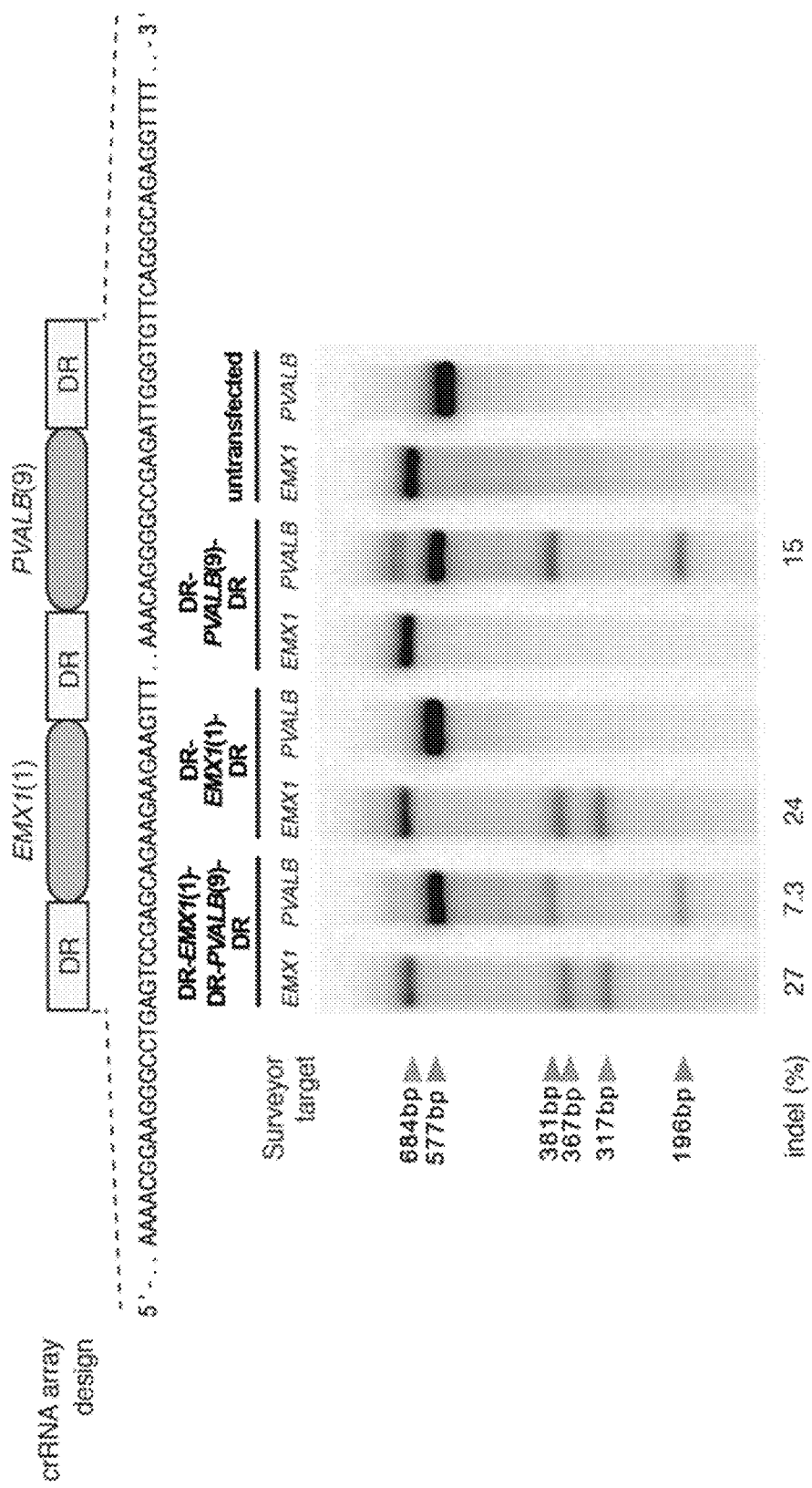
Figure 4G:
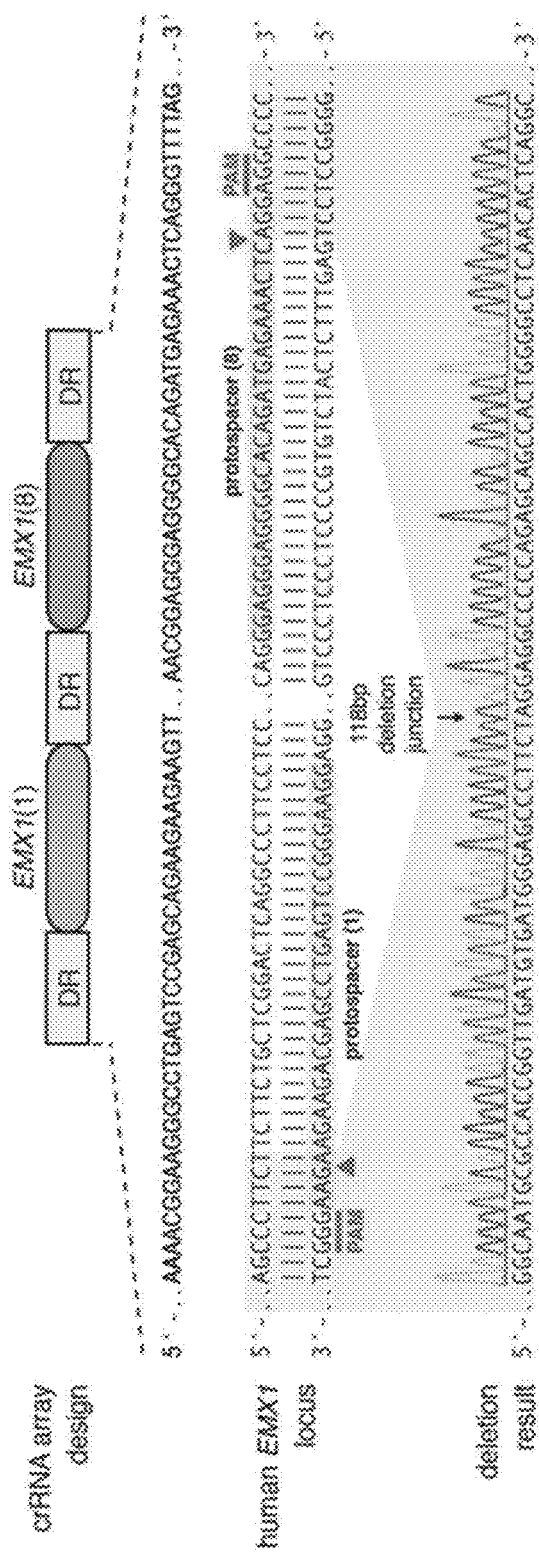

Expression constructs mimicking the natural architecture of CRISPR loci with arrayed spacers (FIG. 2A) were constructed to test the possibility of multiplexed sequence targeting. Using a single CRISPR array encoding a pair of EMX1- and PVALB-targeting spacers, efficient cleavage at both loci was detected (FIG. 4F, showing both a schematic design of the crRNA array and a Surveyor blot showing efficient mediation of cleavage). Targeted deletion of larger genomic regions through concurrent DSBs using spacers against two targets within EMX1 spaced by 119 bp was also tested, and a 1.6% deletion efficacy (3 out of 182 amplicons;

FIG. 4G) was detected. This demonstrates that the CRISPR system can mediate multiplexed editing within a single genome.

Example 2: CRISPR System Modifications and Alternatives

Figure 10D:
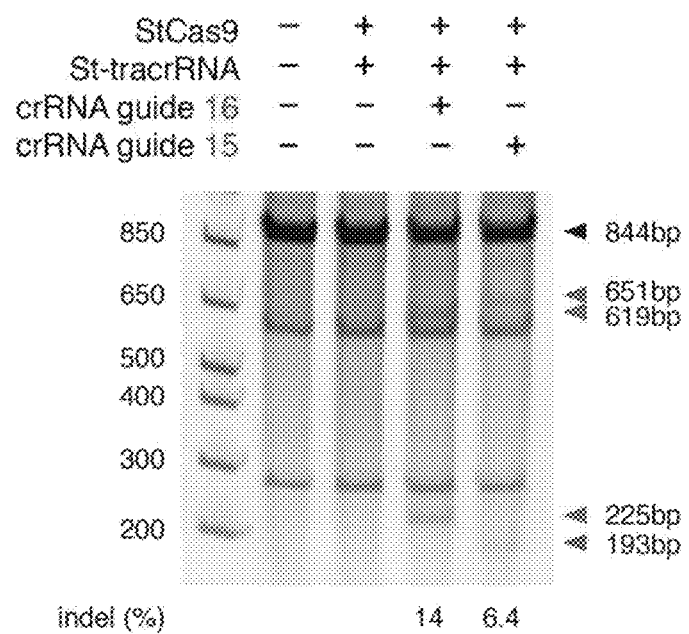
Figure 14:
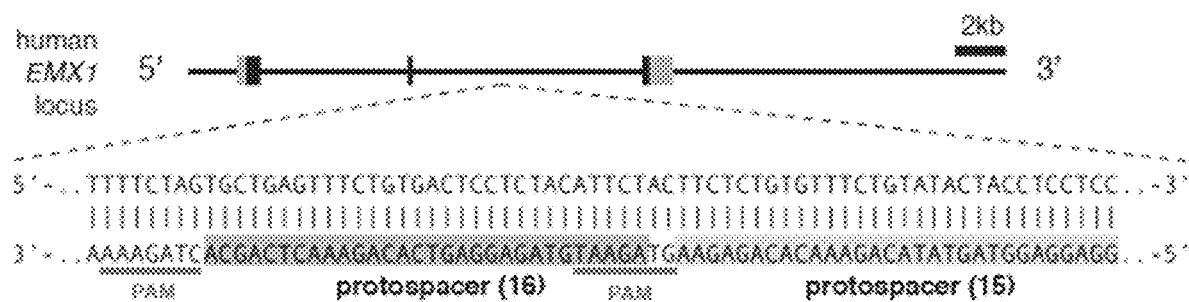
FIG. 14 shows example protospacer and corresponding PAM sequence targets of the *S. thermophilus* CRISPR system in the human EMX1 locus.

The ability to use RNA to program sequence-specific DNA cleavage defines a new class of genome engineering tools for a variety of research and industrial applications. Several aspects of the CRISPR system can be further improved to increase the efficiency and versatility of CRISPR targeting. Optimal Cas9 activity may depend on the availability of free $Mg^{2+}$ at levels higher than that present in the mammalian nucleus (see e.g. Jinek et al., 2012, Science, 337:816), and the preference for an NGG motif immediately downstream of the protospacer restricts the ability to target on average every 12-bp in the human genome (FIG. 9, evaluating both plus and minus strands of human chromosomal sequences). Some of these constraints can be overcome by exploring the diversity of CRISPR loci across the microbial metagenome (see e.g. Makarova et al., 2011, Nat Rev Microbiol, 9:467). Other CRISPR loci may be transplanted into the mammalian cellular milieu by a process similar to that described in Example 1. For example, FIG. 10 illustrates adaptation of the Type II CRISPR system from CRISPR 1 of Streptococcus thermophilus LMD-9 for heterologous expression in mammalian cells to achieve CRISPR-mediated genome editing. FIG. 10A provides a Schematic illustration of CRISPR 1 from S. thermophilus LMD-9. FIG. 10B illustrates the design of an expression system for the S. thermophilus CRISPR system. Human codon-optimized hStCas9 is expressed using a constitutive EF1a promoter. Mature versions of tracrRNA and crRNA are expressed using the U6 promoter to promote precise transcription initiation. Sequences from the mature crRNA and tracrRNA are illustrated. A single base indicated by the lower case "a" in the crRNA sequence is used to remove the polyU sequence, which serves as a RNA polIII transcriptional terminator. FIG. 10C provides a schematic showing guide sequences targeting the human EMX1 locus. FIG. 10D shows the results of hStCas9-mediated cleavage in the target locus using the Surveyor assay. RNA guide spacers 1 and 2 induced 14% and 6.4%, respectively. Statistical analysis of cleavage activity across biological replica at these two protospacer sites is also provided in FIG. 5. FIG. 14 provides a schematic of additional protospacer and corresponding PAM sequence targets of the S. thermophilus CRISPR system in the human EMX1 locus. Two protospacer sequences are highlighted and their corresponding PAM sequences satisfying NNAGAAW motif are indicated by underlining 3' with respect to the corresponding highlighted sequence. Both protospacers target the anti-sense strand.

Example 3: Sample Target Sequence Selection Algorithm

A software program is designed to identify candidate CRISPR target sequences on both strands of an input DNA sequence based on desired guide sequence length and a CRISPR motif sequence (PAM) for a specified CRISPR enzyme. For example, target sites for Cas9 from S. pyogenes, with PAM sequences NGG, may be identified by searching for 5'-$N_x$-NGG-3' both on the input sequence and on the reverse-complement of the input. Likewise, target sites for Cas9 of S. thermophilus CRISPR1, with PAM sequence NNAGAAW, may be identified by searching for 5'-$N_x$-NNAGAAW-3' (SEQ ID NO: 90) both on the input sequence and on the reverse-complement of the input. Likewise, target sites for Cas9 of S. thermophilus CRISPR3, with PAM sequence NGGNG, may be identified by searching for 5'-$N_x$-NGGNG-3' both on the input sequence and on the reverse-complement of the input. The value "x" in $N_x$ may be fixed by the program or specified by the user, such as 20.

Figure 18:
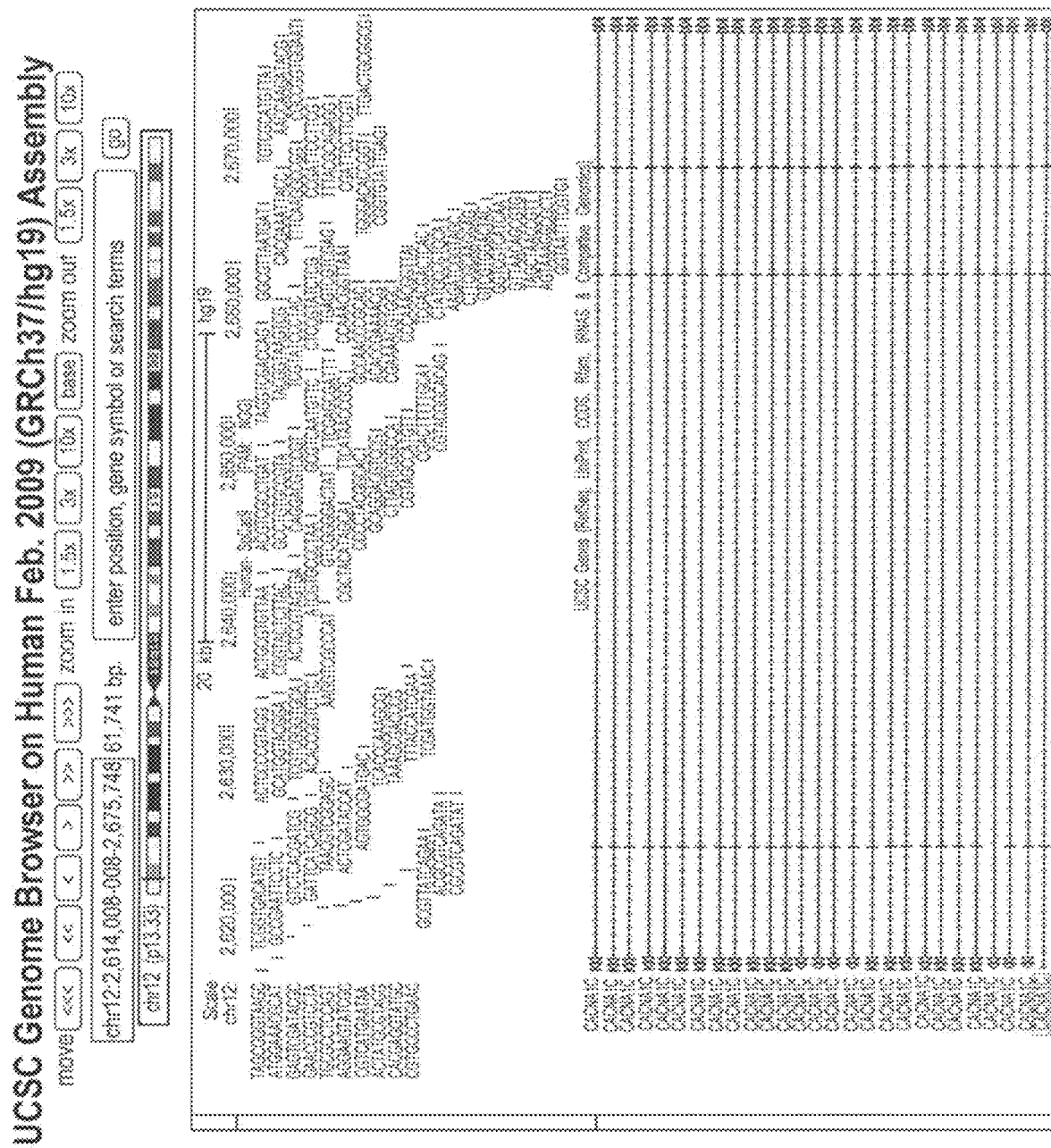
FIG. 18 shows an exemplary visualization of some *S. pyogenes* Cas9 target sites in the human genome using the UCSC genome browser.
Figure 19A:
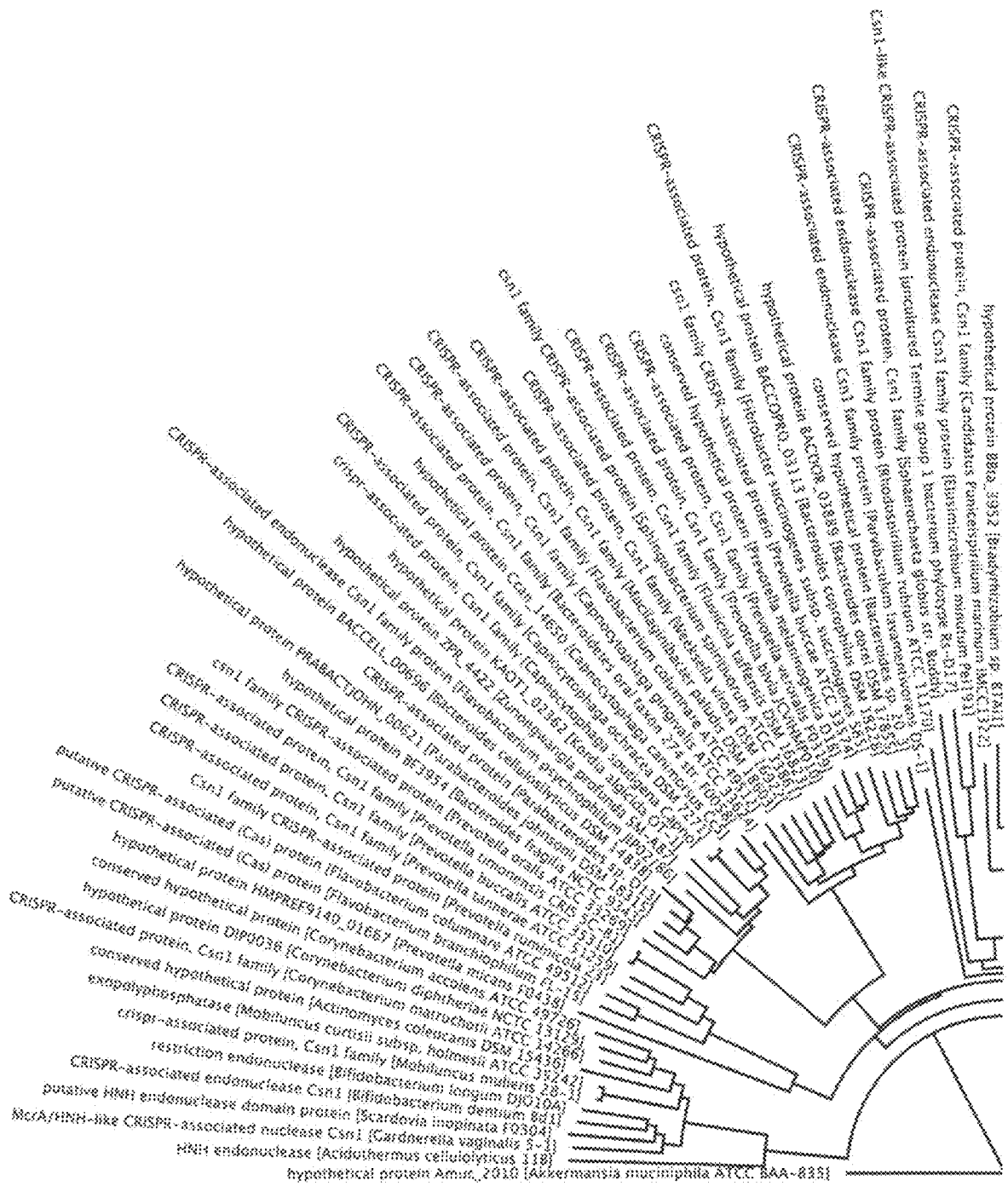
FIG. 19A-D shows a circular depiction of the phylogenetic analysis revealing five families of Cas9s, including three groups of large Cas9s (~1400 amino acids) and two of small Cas9s (~1100 amino acids).
Figure 19B:
Figure 19C:
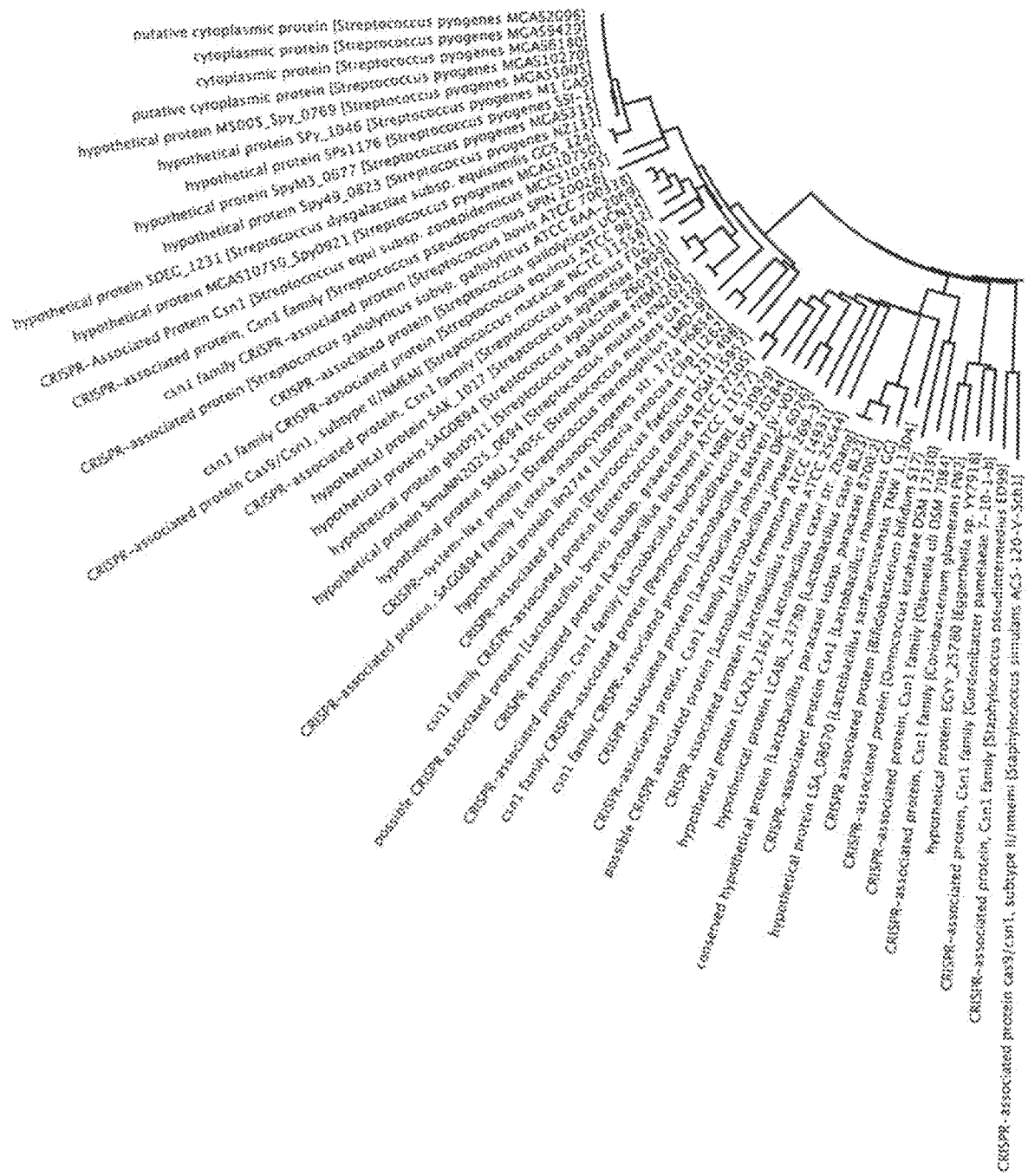
Figure 19D:
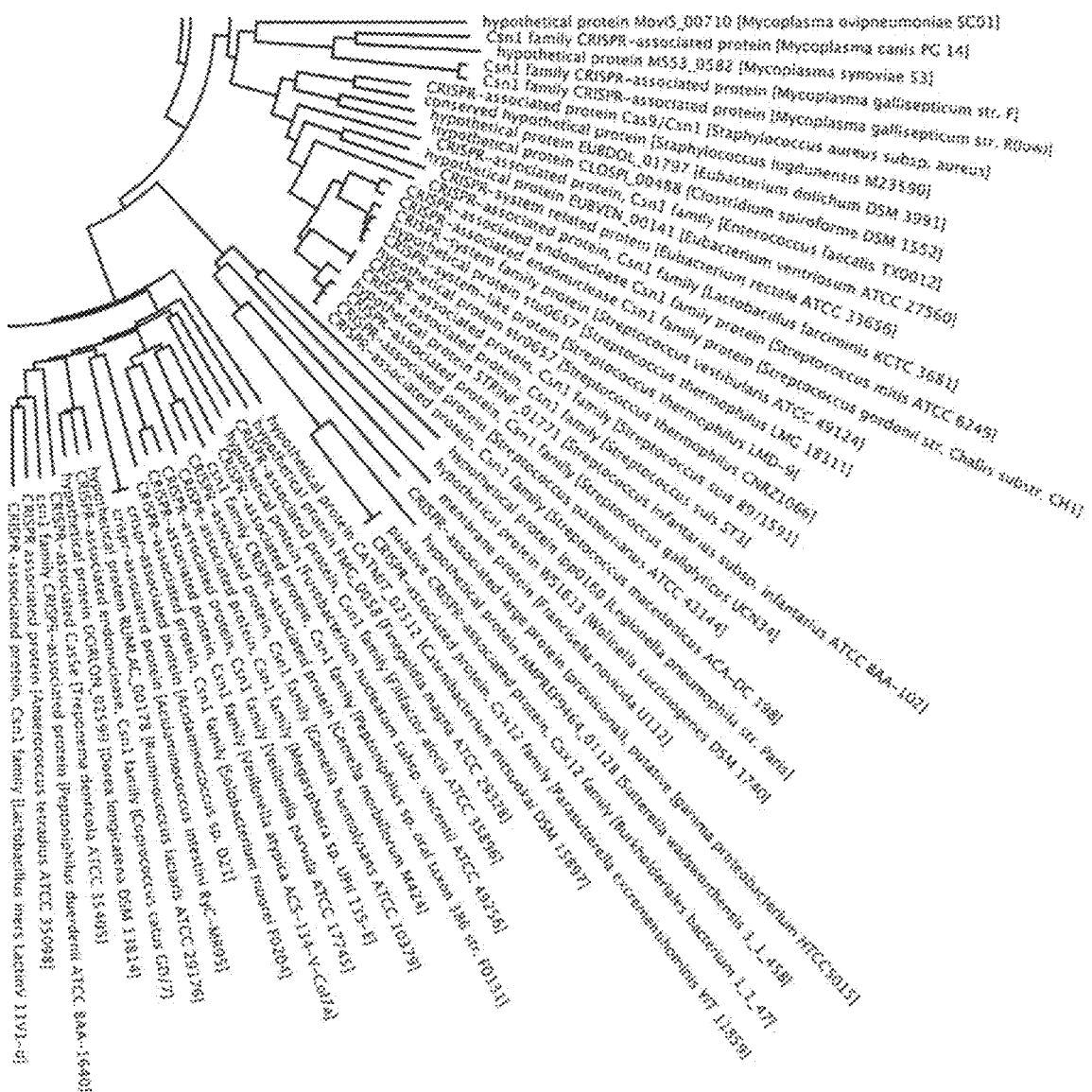
Figure 20A:
Figure 20C:
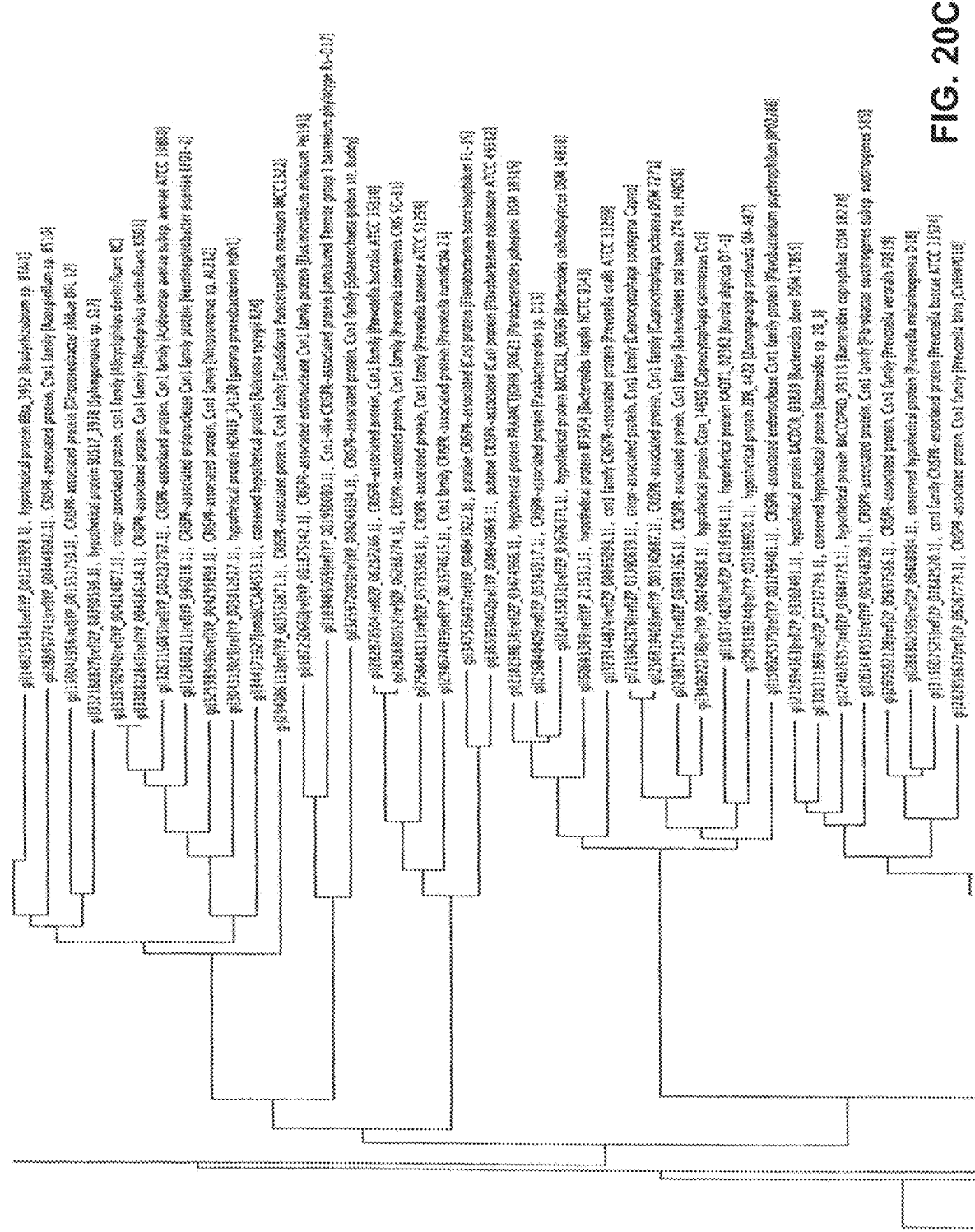
Figure 20E:
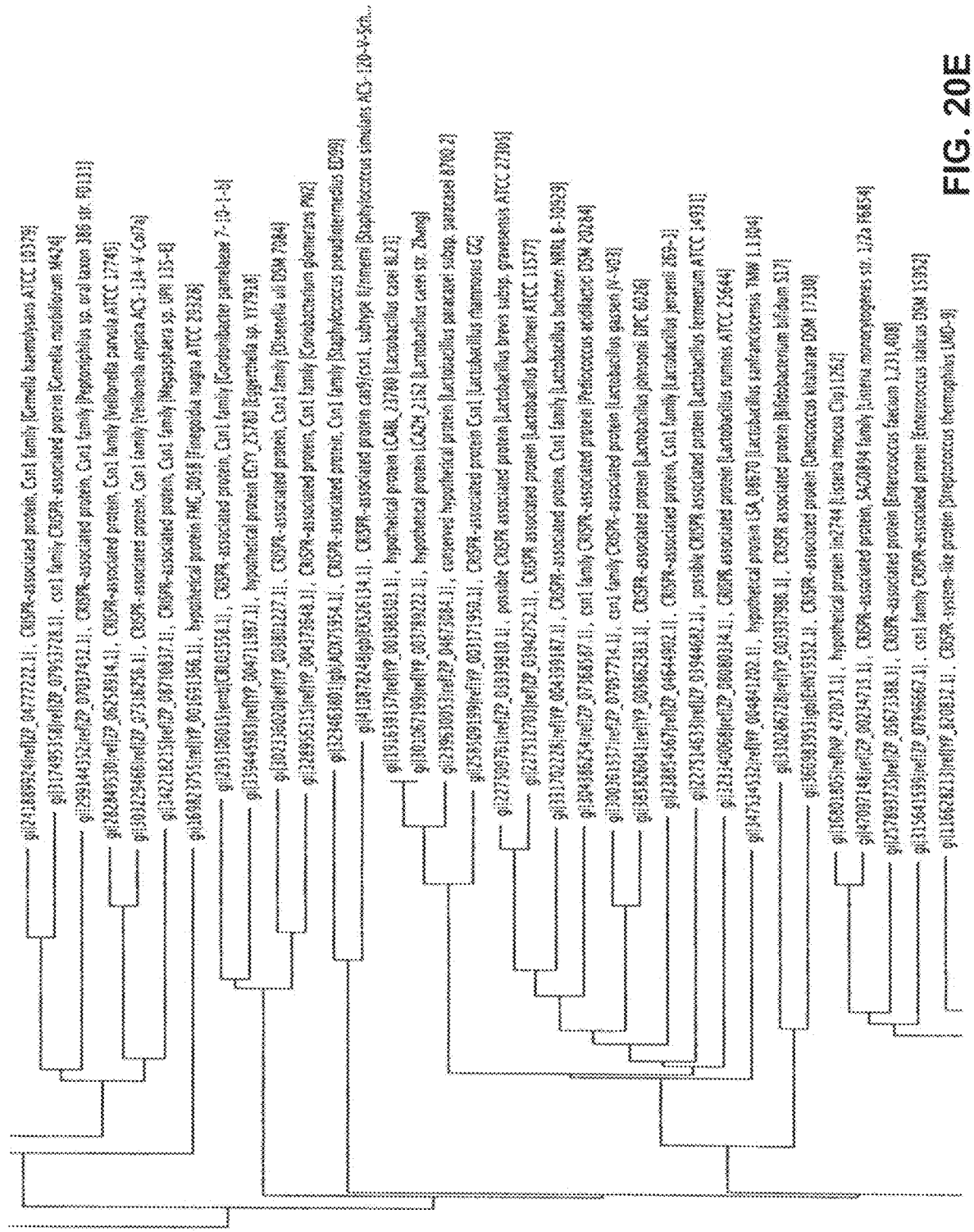
Figure 20F:
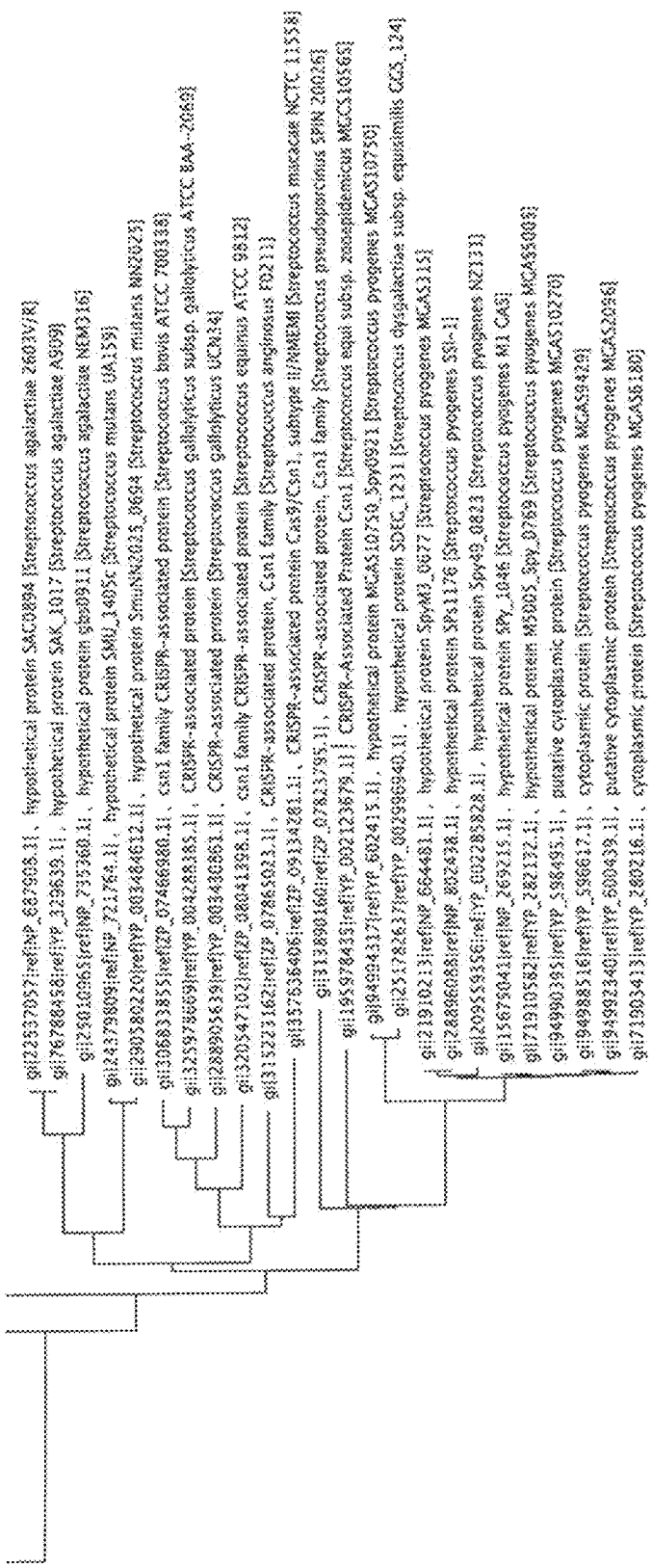
Figure 21A:
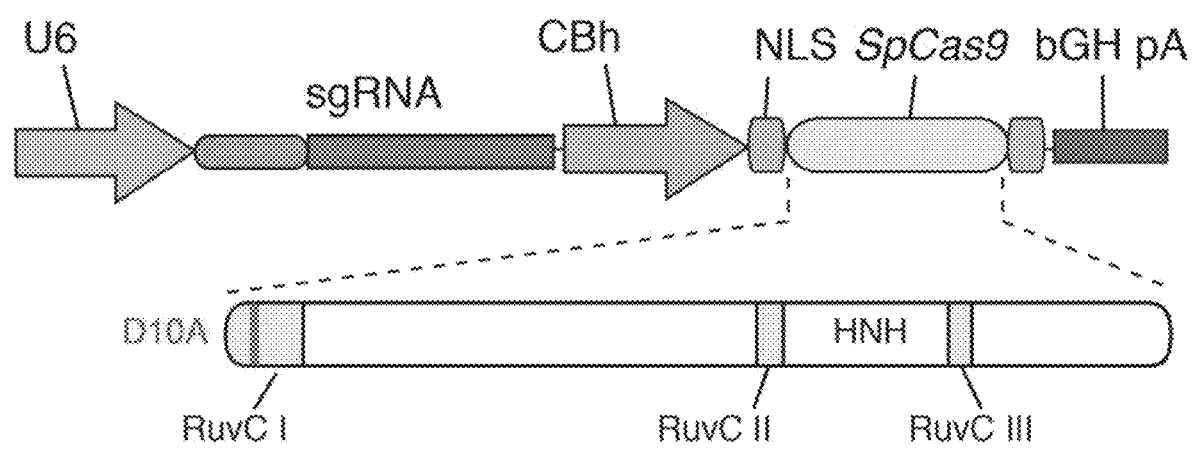
FIG. 21A-D shows genome editing via homologous recombination. (a) Schematic of SpCas9 nickase, with D10A mutation in the RuvC I catalytic domain. (b) Schematic representing homologous recombination (HR) at the human EMX1 locus using either sense or antisense single stranded oligonucleotides as repair templates. Red arrow above indicates sgRNA cleavage site; PCR primers for genotyping (Tables J and K) are indicated as arrows in right panel. (c) Sequence of region modified by HR. d, SURVEYOR assay for wildtype (wt) and nickase (D10A) SpCas9-mediated indels at the EMX1 target 1 locus (n=3). Arrows indicate positions of expected fragment sizes.
Figure 21B:
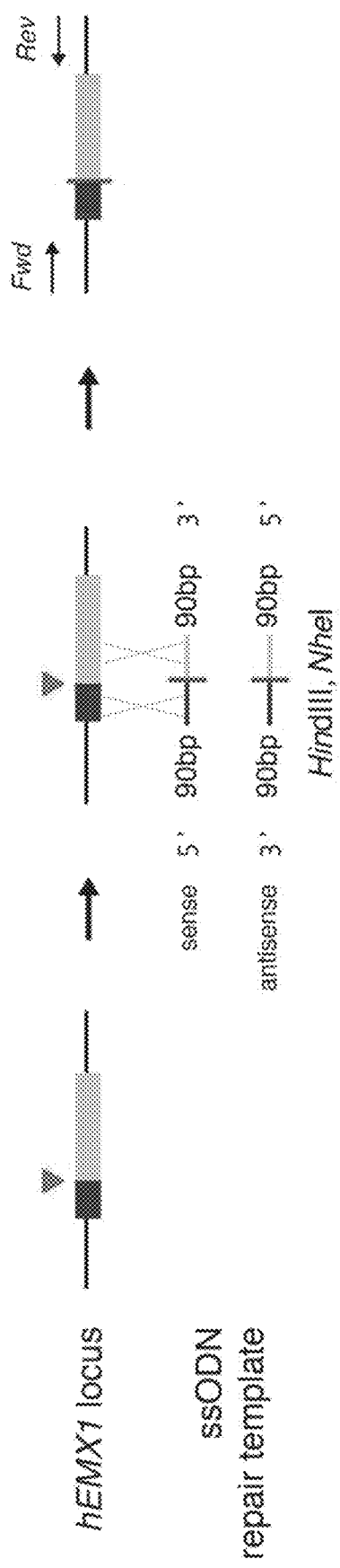
Figure 21C:
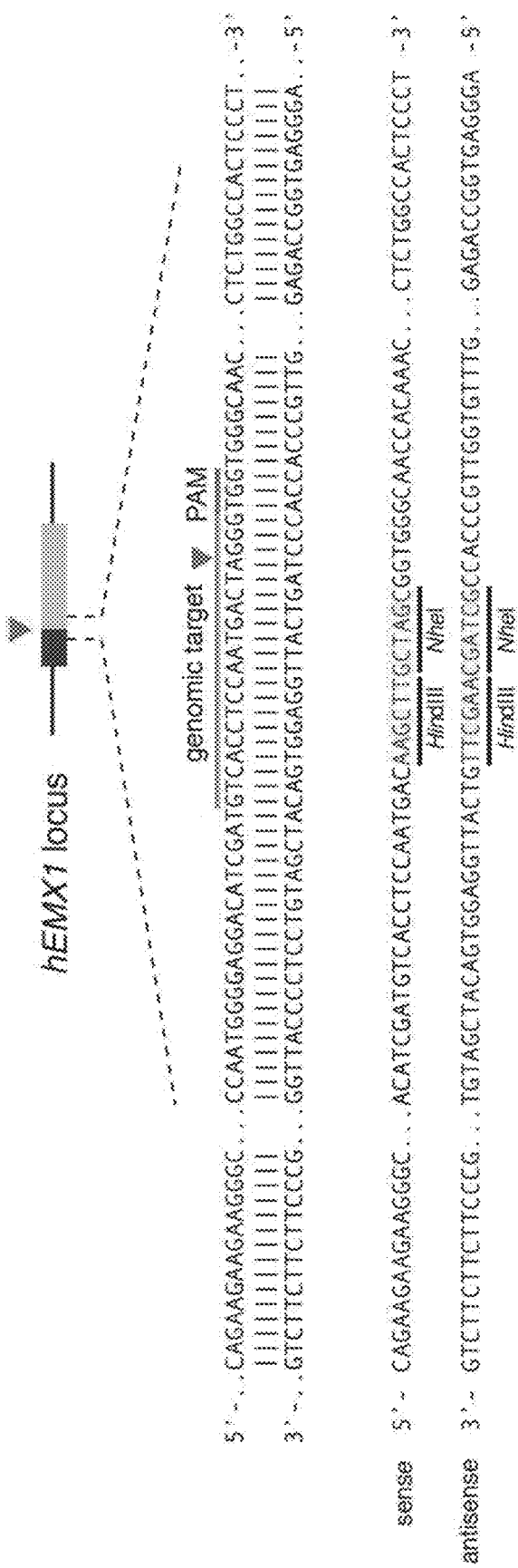
Figure 21D:
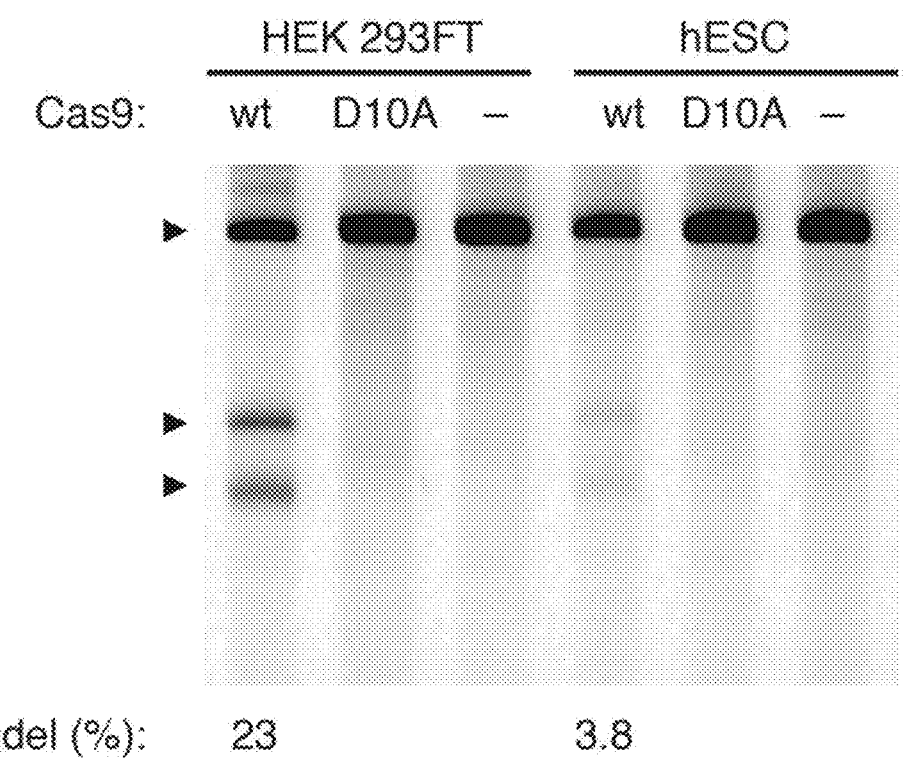

Since multiple occurrences in the genome of the DNA target site may lead to nonspecific genome editing, after identifying all potential sites, the program filters out sequences based on the number of times they appear in the relevant reference genome. For those CRISPR enzymes for which sequence specificity is determined by a 'seed' sequence, such as the 11-12 bp 5' from the PAM sequence, including the PAM sequence itself, the filtering step may be based on the seed sequence. Thus, to avoid editing at additional genomic loci, results are filtered based on the number of occurrences of the seed:PAM sequence in the relevant genome. The user may be allowed to choose the length of the seed sequence. The user may also be allowed to specify the number of occurrences of the seed:PAM sequence in a genome for purposes of passing the filter. The default is to screen for unique sequences. Filtration level is altered by changing both the length of the seed sequence and the number of occurrences of the sequence in the genome. The program may in addition or alternatively provide the sequence of a guide sequence complementary to the reported target sequence(s) by providing the reverse complement of the identified target sequence(s). An example visualization of some target sites in the human genome is provided in FIG. 18.

Further details of methods and algorithms to optimize sequence selection can be found in U.S. application Ser. No. 61/064,798; Broad Reference BI-2012/084); incorporated herein by reference.

Example 4: Evaluation of Multiple Chimeric crRNA-tracrRNA Hybrids

Figure 16A:
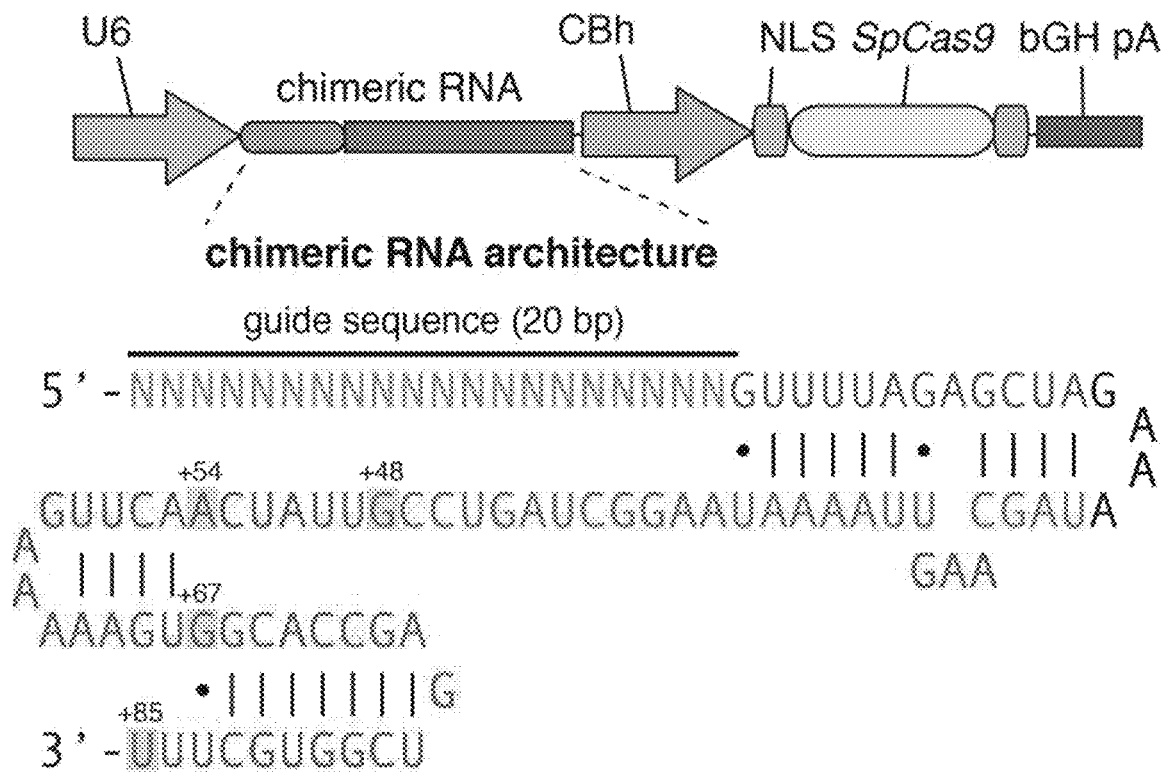
FIG. 16A-C shows exemplary manipulation of a CRISPR system with chimeric RNAs and results of SURVEYOR assays for system activity in eukaryotic cells.
Figure 16B:
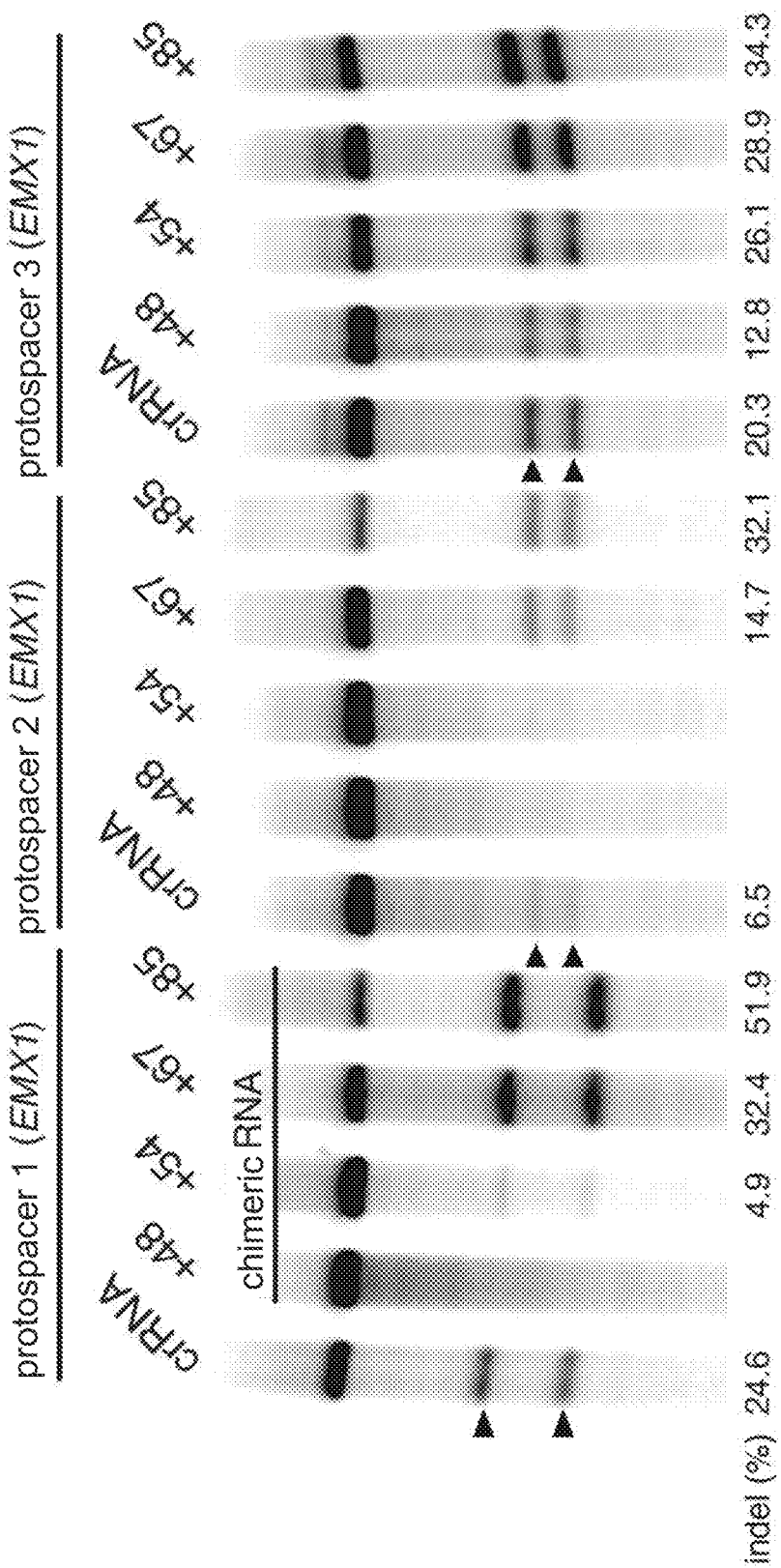
Figure 16C:
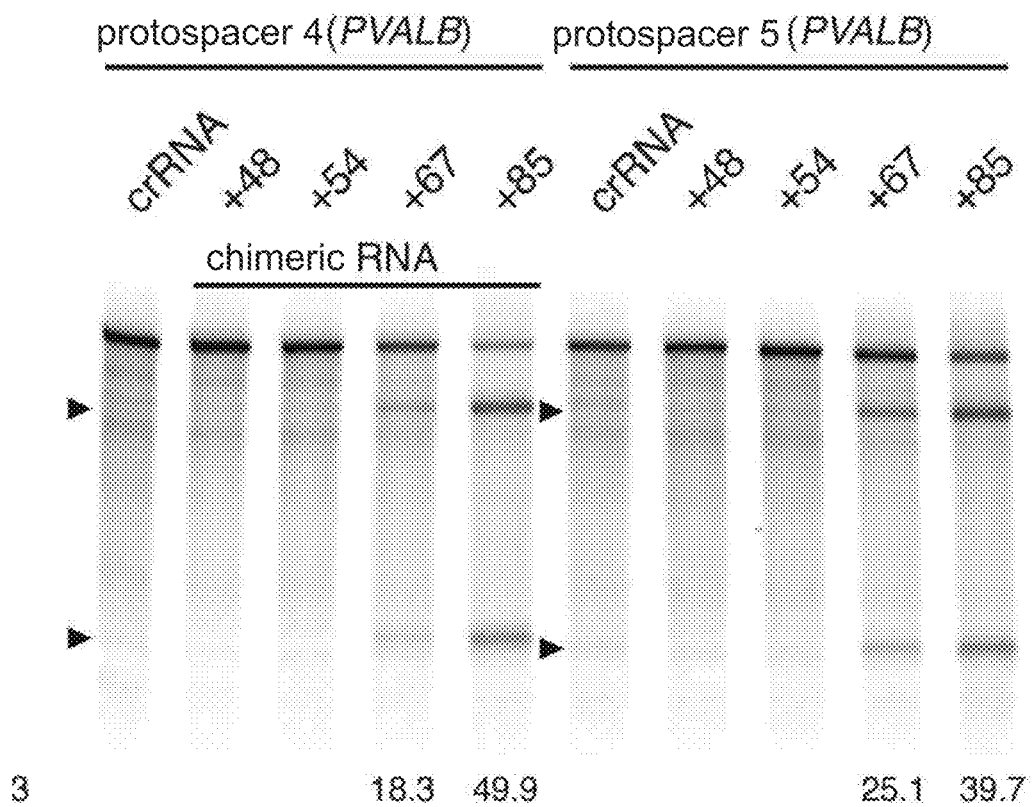

This example describes results obtained for chimeric RNAs (chiRNAs; comprising a guide sequence, a tracr mate sequence, and a tracr sequence in a single transcript) having tracr sequences that incorporate different lengths of wild-type tracrRNA sequence. FIG. 16a illustrates a schematic of a bicistronic expression vector for chimeric RNA and Cas9. Cas9 is driven by the CBh promoter and the chimeric RNA is driven by a U6 promoter. The chimeric guide RNA consists of a 20 bp guide sequence (Ns) joined to the tracr sequence (running from the first "U" of the lower strand to the end of the transcript), which is truncated at various positions as indicated. The guide and tracr sequences are separated by the tracr-mate sequence GUUUUAGAGCUA (SEQ ID NO: 61) followed by the loop sequence GAAA. Results of SURVEYOR assays for Cas9-mediated indels at the human EMX1 and PVALB loci are illustrated in FIGS. 16b and 16c, respectively. Arrows indicate the expected SURVEYOR fragments. ChiRNAs are indicated by their "+n" designation, and crRNA refers to a hybrid RNA where guide and tracr sequences are expressed as separate transcripts. Quantification of these results, performed in triplicate, are illustrated by histogram in FIGS. 17a and 17b, corresponding to FIGS. 16b and 16c, respectively ("N.D." indicates no indels detected). Protospacer IDs and their corresponding genomic target, protospacer sequence, PAM sequence, and strand location are provided in Table D. Guide sequences were designed to be complementary to the entire protospacer sequence in the case of separate transcripts in the hybrid system, or only to the underlined portion in the case of chimeric RNAs.

TABLE D

| protospacer ID | genomic target | protospacer sequence (5' to 3') | PAM | SEQ ID NO: | strand |
|---|---|---|---|---|---|
| 1 | EMX1 | GGACATCGAT<u>GTCACCTCCAATGACTAGGG</u> | TGG | 91 | + |
| 2 | EMX1 | CATTGGAGGT<u>GACATCGATGTCCTCCCCAT</u> | TGG | 92 | − |
| 3 | EMX1 | GGAAGGGCCT<u>GAGTCCGAGCAGAAGAAGAA</u> | GGG | 93 | + |
| 4 | PVALB | GGTGGCGAGA<u>GGGGCCGAGATTGGGTGTTC</u> | AGG | 94 | + |
| 5 | PVALB | ATGCAGGAGG<u>GTGGCGAGAGGGGCCGAGAT</u> | TGG | 95 | + |

Further details to optimize guide sequences can be found in U.S. application Ser. No. 61/836,127; Broad Reference BI-2013/004G); incorporated herein by reference.

Figure 17B:
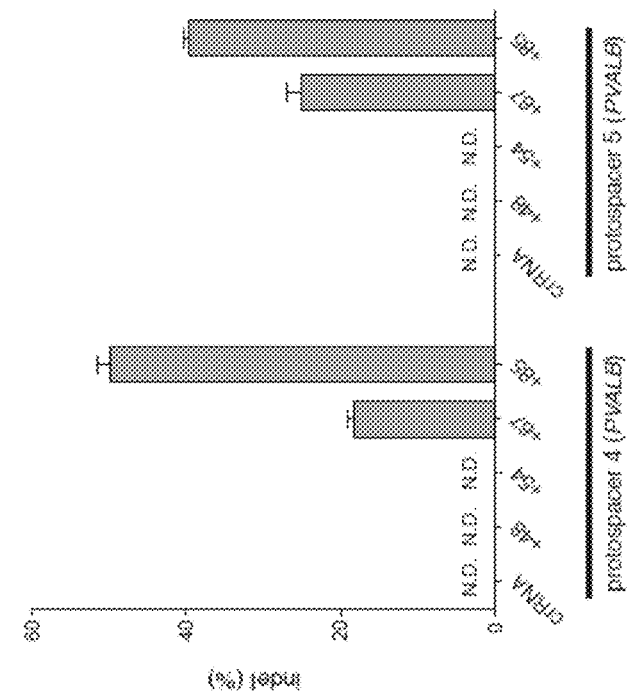
FIG. 17A-B shows a graphical representation of the results of SURVEYOR assays for CRISPR system activity in eukaryotic cells.
Figure 17A:
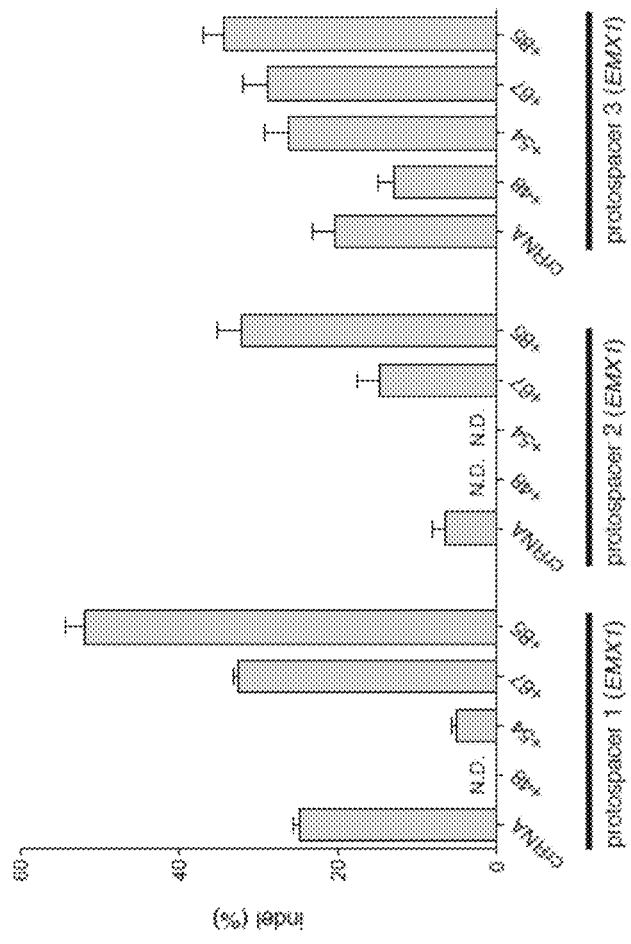

Initially, three sites within the EMX1 locus in human HEK 293FT cells were targeted. Genome modification efficiency of each chiRNA was assessed using the SURVEYOR nuclease assay, which detects mutations resulting from DNA double-strand breaks (DSBs) and their subsequent repair by the non-homologous end joining (NHEJ) DNA damage repair pathway. Constructs designated chiRNA(+n) indicate that up to the +n nucleotide of wild-type tracrRNA is included in the chimeric RNA construct, with values of 48, 54, 67, and 85 used for n. Chimeric RNAs containing longer fragments of wild-type tracrRNA (chiRNA(+67) and chiRNA(+85)) mediated DNA cleavage at all three EMX1 target sites, with chiRNA(+85) in particular demonstrating significantly higher levels of DNA cleavage than the corresponding crRNA/tracrRNA hybrids that expressed guide and tracr sequences in separate transcripts (FIGS. 16b and 17a). Two sites in the PVALB locus that yielded no detectable cleavage using the hybrid system (guide sequence and tracr sequence expressed as separate transcripts) were also targeted using chiRNAs. chiRNA(+67) and chiRNA(+85) were able to mediate significant cleavage at the two PVALB protospacers (FIGS. 16c and 17b).

For all five targets in the EMX1 and PVALB loci, a consistent increase in genome modification efficiency with increasing tracr sequence length was observed. Without wishing to be bound by any theory, the secondary structure formed by the 3' end of the tracrRNA may play a role in enhancing the rate of CRISPR complex formation.

Example 5: Cas9 Diversity

The CRISPR-Cas system is an adaptive immune mechanism against invading exogenous DNA employed by diverse species across bacteria and archaea. The type II CRISPR-Cas9 system consists of a set of genes encoding proteins responsible for the "acquisition" of foreign DNA into the CRISPR locus, as well as a set of genes encoding the "execution" of the DNA cleavage mechanism; these include the DNA nuclease (Cas9), a non-coding transactivating cr-RNA (tracrRNA), and an array of foreign DNA-derived spacers flanked by direct repeats (crRNAs). Upon maturation by Cas9, the tracRNA and crRNA duplex guide the Cas9 nuclease to a target DNA sequence specified by the spacer guide sequences, and mediates double-stranded breaks in the DNA near a short sequence motif in the target DNA that is required for cleavage and specific to each CRISPR-Cas system. The type II CRISPR-Cas systems are found throughout the bacterial kingdom and highly diverse in in Cas9 protein sequence and size, tracrRNA and crRNA direct repeat sequence, genome organization of these elements, and the motif requirement for target cleavage. One species may have multiple distinct CRISPR-Cas systems.

Applicants evaluated 207 putative Cas9s from bacterial species identified based on sequence homology to known Cas9s and structures orthologous to known subdomains, including the HNH endonuclease domain and the RuvC endonuclease domains [information from the Eugene Koonin and Kira Makarova]. Phylogenetic analysis based on the protein sequence conservation of this set revealed five families of Cas9s, including three groups of large Cas9s (1400 amino acids) and two of small Cas9s (1100 amino acids) (see FIGS. 19 and 20A-F).

Further details of Cas9s and mutations of the Cas9 enzyme to convert into a nickase or DNA binding protein and use of same with altered functionality can be found in U.S. application Ser. Nos. 61/836,101 and 61/835,936 and Broad Reference BI-2013/004E and BI-2013/004F respectively) incorporated herein by reference.

Example 6: Cas9 Orthologs

Applicants analyzed Cas9 orthologs to identify the relevant PAM sequences and the corresponding chimeric guide RNA. Having an expanded set of PAMs provides broader targeting across the genome and also significantly increases the number of unique target sites and provides potential for identifying novel Cas9s with increased levels of specificity in the genome.

The specificity of Cas9 orthologs can be evaluated by testing the ability of each Cas9 to tolerate mismatches between the guide RNA and its DNA target. For example, the specificity of SpCas9 has been characterized by testing the effect of mutations in the guide RNA on cleavage efficiency. Libraries of guide RNAs were made with single or multiple mismatches between the guide sequence and the target DNA. Based on these findings, target sites for SpCas9 can be selected based on the following guidelines:

To maximize SpCas9 specificity for editing a particular gene, one should choose a target site within the locus of interest such that potential 'off-target' genomic sequences abide by the following four constraints: First and foremost, they should not be followed by a PAM with either 5'-NGG or NAG sequences. Second, their global sequence similarity to the target sequence should be minimized. Third, a maximal number of mismatches should lie within the PAM-proximal region of the off-target site. Finally, a maximal number of mismatches should be consecutive or spaced less than four bases apart.

Similar methods can be used to evaluate the specificity of other Cas9 orthologs and to establish criteria for the selection of specific target sites within the genomes of target species. As mentioned previously phylogenetic analysis based on the protein sequence conservation of this set revealed five families of Cas9s, including three groups of large Cas9s (~1400 amino acids) and two of small Cas9s (~1100 amino acids) (see FIGS. 19 and 20A-F). Further details on Cas orthologs can be found in U.S. application Serial Nos 61/836,101 and 61/835,936 and Broad Reference BI-2013/004E and BI-2013/004F respectively) incorporated herein by reference.

Example 7: Methodological Improvement to Simplify Cloning and Delivery

Rather than encoding the U6-promoter and guide RNA on a plasmid, Applicants amplified the U6 promoter with a DNA oligo to add on the guide RNA. The resulting PCR product may be transfected into cells to drive expression of the guide RNA.

Example primer pair that allows the generation a PCR product consisting of U6-promoter::guideRNA targeting human Emx1 locus:

Forward Primer: AAACTCTAGAgagggcctatttcccatgattc (SEQ ID NO: 96)

Reverse Primer (carrying the guide RNA, which is underlined):

```
                                        (SEQ ID NO: 97)
acctctagAAAAAAAGCACCGACTCGGTGCCACTTTTTCAAGTTGATAAC

GGACTAGCCTTATTTTAACTTGCTATGCTGTTTTGTTTCCAAAACAGCAT

AGCTCTAAAACCCCTAGTCATTGGAGGTGACGGTGTTTCGTCCTTTCCA

Caag
```

Example 8: Methodological Improvement to Improve Activity

Rather than use pol3 promoters, in particular RNA polymerase III (e.g. U6 or H1 promoters), to express guide RNAs in eukaryotic cells, Applicants express the T7 polymerase in eukaryotic cells to drive expression of guide RNAs using the T7 promoter.

One example of this system may involve introduction of three pieces of DNA:

1. expression vector for Cas9
2. expression vector for T7 polymerase
3. expression vector containing guideRNA fused to the T7 promoter

Example 9: Methodological Improvement to Reduce Toxicity of Cas9: Delivery of Cas9 in the Form of mRNA Delivery of Cas9 in the form of mRNA enables transient expression of Cas9 in cells, to reduce toxicity. For example, humanized SpCas9 may be amplified using the following primer pair:

Forward Primer (to add on T7 promoter for in vitro transcription):

```
                                        (SEQ ID NO: 98)
TAATACGACTCACTATAGGAAGTGCGCCACCATGGCCCCAAAGAAGAAGC

GG
```

Reverse Primer (to add on polyA tail):

```
                                        (SEQ ID NO: 99)
GGTTTTTTTTTTTTTTTTTTTTTTTTTTTTTTttcttaCTTTTTCTTTT

TTGCCTGGCCG
```

Applicants transfect the Cas9 mRNA into cells with either guide RNA in the form of RNA or DNA cassettes to drive guide RNA expression in eukaryotic cells.

Example 10: Methodological Improvement to Reduce Toxicity of Cas9: Use of an Inducible Promoter Applicants transiently turn on Cas9 expression only when it is needed for carrying out genome modification. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome).

Example 11: Improvement of the Cas9 System for In Vivo Application

Figure 23:
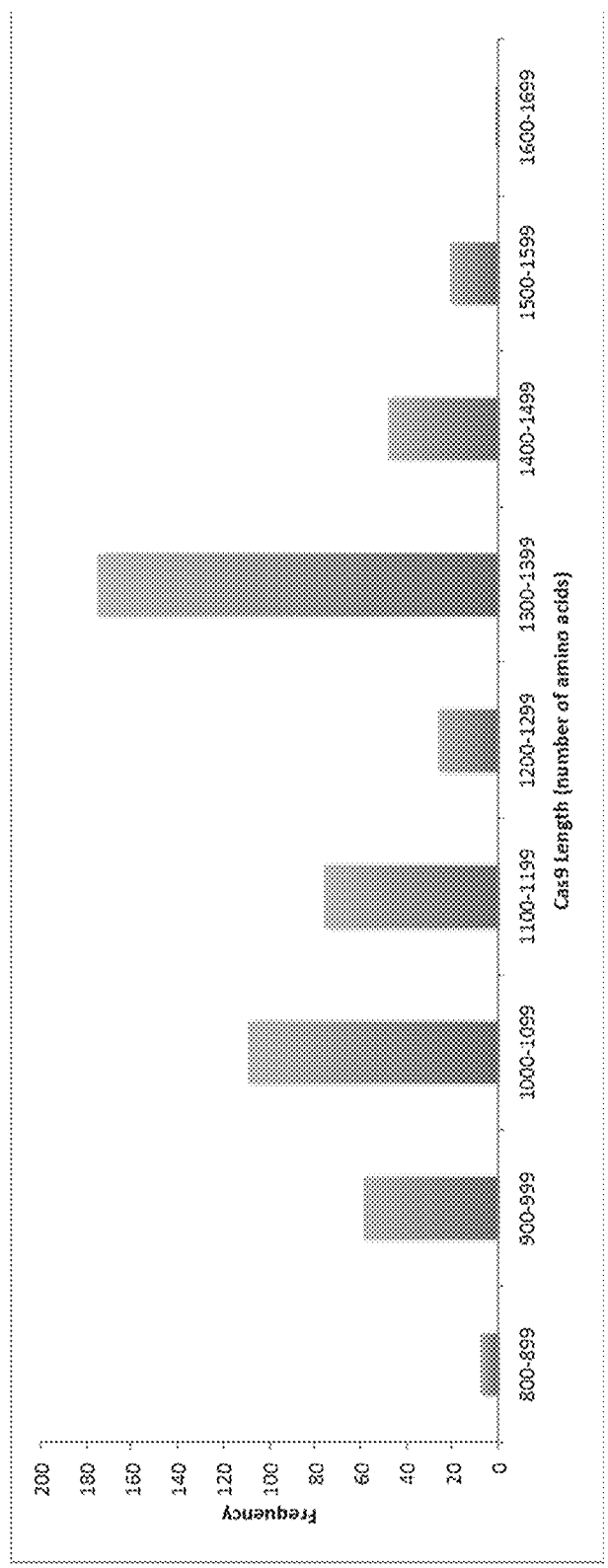
FIG. 23 shows a graph representing the length distribution of Cas9 orthologs.

Applicants conducted a Metagenomic search for a Cas9 with small molecular weight. Most Cas9 homologs are fairly large. For example the SpCas9 is around 1368aa long, which is too large to be easily packaged into viral vectors for delivery. A graph representing the length distribution of Cas9-homologs is generated from sequences deposited in GenBank (FIG. 23). Some of the sequences may have been mis-annotated and therefore the exact frequency for each length may not necessarily be accurate. Nevertheless it provides a glimpse at distribution of Cas9 proteins and suggest that there are shorter Cas9 homologs.

Through computational analysis, Applicants found that in the bacterial strain *Campylobacter*, there are two Cas9 proteins with less than 1000 amino acids. The sequence for one Cas9 from *Campylobacter jejuni* is presented below. At this length, CjCas9 can be easily packaged into AAV, lentiviruses, Adenoviruses, and other viral vectors for robust delivery into primary cells and in vivo in animal models. In a preferred embodiment of the invention, the Cas9 protein from *S. aureus* is used.

*Campylobacter jejuni* Cas9 (CjCas9)

```
                                       (SEQ ID NO: 100)
MARILAFDIGISSIGWAFSENDELKDCGVRIFTKVENPKTGESLALPRRL

ARSARKRLARRKARLNHLKHLIANEFKLNYEDYQSFDESLAKAYKGSLIS

PYELRFRALNELLSKQDFARVILHIAKRRGYDDIKNSDDKEKGAILKAIK

QNEEKLANYQSVGEYLYKEYFQKFKENSKEFTNVRNKKESYERCIAQSFL

KDELKLIFKKQREFGFSFSKKFEEEVLSVAFYKRALKDFSHLVGNCSFFT

DEKRAPKNSPLAFMFVALTRIINLLNNLKNTEGILYTKDDLNALLNEVLK

NGTLTYKQTKKLLGLSDDYEFKGEKGTYFIEFKKYKEFIKALGEHNLSQD

DLNEIAKDITLIKDEIKLKKALAKYDLNQNQIDSLSKLEFKDHLNISFKA
```

LKLVTPLMLEGKKYDEACNELNLKVAINEDKKDFLPAFNETYYKDEVTNP

VVLRAIKEYRKVLNALLKKYGKVHKINIELAREVGKNHSQRAKIEKEQNE

NYKAKKDAELECEKLGLKINSKNILKLRLFKEQKEFCAYSGEKIKISDLQ

DEKMLEIDHIYPYSRSFDDSYMNKVLVFTKQNQEKLNQTPFEAFGNDSAK

WQKIEVLAKNLPTKKQKRILDKNYKDKEQKNFKDRNLNDTRYIARLVLNY

TKDYLDFLPLSDDENTKLNDTQKGSKVHVEAKSGMLTSALRHTWGFSAKD

RNNHLHHAIDAVIIAYANNSIVKAFSDFKKEQESNSAELYAKKISELDYK

NKRKFFEPFSGFRQKVLDKIDEIFVSKPERKKPSGALHEETFRKEEEFYQ

SYGGKEGVLKALELGKIRKVNGKIVKNGDMFRVDIFKHKKTNKFYAVPIY

TMDFALKVLPNKAVARSKKGEIKDWILMDENYEFCFSLYKDSLILIQTKD

MQEPEFVYYNAFTSSTVSLIVSKHDNKFETLSKNQKILFKNANEKEVIAK

SIGIQNLKVFEKYIVSALGEVTKAEFRQREDFKK.

The putative tracrRNA element for this CjCas9 is:

(SEQ ID NO: 101)
TATAATCTCATAAGAAATTTAAAAAGGGACTAAAATAAAGAGTTTGCG

GGACTCTGCGGGGTTACAATCCCCTAAAACCGCTTTTAAAATT

The Direct Repeat sequence is:

(SEQ ID NO: 102)
ATTTTACCATAAAGAAATTTAAAAAGGGACTAAAAC

An example of a chimeric guideRNA for CjCas9 is:

(SEQ ID NO: 103)
NNNNNNNNNNNNNNNNNNNNGUUUUAGUCCCGAAAGGGACUAAAAU

AAAGAGUUUGCGGGACUCUGCGGGGUUACAAUCCCCUAAAACCGCUUUU

Example 12: Cas9 Optimization

For enhanced function or to develop new functions, Applicants generate chimeric Cas9 proteins by combining fragments from different Cas9 homologs. For example, two example chimeric Cas9 proteins:

For example, Applicants fused the N-term of St1Cas9 (fragment from this protein is in bold) with C-term of SpCas9 (fragment from this protein is underlined).

St1(N)Sp(C)Cas9

(SEQ ID NO: 104)
MSDLVLGLDIGIGSVGVGILNKVTGEIIHKNSRIFPAAQAENNLVRRTN

RQGRRLARRKKHRRVRLNRLFEESGLITDFTKISINLNPYQLRVKGLTDE

LSNEELFIALKNMVKHRGISYLDDASDDGNSSVGDYAQIVKENSKQLETK

TPGQIQLERYQTYGQLRGDFTVEKDGKKHRLINVFPTSAYRSEALRILQT

QQEFNPQITDEFINRYLEILTGKRKYYHGPGNEKSRTDYGRYRTSGETLD

NIFGILIGKCTFYPDEFRAAKASYTAQEFNLLNDLNNLTVPTETKKLSKE

QKNQIINYVKNEKAMGPAKLFKYIAKLLSCDVADIKGYRIDKSGKAEIHT

FEAYRKMKTLETLDIEQMDRETLDKLAYVLTLNTEREGIQEALEHEFADG

SFSQKQVDELVQFRKANSSIFGKGWHNFSVKLMMELIPELYETSEEQMTI

LTRLGKQKTTSSSNKTKYIDEKLLTEEIYNPVVAKSVRQAIKIVNAAIKE

YGDFDNIVIEMARENQTTQKGQKNSRERMKRIEEGIKELGSQILKEHPVE

NTQLQNEKLYLYYLQNGRDMYVDQELDINRLSDYDVDHIVPQSFLKDDSI

DNKVLTRSDKNRGKSDNVPSEEVVKKMKNYWRQLLNAKLITQRKFDNLTK

AERGGLSELDKAGFIKRQLVETRQITKHVAQILDSRMNTKYDENDKLIRE

VKVITLKSKLVSDFRKDFQFYKVREINNYHHAHDAYLNAVVGTALIKKYP

KLESEFVYGDYKVYDVRKMIAKSEQEIGKATAKYFFYSNIMNFFKTEITL

ANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYS

LFELENGRKRMLASAGELQKGNELALPSKYVNFLYLASHYEKLKGSPEDN

EQKQLFVEQHKHYLDEIIEQISEFSKRVILADANLDKVLSAYNKHRDKPI

REQAENIIHLFTLTNLGAPAAFKYFDTTIDRKRYTSTKEVLDATLIHQSI

TGLYETRIDLSQLGGD

Sp(N)St1(C)Cas9

(SEQ ID NO: 105)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARETNEDDEKKAIQKIQKANKDEKDAAMLKAANQYNG

KAELPHSVFHGHKQLATKIRLWHQQGERCLYTGKTISIHDLINNSNQFEV

DHILPLSITFDDSLANKVLVYATANQEKGQRTPYQALDSMDDAWSFRELK

AFVRESKTLSNKKKEYLLTEEDISKFDVRKKFIERNLVDTRYASRVVLNA

LQEHFRAHKIDTKVSVVRGQFTSQLRRHWGIEKTRDTYHHHAVDALIIAA

SSQLNLWKKQKNTLVSYSEDQLLDIETGELISDDEYKESVFKAPYQHFVD

TLKSKEFEDSILFSYQVDSKFNRKISDATIYATRQAKVGKDKADETYVLG

KIKDIYTQDGYDAFMKIYKKDKSKFLMYRHDPQTFEKVIEPILENYPNKQ

-continued

INEKGKEVPCNPFLKYKEEHGYIRKYSKKGNGPEIKSLKYYDSKLGNHID

ITPKDSNNKVVLQSVSPWRADVYFNKTTGKYEILGLKYADLQFEKGTGTY

KISQEKYNDIKKKEGVDSDSEFKFTLYKNDLLLVKDTETKEQQLFRFLSR

TMPKQKHYVELKPYDKQKFEGGEALIKVLGNVANSGQCKKGLGKSNISIY

KVRTDVLGNQHIIKNEGDKPKLDF

The benefit of making chimeric Cas9 include:
reduce toxicity
improve expression in eukaryotic cells
enhance specificity
reduce molecular weight of protein, make protein smaller by combining the smallest domains from different Cas9 homologs.
Altering the PAM sequence requirement Example 13: Utilization of Cas9 as a Generic DNA Binding Protein Applicants used Cas9 as a generic DNA binding protein by mutating the two catalytic domains (D10 and H840) responsible for cleaving both strands of the DNA target. In order to upregulate gene transcription at a target locus Applicants fused the transcriptional activation domain (VP64) to Cas9. Applicants hypothesized that it would be important to see strong nuclear localization of the Cas9-VP64 fusion protein because transcription factor activation strength is a function of time spent at the target. Therefore, Applicants cloned a set of Cas9-VP64-GFP constructs, transfected them into 293 cells and assessed their localization under a fluorescent microscope 12 hours post-transfection.

The same constructs were cloned as a 2A-GFP rather than a direct fusion in order to functionally test the constructs without a bulky GFP present to interfere. Applicants elected to target the Sox2 locus with the Cas9 transactivator because it could be useful for cellular reprogram and the locus has already been validated as a target for TALE-TF mediated transcriptional activation. For the Sox2 locus Applicants chose eight targets near the transcriptional start site (TSS). Each target was 20 bp long with a neighboring NGG protospacer adjacent motif (PAM). Each Cas9-VP64 construct was co-transfected with each PCR generated chimeric crispr RNA (chiRNA) in 293 cells. 72 hours post transfection the transcriptional activation was assessed using RT-qPCR.

To further optimize the transcriptional activator, Applicants titrated the ratio of chiRNA (Sox2.1 and Sox2.5) to Cas9 (NLS-VP64-NLS-hSpCas9-NLS-VP64-NLS), transfected into 293 cells, and quantified using RT-qPCR. These results indicate that Cas9 can be used as a generic DNA binding domain to upregulate gene transcription at a target locus.

Applicants designed a second generation of constructs. (Table below).

pLenti-EF1a-GFP-2A-6xHis-NLS-VP64-NLS-hSpCsn1(D10A, H840A)-NLS ("6xHis" disclosed as SEQ ID NO: 370)
pLenti-EF1a-GFP-2A-6xHis-NLS-VP64-NLS-hSpCsn1(D10A, H840A) ("6xHis" disclosed as SEQ ID NO: 370)
pLenti-EF1a-GFP-2A-6xHis-NLS-VP64-NLS-NLS-hSpCsn1(D10A, H840A) ("6xHis" disclosed as SEQ ID NO: 370)
pLenti-EF1a-GFP-2A-6xHis-NLS-hSpCsn1(D10A, H840A)-NLS ("6xHis" disclosed as SEQ ID NO: 370)
pLenti-EF1a-GFP-2A-6xHis-NLS-hSpCsn1(D10A, H840A) ("6xHis" disclosed as SEQ ID NO: 370)
pLenti-EF1a-GFP-2A-6xHis-NLS-NLS-hSpCsn1(D10A, H840A) ("6xHis" disclosed as SEQ ID NO: 370)

Applicants use these constructs to assess transcriptional activation (VP64 fused constructs) and repression (Cas9 only) by RT-qPCR. Applicants assess the cellular localization of each construct using anti-His antibody, nuclease activity using a Surveyor nuclease assay, and DNA binding affinity using a gel shift assay. In a preferred embodiment of the invention, the gel shift assay is an EMSA gel shift assay.

Example 14: Cas9 Transgenic and Knock in Mice

To generate a mouse that expresses the Cas9 nuclease Applicants submit two general strategies, transgenic and knock in. These strategies may be applied to generate any other model organism of interest, for e.g. Rat. For each of the general strategies Applicants made a constitutively active Cas9 and a Cas9 that is conditionally expressed (Cre recombinase dependent). The constitutively active Cas9 nuclease is expressed in the following context: pCAG-NLS-Cas9-NLS-P2A-EGFP-WPRE-bGHpolyA. pCAG is the promoter, NLS is a nuclear localization signal, P2A is the peptide cleavage sequence, EGFP is enhanced green fluorescent protein, WPRE is the woodchuck hepatitis virus posttranscriptional regulatory element, and bGHpolyA is the bovine growth hormone poly-A signal sequence (FIGS. 25A-B). The conditional version has one additional stop cassette element, loxP-SV40 polyA x3-loxP, after the promoter and before NLS-Cas9-NLS (i.e. pCAG-loxP-SV40polyAx3-loxP-NLS-Cas9-NLS-P2A-EGFP-WPRE-bGHpolyA). The important expression elements can be visualized as in FIG. 26. The constitutive construct should be expressed in all cell types throughout development, whereas, the conditional construct will only allow Cas9 expression when the same cell is expressing the Cre recombinase. This latter version will allow for tissue specific expression of Cas9 when Cre is under the expression of a tissue specific promoter. Moreover, Cas9 expression could be induced in adult mice by putting Cre under the expression of an inducible promoter such as the TET on or off system.

Validation of Cas9 constructs: Each plasmid was functionally validated in three ways: 1) transient transfection in 293 cells followed by confirmation of GFP expression; 2) transient transfection in 293 cells followed by immunofluorescence using an antibody recognizing the P2A sequence; and 3) transient transfection followed by Surveyor nuclease assay. The 293 cells may be 293FT or 293 T cells depending on the cells that are of interest. In a preferred embodiment the cells are 293FT cells. The results of the Surveyor were run out on the top and bottom row of the gel for the conditional and constitutive constructs, respectively. Each was tested in the presence and absence of chimeric RNA targeted to the hEMX1 locus (chimeric RNA hEMX1.1). The results indicate that the construct can successfully target the hEMX1 locus only in the presence of chimeric RNA (and Cre in the conditional case). The gel was quantified and the results are presented as average cutting efficiency and standard deviation for three samples.

Transgenic Cas9 mouse: To generate transgenic mice with constructs, Applicants inject pure, linear DNA into the pronucleus of a zygote from a pseudo pregnant CB56 female. Founders are identified, genotyped, and backcrossed to CB57 mice. The constructs were successfully cloned and verified by Sanger sequencing.

Knock in Cas9 mouse: To generate Cas9 knock in mice Applicants target the same constitutive and conditional constructs to the Rosa26 locus. Applicants did this by cloning each into a Rosa26 targeting vector with the following elements: Rosa26 short homology arm—constitutive/conditional Cas9 expression cassette—pPGK-Neo-Rosa26 long homology arm—pPGK-DTA. pPGK is the promoter for the positive selection marker Neo, which confers resistance to neomycin, a 1 kb short arm, a 4.3 kb long arm, and a negative selection diphtheria toxin (DTA) driven by PGK.

The two constructs were electroporated into R1 mESCs and allowed to grow for 2 days before neomycin selection was applied. Individual colonies that had survived by days 5-7 were picked and grown in individual wells. 5-7 days later the colonies were harvested, half were frozen and the other half were used for genotyping. Genotyping was done by genomic PCR, where one primer annealed within the donor plasmid (AttpF) and the other outside of the short homology arm (Rosa26-R) Of the 22 colonies harvested for the conditional case, 7 were positive (Left). Of the 27 colonies harvested for the constitutive case, zero were positive (Right). It is likely that Cas9 causes some level of toxicity in the mESC and for this reason there were no positive clones. To test this Applicants introduced a Cre expression plasmid into correctly targeted conditional Cas9 cells and found very low toxicity after many days in culture. The reduced copy number of Cas9 in correctly targeted conditional Cas9 cells (1-2 copies per cell) is enough to allow stable expression and relatively no cytotoxicity. Moreover, this data indicates that the Cas9 copy number determines toxicity. After electroporation each cell should get several copies of Cas9 and this is likely why no positive colonies were found in the case of the constitutive Cas9 construct. This provides strong evidence that utilizing a conditional, Cre-dependent strategy should show reduced toxicity. Applicants inject correctly targeted cells into a blastocyst and implant into a female mouse. Chimerics are identified and backcrossed. Founders are identified and genotyped.

Utility of the conditional Cas9 mouse: Applicants have shown in 293 cells that the Cas9 conditional expression construct can be activated by co-expression with Cre. Applicants also show that the correctly targeted R1 mESCs can have active Cas9 when Cre is expressed. Because Cas9 is followed by the P2A peptide cleavage sequence and then EGFP Applicants identify successful expression by observing EGFP. This same concept is what makes the conditional Cas9 mouse so useful. Applicants may cross their conditional Cas9 mouse with a mouse that ubiquitously expresses Cre (ACTB-Cre line) and may arrive at a mouse that expresses Cas9 in every cell. It should only take the delivery of chimeric RNA to induce genome editing in embryonic or adult mice. Interestingly, if the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue.

Example 15: Cas9 Diversity and Chimeric RNAs

The CRISPR-Cas system is an adaptive immune mechanism against invading exogenous DNA employed by diverse species across bacteria and archaea. The type II CRISPR-Cas system consists of a set of genes encoding proteins responsible for the "acquisition" of foreign DNA into the CRISPR locus, as well as a set of genes encoding the "execution" of the DNA cleavage mechanism; these include the DNA nuclease (Cas9), a non-coding transactivating cr-RNA (tracrRNA), and an array of foreign DNA-derived spacers flanked by direct repeats (crRNAs). Upon maturation by Cas9, the tracrRNA and crRNA duplex guide the Cas9 nuclease to a target DNA sequence specified by the spacer guide sequences, and mediates double-stranded breaks in the DNA near a short sequence motif in the target DNA that is required for cleavage and specific to each CRISPR-Cas system. The type II CRISPR-Cas systems are found throughout the bacterial kingdom and highly diverse in in Cas9 protein sequence and size, tracrRNA and crRNA direct repeat sequence, genome organization of these elements, and the motif requirement for target cleavage. One species may have multiple distinct CRISPR-Cas systems.

Applicants evaluated 207 putative Cas9s from bacterial species identified based on sequence homology to known Cas9s and structures orthologous to known subdomains, including the HNH endonuclease domain and the RuvC endonuclease domains [information from the Eugene Koonin and Kira Makarova]. Phylogenetic analysis based on the protein sequence conservation of this set revealed five families of Cas9s, including three groups of large Cas9s (~1400 amino acids) and two of small Cas9s (~1100 amino acids) (FIGS. 19A-D and 20A-F).

Applicants have also optimized Cas9 guide RNA using in vitro methods.

Example 16: Cas9 Mutations

In this example, Applicants show that the following mutations can convert SpCas9 into a nicking enzyme: D10A, E762A, H840A, N854A, N863A, D986A.

Applicants provide sequences showing where the mutation points are located within the SpCas9 gene (FIG. 24A-M). Applicants also show that the nickases are still able to mediate homologous recombination. Furthermore, Applicants show that SpCas9 with these mutations (individually) do not induce double strand break.

Cas9 orthologs all share the general organization of 3-4 RuvC domains and a HNH domain. The 5' most RuvC domain cleaves the non-complementary strand, and the HNH domain cleaves the complementary strand. All notations are in reference to the guide sequence.

The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Franciscilla novicida* type II CRISPR locus), and the conserved Asp residue is mutated to alanine to convert Cas9 into a complementary-strand nicking enzyme. Similarly, the conserved His and Asn residues in the HNH domains are mutated to Alanine to convert Cas9 into a non-complementary-strand nicking enzyme.

Example 17: Cas9 Transcriptional Activation and Cas9 Repressor

Cas9 Transcriptional Activation

A second generation of constructs were designed and tested (Table 1). These constructs are used to assess transcriptional activation (VP64 fused constructs) and repression (Cas9 only) by RT-qPCR. Applicants assess the cellular localization of each construct using anti-His antibody, nuclease activity using a Surveyor nuclease assay, and DNA binding affinity using a gel shift assay.

Cas Repressor

It has been shown previously that dCas9 can be used as a generic DNA binding domain to repress gene expression. Applicants report an improved dCas9 design as well as dCas9 fusions to the repressor domains KRAB and SID4x. From the plasmid library created for modulating transcription using Cas9 in Table 1, the following repressor plasmids were functionally characterized by qPCR: pXRP27, pXRP28, pXRP29, pXRP48, pXRP49, pXRP50, pXRP51, pXRP52, pXRP53, pXRP56, pXRP58, pXRP59, pXRP61, and pXRP62.

Each dCas9 repressor plasmid was co-transfected with two guide RNAs targeted to the coding strand of the beta-catenin gene. RNA was isolated 72 hours after transfection and gene expression was quantified by RT-qPCR. The endogenous control gene was GAPDH. Two validated shRNAs were used as positive controls. Negative controls were certain plasmids transfected without gRNA, these are denoted as "pXRP ## control". The plasmids pXRP28, pXRP29, pXRP48, and pXRP49 could repress the beta-catenin gene when using the specified targeting strategy. These plasmids correspond to dCas9 without a functional domain (pXRP28 and pXRP28) and dCas9 fused to SID4x (pXRP48 and pXRP49).

Further work investigates: repeating the above experiment, targeting different genes, utilizing other gRNAs to determine the optimal targeting position, and multiplexed repression.

TABLE 1

(Table 1 discloses "GGGGS$_3$" as SEQ ID NO: 106, "EAAAK$_3$" as SEQ ID NO: 107 and "GGGGGS$_3$" as SEQ ID NO: 108)

pXRP024-pLenti2-EF1a-VP64-NLS-FLAG-Linker-dCas9-NLS-gLuc-2A-GFP-WPRE pXRP025-pLenti2-EF1a-VP64-NLS-GGGGS$_3$Linker-dCas9-NLS-gLuc-2A-GFP-WPRE pXRP026-pLenti2-EF1a-VP64-NLS-EAAAK$_3$Linker-dCas9-NLS-gLuc-2A-GFP-WPRE pXRP027-pLenti2-EF1a-NLS-FLAG-Linker-dCas9-NLS-gLuc-2A-GFP-WPRE pXRP028-pLenti2-EF1a-NLS-GGGGS$_3$Linker-dCas9-NLS-gLuc-2A-GFP-WPRE pXRP029-pLenti2-EF1a-NLS-EAAAK$_3$Linker-dCas9-NLS-gLuc-2A-GFP-WPRE pXRP030-pLenti2-pSV40-VP64-NLS-FLAG-Linker-dCas9-NLS-gLuc-2A-GFP-WPRE pXRP031-pLenti2-pPGK-VP64-NLS-FLAG-Linker-dCas9-NLS-gLuc-2A-GFP-WPRE pXRP032-pLenti2-LTR-VP64-NLS-FLAG-Linker-dCas9-NLS-gLuc-2A-GFP-WPRE pXRP033-pLenti2-pSV40-VP64-NLS-GGGGS$_3$Linker-dCas9-NLS-gLuc-2A-GFP-WPRE pXRP034-pLenti2-pPGK-VP64-NLS-GGGGS$_3$Linker-dCas9-NLS-gLuc-2A-GFP-WPRE pXRP035-pLenti2-LTR-VP64-NLS-GGGGS$_3$Linker-dCas9-NLS-gLuc-2A-GFP-WPRE pXRP036-pLenti2-pSV40-VP64-NLS-EAAAK$_3$Linker-dCas9-NLS-gLuc-2A-GFP-WPRE pXRP037-pLenti2-pPGK-VP64-NLS-EAAAK$_3$Linker-dCas9-NLS-gLuc-2A-GFP-WPRE pXRP038-pLenti2-LTR-VP64-NLS-EAAAK$_3$Linker-dCas9-NLS-gLuc-2A-GFP-WPRE pXRP048-pLenti2-EF1a-SID4x-NLS-FLAG-Linker-dCas9-NLS-gLuc-2A-GFP-WPRE pXRP049-pLenti2-EF1a-SID4X-NLS-GGGGS$_3$Linker-dCas9-NLS-gLuc-2A-GFP-WPRE pXRP050-pLenti2-EF1a-SID4X-NLS-EAAAK$_3$Linker-dCas9-NLS-gLuc-2A-GFP-WPRE pXRP051-pLenti2-EF1a-KRAB-NLS-FLAG-Linker-dCas9-NLS-gLuc-2A-GFP-WPRE pXRP052-pLenti2-EF1a-KRAB-NLS-GGGGS$_3$Linker-dCas9-NLS-gLuc-2A-GFP-WPRE pXRP053-pLenti2-EF1a-KRAB-NLS-EAAAK$_3$Linker-dCas9-NLS-gLuc-2A-GFP-WPRE pXRP054-pLenti2-EF1a-dCas9-Linker-FLAG-NLS-VP64-gLuc-2A-GFP-WPRE pXRP055-pLenti2-EF1a-dCas9-Linker-FLAG-NLS-SID4X-gLuc-2A-GFP-WPRE pXRP056-pLenti2-EF1a-dCas9-Linker-FLAG-NLS-KRAB-gLuc-2A-GFP-WPRE pXRP057-pLenti2-EF1a-dCas9-GGGGGS$_3$-NLS-VP64-gLuc-2A-GFP-WPRE pXRP058-pLenti2-EF1a-dCas9-GGGGGS$_3$-NLS-SID4X-gLuc-2A-GFP-WPRE pXRP059-pLenti2-EF1a-dCas9-GGGGGS$_3$-NLS-KRAB-gLuc-2A-GFP-WPRE pXRP060-pLenti2-EF1a-dCas9-EAAAK$_3$-NLS-VP64-gLuc-2A-GFP-WPRE pXRP061-pLenti2-EF1a-dCas9-EAAAK$_3$-NLS-SID4X-gLuc-2A-GFP-WPRE

TABLE 1-continued (Table 1 discloses "GGGGS₃" as SEQ ID NO: 106, "EAAAK₃" as SEQ ID NO: 107 and "GGGGGS₃" as SEQ ID NO: 108)

pXRP062-pLenti2-EF1a-dCas9-EAAAK₃-NLS-KRAB-gLuc-2A-GFP-WPRE pXRP024-pLenti2-EF1a-VP64-NLS-FLAG-Linker-Cas9-NLS-gLuc-2A-GFP-WPRE pXRP025-pLenti2-EF1a-VP64-NLS-GGGGS₃Linker-Cas9-NLS-gLuc-2A-GFP-WPRE pXRP026-pLenti2-EF1a-VP64-NLS-EAAAK₃Linker-Cas9-NLS-gLuc-2A-GFP-WPRE pXRP027-pLenti2-EF1a-NLS-FLAG-Linker-Cas9-NLS-gLuc-2A-GFP-WPRE pXRP028-pLenti2-EF1a-NLS-GGGGS₃Linker-Cas9-NLS-gLuc-2A-GFP-WPRE pXRP029-pLenti2-EF1a-NLS-EAAAK₃Linker-Cas9-NLS-gLuc-2A-GFP-WPRE pXRP030-pLenti2-pSV40-VP64-NLS-FLAG-Linker-Cas9-NLS-gLuc-2A-GFP-WPRE pXRP031-pLenti2-pPGK-VP64-NLS-FLAG-Linker-Cas9-NLS-gLuc-2A-GFP-WPRE pXRP032-pLenti2-LTR-VP64-NLS-FLAG-Linker-Cas9-NLS-gLuc-2A-GFP-WPRE pXRP033-pLenti2-pSV40-VP64-NLS-GGGGS₃Linker-Cas9-NLS-gLuc-2A-GFP-WPRE pXRP034-pLenti2-pPGK-VP64-NLS-GGGGS₃Linker-Cas9-NLS-gLuc-2A-GFP-WPRE pXRP035-pLenti2-LTR-VP64-NLS-GGGGS₃Linker-Cas9-NLS-gLuc-2A-GFP-WPRE pXRP036-pLenti2-pSV40-VP64-NLS-EAAAK₃Linker-Cas9-NLS-gLuc-2A-GFP-WPRE pXRP037-pLenti2-pPGK-VP64-NLS-EAAAK₃Linker-Cas9-NLS-gLuc-2A-GFP-WPRE pXRP038-pLenti2-LTR-VP64-NLS-EAAAK₃Linker-Cas9-NLS-gLuc-2A-GFP-WPRE pXRP048-pLenti2-EF1a-SID4x-NLS-FLAG-Linker-Cas9-NLS-gLuc-2A-GFP-WPRE pXRP049-pLenti2-EF1a-SID4X-NLS-GGGGS₃Linker-Cas9-NLS-gLuc-2A-GFP-WPRE pXRP050-pLenti2-EF1a-SID4X-NLS-EAAAK₃Linker-Cas9-NLS-gLuc-2A-GFP-WPRE pXRP051-pLenti2-EF1a-KRAB-NLS-FLAG-Linker-Cas9-NLS-gLuc-2A-GFP-WPRE pXRP052-pLenti2-EF1a-KRAB-NLS-GGGGS₃Linker-Cas9-NLS-gLuc-2A-GFP-WPRE pXRP053-pLenti2-EF1a-KRAB-NLS-EAAAK₃Linker-Cas9-NLS-gLuc-2A-GFP-WPRE pXRP054-pLenti2-EF1a-Cas9-Linker-FLAG-NLS-VP64-gLuc-2A-GFP-WPRE pXRP055-pLenti2-EF1a-Cas9-Linker-FLAG-NLS-SID4X-gLuc-2A-GFP-WPRE pXRP056-pLenti2-EF1a-Cas9-Linker-FLAG-NLS-KRAB-gLuc-2A-GFP-WPRE pXRP057-pLenti2-EF1a-Cas9-GGGGGS₃-NLS-VP64-gLuc-2A-GFP-WPRE pXRP058-pLenti2-EF1a-Cas9-GGGGGS₃-NLS-SID4X-gLuc-2A-GFP-WPRE pXRP059-pLenti2-EF1a-Cas9-GGGGGS₃-NLS-KRAB-gLuc-2A-GFP-WPRE pXRP060-pLenti2-EF1a-Cas9-EAAAK₃-NLS-VP64-gLuc-2A-GFP-WPRE pXRP061-pLenti2-EF1a-Cas9-EAAAK₃-NLS-SID4X-gLuc-2A-GFP-WPRE pXRP062-pLenti2-EF1a-Cas9-EAAAK₃-NLS-KRAB-gLuc-2A-GFP-WPRE Example 18: Targeted Deletion of Genes Involved in Cholesterol Biosynthesis, Fatty Acid Biosynthesis, and Other Metabolic Disorders, Genes Encoding Mis-Folded Proteins Involved in Amyloid and Other Diseases, Oncogenes Leading to Cellular Transformation, Latent Viral Genes, and Genes Leading to Dominant-Negative Disorders, Amongst Other Disorders Applicants demonstrate gene delivery of a CRISPR-Cas system in the liver, brain, ocular, epithelial, hematopoetic, or another tissue of a subject or a patient in need thereof, suffering from metabolic disorders, amyloidosis and protein-aggregation related diseases, cellular transformation arising from genetic mutations and translocations, dominant negative effects of gene mutations, latent viral infections, and other related symptoms, using either viral or nanoparticle delivery system.

Study Design: Subjects or patients in need thereof suffering from metabolic disorders, amyloidosis and protein aggregation related disease which include but are not limited to human, non-primate human, canine, feline, bovine, equine, other domestic animals and related mammals. The CRISPR-Cas system is guided by a chimeric guide RNA and targets a specific site of the human genomic loci to be cleaved. After cleavage and non-homologous end-joining mediated repair, frame-shift mutation results in knock out of genes.

Applicants select guide-RNAs targeting genes involved in above-mentioned disorders to be specific to endogenous loci with minimal off-target activity. Two or more guide RNAs may be encoded into a single CRISPR array to induce simultaneous double-stranded breaks in DNA leading to micro-deletions of affected genes or chromosomal regions.

Identification and Design of Gene Targets

For each candidate disease gene, Applicants select DNA sequences of interest include protein-coding exons, sequences including and flanking known dominant negative mutation sites, sequences including and flanking pathological repetitive sequences. For gene-knockout approaches, early coding exons closest to the start codon offer best options for achieving complete knockout and minimize possibility of truncated protein products retaining partial function.

Applicants analyze sequences of interest for all possible targetable 20-bp sequences immediately 5' to a NGG motif (for SpCas9 system) or a NNAGAAW (for St1Cas9 system). Applicants choose sequences for unique, single RNA-guided Cas9 recognition in the genome to minimize off-target effects based on computational algorithm to determine specificity.

Cloning of Guide Sequences into a Delivery System

Guide sequences are synthesized as double-stranded 20-24 bp oligonucleotides. After 5'-phosphorylation treatment of oligos and annealing to form duplexes, oligos are ligated into suitable vector depending on the delivery method:

Virus-Based Delivery Methods

AAV-based vectors (PX260, 330, 334, 335) have been described elsewhere

Lentiviral-based vectors use a similar cloning strategy of directly ligating guide sequences into a single vector carrying a U6 promoter-driven chimeric RNA scaffold and a EF1a promoter-driven Cas9 or Cas9 nickase.

Virus production is described elsewhere.

Nanoparticle-Based RNA Delivery Methods

1. Guide sequences are synthesized as an oligonucleotide duplex encoding T7 promoter-guide sequence-chimeric RNA. A T7 promoter is added 5' of Cas9 by PCR method.

2. T7-driven Cas9 and guide-chimeric RNAs are transcribed in vitro, and Cas9 mRNA is further capped and A-tailed using commercial kits. RNA products are purified per kit instructions.

Hydrodynamic Tail Vein Delivery Methods (for Mouse)

Guide sequences are cloned into AAV plasmids as described above and elsewhere in this application.

In Vitro Validation on Cell Lines

Transfection

1. DNA plasmid transfection

Plasmids Carrying Guide Sequences are Transfected into Human Embryonic Kidney (HEK293T) or human embryonic stem (hES) cells, other relevant cell types using lipid-, chemical-, or electroporation-based methods. For a 24-well transfection of HEK293T cells (~260,000 cells), 500 ng of total DNA is transfected into each single well using Lipofectamine 2000. For a 12-well transfection of hES cells, 1 μg of total DNA is transfected into a single well using Fugene HD.

2. RNA Transfection

Purified RNA described above is used for transfection into HEK293T cells. 1-2 ug of RNA may be transfected into 260,000 using Lipofectamine 2000 per manufacturer's instruction. RNA delivery of Cas9 and chimeric RNA is shown in FIG. 28.

Assay of Indel Formation In Vitro

Cells are harvested 72-hours post-transfection and assayed for indel formation as an indication of double-stranded breaks.

Briefly, genomic region around target sequence is PCR amplified (~400-600 bp amplicon size) using high-fidelity polymerase. Products are purified, normalized to equal concentration, and slowly annealed from 95° C. to 4° C. to allow formation of DNA heteroduplexes. Post annealing, the Cel-I enzyme is used to cleave heteroduplexes, and resulting products are separated on a polyacrylamide gel and indel efficiency calculated.

In Vivo Proof of Principle in Animal

Delivery Mechanisms

AAV or Lentivirus production is described elsewhere.

Nanoparticle formulation: RNA mixed into nanoparticle formulation

Hydrodynamic Tail Vein Injections with DNA Plasmids in Mice are Conducted Using a Commercial Kit Cas9 and guide sequences are delivered as virus, nanoparticle-coated RNA mixture, or DNA plasmids, and injected into subject animals. A parallel set of control animals is injected with sterile saline, Cas9 and GFP, or guide sequence and GFP alone.

Three weeks after injection, animals are tested for amelioration of symptoms and sacrificed. Relevant organ systems analyzed for indel formation. Phenotypic assays include blood levels of HDL, LDL, lipids, Assay for Indel Formation DNA is extracted from tissue using commercial kits; indel assay will be performed as described for in vitro demonstration.

Therapeutic applications of the CRISPR-Cas system are amenable for achieving tissue-specific and temporally controlled targeted deletion of candidate disease genes. Examples include genes involved in cholesterol and fatty acid metabolism, amyloid diseases, dominant negative diseases, latent viral infections, among other disorders.

Examples of a Single Guide-RNA to Introduce Targeted Indels at a Gene Locus

| Disease | GENE | SPACER | PAM | SEQ ID NO: | Mechanism | References |
|---|---|---|---|---|---|---|
| Hypercholesterolemia | HMG-CR | GCCAAATTG GACGACCCT CG | CGG | 109 | Knockout | Fluvastatin: a review of its pharmacology and use in the management of hypercholesterolaemia. (Plosker GL et al. Drugs 1996, 51(3): 433-459) |

| Disease | GENE | SPACER | PAM | SEQ ID NO: | Mechanism | References |
|---|---|---|---|---|---|---|
| Hypercholesterolemia | SQLE | CGAGGAGACCCCCGTTTCGG | TGG | 110 | Knockout | Potential role of nonstatin cholesterol lowering agents (Trapani et al. IUBMB Life, Volume 63, Issue 11, pages 964-971, November 2011) |
| Hyperlipidemia | DGAT1 | CCCGCCGCCGCCGTGGCTCG | AGG | 111 | Knockout | DGAT inhibitors as anti-obesity and anti-diabetic agents. (Birch AM et al. Current Opinion in Drug Discovery & Development [2010, 13(4): 489-496) |
| Leukemia | BCR-ABL | TGAGCTCTACGAGATCCACA | AGG | 112 | Knockout | Killing of leukemic cells with a BCR/ABL fusion gene by RNA interference (RNAi). (Fuchs et al. Oncogene 2002, 21(37): 5716-5724) |

Examples of a Pair of Guide-RNA to Introduce Chromosomal Microdeletion at a Gene Locus

| Disease | GENE | SPACER | PAM | SEQ ID NO: | Mechanism | References |
|---|---|---|---|---|---|---|
| Hyperlipidemia | PLIN2 guide1 | CTCAAAATTCATACCGGTTG | TGG | 113 | Microdeletion | Perilipin-2 Null Mice are Protected Against Diet-Induced Obesity, Adipose Inflammation and Fatty Liver Disease (McManaman JL et al. The Journal of Lipid Research, jlr.M035063. First Published on Feb. 12, 2013) |
| Hyperlipidemia | PLIN2 guide2 | CGTTAAACAACAACCGGACT | TGG | 114 | Microdeletion | |
| Hyperlipidemia | SREBP guide1 | TTCACCCCGCGGCGCTGAAT | ggg | 115 | Microdeletion | Inhibition of SREBP by a Small Molecule, Betulin, Improves Hyperlipidemia and Insulin Resistance and Reduces Atherosclerotic Plaques (Tang J et al. Cell Metabolism, Volume 13, Issue 1, 44-56, 5 Jan. 2011) |
| Hyperlipidemia | SREBP guide2 | ACCACTACCAGTCCGTCCAC | agg | 116 | Microdeletion | |

Example 19: Targeted Integration of Repair for Genes Carrying Disease-Causing Mutations; Reconstitution of Enzyme Deficiencies and Other Related Diseases Study Design
I. Identification and design of gene targets
Described in Example 22
II. Cloning of guide sequences and repair templates into a delivery system
Described above in Example 22
Applicants clone DNA repair templates to include homology arms with diseased allele as well a wild-type repair template
III. In vitro validation on cell lines
   a. Transfection is described above in Example 22; Cas9, guide RNAs, and repair template are co-transfected into relevant cell types.
   b. Assay for repair in vitro
      i. Applicants harvest cells 72-hours post-transfection and assay for repair
      ii. Briefly, Applicants amplify genomic region around repair template PCR using high-fidelity polymerase. Applicants sequence products for decreased incidence of mutant allele.
IV. In vivo proof of principle in animal
   a. Delivery mechanisms are described above Examples 22 and 34.
   b. Assay for repair in vivo
      i. Applicants perform the repair assay as described in the in vitro demonstration.
V. Therapeutic applications
The CRISPR-Cas system is amenable for achieving tissue-specific and temporally controlled targeted deletion of candidate disease genes. Examples include genes involved in cholesterol and fatty acid metabolism, amyloid diseases, dominant negative diseases, latent viral infections, among other disorders.

Example of One Single Missense Mutation with Repair Template:

| Disease | GENE | SPACER | PAM |
|---|---|---|---|
| Familial amyloid polyneuropathy | TTR | AGCCTTTCTGAACACATGCA (SEQ ID NO: 117) | CGG |

Mechanism References
Transthyretin mutations in health and disease (Joao et al. Human Mutation, V30M repair Volume 5, Issue 3, pages 191-196, 1995)

```
V30M allele
                                        (SEQ ID NO: 118)
CCTGCCATCAATGTGGCCATGCATGTGTTCAGAAAGGCT WT allele
                                        (SEQ ID NO: 119)
CCTGCCATCAATGTGGCCGTGCATGTGTTCAGAAAGGCT
```

Example 20: Therapeutic Application of the CRISPR-Cas System in Glaucoma, Amyloidosis, and Huntington's Disease Glaucoma: Applicants design guide RNAs to target the first exon of the mycilin (MYOC) gene. Applicants use adenovirus vectors (Ad5) to package both Cas9 as well as a guide RNA targeting the MYOC gene. Applicants inject adenoviral vectors into the trabecular meshwork where cells have been implicated in the pathophysiology of glaucoma. Applicants initially test this out in mouse models carrying the mutated MYOC gene to see whether they improve visual acuity and decrease pressure in the eyes. Therapeutic application in humans employ a similar strategy.

Amyloidosis: Applicants design guide RNAs to target the first exon of the transthyretin (TTR) gene in the liver. Applicants use AAV8 to package Cas9 as well as guide RNA targeting the first exon of the TTR gene. AAV8 has been shown to have efficient targeting of the liver and will be administered intravenously. Cas9 can be driven either using liver specific promoters such as the albumin promoter, or using a constitutive promoter. A pol3 promoter drives the guide RNA.

Alternatively, Applicants utilize hydrodynamic delivery of plasmid DNA to knockout the TTR gene. Applicants deliver a plasmid encoding Cas9 and the guideRNA targeting Exon1 of TTR.

As a further alternative approach, Applicants administer a combination of RNA (mRNA for Cas9, and guide RNA). RNA can be packaged using liposomes such as Invivofectamine from Life Technologies and delivered intravenously. To reduce RNA-induced immunogenicity, increase the level of Cas9 expression and guide RNA stability, Applicants modify the Cas9 mRNA using 5' capplng. Applicants also incorporate modified RNA nucleotides into Cas9 mRNA and guide RNA to increase their stability and reduce immunogenicity (e.g. activation of TLR). To increase efficiency, Applicants administer multiple doses of the virus, DNA, or RNA.

Huntington's Disease: Applicants design guide RNA based on allele specific mutations in the HTT gene of patients. For example, in a patient who is heterozygous for HTT with expanded CAG repeat, Applicants identify nucleotide sequences unique to the mutant HTT allele and use it to design guideRNA. Applicants ensure that the mutant base is located within the last 9 bp of the guide RNA (which Applicants have ascertained has the ability to discriminate between single DNA base mismatches between the target size and the guide RNA).

Applicants package the mutant HTT allele specific guide RNA and Cas9 into AAV9 and deliver into the striatum of Huntington's patients. Virus is injected into the striatum stereotactically via a craniotomy. AAV9 is known to transduce neurons efficiently. Applicants drive Cas9 using a neuron specific promoter such as human Synapsin I.

Example 21: Therapeutic Application of the CRISPR-Cas System in HIV

Chronic viral infection is a source of significant morbidity and mortality. While there exists for many of these viruses conventional antiviral therapies that effectively target various aspects of viral replication, current therapeutic modalities are usually non-curative in nature due to "viral latency." By its nature, viral latency is characterized by a dormant phase in the viral life cycle without active viral production. During this period, the virus is largely able to evade both immune surveillance and conventional therapeutics allowing for it to establish long-standing viral reservoirs within the host from which subsequent re-activation can permit continued propagation and transmission of virus. Key to viral latency is the ability to stably maintain the viral genome, accomplished either through episomal or proviral latency, which stores the viral genome in the cytoplasm or integrates it into the host genome, respectively. In the absence of effective vaccinations which would prevent primary infection, chronic viral infections characterized by latent reservoirs and episodes of lytic activity can have significant consequences: human papilloma virus (HPV) can result in cervical cancer, hepatitis C virus (HCV) predisposes to hepatocellular carcinoma, and human immunodeficiency virus eventually destroys the host immune system resulting in susceptibility to opportunistic infections. As such, these infections require life-long use of currently available antiviral therapeutics. Further complicating matters is the high mutability of many of these viral genomes which lead to the evolution of resistant strains for which there exists no effective therapy.

The CRISPR-Cas system is a bacterial adaptive immune system able to induce double-stranded DNA breaks (DSB) in a multiplex-able, sequence-specific manner and has been recently re-constituted within mammalian cell systems. It has been shown that targeting DNA with one or numerous guide-RNAs can result in both indels and deletions of the intervening sequences, respectively. As such, this new technology represents a means by which targeted and multiplexed DNA mutagenesis can be accomplished within a single cell with high efficiency and specificity. Consequently, delivery of the CRISPR-Cas system directed against viral DNA sequences could allow for targeted disruption and deletion of latent viral genomes even in the absence of ongoing viral production.

As an example, chronic infection by HIV-1 represents a global health issue with 33 million individuals infected and an annual incidence of 2.6 million infections. The use of the multimodal highly active antiretroviral therapy (HAART), which simultaneously targets multiple aspects of viral replication, has allowed HIV infection to be largely managed as a chronic, not terminal, illness. Without treatment, progression of HIV to AIDS occurs usually within 9-10 years resulting in depletion of the host immune system and occurrence of opportunistic infections usually leading to death soon thereafter. Secondary to viral latency, discontinuation of HAART invariably leads to viral rebound. Moreover, even temporary disruptions in therapy can select for resistant strains of HIV uncontrollable by available means. Additionally, the costs of HAART therapy are significant: within the US $10,000-15,0000 per person per year. As such, treatment approaches directly targeting the HIV genome rather than the process of viral replication represents a means by which eradication of latent reservoirs could allow for a curative therapeutic option.

Development and delivery of an HIV-1 targeted CRISPR-Cas system represents a unique approach differentiable from existing means of targeted DNA mutagenesis, i.e. ZFN and TALENs, with numerous therapeutic implications. Targeted disruption and deletion of the HIV-1 genome by CRISPR-mediated DSB and indels in conjunction with HAART could allow for simultaneous prevention of active viral production as well as depletion of latent viral reservoirs within the host.

Once integrated within the host immune system, the CRISPR-Cas system allows for generation of a HIV-1 resistant sub-population that, even in the absence of complete viral eradication, could allow for maintenance and re-constitution of host immune activity. This could potentially prevent primary infection by disruption of the viral genome preventing viral production and integration, representing a means to "vaccination". Multiplexed nature of the CRISPR-Cas system allows targeting of multiple aspects of the genome simultaneously within individual cells.

As in HAART, viral escape by mutagenesis is minimized by requiring acquisition of multiple adaptive mutations concurrently. Multiple strains of HIV-1 can be targeted simultaneously which minimizes the chance of super-infection and prevents subsequent creation of new recombinants strains. Nucleotide, rather than protein, mediated sequence-specificity of the CRISPR-Cas system allows for rapid generation of therapeutics without need for significantly altering delivery mechanism.

In order to accomplish this, Applicants generate CRISPR-Cas guide RNAs that target the vast majority of the HIV-1 genome while taking into account HIV-1 strain variants for maximal coverage and effectiveness. Sequence analyses of genomic conservation between HIV-1 subtypes and variants should allow for targeting of flanking conserved regions of the genome with the aims of deleting intervening viral sequences or induction of frame-shift mutations which would disrupt viral gene functions.

Applicants accomplish delivery of the CRISPR-Cas system by conventional adenoviral or lentiviral-mediated infection of the host immune system. Depending on approach, host immune cells could be a) isolated, transduced with CRISPR-Cas, selected, and re-introduced in to the host or b) transduced in vivo by systemic delivery of the CRISPR-Cas system. The first approach allows for generation of a resistant immune population whereas the second is more likely to target latent viral reservoirs within the host.

```
Examples of potential HIV-1 targeted spacers
adapted from Mcintyre et al, which generated
shRNAs against HIV-1 optimized for
maximal coverage of HIV-1 variants.
                                  (SEQ ID NO: 120)
CACTGCTTAAGCCTCGCTCGAGG (SEQ ID NO: 121)
TCACCAGCAATATTCGCTCGAGG (SEQ ID NO: 122)
CACCAGCAATATTCCGCTCGAGG (SEQ ID NO: 123)
TAGCAACAGACATACGCTCGAGG (SEQ ID NO: 124)
GGGCAGTAGTAATACGCTCGAGG (SEQ ID NO: 125)
CCAATTCCCATACATTATTGTAC
```

Example 22: Targeted Correction of deltaF508 or Other Mutations in Cystic Fibrosis An aspect of the invention provides for a pharmaceutical composition that may comprise an CRISPR-Cas gene therapy particle and a biocompatible pharmaceutical carrier. According to another aspect, a method of gene therapy for the treatment of a subject having a mutation in the CFTR gene comprises administering a therapeutically effective amount of a CRISPR-Cas gene therapy particle to the cells of a subject.

This Example demonstrates gene transfer or gene delivery of a CRISPR-Cas system in airways of subject or a patient in need thereof, suffering from cystic fibrosis or from cystic fibrosis related symptoms, using adeno-associated virus (AAV) particles.

Study Design: Subjects or patients in need there of: Human, non-primate human, canine, feline, bovine, equine and other domestic animals, related. This study tests efficacy of gene transfer of a CRISPR-Cas system by a AAV vector. Applicants determine transgene levels sufficient for gene expression and utilize a CRISPR-Cas system comprising a Cas9 enzyme to target deltaF508 or other CFTR-inducing mutations.

The treated subjects receive pharmaceutically effective amount of aerosolized AAV vector system per lung endobronchially delivered while spontaneously breathing. The control subjects receive equivalent amount of a pseudotyped AAV vector system with an internal control gene. The vector system may be delivered along with a pharmaceutically acceptable or biocompatible pharmaceutical carrier. Three weeks or an appropriate time interval following vector administration, treated subjects are tested for amelioration of cystic fibrosis related symptoms.

Applicants Use an Adenovirus or an AAV Particle.

Applicants clone the following gene constructs, each operably linked to one or more regulatory sequences (Cbh or EF1a promoter for Cas9, U6 or H1 promoter for chimeric guide RNA), into one or more adenovirus or AAV vectors or any other compatible vector: A CFTRdelta508 targeting chimeric guide RNA (FIG. 31B), a repair template for deltaF508 mutation (FIG. 31C) and a codon optimized Cas9 enzyme with optionally one or more nuclear localization signal or sequence(s) (NLS(s)), e.g., two (2) NLSs.

Identification of Cas9 Target Site

Figure 31A:
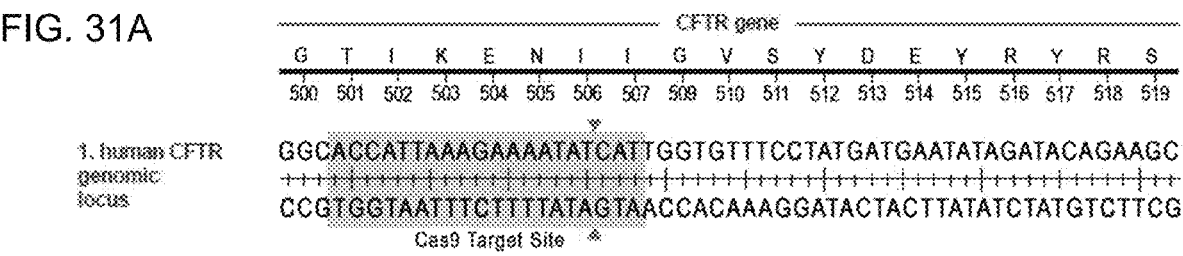
FIG. 31A-C shows the repair strategy for Cystic Fibrosis delta F508 mutation.
Figure 31B:
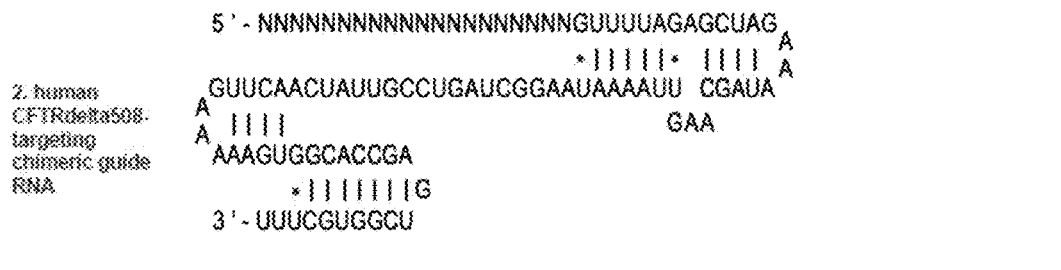
Figure 31C:
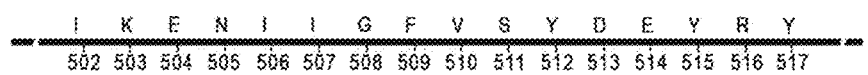

Applicants analyzed the human CFTR genomic locus and identified the Cas9 target site (FIG. 31A). (PAM may contain a NGG or a NNAGAAW motif).

Gene Repair Strategy

Applicants introduce an adenovirus/AAV vector system comprising a Cas9 (or Cas9 nickase) and the guide RNA along with a adenovirus/AAV vector system comprising the homology repair template containing the F508 residue into the subject via one of the methods of delivery discussed earlier. The CRISPR-Cas system is guided by the CFTRdelta 508 chimeric guide RNA and targets a specific site of the CFTR genomic locus to be nicked or cleaved. After cleavage, the repair template is inserted into the cleavage site via homologous recombination correcting the deletion that results in cystic fibrosis or causes cystic fibrosis related symptoms. This strategy to direct delivery and provide systemic introduction of CRISPR systems with appropriate guide RNAs can be employed to target genetic mutations to edit or otherwise manipulate genes that cause metabolic, liver, kidney and protein diseases and disorders such as those in Table B.

Example 23: Generation of Gene Knockout Cell Library

This example demonstrates how to generate a library of cells where each cell has a single gene knocked out:

Applicants make a library of ES cells where each cell has a single gene knocked out, and the entire library of ES cells will have every single gene knocked out. This library is useful for the screening of gene function in cellular processes as well as diseases.

To make this cell library, Applicants integrate Cas9 driven by an inducible promoter (e.g. doxycycline inducible promoter) into the ES cell. In addition, Applicants integrate a single guide RNA targeting a specific gene in the ES cell. To make the ES cell library, Applicants simply mix ES cells with a library of genes encoding guide RNAs targeting each gene in the human genome. Applicants first introduce a single BxB1 attB site into the AAVS1 locus of the human ES cell. Then Applicants use the BxB1 integrase to facilitate the integration of individual guide RNA genes into the BxB1 attB site in AAVS1 locus. To facilitate integration, each guide RNA gene is contained on a plasmid that carries of a single attP site. This way BxB1 will recombine the attB site in the genome with the attP site on the guide RNA containing plasmid.

To generate the cell library, Applicants take the library of cells that have single guide RNAs integrated and induce Cas9 expression. After induction, Cas9 mediates double strand break at sites specified by the guide RNA. To verify the diversity of this cell library, Applicants carry out whole exome sequencing to ensure that Applicants are able to observe mutations in every single targeted gene. This cell library can be used for a variety of applications, including who library-based screens, or can be sorted into individual cell clones to facilitate rapid generation of clonal cell lines with individual human genes knocked out.

Example 24: Engineering of Microalgae Using Cas9

Methods of Delivering Cas9

Method 1: Applicants deliver Cas9 and guide RNA using a vector that expresses Cas9 under the control of a constitutive promoter such as Hsp70A-Rbc S2 or Beta2-tubulin.

Method 2: Applicants deliver Cas9 and T7 polymerase using vectors that expresses Cas9 and T7 polymefase under the control of a constitutive promoter such as Hsp70A-Rbc S2 or Beta2-tubulin. Guide RNA will be delivered using a vector containing T7 promoter driving the guide RNA.

Method 3: Applicants deliver Cas9 mRNA and in vitro transcribed guide RNA to algae cells. RNA can be in vitro transcribed. Cas9 mRNA will consist of the coding region for Cas9 as well as 3'UTR from Cop1 to ensure stabilization of the Cas9 mRNA.

For Homologous recombination, Applicants provide an additional homology directed repair template.

Sequence for a cassette driving the expression of Cas9 under the control of beta-2 tubulin promoter, followed by the 3' UTR of Cop1.

```
                                        (SEQ ID NO: 126)
TCTTTCTTGCGCTATGACACTTCCAGCAAAAGGTAGGGCGGGCTGCGAGA

CGGCTTCCCGGCGCTGCATGCAACACCGATGATGCTTCGACCCCCCGAAG

CTCCTTCGGGGCTGCATGGGCGCTCCGATGCCGCTCCAGGGCGAGCGCTG

TTTAAATAGCCAGGCCCCCGATTGCAAAGACATTATAGCGAGCTACCAAA

GCCATATTCAAACACCTAGATGACTACCACTTCTACACAGGCCACTCGAG

CTTGTGATCGCACTCCGCTAAGGGGCGCCTCTTCCTCTTCGTTTCAGTC

ACAACCCGCAAACATGTACCCATACGATGTTCCAGATTACGCTTCGCCGA

AGAAAAAGCGCAAGGTCGAAGCGTCCGACAAGAAGTACAGCATCGGCCTG

GACATCGGCACCAACTCTGTGGGCTGGGCCGTGATCACCGACGAGTACAA

GGTGCCCAGCAAGAAATTCAAGGTGCTGGGCAACACCGACCGGCACAGCA

TCAAGAAGAACCTGATCGGAGCCCTGCTGTTCGACAGCGGCGAAACAGCC

GAGGCCACCCGGCTGAAGAGAACCGCCAGAAGAAGATACACCAGACGGAA

GAACCGGATCTGCTATCTGCAAGAGATCTTCAGCAACGAGATGGCCAAGG

TGGACGACAGCTTCTTCCACAGACTGGAAGAGTCCTTCCTGGTGGAAGAG

GATAAGAAGCACGAGCGGCACCCCATCTTCGGCAACATCGTGGACGAGGT
```

```
GGCCTACCACGAGAAGTACCCCACCATCTACCACCTGAGAAAGAAACTGG
TGGACAGCACCGACAAGGCCGACCTGCGGCTGATCTATCTGGCCCTGGCC
CACATGATCAAGTTCCGGGGCCACTTCCTGATCGAGGGCGACCTGAACCC
CGACAACAGCGACGTGGACAAGCTGTTCATCCAGCTGGTGCAGACCTACA
ACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGAT
CGCCCAGCTGCCCGGCGAGAAGAAGAATGGCCTGTTCGGCAACCTGATTG
CCCTGAGCCTGGGCCTGACCCCCAACTTCAAGAGCAACTTCGACCTGGCC
GAGGATGCCAAACTGCAGCTGAGCAAGGACACCTACGACGACGACCTGGA
CAACCTGCTGGCCCAGATCGGCGACCAGTACGCCGACCTGTTTCTGGCCG
CCAAGAACCTGTCCGACGCCATCCTGCTGAGCGACATCCTGAGAGTGAAC
ACCGAGATCACCAAGGCCCCCCTGAGCGCCTCTATGATCAAGAGATACGA
CGAGCACCACCAGGACCTGACCCTGCTGAAAGCTCTCGTGCGGCAGCAGC
TGCCTGAGAAGTACAAAGAGATTTTCTTCGACCAGACGAAGAACGGCTAC
GCCGGCTACATTGACGGCGGAGCCAGCCAGGAAGAGTTCTACAAGTTCAT
CAAGCCCATCCTGGAAAAGATGGACGGCACCGAGGAACTGCTCGTGAAGC
TGAACAGAGAGGACCTGCTGCGGAAGCAGCGGACCTTCGACAACGGCAGC
ATCCCCCACCAGATCCACCTGGGAGAGCTGCACGCCATTCTGCGGCGGCA
GGAAGATTTTTACCCATTCCTGAAGGACAACCGGGAAAAGATCGAGAAGA
TCCTGACCTTCCGCATCCCCTACTACGTGGGCCCTCTGGCCAGGGGAAAC
AGCAGATTCGCCTGGATGACCAGAAAGAGCGAGGAAACCATCACCCCCTG
GAACTTCGAGGAAGTGGTGGACAAGGGCGCTTCCGCCCAGAGCTTCATCG
AGCGGATGACCAACTTCGATAAGAACCTGCCCAACGAGAAGGTGCTGCCC
AAGCACAGCCTGCTGTACGAGTACTTCACCGTGTATAACGAGCTGACCAA
AGTGAAATACGTGACCGAGGGAATGAGAAAGCCCGCCTTCCTGAGCGGCG
AGCAGAAAAAGGCCATCGTGGACCTGCTGTTCAAGACCAACCGGAAAGTG
ACCGTGAAGCAGCTGAAAGAGGACTACTTCAAGAAAATCGAGTGCTTCGA
CTCCGTGGAAATCTCCGGCGTGGAAGATCGGTTCAACGCCTCCCTGGGCA
CATACCACGATCTGCTGAAAATTATCAAGGACAAGGACTTCCTGGACAAT
GAGGAAAACGAGGACATTCTGGAAGATATCGTGCTGACCCTGACACTGTT
TGAGGACAGAGAGATGATCGAGGAACGGCTGAAAACCTATGCCCACCTGT
TCGACGACAAAGTGATGAAGCAGCTGAAGCGGCGGAGATACACCGGCTGG
GGCAGGCTGAGCCGGAAGCTGATCAACGGCATCCGGGACAAGCAGTCCGG
CAAGACAATCCTGGATTTCCTGAAGTCCGACGGCTTCGCCAACAGAAACT
TCATGCAGCTGATCCACGACGACAGCCTGACCTTTAAAGAGGACATCCAG
AAAGCCCAGGTGTCCGGCCAGGGCGATAGCCTGCACGAGCACATTGCCAA
TCTGGCCGGCAGCCCCGCCATTAAGAAGGGCATCCTGCAGACAGTGAAGG
TGGTGGACGAGCTCGTGAAAGTGATGGGCCGGCACAAGCCCGAGAACATC
GTGATCGAAATGGCCAGAGAGAACCAGACCACCCAGAAGGGACAAGAAA
CAGCCGCGAGAGAATGAAGCGGATCGAAGAGGGCATCAAAGAGCTGGGCA
GCCAGATCCTGAAAGAACACCCCGTGGAAAACACCCAGCTGCAGAACGAG
AAGCTGTACCTGTACTACCTGCAGAATGGGCGGGATATGTACGTGGACCA
GGAACTGGACATCAACCGGCTGTCCGACTACGATGTGGACCATATCGTGC
CTCAGAGCTTTCTGAAGGACGACTCCATCGACAACAAGGTGCTGACCAGA
AGCGACAAGAACCGGGGCAAGAGCGACAACGTGCCCTCCGAAGAGGTCGT
GAAGAAGATGAAGAACTACTGGCGGCAGCTGCTGAACGCCAAGCTGATTA
CCCAGAGAAAGTTCGACAATCTGACCAAGGCCGAGAGAGGCGGCCTGAGC
GAACTGGATAAGGCCGGCTTCATCAAGAGACAGCTGGTGGAAACCCGGCA
GATCACAAAGCACGTGGCACAGATCCTGGACTCCCGGATGAACACTAAGT
ACGACGAGAATGACAAGCTGATCCGGGAAGTGAAAGTGATCACCCTGAAG
TCCAAGCTGGTGTCCGATTTCCGGAAGGATTTCCAGTTTTACAAAGTGCG
CGAGATCAACAACTACCACCACGCCCACGACGCCTACCTGAACGCCGTCG
TGGGAACCGCCCTGATCAAAAAGTACCCTAAGCTGGAAAGCGAGTTCGTG
TACGGCGACTACAAGGTGTACGACGTGCGGAAGATGATCGCCAAGAGCGA
GCAGGAAATCGGCAAGGCTACCGCCAAGTACTTCTTCTACAGCAACATCA
TGAACTTTTTCAAGACCGAGATTACCCTGGCCAACGGCGAGATCCGGAAG
CGGCCTCTGATCGAGACAAACGGCGAAACCGGGGAGATCGTGTGGGATAA
GGGCCGGGATTTTGCCACCGTGCGGAAAGTGCTGAGCATGCCCCAAGTGA
ATATCGTGAAAAAGACCGAGGTGCAGACAGGCGGCTTCAGCAAAGAGTCT
ATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTG
TGCTGGTGGTGGCCAAAGTGGAAAAGGGCAAGTCCAAGAAACTGAAGAGT
GTGAAAGAGCTGCTGGGGATCACCATCATGGAAAGAAGCAGCTTCGAGAA
GAATCCCATCGACTTTCTGGAAGCCAAGGGCTACAAAGAAGTGAAAAAGG
ACCTGATCATCAAGCTGCCTAAGTACTCCCTGTTCGAGCTGGAAAACGGC
CGGAAGAGAATGCTGGCCTCTGCCGGCGAACTGCAGAAGGGAAACGAACT
GGCCCTGCCCTCCAAATATGTGAACTTCCTGTACCTGGCCAGCCACTATG
AGAAGCTGAAGGGCTCCCCCGAGGATAATGAGCAGAAACAGCTGTTTGTG
GAACAGCACAAGCACTACCTGGACGAGATCATCGAGCAGATCAGCGAGTT
CTCCAAGAGAGTGATCCTGGCCGACGCTAATCTGGACAAAGTGCTGTCCG
CCTACAACAAGCACCGGGATAAGCCCATCAGAGAGCAGGCCGAGAATATC
ATCCACCTGTTTACCCTGACCAATCTGGGAGCCCCTGCCGCCTTCAAGTA
CTTTGACACCACCATCGACCGGAAGAGGTACACCAGCACCAAAGAGGTGC
TGGACGCCACCCTGATCCACCAGAGCATCACCGGCCTGTACGAGACACGG
ATCGACCTGTCTCAGCTGGGAGGCGACAGCCCCAAGAAGAAGAGAAAGGT
GGAGGCCAGCTAAGGATCCGGCAAGACTGGCCCCGCTTGGCAACGCAACA
GTGAGCCCCTCCCTAGTGTGTTTGGGGATGTGACTATGTATTCGTGTGTT
GGCCAACGGGTCAACCCGAACAGATTGATACCCGCCTTGGCATTTCCTGT
CAGAATGTAACGTCAGTTGATGGTACT
```

Sequence for a cassette driving the expression of T7 polymerase under the control of beta-2 tubulin promoter, followed by the 3' UTR of Cop1:

(SEQ ID NO: 127)
TCTTTCTTGCGCTATGACACTTCCAGCAAAAGGTAGGGCGGGCTGCGAGA
CGGCTTCCCGGCGCTGCATGCAACACCGATGATGCTTCGACCCCCCGAAG
CTCCTTCGGGGCTGCATGGGCGCTCCGATGCCGCTCCAGGGCGAGCGCTG
TTTAAATAGCCAGGCCCCCGATTGCAAAGACATTATAGCGAGCTACCAAA
GCCATATTCAAACACCTAGATCACTACCACTTCTACACAGGCCACTCGAG
CTTGTGATCGCACTCCGCTAAGGGGGCGCCTCTTCCTCTTCGTTTCAGTC
ACAACCCGCAAAtgcctaagaagaagaggaaggttaacacgattaaca
tcgctaagaacgacttctctgacatcgaactggctgctatcccgttcaac
actctggctgaccattacggtgagcgtttagctcgcgaacagttggccct
tgagcatgagtcttacgagatgggtgaagcacgcttccgcaagatgtttg
agcgtcaacttaaagctggtgaggttgcggataacgctgccgccaagcct
ctcatcactaccctactccctaagatgattgcacgcatcaacgactggtt
tgaggaagtgaaagctaagcgcggcaagcgcccgacagccttccagttcc
tgcaagaaatcaagccggaagccgtagcgtacatcaccattaagaccact
ctggcttgcctaaccagtgctgacaatacaaccgttcaggctgtagcaag
cgcaatcggtcgggccattgaggacgaggctcgcttcggtcgtatccgtg
accttgaagctaagcacttcaagaaaaacgttgaggaacaactcaacaag
cgcgtagggcacgtctacaagaaagcatttatgcaagttgtcgaggctga
catgctctctaagggtctactcggtggcgaggcgtggtcttcgtggcata
aggaagactctattcatgtaggagtacgctgcatcgagatgctcattgag
tcaaccggaatggttagcttacaccgccaaaatgctggcgtagtaggtca
agactctgagactatcgaactcgcacctgaatacgctgaggctatcgcaa
cccgtgcaggtcgctggctggcatctctccgatgttccaaccttgcgta
gttcctcctaagccgtggactggcattactggtggtggctattgggctaa
cggtcgtcgtcctctggcgctggtgcgtactcacagtaagaaagcactga
tgcgctacgaagacgtttacatgcctgaggtgtacaaagcgattaacatt
gcgcaaaacaccgcatggaaaatcaacaagaaagtcctagcggtcgccaa
cgtaatcaccaagtggaagcattgtccggtcgaggacatccctgcgattg
agcgtgaagaactcccgatgaaaccggaagacatcgacatgaatcctgag
gctctcaccgcgtggaaacgtgctgccgctgctgtgtaccgcaaggacaa
ggctcgcaagtctcgccgtatcagccttgagttcatgcttgagcaagcca
ataagtttgctaaccataaggccatctggttcccttacaacatggactgg
cgcggtcgtgtttacgctgtgtcaatgttcaacccgcaaggtaacgatat
gaccaaaggactgcttacgctggcgaaaggtaaaccaatcggtaaggaag
gttactactggctgaaaatccacggtgcaaactgtgcgggtgtcgacaag
gttccgttcctgagcgcatcaagttcattgaggaaaaccacgagaacat
catggcttcgctaagtctccactggagaacacttggtgggctgagcaag
attctccgttctgcttccttgcgttctgctttgagtacgctggggtacag
caccacggcctgagctataactgctcccttccgctggcgtttgacgggtc
ttgctctggcatccagcacttctccgcgatgctccgagatgaggtaggtg
gtcgcgcggttaacttgcttcctagtgaaaccgttcaggacatctacggg
attgttgctaagaaagtcaacgagattctacaagcagacgcaatcaatgg
gaccgataacgaagtagttaccgtgaccgatgagaacactggtgaaatct
ctgagaaagtcaagctgggcactaaggcactggctggtcaatggctggct
tacggtgttactcgcagtgtgactaagcgttcagtcatgacgctggctta
cgggtccaaagagttcggcttccgtcaacaagtgctggaagataccattc
agccagctattgattccggcaagggtctgatgttcactcagccgaatcag
gctgctggatacatggctaagctgatttgggaatctgtgagcgtgacggt
ggtagctgcggttgaagcaatgaactggcttaagtctgctgctaagctgc
tggctgctgaggtcaaagataagaagactggagagattcttcgcaagcgt
tgcgctgtgcattgggtaactcctgatggtttccctgtgtggcaggaata
caagaagcctattcagacgcgcttgaacctgatgttcctcggtcagttcc
gcttacagcctaccattaacaccaacaaagatagcgagattgatgcacac
aaacaggagtctggtatcgctcctaactttgtacacagccaagacggtag
ccaccttcgtaagactgtagtgtgggcacacgagaagtacggaatcgaat
cttttgcactgattcacgactccttcggtacgattccggctgacgctgcg
aacctgttcaaagcagtgcgcgaaactatggttgacacatatgagtcttg
tgatgtactggctgatttctacgaccagttcgctgaccagttgcacgagt
ctcaattggacaaaatgccagcacttccggctaaaggtaacttgaacctc
cgtgacatcttagagtcggacttcgcgttcgcgtaaGGATCCGGCAAGAC
TGGCCCCGCTTGGCAACGCAACAGTGAGCCCCTCCCTAGTGTGTTTGGGG
ATGTGACTATGTATTCGTGTGTTGGCCAACGGGTCAACCCGAACAGATTG
ATACCCGCCTTGGCATTTCCTGTCAGAATGTAACGTCAGTTGATGGTACT Sequence of guide RNA driven by the T7 promoter (T7 promoter, Ns represent targeting sequence):

(SEQ ID NO: 128)
gaaatTAATACGACTCACTATANNNNNNNNNNNNNNNNNNNNNNNgttttaga
gctaGAAAtagcaagttaaaataaggctagtccgttatcaacttgaaaaa
gtggcaccgagtcggtgcttttttt Gene Delivery:

Chlamydomonas reinhardtii strain CC-124 and CC-125 from the Chlamydomonas Resource Center will be used for electroporation. Electroporation protocol follows standard recommended protocol from the GeneArt Chlamydomonas Engineering kit.

Also, Applicants generate a line of Chlamydomonas reinhardtii that expresses Cas9 constitutively. This can be done by using pChlamy1 (linearized using Pvu1) and selecting for hygromycin resistant colonies. Sequence for pChlamy1 containing Cas9 is below. In this way to achieve gene knockout one simply needs to deliver RNA for the guideRNA. For homologous recombination Applicants deliver guideRNA as well as a linearized homologous recombination template.

pChlamy1-Cas9:

(SEQ ID NO: 129)
TGCGGTATTTCACACCGCATCAGGTGGCACTTTTCGGGGAAATGTGCGCG
GAACCCCTATTTGTTTATTTTTCTAAATACATTCAAATATGTATCCGCTC
ATGAGATTATCAAAAAGGATCTTCACCTAGATCCTTTTAAATTAAAAATG
AAGTTTTAAATCAATCTAAAGTATATATGAGTAAACTTGGTCTGACAGTT
ACCAATGCTTAATCAGTGAGGCACCTATCTCAGCGATCTGTCTATTTCGT
TCATCCATAGTTGCCTGACTCCCCGTCGTGTAGATAACTACGATACGGGA
GGGCTTACCATCTGGCCCCAGTGCTGCAATGATACCGCGAGACCCACGCT
CACCGGCTCCAGATTTATCAGCAATAAACCAGCCAGCCGGAAGGGCCGAG
CGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACG
TTGTTGCCATTGCTACAGGCATCGTGGTGTCACGCTCGTCGTTTGGTATG
GCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCA
GAAGTAAGTTGGCCGCAGTGTTATCACTCATGGTTATGGCAGCACTGCAT
AATTCTCTTACTGTCATGCCATCCGTAAGATGCTTTTCTGTGACTGGTGA
GTACTCAACCAAGTCATTCTGAGAATAGTGTATGCGGCGACCGAGTTGCT
CTTGCCCGGCGTCAATACGGGATAATACCGCGCCACATAGCAGAACTTTA
AAAGTGCTCATCATTGGAAAACGTTCTTCGGGGCGAAAACTCTCAAGGAT
CTTACCGCTGTTGAGATCCAGTTCGATGTAACCCACTCGTGCACCCAACT
GATCTTCAGCATCTTTTACTTTCACCAGCGTTTCTGGGTGAGCAAAAACA
GGAAGGCAAAATGCCGCAAAAAAGGGAATAAGGGCGACACGGAAATGTTG
AATACTCATACTCTTCCTTTTTCAATATTATTGAAGCATTTATCAGGGTT
ATTGTCTCATGACCAAAATCCCTTAACGTGAGTTTTCGTTCCACTGAGCG
TCAGACCCCGTAGAAAAGATCAAAGGATCTTCTTGAGATCCTTTTTTTCT
GCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGC
TTCAGCAGAGCGCAGATACCAAATACTGTTCTTCTAGTGTAGCCGTAGTT
AGGCCACCACTTCAAGAACTCTGTAGCACCGCCTACATACCTCGCTCTGC
TAATCCTGTTACCAGTGGCTGTTGCCAGTGGCGATAAGTCGTGTCTTACC
GGGTTGGACTCAAGACGATAGTTACCGGATAAGGCGCAGCGGTCGGGCTG
AACGGGGGGTTCGTGCACACAGCCCAGCTTGGAGCGAACGACCTACACCG
AACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGA
GCGCACGAGGGAGCTTCCAGGGGGAAACGCCTGGTATCTTTATAGTCCTG
TCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTT
CCTGGCCTTTTGCTGGCCTTTTGCTCACATGTTCTTTCCTGCGTTATCCC
CTGATTCTGTGGATAACCGTATTACCGCCTTTGAGTGAGCTGATACCGCT
CGCCGCAGCCGAACGACCGAGCGCAGCGAGTCAGTGAGCGAGGAAGCGGT
CGCTGAGGCTTGACATGATTGGTGCGTATGTTTGTATGAAGCTACAGGAC
TGATTTGGCGGGCTATGAGGGCGGGGGAAGCTCTGGAAGGGCCGCGATGG
GGCGCGCGGCGTCCAGAAGGCGCCATACGGCCCGCTGGCGGCACCCATCC
GGTATAAAAGCCCGCGACCCCGAACGGTGACCTCCACTTTCAGCGACAAA
CGAGCACTTATACATACGCGACTATTCTGCCGCTATACATAACCACTCAG
CTAGCTTAAGATCCCATCAAGCTTGCATGCCGGGCGCGCCAGAAGGAGCG
CAGCCAAACCAGGATGATGTTTGATGGGGTATTTGAGCACTTGCAACCCT
TATCCGGAAGCCCCCTGGCCCACAAAGGCTAGGCGCCAATGCAAGCAGTT
CGCATGCAGCCCCTGGAGCGGTGCCCTCCTGATAAACCGGCCAGGGGCC
TATGTTCTTTACTTTTTTACAAGAGAAGTCACTCAACATCTTAAAATGGC
CAGGTGAGTCGACGAGCAAGCCCGGCGGATCAGGCAGCGTGCTTGCAGAT
TTGACTTGCAACGCCCGCATTGTGTCGACGAAGGCTTTTGGCTCCTCTGT
CGCTGTCTCAAGCAGCATCTAACCCTGCGTCGCCGTTTCCATTTGCAGGA
GATTCGAGGTACCATGTACCCATACGATGTTCCAGATTACGCTTCGCCGA
AGAAAAAGCGCAAGGTCGAAGCGTCCGACAAGAAGTACAGCATCGGCCTG
GACATCGGCACCAACTCTGTGGGCTGGGCCGTGATCACCGACGAGTACAA
GGTGCCCAGCAAGAAATTCAAGGTGCTGGGCAACACCGACCGGCACAGCA
TCAAGAAGAACCTGATCGGAGCCCTGCTGTTCGACAGCGGCGAAACAGCC
GAGGCCACCCGGCTGAAGAGAACCGCCAGAAGAAGATACACCAGACGGAA
GAACCGGATCTGCTATCTGCAAGAGATCTTCAGCAACGAGATGGCCAAGG
TGGACGACAGCTTCTTCCACAGACTGGAAGAGTCCTTCCTGGTGGAAGAG
GATAAGAAGCACGAGCGGCACCCCATCTTCGGCAACATCGTGGACGAGGT
GGCCTACCACGAGAAGTACCCCACCATCTACCACCTGAGAAAGAAACTGG
TGGACAGCACCGACAAGGCCGACCTGCGGCTGATCTATCTGGCCCTGGCC
CACATGATCAAGTTCCGGGGCCACTTCCTGATCGAGGGCGACCTGAACCC
CGACAACAGCGACGTGGACAAGCTGTTCATCCAGCTGGTGCAGACCTACA
ACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGAT
CGCCCAGCTGCCCGGCGAGAAGAAGAATGGCCTGTTCGGCAACCTGATTG
CCCTGAGCCTGGGCCTGACCCCCAACTTCAAGAGCAACTTCGACCTGGCC
GAGGATGCCAAACTGCAGCTGAGCAAGGACACCTACGACGACGACCTGGA
CAACCTGCTGGCCCAGATCGGCGACCAGTACGCCGACCTGTTTCTGGCCG
CCAAGAACCTGTCCGACGCCATCCTGCTGAGCGACATCCTGAGAGTGAAC
ACCGAGATCACCAAGGCCCCCCTGAGCGCCTCTATGATCAAGAGATACGA
CGAGCACCACCAGGACCTGACCCTGCTGAAAGCTCTCGTGCGGCAGCAGC
TGCCTGAGAAGTACAAAGAGATTTTCTTCGACCAGAGCAAGAACGGCTAC
GCCGGCTACATTGACGGCGGAGCCAGCCAGGAAGAGTTCTACAAGTTCAT
CAAGCCCATCCTGGAAAAGATGGACGGCACCGAGGAACTGCTCGTGAAGC
TGAACAGAGAGGACCTGCTGCGGAAGCAGCGGACCTTCGACAACGGCAGC
ATCCCCCACCAGATCCACCTGGGAGAGCTGCACGCCATTCTGCGGCGGCA

201

-continued

```
GGAAGATTTTTACCCATTCCTGAAGGACAACCGGGAAAAGATCGAGAAGA
TCCTGACCTTCCGCATCCCCTACTACGTGGGCCCTCTGGCCAGGGGAAAC
AGCAGATTCGCCTGGATGACCAGAAAGAGCGAGGAAACCATCACCCCCTG
GAACTTCGAGGAAGTGGTGGACAAGGGCGCTTCCGCCCAGAGCTTCATCG
AGCGGATGACCAACTTCGATAAGAACCTGCCCAACGAGAAGGTGCTGCCC
AAGCACAGCCTGCTGTACGAGTACTTCACCGTGTATAACGAGCTGACCAA
AGTGAAATACGTGACCGAGGGAATGAGAAAGCCCGCCTTCCTGAGCGGCG
AGCAGAAAAAGGCCATCGTGGACCTGCTGTTCAAGACCAACCGGAAAGTG
ACCGTGAAGCAGCTGAAAGAGGACTACTTCAAGAAAATCGAGTGCTTCGA
CTCCGTGGAAATCTCCGGCGTGGAAGATCGGTTCAACGCCTCCCTGGGCA
CATACCACGATCTGCTGAAAATTATCAAGGACAAGGACTTCCTGGACAAT
GAGGAAAACGAGGACATTCTGGAAGATATCGTGCTGACCCTGACACTGTT
TGAGGACAGAGAGATGATCGAGGAACGGCTGAAAACCTATGCCCACCTGT
TCGACGACAAAGTGATGAAGCAGCTGAAGCGGCGGAGATACACCGGCTGG
GGCAGGCTGAGCCGGAAGCTGATCAACGGCATCCGGGACAAGCAGTCCGG
CAAGACAATCCTGGATTTCCTGAAGTCCGACGGCTTCGCCAACAGAAACT
TCATGCAGCTGATCCACGACGACAGCCTGACCTTTAAAGAGGACATCCAG
AAAGCCCAGGTGTCCGGCCAGGGCGATAGCCTGCACGAGCACATTGCCAA
TCTGGCCGGCAGCCCCGCCATTAAGAAGGGCATCCTGCAGACAGTGAAGG
TGGTGGACGAGCTCGTGAAAGTGATGGGCCGGCACAAGCCCGAGAACATC
GTGATCGAAATGGCCAGAGAGAACCAGACCACCCAGAAGGGACAGAAGAA
CAGCCGCGAGAGAATGAAGCGGATCGAAGAGGGCATCAAAGAGCTGGGCA
GCCAGATCCTGAAAGAACACCCCGTGGAAAACACCCAGCTGCAGAACGAG
AAGCTGTACCTGTACTACCTGCAGAATGGGCGGGATATGTACGTGGACCA
GGAACTGGACATCAACCGGCTGTCCGACTACGATGTGGACCATATCGTGC
CTCAGAGCTTTCTGAAGGACGACTCCATCGACAACAAGGTGCTGACCAGA
AGCGACAAGAACCGGGGCAAGAGCGACAACGTGCCCTCCGAAGAGGTCGT
GAAGAAGATGAAGAACTACTGGCGGCAGCTGCTGAACGCCAAGCTGATTA
CCCAGAGAAAGTTCGACAATCTGACCAAGGCCGAGAGAGGCGGCCTGAGC
GAACTGGATAAGGCCGGCTTCATCAAGAGACAGCTGGTGGAAACCCGGCA
GATCACAAAGCACGTGGCACAGATCCTGGACTCCCGGATGAACACTAAGT
ACGACGAGAATGACAAGCTGATCCGGGAAGTGAAAGTGATCACCCTGAAG
TCCAAGCTGGTGTCCGATTTCCGGAAGGATTTCCAGTTTTACAAAGTGCG
CGAGATCAACAACTACCACCACGCCCACGACGCCTACCTGAACGCCGTCG
TGGGAACCGCCCTGATCAAAAAGTACCCTAAGCTGGAAAGCGAGTTCGTG
TACGGCGACTACAAGGTGTACGACGTGCGCAAGATGATCGCCAAGAGCGA
GCAGGAAATCGGCAAGGCTACCGCCAAGTACTTCTTCTACAGCAACATCA
TGAACTTTTTCAAGACCGAGATTACCCTGGCCAACGGCGAGATCCGGAAG
CGGCCTCTGATCGAGACAAACGGCGAAACCGGGGAGATCGTGTGGGATAA
GGGCCGGGATTTTGCCACCGTGCGGAAAGTGCTGAGCATGCCCCAAGTGA
ATATCGTGAAAAAGACCGAGGTGCAGACAGGCGGCTTCAGCAAAGAGTCT
```

202

-continued

```
ATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTG
TGCTGGTGGTGGCCAAAGTGGAAAAGGGCAAGTCCAAGAAACTGAAGAGT
GTGAAAGAGCTGCTGGGGATCACCATCATGGAAAGAAGCAGCTTCGAGAA
GAATCCCATCGACTTTCTGGAAGCCAAGGGCTACAAAGAAGTGAAAAAGG
ACCTGATCATCAAGCTGCCTAAGTACTCCCTGTTCGAGCTGGAAAACGGC
CGGAAGAGAATGCTGGCCTCTGCCGGCGAACTGCAGAAGGGAAACGAACT
GGCCCTGCCCTCCAAATATGTGAACTTCCTGTACCTGGCCAGCCACTATG
AGAAGCTGAAGGGCTCCCCCGAGGATAATGAGCAGAAACAGCTGTTTGTG
GAACAGCACAAGCACTACCTGGACGAGATCATCGAGCAGATCAGCGAGTT
CTCCAAGAGAGTGATCCTGGCCGACGCTAATCTGGACAAAGTGCTGTCCG
CCTACAACAAGCACCGGGATAAGCCCATCAGAGAGCAGGCCGAGAATATC
ATCCACCTGTTTACCCTGACCAATCTGGGAGCCCCTGCCGCCTTCAAGTA
CTTTGACACCACCATCGACCGGAAGAGGTACACCAGCACCAAAGAGGTGC
TGGACGCCACCCTGATCCACCAGAGCATCACCGGCCTGTACGAGACACGG
ATCGACCTGTCTCAGCTGGGAGGCGACAGCCCCAAGAAGAAGAGAAAGGT
GGAGGCCAGCTAACATATGATTCGAATGTCTTTCTTGCGCTATGACACTT
CCAGCAAAGGTAGGGCGGGCTGCGAGACGGCTTCCCGGCGCTGCATGCA
ACACCGATGATGCTTCGACCCCCCGAAGCTCCTTCGGGGCTGCATGGGCG
CTCCGATGCCGCTCCAGGGCGAGCGCTGTTTAAATAGCCAGGCCCCCGAT
TGCAAAGACATTATAGCGAGCTACCAAAGCCATATTCAAACACCTAGATC
ACTACCACTTCTACACAGGCCACTCGAGCTTGTGATCGCACTCCGCTAAG
GGGGCGCCTCTTCCTCTTCGTTTCAGTCACAACCCGCAAACATGACACAA
GAATCCCTGTTACTTCTCGACCGTATTGATTCGGATGATTCCTACGCGAG
CCTGCGGAACGACCAGGAATTCTGGGAGGTGAGTCGACGAGCAAGCCCGG
CGGATCAGGCAGCGTGCTTGCAGATTTGACTTGCAACGCCCGCATTGTGT
CGACGAAGGCTTTTGGCTCCTCTGTCGCTGTCTCAAGCAGCATCTAACCC
TGCGTCGCCGTTTCCATTTGCAGCCGCTGGCCCGCCGAGCCCTGGAGGAG
CTCGGGCTGCCGGTGCCGCCGGTGCTGCGGGTGCCCGGCGAGAGCACCAA
CCCCGTACTGGTCGGCGAGCCCGGCCCGGTGATCAAGCTGTTCGGCGAGC
ACTGGTGCGGTCCGGAGAGCCTCGCGTCGGAGTCGGAGGCGTACGCGGTC
CTGGCGGACGCCCCGGTGCCGGTGCCCCGCCTCCTCGGCCGCGGCGAGCT
GCGGCCCGGCACCGGAGCCTGGCCGTGGCCCTACCTGGTGATGAGCCGGA
TGACCGGCACCACCTGGCGGTCCGCGATGGACGGCACGACCGACCGGAAC
GCGCTGCTCGCCCTGGCCCGCGAACTCGGCCGGGTGCTCGGCCGGCTGCA
CAGGGTGCCGCTGACCGGGAACACCGTGCTCACCCCCCATTCCGAGGTCT
TCCCGGAACTGCTGCGGGAACGCCGCGCGGCGACCGTCGAGGACCACCGC
GGGTGGGGCTACCTCTCGCCCCGGCTGCTGGACCGCCTGGAGGACTGGCT
GCCGGACGTGGACACGCTGCTGGCCGGCCGCGAACCCCGGTTCGTCCACG
GCGACCTGCACGGGACCAACATCTTCGTGGACCTGGCCGCGACCGAGGTC
```

-continued
```
ACCGGGATCGTCGACTTCACCGACGTCTATGCGGGAGACTCCCGCTACAG

CCTGGTGCAACTGCATCTCAACGCCTTCCGGGGCGACCGCGAGATCCTGG

CCGCGCTGCTCGACGGGCGCAGTGGAAGCGGACCGAGGACTTCGCCCGC

GAACTGCTCGCCTTCACCTTCCTGCACGACTTCGAGGTGTTCGAGGAGAC

CCCGCTGGATCTCTCCGGCTTCACCGATCCGGAGGAACTGGCGCAGTTCC

TCTGGGGGCCGCCGGACACCGCCCCGGCGCCTGATAAGGATCCGGCAAG

ACTGGCCCCGCTTGGCAACGCAACAGTGAGCCCCTCCCTAGTGTGTTTGG

GGATGTGACTATGTATTCGTGTGTTGGCCAACGGGTCAACCCGAACAGAT

TGATACCCGCCTTGGCATTTCCTGTCAGAATGTAACGTCAGTTGATGGTA

CT
```

For all modified *Chlamydomonas reinhardtii* cells, Applicants use PCR, SURVEYOR nuclease assay, and DNA sequencing to verify successful modification.

Example 25: Use of Cas9 to Target a Variety of Disease Types

Diseases that involve mutations in protein coding sequence:

Dominant disorders may be targeted by inactivating the dominant negative allele. Applicants use Cas9 to target a unique sequence in the dominant negative allele and introduce a mutation via NHEJ. The NHEJ-induced indel may be able to introduce a frame-shift mutation in the dominant negative allele and eliminate the dominant negative protein. This may work if the gene is haplo-sufficient (e.g. MYOC mutation induced glaucoma and Huntington's disease).

Recessive disorders may be targeted by repairing the disease mutation in both alleles. For dividing cells, Applicants use Cas9 to introduce double strand breaks near the mutation site and increase the rate of homologous recombination using an exogenous recombination template. For dividing cells, this may be achieved using multiplexed nickase activity to catalyze the replacement of the mutant sequence in both alleles via NHEJ-mediated ligation of an exogenous DNA fragment carrying complementary overhangs.

Applicants also use Cas9 to introduce protective mutations (e.g. inactivation of CCR5 to prevent HIV infection, inactivation of PCSK9 for cholesterol reduction, or introduction of the A673T into APP to reduce the likelihood of Alzheimer's disease).

Diseases that Involve Non-Coding Sequences

Applicants use Cas9 to disrupt non-coding sequences in the promoter region, to alter transcription factor binding sites and alter enhancer or repressor elements. For example, Cas9 may be used to excise out the Klf1 enhancer EHS1 in hematopoietic stem cells to reduce BCL11a levels and reactivate fetal globin gene expression in differentiated erythrocytes Applicants also use Cas9 to disrupt functional motifs in the 5' or 3' untranslated regions. For example, for the treatment of myotonic dystrophy, Cas9 may be used to remove CTG repeat expansions in the DMPK gene.

Example 26: Multiplexed Nickase

Aspects of optimization and the teachings of Cas9 detailed in this application may also be used to generate Cas9 nickases. Applicants use Cas9 nickases in combination with pairs of guide RNAs to generate DNA double strand breaks with defined overhangs. When two pairs of guide RNAs are used, it is possible to excise an intervening DNA fragment. If an exogenous piece of DNA is cleaved by the two pairs of guide RNAs to generate compatible overhangs with the genomic DNA, then the exogenous DNA fragment may be ligated into the genomic DNA to replace the excised fragment. For example, this may be used to remove trinucleotide repeat expansion in the huntintin (HTT) gene to treat Huntington's Disease.

If an exogenous DNA that bears fewer number of CAG repeats is provided, then it may be able to generate a fragment of DNA that bears the same overhangs and can be ligated into the HTT genomic locus and replace the excised fragment (fragments below disclosed as SEQ ID NOS 130-137, respectively, in order of appearance).

```
HTT locus with     ...CCGTGCCGGGCGGGAGACCGCCATGG            GGCCCGGCTGTGGCTGAG-
                      GAGC...
fragment           ...GGCACGGCCCGCCCTCTGGC                 TGGGCCGGGCCGACACCGACTCCTCG...
excised by
Cas9 nickase
and two
pairs of
guide RNAs

+ exogenous DNA              CGACCCTGGAAA..... reduced number of CAG repeats .....CCCCGCCGCCACCC
fragment with              GGTACCGCTGGGACCTTT.....                              .....GGGGCGGCGG
fewer number
of CAG repeats
also cleaved
by Cas9
nicakse and
the two pairs
of guide
RNAs
```

The ligation of the exogenous DNA fragment into the genome does not require homologous recombination machineries and therefore this method may be used in post-mitotic cells such as neurons.

Example 27: Delivery of CRISPR System

Cas9 and its chimeric guide RNA, or combination of tracrRNA and crRNA, can be delivered either as DNA or RNA. Delivery of Cas9 and guide RNA both as RNA (normal or containing base or backbone modifications)

molecules can be used to reduce the amount of time that Cas9 protein persist in the cell. This may reduce the level of off-target cleavage activity in the target cell. Since delivery of Cas9 as mRNA takes time to be translated into protein, it might be advantageous to deliver the guide RNA several hours following the delivery of Cas9 mRNA, to maximize the level of guide RNA available for interaction with Cas9 protein.

In situations where guide RNA amount is limiting, it may be desirable to introduce Cas9 as mRNA and guide RNA in the form of a DNA expression cassette with a promoter driving the expression of the guide RNA. This way the amount of guide RNA available will be amplified via transcription.

A variety of delivery systems can be introduced to introduce Cas9 (DNA or RNA) and guide RNA (DNA or RNA) into the host cell. These include the use of liposomes, viral vectors, electroporation, nanoparticles, nanowires (Shalek et al., Nano Letters, 2012), exosomes. Molecular trojan horses liposomes (Pardridge et al., Cold Spring Harb Protoc; 2010; doi:10.1101/pdb.prot5407) may be used to deliver Cas9 and guide RNA across the blood brain barrier.

Example 28: Therapeutic Strategies for Trinucleotide Repeat Disorders

As previously mentioned in the application, the target polynucleotide of a CRISPR complex may include a number of disease-associated genes and polynucleotides and some of these disease associated gene may belong to a set of genetic disorders referred to as Trinucleotide repeat disorders (referred to as also trinucleotide repeat expansion disorders, triplet repeat expansion disorders or codon reiteration disorders).

These diseases are caused by mutations in which the trinucleotide repeats of certain genes exceed the normal, stable threshold which may usually differ in a gene. The discovery of more repeat expansion disorders has allowed for the classification of these disorders into a number of categories based on underlying similar characteristics. Huntington's disease (HD) and the spinocerebellar ataxias that are caused by a CAG repeat expansion in protein-coding portions of specific gene are included in Category I. Diseases or disorders with expansions that tend to make them phenotypically diverse and include expansions are usually small in magnitude and also found in exons of genes are included in Category II. Category III includes disorders or diseases which are characterized by much larger repeat expansions than either Category I or II and are generally located outside protein coding regions. Examples of Category III diseases or disorders include but are not limited to Fragile X syndrome, myotonic dystrophy, two of the spinocerebellar ataxias, juvenile myoclonic epilepsy, and Friedreich's ataxia.

Figure 32A:
FIG. 32A-B (a) shows a schematic of the GAA repeat expansion in FXN intron 1 and (b) shows a schematic of the strategy adopted to excise the GAA expansion region using the CRISPR/Cas system.

Similar therapeutic strategies, like the one mentioned for Friedreich's ataxia below may be adopted to address other trinucleotide repeat or expansion disorders as well. For example, another triple repeat disease that can be treated using almost identical strategy is dystrophia myotonica 1 (DM1), where there is an expanded CTG motif in the 3' UTR. In Friedreich's ataxia, the disease results from expansion of GAA trinucleotides in the first intron of frataxin (FXN). One therapeutic strategy using CRISPR is to excise the GAA repeat from the first intron. The expanded GAA repeat is thought to affect the DNA structure and leads to recruit the formation of heterochromatin which turn off the frataxin gene (FIG. 32A).

Competitive Advantage over other therapeutic strategies are listed below:

siRNA knockdown is not applicable in this case, as disease is due to reduced expression of frataxin. Viral gene therapy is currently being explored. HSV-1 based vectors were used to deliver the frataxin gene in animal models and have shown therapeutic effect. However, long term efficacy of virus-based frataxin delivery suffer from several problems: First, it is difficult to regulate the expression of frataxin to match natural levels in health individuals, and second, long term over expression of frataxin leads to cell death.

Nucleases may be used to excise the GAA repeat to restore healthy genotype, but Zinc Finger Nuclease and TALEN strategies require delivery of two pairs of high efficacy nucleases, which is difficult for both delivery as well as nuclease engineering (efficient excision of genomic DNA by ZFN or TALEN is difficult to achieve).

In contrast to above strategies, the CRISPR-Cas system has clear advantages. The Cas9 enzyme is more efficient and more multiplexible, by which it is meant that one or more targets can be set at the same time. So far, efficient excision of genomic DNA >30% by Cas9 in human cells and may be as high as 30%, and may be improved in the future. Furthermore, with regard to certain trinucleotide repeat disorders like Huntington's disease (HD), trinucleotide repeats in the coding region may be addressed if there are differences between the two alleles. Specifically, if a HD patient is heterozygous for mutant HTT and there are nucleotide differences such as SNPs between the wt and mutant HTT alleles, then Cas9 may be used to specifically target the mutant HTT allele. ZFN or TALENs will not have the ability to distinguish two alleles based on single base differences.

Figure 32B:
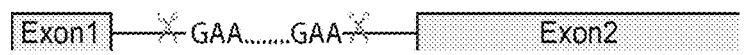

In adopting a strategy using the CRISPR-Cas 9 enzyme to address Friedreich's ataxia, Applicants design a number of guide RNAs targeting sites flanking the GAA expansion and the most efficient and specific ones are chosen (FIG. 32B).

Applicants deliver a combination of guide RNAs targeting the intron 1 of FXN along with Cas9 to mediate excision of the GAA expansion region. AAV9 may be used to mediate efficient delivery of Cas9 and in the spinal cord.

If the Alu element adjacent to the GAA expansion is considered important, there may be constraints to the number of sites that can be targeted but Applicants may adopt strategies to avoid disrupting it.

Alternative Strategies:

Rather than modifying the genome using Cas9, Applicants may also directly activate the FXN gene using Cas9 (nuclease activity deficient)-based DNA binding domain to target a transcription activation domain to the FXN gene. Applicants may have to address the robustness of the Cas9-mediated artificial transcription activation to ensure that it is robust enough as compared to other methods (Tremblay et al., Transcription Activator-Like Effector Proteins Induce the Expression of the Frataxin Gene; Human Gene Therapy. August 2012, 23(8): 883-890.)

Example 29: Strategies for Minimizing Off-Target Cleavage Using Cas9 Nickase

As previously mentioned in the application, Cas9 may be mutated to mediate single strand cleavage via one or more of the following mutations: D10A, E762A, and H840A.

To mediate gene knockout via NHEJ, Applicants use a nickase version of Cas9 along with two guide RNAs. Off-target nicking by each individual guide RNA may be primarily repaired without mutation, double strand breaks (which can lead to mutations via NHEJ) only occur when the target sites are adjacent to each other. Since double strand breaks introduced by double nicking are not blunt, co-expression of end-processing enzymes such as TREX1 will increase the level of NHEJ activity.

The following list of targets in tabular form are for genes involved in the following diseases:

Lafora's Disease—target GSY1 or PPP1R3C (PTG) to reduce glycogen in neurons.

Hypercholesterolemia—target PCSK9

Target sequences are listed in pairs (L and R) with different number of nucleotides in the spacer (0 to 3 bp). Each spacer may also be used by itself with the wild type Cas9 to introduce double strand break at the target locus.

| Gene | Target | Sequence | SEQ ID |
|---|---|---|---|
| GYS1 (human) | GGCC-L | ACCCTTGTTAGCCACCTCCC | (SEQ ID NO: 138) |
| | GGCC-R | GAACGCAGTGCTCTTCGAAG | (SEQ ID NO: 139) |
| | GGNCC-L | CTCACGCCCTGCTCCGTGTA | (SEQ ID NO: 140) |
| | GGNCC-R | GGCGACAACTACTTCCTGGT | (SEQ ID NO: 141) |
| | GGNNCC-L | CTCACGCCCTGCTCCGTGTA | (SEQ ID NO: 142) |
| | GGNNCC-R | GGGCGACAACTACTTCCTGG | (SEQ ID NO: 143) |
| | GGNNNCC-L | CCTCTTCAGGGCCGGGGTGG | (SEQ ID NO: 144) |
| | GGNNNCC-R | GAGGACCCAGGTGGAACTGC | (SEQ ID NO: 145) |
| PCSK9 (human) | GGCC-L | TCAGCTCCAGGCGGTCCTGG | (SEQ ID NO: 146) |
| | GGCC-R | AGCAGCAGCAGCAGTGGCAG | (SEQ ID NO: 147) |
| | GGNCC-L | TGGGCACCGTCAGCTCCAGG | (SEQ ID NO: 148) |
| | GGNCC-R | CAGCAGTGGCAGCGGCCACC | (SEQ ID NO: 149) |
| | GGNNCC-L | ACCTCTCCCTGGCCCTCAT | (SEQ ID NO: 150) |
| | GGNNCC-R | CCAGGACCGCCTGGAGCTGA | (SEQ ID NO: 151) |
| | GGNNNCC-L | CCGTCAGCTCCAGGCGGTCC | (SEQ ID NO: 152) |
| | GGNNNCC-R | AGCAGCAGCAGCAGTGGCAG | (SEQ ID NO: 153) |
| PPP1R3C (PTG) (human) | GGCC-L | ATGTGCCAAGCAAAGCCTCA | (SEQ ID NO: 154) |
| | GGCC-R | TTCGGTCATGCCCGTGGATG | (SEQ ID NO: 155) |
| | GGNCC-L | GTCGTTGAAATTCATCGTAC | (SEQ ID NO: 156) |
| | GGNCC-R | ACCACCTGTGAAGAGTTTCC | (SEQ ID NO: 157) |
| | GGNNCC-L | CGTCGTTGAAATTCATCGTA | (SEQ ID NO: 158) |
| | GGNNCC-R | ACCACCTGTGAAGAGTTTCC | (SEQ ID NO: 159) |
| Gys1 (mouse) | GGCC-L | GAACGCAGTGCTTTTCGAGG | (SEQ ID NO: 160) |
| | GGCC-R | ACCCTTGTTGGCCACCTCCC | (SEQ ID NO: 161) |
| | GGNCC-L | GGTGACAACTACTATCTGGT | (SEQ ID NO: 162) |
| | GGNCC-R | CTCACACCCTGCTCCGTGTA | (SEQ ID NO: 163) |
| | GGNNCC-L | GGGTGACAACTACTATCTGG | (SEQ ID NO: 164) |
| | GGNNCC-R | CTCACACCCTGCTCCGTGTA | (SEQ ID NO: 165) |
| | GGNNNCC-L | CGAGAACGCAGTGCTTTTCG | (SEQ ID NO: 166) |
| | GGNNNCC-R | ACCCTTGTTGGCCACCTCCC | (SEQ ID NO: 167) |
| PPP1R3C (PTG) (mouse) | GGCC-L | ATGAGCCAAGCAAATCCTCA | (SEQ ID NO: 168) |
| | GGCC-R | TTCCGTCATGCCCGTGGACA | (SEQ ID NO: 169) |
| | GGNCC-L | CTTCGTTGAAAACCATTGTA | (SEQ ID NO: 170) |
| | GGNCC-R | CCACCTCTGAAGAGTTTCCT | (SEQ ID NO: 171) |
| | GGNNCC-L | CTTCGTTGAAAACCATTGTA | (SEQ ID NO: 172) |
| | GGNNCC-R | ACCACCTCTGAAGAGTTTCC | (SEQ ID NO: 173) |
| | GGNNNCC-L | CTTCCACTCACTCTGCGATT | (SEQ ID NO: 174) |
| | GGNNNCC-R | ACCATGTCTCAGTGTCAAGC | (SEQ ID NO: 175) |
| PCSK9 (mouse) | GGCC-L | GGCGGCAACAGCGGCAACAG | (SEQ ID NO: 176) |
| | GGCC-R | ACTGCTCTGCGTGGCTGCGG | (SEQ ID NO: 177) |
| | GGNNCC-L | CCGCAGCCACGCAGAGCAGT | (SEQ ID NO: 178) |
| | GGNNCC-R | GCACCTCTCCTCGCCCCGAT | (SEQ ID NO: 179) |

Alternative strategies for improving stability of guide RNA and increasing specificity 1. Nucleotides in the 5' of the guide RNA may be linked via thiolester linkages rather than phosphoester linkage like in natural RNA. Thiolester linkage may prevent the guide RNA from being digested by endogenous RNA degradation machinery.

2. Nucleotides in the guide sequence (5' 20 bp) of the guide RNA can use bridged nucleic acids (BNA) as the bases to improve the binding specificity.

Example 30: CRISPR-Cas for Rapid, Multiplex Genome Editing

Aspects of the invention relate to protocols and methods by which efficiency and specificity of gene modification may be tested within 3-4 days after target design, and modified clonal cell lines may be derived within 2-3 weeks.

Programmable nucleases are powerful technologies for mediating genome alteration with high precision. The RNA-guided Cas9 nuclease from the microbial CRISPR adaptive immune system can be used to facilitate efficient genome editing in eukaryotic cells by simply specifying a 20-nt targeting sequence in its guide RNA. Applicants describe a set of protocols for applying Cas9 to facilitate efficient genome editing in mammalian cells and generate cell lines for downstream functional studies. Beginning with target design, efficient and specific gene modification can be achieved within 3-4 days, and modified clonal cell lines can be derived within 2-3 weeks.

The ability to engineer biological systems and organisms holds enormous potential for applications across basic science, medicine, and biotechnology. Programmable sequence-specific endonucleases that facilitate precise editing of endogenous genomic loci are now enabling systematic interrogation of genetic elements and causal genetic variations in a broad range of species, including those that have not been genetically tractable previously. A number of genome editing technologies have emerged in recent years, including zinc finger nucleases (ZFNs), transcription activator-like effector nucleases (TALENs), and the RNA-guided CRISPR-Cas nuclease system. The first two technologies use a common strategy of tethering endonuclease catalytic domains to modular DNA-binding proteins for inducing targeted DNA double stranded breaks (DSB) at specific genomic loci. By contrast, Cas9 is a nuclease guided by small RNAs through Watson-Crick base-pairing with target DNA, presenting a system that is easy to design, efficient, and well-suited for high-throughput and multiplexed gene editing for a variety of cell types and organisms. Here Applicants describe a set of protocols for applying the recently developed Cas9 nuclease to facilitate efficient genome editing in mammalian cells and generate cell lines for downstream functional studies.

Like ZFNs and TALENs, Cas9 promotes genome editing by stimulating DSB at the target genomic loci. Upon cleavage by Cas9, the target locus undergoes one of two major pathways for DNA damage repair, the error-prone non-homologous end joining (NHEJ) or the high-fidelity homology directed repair (HDR) pathway. Both pathways may be utilized to achieve the desired editing outcome.

NHEJ: In the absence of a repair template, the NHEJ process re-ligates DSBs, which may leave a scar in the form of indel mutations. This process can be harnessed to achieve gene knockouts, as indels occurring within a coding exon may lead to frameshift mutations and a premature stop codon. Multiple DSBs may also be exploited to mediate larger deletions in the genome.

HDR: Homology directed repair is an alternate major DNA repair pathway to NHEJ. Although HDR typically occurs at lower frequencies than NHEJ, it may be harnessed to generate precise, defined modifications at a target locus in the presence of an exogenously introduced repair template. The repair template may be either in the form of double stranded DNA, designed similarly to conventional DNA targeting constructs with homology arms flanking the insertion sequence, or single-stranded DNA oligonucleotides (ssODNs). The latter provides an effective and simple method for making small edits in the genome, such as the introduction of single nucleotide mutations for probing causal genetic variations. Unlike NHEJ, HDR is generally active only in dividing cells and its efficiency varies depending on the cell type and state.

Overview of CRISPR: The CRISPR-Cas system, by contrast, is at minimum a two-component system consisting of the Cas9 nuclease and a short guide RNA. Re-targeting of Cas9 to different loci or simultaneous editing of multiple genes simply requires cloning a different 20-bp oligonucleotide. Although specificity of the Cas9 nuclease has yet to be thoroughly elucidated, the simple Watson-Crick base-pairing of the CRISPR-Cas system is likely more predictable than that of ZFN or TALEN domains.

The type II CRISPR-Cas (clustered regularly interspaced short palindromic repeats) is a bacterial adaptive immune system that uses Cas9, to cleave foreign genetic elements. Cas9 is guided by a pair of non-coding RNAs, a variable crRNA and a required auxiliary tracrRNA. The crRNA contains a 20-nt guide sequence determines specificity by locating the target DNA via Watson-Crick base-pairing. In the native bacterial system, multiple crRNAs are co-transcribed to direct Cas9 against various targets. In the CRISPR-Cas system derived from *Streptococcus pyogenes*, the target DNA must immediately precede a 5'-NGG/NRG protospacer adjacent motif (PAM), which can vary for other CRISPR systems.

CRISPR-Cas is reconstituted in mammalian cells through the heterologous expression of human codon-optimized Cas9 and the requisite RNA components. Furthermore, the crRNA and tracrRNA can be fused to create a chimeric, synthetic guide RNA (sgRNA). Cas9 can thus be re-directed toward any target of interest by altering the 20-nt guide sequence within the sgRNA.

Given its ease of implementation and multiplex capability, Cas9 has been used to generate engineered eukaryotic cells carrying specific mutations via both NHEJ and HDR. In addition, direct injection of sgRNA and mRNA encoding Cas9 into embryos has enabled the rapid generation of transgenic mice with multiple modified alleles; these results hold promise for editing organisms that are otherwise genetically intractable.

A mutant Cas9 carrying a disruption in one of its catalytic domains has been engineered to nick rather than cleave DNA, allowing for single-stranded breaks and preferential repair through HDR, potentially ameliorating unwanted indel mutations from off-target DSBs. Additionally, a Cas9 mutant with both DNA-cleaving catalytic residues mutated has been adapted to enable transcriptional regulation in *E. coli*, demonstrating the potential of functionalizing Cas9 for diverse applications. Certain aspects of the invention relate to the construction and application of Cas9 for multiplexed editing of human cells.

Applicants have provided a human codon-optimized, nuclear localization sequence-flanked Cas9 to facilitate eukaryotic gene editing. Applicants describe considerations for designing the 20-nt guide sequence, protocols for rapid construction and functional validation of sgRNAs, and finally use of the Cas9 nuclease to mediate both NHEJ- and HDR-based genome modifications in human embryonic kidney (HEK-293FT) and human stem cell (HUES9) lines. This protocol can likewise be applied to other cell types and organisms.

Target selection for sgRNA: There are two main considerations in the selection of the 20-nt guide sequence for gene targeting: 1) the target sequence should precede the 5'-NGG PAM for *S. pyogenes* Cas9, and 2) guide sequences should be chosen to minimize off-target activity. Applicants provided an online Cas9 targeting design tool that takes an input sequence of interest and identifies suitable target sites. To experimentally assess off-target modifications for each sgRNA, Applicants also provide computationally predicted off-target sites for each intended target, ranked according to Applicants' quantitative specificity analysis on the effects of base-pairing mismatch identity, position, and distribution.

The detailed information on computationally predicted off-target sites is as follows:

Considerations for Off-target Cleavage Activities: Similar to other nucleases, Cas9 can cleave off-target-DNA targets in the genome at reduced frequencies. The extent to which a given guide sequence exhibit off-target activity depends on a combination of factors including enzyme concentration, thermodynamics of the specific guide sequence employed, and the abundance of similar sequences in the target genome. For routine application of Cas9, it is important to consider ways to minimize the degree of off-target cleavage and also to be able to detect the presence of off-target cleavage.

Minimizing off-target activity: For application in cell lines, Applicants recommend following two steps to reduce the degree of off-target genome modification. First, using our online CRISPR target selection tool, it is possible to computationally assess the likelihood of a given guide sequence to have off-target sites. These analyses are performed through an exhaustive search in the genome for off-target sequences that are similar sequences as the guide sequence. Comprehensive experimental investigation of the effect of mismatching bases between the sgRNA and its target DNA revealed that mismatch tolerance is 1) position dependent—the 8-14 bp on the 3' end of the guide sequence are less tolerant of mismatches than the 5' bases, 2) quantity dependent—in general more than 3 mismatches are not tolerated, 3) guide sequence dependent—some guide sequences are less tolerant of mismatches than others, and 4) concentration dependent—off-target cleavage is highly sensitive to the amount of transfected DNA. The Applicants' target site analysis web tool (available at the website genome-engineering.org/tools) integrates these criteria to provide predictions for likely off-target sites in the target genome. Second, Applicants recommend titrating the amount of Cas9 and sgRNA expression plasmid to minimize off-target activity.

Detection of off-target activities: Using Applicants' CRISPR targeting web tool, it is possible to generate a list of most likely off-target sites as well as primers performing SURVEYOR or sequencing analysis of those sites. For isogenic clones generated using Cas9, Applicants strongly recommend sequencing these candidate off-target sites to check for any undesired mutations. It is worth noting that there may be off target modifications in sites that are not included in the predicted candidate list and full genome sequence should be performed to completely verify the absence of off-target sites. Furthermore, in multiplex assays where several DSBs are induced within the same genome, there may be low rates of translocation events and can be evaluated using a variety of techniques such as deep sequencing.

The online tool provides the sequences for all oligos and primers necessary for 1) preparing the sgRNA constructs, 2) assaying target modification efficiency, and 3) assessing cleavage at potential off-target sites. It is worth noting that because the U6 RNA polymerase III promoter used to express the sgRNA prefers a guanine (G) nucleotide as the first base of its transcript, an extra G is appended at the 5' of the sgRNA where the 20-nt guide sequence does not begin with G.

Approaches for sgRNA construction and delivery: Depending on the desired application, sgRNAs may be delivered as either 1) PCR amplicons containing an expression cassette or 2) sgRNA-expressing plasmids. PCR-based sgRNA delivery appends the custom sgRNA sequence onto the reverse PCR primer used to amplify a U6 promoter template. The resulting amplicon may be co-transfected with a plasmid containing Cas9 (PX165). This method is optimal for rapid screening of multiple candidate sgRNAs, as cell transfections for functional testing can be performed mere hours after obtaining the sgRNA-encoding primers. Because this simple method obviates the need for plasmid-based cloning and sequence verification, it is well suited for testing or co-transfecting a large number of sgRNAs for generating large knockout libraries or other scale-sensitive applications. Note that the sgRNA-encoding primers are over 100-bp, compared to the ~20-bp oligos required for plasmid-based sgRNA delivery.

Construction of an expression plasmid for sgRNA is also simple and rapid, involving a single cloning step with a pair of partially complementary oligonucleotides. After annealing the oligo pairs, the resulting guide sequences may be inserted into a plasmid bearing both Cas9 and an invariant scaffold bearing the remainder of the sgRNA sequence (PX330). The transfection plasmids may also be modified to enable virus production for in vivo delivery.

In addition to PCR and plasmid-based delivery methods, both Cas9 and sgRNA can be introduced into cells as RNA.

Design of repair template: Traditionally, targeted DNA modifications have required use of plasmid-based donor repair templates that contain homology arms flanking the site of alteration. The homology arms on each side can vary in length, but are typically longer than 500 bp. This method can be used to generate large modifications, including insertion of reporter genes such as fluorescent proteins or antibiotic resistance markers. The design and construction of targeting plasmids has been described elsewhere.

More recently, single-stranded DNA oligonucleotides (ssODNs) have been used in place of targeting plasmids for short modifications within a defined locus without cloning. To achieve high HDR efficiencies, ssODNs contain flanking sequences of at least 40 bp on each side that are homologous to the target region, and can be oriented in either the sense or antisense direction relative to the target locus.

Functional Testing

SURVEYOR nuclease assay: Applicants detected indel mutations either by the SURVEYOR nuclease assay (or PCR amplicon sequencing. Applicants online CRISPR target design tool provides recommended primers for both approaches. However, SURVEYOR or sequencing primers may also be designed manually to amplify the region of interest from genomic DNA and to avoid non-specific amplicons using NCBI Primer-BLAST. SURVEYOR primers should be designed to amplify 300-400 bp (for a 600-800 bp total amplicon) on either side of the Cas9 target for allowing clear visualization of cleavage bands by gel electrophoresis. To prevent excessive primer dimer formation, SURVEYOR primers should be designed to be typically under 25-nt long with melting temperatures of ~60° C. Applicants recommend testing each pair of candidate primers for specific PCR amplicons as well as for the absence of non-specific cleavage during the SURVEYOR nuclease digestion process.

Plasmid- or ssODN-mediated HDR: HDR can be detected via PCR-amplification and sequencing of the modified region. PCR primers for this purpose should anneal outside the region spanned by the homology arms to avoid false detection of residual repair template (HDR Fwd and Rev, FIG. 30). For ssODN-mediated HDR, SURVEYOR PCR primers can be used.

Detection of indels or HDR by sequencing: Applicants detected targeted genome modifications by either Sanger or next-generation deep sequencing (NGS). For the former, genomic DNA from modified region can be amplified using either SURVEYOR or HDR primers. Amplicons should be subcloned into a plasmid such as pUC19 for transformation; individual colonies can be sequenced to reveal clonal genotype.

Applicants designed next-generation sequencing (NGS) primers for shorter amplicons, typically in the 100-200 bp size range. For detecting NHEJ mutations, it is important to design primers with at least 10-20 bp between the priming regions and the Cas9 target site to allow detection of longer indels. Applicants provide guidelines for a two-step PCR method to attach barcoded adapters for multiplex deep sequencing. Applicants recommend the Illumina platform, due to its generally low levels of false positive indels. Off-target analysis (described previously) can then be performed through read alignment programs such as ClustalW, Geneious, or simple sequence analysis scripts.

Materials and Reagents sgRNA Preparation:

UltraPure DNaseRNase-free distilled water (Life Technologies, cat. no. 10977-023) Herculase II fusion polymerase (Agilent Technologies, cat. no. 600679) CRITICAL. Standard Taq polymerase, which lacks 3'-5' exonuclease proofreading activity, has lower fidelity and can lead to amplification errors. Herculase II is a high-fidelity polymerase (equivalent fidelity to Pfu) that produces high yields of PCR product with minimal optimization. Other high-fidelity polymerases may be substituted.

Herculase II reaction buffer (5×; Agilent Technologies, included with polymerase)

dNTP solution mix (25 mM each; Enzymatics, cat. no. N205L)

MgCl2 (25 mM; ThermoScientific, cat. no. R0971)

QIAquick gel extraction kit (Qiagen, cat. no. 28704)

QIAprep spin miniprep kit (Qiagen, cat. no. 27106)

UltraPure TBE buffer (10×; Life Technologies, cat. no. 15581-028)

SeaKem LE agarose (Lonza, cat. no. 50004)

SYBR Safe DNA stain (10,000×; Life Technologies, cat. no. 533102)

1-kb Plus DNA ladder (Life Technologies, cat. no. 10787-018)

TrackIt CyanOrange loading buffer (Life Technologies, cat. no. 10482-028)

FastDigest BbsI (BpiI) (Fermentas/ThermoScientific, cat. no. FD1014)

Fermentas Tango Buffer (Fermentas/ThermoScientific, cat. no. BY5)

DL-dithiothreitol (DTT; Fermentas/ThermoScientific, cat. no. R0862)

T7 DNA ligase (Enzymatics, cat. no. L602L)

Critical: Do not substitute the more commonly used T4 ligase. T7 ligase has 1,000-fold higher activity on the sticky ends than on the blunt ends and higher overall activity than commercially available concentrated T4 ligases.

T7 2× Rapid Ligation Buffer (included with T7 DNA ligase, Enzymatics, cat. no.
L602L)

T4 Polynucleotide Kinase (New England Biolabs, cat. no M0201S)

T4 DNA Ligase Reaction Buffer (10×; New England Biolabs, cat. no B0202S)

Adenosine 5'-triphosphate (10 mM; New England Biolabs, cat. no. P0756S)

PlasmidSafe ATP-dependent DNase (Epicentre, cat. no. E3101K)

One Shot Stbl3 chemically competent *Escherichia coli* (*E. coli*) (Life Technologies, cat. no. C7373-03)

SOC medium (New England Biolabs, cat. no. B9020S)

LB medium (Sigma, cat. no. L3022)

LB agar medium (Sigma, cat. no. L2897)

Ampicillin, sterile filtered (100 mg ml−1; Sigma, cat. no. A5354)

Mammalian Cell Culture:

HEK293FT cells (Life Technologies, cat. no. R700-07)

Dulbecco's minimum Eagle's medium (DMEM, 1×, high glucose; Life Technologies, cat. no. 10313-039)

Dulbecco's minimum Eagle's medium (DMEM, 1×, high glucose, no phenol red; Life Technologies, cat. no. 31053-028)

Dulbecco's phosphate-buffered saline (DPBS, 1×; Life Technologies, cat. no. 14190-250)

Fetal bovine serum, qualified and heat inactivated (Life Technologies, cat. no. 10438-034)

Opti-MEM I reduced-serum medium (FBS; Life Technologies, cat. no. 11058-021)

Penicillin-streptomycin (100×; Life Technologies, cat. no. 15140-163)

TrypLET™ Express (1×, no Phenol Red; Life Technologies, cat. no. 12604-013)

Lipofectamine 2000 transfection reagent (Life Technologies, cat. no. 11668027)

Amaxa SF Cell Line 4D-Nucleofector® X Kit S (32 RCT; Lonza, cat. no V4XC-2032)

HUES 9 cell line (HARVARD STEM CELL SCIENCE)

Geltrex LDEV-Free Reduced Growth Factor Basement Membrane Matrix (Life Technologies, cat. no. A1413201)

mTeSR1 medium (Stemcell Technologies, cat. no. 05850)

Accutase cell detachment solution (Stemcell Technologies, cat. no. 07920) ROCK Inhibitor (Y-27632; Millipore, cat. no. SCM075)

Amaxa P3 Primary Cell 4D-Nucleofector® X Kit S (32 RCT; Lonza cat. no. V4XP-3032)

Genotyping Analysis:

QuickExtract DNA extraction solution (Epicentre, cat. no. QE09050)

PCR primers for SURVEYOR, RFLP analysis, or sequencing (see Primer table)

Herculase II fusion polymerase (Agilent Technologies, cat. no. 600679)

CRITICAL. As Surveyor assay is sensitive to single-base mismatches, it is particularly important to use a high-fidelity polymerase. Other high-fidelity polymerases may be substituted.

Herculase II reaction buffer (5×; Agilent Technologies, included with polymerase)

dNTP solution mix (25 mM each; Enzymatics, cat. no. N205L)

QIAquick gel extraction kit (Qiagen, cat. no. 28704)

Taq Buffer (10×; Genscript, cat. no. B0005)

SURVEYOR mutation detection kit for standard gel electrophoresis (Transgenomic, cat. no. 706025)

UltraPure TBE buffer (10×; Life Technologies, cat. no. 15581-028)

SeaKem LE agarose (Lonza, cat. no. 50004)

4-20% TBE Gels 1.0 mm, 15 Well (Life Technologies, cat. no. EC62255BOX)

Novex® Hi-Density TBE Sample Buffer (5×; Life Technologies, cat. no. LC6678)

SYBR Gold Nucleic Acid Gel Stain (10,000×; Life Technologies, cat. no. S-11494)

1-kb Plus DNA ladder (Life Technologies, cat. no. 10787-018)

TrackIt CyanOrange loading buffer (Life Technologies, cat. no. 10482-028)

FastDigest HindIII (Fermentas/ThermoScientific, cat. no. FD0504)

Equipment

Filtered sterile pipette tips (Corning)

Standard 1.5 ml microcentrifuge tubes (Eppendorf, cat. no. 0030 125.150)

Axygen 96-well PCR plates (VWR, cat. no. PCR-96M2-HSC)

Axygen 8-Strip PCR tubes (Fischer Scientific, cat. no. 14-222-250)

Falcon tubes, polypropylene, 15 ml (BD Falcon, cat. no. 352097)

Falcon tubes, polypropylene, 50 ml (BD Falcon, cat. no. 352070)

Round-bottom Tube with cell strainer cap, 5 ml (BD Falcon, cat. no. 352235)

Petri dishes (60 mm×15 mm; BD Biosciences, cat. no. 351007)

Tissue culture plate (24 well; BD Falcon, cat. no. 353047)

Tissue culture plate (96 well, flat bottom; BD Falcon, cat. no. 353075)

Tissue culture dish (100 mm; BD Falcon, 353003)

96-well thermocycler with programmable temperature stepping functionality (Applied Biosystems Veriti, cat. no. 4375786).

Desktop microcentrifuges 5424, 5804 (Eppendorf)

Gel electrophoresis system (PowerPac basic power supply, Bio-Rad, cat. no. 164-5050, and Sub-Cell GT System gel tray, Bio-Rad, cat. no. 170-4401)

Novex XCell SureLock Mini-Cell (Life Technologies, cat. no. EI0001)

Digital gel imaging system (GelDoc EZ, Bio-Rad, cat. no. 170-8270, and blue sample tray, Bio-Rad, cat. no. 170-8273)

Blue light transilluminator and orange filter goggles (SafeImager 2.0; Invitrogen, cat. no. G6600)

Gel quantification software (Bio-Rad, ImageLab, included with GelDoc EZ, or open-source ImageJ from the National Institutes of Health, available at the website rsbweb.nih.gov/ij/) UV spectrophotometer (NanoDrop 2000c, Thermo Scientific)

Reagent Setup

Tris-borate EDTA (TBE) electrophoresis solution Dilute TBE buffer in distilled water to 1× working solution for casting agarose gels and for use as a buffer for gel electrophoresis. Buffer may be stored at room temperature (18-22° C.) for at least 1 year.

- ATP, 10 mM Divide 10 mM ATP into 50-μl aliquots and store at −20° C. for up to 1 year; avoid repeated freeze-thaw cycles.
- DTT, 10 mM Prepare 10 mM DTT solution in distilled water and store in 20-μl aliquots at −70° C. for up to 2 years; for each reaction, use a new aliquot, as DTT is easily oxidized.
- D10 culture medium For culture of HEK293FT cells, prepare D10 culture medium by supplementing DMEM with 1× GlutaMAX and 10% (vol/vol) fetal bovine serum. As indicated in the protocol, this medium can also be supplemented with 1× penicillin-streptomycin D10 medium can be made in advance and stored at 4° C. for up to 1 month.
- mTeSR1 culture medium For culture of human embryonic stem cells, prepare mTeSR1 medium by supplementing the 5× supplement (included with mTeSR1 basal medium), and 100 ug/ml Normocin.

Procedure

Design of Targeting Components and Use of the Online Tool•Timing 1 d

1| Input target genomic DNA sequence. Applicants provide an online Cas9 targeting design tool that takes an input sequence of interest, identifies and ranks suitable target sites, and computationally predicts off-target sites for each intended target. Alternatively, one can manually select guide sequence by identifying the 20-bp sequence directly upstream of any 5'-NGG.

2| Order necessary oligos and primers as specified by the online tool. If the site is chosen manually, the oligos and primers should be designed.

Preparation of sgRNA Expression Construct

3| To generate the sgRNA expression construct, either the PCR- or plasmid-based protocol can be used.

(A) via PCR amplification•Timing 2 h (i) Applicants prepare diluted U6 PCR template. Applicants recommend using PX330 as a PCR template, but any U6-containing plasmid may likewise be used as the PCR template. Applicants diluted template with ddH$_2$O to a concentration of 10 ng/ul. Note that if a plasmid or cassette already containing an U6-driven sgRNA is used as a template, a gel extraction needs to be performed to ensure that the product contains only the intended sgRNA and no trace sgRNA carryover from template.

(ii) Applicants prepared diluted PCR oligos. U6-Fwd and U6-sgRNA-Rev primers are diluted to a final concentration of 10 uM in ddH$_2$O (add 10 ul of 100 uM primer to 90 ul ddH$_2$O).

(iii) U6-sgRNA PCR reaction. Applicants set up the following reaction for each U6-sgRNA-Rev primer and mastermix as needed:

| Component: | Amount (ul) | Final concentration |
|---|---|---|
| Herculase II PCR buffer, 5X | 10 | 1X |
| dNTP, 100 mM (25 mM each) | 0.5 | 1 mM |
| U6 template (PX330) | 1 | 0.2 ng/ul |
| U6-Fwd primer | 1 | 0.2 uM |
| U6-sgRNA-Rev primer (variable) | 1 | 0.2 uM |
| Herculase II Fusion polymerase | 0.5 | |
| Distilled water | 36 | |
| Total | 50 | |

(iv) Applicants performed PCR reaction on the reactions from step (iii) using the following cycling conditions:

| Cycle number | Denature | Anneal | Extend |
|---|---|---|---|
| 1 | 95° C., 2 m | | |
| 2-31 | 95° C., 20 s | 60° C., 20 s | 72° C., 20 s |
| 32 | | | 72° C., 3 m |

(v) After the reaction is completed, Applicants ran the product on a gel to verify successful, single-band amplification. Cast a 2% (wt/vol) agarose gel in 1×TBE buffer with 1× SYBR Safe dye. Run 5 ul of the PCR product in the gel at 15 V cm−1 for 20-30 min. Successful amplicons should yield one single 370-bp product and the template should be invisible. It should not be necessary to gel extract the PCR amplicon.

(vi) Applicants purified the PCR product using the QIAquick PCR purification kit according to the manufacturer's directions. Elute the DNA in 35 ul of Buffer EB or water. Purified PCR products may be stored at 4° C. or −20° C.

(B) Cloning sgRNA into Cas9-Containing Bicistronic Expression Vector •Timing 3d (i) Prepare the sgRNA oligo inserts. Applicants resuspended the top and bottom strands of oligos for each sgRNA design to a final concentration of 100 uM. Phosphorylate and anneal the oligo as follows:

| | |
|---|---|
| Oligo 1 (100 uM) | 1 ul |
| Oligo 2 (100 uM) | 1 ul |
| T4 Ligation Buffer, 10X | 1 ul |
| T4 PNK | 1 ul |
| ddH$_2$O | 6 ul |
| Total | 10 ul |

(ii) Anneal in a thermocycler using the following parameters:

37° C. for 30 m
95° C. for 5 m
Ramp down to 25° C. at 5° C. per m (iii) Applicants diluted phosphorylated and annealed oligos 1:200 by add 1 ul of oligo to 199 ul room temperature ddH₂O.

(iv) Clone sgRNA oligo into PX330. Applicants set up Golden Gate reaction for each sgRNA. Applicants recommend also setting up a no-insert, PX330 only negative control.

| | |
|---|---|
| PX330 (100 ng) | x ul |
| Diluted oligo duplex from step (iii) | 2 ul |
| Tango Buffer, 10X | 2 ul |
| DTT, 10 mM | 1 ul |
| ATP, 10 mM | 1 ul |
| FastDigest BbsI | 1 ul |
| T7 Ligase | 0.5 ul |
| ddH₂O | x ul |
| Total | 20 ul |

(v) Incubate the Golden Gate reaction for a total of 1 h:

| Cycle number | Condition |
|---|---|
| 1-6 | 37° C. for 5 m, 21° C. for 5 m |

(vi) Applicants treated Golden Gate reaction with PlasmidSafe exonuclease to digest any residual linearized DNA. This step is optional but highly recommended.

| | |
|---|---|
| Golden Gate reaction from step 4 | 11 ul |
| 10X PlasmidSafe Buffer | 1.5 ul |
| ATP, 10 mM | 1.5 ul |
| PlasmidSafe exonuclease | 1 ul |
| Total | 15 ul |

(vii) Applicants incubated the PlasmidSafe reaction at 37° C. for 30 min, followed by inactivation at 70° C. for 30 min. Pause point: after completion, the reaction may be frozen and continued later. The circular DNA should be stable for at least 1 week.

(viii) Transformation. Applicants transformed the PlasmidSafe-treated plasmid into a competent *E. coli* strain, according to the protocol supplied with the cells. Applicants recommend Stbl3 for quick transformation. Briefly, Applicants added 5 ul of the product from step (vii) into 20 ul of ice-cold chemically competent Stbl3 cells. This is then incubated on ice for 10 m, heat shocked at 42° C. for 30 s, returned immediately to ice for 2 m, 100 ul of SOC medium is added, and this is plated onto an LB plate containing 100 ug/ml ampicillin with incubation overnight at 37° C.

(ix) Day 2: Applicants inspected plates for colony growth. Typically, there are no colonies on the negative control plates (ligation of BbsI-digested PX330 only, no annealed sgRNA oligo), and tens to hundreds of colonies on the PX330-sgRNA cloning plates.

(x) From each plate, Applicants picked 2-3 colonies to check correct insertion of sgRNA. Applicants used a sterile pipette tip to inoculate a single colony into a 3 ml culture of LB medium with 100 ug/ml ampicillin. Incubate and shake at 37° C. overnight.

(xi) Day 3: Applicants isolated plasmid DNA from overnight cultures using a QiAprep Spin miniprep kit according to the manufacturer's instructions.

(xii) Sequence validate CRISPR plasmid. Applicants verified the sequence of each colony by sequencing from the U6 promoter using the U6-Fwd primer. Optional: sequence the Cas9 gene using primers listed in the following Primer table.

| Primer | Sequence (5' to 3') | Purpose |
|---|---|---|
| U6-For | GAGGGCCTATTTCCCATGATTCC (SEQ ID NO: 180) | Amplify U6-sgRNA |
| U6-Rev | AAAAAAAGCACCGACTCGGTGCCACTTTTTCAAGTTGATAACGGACTAGCCTTATTTTAACTTGCTATTTCTAGCTCTAAAACNNNNNNNNNNNNNNNNNNNNNNCCGGTGTTTCGTCCTTTCCACAAG (SEQ ID NO: 181) | Amplify U6-sgRNA; N is reverse complement of target |
| sgRNA-top | CACCGNNNNNNNNNNNNNNNNNNNN (SEQ ID NO: 182) | Clone sgRNA into PX330 |
| sgRNA-bottom | AAACNNNNNNNNNNNNNNNNNNNNC (SEQ ID NO: 183) | Clone sgRNA into PX330 |
| U6-EMX1-Rev | AAAAAAAGCACCGACTCGGTGCCACTTTTTCAAGTTGATAACGGACTAGCCTTATTTTAACTTGCTATTTCTAGCTCTAAAACCCCTAGTCATTGGAGGTGACCGGTGTTTCGTCCTTTCCACAAG (SEQ ID NO: 184) | Amplify U6-EMX1 sgRNA |
| EMX1-top | CACCGTCACCTCCAATGACTAGGG (SEQ ID NO: 185) | Clone EMX1 sgRNA into PX330 |
| EMX1-bottom | AAACCCCTAGTCATTGGAGGTGAC (SEQ ID NO: 186) | Clone EMX1 sgRNA into PX330 |
| ssODN-sense | CAGAAGAAGAAGGGCTCCCATCACATCAACCGGTGGCGCATTGCCACGAAGCAGGCCAATGGGGAGGACATCGATGTCACCTCCAATGAC<u>AAGCTTGCTAGC</u>GGTGGGCAACCACAAACCCACGAGGGCAGAGTGCTGCTTGCTG | EMX1 HDR (sense; insertion underlined) |

| Primer | Sequence (5' to 3') | Purpose |
|---|---|---|
| | CTGGCCAGGCCCCTGCGTGGGCCCAAGCTGGACTCTGG<br>CCACTCCCT (SEQ ID NO: 187) | |
| ssODN-<br>antisense | AGGGAGTGGCCAGAGTCCAGCTTGGGCCCACGCAGGGG<br>CCTGGCCAGCAGCAAGCAGCACTCTGCCCTCGTG<br>GGTTTGTGGTTGCCCACC<u>GCTAGCAAGCTT</u>GTCATTGGA<br>GGTGACATCGATGTCCTCCCCATTGGCCTGCTTCG<br>TGGCAATGCGCCACCGGTTGATGTGATGGGAGCCCTTC<br>TTCTTCTG (SEQ ID NO: 188) | EMX1 HDR<br>(antisense;<br>insertion<br>underlined) |
| EMX1-<br>SURV-F | CCATCCCCTTCTGTGAATGT (SEQ ID NO: 189) | EMX1<br>SURVEYOR<br>assay PCR,<br>sequencing |
| EMX1-<br>SURV-R | GGAGATTGGAGACACGGAGA (SEQ ID NO: 190) | EMX1<br>SURVEYOR<br>assay PCR,<br>sequencing |
| EMX1-<br>HDR-F | GGCTCCCTGGGTTCAAAGTA (SEQ ID NO: 191) | EMX1 RFLP<br>analysis PCR,<br>sequencing |
| EMX1-<br>HDR-R | AGAGGGGTCTGGATGTCGTAA (SEQ ID NO: 192) | EMX1 RFLP<br>analysis PCR,<br>sequencing |
| pUC19-F | CGCCAGGGTTTTCCCAGTCACGAC (SEQ ID NO: 193) | pUC19<br>multiple<br>cloning site F<br>primer, for<br>Sanger<br>sequencing |

Applicants referenced the sequencing results against the PX330 cloning vector sequence to check that the 20 bp guide sequence was inserted between the U6 promoter and the remainder of the sgRNA scaffold. Details and sequence of the PX330 map in GenBank vector map format (*.gb file) can be found at the website crispr.genome-engineering.org.

(Optional) Design of ssODN Template•Timing 3 d Planning Ahead

3| Design and order ssODN. Either the sense or antisense ssODN can be purchased directly from supplier. Applicants recommend designing homology arms of at least 40 bp on either side and 90 bp for optimal HDR efficiency. In Applicants' experience, antisense oligos have slightly higher modification efficiencies.

4| Applicants resuspended and diluted ssODN ultramers to a final concentration of 10 uM. Do not combine or anneal the sense and antisense ssODNs. Store at −20° C.

5| Note for HDR applications, Applicants recommend cloning sgRNA into the PX330 plasmid.

Functional Validation of sgRNAs: Cell Culture and Transfections •Timing 3-4 d

The CRISPR-Cas system has been used in a number of mammalian cell lines. Conditions may vary for each cell line. The protocols below details transfection conditions for HEK239FT cells. Note for ssODN-mediated HDR transfections, the Amaxa SF Cell Line Nucleofector Kit is used for optimal delivery of ssODNs. This is described in the next section.

7| HEK293FT maintenance. Cells are maintained according to the manufacturer's recommendations. Briefly, Applicants cultured cells in D10 medium (GlutaMax DMEM supplemented with 10% Fetal Bovine Serum), at 37° C. and 5% CO2.

8| To passage, Applicants removed medium and rinsed once by gently adding DPBS to side of vessel, so as not to dislodge cells. Applicants added 2 ml of TrypLE to a T75 flask and incubated for 5 m at 37° C. 10 ml of warm D10 medium is added to inactivate and transferred to a 50 ml Falcon tube. Applicants dissociated cells by triturating gently, and re-seeded new flasks as necessary. Applicants typically passage cells every 2-3 d at a split ratio of 1:4 or 1:8, never allowing cells to reach more than 70% confluency. Cell lines are restarted upon reaching passage number 15.

9| Prepare cells for transfection. Applicants plated well-dissociated cells onto 24-well plates in D10 medium without antibiotics 16-24 h before transfection at a seeding density of $1.3 \times 10^5$ cells per well and a seeding volume of 500 ul. Scale up or down according to the manufacturer's manual as needed. It is suggested to not plate more cells than recommended density as doing so may reduce transfection efficiency.

10| On the day of transfection, cells are optimal at 70-90% confluency. Cells may be transfected with Lipofectamine 2000 or Amaxa SF Cell Line Nucleofector Kit according to the manufacturers' protocols.

(A) For sgRNAs cloned into PX330, Applicants transfected 500 ng of sequence-verified CRISPR plasmid; if transfecting more than one plasmid, mix at equimolar ratio and no more than 500 ng total.

(B) For sgRNA amplified by PCR, Applicants mixed the following:

| | |
|---|---|
| PX165 (Cas9 only) | 200 ng |
| sgRNA amplicon (each) | 40 ng |
| pUC19 | fill up total DNA to 500 ng |

Applicants recommend transfecting in technical triplicates for reliable quantification and including transfection controls (e.g. GFP plasmid) to monitor transfection efficiency. In addition, PX330 cloning plasmid and/or sgRNA amplicon may be transfected alone as a negative control for downstream functional assays.

11| Applicants added Lipofectamine complex to cells gently as HEK293FT cells may detach easily from plate easily and result in lower transfection efficiency.

12| Applicants checked cells 24 h after transfection for efficiency by estimating the fraction of fluorescent cells in the control (e.g., GFP) transfection using a fluorescence microscope. Typically cells are more than 70% transfected.

13| Applicants supplemented the culture medium with an additional 500 ul of warm D10 medium. Add D10 very slowly to the side of the well and do not use cold medium, as cells can detach easily.

14| Cells are incubated for a total of 48-72 h post-transfection before harvested for indel analysis. Indel efficiency does not increase noticeably after 48 h.

(Optional) Co-Transfection of CRISPR Plasmids and ssODNs or Targeting Plasmids for HR •Timing 3-4 d 15| Linearize targeting plasmid. Targeting vector is linearized if possible by cutting once at a restriction site in the vector backbone near one of the homology arms or at the distal end of either homology arm.

16| Applicants ran a small amount of the linearized plasmid alongside uncut plasmid on a 0.8-1% agarose gel to check successful linearization. Linearized plasmid should run above the supercoiled plasmid.

17| Applicants purified linearized plasmid with the QIAQuick PCR Purification kit.

18| Prepare cells for transfection. Applicants cultured HEK293FT in T75 or T225 flasks. Sufficient cell count before day of transfection is planned for. For the Amaxa strip-cuvette format, $2 \times 10^6$ cells are used per transfection.

19| Prepare plates for transfection. Applicants added 1 ml of warm D10 medium into each well of a 12 well plate. Plates are placed into the incubator to keep medium warm.

20| Nucleofection. Applicants transfected HEK293FT cells according to the Amaxa SF Cell Line Nucleofector 4D Kit manufacturer's instructions, adapted in the steps below.

a: For ssODN and CRISPR cotransfection, pre-mix the following DNA in PCR tubes:

| pCRISPR plasmid (Cas9 + sgRNA) | 500 ng |
|---|---|
| ssODN template (10 uM) | 1 ul | b. For HDR targeting plasmid and CRISPR cotransfection, pre-mix the following DNA in PCR tubes:

| CRISPR plasmid (Cas9 + sgRNA) | 500 ng |
|---|---|
| Linearized targeting plasmid | 500 ng |

For transfection controls, see previous section. In addition, Applicants recommend transfecting ssODN or targeting plasmid alone as a negative control.

21| Dissociate to single cells. Applicants removed medium and rinsed once gently with DPBS, taking care not to dislodge cells. 2 ml of TrypLE is added to a T75 flask and incubated for 5 m at 37° C. 10 ml of warm D10 medium is added to inactivate and triturated gently in a 50 ml Falcon tube. It is recommended that cells are triturated gently and dissociated to single cells. Large clumps will reduce transfection efficiency. Applicants took a 10 ul aliquot from the suspension and diluted into 90 ul of D10 medium for counting. Applicants counted cells and calculated the number of cells and volume of suspension needed for transfection. Applicants typically transfected $2 \times 10^5$ cells per condition using the Amaxa Nucleocuvette strips, and recommend calculating for 20% more cells than required to adjust for volume loss in subsequent pipetting steps. The volume needed is transferred into a new Falcon tube.

23| Applicants spun down the new tube at 200×g for 5 m.

Applicants prepared the transfection solution by mixing the SF solution and S1 supplement as recommended by Amaxa. For Amaxa strip-cuvettes, a total of 20 ul of supplemented SF solution is needed per transfection. Likewise, Applicants recommend calculating for 20% more volume than required.

25| Applicants removed medium completely from pelleted cells from step 23 and gently resuspended in appropriate volume (20 ul per $2 \times 10^5$ cells) of S1-supplemented SF solution. Do not leave cells in SF solution for extended period of time.

26| 20 ul of resuspended cells is pipetted into each DNA pre-mix from step 20. Pipette gently to mix and transfer to Nucleocuvette strip chamber. This is repeated for each transfection condition.

Electroporate cells using the Nucleofector 4D program recommended by Amaxa, CM-130.

28| Applicants gently and slowly pipetted 100 ul of warm D10 medium into each Nucleocuvette strip chamber, and transferred all volume into the pre-warmed plate from step 19. CRITICAL. Cells are very fragile at this stage and harsh pipetting can cause cell death. Incubate for 24 h. At this point, transfection efficiency can be estimated from fraction of fluorescent cells in positive transfection control. Nucleofection typically results in greater than 70-80% transfection efficiency. Applicants slowly added 1 ml warm D10 medium to each well without dislodging the cells. Incubate cells for a total of 72 h.

Human Embryonic Stem Cell (HUES 9) Culture and Transfection•Timing 3-4 d

Maintaining hESC (HUES9) line. Applicants routinely maintain HUES9 cell line in feeder-free conditions with mTesR1 medium. Applicants prepared mTeSR1 medium by adding the 5× supplement included with basal medium and 100 ug/ml Normocin. Applicants prepared a 10 ml aliquot of mTeSR1 medium supplemented further with 10 uM Rock Inhibitor. Coat tissue culture plate. Dilute cold GelTrex 1:100 in cold DMEM and coat the entire surface of a 100 mm tissue culture plate.

Place plate in incubator for at least 30 m at 37° C. Thaw out a vial of cells at 37° C. in a 15 ml Falcon tube, add 5 ml of mTeSR1 medium, and pellet at 200×g for 5 m. Aspirate off GelTrex coating and seed ~1×106 cells with 10 ml mTeSR1 medium containing Rock Inhibitor. Change to normal mTeSR1 medium 24 h after transfection and re-feed daily. Passaging cells. Re-feed cells with fresh mTeSR1 medium daily and passage before reaching 70% confluency. Aspirate off mTeSR1 medium and wash cells once with DPBS. Dissociate cells by adding 2 ml Accutase and incubating at 37° C. for 3-5 m. Add 10 ml mTeSR1 medium to detached cells, transfer to 15 ml Falcon tube and resuspend gently. Re-plate onto GelTrex-coated plates in mTeSR1 medium with 10 uM Rock Inhibitor. Change to normal mTeSR1 medium 24 h after plating.

Transfection. Applicants recommend culturing cells for at least 1 week post-thaw before transfecting using the Amaxa P3 Primary Cell 4-D Nucleofector Kit (Lonza). Re-feed log-phase growing cells with fresh medium 2 h before transfection. Dissociate to single cells or small clusters of no more than 10 cells with accutase and gentle resuspension. Count the number of cells needed for nucleofection and spin down at 200×g for 5 m. Remove medium completely and resuspend in recommended volume of S1-supplemented P3 nucleofection solution. Gently plate electroporated cells into coated plates in presence of 1× Rock Inhibitor.

Check transfection success and re-feed daily with regular mTeSR1 medium beginning 24 h after nucleofection. Typically, Applicants observe greater than 70% transfection efficiency with Amaxa Nucleofection. Harvest DNA. 48-72 h post transfection, dissociate cells using accutase and inactivate by adding 5 x volume of mTeSR1. Spin cells down at 200×g for 5 m. Pelleted cells can be directed processed for DNA extraction with QuickExtract solution. It is recommended to not mechanically dissociate cells without accutase. It is recommended to not spin cells down without inactivating accutase or above the recommended speed; doing so may cause cells to lyse.

Isolation of Clonal Cell Lines by FACS. Timing•2-3 h Hands-on; 2-3 Weeks Expansion Clonal isolation may be performed 24 h post-transfection by FACS or by serial dilution.

54| Prepare FACS buffer. Cells that do not need sorting using colored fluorescence may be sorted in regular D10 medium supplemented with IX penicillin/streptinomycin. If colored fluorescence sorting is also required, a phenol-free DMEM or DPBS is substituted for normal DMEM. Supplement with IX penicillin/streptinomycin and filter through a 0.22 urn Steriflip filter.

55| Prepare 96 well plates. Applicants added 100 ul of D10 media supplemented with 1× penicillin/streptinomycin per well and prepared the number of plates as needed for the desired number of clones.

56| Prepare cells for FACS. Applicants dissociated cells by aspirating the medium completely and adding 100 ul TrypLE per well of a 24-well plate. Incubate for 5 m and add 400 ul warm D10 media.

57| Resuspended cells are transferred into a 15 ml Falcon tube and gently triturated 20 times. Recommended to check under the microscope to ensure dissociation to single cells.

58| Spin down cells at 200×g for 5 minutes.

59| Applicants aspirated the media, and resuspended the cells in 200 ul of FACS media.

60| Cells are filtered through a 35 urn mesh filter into labeled FACS tubes. Applicants recommend using the BD Falcon 12×75 mm Tube with Cell Strainer cap. Place cells on ice until sorting.

61| Applicants sorted single cells into 96-well plates prepared from step 55. Applicants recommend that in one single designated well on each plate, sort 100 cells as a positive control.

NOTE. The remainder of the cells may be kept and used for genotyping at the population level to gauge overall modification efficiency.

62| Applicants returned cells into the incubator and allowed them to expand for 2-3 weeks. 100 ul of warm D10 medium is added 5 d post sorting. Change 100 ul of medium every 3-5 d as necessary.

63| Colonies are inspected for "clonal" appearance 1 week post sorting: rounded colonies radiating from a central point. Mark off wells that are empty or may have been seeded with doublets or multiplets.

64| When cells are more than 60% confluent, Applicants prepared a set of replica plates for passaging. 100 ul of D10 medium is added to each well in the replica plates. Applicants dissociated cells directly by pipetting up and down vigorously 20 times. 20% of the resuspended volume was plated into the prepared replica plates to keep the clonal lines. Change the medium every 2-3 d thereafter and passage accordingly.

65| Use the remainder 80% of cells for DNA isolation and genotyping.

Optional: Isolation of Clonal Cell Lines by Dilution. Timing•2-3 h Hands-on; 2-3 Weeks Expansion 66| Applicants dissociated cells from 24-well plates as described above. Make sure to dissociate to single cells. A cell strainer can be used to prevent clumping of cells.

67| The number of cells are counted in each condition. Serially dilute each condition in D10 medium to a final concentration of 0.5 cells per 100 ul. For each 96 well plate, Applicants recommend diluting to a final count of 60 cells in 12 ml of D10. Accurate count of cell number is recommended for appropriate clonal dilution. Cells may be recounted at an intermediate serial dilution stage to ensure accuracy.

68| Multichannel pipette was used to pipette 100 ul of diluted cells to each well of a 96 well plate.

NOTE. The remainder of the cells may be kept and used for genotyping at the population level to gauge overall modification efficiency.

69| Applicants inspected colonies for "clonal" appearance ~1 week post plating: rounded colonies radiating from a central point. Mark off wells that may have seeded with doublets or multiplets.

70| Applicants returned cells to the incubator and allowed them to expand for 2-3 weeks. Re-feed cells as needed as detailed in previous section.

SURVEYOR Assay for CRISPR Cleavage Efficiency. Timing•5-6 h

Before assaying cleavage efficiency of transfected cells, Applicants recommend testing each new SURVEYOR primer on negative (untransfected) control samples through the step of SURVEYOR nuclease digestion using the protocol described below. Occasionally, even single-band clean SURVEYOR PCR products can yield non-specific SURVEYOR nuclease cleavage bands and potentially interfere with accurate indel analysis.

71| Harvest cells for DNA. Dissociate cells and spin down at 200×g for 5 m. NOTE. Replica plate at this stage as needed to keep transfected cell lines.

72| Aspirate the supernatant completely.

73| Applicants used QuickExtract DNA extraction solution according to the manufacturer's instructions. Applicants typically used 50 ul of the solution for each well of a 24 well plate and 10 ul for a 96 well plate.

74| Applicants normalized extracted DNA to a final concentration of 100-200 ng/ul with ddH$_2$O. Pause point: Extracted DNA may be stored at $-20°$ C. for several months.

75| Set up the SURVEYOR PCR. Master mix the following using SURVEYOR primers provided by Applicants online/computer algorithm tool:

| Component: | Amount (ul) | Final concentration |
| --- | --- | --- |
| Herculase II PCR buffer, 5X | 10 | 1X |
| dNTP, 100 mM (25 mM each) | 1 | 1 mM |
| SURVEYOR Fwd primer (10 uM) | 1 | 0.2 uM |

| Component: | Amount (ul) | Final concentration |
|---|---|---|
| SURVEYOR Rev primer (10 uM) | 1 | 0.2 uM |
| Herculase II Fusion polymerase | 1 | |
| MgCl$_2$ (25 mM) | 2 | 1 mM |
| Distilled water | 33 | |
| Total | 49 (for each reaction) | |

76| Applicants added 100-200 ng of normalized genomic DNA template from step 74 for each reaction.

77| PCR reaction was performed using the following cycling conditions, for no more than 30 amplification cycles:

| Cycle number | Denature | Anneal | Extend |
|---|---|---|---|
| 1 | 95° C., 2 min | | |
| 2-31 | 95° C., 20 s | 60° C., 20 s | 72° C., 30 s |
| 32 | | | 72° C., 3 min |

78| Applicants ran 2-5 ul of PCR product on a 1% gel to check for single-band product. Although these PCR conditions are designed to work with most pairs of SURVEYOR primers, some primers may need additional optimization by adjusting the template concentration, MgCl$_2$ concentration, and/or the annealing temperature.

79| Applicants purified the PCR reactions using the QIA-Quick PCR purification kit and normalized eluant to 20 ng/ul. Pause point: Purified PCR product may be stored at −20° C.

80| DNA heteroduplex formation. The annealing reaction was set up as follows:

| | |
|---|---|
| Taq PCR buffer, 10X | 2 ul |
| Normalized DNA (20 ng/ul) | 18 ul |
| Total volume | 20 ul |

81| Anneal the reaction using the following conditions:

| Cycle number | Condition |
|---|---|
| 1 | 95° C., 10 mn |
| 2 | 95° C.-85° C., −2° C./s |
| 3 | 85° C., 1 min |
| 4 | 85° C.-75° C., −0.3° C./s |
| 5 | 75° C., 1 min |
| 6 | 75° C.-65° C., −0.3° C./s |
| 7 | 65° C., 1 min |
| 8 | 65° C.-55° C., −0.3° C./s |
| 9 | 55° C., 1 min |
| 10 | 55° C.-45° C., −0.3° C./s |
| 11 | 45° C., 1 min |
| 12 | 45° C.-35° C., −0.3° C./s |
| 13 | 35° C., 1 min |
| 14 | 35° C.-25° C., −0.3° C./s |
| 15 | 25° C., 1 min |

82| SURVEYOR nuclease S digestion. Applicants prepared master-mix and added the following components on ice to annealed heteroduplexes from step 81 for a total final volume of 25 ul:

| Component | Amount (ul) | Final Concentration |
|---|---|---|
| MgCl$_2$ solution, 0.15M | 2.5 | 15 mM |
| ddH$_2$O | 0.5 | |
| SURVEYOR nuclease S | 1 | 1X |
| SURVEYOR enhancer S | 1 | 1X |
| Total | 5 | |

83| Vortex well and spin down. Incubate the reaction at 42° C. for 1 h.

84| Optional: 2 ul of the Stop Solution from the SURVEYOR kit may be added. Pause point. The digested product may be stored at −20° C. for analysis at a later time.

85| Visualize the SURVEYOR reaction. SURVEYOR nuclease digestion products may be visualized on a 2% agarose gel. For better resolution, products may be run on a 4-20% gradient Polyacrylamide TBE gel. Applicants loaded 10 ul of product with the recommended loading buffer and ran the gel according to manufacturer's instructions. Typically, Applicants run until the bromophenol blue dye has migrated to the bottom of the gel. Include DNA ladder and negative controls on the same gel.

86| Applicants stained the gel with 1×SYBR Gold dye diluted in TBE. The gel was gently rocked for 15 m.

87| Applicants imaged the gel using a quantitative imaging system without overexposing the bands. The negative controls should have only one band corresponding to the size of the PCR product, but may have occasionally non-specific cleavage bands of other sizes. These will not interfere with analysis if they are different in size from target cleavage bands. The sum of target cleavage band sizes, provided by Applicants online/computer algorithm tool, should be equal to the size of the PCR product.

88| Estimate the cleavage intensity. Applicants quantified the integrated intensity of each band using ImageJ or other gel quantification software.

89| For each lane, Applicants calculated the fraction of the PCR product cleaved ($f_{cut}$) using the following formula: $f_{cut}$=(b+c)/(a+b+c), where a is the integrated intensity of the undigested PCR product and b and c are the integrated intensities of each cleavage product. 90| Cleavage efficiency may be estimated using the following formula, based on the binomial probability distribution of duplex formation:

91| indel (%)=100×$\sqrt{(1-(1-f_{cut}))}$

Sanger Sequencing for Assessing CRISPR Cleavage Efficiency. Timing•3 d

Initial steps are identical to Steps 71-79 of the SURVEYOR assay. Note: SURVEYOR primers may be used for Sanger sequencing if appropriate restriction sites are appended to the Forward and Reverse primers. For cloning into the recommended pUC19 backbone, EcoRI may be used for the Fwd primer and HindIII for the Rev primer.

92| Amplicon digestion. Set up the digestion reaction as follows:

| Component | Amount (ul) |
|---|---|
| Fast Digest buffer, 10X | 3 |
| FastDigest EcoRI | 1 |
| FastDigest HindIII | 1 |
| Normalized DNA (20 ng/ul) | 10 |
| ddH$_2$O | 15 |
| Total volume | 30 |

93| pUC19 backbone digestion. Set up the digestion reaction as follows:

| Component | Amount (ul) |
|---|---|
| Fast Digest buffer, 10X | 3 |
| FastDigest EcoRI | 1 |
| FastDigest HindIII | 1 |
| FastAP Alkaline Phosphatase | 1 |
| pUC19 vector (200 ng/ul) | 5 |
| ddH$_2$O | 20 |
| Total volume | 30 |

94| Applicants purified the digestion reactions using the QIAQuick PCR purification kit. Pause point: Purified PCR product may be stored at −20° C.

95| Applicants ligated the digested pUC19 backbone and Sanger amplicons at a 1:3 vector:insert ratio as follows:

| Component | Amount (ul) |
|---|---|
| Digested pUC19 | x (50 ng) |
| Digested insert | x (1:3 vector:insert molar ratio) |
| T7 ligase | 1 |
| 2X Rapid Ligation Buffer | 10 |
| ddH$_2$O | x |
| Total volume | 20 |

96| Transformation. Applicants transformed the Plasmid-Safe-treated plasmid into a competent *E. coli* strain, according to the protocol supplied with the cells. Applicants recommend Stbl3 for quick transformation. Briefly, 5 ul of the product from step 95 is added into 20 ul of ice-cold chemically competent Stbl3 cells, incubated on ice for 10 m, heat shocked at 42° C. for 30 s, returned immediately to ice for 2 m, 100 ul of SOC medium is added, and plated onto an LB plate containing 100 ug/ml ampicillin. This is incubated overnight at 37° C.

97| Day 2: Applicants inspected plates for colony growth. Typically, there are no colonies on the negative control plates (ligation of EcoRI-HindIII digested pUC19 only, no Sanger amplicon insert), and tens to hundreds of colonies on the pUC19-Sanger amplicon cloning plates.

98| Day 3: Applicants isolated plasmid DNA from overnight cultures using a QIAprep Spin miniprep kit according to the manufacturer's instructions.

99| Sanger sequencing. Applicants verified the sequence of each colony by sequencing from the pUC19 backbone using the pUC19-For primer. Applicants referenced the sequencing results against the expected genomic DNA sequence to check for the presence of Cas9-induced NHEJ mutations. % editing efficiency=(# modified clones)/(# total clones). It is important to pick a reasonable number of clones (>24) to generate accurate modification efficiencies.

Genotyping for Microdeletion. Timing•2-3 d Hands on; 2-3 Weeks Expansion

100| Cells were transfected as described above with a pair of sgRNAs targeting the region to be deleted.

101| 24 h post-transfection, clonal lines are isolated by FACS or serial dilution as described above.

102| Cells are expanded for 2-3 weeks.

103| Applicants harvested DNA from clonal lines as described above using 10 ul QuickExtract solution and normalized genomic DNA with ddH$_2$O to a final concentration of 50-100 ng/ul.

104| PCR Amplify the modified region. The PCR reaction is set up as follows:

| Component: | Amount (ul) | Final concentration |
|---|---|---|
| Herculase II PCR buffer, 5X | 10 | 1X |
| dNTP, 100 mM (25 mM each) | 1 | 1 mM |
| Out Fwd primer (10 uM) | 1 | 0.2 uM |
| Out Rev primer (10 uM) | 1 | 0.2 uM |
| Herculase II Fusion polymerase | 1 | |
| MgCl2 (25 mM) | 2 | 1 mM |
| ddH$_2$O | 32 | |
| Total | 48 (for each reaction) | |

Note: if deletion size is more than 1 kb, set up a parallel set of PCR reactions with In-Fwd and In-Rev primers to screen for the presence of the wt allele.

105| To screen for inversions, a PCR reaction is set up as follows:

| Component: | Amount (ul) | Final concentration |
|---|---|---|
| Herculase II PCR buffer, 5X | 10 | 1X |
| dNTP, 100 mM (25 mM each) | 1 | 1 mM |
| Out Fwd or Out-Rev primer (10 uM) | 1 | 0.2 uM |
| In Fwd or In-Rev primer (10 uM) | 1 | 0.2 uM |
| Herculase II Fusion polymerase | 1 | |
| MgCl$_2$ (25 mM) | 2 | 1 mM |
| ddH$_2$O | 32 | |
| Total | 48 (for each reaction) | |

Note: primers are paired either as Out-Fwd + In Fwd, or Out-Rev + In-Rev.

106| Applicants added 100-200 ng of normalized genomic DNA template from step 103 for each reaction.

107| PCR reaction was performed using the following cycling conditions:

| Cycle number | Denature | Anneal | Extend |
|---|---|---|---|
| 1 | 95° C., 2 min | | |
| 2-31 | 95° C., 20 s | 60° C., 20 s | 72° C., 30 s |
| 32 | | | 72° C., 3 m |

108| Applicants run 2-5 ul of PCR product on a 1-2% gel to check for product. Although these PCR conditions are designed to work with most primers, some primers may need additional optimization by adjusting the template concentration, MgCl$_2$ concentration, and/or the annealing temperature.

Genotyping for Targeted Modifications Via HDR. Timing•2-3 d, 2-3 h Hands on

109| Applicants harvested DNA as described above using QuickExtract solution and normalized genomic DNA with TE to a final concentration of 100-200 ng/ul.

110| PCR Amplify the modified region. The PCR reaction is set up as follows:

| Component: | Amount (ul) | Final concentration |
|---|---|---|
| Herculase II PCR buffer, 5X | 10 | 1X |
| dNTP, 100 mM (25 mM each) | 1 | 1 mM |
| HDR Fwd primer (10 uM) | 1 | 0.2 uM |
| HDR Rev primer (10 uM) | 1 | 0.2 uM |
| Herculase II Fusion polymerase | 1 | |

| Component: | Amount (ul) | Final concentration |
|---|---|---|
| $MgCl_2$ (25 mM) | 2 | 1 mM |
| $ddH_2O$ | 33 | |
| Total | 49 (for each reaction) | |

|111| Applicants added 100-200 ng of genomic DNA template from step 109 for each reaction and run the following program.

| Cycle number | Denature | Anneal | Extend |
|---|---|---|---|
| 1 | 95° C., 2 min | | |
| 2-31 | 95° C., 20 s | 60° C., 20 s | 72° C., 30-60 s per kb |
| 32 | | | 72° C., 3 min |

|112| Applicants ran 5 ul of PCR product on a 0.8-1% gel to check for single-band product. Primers may need additional optimization by adjusting the template concentration, $MgCl_2$ concentration, and/or the annealing temperature.

|113| Applicants purified the PCR reactions using the QIAQuick PCR purification kit.

|114| In the HDR example, a HindIII restriction site is inserted into the EMX1 gene. These are detected by a restriction digest of the PCR amplicon:

| Component | Amount (ul) |
|---|---|
| Purified PCR amplicon (200-300 ng) | x |
| F.D. buffer, Green | 1 |
| HindIII | 0.5 |
| ddH2O | x |
| Total | 10 | i. The DNA is digested for 10 m at 37° C.:

ii. Applicants ran 10 ul of the digested product with loading dye on a 4-20% gradient polyacrylamide TBE gel until the xylene cyanol band had migrated to the bottom of the gel.

iii. Applicants stained the gel with 1×SYBR Gold dye while rocking for 15 m.

iv. The cleavage products are imaged and quantified as described above in the SURVEYOR assay section. HDR efficiency is estimated by the formula: (b+c)/(a+b+c), where a is the integrated intensity for the undigested HDR PCR product, and b and c are the integrated intensities for the HindIII-cut fragments.

|115| Alternatively, purified PCR amplicons from step 113 may be cloned and genotyped using Sanger sequencing or NGS.

Deep Sequencing and Off-Target Analysis•Timing 1-2 d

The online CRISPR target design tool generates candidate genomic off-target sites for each identified target site. Off-target analysis at these sites can be performed by SURVEYOR nuclease assay, Sanger sequencing, or next-generation deep sequencing. Given the likelihood of low or undetectable modification rates at many of these sites, Applicants recommend deep sequencing with the Illumina Miseq platform for high sensitivity and accuracy. Protocols will vary with sequencing platform; here, Applicants briefly describe a fusion PCR method for attaching sequencing adapters.

|116| Design deep sequencing primers. Next-generation sequencing (NGS) primers are designed for shorter amplicons, typically in the 100-200 bp size range. Primers may be manually designed using NCBI Primer-Blast or generated with online CRISPR target design tools (website at genome-engineering.org/tools).

|117| Harvest genomic DNA from Cas9-targeted cells. Normalize QuickExtract genomic DNA to 100-200 ng/ul with $ddH_2O$.

|118| Initial library preparation PCR. Using the NGS primers from step 116, prepare the initial library preparation PCR

| Component: | Amount (ul) | Final concentration |
|---|---|---|
| Herculase II PCR buffer, 5X | 10 | 1X |
| dNTP, 100 mM (25 mM each) | 1 | 1 mM |
| NGS Fwd primer (10 uM) | 1 | 0.2 uM |
| NGS Rev primer (10 uM) | 1 | 0.2 uM |
| Herculase II Fusion polymerase | 1 | |
| MgCl2 (25 mM) | 2 | 1 mM |
| ddH2O | 33 | |
| Total | 49 (for each reaction) | |

|119| Add 100-200 ng of normalized genomic DNA template for each reaction.

|120| Perform PCR reaction using the following cycling conditions, for no more than 20 amplification cycles:

| Cycle number | Denature | Anneal | Extend |
|---|---|---|---|
| 1 | 95° C., 2 min | | |
| 2-21 | 95° C., 20 s | 60° C., 20 s | 72° C., 15 s |
| 22 | | | 72° C., 3 min |

|121| Run 2-5 ul of PCR product on a 1% gel to check for single-band product. As with all genomic DNA PCRs, NGS primers may require additional optimization by adjusting the template concentration, MgCl2 concentration, and/or the annealing temperature.

|122| Purify the PCR reactions using the QIAQuick PCR purification kit and normalize eluant to 20 ng/ul. Pause point: Purified PCR product may be stored at −20° C.

|123| Nextera XT DNA Sample Preparation Kit. Following the manufacturer's protocol, generate Miseq sequencing-ready libraries with unique barcodes for each sample.

|124| Analyze sequencing data. Off-target analysis may be performed through read alignment programs such as ClustalW, Geneious, or simple sequence analysis scripts.

Timing

Steps 1-2 Design and synthesis of sgRNA oligos and ssODNs: 1-5 d, variable depending on supplier Steps 3-5 Construction of CRISPR plasmid or PCR expression cassette: 2 h to 3 d Steps 6-53 Transfection into cell lines: 3 d (1 h hands-on time)

Steps 54-70 Optional derivation of clonal lines: 1-3 weeks, variable depending on cell type Steps 71-91 Functional validation of NHEJ via SURVEYOR: 5-6 h Steps 92-124 Genotyping via Sanger or next-gen deep sequencing: 2-3 d (3-4 h hands on time)

Addressing Situations Concerning Herein Examples

| Situation | Solution |
|---|---|
| No amplification of sgRNA | Titrate U6-template concentration |
| SURVEYOR or HDR PCR dirty or no amplification | Titrate MgCl2; normalize and titrate template concentration; annealing temp gradient; redesign primers |
| Unequal amplification of alleles in microdeletion PCRs | Set up separate PCRs to detect wildtype and deletion alleles; Redesign primers with similar sized amplicons |
| Colonies on negative control plate | Increase BbsI; increase Golden Gate reaction cycle number, cut PX330 separately with Antarctic Phosphate treatment |
| No sgRNA sequences or wrong sequences | Screen additional colonies |
| Low lipofectamine transfection efficiency | Check cell health and density; titrate DNA; add GFP transfection control |
| Low nucleofection transfection efficiency | Check cell health and density; titrate DNA; suspend to single cell |
| Clumps or no cells after FACS | Filter cells before FACS; dissociate to single cells; resuspend in appropriate density |
| Clumps or no cells in serial dilution | Recount cells; dissociate to single cells and filter through strainer; check serial dilution |
| High SURVEYOR background on negative sample | Redesign primers to prime from different locations |
| Dirty SURVEYOR result on gel | Purify PCR product; reduce input DNA; reduce 42° C. incubation to 30 m |
| No SURVEYOR cleavage | Purify and normalize PCR product; re-anneal with TaqB buffer; Redesign sgRNAs; sequence verify Cas9 on px330 backbone |
| Samples do not sink in TBE acrylamide gel | Supplement with MgCl2 to a final concentration of 15 mM or add loading buffer containing glycerol |

Discussion

CRISPR-Cas may be easily multiplexed to facilitate simultaneous modification of several genes and mediate chromosomal microdeletions at high efficiencies. Applicants used two sgRNAs to demonstrate simultaneous targeting of the human GRIN2B and DYRK1A loci at efficiencies of up to 68% in HEK293FT cells. Likewise, a pair of sgRNAs may be used to mediate microdeletions, such as excision of an exon, which can be genotyped by PCR on a clonal level. Note that the precise location of exon junctions can vary. Applicants also demonstrated the use of ssODNs and targeting vector to mediate HDR with both wildtype and nickase mutant of Cas9 in HEK 293FT and HUES9 cells (FIG. 30). Note that Applicants have not been able to detect HDR in HUES9 cells using the Cas9 nickase, which may be due to low efficiency or a potential difference in repair activities in HUES9 cells. Although these values are typical, there is some variability in the cleavage efficiency of a given sgRNA, and on rare occasions certain sgRNAs may not work for reasons yet unknown. Applicants recommend designing two sgRNAs for each locus, and testing their efficiencies in the intended cell type.

Example 31: NLSs

Cas9 Transcriptional Modulator: Applicants set out to turn the Cas9/gRNA CRISPR system into a generalized DNA binding system in which functions beyond DNA cleavage can be executed. For instance, by fusing functional domain(s) onto a catalytically inactive Cas9 Applicants have imparted novel functions, such as transcriptional activation/repression, methylation/demethylation, or chromatin modifications. To accomplish this goal Applicants made a catalytically inactive Cas9 mutant by changing two residues essential for nuclease activity, D10 and H840, to alanine. By mutating these two residues the nuclease activity of Cas9 is abolished while maintaining the ability to bind target DNA. The functional domains Applicants decided to focus on to test Applicants' hypothesis are the transcriptional activator VP64 and the transcriptional repressors SID and KRAB.

Cas9 Nuclear localization: Applicants hypothesized that the most effective Cas9 transcriptional modulator would be strongly localized to the nucleus where it would have its greatest influence on transcription. Moreover, any residual Cas9 in the cytoplasm could have unwanted effects. Applicants determined that wild-type Cas9 does not localize into the nucleus without including multiple nuclear localization signals (NLSs) (although a CRISPR system need not have one or more NLSs but advantageously has at least one or more NLS(s)). Because multiple NLS sequences were required it was reasoned that it is difficult to get Cas9 into the nucleus and any additional domain that is fused to Cas9 could disrupt the nuclear localization. Therefore, Applicants made four Cas9-VP64-GFP fusion constructs with different NLS sequences (pXRP02-pLenti2-EF1a-NLS-hSpCsn1(10A,840A)-NLS-VP64-EGFP, pXRP04-pLenti2-EF1a-NLS-hSpCsn1(10A,840A)-NLS-VP64-2A-EGFP-NLS, pXRP06-pLenti2-EF1a-NLS-EGFP-VP64-NLS-hSpCsn1(10A,840A)-NLS, pXRP08-pLenti2-EF1a-NLS-VP64-NLS-hSpCsn1(10A,840A)-NLS-VP64-EGFP-NLS). These constructs were cloned into a lenti backbone under the expression of the human EF1a promoter. The WPRE element was also added for more robust protein expression. Each construct was transfected into HEK 293FT cells using Lipofectame 2000 and imaged 24 hours post-transfection. The best nuclear localization is obtained when the fusion proteins have NLS sequences on both the N- and C-term of the fusion protein. The highest observed nuclear localization occurred in the construct with four NLS elements.

To more robustly understand the influence of NLS elements on Cas9 Applicants made 16 Cas9-GFP fusions by adding the same alpha importin NLS sequence on either the N- or C-term looking at zero to three tandem repeats. Each construct was transfected into HEK 293FT cells using Lipofectame 2000 and imaged 24 hours post-transfection. Notably, the number of NLS elements does not directly correlate with the extent of nuclear localization. Adding an NLS on the C-term has a greater influence on nuclear localization than adding on the N-term.

Cas9 Transcriptional Activator: Applicants functionally tested the Cas9-VP64 protein by targeting the Sox2 locus and quantifying transcriptional activation by RT-qPCR. Eight DNA target sites were chosen to span the promoter of Sox2. Each construct was transfected into HEK 293FT cells using Lipofectame 2000 and 72 hours post-transfection total RNA was extracted from the cells. 1 ug of RNA was reverse transcribed into cDNA (qScript Supermix) in a 40 ul reaction. 2 ul of reaction product was added into a single 20 ul TaqMan assay qPCR reaction. Each experiment was performed in biological and technical triplicates. No RT control and no template control reactions showed no amplification. Constructs that do not show strong nuclear localization, pXRP02 and pXRP04, result in no activation. For the construct that did show strong nuclear localization, pXRP08, moderate activation was observed. Statistically significant activation was observed in the case of guide RNAs Sox2.4 and Sox2.5.

Example 32: In Vivo Mouse Data

Material and Reagents
Herculase II fusion polymerase (Agilent Technologies, cat. no. 600679)
10×NEBuffer 4 (NEB, cat. No. B7004S)
BsaI HF (NEB, cat. No. R3535S)
T7 DNA ligase (Enzymatics, cat. no. L602L)
Fast Digest buffer, 10× (ThermoScientific, cat. No. B64)
FastDigest NotI (ThermoScientific, cat. No. FD0594)
FastAP Alkaline Phosphatase (ThermoScientific, cat. No. EF0651)
Lipofectamine2000 (Life Technologies, cat. No. 11668-019)
Trypsin (Life Technologies, cat. No. 15400054)
Forceps #4 (Sigma, cat. No. Z168777-1EA)
Forceps #5 (Sigma, cat. No. F6521-1EA)
10× Hank's Balanced Salt Solution (Sigma, cat. No. H4641-500ML)
Penicillin/Streptomycin solution (Life Technologies, cat. No. P4333)
Neurobasal (Life Technologies, cat. No. 21103049)
B27 Supplement (Life Technologies, cat. No. 17504044)
L-glutamine (Life Technologies, cat. No. 25030081)
Glutamate (Sigma, cat. No. RES5063G-A7)
β-mercaptoethanol (Sigma, cat. No. M6250-100ML)
HA rabbit antibody (Cell Signaling, cat. No. 3724S)
LIVE/DEAD® Cell Imaging Kit (Life Technologies, cat. No. R37601)
30G World Precision Instrument syringe (World Precision Instruments, cat. No. NANOFIL)
Stereotaxic apparatus (Kopf Instruments)
UltraMicroPump3 (World Precision Instruments, cat. No. UMP3-4)
Sucrose (Sigma, cat. No. S7903)
Calcium chloride (Sigma, cat. No. C1016)
Magnesium acetate (Sigma, cat. No. M0631)
Tris-HCl (Sigma, cat: no T5941)
EDTA (Sigma, cat. No. E6758)
NP-40 (Sigma, cat. No. NP40)
Phenylmethanesulfonyl fluoride (Sigma, cat. No. 78830)
Magnesium chloride (Sigma, cat. No. M8266)
Potassium chloride (Sigma, cat. No. P9333)
β-glycerophosphate (Sigma, cat. No. G9422)
Glycerol (Sigma, cat. No. G9012)
Vybrant® DyeCycle™ Ruby Stain (Life technologies, cat. No. S4942)
FACS Aria Flu-act-cell sorter (Koch Institute of MIT, Cambridge US)
DNAeasy Blood & Tissue Kit (Qiagen, cat. No. 69504)

Procedure
Constructing gRNA Multiplexes for Using In Vivo in the Brain

Figure 33:
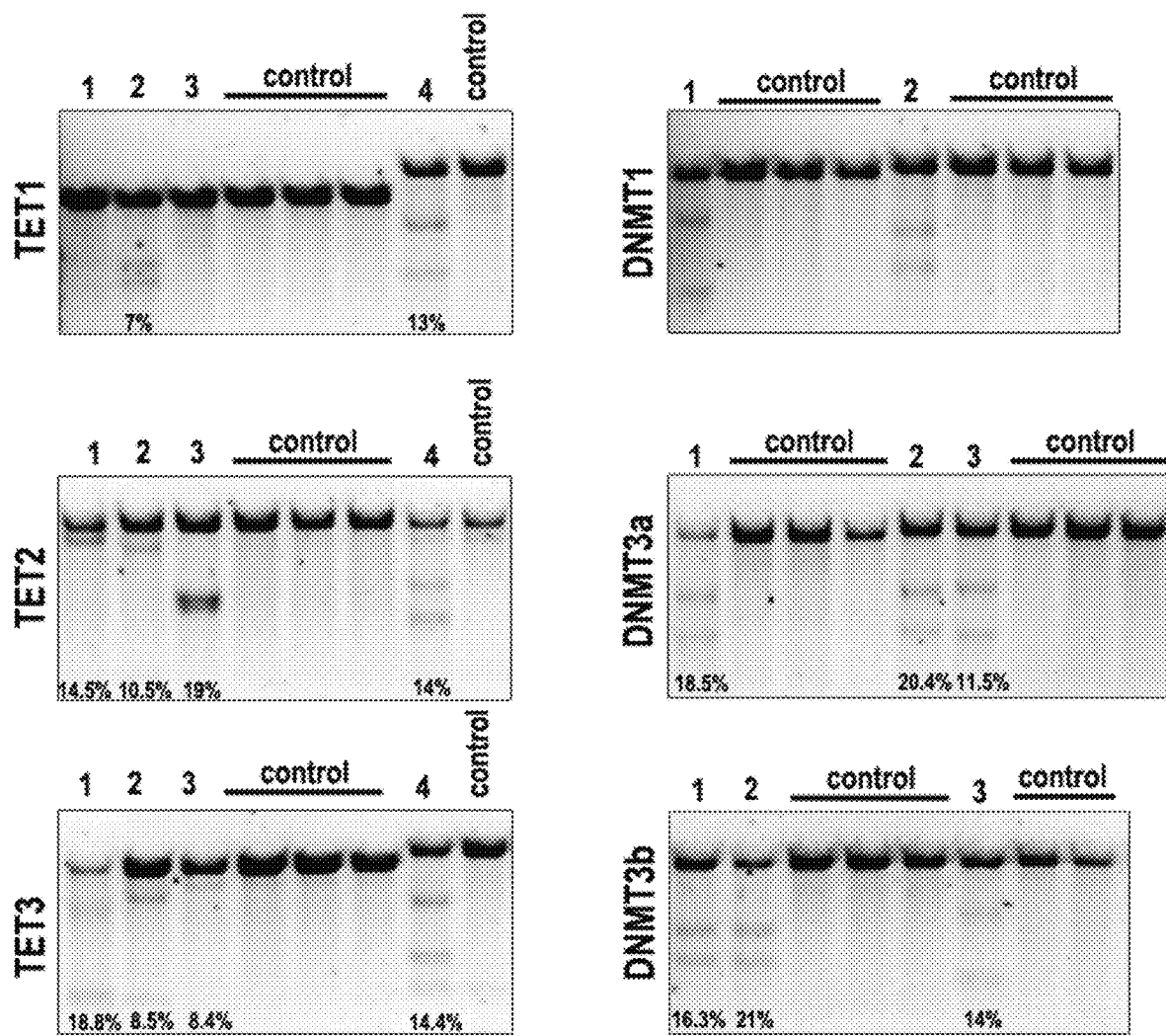
FIG. 33 shows a screen for efficient SpCas9 mediated targeting of Tet1-3 and Dnmt1, 3a and 3b gene loci. Surveyor assay on DNA from transfected N2A cells demonstrates efficient DNA cleavage by using different gRNAs.
Figure 34:
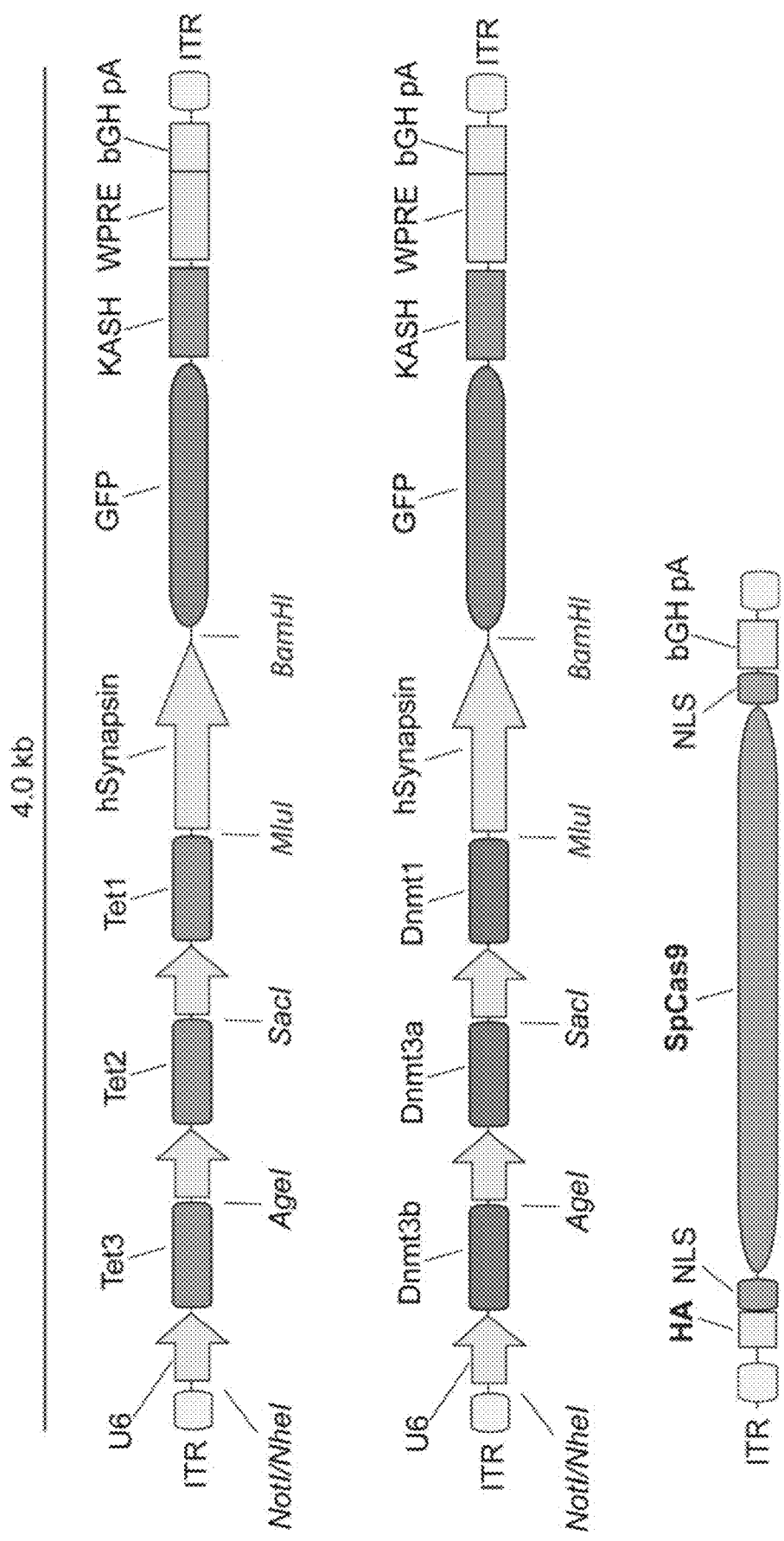
FIG. 34 shows a strategy of multiplex genome targeting using a 2-vector system in an AAV1/2 delivery system. Tet1-3 and Dnmt1, 3a and 3b gRNA under the control of the U6 promoter. GFP-KASH under the control of the human synapsin promoter. Restriction sides shows simple gRNA replacement strategy by subcloning. HA-tagged SpCas9 flanked by two nuclear localization signals (NLS) is shown. Both vectors are delivered into the brain by AAV1/2 virus in a 1:1 ratio.

Applicants designed and PCR amplified single gRNAs targeting mouse TET and DNMT family members (as described herein) Targeting efficiency was assessed in N2a cell line (FIG. 33). To obtain simultaneous modification of several genes in vivo, efficient gRNA was multiplexed in AAV-packaging vector (FIG. 34). To facilitate further analysis of system efficiency applicants added to the system expression cassette consistent of GFP-KASH domain fusion protein under control of human Synapsin I promoter (FIG. 34). This modification allows for further analysis of system efficiency in neuronal population (more detail procedure in section Sorting nuclei and in vivo results).

All 4 parts of the system were PCR amplified using Herculase II Fusion polymerase using following primers:

1st U6 Fw:
(SEQ ID NO: 194)
gagggtctcgtccttgcggccgcgctagcgagggcctatttcccatgattc

1st gRNA Rv:
(SEQ ID NO: 195)
ctcggtctcggtAAAAAAgcaccgactcggtgccacttttcaagttgat
aacggactagccttatttaacttgctaTTTCtagctctaaaacNNNNNN
NNNNNNNNNNNNNNNNNGGTGTTTCGTCCTTTCCAC 2nd U6 Fw:
(SEQ ID NO: 196)
gagggtctcTTTaccggtgagggcctatttcccatgattcc 2nd gRNA Rv:
(SEQ ID NO: 197)
ctcggtctcctcAAAAAAgcaccgactcggtgccacttttcaagttgat
aacggactagc cttatttaacttgctaTTTCtagctctaaaacNNNNN
NNNNNNNNNNNNNNNNGGTGTTTCGTCCTTTCCAC 3rd U6 Fw:
(SEQ ID NO: 198)
gagggtctcTTTgagctcgagggcctatttcccatgattc 3rd gRNA Rv:
(SEQ ID NO: 199)
ctcggtctcgcgtAAAAAAgcaccgactcggtgccacttttcaagttga
taacggactag ccttatttaacttgctaTTTCtagctctaaaacNNNN
NNNNNNNNNNNNNNNNNGGTGTTTCGTCCTTTCCA hSyn_GFP-kash Fw:
(SEQ ID NO: 200)
gagggtctcTTacgcgtgtgtctagac hSyn_GFP-kash Rv:
(SEQ ID NO: 201)
ctcggtctcAaggaCAGGGAAGGGAGCAGTGGTTCACGCCTGTAATCCCA
GCAATTTGGGA GGCCAAGGTGGGTAGATCACCTGAGATTAGGAGTTGC (NNNNNNNNNNNNNNNNNNNN is a reverse compliment targeted genomic sequence)

Applicants used Golden Gate strategy to assemble all parts (1:1 molecular ratio) of the system in a single step reaction:

| | |
|---|---|
| 1$^{st}$ U6_gRNA | 18 ng |
| 2$^{nd}$ U6_gRNA | 18 ng |
| 3$^{rd}$ U6_gRNA | 18 ng |
| Syn_GFP-kash | 100 ng |
| 10x NEBuffer 4 | 1.0 µl |
| 10x BSA | 1.0 µl |
| 10 mM ATP | 1.0 µl |
| BsaI HF | 0.75 µl |
| T7 ligase | 0.25 µl |
| ddH$_2$O | 10 µl |

| Cycle number | Condition |
|---|---|
| 1-50 | 37° C. for 5 m, 21° C. for 5 m |

Golden Gate reaction product was PCR amplified using Herculase II fusion polymerase and following primers:

Fw
(SEQ ID NO: 202)
5' cctgtccttgcggccgcgctagcgagggcc

Rv
(SEQ ID NO: 203)
5' cacgcggccgcaaggacagggaagggagcag

PCR product was cloned into AAV backbone, between ITR sequences using NotI restriction sites:
PCR Product Digestion:

| Fast Digest buffer, 10X | 3 µl |
| FastDigest NotI | 1 µl |
| DNA | 1 µg |
| ddH$_2$O | up to 30 µl |

AAV Backbone Digestion:

| Fast Digest buffer, 10X | 3 µl |
| FastDigest NotI | 1 µl |
| FastAP Alkaline Phosphatase | 1 µl |
| AAV backbone | 1 µg |
| ddH$_2$O | up to 30 µl |

After 20 min incubation in 37° C. samples were purified using QIAQuick PCR purification kit. Standardized samples were ligated at a 1:3 vector:insert ratio as follows:

| Digested pUC19 | 50 ng |
| Digested insert | 1:3 vector:insert molar ratio |
| T7 ligase | 1 µl |
| 2X Rapid Ligation Buffer | 5 µl |
| ddH$_2$O | up to 10 µl |

After transformation of bacteria with ligation reaction product, applicants confirmed obtained clones with Sanger sequencing.

Figure 35:
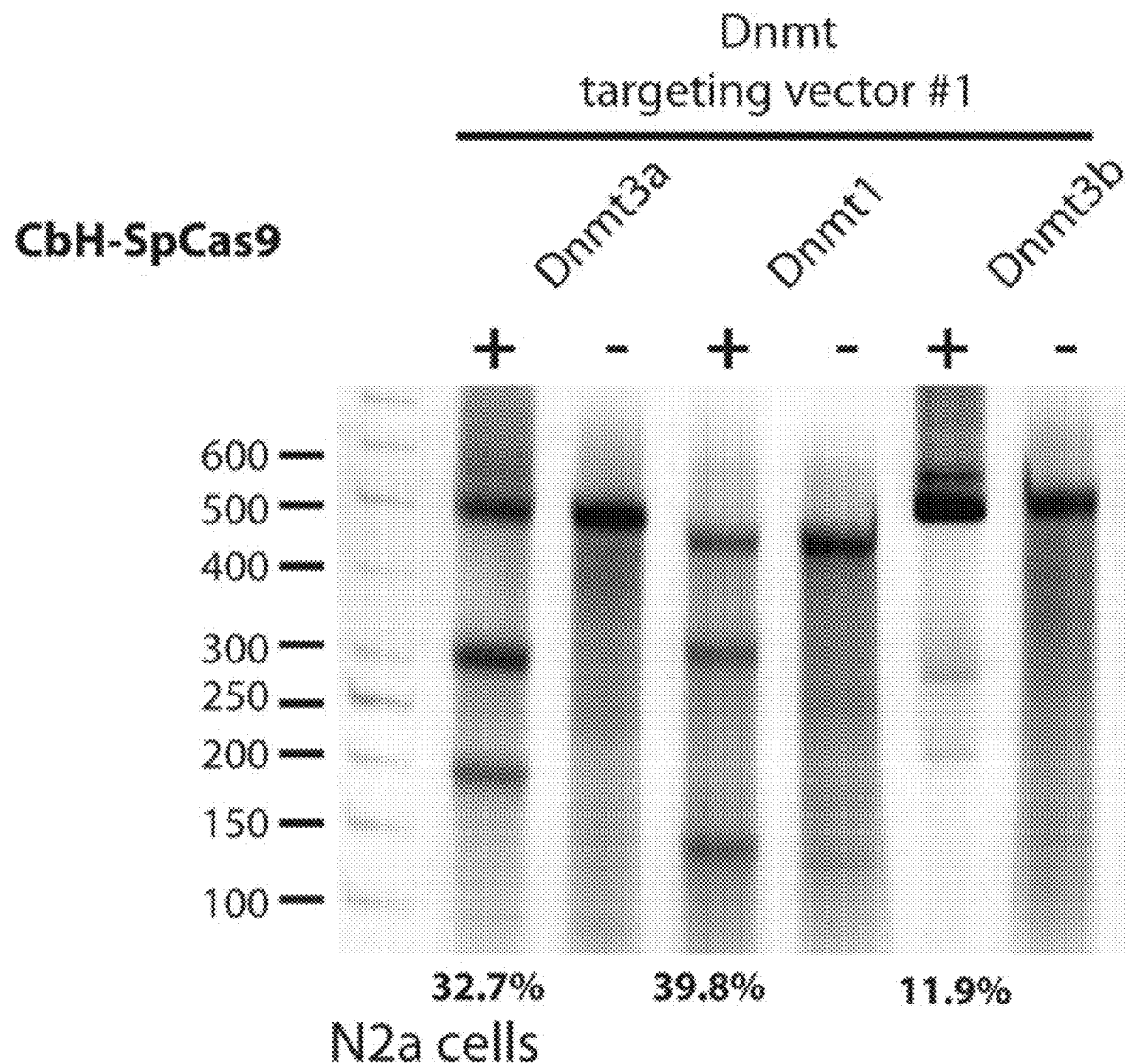
FIG. 35 shows verification of multiplex DNMT targeting vector #1 functionality using Surveyor assay. N2A cells were co-transfected with the DNMT targeting vector #1 (+) and the SpCas9 encoding vector for testing SpCas9 mediated cleavage of DNMTs genes family loci. gRNA only (−) is negative control. Cells were harvested for DNA purification and downstream processing 48 h after transfection.
Figure 36:
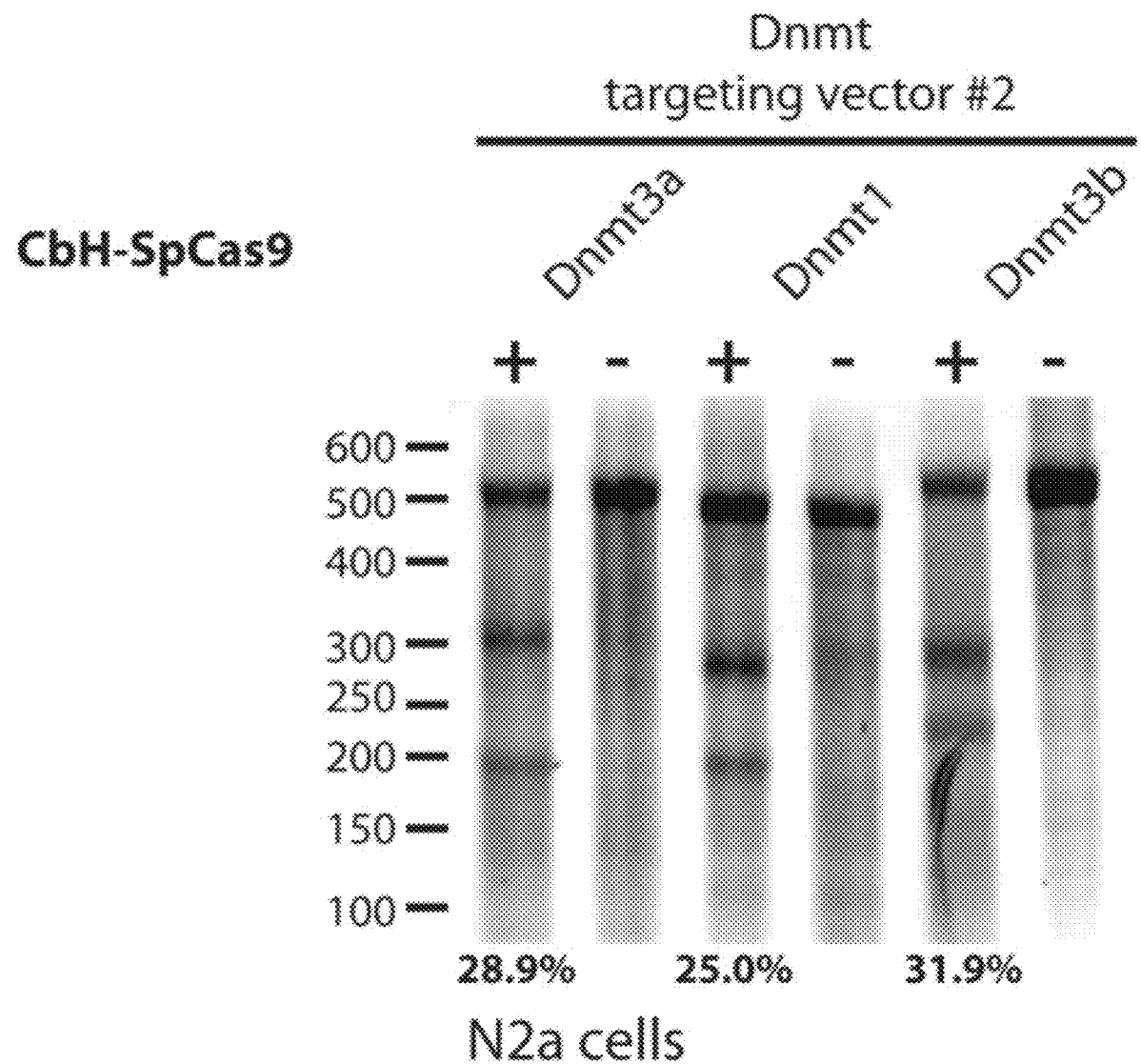
FIG. 36 shows verification of multiplex DNMT targeting vector #2 functionality using Surveyor assay. N2A cells were co-transfected with the DNMT targeting vector #1 (+) and the SpCas9 encoding vector for testing SpCas9 mediated cleavage of DNMTs genes family loci. gRNA only (−) is negative control. Cells were harvested for DNA purification and downstream processing 48 h after transfection.

Positive DNA clones were tested in N2a cells after co-transfection with Cas9 construct (FIGS. 35 and 36).

Design of New Cas9 Constructs for AAV Delivery

Figure 37:
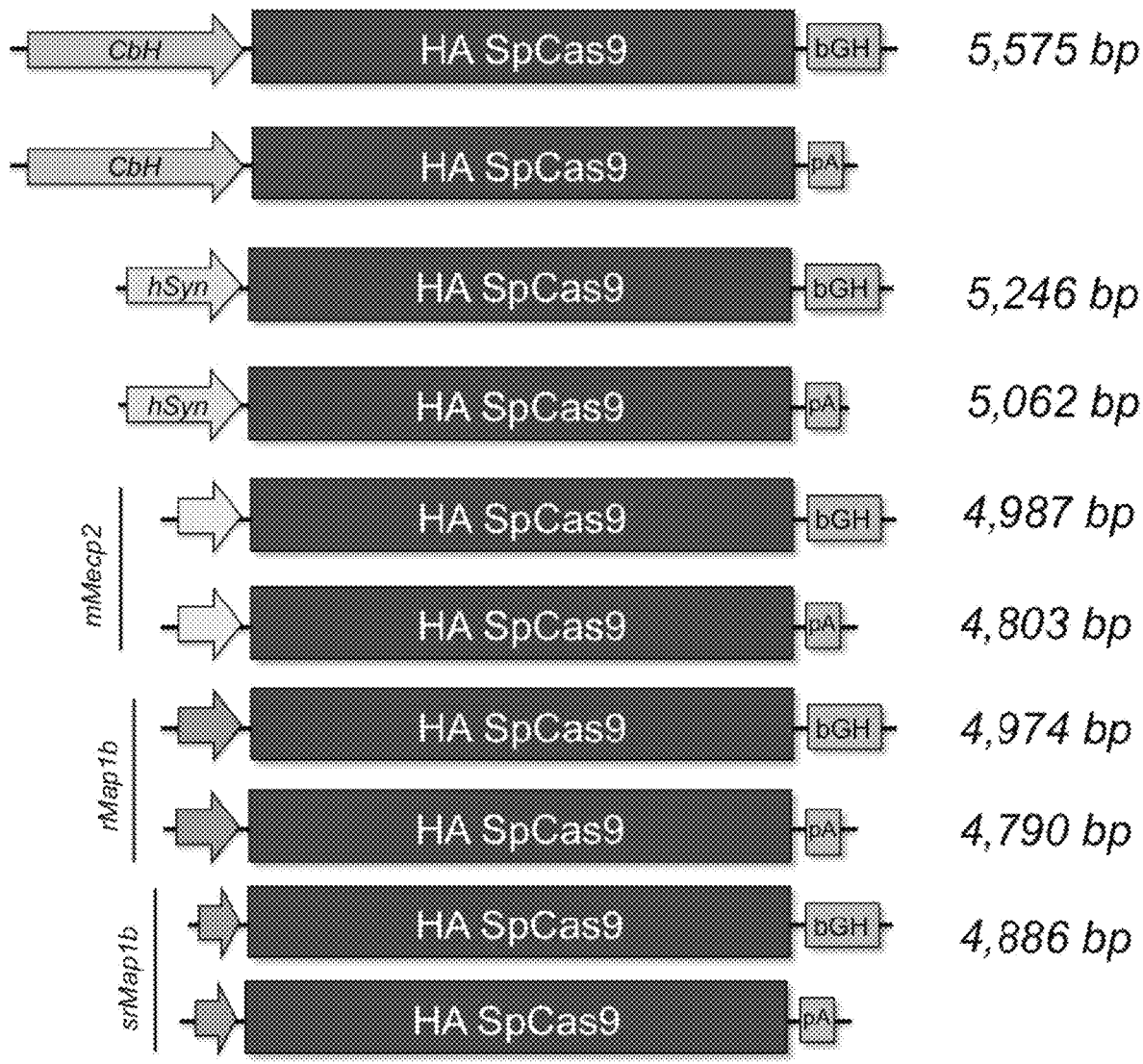
FIG. 37 shows schematic overview of short promoters and short polyA versions used for HA-SpCas9 expression in vivo. Sizes of the encoding region from L-ITR to R-ITR are shown on the right.
Figure 38:
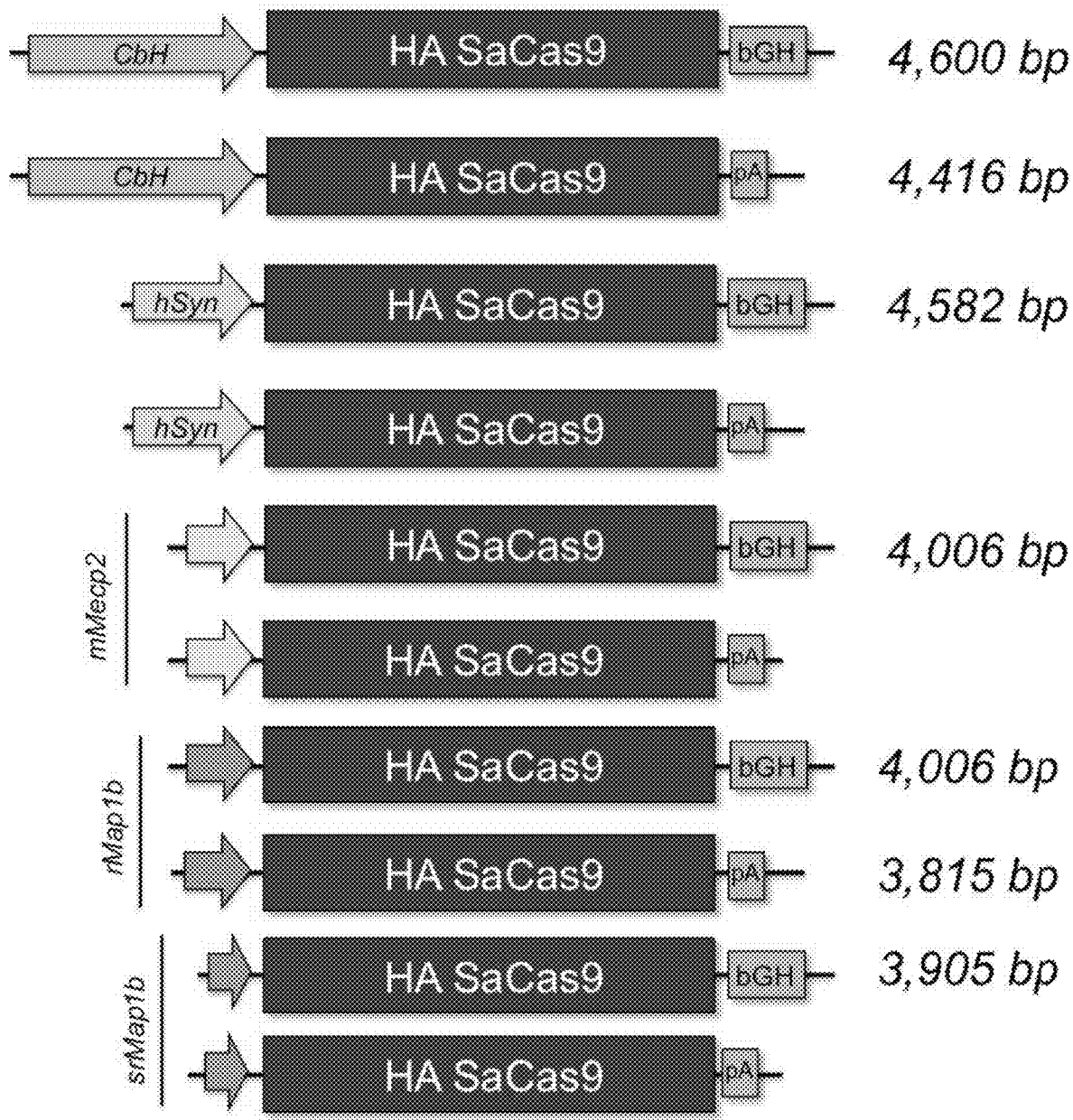
FIG. 38 shows schematic overview of short promoters and short polyA versions used for HA-SaCas9 expression in vivo. Sizes of the encoding region from L-ITR to R-ITR are shown on the right.
Figure 39:
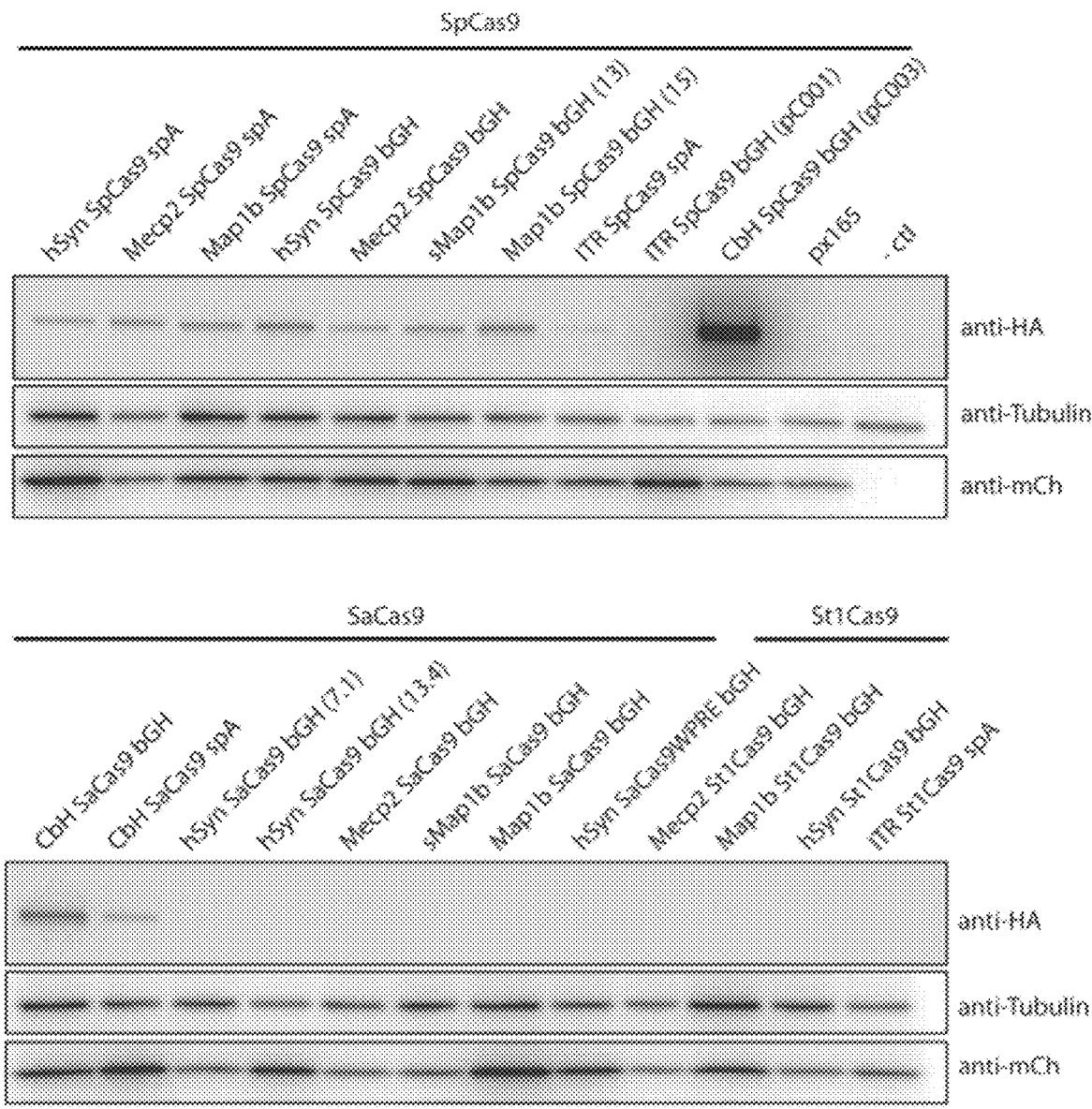
FIG. 39 shows expression of SpCas9 and SaCas9 in N2A cells. Representative Western blot of HA-tagged SpCas9 and SaCas9 versions under the control of different short promoters and with or short polyA (spA) sequences. Tubulin is loading control. mCherry (mCh) is a transfection control. Cells were harvested and further processed for Western blotting 48 h after transfection.
Figure 40:
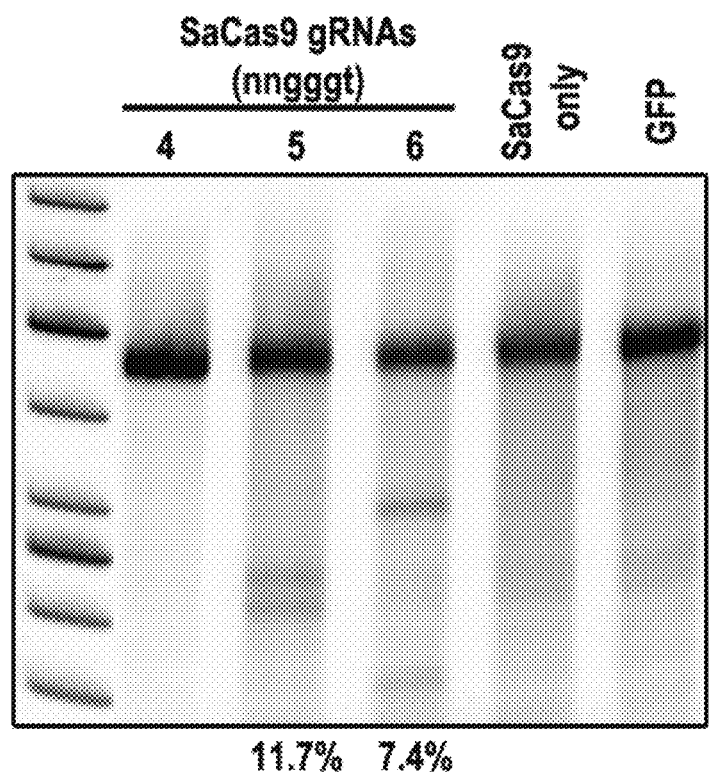
FIG. 40 shows screen for efficient SaCas9 mediated targeting of Tet3 gene locus. Surveyor assay on DNA from transfected N2A cells demonstrates efficient DNA cleavage by using different gRNAs with NNGGGT PUM sequence. GFP transfected cells and cells expressing only SaCas9 are controls.
Figure 41:
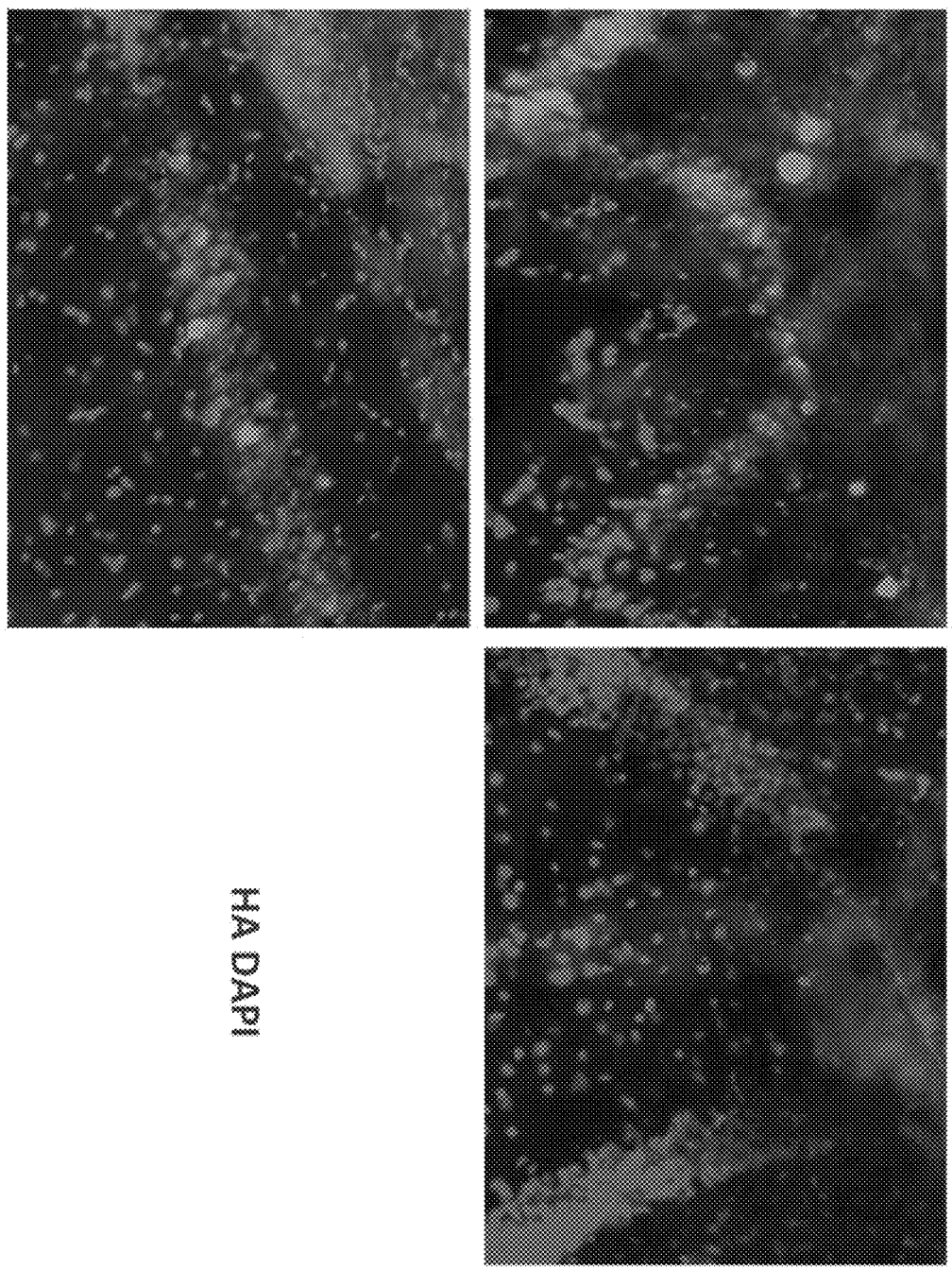
FIG. 41 shows expression of HA-SaCas9 in the mouse brain. Animals were injected into dentate gyri with virus driving expression of HA-SaCas9 under the control of human Synapsin promoter. Animals were sacrificed 2 weeks after surgery. HA tag was detected using rabbit monoclonal antibody C29F4 (Cell Signaling). Cell nuclei stained in blue with DAPI stain.

AAV delivery system despite its unique features has packing limitation—to successfully deliver expressing cassette in vivo it has to be in size <then 4.7 kb. To decrease the size of SpCas9 expressing cassette and facilitate delivery applicants tested several alteration: different promoters, shorter polyA signal and finally a smaller version of Cas9 from *Staphylococcus aureus* (SaCas9) (FIGS. 37 and 38). All tested promoters were previously tested and published to be active in neurons, including mouse Mecp2 (Gray et al., 2011), rat Map1b and truncated rat Map1b (Liu and Fischer, 1996). Alternative synthetic polyA sequence was previously shown to be functional as well (Levitt et al., 1989; Gray et al., 2011). All cloned constructs were expressed in N2a cells after transfection with Lipofectamine 2000, and tested with Western blotting method (FIG. 39).

Testing AAV Multiplex System in Primary Neurons

To confirm functionality of developed system in neurons, Applicants use primary neuronal cultures in vitro. Mouse cortical neurons was prepared according to the protocol published previously by Banker and Goslin (Banker and Goslin, 1988).

Neuronal cells are obtained from embryonic day 16. Embryos are extracted from the euthanized pregnant female and decapitated, and the heads are placed in ice-cold HBSS. The brains are then extracted from the skulls with forceps (#4 and #5) and transferred to another change of ice-cold HBSS. Further steps are performed with the aid of a stereoscopic microscope in a Petri dish filled with ice-cold HBSS and #5 forceps. The hemispheres are separated from each other and the brainstem and cleared of meninges. The hippocampi are then very carefully dissected and placed in a 15 ml conical tube filled with ice-cold HBSS. Cortices that remain after hippocampal dissection can be used for further cell isolation using an analogous protocol after removing the brain steam residuals and olfactory bulbs. Isolated hippocampi are washed three times with 10 ml ice-cold HBSS and dissociated by 15 min incubation with trypsin in HBSS (4 ml HBSS with the addition of 10 µl 2.5% trypsin per hippocampus) at 37° C. After trypsinization, the hippocampi are very carefully washed three times to remove any traces of trypsin with HBSS preheated to 37° C. and dissociated in warm HBSS. Applicants usually dissociate cells obtained from 10-12 embryos in 1 ml HBSS using 1 ml pipette tips and dilute dissociated cells up to 4 ml. Cells are plated at a density of 250 cells/mm2 and cultured at 37° C. and 5% CO2 for up to 3 week HBSS
435 ml H2O
50 ml 10× Hank's Balanced Salt Solution
16.5 ml 0.3M HEPES pH 7.3
5 ml penicillin-streptomycin solution
Filter (0.2 µm) and store 4° C.
Neuron Plating Medium (100 ml)
97 ml Neurobasal
2 ml B27 Supplement
1 ml penicillin-streptomycin solution
250 µl glutamine
125 µl glutamate Neurons are transduced with concentrated AAV1/2 virus or AAV1 virus from filtered medium of HEK293FT cells, between 4-7 days in culture and keep for at least one week in culture after transduction to allow for delivered gene expression.

AAV-Driven Expression of the System

Applicants confirmed expression of SpCas9 and SaCas9 in neuronal cultures after AAV delivery using Western blot method (FIG. 42). One week after transduction neurons were collected in NuPage SDS loading buffer with β-mercaptoethanol to denaturate proteins in 95° C. for 5 min. Samples were separated on SDS PAGE gel and transferred on PVDF membrane for WB protein detection. Cas9 proteins were detected with HA antibody.

Figure 50:
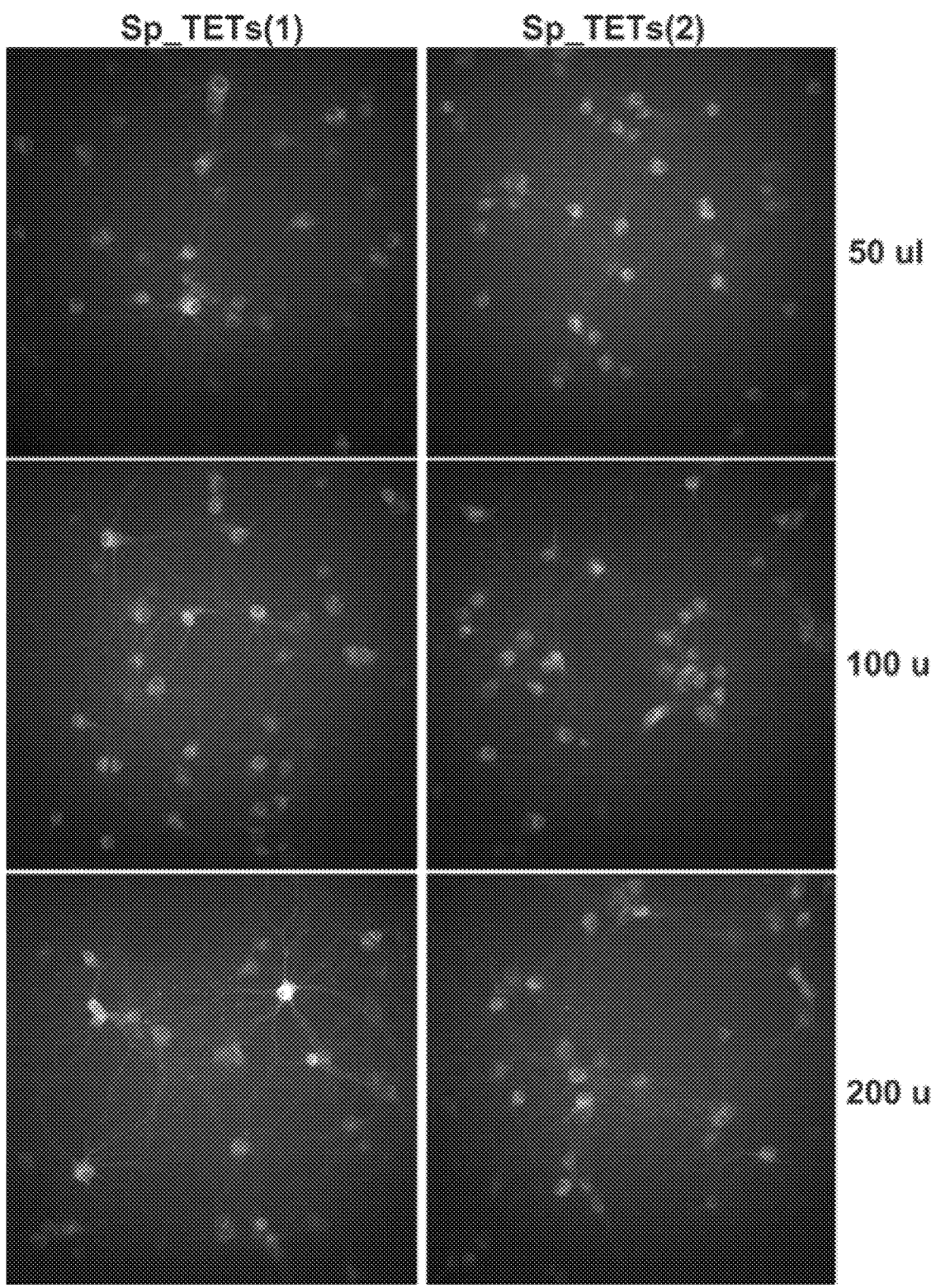
FIG. 50 shows GFP-KASH expression in cortical neurons in culture. Neurons were transduced with AAV1 virus carrying gRNA multiplex constructs targeting TET genes loci. The strongest signal localize around cells nuclei due to KASH domain localization.

Expression of Syn-GFP-kash from gRNA multiplex AAV was confirmed with fluorescent microscopy (FIG. 50).

Toxicity

Figure 43:
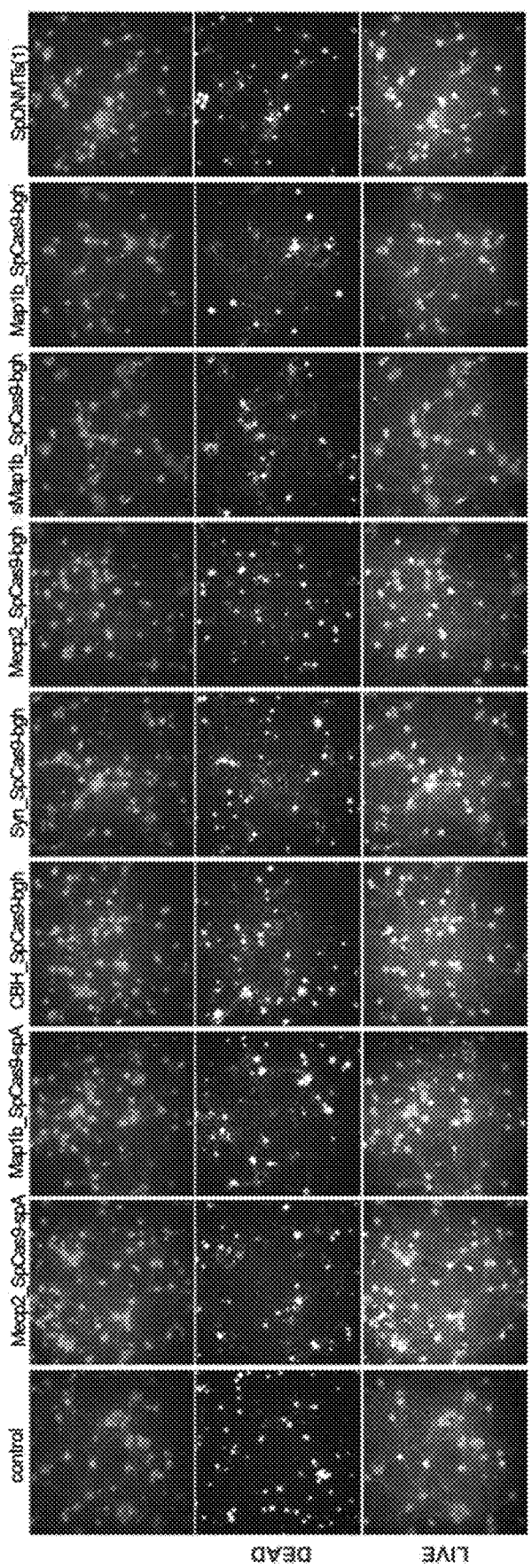
FIG. 43 shows LIVE/DEAD stain of primary cortical neurons 7 days after transduction with AAV1 particles carrying SpCas9 with different promoters and multiplex gRNAs constructs (example shown on the last panel for DNMT5). Neurons after AAV transduction were compared with control untransduced neurons. Red nuclei indicate permeabilized, dead cells (second line of panels). Live cells are marked in green color (third line of panels).
Figure 44:
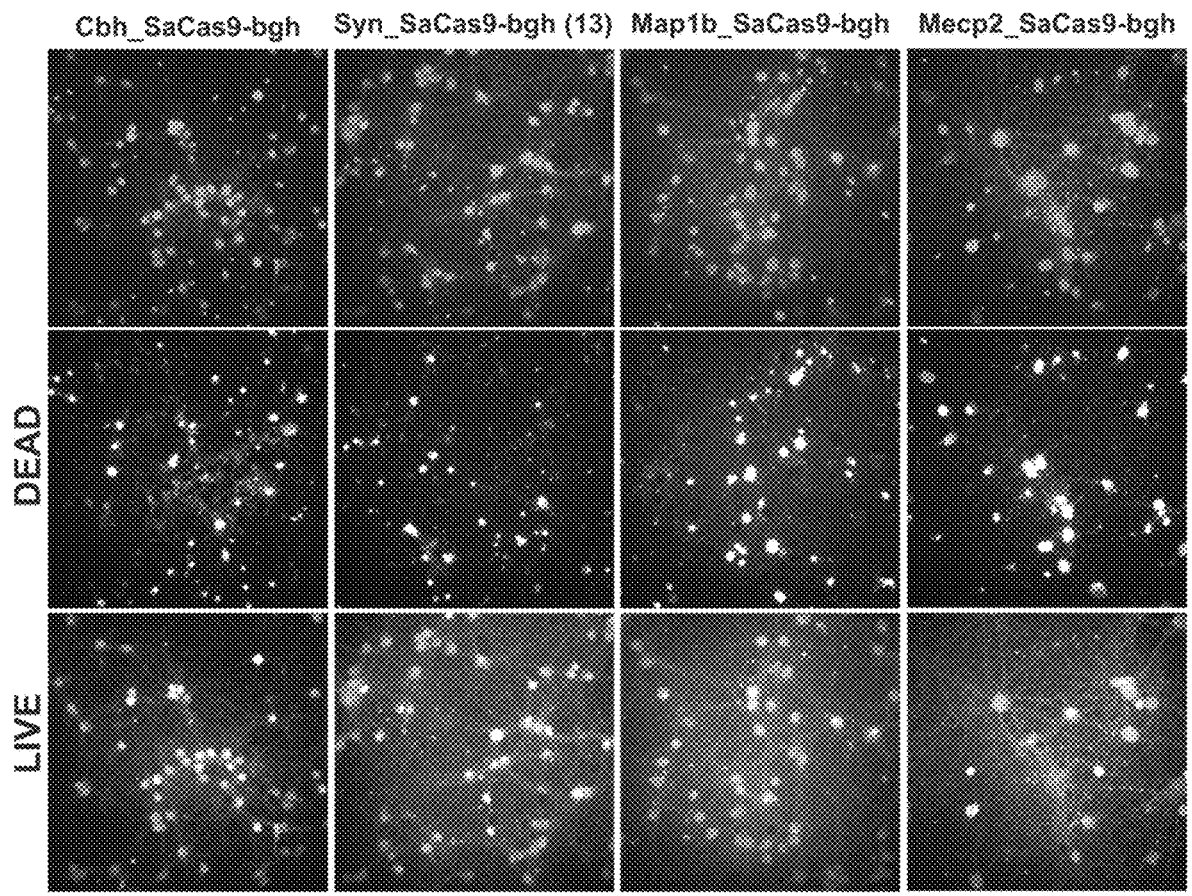
FIG. 44 shows LIVE/DEAD stain of primary cortical neurons 7 days after transduction with AAV1 particles carrying SaCas9 with different promoters. Red nuclei indicate permeabilized, dead cells (second line of panels). Live cells are marked in green color (third line of panels).
Figure 45:
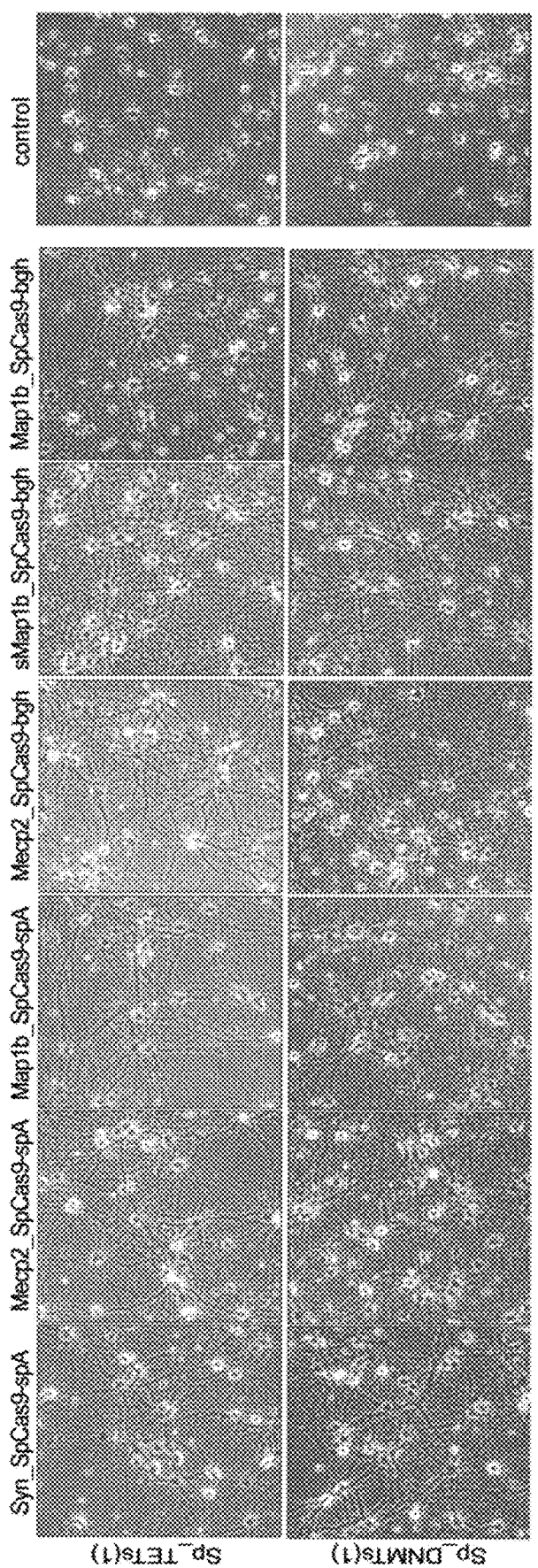
FIG. 45 shows comparison of morphology of neurons after transduction with AAV1 virus carrying SpCas9 and gRNA multiplexes for TETs and DNMTs genes loci. Neurons without transduction are shown as a control.
Figure 46:
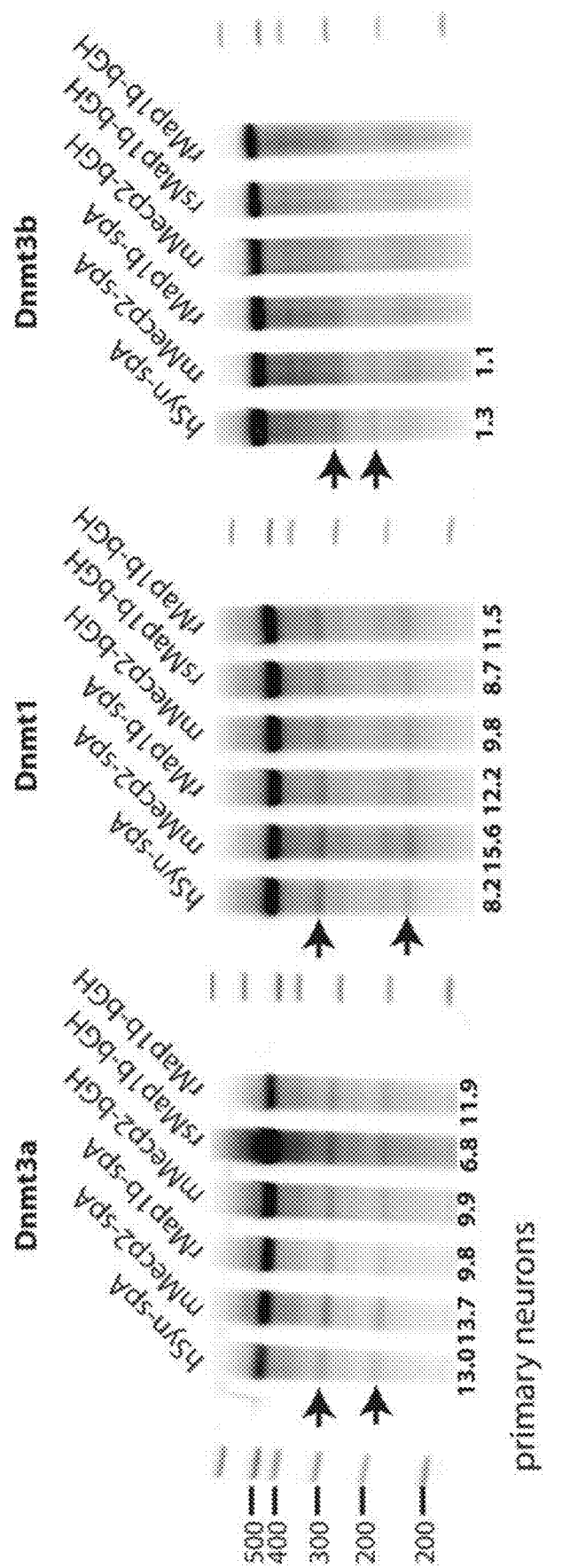
FIG. 46 shows verification of multiplex DNMT targeting vector #1 functionality using Surveyor assay in primary cortical neurons. Cells were co-transduced with the DNMT targeting vector #1 and the SpCas9 viruses with different promoters for testing SpCas9 mediated cleavage of DNMTs genes family loci.
Figure 47:
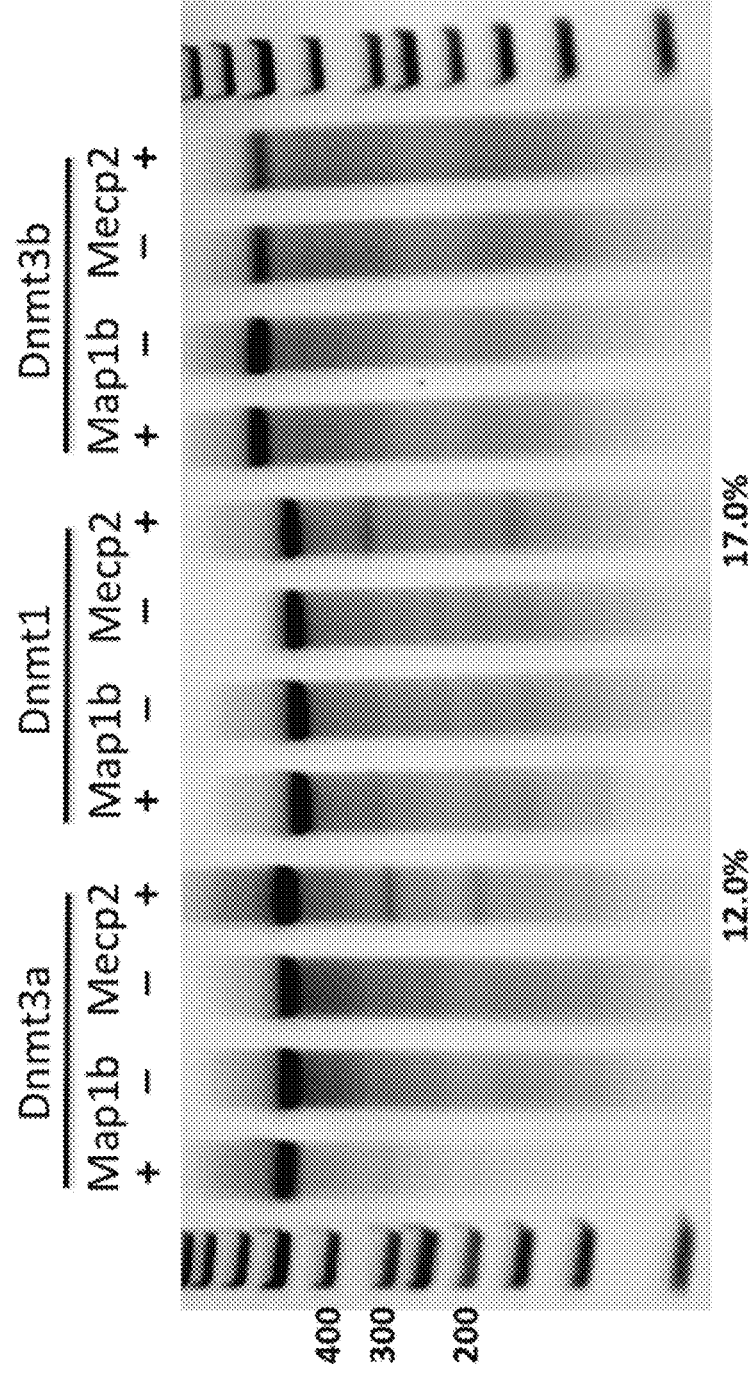
FIG. 47 shows in vivo efficiency of SpCas9 cleavage in the brain. Mice were injected with AAV1/2 virus carrying gRNA multiplex targeting DNMT family genes loci together with SpCas9 viruses under control of 2 different promoters: mouse Mecp2 and rat Map1b. Two weeks after injection brain tissue was extracted and nuclei were prepped and sorted using FACS, based on the GFP expression driven by Synapsin promoter from gRNA multiplex construct. After gDNA extraction Surveyor assay was run. + indicates GFP positive nuclei and − control, GFP-negative nuclei from the same animal. Numbers on the gel indicate assessed SpCas9 efficiency.
Figure 48:
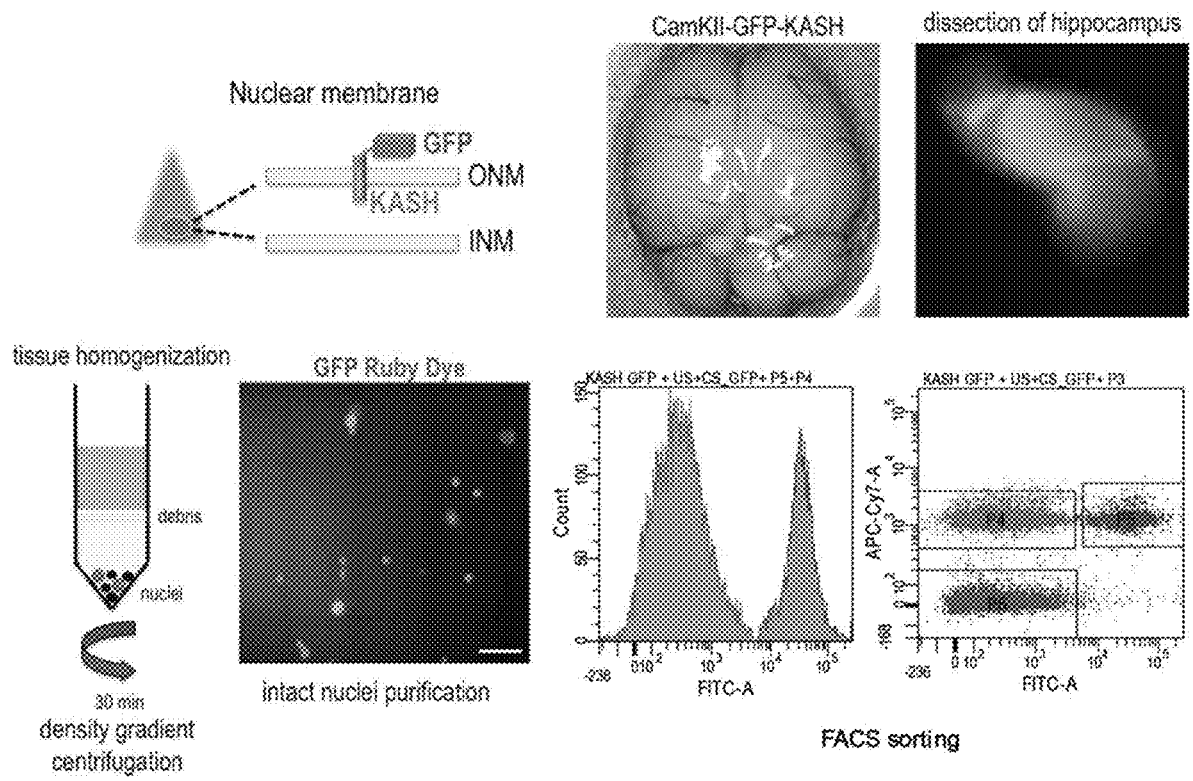
FIG. 48 shows purification of GFP-KASH labeled cell nuclei from hippocampal neurons. The outer nuclear membrane (ONM) of the cell nuclear membrane is tagged with a fusion of GFP and the KASH protein transmembrane domain. Strong GFP expression in the brain after one week of stereotactic surgery and AAV1/2 injection. Density gradient centrifugation step to purify cell nuclei from intact brain. Purified nuclei are shown. Chromatin stain by Vybrant® DyeCycle™ Ruby Stain is shown in red, GFP labeled nuclei are green. Representative FACS profile of GFP+ and GFP− cell nuclei (Magenta: Vybrant® DyeCycle™ Ruby Stain, Green: GFP).

To assess the toxicity of AAV with CRISPR system Applicants tested overall morphology of neurons one week after virus transduction (FIG. 45). Additionally, Applicants tested potential toxicity of designed system with the LIVE/DEAD® Cell Imaging Kit, which allows to distinguish live and dead cells in culture. It is based on the presence of intracellular esterase activity (as determined by the enzymatic conversion of the non-fluorescent calcein AM to the intensely green fluorescent calcein). On the other hand, the red, cell-impermeant component of the Kit enters cells with damaged membranes only and bind to DNA generating fluorescence in dead cells. Both flourophores can be easily visualized in living cells with fluorescent microscopy. AAV-driven expression of Cas9 proteins and multiplex gRNA constructs in the primary cortical neurons was well tolerated and not toxic (FIGS. 43 and 44), what indicates that designed AAV system is suitable for in vivo tests.

Virus Production

Concentrated virus was produced according to the methods described in McClure et al., 2011. Supernatant virus production occurred in HEK293FT cells.

Brain Surgeries

For viral vector injections 10-15 week old male C57BL/6N mice were anesthetized with a Ketamine/Xylazine cocktail (Ketamine dose of 100 mg/kg and Xylazine dose of 10 mg/kg) by intraperitoneal injection. Intraperitonial administration of Buprenex was used as a pre-emptive analgesic (1 mg/kg). Animals were immobilized in a Kopf stereotaxic apparatus using intra-aural positioning studs and tooth bar to maintain an immobile skull. Using a hand-held drill, a hole (1-2 mm) at −3.0 mm posterior to Bregma and 3.5 mm lateral for injection in the CA1 region of the hippocampus was made. Using 30G World Precision Instrument syringe at a depth of 2.5 mm, the solution of AAV viral particles in a total volume of 1 ul was injected. The injection was monitored by a 'World Precision Instruments UltraMicroPump3' injection pump at a flow rate of 0.5 ul/min to prevent tissue damage. When the injection was complete, the injection needle wase removed slowly, at a rate of 0.5 mm/min. After injection, the skin was sealed with 6-0 Ethilon sutures. Animals were postoperatively hydrated with 1 mL lactated Ringer's (subcutaneous) and housed in a temperature controlled (37° C.) environment until achieving an ambulatory recovery. 3 weeks after surgery animals were euthanized by deep anesthesia followed by tissue removal for nuclei sorting or with 4% paraformaldehyde perfusion for immunochemistry.

Sorting Nuclei and In Vivo Results

Applicants designed a method to specifically genetically tag the gRNA targeted neuronal cell nuclei with GFP for Fluorescent Activated Cell Sorting (FACS) of the labeled cell nuclei and downstream processing of DNA, RNA and nuclear proteins. To that purpose the applicants' multiplex targeting vector was designed to express both a fusion protein between GFP and the mouse nuclear membrane protein domain KASH (Starr DA, 2011, Current biology) and the 3 gRNAs to target specific gene loci of interest (FIG. 34). GFP-KASH was expressed under the control of the human Synapsin promoter to specifically label neurons. The amino acid of the fusion protein GFP-KASH was:

(SEQ ID NO: 204)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYKSGLRSREEEEE

TDSRMPHLDSPGSSQPRRSFLSRVIRAALPLQLLLLLLLLLACLLPASED

DYSCTQANNFARSFYPMLRYTNGPPPT

One week after AAV1/2 mediated delivery into the brain a robust expression of GFP-KASH was observed. For FACS and downstream processing of labeled nuclei, the hippocampi were dissected 3 weeks after surgery and processed for cell nuclei purification using a gradient centrifugation step. For that purpose the tissue was homogenized in 320 mM Sucrose, 5 mM CaCl, 3 mM Mg(Ac)2, 10 mM Tris pH 7.8, 0.1 mM EDTA, 0.1% NP40, 0.1 mM Phenylmethanesulfonyl fluoride (PMSF), 1 mM β-mercaptoethanol using 2 ml Dounce homogenizer (Sigma) The homogenisate was centrifuged on a 25% to 29% Optiprep® gradient according to the manufacture's protocol for 30 min at 3.500 rpm at 4° C. The nuclear pellet was resuspended in 340 mM Sucrose, 2 mM MgCl2, 25 mM KCl, 65 mM glycerophosphate, 5% glycerol, 0.1 mM PMSF, 1 mM β-mercaptoethanol and Vybrant® DyeCycle™ Ruby Stain (Life technologies) was added to label cell nuclei (offers near-infrared emission for DNA). The labeled and purified nuclei were sorted by FACS using an Aria Flu-act-cell sorter and BDFACS Diva software. The sorted GFP+ and GFP− nuclei were finally used to purify genomic DNA using DNAeasy Blood & Tissue Kit (Qiagen) for Surveyor assay analysis of the targeted genomic regions. The same approach can be easily used to purify nuclear RNA or protein from targeted cells for downstream processing. Due to the 2-vector system (FIG. 34) the applicants using in this approach efficient Cas9 mediated DNA cleavage was expected to occur only in a small subset of cells in the brain (cells which were co-infected with both the multiplex targeting vector and the Cas9 encoding vector). The method described here enables the applicants to specifically purify DNA, RNA and nuclear proteins from the cell population expressing the 3 gRNAs of interest and therefore are supposed to undergo Cas9 mediated DNA cleavage. By using this method the applicants were able to visualize efficient DNA cleavage in vivo occurring only in a small subset of cells.

Essentially, what Applicants have shown here is targeted in vivo cleavage. Furthermore, Applicants used a multiple approach, with several different sequences targeted at the same time, but independently. Presented system can be applied for studying brain pathologic conditions (gene knock out, e.g. Parkinson disease) and also open a field for further development of genome editing tools in the brain. By replacing nuclease activity with gene transcription regulators or epigenetic regulators it will be possible to answer whole spectrum of scientific question about role of gene regulation and epigenetic changes in the brain in not only in the pathologic conditions but also in physiological process as learning and memory formation. Finally, presented technology can be applied in more complex mammalian system as primates, what allows to overcome current technology limitations.

Example 33: Model Data

Several disease models have been specifically investigated. These include de novo autism risk genes CHD8, KATNAL2, and SCN2A; and the syndromic autism (Angelman Syndrome) gene UBE3A. These genes and resulting autism models are of course preferred, but show that the invention may be applied to any gene and therefore any model is possible.

Applicants have made these cells lines using Cas9 nuclease in human embryonic stem cells (hESCs). The lines were created by transient transfection of hESCs with Cbh-Cas9-2A-EGFP and pU6-sgRNA. Two sgRNAs are designed for each gene targeting most often the same exons in which patient nonsense (knock-out) mutations have been recently described from whole exome sequencing studies of autistic patients. The Cas9-2A-EGFP and pU6 plasmids were created specifically for this project.

Example 34: AAV Production System or Protocol

An AAV production system or protocol that was developed for, and works particularly well with, high through put screening uses is provided herein, but it has broader applicability in the present invention as well. Manipulating endogenous gene expression presents various challenges, as the rate of expression depends on many factors, including regulatory elements, mRNA processing, and transcript stability. To overcome this challenge, Applicants developed an adeno-associated virus (AAV)-based vector for the delivery. AAV has an ssDNA-based genome and is therefore less susceptible to recombination.

AAV1/2 (serotype AAV1/2, i.e., hybrid or mosaic AAV1/AAV2 capsid AAV) heparin purified concentrated virus protocol
Media: D10+HEPES
500 ml bottle DMEM high glucose+Glutamax (GIBCO)
50 ml Hyclone FBS (heat-inactivated) (Thermo Fischer)
5.5 ml HEPES solution (1M, GIBCO)
Cells: low passage HEK293FT (passage <10 at time of virus production, thaw new cells of passage 2-4 for virus production, grow up for 3-5 passages)
Transfection Reagent: Polyethylenimine (PEI) "Max"
Dissolve 50 mg PEI "Max" in 50 ml sterile Ultrapure H2O
Adjust pH to 7.1
Filter with 0.22 um fliptop filter
Seal tube and wrap with parafilm
Freeze aliquots at −20° C. (for storage, can also be used immediately)
Cell Culture
Culture low passage HEK293FT in D10+HEPES
Passage everyday between 1:2 and 1:2.5
Advantageously do not allow cells to reach more than 85% confluency
For T75
Warm 10 ml HBSS (—Mg2+, —Ca2+, GIBCO)+1 ml TrypLE Express (GIBCO) per flask to 37° C.
(Waterbath) Aspirate media fully
Add 10 ml warm HBSS gently (to wash out media completely)
Add 1 ml TrypLE per Flask
Place flask in incubator (37° C.) for 1 min
Rock flask to detach cells
Add 9 ml D10+HEPES media (37° C.)
Pipette up and down 5 times to generate single cell suspension
Split at 1:2-1:2.5 (12 ml media for T75) ratio (if cells are growing more slowly, discard and thaw a new batch, they are not in optimal growth)
transfer to T225 as soon as enough cells are present (for ease of handling large amounts of cells)
AAV Production (5*15 cm Dish Scale Per Construct):
Plate 10 million cells in 21.5 ml media into a 15 cm dish
Incubate for 18-22 hours at 37° C.
Transfection is ideal at 80% confluence
Per Plate
Prewarm 22 ml media (D10+HEPES)
Prepare Tube with DNA Mixture (Use Endofree Maxiprep DNA):
5.2 ug vector of interest plasmid
4.35 ug AAV 1 serotype plasmid
4.35 ug AAV 2 serotype plasmid
10.4 ug pDF6 plasmid (adenovirus helper genes)☐Vortex to mix
Add 434 uL DMEM (no serum!)
Add 130 ul PEI solution
Vortex 5-10 seconds
Add DNA/DMEM/PEI mixture to prewarmed media
Vortex briefly to mix
Replace media in 15 cm dish with DNA/DMEM/PEI mixture
Return to 37° C. incubator
Incubate 48 h before harvesting (make sure medium isn't turning too acidic)
Virus Harvest:
1. aspirate media carefully from 15 cm dish dishes (advantageously do not dislodge cells)
2. Add 25 ml RT DPBS (Invitrogen) to each plate and gently remove cells with a cell scraper. Collect suspension in 50 ml tubes.
3. Pellet cells at 800×g for 10 minutes.
4. Discard supernatant
Pause Point: Freeze Cell Pellet at −80 C if Desired
5. resuspend pellet in 150 mM NaCl, 20 mM Tris pH 8.0, use 10 ml per tissue culture plate.
6. Prepare a fresh solution of 10% sodium deoxycholate in dH2O. Add 1.25 ml of this per tissue culture plate for a final concentration of 0.5%. Add benzonase nuclease to a final concentration of 50 units per ml. Mix tube thoroughly.
7. Incubate at 37° C. for 1 hour (Waterbath).
8. Remove cellular debris by centrifuging at 3000×g for 15 mins. Transfer to fresh 50 ml tube and ensure all cell debris has been removed to prevent blocking of heparin columns.
Heparin Column Purification of AAV1/2:
1. Set up HiTrap heparin columns using a peristaltic pump so that solutions flow through the column at 1 ml per minute. It is important to ensure no air bubbles are introduced into the heparin column.
2. Equilibrate the column with 10 ml 150 mM NaCl, 20 mM Tris, pH 8.0 using the peristaltic pump.
3. Binding of virus: Apply 50 ml virus solution to column and allow to flow through.
4. Wash step 1: column with 20 ml 100 mM NaCl, 20 mM Tris, pH 8.0. (using the peristaltic pump)
5. Wash step 2: Using a 3 ml or 5 ml syringe continue to wash the column with 1 ml 200 mM NaCl, 20 mM Tris, pH 8.0, followed by 1 ml 300 mM NaCl, 20 mM Tris, pH 8.0.
Discard the Flow-Through.
(prepare the syringes with different buffers during the 50 min flow through of virus solution above)
6. Elution Using 5 ml syringes and gentle pressure (flow rate of <1 ml/min) elute the virus from the column by applying:
1.5 ml 400 mM NaCl, 20 mM Tris, pH 8.0
3.0 ml 450 mM NaCl, 20 mM Tris, pH 8.0
1.5 ml 500 mM NaCl, 20 mM Tris, pH 8.0
Collect these in a 15 ml centrifuge tube.
Concentration of AAV1/2:
1. Concentration step 1: Concentrate the eluted virus using Amicon ultra 15 ml centrifugal filter units with a 100,000 molecular weight cutoff. Load column eluate into the concentrator and centrifuge at 2000×g for 2 minutes (at room temperature. Check concentrated volume—it should be approximately 500 µl. If necessary, centrifuge in 1 min intervals until correct volume is reached.
2. buffer exchange: Add 1 ml sterile DPBS to filter unit, centrifuge in 1 min intervals until correct volume (500 ul) is reached.
3. Concentration step 2: Add 500 ul concentrate to an Amicon Ultra 0.5 ml 100K filter unit. Centrifuge at 6000 g for 2 min. Check concentrated volume—it should be approximately 100 If necessary, centrifuge in 1 min intervals until correct volume is reached.
4. Recovery: Invert filter insert and insert into fresh collection tube. Centrifuge at 1000 g for 2 min.

Aliquot and freeze at −80° C.
1 ul is typically required per injection site, small aliquots (e.g. 5 ul) are therefore recommended (avoid freeze-thaw of virus).
determine DNaseI-resistant GC particle titer using qPCR (see separate protocol)
  Materials.
Amicon Ultra, 0.5 ml, 100K; MILLIPORE; UFC510024
Amicon Ultra, 15 ml, 100K; MILLIPORE; UFC910024
Benzonase nuclease; Sigma-Aldrich, E1014
HiTrap Heparin cartridge; Sigma-Aldrich; 54836
Sodium deoxycholate; Sigma-Aldrich; D5670
  AAV1 Supernatant Production Protocol
Media: D10+HEPES
500 ml bottle DMEM high glucose+Glutamax (Invitrogen)
50 ml Hyclone FBS (heat-inactivated) (Thermo Fischer)
5.5 ml HEPES solution (1M, GIBCO)
Cells: low passage HEK293FT (passage <10 at time of virus production)
Thaw new cells of passage 2-4 for virus production, grow up for 2-5 passages
Transfection reagent: Polyethylenimine (PEI) "Max"
Dissolve 50 mg PEI "Max" in 50 ml sterile Ultrapure H2O
Adjust pH to 7.1
Filter with 0.22 um fliptop filter
Seal tube and wrap with parafilm
Freeze aliquots at −20° C. (for storage, can also be used immediately)
Cell Culture
Culture low passage HEK293FT in D10+HEPES Passage everyday between 1:2 and 1:2.5 Advantageously do let cells reach more than 85% confluency
For T75
  Warm 10 ml HBSS (—Mg2+, —Ca2+, GIBCO)+1 ml TryPLE Express (GIBCO) per flask to 37° C. (Waterbath)
  Aspirate media fully
  Add 10 ml warm HBSS gently (to wash out media completely)
  Add 1 ml TryPLE per Flask
  Place flask in incubator (37° C.) for 1 min
  Rock flask to detach cells
  Add 9 ml D10+HEPES media (37° C.)
  Pipette up and down 5 times to generate single cell suspension
  Split at 1:2-1:2.5 (12 ml media for T75) ratio (if cells are growing more slowly, discard and thaw a new batch, they are not in optimal growth)
  transfer to T225 as soon as enough cells are present (for ease of handling large amounts of cells)
AAV production (single 15 cm dish scale)
Plate 10 million cells in 21.5 ml media into a 15 cm dish
Incubate for 18-22 hours at 37° C.
Transfection is ideal at 80% confluence per plate
Prewarm 22 ml media (D10+HEPES)
Prepare tube with DNA mixture (use endofree maxiprep DNA):
5.2 ug vector of interest plasmid
8.7 ug AAV 1 serotype plasmid
10.4 ug DF6 plasmid (adenovirus helper genes)
Vortex to mix
Add 434 uL DMEM (no serum!) Add 130 ul PEI solution
Vortex 5-10 seconds
Add DNA/DMEM/PEI mixture to prewarmed media
Vortex briefly to mix
Replace media in 15 cm dish with DNA/DMEM/PEI mixture
Return to 37° C. incubator Incubate 48 h before harvesting (advantageously monitor to ensure medium is not turning too acidic)
  Virus Harvest:
Remove supernatant from 15 cm dish
Filter with 0.45 um filter (low protein binding) Aliquot and freeze at −80° C.
Transduction (primary neuron cultures in 24-well format, SDIV)
Replace complete neurobasal media in each well of neurons to be transduced with fresh neurobasal (usually 400 ul out of 500 ul per well is replaced)
Thaw AAV supernatant in 37° C. waterbath
Let equilibrate in incubator for 30 min
Add 250 ul AAV supernatant to each well
Incubate 24 h at 37° C.
Remove media/supernatant and replace with fresh complete neurobasal
Expression starts to be visible after 48 h, saturates around 6-7 Days Post Infection
Constructs for pAAV plasmid with GOI should not exceed 4.8 kb including both ITRS.
  Example of a human codon optimized sequence (i.e. being optimized for expression in humans) sequence: SaCas9 is provided below:

(SEQ ID NO: 205)
ACCGGTGCCACCATGTACCCATACGATGTTCCAGATTACGCTTCGCCGAA

GAAAAAGCGCAAGGTCGAAGCGTCCATGAAAAGGAACTACATTCTGGGGC

TGGACATCGGGATTACAAGCGTGGGGTATGGGATTATTGACTATGAAACA

AGGGACGTGATCGACGCAGGCGTCAGACTGTTCAAGGAGGCCAACGTGGA

AAACAATGAGGGACGGAGAAGCAAGAGGGGAGCCAGGCGCCTGAAACGAC

GGAGAAGGCACAGAATCCAGAGGGTGAAGAAACTGCTGTTCGATTACAAC

CTGCTGACCGACCATTCTGAGCTGAGTGGAATTAATCCTTATGAAGCCAG

GGTGAAAGGCCTGAGTCAGAAGCTGTCAGAGGAAGAGTTTTCCGCAGCTC

TGCTGCACCTGGCTAAGCGCCGAGGAGTGCATAACGTCAATGAGGTGGAA

GAGGACACCGGCAACGAGCTGTCTACAAAGGAACAGATCTCACGCAATAG

CAAAGCTCTGGAAGAGAAGTATGTCGCAGAGCTGCAGCTGGAACGGCTGA

AGAAAGATGGCGAGGTGAGAGGGTCAATTAATAGGTTCAAGACAAGCGAC

TACGTCAAAGAAGCCAAGCAGCTGCTGAAAGTGCAGAAGGCTTACCACCA

GCTGGATCAGAGCTTCATCGATACTTATATCGACCTGCTGGAGACTCGGA

GAACCTACTATGAGGGACCAGGAGAAGGGAGCCCCTTCGGATGGAAAGAC

ATCAAGGAATGGTACGAGATGCTGATGGGACATTGCACCTATTTTCCAGA

AGAGCTGAGAAGCGTCAAGTACGCTTATAACGCAGATCTGTACAACGCCC

TGAATGACCTGAACAACCTGGTCATCACCAGGGATGAAAACGAGAAACTG

GAATACTATGAGAAGTTCCAGATCATCGAAAACGTGTTTAAGCAGAAGAA

AAAGCCTACACTGAAACAGATTGCTAAGGAGATCCTGGTCAACGAAGAGG

ACATCAAGGGCTACCGGGTGACAAGCACTGGAAAACCAGAGTTCACCAAT

CTGAAAGTGTATCACGATATTAAGGACATCACAGCACGGAAAGAAATCAT

TGAGAACGCCGAACTGCTGGATCAGATTGCTAAGATCCTGACTATCTACC

AGAGCTCCGAGGACATCCAGGAAGAGCTGACTAACCTGAACAGCGAGCTG

ACCCAGGAAGAGATCGAACAGATTAGTAATCTGAAGGGGTACACCGGAAC

-continued

```
ACACAACCTGTCCCTGAAAGCTATCAATCTGATTCTGGATGAGCTGTGGC
ATACAAACGACAATCAGATTGCAATCTTTAACCGGCTGAAGCTGGTCCCA
AAAAAGGTGGACCTGAGTCAGCAGAAAGAGATCCCAACCACACTGGTGGA
CGATTTCATTCTGTCACCCGTGGTCAAGCGGAGCTTCATCCAGAGCATCA
AAGTGATCAACGCCATCATCAAGAAGTACGGCCTGCCCAATGATATCATT
ATCGAGCTGGCTAGGGAGAAGAACAGCAAGGACGCACAGAAGATGATCAA
TGAGATGCAGAAACGAAACCGGCAGACCAATGAACGCATTGAAGAGATTA
TCCGAACTACCGGGAAAGAACGCAAAGTACCTGATTGAAAAAATCAAG
CTGCACGATATGCAGGAGGGAAAGTGTCTGTATTCTCTGGAGGCCATCCC
CCTGGAGGACCTGCTGAACAATCCATTCAACTACGAGGTCGATCATATTA
TCCCCAGAAGCGTGTCCTTCGACAATTCCTTTAACAACAAGGTGCTGGTC
AAGCAGGAAGAGAACTCTAAAAAGGGCAATAGGACTCCTTTCCAGTACCT
GTCTAGTTCAGATTCCAAGATCTCTTACGAAACCTTTAAAAAGCACATTC
TGAATCTGGCCAAAGGAAAGGGCCGCATCAGCAAGACCAAAAAGGAGTAC
CTGCTGGAAGAGCGGGACATCAACAGATTCTCCGTCCAGAAGGATTTTAT
TAACCGGAATCTGGTGGACACAAGATACGCTACTCGCGGCCTGATGAATC
TGCTGCGATCCTATTTCCGGGTGAACAATCTGGATGTGAAAGTCAAGTCC
ATCAACGGCGGGTTCACATCTTTTCTGAGGCGCAAATGGAAGTTTAAAAA
GGAGCGCAACAAAGGGTACAAGCACCATGCCGAAGATGCTCTGATTATCG
CAAATGCCGACTTCATCTTTAAGGAGTGGAAAAAGCTGGACAAAGCCAAG
AAAGTGATGGAGAACCAGATGTTCGAAGAGAAGCAGGCCGAATCTATGCC
CGAAATCGAGACAGAACAGGAGTACAAGGAGATTTTCATCACTCCTCACC
AGATCAAGCATATCAAGGATTTCAAGGACTACAAGTACTCTCACCGGGTG
GATAAAAAGCCCAACAGAGAGCTGATCAATGACACCCTGTATAGTACAAG
AAAAGACGATAAGGGGAATACCCTGATTGTGAACAATCTGAACGGACTGT
ACGACAAAGATAATGACAAGCTGAAAAAGCTGATCAACAAAAGTCCCGAG
AAGCTGCTGATGTACCACCATGATCCTCAGACATATCAGAAACTGAAGCT
GATTATGGAGCAGTACGGCGACGAGAAGAACCCACTGTATAAGTACTATG
AAGAGACTGGGAACTACCTGACCAAGTATAGCAAAAAGGATAATGGCCCC
GTGATCAAGAAGATCAAGTACTATGGGAACAAGCTGAATGCCCATCTGGA
CATCACAGACGATTACCCTAACAGTCGCAACAAGGTGGTCAAGCTGTCAC
TGAAGCCATACAGATTCGATGTCTATCTGGACAACGGCGTGTATAAATTT
GTGACTGTCAAGAATCTGGATGTCATCAAAAAGGAGAACTACTATGAAGT
GAATAGCAAGTGCTACGAAGAGGCTAAAAAGCTGAAAAAGATTAGCAACC
AGGCAGAGTTCATCGCCTCCTTTTACAACAACGACCTGATTAAGATCAAT
GGCGAACTGTATAGGGTCATCGGGGTGAACAATGATCTGCTGAACCGCAT
TGAAGTGAATATGATTGACATCACTTACCGAGAGTATCTGGAAAACATGA
ATGATAAGCGCCCCCCTCGAATTATCAAAACAATTGCCTCTAAGACTCAG
AGTATCAAAAAGTACTCAACCGACATTCTGGGAAACCTGTATGAGGTGAA
GAGCAAAAAGCACCCTCAGATTATCAAAAAGGGCTAAGAATTC
```

Example 35: Minimizing Off-Target Cleavage Using Cas9 Nickase and Two Guide RNAs Cas9 is a RNA-guided DNA nuclease that may be targeted to specific locations in the genome with the help of a 20 bp RNA guide. However the guide sequence may tolerate some mismatches between the guide sequence and the DNA-target sequence. The flexibility is undesirable due to the potential for off-target cleavage, when the guide RNA targets Cas9 to a an off-target sequence that has a few bases different from the guide sequence. For all experimental applications (gene targeting, crop engineering, therapeutic applications, etc) it is important to be able to improve the specificity of Cas9 mediated gene targeting and reduce the likelihood of off-target modification by Cas9.

Applicants developed a method of using a Cas9 nickase mutant in combination with two guide RNAs to facilitate targeted double strand breaks in the genome without off-target modifications. The Cas9 nickase mutant may be generated from a Cas9 nuclease by disabling its cleavage activity so that instead of both strands of the DNA duplex being cleaved only one strand is cleaved. The Cas9 nickase may be generated by inducing mutations in one ore more domains of the Cas9 nuclease, e.g. Ruvc1 or HNH. These mutations may include but are not limited to mutations in a Cas9 catalytic domain, e.g in SpCas9 these mutations may be at positions D10 or H840. These mutations may include but are not limited to D10A, E762A, H840A, N854A, N863A or D986A in SpCas9 but nickases may be generated by inducing mutations at corresponding positions in other CRISPR enzymes or Cas9 orthologs. In a most preferred embodiment of the invention the Cas9 nickase mutant is a SpCas9 nickase with a D10A mutation.

The way this works is that each guide RNA in combination with Cas9 nickase would induce the targeted single strand break of a duplex DNA target. Since each guide RNA nicks one strand, the net result is a double strand break. The reason this method eliminates off-target mutations is because it is very unlikely to have an off-target site that has high degrees of similarity for both guide sequences (20 bp+2 bp(PAM)=22 bp specificity for each guide, and two guides means any off-target site will have to have close to 44 bp of homologous sequence). Although it is still likely that individual guides may have off-targets, but those off-targets will only be nicked, which is unlikely to be repaired by the mutagenic NHEJ process. Therefore the multiplexing of DNA double strand nicking provides a powerful way of introducing targeted DNA double strand breaks without off-target mutagenic effects.

Figure 52:
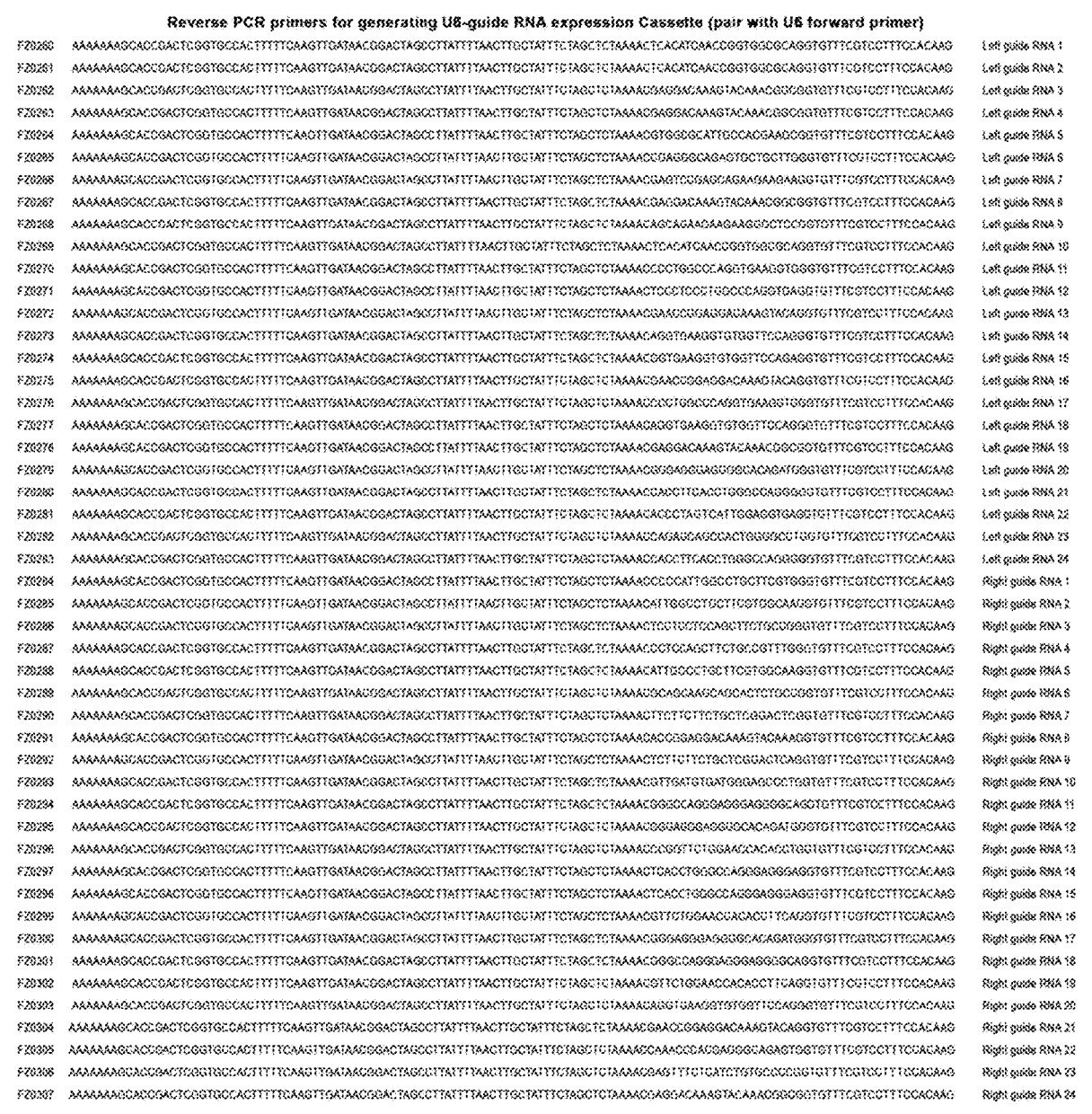
Figure 53:
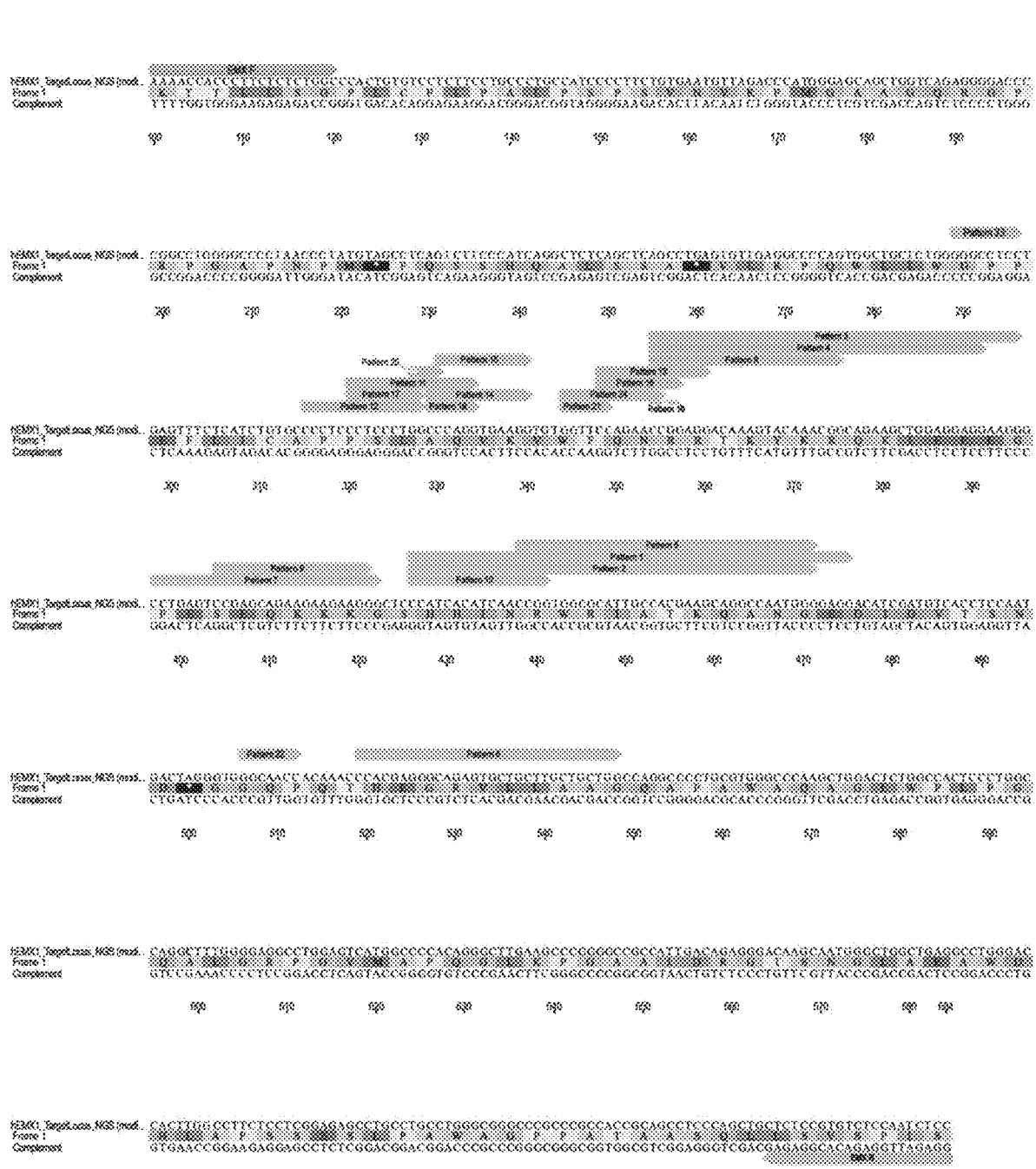
FIG. 53 shows a Genomic sequence map from the human Emx1 locus showing the locations of the 24 patterns listed in FIG. 33.

Applicants carried out experiments involving the co-transfection of HEK293FT cells with a plasmid encoding Cas9(D10A) nickase as well as DNA expression cassettes for one or more guides. Applicants transfected cells using Lipofectamine 2000, and transfected cells were harvested 48 or 72 hours after transfections. Double nicking-induced NHEJ were detected using the SURVEYOR nuclease assay as described previously herein (FIGS. 51, 52 and 53).

Figure 55:
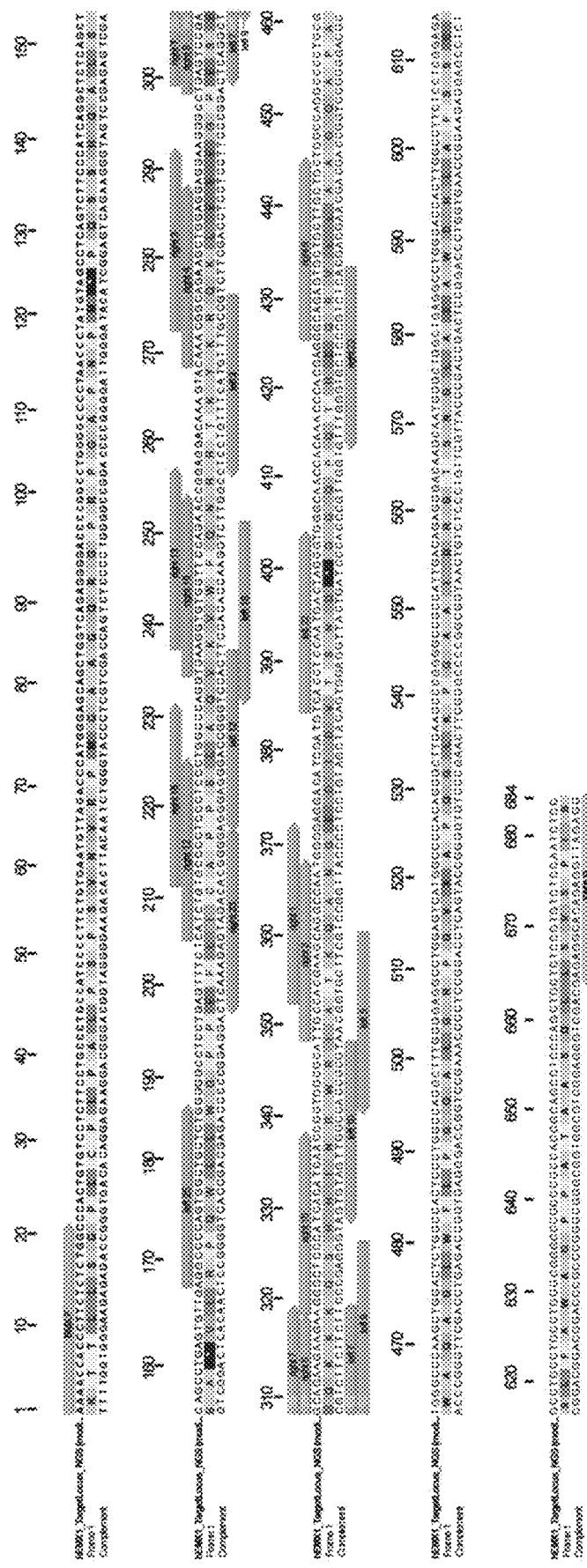
FIG. 55 shows a Genomic sequence map from the human Emx1 locus showing the locations of the different pairs of guide RNAs that result in the gel patterns of FIG. 54 (right) and which are further described in Example 35.
Figure 56:
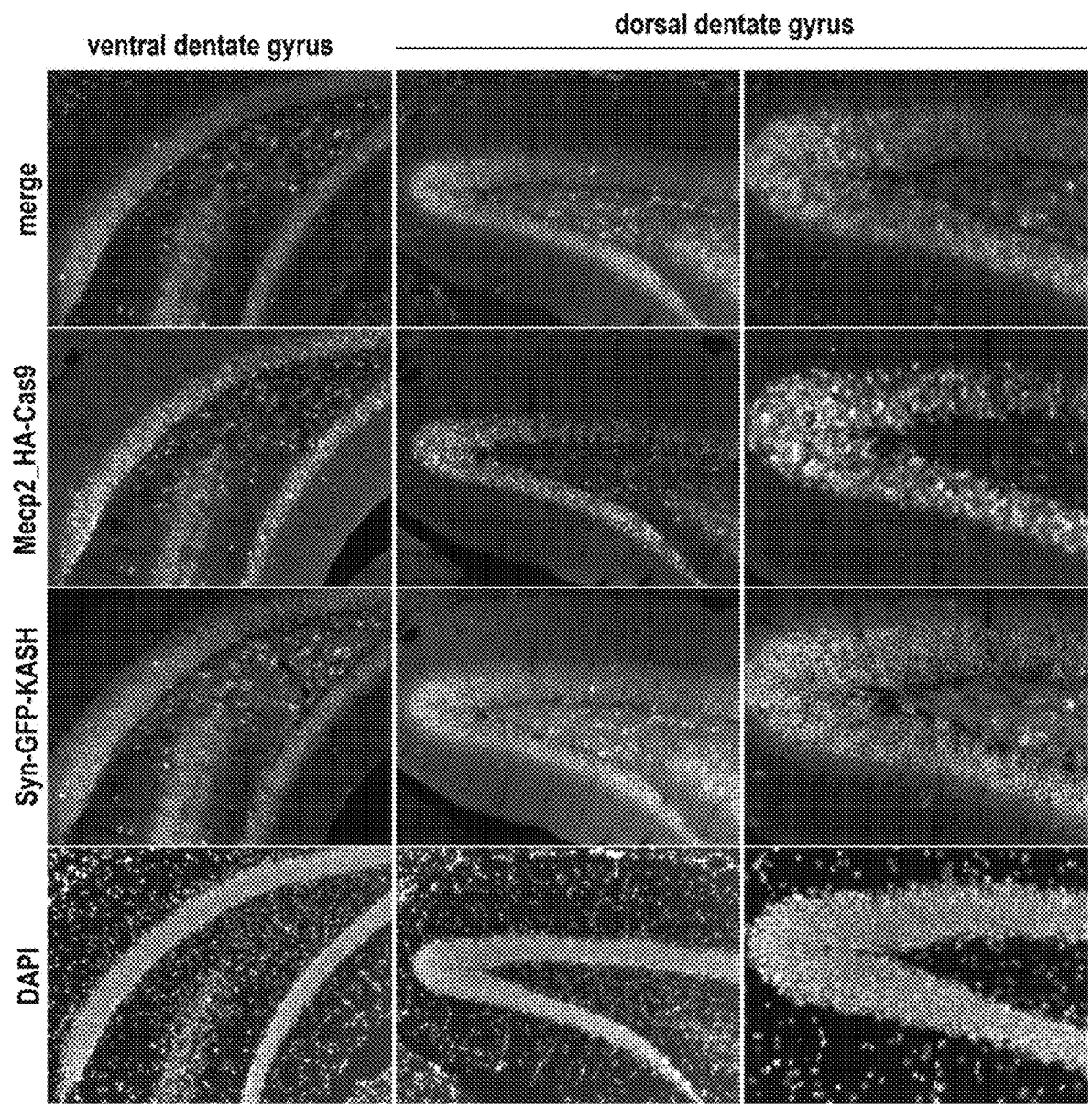
FIG. 56 shows staining of HA-SpCas9 in dorsal and ventral hippocampus 8 weeks after injection of viruses encoding Mecp2-HA-SpCas9 and 3×gRNA-TETS with Syn-KASH-GFP.
Figure 58A:
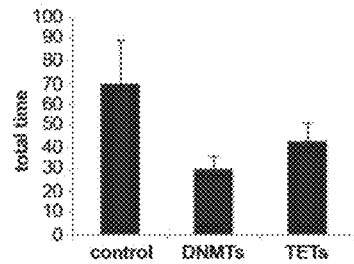
FIG. 58A-I shows behavior tests conducted 5 weeks after CRISPR-mediated KD of TETs and DNMTs in dentate gyrus (ventral and dorsal part) showed increased level of anxiety and learning deficits. A) time spend in the open arm during elevated plus maze test. B) open field test, time spent in the center of arena vs time in the corners was measured. C) Novel object recognition test, results were measured 3 h after familiarization phase. D) Barnes maze; efficiency in finding escape within 3 days of training. E) Barnes maze results. F) Freezing behavior during contextual fear conditioning. G) Latency to first freezing episode during contextual fear conditioning. H) Trace fear conditioning results for TETs KD and DNMTs KD (I). Control—animals injected with SpCas9 virus and GFP-KASH construct without gRNAs. TETs—animals injected with both SpCas9 and construct encoding gRNAs against Tet1, Tet2 and Tet3. DNMTs—animals injected with both SpCas9 and construct encoding gRNAs against Dnmt1, Dnmt3a and Dnmt3b.
Figure 58B:
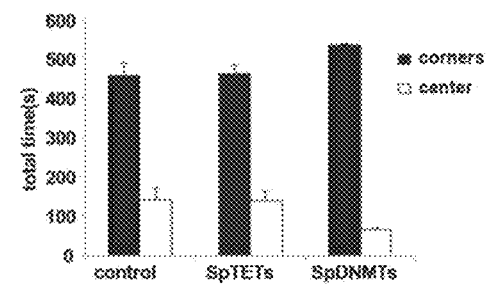
Figure 58C:
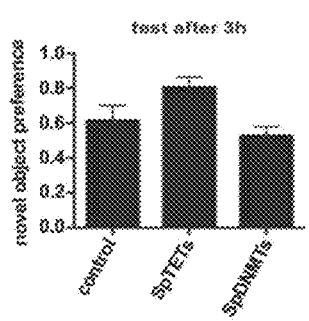
Figure 58D:
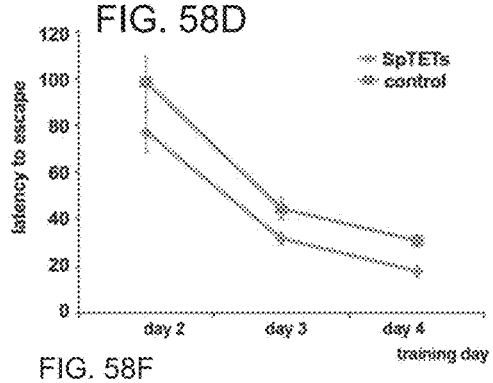
Figure 58E:
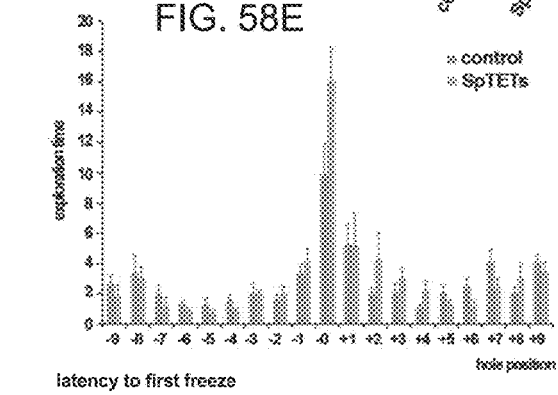
Figure 58F:
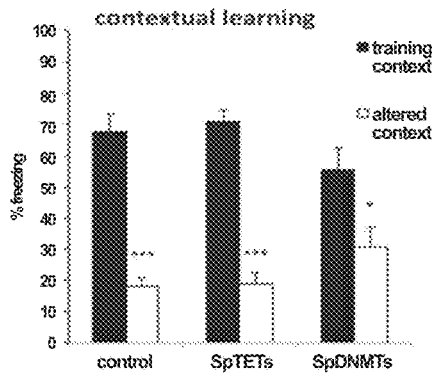
Figure 58G:
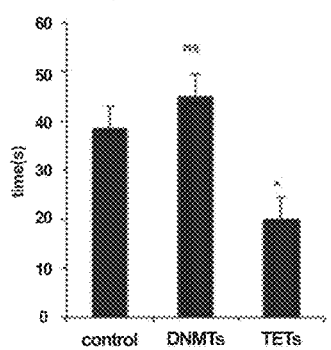
Figure 58H:
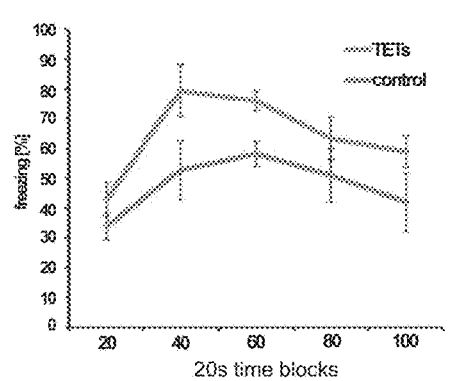
Figure 58I:
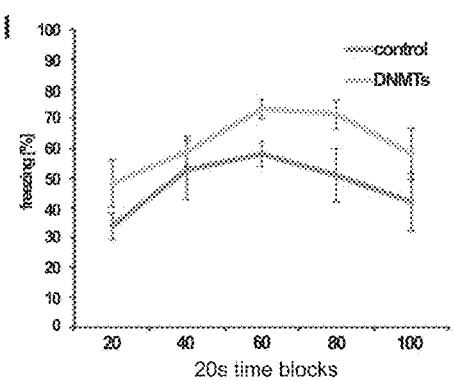
Figure 59:
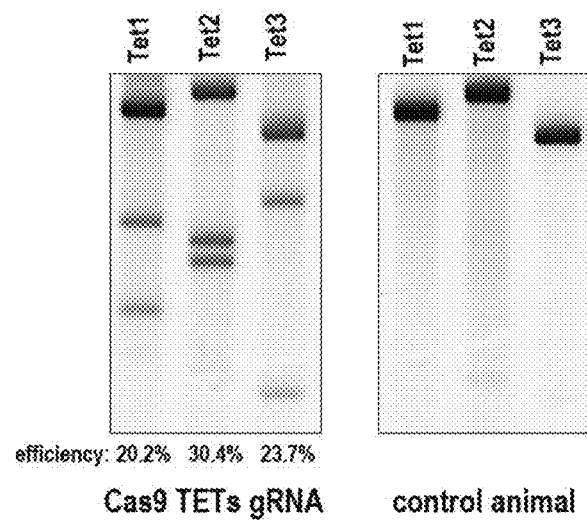
FIG. 59 shows cutting efficiency of Tet loci in the brain, 8 weeks after Mecp_SpCas9 virus injection in compare to control animals injected with Mecp2_SpCas9 virus only.
Figure 60:
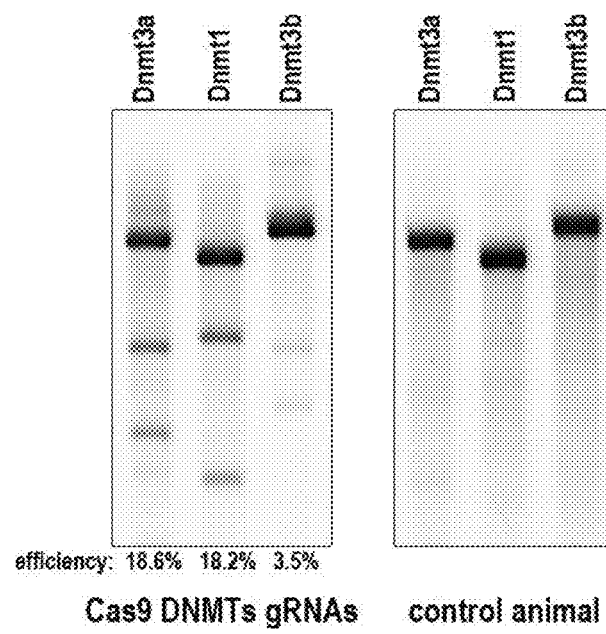
FIG. 60 shows cutting efficiency of Dnmt loci in the brain, 8 weeks after Mecp_SpCas9 virus injection in compare to control animals injected with Mecp2_SpCas9 virus only.
Figure 61:
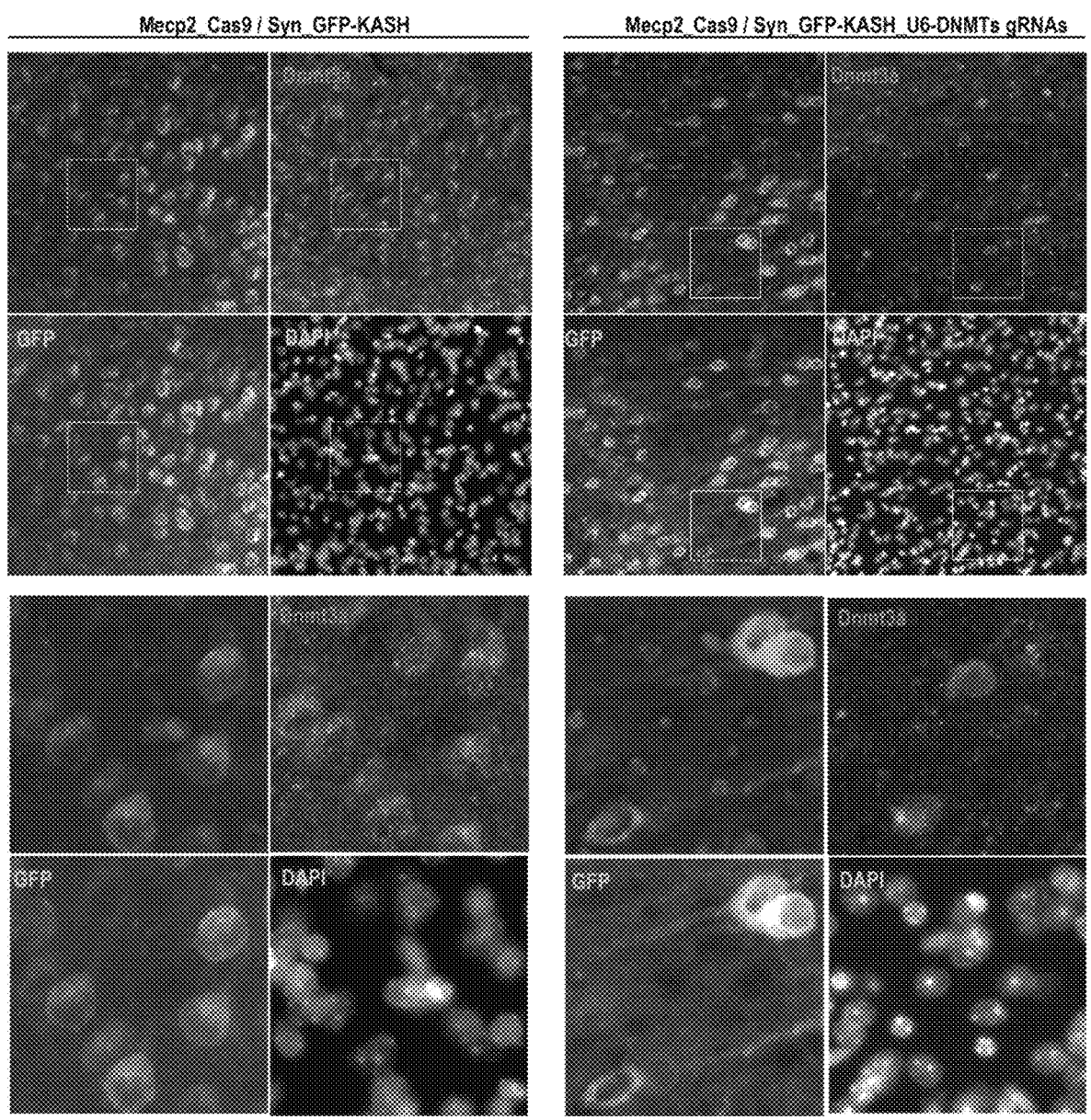
FIG. 61 shows Dnmt3a staining in the brain, 8 weeks after stereotaxic injection of virus encoding Mecp2_SpCas9 and gRNAs targeting Dnmt loci. Bottom panel shows magnification of ROI indicated on the upper panel.
Figure 62:
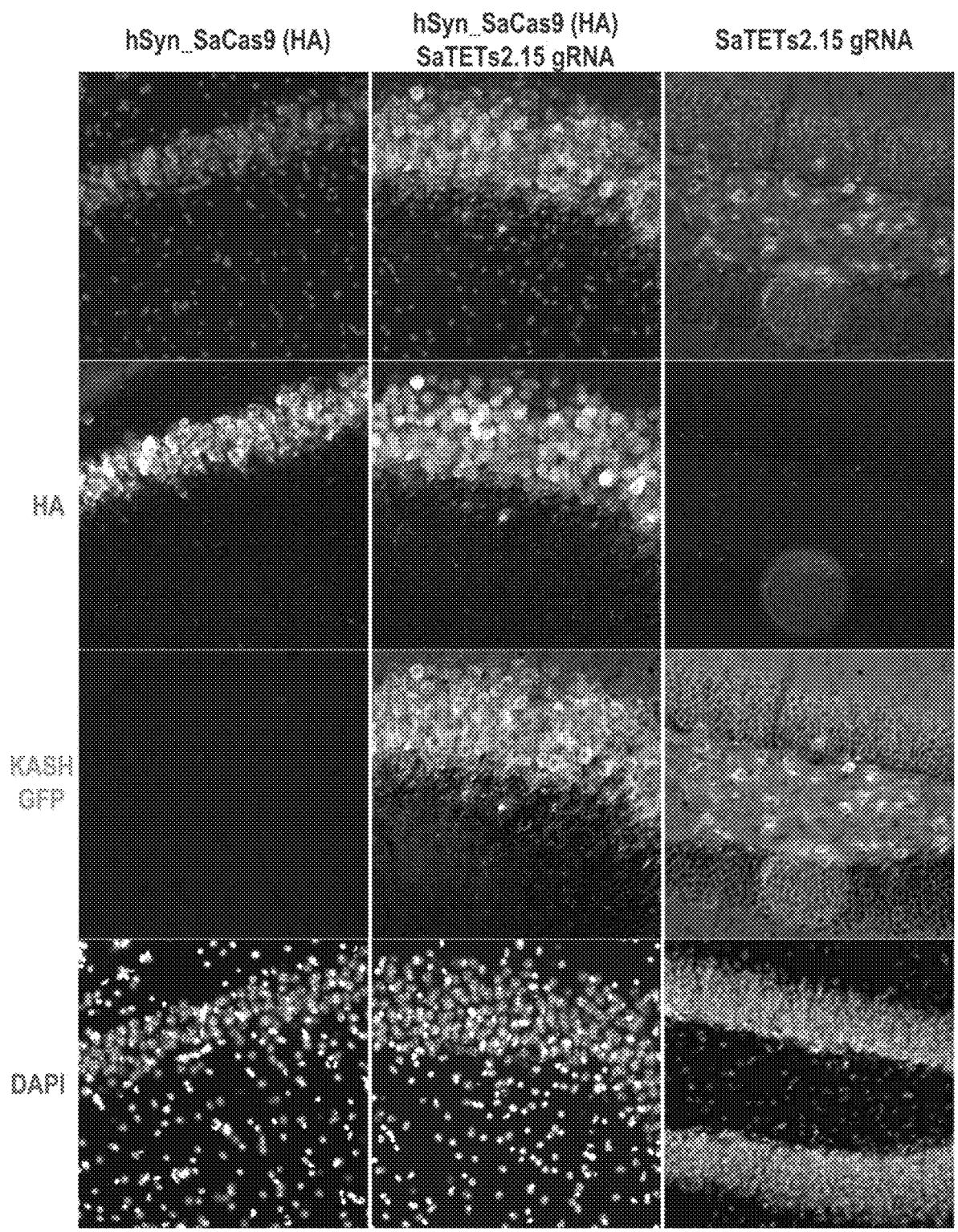
FIG. 62 shows staining of Syn_HA-SaCas9 in the dorsal hippocampus, 4 weeks after injection of virus. First column shows animal injected with Sa-Cas9 only, middle column animal injected with both SaCas9 and gRNAs against TETs loci and the right column represents animal injected with only gRNAs encoding virus. SaCas9 nuclear localization depends on the presence of gRNA.

Applicants have further identified parameters that relate to efficient cleavage by the Cas9 nickase mutant when combined with two guide RNAs and these parameters include but are not limited to the length of the 5' overhang. Efficient cleavage is reported for 5' overhang of at least 26 base pairs. In a preferred embodiment of the invention, the 5' overhang is at least 30 base pairs and more preferably at least 34 base pairs. Overhangs of up to 200 base pairs may be acceptable for cleavage, while 5' overhangs less than 100 base pairs are preferred and 5' overhangs less than 5.0 base pairs are most preferred (FIGS. 54 and 55).

Example 36: Behavior Protocols

Elevated Plus Maze. The Elevated Plus-Maze is used to assess anxiety-like behavior, exploiting the conflict between the innate fear that rodents have of open areas versus their desire to explore novel environments.

The apparatus used for the elevated plus maze test is made of stainless steel and consists of four arms (two open without walls and two enclosed by 15 cm high walls) 35 cm long and 5 cm wide. Each arm of the maze is attached to sturdy metal legs such that it is elevated 40 cm off of the floor:

Mice are housed up to three per cage in a room with a 12 hr light/dark cycle with ad libitum access to food and water.

Behavioral testing is performed between 9:00 A.M. and 6:00 P.M in the brightly lighted room. All the cages containing mice are transferred to the behavior testing room 30 min before the first trial begins.

A mouse is taken out of its cage and place at the junction of the open and closed arms, facing the open arm opposite to where the experimenter is and let for freely explore the maze for 5 min. During that time animal is recorded and behavior is tracked. The total distance traveled in the open arms, time spent in open arms, the total number of transitions between arms, and the latency to enter the open arm are measured automatically with the Noldus software. At the end of the 5-min test, remove the rodent from the plus maze and place into a transport cage. Place back inside its homecage. The elevated plus maze is cleaned carefully and dry with paper towels before testing with another mouse.

Fear Conditioning

Animals: 4-weeks old male mice (BL6J/57); 10 per group

Foot shock: 2 s; 0.5 mA

Protocol involved three phases:

1. Exposure, which allowed the mice to acclimate and become familiar with the training chamber. For unpaired group: 2 min of acclimation, followed by presentation of the 20-sec tone cue, followed by an 80-sec interval, repeated six times. For paired group the acclimation period was 12 min.

2. Training; mice were presented with the CS and or US stimuli. Acclimation period—4 min. Six conditioning trials involving a tone (CS) and a shock (US) were run in trial epochs that lasted 100 sec (including the intertrial interval). For the paired group, each trial consisted of a 20-sec "baseline" interval, a 20-sec tone presentation, an 18-sec trace interval, a 2-sec shock, and a 40-sec post-shock interval. Trials were the same for the unpaired groups of mice except that the tone was omitted.

3. Testing; mice were observed for freezing in response to each context and to the tone and trace-CS. Each phase occurred at 24-h intervals. Mice were allowed to move freely in the training (familiar) and test (altered; flat floor with a grid, bw patterns on the walls; vanillin scent) contexts for 3 min. All mice received four 100-sec testing trials. For all mice, each trial began with a 20-sec interval and the 20-sec tone presentation was followed by a 60-sec interval.

Scoring: All scoring was done based on video. The % of freezing was observed in 5-sec increments throughout each context test exposure and each 100-sec trial epoch. Freezing was scored as 1 or 0 in each time bin, if animal froze for at least 2 s.

The data presented on the column charts is the average for the group of 7 animals, error bars represent SEM. The data on the line charts representing training/testing process in time, and each point is the average of 7 animals, from 6 or 4 trials (training and testing protocol, respectively). Error bars represent SEM.

Open field. The Open Field apparatus is broadly used to assess exploratory behaviour and is validated for use in the measurement of anxiety related behaviours. Animals are placed in the square arena (40×40 cm) for 10 min while their behavior is recorded. The total distance moved, velocity and time spent in the center of arena are scored.

Novel object recognition. The Novel Object Recognition test (NOR) is a popular test to study learning and memory in rodents. It is based on their tendency to interact more with a novel object than with a familiar object. In general, animals are first placed in an apparatus and allowed to explore an object. After a prescribed interval, the animal is returned to the apparatus, which now contains the familiar object and a novel object. Object recognition is distinguished by more time spent interacting with the novel object. The NOR task is particularly attractive because it requires no external motivation, reward, or punishment but a little training or habituation is required, and it can be completed in a relatively short time.

I Pretraining:
1. Following arrival in the colony, the animals are allowed to acclimatize for at least 3-7 d.
2. At test 3 days before starting experiment animals are handled daily for at least 3 min per day and exposed to the transport routine.
3. Familiarization with the testing environment—24 h before experiment animals are exposed to testing arena (40×40×35 cm, clear walls) in the behavior room for 10 min.

II Object recognition training:
1. Two 'identical' to-be-familiarized (sample) objects are placed in the back left and right corners of the apparatus
2. Animal is placed at the mid-point of the wall opposite the sample objects, what prevents any unintentional bias in placing the animal such that it is oriented more towards a particular side/object
3. The experimenter is recording the animal behavior using camera, staying behind the curtain so as not to serve as a cue for the animal or to introduce unintentional bias into the study.
4. After the planned sample-object exposure time (5-10 min), the animal is removed from the apparatus and return to the colony for planned training-to-testing interval. The apparatus is cleaned with 70% ethanol between animals.

III Delay phase. Commonly used training-to-testing intervals vary from 1 h (for robust object recognition) to 24 h.

IV Object recognition test:
1. To test for object recognition after the training-to-testing interval, one of the familiar sample objects is placed in one back corner of the apparatus; the novel object is placed in the other back corner.
2. Animal is placed in the apparatus as in step 11.2. The experimenter is recording animal behavior, staying behind the curtain.
3. After the planned objects exposure time (3-5 min) animals is removed from apparatus and returned to colony. The apparatus is cleaned with 70% ethanol between animals.

Data analysis: Recorded videos are used for later data analysis: a) directed contact scoring (total duration of animal contact with an object); b) within area scoring (an animal as "interacting" with the object when its nose is in contact with the object or directed at the object within minimal distance of 2 cm). Commonly used measures include time with familiar object versus novel object, a difference score (novel object interaction—familiar object interaction), a discrimination ratio (novel object interaction/total interaction with both objects). Object recognition in these measures is reflected by more time interacting with the novel than familiar object, a positive difference score or a discrimination ratio above 0.5, respectively.

Barnes maze. Carol Barnes developed a dry-land maze test for spatial learning and memory in 1979 where animals escaped from a brightly lit, exposed circular open platform surface to a small dark recessed chamber located under one of the 18 holes around the perimeter of the platform. Although it was initially invented for rats, the Barnes maze (BM) has become more popular to assess spatial memory in mice, taking advantage of their superior abilities to find and escape through small holes.

Procedure:

1. Adaptaiion. Mouse is placed in a cylindrical black start chamber in the middle of the maze. After 10 s have elapsed chamber is removed and the buzzer is turned on together with strong light. Mouse is gently guided to the escape box. Once the mouse is inside the box, buzzer and light are turned off. The mouse should stay in the escape box for 2 min.

2. Spatial acquisition. Mouse is placed in the cylindrical black start chamber in the middle of the maze. After 10 s have the chamber is lifted and the buzzer and light are on. Mouse is allowed to explore the maze for 3 minutes. The trial ends when the mouse enters the goal tunnel or after 3 min have elapsed. Immediately after the mouse enters the tunnel, the buzzer and the light are turned off and the mouse is allowed to stay in the tunnel for 1 min. If the mouse does not reach the goal within 3 minutes the experimenter is guiding it gently to the escape box and leave the mouse inside for 1 min. Mouse stays in the home cage until next trial. Whole trial is repeated 4 times in 15 minutes intervals during next 3-4 days.

3. Reference memory trial. 24 h after the last training day, the probe trial is conducted. The target hole must be closed. Animal is placed in the middle of the maze under the cylindrical black start chamber and after 10 s the chamber is removed, the buzzer and the light are turned on. Mouse is removed from the maze after 90 s. The probe trial is done in order to determine if the animal remembers where the target goal was located. Number of pokes (errors) in each hole and latency and path length to reach the virtually target hole are measured.

Example 37: SaCas9 Update

Figure 69:
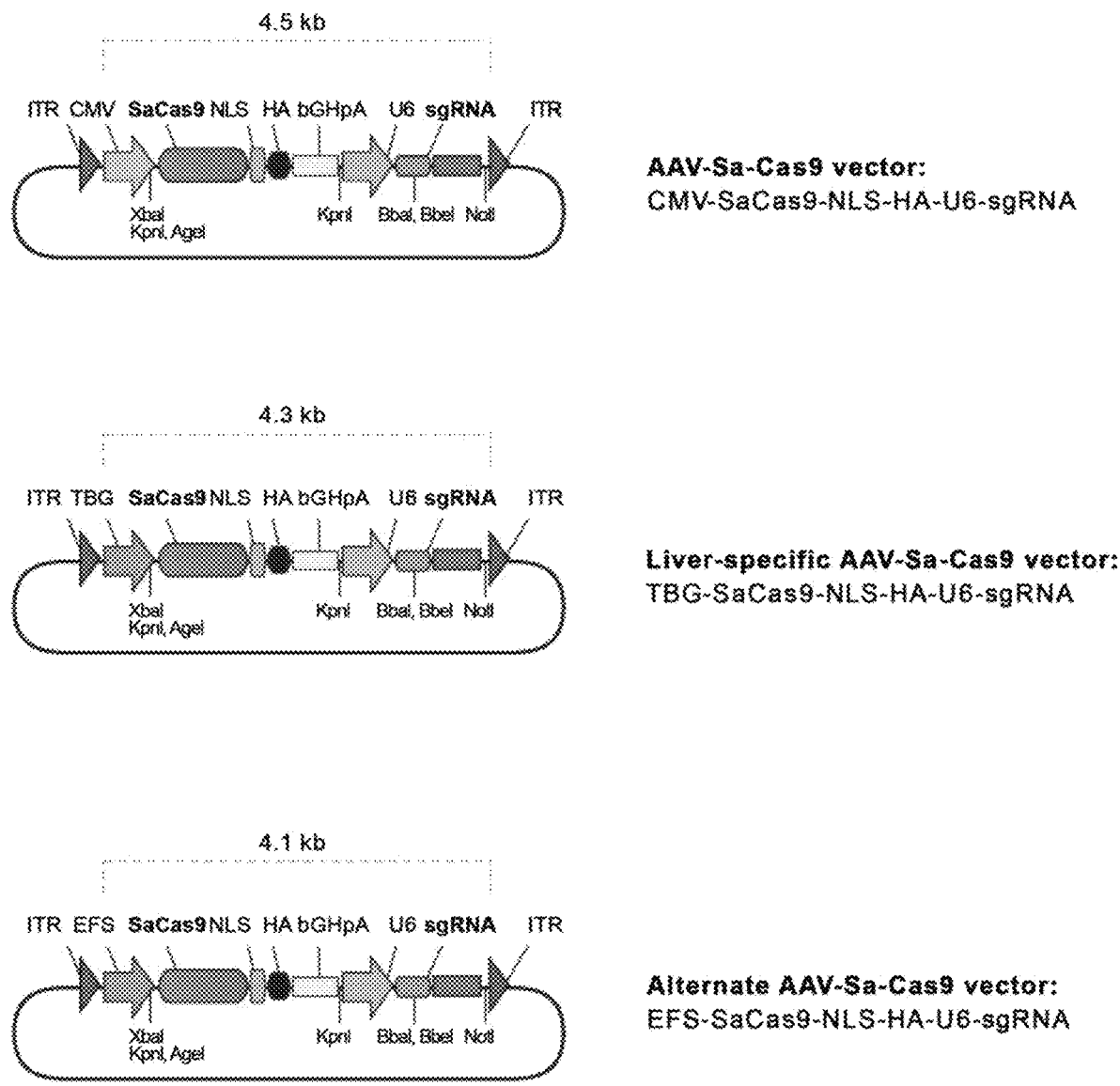
FIG. 69 shows an AAV-Sa-Cas9 vector, a liver-specific AAV-Sa-Cas9 vector and an alternate AAV-Sa-Cas9 vector.

FIG. 69 shows an AAV-Sa-Cas9 vector, a liver-specific AAV-Sa-Cas9 vector and an alternate AAV-Sa-Cas9 vector.

Figure 70:
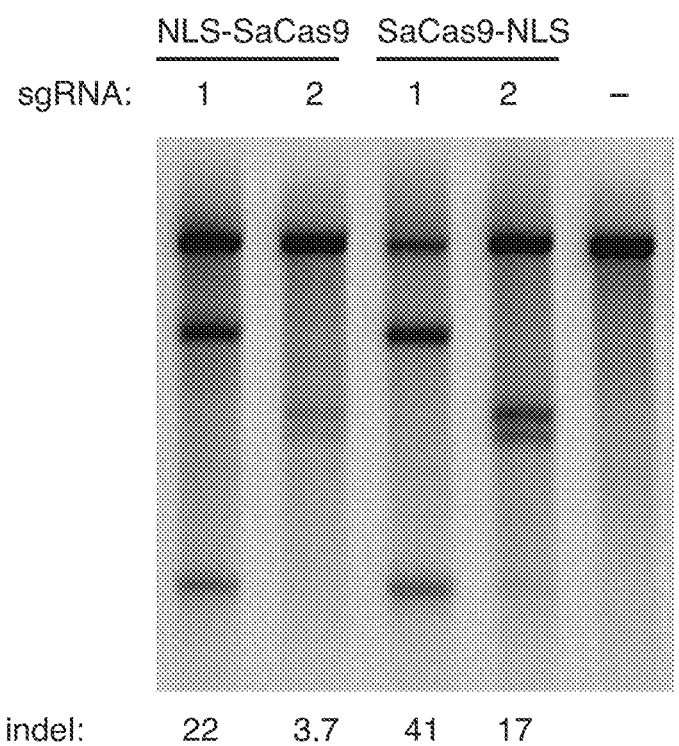
FIG. 70 shows data on optimized CMV-SaCas9-NLS-U6-sgRNA vector (submitted vector design last time); new data compares N'-term vs C'-term tagged SaCas9 and shows enhanced cleavage efficiency using C'-term NLS tagging.

FIG. 70 shows data on optimized CMV-SaCas9-NLS-U6-sgRNA vector (submitted vector design last time); new data compares N'-term vs C'-term tagged SaCas9 and shows enhanced cleavage efficiency using C'-term NLS tagging.

New targets were chosen in exons 4 and 5 of the mouse Pcsk9 gene (sequences and locations below). Exons 4-5 lie downstream of a Pcsk9 N-terminal pro-domain region that is proteolytically cleaved upon protein maturation, and indels in this downstream region are expected to lead to protein degradation. Pcsk9 is involved in cycling and negative regulation of the LDL-receptor, and loss of Pcsk9 should indirectly lead to lowered plasma cholesterol levels.

SgRNAs were cloned into AAV vector and tested for indel activity in Hepa1-6 mouse hepatocyte cell line in single vector transfection. 500 ng of vector was transfected into 200,000 Hepa1-6 cells by Lipofectamine 2000 and DNA collected for SURVEYOR assay, showing cleavage of Pcsk9.

pAAV-CMV-SaCas9-NLS-U6-sgRNA(231: atctcttagataccagcatc (SEQ ID NO: 206))

pAAV-CMV-SaCas9-NLS-U6-sgRNA(232: tcaatctcccgatgggcacc (SEQ ID NO: 207))

pAAV-CMV-SaCas9-NLS-U6-sgRNA(233: gcccatcggagattgaggg (SEQ ID NO: 208))

pAAV-CMV-SaCas9-NLS-U6-sgRNA(234: acttcaacagcgtgccggag (SEQ ID NO: 209))

pAAV-CMV-SaCas9-NLS-U6-sgRNA(235: ccgctgaccacacctgccag (SEQ ID NO: 210))

pAAV-CMV-SaCas9-NLS-U6-sgRNA(236: tggcaggtgtggtcagcggc (SEQ ID NO: 211))

Figure 71:
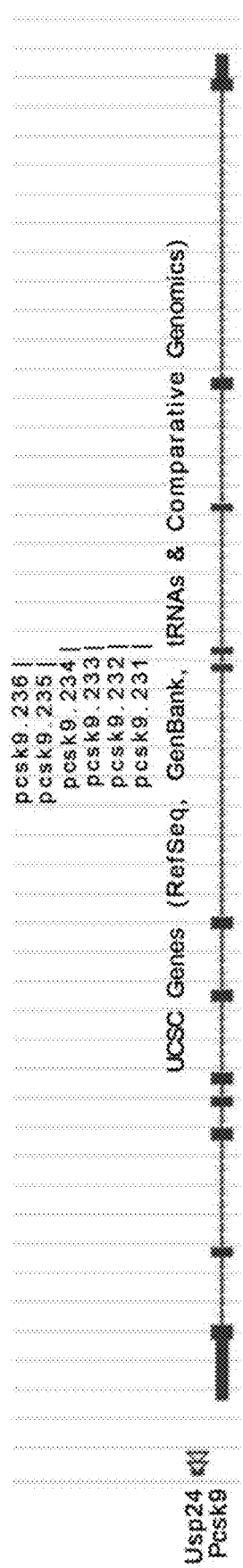
FIG. 71 shows SURVEYOR image showing indels generated by new Pcsk9 targets.

FIG. 71 shows SURVEYOR image showing indels generated by new Pcsk9 targets.

Figure 72:
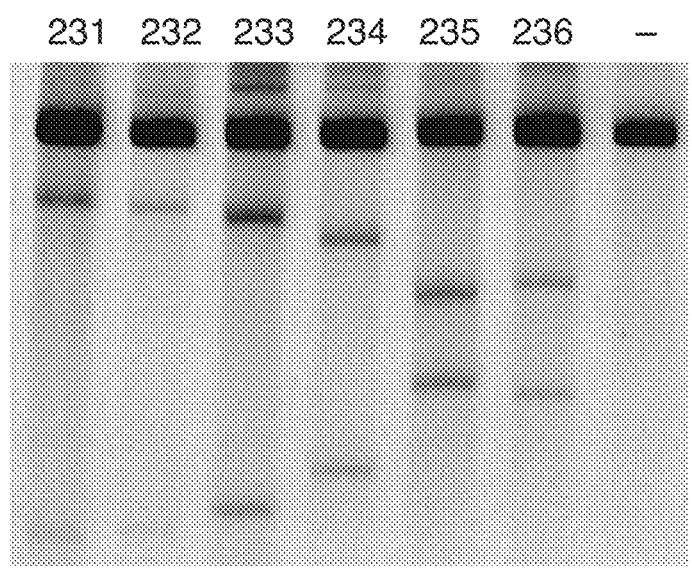
FIG. 72 shows SaCas9 specificity: genome-wide off target sites (GWOTs) are predicted based on 2 criteria: they contain 4 or fewer mismatched bases to intended SaCas9 target and bear the least restrictive PAM for SaCas9, NNGRR. HEK 293FT cells are transfected with either SpCas9 or SaCas9 with their corresponding sgRNAs at a target site (EMX1: TAGGGTTAGGGGCCCCAGGC (SEQ ID NO: 2)) that has CGGGGT as a PAM (sequence including PAM disclosed as SEQ ID NO: 369) so that it can be cut by either SpCas9 (CGG) or SaCas9 (CGGGGT). DNAs from cells are harvested and analyzed for indels by Illumina sequencing at on-target and 41 predicted off-target loci (following protocols from Hsu et al. Nature Biotech 2013 and data analysis pipeline developed by David Scott and Josh Weinstein).

FIG. 72 shows SaCas9 specificity: genome-wide off target sites (GWOTs) are predicted based on 2 criteria: they contain 4 or fewer mismatched bases to intended SaCas9 target and bear the least restrictive PAM for SaCas9, NNGRR. HEK 293FT cells are transfected with either SpCas9 or SaCas9 with their corresponding sgRNAs at a target site (EMX1: TAGGGTTAGGGGCCCCAGGC (SEQ ID NO: 2)) that has CGGGGT as a PAM (sequence including PAM disclosed as SEQ ID NO: 369) so that it can be cut by either SpCas9 (CGG) or SaCas9 (CGGGGT). DNAs from cells are harvested and analyzed for indels by Illumina sequencing at on-target and 41 predicted off-target loci (following protocols from Hsu et al. Nature Biotech 2013 and data analysis pipeline developed by David Scott and Josh Weinstein).

Figure 73:
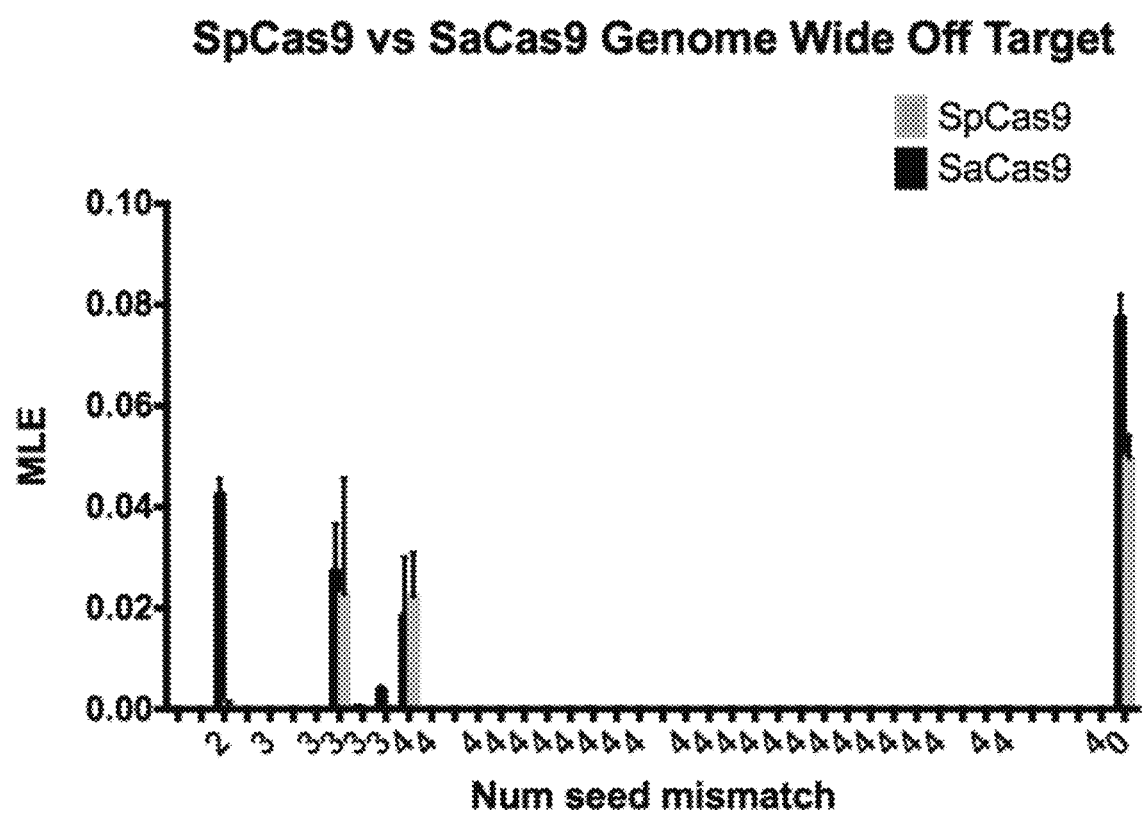
FIG. 73 shows that that SaCas9 may have a higher level of off-target activity than SpCas9 at certain loci.

FIG. 73 shows that that SaCas9 may have a higher level of off-target activity than SpCas9 at certain loci.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

PARTIES TO A JOINT RESEARCH AGREEMENT

The claimed invention was made by, on behalf of, and/or in connection with one or more of the following parties to a joint research agreement: the Broad Institute, Inc., Massachusetts Institute of Technology, and President and Fellows of Harvard College. The joint research agreement was in effect on or before the date the claimed invention was made, and the claimed invention was made as a result of activities undertaken within the scope of the joint research agreement.

REFERENCES

Banker G, Goslin K. Developments in neuronal cell culture. Nature. 1988 Nov. 10; 336(6195): 185-6.

Bedell, V. M. et al. In vivo genome editing using a high-efficiency TALEN system. Nature 491, 114-U133 (2012).

Bhaya, D., Davison, M. & Barrangou, R. CRISPR-Cas systems in bacteria and archaea: versatile small RNAs for adaptive defense and regulation. Annu Rev Genet 45, 273-297 (2011).

Bobis-Wozowicz, S., Osiak, A., Rahman, S. H. & Cathomen, T. Targeted genome editing in pluripotent stem cells using zinc-finger nucleases. Methods 53, 339-346 (2011).

Boch, J. et al. Breaking the code of DNA binding specificity of TAL-type III effectors. Science 326, 1509-1512 (2009).

Bogenhagen, D. F. & Brown, D. D. Nucleotide sequences in *Xenopus* 5S DNA required for transcription termination. Cell 24, 261-270 (1981).

Bultmann, S. et al. Targeted transcriptional activation of silent oct4 pluripotency gene by combining designer TALEs and inhibition of epigenetic modifiers. Nucleic Acids Res 40, 5368-5377 (2012).

Carlson, D. F. et al. Efficient TALEN-mediated gene knockout in livestock. Proc Natl Acad Sci USA 109, 17382-17387 (2012).

Chen, F. Q. el al. High-frequency genome editing using ssDNA oligonucleotides with zinc-finger nucleases. Nat Methods 8, 753-U796 (2011).

Cho, S. W., Kim, S., Kim, J. M. & Kim, J. S. Targeted genome engineering in human cells with the Cas9 RNA-guided endonuclease. Nat Biotechnol 31, 230-232 (2013).

Christian, M. et al. Targeting DNA double-strand breaks with TAL effector nucleases. Genetics 186, 757-761 (2010).

Cong, L. et al. Multiplex genome engineering using CRISPR-Cas systems. Science 339, 819-823 (2013).

Deltcheva, E. et al. CRISPR RNA maturation by trans-encoded small RNA and host factor RNase III. Nature 471, 602-607 (2011).

Deveau, H., Garneau, J. E. & Moineau, S. CRISPR-Cas system and its role in phage-bacteria interactions. Annu Rev Microbiol 64, 475-493 (2010).

Ding, Q. et al. A TALEN genome-editing system for generating human stem cell-based disease models. Cell Stem Cell 12, 238-251 (2013).

Garneau, J. E. et al. The CRISPR-Cas bacterial immune system cleaves bacteriophage and plasmid DNA. Nature 468, 67-71 (2010).

Gasiunas, G., Barrangou, R., Horvath, P. & Siksnys, V. Cas9-crRNA ribonucleoprotein complex mediates specific DNA cleavage for adaptive immunity in bacteria. Proc Natl Acad Sci USA 109, E2579-2586 (2012).

Geurts, A. M. et al. Knockout Rats via Embryo Microinjection of Zinc-Finger Nucleases. Science 325, 433-433 (2009).

Gray S J, Foti S B, Schwartz J W, Bachaboina L, Taylor-Blake B, Coleman J, Ehlers M D, Zylka M J, McCown T J, Samulski R J. Optimizing promoters for recombinant adeno-associated virus-mediated gene expression in the peripheral and central nervous system using self-complementary vectors. Hum Gene Ther. 2011 September; 22(9): 1143-53. doi: 10.1089/hum.2010.245.

Guschin, D. Y. et al. A rapid and general assay for monitoring endogenous gene modification. Methods Mol Biol 649, 247-256 (2010).

Hasty, P., Rivera-Perez, J. & Bradley, A. The length of homology required for gene targeting in embryonic stem cells. Mol Cell Biol 11, 5586-5591 (1991).

Horvath, P. & Barrangou, R. CRISPR-Cas, the immune system of bacteria and archaea. Science 327, 167-170 (2010).

Hsu, P. D. & Zhang, F. Dissecting neural function using targeted genome engineering technologies. ACS Chem Neurosci 3, 603-610 (2012).

Hwang, W. Y. et al. Efficient genome editing in zebrafish using a CRISPR-Cas system. Nat Biotechnol 31, 227-229 (2013).

Jiang, W., Bikard, D., Cox, D., Zhang, F. & Marraffini, L. A. RNA-guided editing of bacterial genomes using CRISPR-Cas systems. Nat Biotechnol 31, 233-239 (2013).

Jinek, M. et al. A programmable dual-RNA-guided DNA endonuclease in adaptive bacterial immunity. Science 337, 816-821 (2012).

Jinek, M. et al. RNA-programmed genome editing in human cells. eLife 2, e00471 (2013).

Kaplitt, M. G., et al., Safety and tolerability of gene therapy with an adeno-associated virus (AAV) borne GAD gene for Parkinson's disease: an open label, phase I trial. Lancet. 2007 Jun. 23; 369(9579):2097-105.

Levitt N. Briggs D. Gil A. Proudfoot N. J. Definition of an efficient synthetic poly(A) site. Genes Dev. 1989; 3:1019-1025.

Liu D, Fischer I. Two alternative promoters direct neuron-specific expression of the rat microtubule-associated protein 1B gene. J Neurosci. 1996 Aug. 15; 16(16):5026-36.

Lopes, V. S., etc al., Retinal gene therapy with a large MYO7A cDNA using adeno-assocaited virus. Gene Ther, 2013 Jan. 24. doi: 10.1038/gt 2013.3.[Epub ahead of print]

Mahfouz, M. M. et al. De novo-engineered transcription activator-like effector (TALE) hybrid nuclease with novel DNA binding specificity creates double-strand breaks. Proc Natl Acad Sci USA 108, 2623-2628 (2011).

Makarova, K. S. et al. Evolution and classification of the CRISPR-Cas systems. Nat Rev Microbiol 9, 467-477 (2011).

Mali, P. et al. RNA-guided human genome engineering via Cas9. Science 339, 823-826 (2013).

McClure C, Cole K L, Wulff P, Klugmann M, Murray A J. Production and titering of recombinant adeno-associated viral vectors. J Vis Exp. 2011 Nov. 27; (57):e3348. doi: 10.3791/3348.

Michaelis, L. M., Maud "Die kinetik der invertinwirkung.". Biochem. z (1913).

Miller, J. C. et al. An improved zinc-finger nuclease architecture for highly specific genome editing. Nat Biotechnol 25, 778-785 (2007).

Miller, J. C. et al. A TALE nuclease architecture for efficient genome editing. Nat Biotechnol 29, 143-148 (2011).

Moscou, M. J. & Bogdanove, A. J. A simple cipher governs DNA recognition by TAL effectors. Science 326, 1501 (2009). Porteus, M. H. & Baltimore, D. Chimeric nucleases stimulate gene targeting in human cells. Science 300, 763 (2003).

Mussolino, C. et al. A novel TALE nuclease scaffold enables high genome editing activity in combination with low toxicity. Nucleic acids research 39, 9283-9293 (2011).

Nathwani, A. C., et al., Adenovirus-associated virus vector-mediated gene transfer in hemophilia B. N Engl J Med. 2011 Dec. 22; 365(25):2357-65. doi: 10.1056/NEJMoa1108046. Epub 2011 Dec. 10.

Oliveira, T. Y. et al. Translocation capture sequencing: a method for high throughput mapping of chromosomal rearrangements. J Immunol Methods 375, 176-181 (2012).

Perez, E. E. et al. Establishment of HIV-1 resistance in CD4(+) T cells by genome editing using zinc-finger nucleases. Nat Biotechnol 26, 808-816 (2008).

Qi, L. S. et al. Repurposing CRISPR as an RNA-guided platform for sequence-specific control of gene expression. Cell 152, 1173-1183 (2013).

REMINGTON'S PHARMACEUTICAL SCIENCES (Mack Pub. Co., N.J. 1991)

Reyon, D. et al. FLASH assembly of TALENs for high-throughput genome editing. Nat Biotechnol 30, 460-465 (2012).

Saleh-Gohari, N. & Helleday, T. Conservative homologous recombination preferentially repairs DNA double-strand breaks in the S phase of the cell cycle in human cells. Nucleic Acids Res 32, 3683-3688 (2004).

Sander, J. D. et al. Selection-free zinc-finger-nuclease engineering by context-dependent assembly (CoDA). Nat Methods 8, 67-69 (2011).

Sanjana, N. E. et al. A transcription activator-like effector toolbox for genome engineering. Nat Protoc 7, 171-192 (2012).

Sapranauskas, R. et al. The *Streptococcus thermophilus* CRISPR-Cas system provides immunity in *Escherichia coli*. Nucleic Acids Res 39, 9275-9282 (2011).

Shen, B. et al: Generation of gene-modified mice via Cas9/RNA-mediated gene targeting. Cell Res 23, 720-723 (2013).

Smithies, O., Gregg, R. G., Boggs, S. S., Koralewski, M. A. & Kucherlapati, R. S. Insertion of DNA sequences into the human chromosomal beta-globin locus by homologous recombination. Nature 317, 230-234 (1985).

Soldner, F. et al. Generation of isogenic pluripotent stem cells differing exclusively at two early onset Parkinson point mutations. Cell 146, 318-331 (2011).

Takasu, Y. et al. Targeted mutagenesis in the silkworm *Bombyx mori* using zinc finger nuclease mRNA injection. Insect Biochem Molec 40, 759-765 (2010).

Tangri S, et al., Rationally engineered therapeutic proteins with reduced immunogenicity, J Immunol. 2005 Mar. 15; 174(6):3187-96.

Thomas, K. R., Folger, K. R. & Capecchi, M. R. High frequency targeting of genes to specific sites in the mammalian genome. Cell 44, 419-428 (1986).

Tuschl, T. Expanding small RNA interference. Nat Biotechnol 20, 446-448 (2002).

Urnov, F. D., Rebar, E. J., Holmes, M. C., Zhang, H. S. & Gregory, P. D. Genome editing with engineered zinc finger nucleases. Nat Rev Genet 11, 636-646 (2010).

Valton, J. et al. Overcoming transcription activator-like effector (TALE) DNA binding domain sensitivity to cytosine methylation. J Biol Chem 287, 38427-38432 (2012).

Wang, H. et al. One-Step Generation of Mice Carrying Mutations in Multiple Genes by CRISPR-Cas-Mediated Genome Engineering. Cell 153, 910-918 (2013).

Watanabe, T. et al. Non-transgenic genome modifications in a hemimetabolous insect using zinc-finger and TAL effector nucleases. Nat Commun 3 (2012).

Wilson, E. B. Probable inference, the law of succession, and statistical inference. J Am Stat Assoc 22, 209-212 (1927).

Wood, A. J. et al. Targeted genome editing across species using ZFNs and TALENs. Science 333, 307 (2011).

Wu, S., Ying, G. X., Wu, Q. & Capecchi, M. R. A protocol for constructing gene targeting vectors: generating knockout mice for the cadherin family and beyond. Nat Protoc 3, 1056-1076 (2008).

Zhang, F. et al. Efficient construction of sequence-specific TAL effectors for modulating mammalian transcription. Nat Biotechnol 29, 149-153 (2011).

---

The invention claimed is:

1. A vector comprising a nucleic acid encoding Cas9 operably linked to at least one nuclear localization signal (NLS), wherein the nucleic acid is under the control of a promoter which is inducible in a eukaryotic cell or a control element which allows for conditional expression of the Cas9 in a eukaryotic cell, and wherein the Cas9 is a Cre recombinase dependent Cas9.

2. The vector of claim 1, wherein the vector comprises a nucleic acid encoding a stop cassette element, wherein the stop cassette element is loxP-SV40 polyA x3-loxP.

3. The vector of claim 2, wherein the nucleic acid encoding the stop element is between the promoter and the nucleic acid encoding Cas9.

4. A eukaryotic cell comprising the vector of claim 2.

5. The vector of claim 1, wherein the Cas9 is a *Streptococcus pyogenes* Cas9.

6. The vector of claim 1, further comprising a nucleic acid encoding a peptide cleavage sequence.

7. The vector of claim 1, further comprising a nucleic acid encoding a woodchuck hepatitis virus posttranscriptional regulatory element (WPRE).

8. The vector of claim 1, further comprising a nucleic acid encoding a bovine growth hormone poly-A signal sequence (bGHpolyA).

9. The vector of claim 1, further comprising a nucleic acid encoding a peptide cleavage sequence, a WPRE and a bGHpolyA.

10. A eukaryotic cell comprising the vector of claim 1.

11. The eukaryotic cell of claim 10, wherein the cell is a mouse cell.

12. The vector of claim 1, wherein the vector further comprises nucleic acid(s) to target insertion of the nucleic acid encoding the Cas9 and the at least one NLS, and the promoter or the control element, to a Rosa26 locus.

13. The vector of claim 1, wherein the at least one NLS is selected from the group consisting of: PKKKRKV (SEQ ID NO:62), KRPAATKKAGQAKKKK (SEQ ID NO:63), PAAKRVKLD (SEQ ID NO:64), RQRRNELKRSP (SEQ ID NO:65), NQSSNFGPMKGGNFG-GRSSGPYGGGGQYFAKPRNQGGY (SEQ ID NO:66), RMRIZFKNKGKDTAELRRRRVEVSVELRKAKKD-EQILKRRNV (SEQ ID NO:67), VSRKRPRP (SEQ ID NO:68), PPKKARED (SEQ ID NO:69), PQPKKKPL (SEQ ID NO:70), SALIKKKKKMAP (SEQ ID NO:71), DRLRR (SEQ ID NO:72), PKQKKRK (SEQ ID NO:73), RKLKK-KIKKL (SEQ ID NO:74), REKKKFLKRR (SEQ ID NO:75), KRKGDEVDGVDEVAKKKSKK (SEQ ID NO:76), and RKCLQAGMNLEARKTKK (SEQ ID NO:77).

14. A vector comprising a nucleic acid encoding Cas9 operably liked to a first NLS at the amino-terminus (N-terminus) of the Cas9 and a second NLS at the carboxy-terminus (C-terminus) of the Cas9, wherein the nucleic acid is under the control of a promoter which is inducible in a eukaryotic cell or a control element which allows for conditional expression of the Cas9 in a eukaryotic cell.

15. A vector comprising a nucleic acid encoding Cas9 operably linked to a first NLS near the N-terminus of the Cas9 and a second NLS near the C-terminus of the Cas9, wherein the nucleic acid is under the control of a promoter which is inducible in a eukaryotic cell or a control element which allows for conditional expression of Cas9 in a eukaryotic cell, wherein the first NLS is considered near the N-terminus of the Cas9 when the nearest amino acid of the first NLS is within about 50 amino acids along the polypeptide chain from the N-terminus of the Cas9, and wherein the second NLS is considered near the C-terminus of the Cas9 when the nearest amino acid of the second NLS is within about 50 amino acids along the polypeptide chain from the C-terminus of the Cas9.

* * * * *